United States Patent
Solis Escalante et al.

(10) Patent No.: US 12,252,727 B2
(45) Date of Patent: Mar. 18, 2025

(54) METHOD FOR PRODUCING DRIMANYL ACETATE COMPOUNDS

(71) Applicant: FIRMENICH SA, Satigny (CH)

(72) Inventors: Daniel Solis Escalante, Satigny (CH); Christian Görner, Satigny (CH); Laurent Daviet, Satigny (CH); Qi Wang, Shanghai (CN)

(73) Assignee: FIRMENICH SA, Satigny (CH)

( * ) Notice: Subject to any disclaimer, the term of this patent is extended or adjusted under 35 U.S.C. 154(b) by 337 days.

(21) Appl. No.: 17/271,474

(22) PCT Filed: Oct. 14, 2019

(86) PCT No.: PCT/EP2019/077716
§ 371 (c)(1),
(2) Date: Feb. 25, 2021

(87) PCT Pub. No.: WO2020/078871
PCT Pub. Date: Apr. 23, 2020

(65) Prior Publication Data
US 2021/0310031 A1    Oct. 7, 2021

(30) Foreign Application Priority Data

Oct. 15, 2018   (EP) .................................. 18200539

(51) Int. Cl.
*C12P 7/62* (2022.01)
*C12P 7/02* (2006.01)

(52) U.S. Cl.
CPC .. *C12P 7/62* (2013.01); *C12P 7/02* (2013.01)

(58) Field of Classification Search
CPC . C12P 7/62; C12P 7/02; C12N 9/1025; C12N 9/10; C12N 15/09; C12N 1/15; C12Y 203/00
USPC ................................................ 435/135, 193
See application file for complete search history.

(56) References Cited

FOREIGN PATENT DOCUMENTS

| JP | 2017518741 A | 7/2017 |
|----|--------------|--------|
| WO | 2013058655 A1 | 4/2013 |
| WO | 2015169871 A2 | 11/2015 |

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340.*
Witkowski et al., (Biochemistry 38:11643-11650, 1999.*
Achenbernner et al. Eur J of chem, 2009, pp. 1-31.*
International Search Report and Written Opinion for corresponding PCT/EP2019/077716 mailed Jan. 13, 2020, 12 Pages.
Hiroyuki Akita et al. Tetrahedron Asymmetry vol. 11 Published 2000 pp. 1375-1388.
Anilkumar A. T. et al. Tetrahedron Studies in Lipase Catalyzed Transesterifications vol. 56 Published 2000 pp. 1899-1903.
Moonhyuk Kwon et al. FEBS Letters Elsevier vol. 588 No. 24 published 2014 pp. 4597-4603.

* cited by examiner

*Primary Examiner* — Robert B Mondesi
*Assistant Examiner* — Mohammad Y Meah
(74) *Attorney, Agent, or Firm* — Armstrong Teasdale LLP

(57) ABSTRACT

Described herein are novel methods for the acetyl transferase-catalyzed production of drimanyl-acetate compounds by the acetylation of the respective drimanyl alcohol sources performed in vitro or in vivo. Also described herein is the identification of enzymes having corresponding acetyl transferase activity from different microbial and plant sources. Also described herein is the provision of enzyme mutants derived from the newly identified enzymes. Further described herein is the provision of corresponding coding sequences of such enzymes and mutants, recombinant vectors, and recombinant host cells suitable for the production of such acetyl transferases and mutants and for performing the novel production methods of drimanyl acetate compounds. Still further described herein is a method of using such drimanyl acetates as intermediates for the production of odorant, flavor or fragrance or insect/pest control ingredients.

11 Claims, 12 Drawing Sheets

Specification includes a Sequence Listing.

drimane structure (+)-albicanol (-)-drimenol

Bicyclofarnesol

SEQUENCE LISTING

<160> NUMBER OF SEQ ID NOS: 144

<210> SEQ ID NO 1
<211> LENGTH: 5689
<212> TYPE: DNA
<213> ORGANISM: Artificial Sequence
<220> FEATURE:
<223> OTHER INFORMATION: Plasmid pF167

<400> SEQUENCE: 1
tggtcagcaa caacgccgaa gaatcactct cgtgttgaga attgcacgcc ttgaccacga    60
cacgttaagg gattttggtc atgagattat caaaaaggat cttcacctag atccttttaa   120

```
attaaaaatg aagttttaaa tcaatctaaa gtatatatga gtaaacttgg tctgacagtt      180
accaatgctt aatcagtgag gcacctatct cagcgatctg tctatttcgt tcatccatag      240
ttgcctgact ccccgtcgtg tagataacta cgatacggga gggcttacca tctggcccca      300
gtgctgcaat gataccgcga gacccacgct caccggctcc agatttatca gcaataaacc      360
agccagccgg aagggccgag cgcagaagtg gtcctgcaac tttatccgcc tccatccagt      420
ctattaattg ttgccgggaa gctagagtaa gtagttcgcc agttaatagt ttgcgcaacg      480
ttgttgccat tgctacaggc atcgtggtgt cacgctcgtc gtttggtatg gcttcattca      540
gctccggttc ccaacgatca aggcgagtta catgatcccc catgttgtgc aaaaaagcgg      600
ttagctcctt cggtcctccg atcgttgtca gaagtaagtt ggccgcagtg ttatcactca      660
tggttatggc agcactgcat aattctctta ctgtcatgcc atccgtaaga tgcttttctg      720
tgactggtga gtactcaacc aagtcattct gagaatagtg tatgcggcga ccgagttgct      780
cttgcccggc gtcaatacgg gataataccg cgccacatag cagaacttta aaagtgctca      840
tcattggaaa acgttcttcg gggcgaaaac tctcaaggat cttaccgctg ttgagatcca      900
gttcgatgta acccactcgt gcacccaact gatcttcagc atcttttact ttcaccagcg      960
tttctgggtg agcaaaaaca ggaaggcaaa atgccgcaaa aaagggaata agggcgacac     1020
ggaaatgttg aatactcata ctcttccttt tcaatattta ttgaagcatt tatcagggtt     1080
attgtctcat gagcggatac atatttgaat gtatttagaa aaataaacaa ataggggttc     1140
cgcgcacatt tttggcattg gcaaagtgcg gactgcatag tcactgtggt gccgtactta     1200
gggtacgcgt tcctgaacga agcatctgtg cttcattttg tagaacaaaa atgcaacgcg     1260
agagcgctaa ttttttcaaac aaagaatctg agctgcattt ttacagaaca gaaatgcaac     1320
gcgaaagcgc tattttacca acgaagaatc tgtgcttcat ttttgtaaaa caaaaatgca     1380
acgcgagagc gctaattttt caaacaaaga atctgagctg catttttaca gaacagaaat     1440
gcaacgcgag agcgctattt taccaacaaa gaatctatac ttcttttttg ttctacaaaa     1500
atgcatcccg agagcgctat ttttctaaca aagcatctta gattactttt tttctccttt     1560
gtgcgctcta taatgcagtc tcttgataac ttttttgcact gtaggtccgt taaggttaga     1620
agaaggctac tttggtgtct attttctctt ccataaaaaa agcctgactc cacttcccgc     1680
gtttactgat tactagcgaa gctgcgggtg cattttttca agataaaggc atccccgatt     1740
atattctata ccgatgtgga ttgcgcatac tttgtgaaca gaaagtgata gcgttgatga     1800
ttcttcattg gtcagaaaat tatgaacggt ttcttctatt ttgtctctat atactacgta     1860
taggaaatgt ttacattttc gtattgtttt cgattcactc tatgaatagt tcttactaca     1920
atttttttgt ctaaagagta atactagaga taaacataaa aaatgtagag gtcgagttta     1980
gatgcaagtt caaggagcga aaggtggatg ggtaggttat ataggatat agcacagaga     2040 tatatagcaa agagatactt ttgagcaatg tttgtggaag cggtattcgc aatattttag     2100
tagctcgtta cagtccggtg cgttttggt tttttgaaag tgcgtcttca gagcgctttt     2160
ggttttcaaa agcgctctga agttcctata cttctagag aataggaact tcggaatagg     2220
aacttcaaag cgtttccgaa aacgagcgct tccgaaaatg caacgcgagc tgcgcacata     2280
cagctcactg ttcacgtcgc acctatatct gcgtgttgcc tgtatatata tatacatgag     2340
aagaacggca tagtgcgtgt ttatgcttaa atgcgtactt atatgcgtct atttatgtag     2400
gatgaaaggt agtctagtac ctcctgtgat attatcccat tccatgcggg gtatcgtatg     2460
```

```
cttccttcag cactacccett tagctgttct atatgctgcc actcctcaat tggattagtc    2520
tcatccttca atgctatcat tatgtcaccc gcagttctgt gtcgtagtca tcaacatagc    2580
acctatcctt tggcatctcg gtgagcaaaa ggccagcaaa aggccaggaa ccgtaaaaag    2640
gccgcgttgc tggcgttttt ccataggctc cgcccccctg acgagcatca caaaaatcga    2700
cgctcaagtc agaggtggcg aaacccgaca ggactataaa gataccaggc gtttccccct    2760
ggaagctccc tcgtgcgctc tcctgttccg accctgccgc ttaccggata cctgtccgcc    2820
tttctccctt cgggaagcgt ggcgctttct catagctcac gctgtaggta tctcagttcg    2880
gtgtaggtcg ttcgctccaa gctgggctgt gtgcacgaac ccccegttca gcccgaccgc    2940 tgcgccttat ccggtaacta tcgtcttgag tccaacccgg taagacacga cttatcgcca    3000
ctggcagcag ccactggtaa caggattagc agagcgaggt atgtaggcgg tgctacagag    3060
ttcttgaagt ggtggcctaa ctacggctac actagaagga cagtatttgg tatctgcgct    3120
ctgctgaagc cagttacctt cggaaaaaga gttggtagct cttgatccgg caaacaaacc    3180
accgctggta gcggtggttt ttttgtttgc aagcagcaga ttacgcgcag aaaaaaagga    3240
tctcaagaag atccttttgat cttttctacg gggtctgacg ctcagcactt gctacactgt    3300
caggatagct tccgtcacat ggtggcgatc accgtacatc tgagtgagac gttaattaaa    3360
gtagaccgct cacacatggg cggccgccgt ctcaaggtgc agttcgcgtg caattataac    3420
gtcgtggcaa ctgttatcag tcgtaccgcg ccattcgact acgtcgtaag gccgtttctg    3480
acagagtaaa attcttgagg gaactttcac cattatggga aatgcttcaa gaaggtattg    3540
acttaaactc catcaaatgg tcaggtcatt gagtgttttt tatttgttgt atttttttt    3600 ttttagagaa aatcctccaa tatcaaatta ggaatcgtag tttcatgatt ttctgttaca    3660
cctaactttt tgtgtggtgc cctcctcctt gtcaatatta atgttaaagt gcaattcttt    3720
ttccttatca cgttgagcca ttagtatcaa tttgcttacc tgtattcctt tactatcctc    3780 cttttttctcc ttcttgataa atgtatgtag attgcgtata tagtttcgtc taccctatga    3840
acatattcca ttttgtaatt tcgtgtcgtt tctattatga atttcattta taaagtttat    3900
gtacaaatat cataaaaaaa gagaatcttt ttaagcaagg attttcttaa cttcttcggc    3960
gacagcatca ccgacttcgg tggtactgtt ggaaccacct aaatcaccag ttctgatacc    4020
tgcatccaaa accttttttaa ctgcatcttc aatggcctta ccttcttcag gcaagttcaa    4080
tgacaatttc aacatcattg cagcagacaa gatagtggcg atagggtcaa ccttattctt    4140
tggcaaatct ggagcagaac cgtggcatgg ttcgtacaaa ccaaatgcgg tgttcttgtc    4200
tggcaaagag gccaaggacg cagatggcaa caaacccaag gaacctggga taacggaggc    4260
ttcatcggag atgatatcac caaacatgtt gctggtgatt ataataccat ttaggtgggt    4320
tgggttctta actaggatca tggcggcaga atcaatcaat tgatgttgaa ccttcaatgt    4380
agggaattcg ttcttgatgg tttcctccac agttttttctc cataatcttg aagaggccaa    4440
aagattagct ttatccaagg accaaatagg caatggtggc tcatgttgta gggccatgaa    4500
agcggccatt cttgtgattc tttgcacttc tggaacggtg tattgttcac tatcccaagc    4560
gacaccatca ccatcgtctt cctttctctt accaaagtaa atacctccca ctaattctct    4620
gacaacaacg aagtcagtac ctttagcaaa ttgtggcttg attggagata agtctaaaag    4680
agagtcggat gcaaagttac atggtcttaa gttggcgtac aattgaagtt ctttacggat    4740
ttttagtaaa ccttgttcag gtctaacact accggtaccc catttaggac cagccacagc    4800
acctaacaaa acggcatcaa ccttcttgga ggcttccagc gcctcatctg gaagtgggac    4860
```

```
acctgtagca tcgatagcag caccaccaat taaatgattt tcgaaatcga acttgacatt    4920
ggaacgaaca tcagaaatag ctttaagaac cttaatggct tcggctgtga tttcttgacc    4980
aacgtggtca cctggcaaaa cgacgatctt cttaggggca gacatagggg cagacattag    5040
aatggtatat ccttgaaata tatatatata ttgctgaaat gtaaaaggta agaaaagtta    5100
gaaagtaaga cgattgctaa ccacctattg gaaaaaacaa taggtcctta aataatattg    5160
tcaacttcaa gtattgtgat gcaagcattt agtcatgaac gcttctctat tctatatgaa    5220
aagccggttc cggcctctca cctttccttt ttctcccaat ttttcagttg aaaaaggtat    5280
atgcgtcagg cgacctctga aattaacaaa aaatttccag tcatcgaatt tgattctgtg    5340
cgatagcgcc cctgtgtgtt ctcgttatgt tgaggaaaaa aataatggtt gctaagagat    5400
tcgaactctt gcatcttacg atacctgagt attcccacag ttaactgcgg tcaagatatt    5460
tcttgaatca ggcgccttag accgctcggc caaacaacca attacttgtt gagaaataga    5520
gtataattat cctataaata taacgttttt gaacacacat gaacaaggaa gtacaggaca    5580
attgattttg aagagaatgt ggattttgat gtaattgttg ggattccatt tttaataagg    5640
caataatatt aggtatgtgg atatactaga agttctcctc gaccgtcga               5689

<210> SEQ ID NO 2
<211> LENGTH: 60
<212> TYPE: DNA
<213> ORGANISM: Artificial Sequence
<220> FEATURE:
<223> OTHER INFORMATION: Sequence for homologous recombination

<400> SEQUENCE: 2
gcacttgcta cactgtcagg atagcttccg tcacatggtg gcgatcaccg tacatctgag    60

<210> SEQ ID NO 3
<211> LENGTH: 60
<212> TYPE: DNA
<213> ORGANISM: Artificial Sequence
<220> FEATURE:
<223> OTHER INFORMATION: Sequence for homologous recombination

<400> SEQUENCE: 3
aggtgcagtt cgcgtgcaat tataacgtcg tggcaactgt tatcagtcgt accgcgccat    60

<210> SEQ ID NO 4
<211> LENGTH: 1584
<212> TYPE: DNA
<213> ORGANISM: Artificial Sequence
<220> FEATURE:
<223> OTHER INFORMATION: Dichomitus squalens Albicanol synthase codon
      optimized for its expression in S. cerevisiae
<220> FEATURE:
<221> NAME/KEY: CDS
<222> LOCATION: (1)..(1584)

<400> SEQUENCE: 4 atg gct tct atc cac aga aga tac act act ttg atc ttg gac ttg ggt    48
Met Ala Ser Ile His Arg Arg Tyr Thr Thr Leu Ile Leu Asp Leu Gly
1               5                   10                  15 gac gtt ttg ttc aga tgg tct cca aag act gaa act gct atc cca cca    96
Asp Val Leu Phe Arg Trp Ser Pro Lys Thr Glu Thr Ala Ile Pro Pro
            20                  25                  30 caa caa ttg aag gac atc ttg tct tct gtt act tgg ttc gaa tac gaa   144
Gln Gln Leu Lys Asp Ile Leu Ser Ser Val Thr Trp Phe Glu Tyr Glu
        35                  40                  45
```

```
aga ggt aga ttg tct caa gaa gct tgt tac gaa aga tgt gct gaa gaa         192
Arg Gly Arg Leu Ser Gln Glu Ala Cys Tyr Glu Arg Cys Ala Glu Glu
     50              55                  60 ttc aag atc gaa gct tct gtt atc gct gaa gct ttc aag caa gct aga         240
Phe Lys Ile Glu Ala Ser Val Ile Ala Glu Ala Phe Lys Gln Ala Arg
 65              70                  75                  80 ggt tct ttg aga cca aac gaa gaa ttc atc gct ttg atc aga gac ttg         288
Gly Ser Leu Arg Pro Asn Glu Glu Phe Ile Ala Leu Ile Arg Asp Leu
                 85                  90                  95 aga aga gaa atg cac ggt gac ttg act gtt ttg gct ttg tct aac atc         336
Arg Arg Glu Met His Gly Asp Leu Thr Val Leu Ala Leu Ser Asn Ile
                    100                 105                 110 tct ttg cca gac tac gaa tac atc atg tct ttg tct tct gac tgg act         384
Ser Leu Pro Asp Tyr Glu Tyr Ile Met Ser Leu Ser Ser Asp Trp Thr
             115                 120                 125 act gtt ttc gac aga gtt ttc cca tct gct ttg gtt ggt gaa aga aag         432
Thr Val Phe Asp Arg Val Phe Pro Ser Ala Leu Val Gly Glu Arg Lys
         130                 135                 140 cca cac ttg ggt tgt tac aga aag gtt atc tct gaa atg aac ttg gaa         480
Pro His Leu Gly Cys Tyr Arg Lys Val Ile Ser Glu Met Asn Leu Glu
145                 150                 155                 160 cca caa act act gtt ttc gtt gac gac aag ttg gac aac gtt gct tct         528
Pro Gln Thr Thr Val Phe Val Asp Asp Lys Leu Asp Asn Val Ala Ser
                 165                 170                 175 gct aga tct ttg ggt atg cac ggt atc gtt ttc gac aac caa gct aac         576
Ala Arg Ser Leu Gly Met His Gly Ile Val Phe Asp Asn Gln Ala Asn
             180                 185                 190 gtt ttc aga caa ttg aga aac atc ttc ggt gac cca atc aga aga ggt         624
Val Phe Arg Gln Leu Arg Asn Ile Phe Gly Asp Pro Ile Arg Arg Gly
         195                 200                 205 caa gaa tac ttg aga ggt cac gct ggt aag ttg gaa tct tct act gac         672
Gln Glu Tyr Leu Arg Gly His Ala Gly Lys Leu Glu Ser Ser Thr Asp
     210                 215                 220 aac ggt ttg atc ttc gaa gaa aac ttc act caa ttg atc atc tac gaa         720
Asn Gly Leu Ile Phe Glu Glu Asn Phe Thr Gln Leu Ile Ile Tyr Glu
225                 230                 235                 240 ttg act caa gac aga act ttg atc tct ttg tct gaa tgt cca aga act         768
Leu Thr Gln Asp Arg Thr Leu Ile Ser Leu Ser Glu Cys Pro Arg Thr
                 245                 250                 255 tgg aac ttc ttc aga ggt gaa cca ttg ttc tct gaa act ttc cca gac         816
Trp Asn Phe Phe Arg Gly Glu Pro Leu Phe Ser Glu Thr Phe Pro Asp
             260                 265                 270 gac gtt gac act act tct gtt gct ttg act gtt ttg caa cca gac aga         864
Asp Val Asp Thr Thr Ser Val Ala Leu Thr Val Leu Gln Pro Asp Arg
         275                 280                 285 gct ttg gtt aac tct gtt ttg gac gaa atg ttg gaa tac gtt gac gct         912
Ala Leu Val Asn Ser Val Leu Asp Glu Met Leu Glu Tyr Val Asp Ala
     290                 295                 300 gac ggt atc atg caa act tac ttc gac aga tct aga cca aga atg gac         960
Asp Gly Ile Met Gln Thr Tyr Phe Asp Arg Ser Arg Pro Arg Met Asp
305                 310                 315                 320 cca ttc gtt tgt gtt aac gtt ttg tct ttg ttc tac gaa aac ggt aga        1008
Pro Phe Val Cys Val Asn Val Leu Ser Leu Phe Tyr Glu Asn Gly Arg
                 325                 330                 335 ggt cac gaa ttg cca aga act ttg gac tgg gtt tac gaa gtt ttg ttg        1056
Gly His Glu Leu Pro Arg Thr Leu Asp Trp Val Tyr Glu Val Leu Leu
             340                 345                 350 cac aga gct tac cac ggt ggt tct aga tac tac ttg tct cca gac tgt        1104
His Arg Ala Tyr His Gly Gly Ser Arg Tyr Tyr Leu Ser Pro Asp Cys
         355                 360                 365
```

```
ttc ttg ttc ttc atg tct aga ttg ttg aag aga gct gac gac cca gct     1152
Phe Leu Phe Phe Met Ser Arg Leu Leu Lys Arg Ala Asp Asp Pro Ala
370                 375                 380 gtt caa gct aga ttg aga cca ttg ttc gtt gaa aga gtt aac gaa aga     1200
Val Gln Ala Arg Leu Arg Pro Leu Phe Val Glu Arg Val Asn Glu Arg
385                 390                 395                 400 gtt ggt gct gct ggt gac tct atg gac ttg gct ttc aga atc ttg gct     1248
Val Gly Ala Ala Gly Asp Ser Met Asp Leu Ala Phe Arg Ile Leu Ala
                405                 410                 415 gct gct tct gtt ggt gtt caa tgt cca aga gac ttg gaa aga ttg act     1296
Ala Ala Ser Val Gly Val Gln Cys Pro Arg Asp Leu Glu Arg Leu Thr
                420                 425                 430 gct ggt caa tgt gac gac ggt ggt tgg gac ttg tgt tgg ttc tac gtt     1344
Ala Gly Gln Cys Asp Asp Gly Gly Trp Asp Leu Cys Trp Phe Tyr Val
            435                 440                 445 ttc ggt tct act ggt gtt aag gct ggt aac aga ggt ttg act act gct     1392
Phe Gly Ser Thr Gly Val Lys Ala Gly Asn Arg Gly Leu Thr Thr Ala
450                 455                 460 ttg gct gtt act gct atc caa act gct atc ggt aga cca cca tct cca     1440
Leu Ala Val Thr Ala Ile Gln Thr Ala Ile Gly Arg Pro Pro Ser Pro
465                 470                 475                 480 tct cca tct gct gct tct tct tct ttc aga cca tct tct cca tac aag     1488
Ser Pro Ser Ala Ala Ser Ser Ser Phe Arg Pro Ser Ser Pro Tyr Lys
                485                 490                 495 ttc ttg ggt atc tct aga cca gct tct cca atc aga ttc ggt gac ttg     1536
Phe Leu Gly Ile Ser Arg Pro Ala Ser Pro Ile Arg Phe Gly Asp Leu
                500                 505                 510 ttg aga cca tgg aga aag atg tct aga tct aac ttg aag tct caa taa    1584
Leu Arg Pro Trp Arg Lys Met Ser Arg Ser Asn Leu Lys Ser Gln
                515                 520                 525

<210> SEQ ID NO 5
<211> LENGTH: 527
<212> TYPE: PRT
<213> ORGANISM: Artificial Sequence
<220> FEATURE:
<223> OTHER INFORMATION: Synthetic Construct

<400> SEQUENCE: 5

Met Ala Ser Ile His Arg Arg Tyr Thr Thr Leu Ile Leu Asp Leu Gly
1               5                   10                  15

Asp Val Leu Phe Arg Trp Ser Pro Lys Thr Glu Thr Ala Ile Pro Pro
            20                  25                  30

Gln Gln Leu Lys Asp Ile Leu Ser Ser Val Thr Trp Phe Glu Tyr Glu
        35                  40                  45

Arg Gly Arg Leu Ser Gln Glu Ala Cys Tyr Glu Arg Cys Ala Glu Glu
    50                  55                  60

Phe Lys Ile Glu Ala Ser Val Ile Ala Glu Ala Phe Lys Gln Ala Arg
65                  70                  75                  80

Gly Ser Leu Arg Pro Asn Glu Glu Phe Ile Ala Leu Ile Arg Asp Leu
                85                  90                  95

Arg Arg Glu Met His Gly Asp Leu Thr Val Leu Ala Leu Ser Asn Ile
            100                 105                 110

Ser Leu Pro Asp Tyr Glu Tyr Ile Met Ser Leu Ser Ser Asp Trp Thr
        115                 120                 125

Thr Val Phe Asp Arg Val Phe Pro Ser Ala Leu Val Gly Glu Arg Lys
    130                 135                 140

Pro His Leu Gly Cys Tyr Arg Lys Val Ile Ser Glu Met Asn Leu Glu
```

```
            145                 150                 155                 160
        Pro Gln Thr Thr Val Phe Val Asp Asp Lys Leu Asp Asn Val Ala Ser
                        165                 170                 175

Ala Arg Ser Leu Gly Met His Gly Ile Val Phe Asp Asn Gln Ala Asn
                    180                 185                 190

Val Phe Arg Gln Leu Arg Asn Ile Phe Gly Asp Pro Ile Arg Arg Gly
                195                 200                 205

Gln Glu Tyr Leu Arg Gly His Ala Gly Lys Leu Glu Ser Ser Thr Asp
            210                 215                 220

Asn Gly Leu Ile Phe Glu Glu Asn Phe Thr Gln Leu Ile Ile Tyr Glu
        225                 230                 235                 240

Leu Thr Gln Asp Arg Thr Leu Ile Ser Leu Ser Glu Cys Pro Arg Thr
                        245                 250                 255

Trp Asn Phe Phe Arg Gly Glu Pro Leu Phe Ser Glu Thr Phe Pro Asp
                    260                 265                 270

Asp Val Asp Thr Thr Ser Val Ala Leu Thr Val Leu Gln Pro Asp Arg
                275                 280                 285

Ala Leu Val Asn Ser Val Leu Asp Glu Met Leu Glu Tyr Val Asp Ala
            290                 295                 300

Asp Gly Ile Met Gln Thr Tyr Phe Asp Arg Ser Arg Pro Arg Met Asp
        305                 310                 315                 320

Pro Phe Val Cys Val Asn Val Leu Ser Leu Phe Tyr Glu Asn Gly Arg
                        325                 330                 335

Gly His Glu Leu Pro Arg Thr Leu Asp Trp Val Tyr Glu Val Leu Leu
                    340                 345                 350

His Arg Ala Tyr His Gly Gly Ser Arg Tyr Tyr Leu Ser Pro Asp Cys
                355                 360                 365

Phe Leu Phe Phe Met Ser Arg Leu Leu Lys Arg Ala Asp Asp Pro Ala
            370                 375                 380

Val Gln Ala Arg Leu Arg Pro Leu Phe Val Glu Arg Val Asn Glu Arg
        385                 390                 395                 400

Val Gly Ala Ala Gly Asp Ser Met Asp Leu Ala Phe Arg Ile Leu Ala
                        405                 410                 415

Ala Ala Ser Val Gly Val Gln Cys Pro Arg Asp Leu Glu Arg Leu Thr
                    420                 425                 430

Ala Gly Gln Cys Asp Asp Gly Gly Trp Asp Leu Cys Trp Phe Tyr Val
                435                 440                 445

Phe Gly Ser Thr Gly Val Lys Ala Gly Asn Arg Gly Leu Thr Thr Ala
            450                 455                 460

Leu Ala Val Thr Ala Ile Gln Thr Ala Ile Gly Arg Pro Pro Ser Pro
        465                 470                 475                 480

Ser Pro Ser Ala Ala Ser Ser Phe Arg Pro Ser Pro Tyr Lys
                        485                 490                 495

Phe Leu Gly Ile Ser Arg Pro Ala Ser Pro Ile Arg Phe Gly Asp Leu
                    500                 505                 510

Leu Arg Pro Trp Arg Lys Met Ser Arg Ser Asn Leu Lys Ser Gln
                515                 520                 525

<210> SEQ ID NO 6
<211> LENGTH: 1623
<212> TYPE: DNA
<213> ORGANISM: Artificial Sequence
<220> FEATURE:
<223> OTHER INFORMATION: Agaricus bisporus Drimeol synthase sequence
      codon optimized for its expression in S. cerevisiae
```

```
<220> FEATURE:
<221> NAME/KEY: CDS
<222> LOCATION: (1)..(1623)

<400> SEQUENCE: 6 atg gct cca cca caa aga cca ttc act gct atc gtt ttc gac atc ggt      48
Met Ala Pro Pro Gln Arg Pro Phe Thr Ala Ile Val Phe Asp Ile Gly
1               5                   10                  15 gac gtt ttg ttc caa tgg tct gct act act aag act tct atc tct cca      96
Asp Val Leu Phe Gln Trp Ser Ala Thr Thr Lys Thr Ser Ile Ser Pro
            20                  25                  30 aag act ttg aga tct atc ttg aac tgt cca act tgg ttc gac tac gaa      144
Lys Thr Leu Arg Ser Ile Leu Asn Cys Pro Thr Trp Phe Asp Tyr Glu
        35                  40                  45 aga ggt aga ttg gct gaa aac gct tgt tac gct gct atc tct caa gaa      192
Arg Gly Arg Leu Ala Glu Asn Ala Cys Tyr Ala Ala Ile Ser Gln Glu
50                  55                  60 ttc aac gtt aac cca gac gaa gtt aga gac gct ttc tct caa gct aga      240
Phe Asn Val Asn Pro Asp Glu Val Arg Asp Ala Phe Ser Gln Ala Arg
65                  70                  75                  80 gac tct ttg caa gct aac cac gac ttc atc tct ttg atc aga gaa ttg      288
Asp Ser Leu Gln Ala Asn His Asp Phe Ile Ser Leu Ile Arg Glu Leu
                85                  90                  95 aag gct caa gct aac ggt aga ttg aga gtt tac gct atg tct aac atc      336
Lys Ala Gln Ala Asn Gly Arg Leu Arg Val Tyr Ala Met Ser Asn Ile
            100                 105                 110 tct ttg cca gac tgg gaa gtt ttg aga atg aag cca gct gac tgg gac      384
Ser Leu Pro Asp Trp Glu Val Leu Arg Met Lys Pro Ala Asp Trp Asp
        115                 120                 125 atc ttc gac cac gtt ttc act tct ggt gct gtt ggt gaa aga aag cca      432
Ile Phe Asp His Val Phe Thr Ser Gly Ala Val Gly Glu Arg Lys Pro
130                 135                 140 aac ttg gct ttc tac aga cac gtt atc gct gct act gac ttg caa cca      480
Asn Leu Ala Phe Tyr Arg His Val Ile Ala Ala Thr Asp Leu Gln Pro
145                 150                 155                 160 cac caa act atc ttc gtt gac gac aag ttg gaa aac gtt ttg tct gct      528
His Gln Thr Ile Phe Val Asp Asp Lys Leu Glu Asn Val Leu Ser Ala
                165                 170                 175 aga tct ttg ggt ttc act ggt atc gtt ttc gac gaa cca tct gaa gtt      576
Arg Ser Leu Gly Phe Thr Gly Ile Val Phe Asp Glu Pro Ser Glu Val
            180                 185                 190 aag aga gct ttg aga aac ttg atc ggt gac cca gtt caa aga ggt ggt      624
Lys Arg Ala Leu Arg Asn Leu Ile Gly Asp Pro Val Gln Arg Gly Gly
        195                 200                 205 gaa ttc ttg gtt aga aac gct ggt aag ttg ggt tct atc act aga act      672
Glu Phe Leu Val Arg Asn Ala Gly Lys Leu Gly Ser Ile Thr Arg Thr
210                 215                 220 act gct aag cac gaa tct atc cca ttg gac gaa aac ttc gct caa ttg      720
Thr Ala Lys His Glu Ser Ile Pro Leu Asp Glu Asn Phe Ala Gln Leu
225                 230                 235                 240 ttg atc ttg gaa atc act ggt aac aga gct ttg gtt aac ttg gtt gaa      768
Leu Ile Leu Glu Ile Thr Gly Asn Arg Ala Leu Val Asn Leu Val Glu
                245                 250                 255 cac cca caa act tgg aac ttc ttc caa ggt aag ggt caa ttg act act      816
His Pro Gln Thr Trp Asn Phe Phe Gln Gly Lys Gly Gln Leu Thr Thr
            260                 265                 270 gaa gaa ttc cca ttc gac ttg gac act act tct ttg ggt ttg act atc      864
Glu Glu Phe Pro Phe Asp Leu Asp Thr Thr Ser Leu Gly Leu Thr Ile
        275                 280                 285 ttg aag aga tct aga gaa atc gct gac tct gtt atg gac gaa atg ttg      912
Leu Lys Arg Ser Arg Glu Ile Ala Asp Ser Val Met Asp Glu Met Leu
```

```
                    Leu Lys Arg Ser Arg Glu Ile Ala Asp Ser Val Met Asp Glu Met Leu
                        290                 295                 300 gaa tac gtt gac cca gac ggt atc atc caa act tac ttc gac cac aga       960
Glu Tyr Val Asp Pro Asp Gly Ile Ile Gln Thr Tyr Phe Asp His Arg
305                 310                 315                 320 aga cca aga ttc gac cca gtt gtt tgt gtt aac gct ttg tct ttg ttc      1008
Arg Pro Arg Phe Asp Pro Val Val Cys Val Asn Ala Leu Ser Leu Phe
                    325                 330                 335 tac gct tac ggt aga ggt gaa caa ttg aga tct act ttg act tgg gtt      1056
Tyr Ala Tyr Gly Arg Gly Glu Gln Leu Arg Ser Thr Leu Thr Trp Val
                340                 345                 350 cac gaa gtt ttg ttg aac aga gct tac ttg gac ggt act aga tac tac      1104
His Glu Val Leu Leu Asn Arg Ala Tyr Leu Asp Gly Thr Arg Tyr Tyr
            355                 360                 365 gaa act gct gaa tgt ttc ttg tac ttc atg tct aga ttg ttg gct act      1152
Glu Thr Ala Glu Cys Phe Leu Tyr Phe Met Ser Arg Leu Leu Ala Thr
        370                 375                 380 tct ggt gac cca gac ttg cac tct ttg ttg aag cca ttg ttg aag gaa      1200
Ser Gly Asp Pro Asp Leu His Ser Leu Leu Lys Pro Leu Leu Lys Glu
385                 390                 395                 400 aga gtt caa gaa aga atc ggt gct gac ggt gac tct ttg gct ttg gct      1248
Arg Val Gln Glu Arg Ile Gly Ala Asp Gly Asp Ser Leu Ala Leu Ala
                    405                 410                 415 atg aga atc ttg gct tgt gac ttc gtt ggt atc aga gac gaa gtt gac      1296
Met Arg Ile Leu Ala Cys Asp Phe Val Gly Ile Arg Asp Glu Val Asp
                420                 425                 430 ttg aga act ttg ttg act ttg caa tgt gaa gac ggt ggt tgg gaa gtt      1344
Leu Arg Thr Leu Leu Thr Leu Gln Cys Glu Asp Gly Gly Trp Glu Val
            435                 440                 445 ggt tgg atg tac aag tac ggt tct tct ggt atc tct atc ggt aac aga      1392
Gly Trp Met Tyr Lys Tyr Gly Ser Ser Gly Ile Ser Ile Gly Asn Arg
        450                 455                 460 ggt ttg gct act gct ttg gct atc aag gct gtt gac act atg ttc caa      1440
Gly Leu Ala Thr Ala Leu Ala Ile Lys Ala Val Asp Thr Met Phe Gln
465                 470                 475                 480 cca caa atc aga ttc tct gaa tct cca act gac act ttg gtt gaa aac      1488
Pro Gln Ile Arg Phe Ser Glu Ser Pro Thr Asp Thr Leu Val Glu Asn
                    485                 490                 495 gct atc cac aag aga aga cca tct ttc tct gaa aag ttc ttg ggt aag      1536
Ala Ile His Lys Arg Arg Pro Ser Phe Ser Glu Lys Phe Leu Gly Lys
                500                 505                 510 aga cca aga tct ggt tct ttc aga aag cca ttg caa tgg atc ttg caa      1584
Arg Pro Arg Ser Gly Ser Phe Arg Lys Pro Leu Gln Trp Ile Leu Gln
            515                 520                 525 ggt tct aag ttg aga aag tct gtt gaa atc ggt tct taa                  1623
Gly Ser Lys Leu Arg Lys Ser Val Glu Ile Gly Ser
        530                 535                 540

<210> SEQ ID NO 7
<211> LENGTH: 540
<212> TYPE: PRT
<213> ORGANISM: Artificial Sequence
<220> FEATURE:
<223> OTHER INFORMATION: Synthetic Construct

<400> SEQUENCE: 7

Met Ala Pro Pro Gln Arg Pro Phe Thr Ala Ile Val Phe Asp Ile Gly
1               5                   10                  15

Asp Val Leu Phe Gln Trp Ser Ala Thr Thr Lys Thr Ser Ile Ser Pro
            20                  25                  30
```

```
Lys Thr Leu Arg Ser Ile Leu Asn Cys Pro Thr Trp Phe Asp Tyr Glu
         35                  40                  45

Arg Gly Arg Leu Ala Glu Asn Ala Cys Tyr Ala Ala Ile Ser Gln Glu
 50                  55                  60

Phe Asn Val Asn Pro Asp Glu Val Arg Asp Ala Phe Ser Gln Ala Arg
 65                  70                  75                  80

Asp Ser Leu Gln Ala Asn His Asp Phe Ile Ser Leu Ile Arg Glu Leu
             85                  90                  95

Lys Ala Gln Ala Asn Gly Arg Leu Arg Val Tyr Ala Met Ser Asn Ile
            100                 105                 110

Ser Leu Pro Asp Trp Glu Val Leu Arg Met Lys Pro Ala Asp Trp Asp
            115                 120                 125

Ile Phe Asp His Val Phe Thr Ser Gly Ala Val Gly Glu Arg Lys Pro
    130                 135                 140

Asn Leu Ala Phe Tyr Arg His Val Ile Ala Ala Thr Asp Leu Gln Pro
145                 150                 155                 160

His Gln Thr Ile Phe Val Asp Asp Lys Leu Glu Asn Val Leu Ser Ala
                165                 170                 175

Arg Ser Leu Gly Phe Thr Gly Ile Val Phe Asp Glu Pro Ser Glu Val
            180                 185                 190

Lys Arg Ala Leu Arg Asn Leu Ile Gly Asp Pro Val Gln Arg Gly Gly
        195                 200                 205

Glu Phe Leu Val Arg Asn Ala Gly Lys Leu Gly Ser Ile Thr Arg Thr
    210                 215                 220

Thr Ala Lys His Glu Ser Ile Pro Leu Asp Glu Asn Phe Ala Gln Leu
225                 230                 235                 240

Leu Ile Leu Glu Ile Thr Gly Asn Arg Ala Leu Val Asn Leu Val Glu
                245                 250                 255

His Pro Gln Thr Trp Asn Phe Phe Gln Gly Lys Gly Gln Leu Thr Thr
            260                 265                 270

Glu Glu Phe Pro Phe Asp Leu Asp Thr Thr Ser Leu Gly Leu Thr Ile
            275                 280                 285

Leu Lys Arg Ser Arg Glu Ile Ala Asp Ser Val Met Asp Glu Met Leu
    290                 295                 300

Glu Tyr Val Asp Pro Asp Gly Ile Ile Gln Thr Tyr Phe Asp His Arg
305                 310                 315                 320

Arg Pro Arg Phe Asp Pro Val Val Cys Val Asn Ala Leu Ser Leu Phe
                325                 330                 335

Tyr Ala Tyr Gly Arg Gly Glu Gln Leu Arg Ser Thr Leu Thr Trp Val
            340                 345                 350

His Glu Val Leu Leu Asn Arg Ala Tyr Leu Asp Gly Thr Arg Tyr Tyr
            355                 360                 365

Glu Thr Ala Glu Cys Phe Leu Tyr Phe Met Ser Arg Leu Leu Ala Thr
    370                 375                 380

Ser Gly Asp Pro Asp Leu His Ser Leu Leu Lys Pro Leu Leu Lys Glu
385                 390                 395                 400

Arg Val Gln Glu Arg Ile Gly Ala Asp Gly Asp Ser Leu Ala Leu Ala
                405                 410                 415

Met Arg Ile Leu Ala Cys Asp Phe Gly Ile Arg Asp Glu Val Asp
            420                 425                 430

Leu Arg Thr Leu Leu Thr Leu Gln Cys Glu Asp Gly Gly Trp Glu Val
            435                 440                 445

Gly Trp Met Tyr Lys Tyr Gly Ser Ser Gly Ile Ser Ile Gly Asn Arg
```

```
                450           455           460
Gly Leu Ala Thr Ala Leu Ala Ile Lys Ala Val Asp Thr Met Phe Gln
465                 470                 475                 480

Pro Gln Ile Arg Phe Ser Glu Ser Pro Thr Asp Thr Leu Val Glu Asn
                485                 490                 495

Ala Ile His Lys Arg Arg Pro Ser Phe Ser Glu Lys Phe Leu Gly Lys
            500                 505                 510

Arg Pro Arg Ser Gly Ser Phe Arg Lys Pro Leu Gln Trp Ile Leu Gln
        515                 520                 525

Gly Ser Lys Leu Arg Lys Ser Val Glu Ile Gly Ser
530                 535                 540

<210> SEQ ID NO 8
<211> LENGTH: 1320
<212> TYPE: DNA
<213> ORGANISM: Artificial Sequence
<220> FEATURE:
<223> OTHER INFORMATION: CrDAT codon optimized for its expression in S.
      cerevisiae
<220> FEATURE:
<221> NAME/KEY: CDS
<222> LOCATION: (1)..(1320)

<400> SEQUENCE: 8 atg gaa agt ggt aaa ata tct gta gaa acg gaa acc cta tcg aaa acc     48
Met Glu Ser Gly Lys Ile Ser Val Glu Thr Glu Thr Leu Ser Lys Thr
1               5                   10                  15 ctt atc aag ccg tcc tcg ccc acg cca cag tct ctt tcc cgt tac aac     96
Leu Ile Lys Pro Ser Ser Pro Thr Pro Gln Ser Leu Ser Arg Tyr Asn
            20                  25                  30 tta tct tac aat gat cag aac att tat cag acc tgc gta tct gta ggg    144
Leu Ser Tyr Asn Asp Gln Asn Ile Tyr Gln Thr Cys Val Ser Val Gly
        35                  40                  45 ttc ttt tac gaa aat cct gat ggc atc gag ata tcc acg atc cgt gag    192
Phe Phe Tyr Glu Asn Pro Asp Gly Ile Glu Ile Ser Thr Ile Arg Glu
50                  55                  60 cag ctg cag aac agc ctg tcc aaa act ctg gtc tca tac tat ccc ttc    240
Gln Leu Gln Asn Ser Leu Ser Lys Thr Leu Val Ser Tyr Tyr Pro Phe
65                  70                  75                  80 gca ggc aaa gta gtg aag aac gac tac ata cat tgt aac gac gat ggc    288
Ala Gly Lys Val Val Lys Asn Asp Tyr Ile His Cys Asn Asp Asp Gly
                85                  90                  95 att gag ttc gtc gaa gtc aga att aga tgc agg atg aat gat ata ctt    336
Ile Glu Phe Val Glu Val Arg Ile Arg Cys Arg Met Asn Asp Ile Leu
            100                 105                 110 aaa tac gaa cta cgt tct tac gct cgt gat tta gtc ctg cca aag agg    384
Lys Tyr Glu Leu Arg Ser Tyr Ala Arg Asp Leu Val Leu Pro Lys Arg
        115                 120                 125 gtt acc gtg ggc tct gaa gat acc acc gct atc gtg cag ctg tcc cat    432
Val Thr Val Gly Ser Glu Asp Thr Thr Ala Ile Val Gln Leu Ser His
130                 135                 140 ttc gac tgt ggc ggt ttg gcc gtg gct ttt ggt atc tcc cac aag gtg    480
Phe Asp Cys Gly Gly Leu Ala Val Ala Phe Gly Ile Ser His Lys Val
145                 150                 155                 160 gcc gat ggt ggt act ata gcc tct ttc atg aag gac tgg gcg gcc tct    528
Ala Asp Gly Gly Thr Ile Ala Ser Phe Met Lys Asp Trp Ala Ala Ser
                165                 170                 175 gct tgc tac ttg tcc tca agt cac cac gtt cca acg cct cta ttg gtc    576
Ala Cys Tyr Leu Ser Ser Ser His His Val Pro Thr Pro Leu Leu Val
            180                 185                 190
```

```
tca gac agt att ttc cca aga cag gac aac ata ata tgc gaa caa ttt       624
Ser Asp Ser Ile Phe Pro Arg Gln Asp Asn Ile Ile Cys Glu Gln Phe
        195                 200                 205 ccc acc tca aag aat tgc gtg gag aag aca ttc att ttc cca cca gaa       672
Pro Thr Ser Lys Asn Cys Val Glu Lys Thr Phe Ile Phe Pro Pro Glu
    210                 215                 220 gca atc gaa aag tta aag agt aag gcc gtt gaa ttc ggc att gag aaa       720
Ala Ile Glu Lys Leu Lys Ser Lys Ala Val Glu Phe Gly Ile Glu Lys
225                 230                 235                 240 ccg acc aga gta gag gtc ctg act gca ttc tta tct aga tgc gcc acc       768
Pro Thr Arg Val Glu Val Leu Thr Ala Phe Leu Ser Arg Cys Ala Thr
                245                 250                 255 gta gca ggt aag tcg gca gct aag aac aac aat tgt ggt caa agc ctg       816
Val Ala Gly Lys Ser Ala Ala Lys Asn Asn Asn Cys Gly Gln Ser Leu
            260                 265                 270 ccc ttt ccg gtt cta cag gcc att aat ttg agg ccg att cta gaa ttg       864
Pro Phe Pro Val Leu Gln Ala Ile Asn Leu Arg Pro Ile Leu Glu Leu
        275                 280                 285 cca cag aac tct gtg ggt aat cta gtt tcg atc tac ttc agc agg aca       912
Pro Gln Asn Ser Val Gly Asn Leu Val Ser Ile Tyr Phe Ser Arg Thr
    290                 295                 300 att aag gaa aac gac tac cta aat gaa aag gag tac act aaa ttg gtg       960
Ile Lys Glu Asn Asp Tyr Leu Asn Glu Lys Glu Tyr Thr Lys Leu Val
305                 310                 315                 320 ata aac gag ttg cgt aaa gaa aag caa aag atc aag aat ttg agc aga      1008
Ile Asn Glu Leu Arg Lys Glu Lys Gln Lys Ile Lys Asn Leu Ser Arg
                325                 330                 335 gag aag ttg acc tac gtc gcc cag atg gaa gag ttc gtt aag tca ctt      1056
Glu Lys Leu Thr Tyr Val Ala Gln Met Glu Glu Phe Val Lys Ser Leu
            340                 345                 350 aaa gag ttc gat atc tcc aac ttc cta gat atc gat gcc tac tta agc      1104
Lys Glu Phe Asp Ile Ser Asn Phe Leu Asp Ile Asp Ala Tyr Leu Ser
        355                 360                 365 gat agt tgg tgc agg ttt cct ttc tac gac gtc gac ttc gga tgg gga      1152
Asp Ser Trp Cys Arg Phe Pro Phe Tyr Asp Val Asp Phe Gly Trp Gly
    370                 375                 380 aag cct atc tgg gtc tgc cta ttc cag cct tac atc aag aac tgc gtt      1200
Lys Pro Ile Trp Val Cys Leu Phe Gln Pro Tyr Ile Lys Asn Cys Val
385                 390                 395                 400 gtt atg atg gac tat cct ttc ggt gac gat tat ggt atc gag gct att      1248
Val Met Met Asp Tyr Pro Phe Gly Asp Asp Tyr Gly Ile Glu Ala Ile
                405                 410                 415 gtt tct ttc gag caa gag aaa atg tcc gcg ttc gag aag aac gaa cag      1296
Val Ser Phe Glu Gln Glu Lys Met Ser Ala Phe Glu Lys Asn Glu Gln
            420                 425                 430 tta ctg cag ttt gtg tct aac taa                                      1320
Leu Leu Gln Phe Val Ser Asn
        435
```

<210> SEQ ID NO 9
<211> LENGTH: 439
<212> TYPE: PRT
<213> ORGANISM: Artificial Sequence
<220> FEATURE:
<223> OTHER INFORMATION: Synthetic Construct

<400> SEQUENCE: 9

```
Met Glu Ser Gly Lys Ile Ser Val Glu Thr Glu Thr Leu Ser Lys Thr
1               5                   10                  15

Leu Ile Lys Pro Ser Ser Pro Thr Pro Gln Ser Leu Ser Arg Tyr Asn
            20                  25                  30
```

Leu Ser Tyr Asn Asp Gln Asn Ile Tyr Gln Thr Cys Val Ser Val Gly
                35                  40                  45

Phe Phe Tyr Glu Asn Pro Asp Gly Ile Glu Ile Ser Thr Ile Arg Glu
 50                  55                  60

Gln Leu Gln Asn Ser Leu Ser Lys Thr Leu Val Ser Tyr Tyr Pro Phe
 65                  70                  75                  80

Ala Gly Lys Val Val Lys Asn Asp Tyr Ile His Cys Asn Asp Asp Gly
                85                  90                  95

Ile Glu Phe Val Glu Val Arg Ile Arg Cys Arg Met Asn Asp Ile Leu
                100                 105                 110

Lys Tyr Glu Leu Arg Ser Tyr Ala Arg Asp Leu Val Leu Pro Lys Arg
                115                 120                 125

Val Thr Val Gly Ser Glu Asp Thr Thr Ala Ile Val Gln Leu Ser His
                130                 135                 140

Phe Asp Cys Gly Gly Leu Ala Val Ala Phe Gly Ile Ser His Lys Val
145                 150                 155                 160

Ala Asp Gly Gly Thr Ile Ala Ser Phe Met Lys Asp Trp Ala Ala Ser
                165                 170                 175

Ala Cys Tyr Leu Ser Ser His His Val Pro Thr Pro Leu Leu Val
                180                 185                 190

Ser Asp Ser Ile Phe Pro Arg Gln Asp Asn Ile Ile Cys Glu Gln Phe
                195                 200                 205

Pro Thr Ser Lys Asn Cys Val Glu Lys Thr Phe Ile Phe Pro Pro Glu
                210                 215                 220

Ala Ile Glu Lys Leu Lys Ser Lys Ala Val Glu Phe Gly Ile Glu Lys
225                 230                 235                 240

Pro Thr Arg Val Glu Val Leu Thr Ala Phe Leu Ser Arg Cys Ala Thr
                245                 250                 255

Val Ala Gly Lys Ser Ala Ala Lys Asn Asn Asn Cys Gly Gln Ser Leu
                260                 265                 270

Pro Phe Pro Val Leu Gln Ala Ile Asn Leu Arg Pro Ile Leu Glu Leu
                275                 280                 285

Pro Gln Asn Ser Val Gly Asn Leu Val Ser Ile Tyr Phe Ser Arg Thr
                290                 295                 300

Ile Lys Glu Asn Asp Tyr Leu Asn Glu Lys Glu Tyr Thr Lys Leu Val
305                 310                 315                 320

Ile Asn Glu Leu Arg Lys Glu Lys Gln Lys Ile Lys Asn Leu Ser Arg
                325                 330                 335

Glu Lys Leu Thr Tyr Val Ala Gln Met Glu Glu Phe Val Lys Ser Leu
                340                 345                 350

Lys Glu Phe Asp Ile Ser Asn Phe Leu Asp Ile Asp Ala Tyr Leu Ser
                355                 360                 365

Asp Ser Trp Cys Arg Phe Pro Phe Tyr Asp Val Asp Phe Gly Trp Gly
                370                 375                 380

Lys Pro Ile Trp Val Cys Leu Phe Gln Pro Tyr Ile Lys Asn Cys Val
385                 390                 395                 400

Val Met Met Asp Tyr Pro Phe Gly Asp Asp Tyr Gly Ile Glu Ala Ile
                405                 410                 415

Val Ser Phe Glu Gln Glu Lys Met Ser Ala Phe Glu Lys Asn Glu Gln
                420                 425                 430

Leu Leu Gln Phe Val Ser Asn
                435

<210> SEQ ID NO 10
<211> LENGTH: 1320
<212> TYPE: DNA
<213> ORGANISM: Artificial Sequence
<220> FEATURE:
<223> OTHER INFORMATION: TcTAT codon optimized for its expression in S. cerevisiae
<220> FEATURE:
<221> NAME/KEY: CDS
<222> LOCATION: (1)..(1320)

<400> SEQUENCE: 10

| | | | | | | | | | | | | | | | | |
|---|---|---|---|---|---|---|---|---|---|---|---|---|---|---|---|---|
| atg | gag | aag | acg | gat | tta | cac | gtg | aac | ctt | atc | gaa | aag | gtt | atg | gtc | 48 |
| Met | Glu | Lys | Thr | Asp | Leu | His | Val | Asn | Leu | Ile | Glu | Lys | Val | Met | Val | |
| 1 | | | | 5 | | | | | 10 | | | | | 15 | | |
| ggt | cca | agc | cca | cct | ttg | ccg | aag | act | aca | cta | caa | cta | tcc | tca | atc | 96 |
| Gly | Pro | Ser | Pro | Pro | Leu | Pro | Lys | Thr | Thr | Leu | Gln | Leu | Ser | Ser | Ile | |
| | | | 20 | | | | | 25 | | | | | 30 | | | |
| gat | aac | cta | cct | ggt | gtt | aga | ggc | tcg | atc | ttt | aat | gcc | ttg | tta | ata | 144 |
| Asp | Asn | Leu | Pro | Gly | Val | Arg | Gly | Ser | Ile | Phe | Asn | Ala | Leu | Leu | Ile | |
| | 35 | | | | | 40 | | | | | 45 | | | | | |
| tat | aat | gct | tca | ccg | tct | ccc | acg | atg | atc | tcc | gct | gat | cca | gct | aaa | 192 |
| Tyr | Asn | Ala | Ser | Pro | Ser | Pro | Thr | Met | Ile | Ser | Ala | Asp | Pro | Ala | Lys | |
| 50 | | | | | 55 | | | | | 60 | | | | | | |
| cct | atc | aga | gaa | gct | ttg | gcc | aaa | atc | ctg | gtt | tac | tac | cca | cct | ttc | 240 |
| Pro | Ile | Arg | Glu | Ala | Leu | Ala | Lys | Ile | Leu | Val | Tyr | Tyr | Pro | Pro | Phe | |
| 65 | | | | | 70 | | | | | 75 | | | | | 80 | |
| gct | ggc | agg | cta | cgt | gag | act | gag | aat | ggc | gat | cta | gag | gta | gag | tgc | 288 |
| Ala | Gly | Arg | Leu | Arg | Glu | Thr | Glu | Asn | Gly | Asp | Leu | Glu | Val | Glu | Cys | |
| | | | | 85 | | | | | 90 | | | | | 95 | | |
| acg | gga | gag | ggt | gcg | atg | ttt | ctt | gaa | gcg | atg | gcc | gat | aat | gaa | tta | 336 |
| Thr | Gly | Glu | Gly | Ala | Met | Phe | Leu | Glu | Ala | Met | Ala | Asp | Asn | Glu | Leu | |
| | | | 100 | | | | | 105 | | | | | 110 | | | |
| agt | gtc | tta | ggg | gat | ttc | gac | gac | agt | aac | cct | agc | ttc | cag | caa | ttg | 384 |
| Ser | Val | Leu | Gly | Asp | Phe | Asp | Asp | Ser | Asn | Pro | Ser | Phe | Gln | Gln | Leu | |
| | | 115 | | | | | 120 | | | | | 125 | | | | |
| ttg | ttc | tcc | ctt | cca | ctg | gac | act | aac | ttc | aag | gat | cta | tcc | ctg | tta | 432 |
| Leu | Phe | Ser | Leu | Pro | Leu | Asp | Thr | Asn | Phe | Lys | Asp | Leu | Ser | Leu | Leu | |
| | 130 | | | | | 135 | | | | | 140 | | | | | |
| gtc | gtg | cag | gtg | aca | agg | ttt | aca | tgc | ggc | ggg | ttc | gtc | gtt | ggg | gtt | 480 |
| Val | Val | Gln | Val | Thr | Arg | Phe | Thr | Cys | Gly | Gly | Phe | Val | Val | Gly | Val | |
| 145 | | | | | 150 | | | | | 155 | | | | | 160 | |
| tca | ttt | cac | cac | ggt | gta | tgc | gat | ggg | aga | gga | gct | gca | caa | ttt | ctg | 528 |
| Ser | Phe | His | His | Gly | Val | Cys | Asp | Gly | Arg | Gly | Ala | Ala | Gln | Phe | Leu | |
| | | | | 165 | | | | | 170 | | | | | 175 | | |
| aag | gga | cta | gcc | gaa | atg | gca | agg | gga | gaa | gtt | aag | ttg | tcg | ctg | gag | 576 |
| Lys | Gly | Leu | Ala | Glu | Met | Ala | Arg | Gly | Glu | Val | Lys | Leu | Ser | Leu | Glu | |
| | | | 180 | | | | | 185 | | | | | 190 | | | |
| ccg | atc | tgg | aat | cgt | gaa | cta | gtt | aag | ctg | gac | gat | ccc | aag | tat | ttg | 624 |
| Pro | Ile | Trp | Asn | Arg | Glu | Leu | Val | Lys | Leu | Asp | Asp | Pro | Lys | Tyr | Leu | |
| | | 195 | | | | | 200 | | | | | 205 | | | | |
| caa | ttc | ttt | cac | ttc | gaa | ttc | ttg | aga | gca | cca | tca | atc | gtc | gaa | aag | 672 |
| Gln | Phe | Phe | His | Phe | Glu | Phe | Leu | Arg | Ala | Pro | Ser | Ile | Val | Glu | Lys | |
| | 210 | | | | | 215 | | | | | 220 | | | | | |
| ata | gtt | caa | acc | tac | ttc | atc | atc | gat | ttc | gaa | act | att | aac | tac | ata | 720 |
| Ile | Val | Gln | Thr | Tyr | Phe | Ile | Ile | Asp | Phe | Glu | Thr | Ile | Asn | Tyr | Ile | |
| 225 | | | | | 230 | | | | | 235 | | | | | 240 | |
| aag | cag | tca | gta | atg | gaa | gaa | tgt | aaa | gaa | ttc | tgc | agc | tct | ttt | gaa | 768 |
| Lys | Gln | Ser | Val | Met | Glu | Glu | Cys | Lys | Glu | Phe | Cys | Ser | Ser | Phe | Glu | |
| | | | | 245 | | | | | 250 | | | | | 255 | | |
| gtt | gct | tct | gca | atg | acg | tgg | ata | gct | agg | acc | agg | gcc | ttt | caa | ata | 816 |

```
                Val Ala Ser Ala Met Thr Trp Ile Ala Arg Thr Arg Ala Phe Gln Ile
                            260                 265                 270 ccc gag agc gag tac gtg aaa atc cta ttt ggt atg gac atg agg aac           864
Pro Glu Ser Glu Tyr Val Lys Ile Leu Phe Gly Met Asp Met Arg Asn
                275                 280                 285 tct ttt aac ccg cct ctg ccg tca ggt tat tat gga aac tca att ggt           912
Ser Phe Asn Pro Pro Leu Pro Ser Gly Tyr Tyr Gly Asn Ser Ile Gly
290                 295                 300 acg gct tgt gca gtg gac aat gtt caa gac ttg ttg agt ggt tca cta           960
Thr Ala Cys Ala Val Asp Asn Val Gln Asp Leu Leu Ser Gly Ser Leu
305                 310                 315                 320 ctg agg gca ata atg ata atc aag aaa tca aag gta tca ctt aac gac          1008
Leu Arg Ala Ile Met Ile Ile Lys Lys Ser Lys Val Ser Leu Asn Asp
                325                 330                 335 aac ttt aag agc cgt gct gtc gtt aag cct tca gaa ctt gac gta aac          1056
Asn Phe Lys Ser Arg Ala Val Val Lys Pro Ser Glu Leu Asp Val Asn
                340                 345                 350 atg aac cat gag aat gtg gtg gca ttt gct gac tgg tca agg ctg ggg          1104
Met Asn His Glu Asn Val Val Ala Phe Ala Asp Trp Ser Arg Leu Gly
                355                 360                 365 ttc gac gaa gtc gat ttt ggc tgg gga aac gcg gtg tct gtt tcc ccg          1152
Phe Asp Glu Val Asp Phe Gly Trp Gly Asn Ala Val Ser Val Ser Pro
370                 375                 380 gta cag caa cag tcg gca ctt gca atg cag aat tac ttc ctg ttc ttg          1200
Val Gln Gln Gln Ser Ala Leu Ala Met Gln Asn Tyr Phe Leu Phe Leu
385                 390                 395                 400 aag cca agc aag aac aag ccc gat gga att aag att cta atg ttc cta          1248
Lys Pro Ser Lys Asn Lys Pro Asp Gly Ile Lys Ile Leu Met Phe Leu
                405                 410                 415 cca ttg tcc aag atg aaa tcc ttc aaa att gaa atg gaa gcg atg atg          1296
Pro Leu Ser Lys Met Lys Ser Phe Lys Ile Glu Met Glu Ala Met Met
                420                 425                 430 aag aag tac gtc gcc aag gta taa                                          1320
Lys Lys Tyr Val Ala Lys Val
                435

<210> SEQ ID NO 11
<211> LENGTH: 439
<212> TYPE: PRT
<213> ORGANISM: Artificial Sequence
<220> FEATURE:
<223> OTHER INFORMATION: Synthetic Construct

<400> SEQUENCE: 11

Met Glu Lys Thr Asp Leu His Val Asn Leu Ile Glu Lys Val Met Val
1               5                   10                  15

Gly Pro Ser Pro Pro Leu Pro Lys Thr Thr Leu Gln Leu Ser Ser Ile
                20                  25                  30

Asp Asn Leu Pro Gly Val Arg Gly Ser Ile Phe Asn Ala Leu Leu Ile
            35                  40                  45

Tyr Asn Ala Ser Pro Ser Pro Thr Met Ile Ser Ala Asp Pro Ala Lys
        50                  55                  60

Pro Ile Arg Glu Ala Leu Ala Lys Ile Leu Val Tyr Tyr Pro Pro Phe
65                  70                  75                  80

Ala Gly Arg Leu Arg Glu Thr Glu Asn Gly Asp Leu Glu Val Glu Cys
                85                  90                  95

Thr Gly Glu Gly Ala Met Phe Leu Glu Ala Met Ala Asp Asn Glu Leu
                100                 105                 110

Ser Val Leu Gly Asp Phe Asp Asp Ser Asn Pro Ser Phe Gln Gln Leu
```

```
                115                 120                 125
Leu Phe Ser Leu Pro Leu Asp Thr Asn Phe Lys Asp Leu Ser Leu Leu
            130                 135                 140

Val Val Gln Val Thr Arg Phe Thr Cys Gly Gly Phe Val Val Gly Val
145                 150                 155                 160

Ser Phe His His Gly Val Cys Asp Gly Arg Gly Ala Ala Gln Phe Leu
                165                 170                 175

Lys Gly Leu Ala Glu Met Ala Arg Gly Glu Val Lys Leu Ser Leu Glu
            180                 185                 190

Pro Ile Trp Asn Arg Glu Leu Val Lys Leu Asp Asp Pro Lys Tyr Leu
        195                 200                 205

Gln Phe Phe His Phe Glu Phe Leu Arg Ala Pro Ser Ile Val Glu Lys
    210                 215                 220

Ile Val Gln Thr Tyr Phe Ile Ile Asp Phe Glu Thr Ile Asn Tyr Ile
225                 230                 235                 240

Lys Gln Ser Val Met Glu Glu Cys Lys Glu Phe Cys Ser Ser Phe Glu
                245                 250                 255

Val Ala Ser Ala Met Thr Trp Ile Ala Arg Thr Arg Ala Phe Gln Ile
            260                 265                 270

Pro Glu Ser Glu Tyr Val Lys Ile Leu Phe Gly Met Asp Met Arg Asn
        275                 280                 285

Ser Phe Asn Pro Pro Leu Pro Ser Gly Tyr Tyr Gly Asn Ser Ile Gly
    290                 295                 300

Thr Ala Cys Ala Val Asp Asn Val Gln Asp Leu Leu Ser Gly Ser Leu
305                 310                 315                 320

Leu Arg Ala Ile Met Ile Ile Lys Lys Ser Lys Val Ser Leu Asn Asp
                325                 330                 335

Asn Phe Lys Ser Arg Ala Val Val Lys Pro Ser Glu Leu Asp Val Asn
            340                 345                 350

Met Asn His Glu Asn Val Val Ala Phe Ala Asp Trp Ser Arg Leu Gly
        355                 360                 365

Phe Asp Glu Val Asp Phe Gly Trp Gly Asn Ala Val Ser Val Ser Pro
    370                 375                 380

Val Gln Gln Gln Ser Ala Leu Ala Met Gln Asn Tyr Phe Leu Phe Leu
385                 390                 395                 400

Lys Pro Ser Lys Asn Lys Pro Asp Gly Ile Lys Ile Leu Met Phe Leu
                405                 410                 415

Pro Leu Ser Lys Met Lys Ser Phe Lys Ile Glu Met Glu Ala Met Met
            420                 425                 430

Lys Lys Tyr Val Ala Lys Val
        435

<210> SEQ ID NO 12
<211> LENGTH: 1332
<212> TYPE: DNA
<213> ORGANISM: Artificial Sequence
<220> FEATURE:
<223> OTHER INFORMATION: CrMAT codon optimized for its expression in S.
      cerevisiae
<220> FEATURE:
<221> NAME/KEY: CDS
<222> LOCATION: (1)..(1332)

<400> SEQUENCE: 12 atg gat tct att act atg gtt gaa acc gag aca tta tcg aag aca ttg        48
Met Asp Ser Ile Thr Met Val Glu Thr Glu Thr Leu Ser Lys Thr Leu
1               5                   10                  15
```

```
att aag cca tct agc cca acc cca cag agt ctg tca cac tac aac ctg      96
Ile Lys Pro Ser Ser Pro Thr Pro Gln Ser Leu Ser His Tyr Asn Leu
         20                  25                  30 tct tac aac gat cag aat ata tat cca gag tat ata ttt gca ggc ttc     144
Ser Tyr Asn Asp Gln Asn Ile Tyr Pro Glu Tyr Ile Phe Ala Gly Phe
     35                  40                  45 ttc tac agc aac ccg gac gga cac gag atc tcg act att aga gag cag     192
Phe Tyr Ser Asn Pro Asp Gly His Glu Ile Ser Thr Ile Arg Glu Gln
 50                  55                  60 ctg cag aac tct ctt agc aag aca tta gta tct tat tat cca ttc gct     240
Leu Gln Asn Ser Leu Ser Lys Thr Leu Val Ser Tyr Tyr Pro Phe Ala
65                  70                  75                  80 ggt aaa gtg gtc aag aac gat tac att cac tgc aat gac gac gga ata     288
Gly Lys Val Val Lys Asn Asp Tyr Ile His Cys Asn Asp Asp Gly Ile
                 85                  90                  95 gaa ttc gta gac gtc aga atc cac tgc agg atg aac gat att ctt aag     336
Glu Phe Val Asp Val Arg Ile His Cys Arg Met Asn Asp Ile Leu Lys
            100                 105                 110 cct gaa ttg agg tct tac gct tcc gag ctt att cgt ccg aat aga agt     384
Pro Glu Leu Arg Ser Tyr Ala Ser Glu Leu Ile Arg Pro Asn Arg Ser
        115                 120                 125 aca gtg ggg tca gag gac agt act gcg ctt gtc cag tta tct cac ttt     432
Thr Val Gly Ser Glu Asp Ser Thr Ala Leu Val Gln Leu Ser His Phe
    130                 135                 140 gac tgt ggc ggg gta gct gtc gca ttc ggt ata tct cac aaa gtc gca     480
Asp Cys Gly Gly Val Ala Val Ala Phe Gly Ile Ser His Lys Val Ala
145                 150                 155                 160 gac gca gcg act att ctg tcg ttt ata aag gat tgg gcc gct tct acg     528
Asp Ala Ala Thr Ile Leu Ser Phe Ile Lys Asp Trp Ala Ala Ser Thr
                165                 170                 175 tgt gac ttg tca agt agt cac gat gtg tct aca cca gta cta gta tcc     576
Cys Asp Leu Ser Ser Ser His Asp Val Ser Thr Pro Val Leu Val Ser
            180                 185                 190 gat tcc ata ttc ccc cgt caa gat aac atc atc tgt ggc cag ttc cct     624
Asp Ser Ile Phe Pro Arg Gln Asp Asn Ile Ile Cys Gly Gln Phe Pro
        195                 200                 205 gct tca ccg aac tgc gta agg aag cgt ttc tta ttc agc ccg gaa gct     672
Ala Ser Pro Asn Cys Val Arg Lys Arg Phe Leu Phe Ser Pro Glu Ala
    210                 215                 220 atc gaa aga cta aaa tcg aaa gcc att gaa ttt ggg atc gag aag cca     720
Ile Glu Arg Leu Lys Ser Lys Ala Ile Glu Phe Gly Ile Glu Lys Pro
225                 230                 235                 240 acg agg gta gag gtc ctg aca gca ttc ttg tgc cgt tgc gct acc gtt     768
Thr Arg Val Glu Val Leu Thr Ala Phe Leu Cys Arg Cys Ala Thr Val
                245                 250                 255 gca ggt aaa tct gcg gcc aag aac aac aat tgt gga cag tca ctg cct     816
Ala Gly Lys Ser Ala Ala Lys Asn Asn Asn Cys Gly Gln Ser Leu Pro
            260                 265                 270 ttc gct gtt att caa gca gtc aac ctg agg ccc tta cta gaa ctg cca     864
Phe Ala Val Ile Gln Ala Val Asn Leu Arg Pro Leu Leu Glu Leu Pro
        275                 280                 285 aag aat tcc gtc ggc aac ctt ata tca atc tac ttt tct aca atc aaa     912
Lys Asn Ser Val Gly Asn Leu Ile Ser Ile Tyr Phe Ser Thr Ile Lys
    290                 295                 300 gaa aac gac acg gtg aac atc gaa cag gag ttc aca aaa tta gtg atc     960
Glu Asn Asp Thr Val Asn Ile Glu Gln Glu Phe Thr Lys Leu Val Ile
305                 310                 315                 320 gga gag ttg agg aag gct aag gat aag tta aag aac ctg tcg caa gag    1008
Gly Glu Leu Arg Lys Ala Lys Asp Lys Leu Lys Asn Leu Ser Gln Glu
```

```
                   325                 330                 335
aag ctg aat tac gta gct aga atg caa gat ttc gcg aat tgc ctg aag    1056
Lys Leu Asn Tyr Val Ala Arg Met Gln Asp Phe Ala Asn Cys Leu Lys
        340                 345                 350 gaa ttg gac ata agt tca ttc ttc gac atg gaa aac gtg gac ata gac    1104
Glu Leu Asp Ile Ser Ser Phe Phe Asp Met Glu Asn Val Asp Ile Asp
355                 360                 365 gct tat tta ttt tcg agc tgg tgc agg ttc ccc ttc tac gac atc gat    1152
Ala Tyr Leu Phe Ser Ser Trp Cys Arg Phe Pro Phe Tyr Asp Ile Asp
    370                 375                 380 ttc ggt ctg ggg aag cca ata tgg gtc tgc atg ttt cag cct cac ttt    1200
Phe Gly Leu Gly Lys Pro Ile Trp Val Cys Met Phe Gln Pro His Phe
385                 390                 395                 400 aag aat tgt ata att tta atg gat tat ccc ttt ggt gac gat tac ggc    1248
Lys Asn Cys Ile Ile Leu Met Asp Tyr Pro Phe Gly Asp Asp Tyr Gly
                405                 410                 415 atc gaa gcc cta att acg ttg gaa caa gag aag atg ccc gcc ttc gaa    1296
Ile Glu Ala Leu Ile Thr Leu Glu Gln Glu Lys Met Pro Ala Phe Glu
            420                 425                 430 aac aac gag ctg ctg cta agc ttc gcc agc aac taa                    1332
Asn Asn Glu Leu Leu Leu Ser Phe Ala Ser Asn
                435                 440

<210> SEQ ID NO 13
<211> LENGTH: 443
<212> TYPE: PRT
<213> ORGANISM: Artificial Sequence
<220> FEATURE:
<223> OTHER INFORMATION: Synthetic Construct

<400> SEQUENCE: 13

Met Asp Ser Ile Thr Met Val Glu Thr Glu Thr Leu Ser Lys Thr Leu
1               5                   10                  15

Ile Lys Pro Ser Ser Pro Thr Pro Gln Ser Leu Ser His Tyr Asn Leu
            20                  25                  30

Ser Tyr Asn Asp Gln Asn Ile Tyr Pro Glu Tyr Ile Phe Ala Gly Phe
        35                  40                  45

Phe Tyr Ser Asn Pro Asp Gly His Glu Ile Ser Thr Ile Arg Glu Gln
    50                  55                  60

Leu Gln Asn Ser Leu Ser Lys Thr Leu Val Ser Tyr Tyr Pro Phe Ala
65                  70                  75                  80

Gly Lys Val Val Lys Asn Asp Tyr Ile His Cys Asn Asp Asp Gly Ile
                85                  90                  95

Glu Phe Val Asp Val Arg Ile His Cys Arg Met Asn Asp Ile Leu Lys
            100                 105                 110

Pro Glu Leu Arg Ser Tyr Ala Ser Glu Leu Ile Arg Pro Asn Arg Ser
        115                 120                 125

Thr Val Gly Ser Glu Asp Ser Thr Ala Leu Val Gln Leu Ser His Phe
    130                 135                 140

Asp Cys Gly Gly Val Ala Val Ala Phe Gly Ile Ser His Lys Val Ala
145                 150                 155                 160

Asp Ala Ala Thr Ile Leu Ser Phe Ile Lys Asp Trp Ala Ala Ser Thr
                165                 170                 175

Cys Asp Leu Ser Ser Ser His Asp Val Ser Thr Pro Val Leu Val Ser
            180                 185                 190

Asp Ser Ile Phe Pro Arg Gln Asp Asn Ile Ile Cys Gly Gln Phe Pro
        195                 200                 205
```

```
Ala Ser Pro Asn Cys Val Arg Lys Arg Phe Leu Phe Ser Pro Glu Ala
        210             215                 220

Ile Glu Arg Leu Lys Ser Lys Ala Ile Glu Phe Gly Ile Glu Lys Pro
225                 230                 235                 240

Thr Arg Val Glu Val Leu Thr Ala Phe Leu Cys Arg Cys Ala Thr Val
                245                 250                 255

Ala Gly Lys Ser Ala Ala Lys Asn Asn Asn Cys Gly Gln Ser Leu Pro
            260                 265                 270

Phe Ala Val Ile Gln Ala Val Asn Leu Arg Pro Leu Leu Glu Leu Pro
            275                 280                 285

Lys Asn Ser Val Gly Asn Leu Ile Ser Ile Tyr Phe Ser Thr Ile Lys
        290                 295                 300

Glu Asn Asp Thr Val Asn Ile Glu Gln Glu Phe Thr Lys Leu Val Ile
305                 310                 315                 320

Gly Glu Leu Arg Lys Ala Lys Asp Lys Leu Lys Asn Leu Ser Gln Glu
                325                 330                 335

Lys Leu Asn Tyr Val Ala Arg Met Gln Asp Phe Ala Asn Cys Leu Lys
            340                 345                 350

Glu Leu Asp Ile Ser Ser Phe Phe Asp Met Glu Asn Val Asp Ile Asp
        355                 360                 365

Ala Tyr Leu Phe Ser Ser Trp Cys Arg Phe Pro Phe Tyr Asp Ile Asp
370                 375                 380

Phe Gly Leu Gly Lys Pro Ile Trp Val Cys Met Phe Gln Pro His Phe
385                 390                 395                 400

Lys Asn Cys Ile Ile Leu Met Asp Tyr Pro Phe Gly Asp Asp Tyr Gly
            405                 410                 415

Ile Glu Ala Leu Ile Thr Leu Glu Gln Glu Lys Met Pro Ala Phe Glu
                420                 425                 430

Asn Asn Glu Leu Leu Leu Ser Phe Ala Ser Asn
            435                 440

<210> SEQ ID NO 14
<211> LENGTH: 1254
<212> TYPE: DNA
<213> ORGANISM: Artificial Sequence
<220> FEATURE:
<223> OTHER INFORMATION: LiAAT-4 DNA sequence codon optimized for its
      expression in S. cerevisiae
<220> FEATURE:
<221> NAME/KEY: CDS
<222> LOCATION: (1)..(1254)

<400> SEQUENCE: 14 atg gcc atg ata atc acg aag caa ata tta aga cct agt tcc ccg acg      48
Met Ala Met Ile Ile Thr Lys Gln Ile Leu Arg Pro Ser Ser Pro Thr
1               5                   10                  15 ccc caa gcc ttt aag aat cac aag ctg tcc tac tta gac caa ata cag      96
Pro Gln Ala Phe Lys Asn His Lys Leu Ser Tyr Leu Asp Gln Ile Gln
            20                  25                  30 gcg cct att tac ata cct ttg ttg ttc ttc tat aag aac gag gag tca     144
Ala Pro Ile Tyr Ile Pro Leu Leu Phe Phe Tyr Lys Asn Glu Glu Ser
        35                  40                  45 aaa tac cca gac cag atc tcg caa aga ttt aag cag agt ttg tcc gaa     192
Lys Tyr Pro Asp Gln Ile Ser Gln Arg Phe Lys Gln Ser Leu Ser Glu
50                  55                  60 att ttg aca ata ttc tac cct ttg gct ggt acg atg agg cat aac tcg     240
Ile Leu Thr Ile Phe Tyr Pro Leu Ala Gly Thr Met Arg His Asn Ser
65                  70                  75                  80
```

```
ttc gtg gac tgc aat gac agg ggt gtc gaa ttt gta gag gtc agg gtc      288
Phe Val Asp Cys Asn Asp Arg Gly Val Glu Phe Val Glu Val Arg Val
                85                  90                  95 cat gcg aga cta gcc cag ttc att caa gat cct aag atg gaa gag ctt      336
His Ala Arg Leu Ala Gln Phe Ile Gln Asp Pro Lys Met Glu Glu Leu
               100                 105                 110 aag caa ttg ata cct gtg gat tgt ata tct cac act gac gat gat ttc      384
Lys Gln Leu Ile Pro Val Asp Cys Ile Ser His Thr Asp Asp Asp Phe
               115                 120                 125 tta ttg cta gtc aag att agc tat ttt gac tgc ggt gag gtc gtc gtt      432
Leu Leu Leu Val Lys Ile Ser Tyr Phe Asp Cys Gly Glu Val Val Val
    130                 135                 140 gga gtc tgc atg tcg cac aaa att ggt gac gga att agt ctg gca gcg      480
Gly Val Cys Met Ser His Lys Ile Gly Asp Gly Ile Ser Leu Ala Ala
145                 150                 155                 160 ttt atg aac gct tgg gca gca acg tgt agg gga gaa tcg tct agt gag      528
Phe Met Asn Ala Trp Ala Ala Thr Cys Arg Gly Glu Ser Ser Ser Glu
                165                 170                 175 atc att cac cca tct ttt gat ctt gct tta cac ttt ccg cct aaa gac      576
Ile Ile His Pro Ser Phe Asp Leu Ala Leu His Phe Pro Pro Lys Asp
                180                 185                 190 cac ttg tct tca gca tcc tca ttc cgt gtg gcc ata gcc cag gag aac      624
His Leu Ser Ser Ala Ser Ser Phe Arg Val Ala Ile Ala Gln Glu Asn
               195                 200                 205 atc atg acc aag agg cta gta ttt gat aga gaa aag ttg gag aag ctg      672
Ile Met Thr Lys Arg Leu Val Phe Asp Arg Glu Lys Leu Glu Lys Leu
               210                 215                 220 cgt aag aga atc gct gcc agt tct gat ggg gtg aga gac cct agc aga      720
Arg Lys Arg Ile Ala Ala Ser Ser Asp Gly Val Arg Asp Pro Ser Arg
225                 230                 235                 240 gtt gaa gct gta tct gtc ttt att tgg aaa agc tta att gaa gcc cac      768
Val Glu Ala Val Ser Val Phe Ile Trp Lys Ser Leu Ile Glu Ala His
                245                 250                 255 aag gcc gag tca cac atg act gag aca cca gcc gtt tct att gct agc      816
Lys Ala Glu Ser His Met Thr Glu Thr Pro Ala Val Ser Ile Ala Ser
                260                 265                 270 cac gcc gtg aac tta agg cct aga aca gtc cca caa atg gac caa act      864
His Ala Val Asn Leu Arg Pro Arg Thr Val Pro Gln Met Asp Gln Thr
               275                 280                 285 ttc ggt aac tgc tac gct ccc gct tcg gcc gtt gtc tcc tgg gat gaa      912
Phe Gly Asn Cys Tyr Ala Pro Ala Ser Ala Val Val Ser Trp Asp Glu
               290                 295                 300 gac tac gta cat cac agt cgt ttg agg gcg gcc ctt aga gaa atc gac      960
Asp Tyr Val His His Ser Arg Leu Arg Ala Ala Leu Arg Glu Ile Asp
305                 310                 315                 320 gac gac tac att aat aag gtc ttg aaa gcc gac aat aat tat tta acg     1008
Asp Asp Tyr Ile Asn Lys Val Leu Lys Ala Asp Asn Asn Tyr Leu Thr
                325                 330                 335 cag gat caa att ggt gac ttg ttt aaa cca gaa aac tca gtt cta agt     1056
Gln Asp Gln Ile Gly Asp Leu Phe Lys Pro Glu Asn Ser Val Leu Ser
               340                 345                 350 tcg tgg tgg cgt ttc cca gtt tac aag gta gac ttt gga tgg ggt aag     1104
Ser Trp Trp Arg Phe Pro Val Tyr Lys Val Asp Phe Gly Trp Gly Lys
               355                 360                 365 cca gtt tgg gtt tct acg acg acc atc caa tac atg aac ttg att ata     1152
Pro Val Trp Val Ser Thr Thr Thr Ile Gln Tyr Met Asn Leu Ile Ile
370                 375                 380 ttt act tcg acg ccc tca gaa gac ggc ata gag gcg tgg gta act act     1200
Phe Thr Ser Thr Pro Ser Glu Asp Gly Ile Glu Ala Trp Val Thr Thr
385                 390                 395                 400
```

```
act cac aat ttc ttc caa gtt ctg cag gca aac tat aat aaa ctt gac    1248
Thr His Asn Phe Phe Gln Val Leu Gln Ala Asn Tyr Asn Lys Leu Asp
             405                 410                 415 acg taa                                                             1254
Thr
```

<210> SEQ ID NO 15
<211> LENGTH: 417
<212> TYPE: PRT
<213> ORGANISM: Artificial Sequence
<220> FEATURE:
<223> OTHER INFORMATION: Synthetic Construct

<400> SEQUENCE: 15

```
Met Ala Met Ile Ile Thr Lys Gln Ile Leu Arg Pro Ser Ser Pro Thr
1               5                   10                  15

Pro Gln Ala Phe Lys Asn His Lys Leu Ser Tyr Leu Asp Gln Ile Gln
            20                  25                  30

Ala Pro Ile Tyr Ile Pro Leu Leu Phe Phe Tyr Lys Asn Glu Glu Ser
        35                  40                  45

Lys Tyr Pro Asp Gln Ile Ser Gln Arg Phe Lys Gln Ser Leu Ser Glu
    50                  55                  60

Ile Leu Thr Ile Phe Tyr Pro Leu Ala Gly Thr Met Arg His Asn Ser
65                  70                  75                  80

Phe Val Asp Cys Asn Asp Arg Gly Val Glu Phe Val Glu Val Arg Val
                85                  90                  95

His Ala Arg Leu Ala Gln Phe Ile Gln Asp Pro Lys Met Glu Glu Leu
            100                 105                 110

Lys Gln Leu Ile Pro Val Asp Cys Ile Ser His Thr Asp Asp Asp Phe
        115                 120                 125

Leu Leu Leu Val Lys Ile Ser Tyr Phe Asp Cys Gly Glu Val Val Val
    130                 135                 140

Gly Val Cys Met Ser His Lys Ile Gly Asp Gly Ile Ser Leu Ala Ala
145                 150                 155                 160

Phe Met Asn Ala Trp Ala Ala Thr Cys Arg Gly Glu Ser Ser Ser Glu
                165                 170                 175

Ile Ile His Pro Ser Phe Asp Leu Ala Leu His Phe Pro Pro Lys Asp
            180                 185                 190

His Leu Ser Ser Ala Ser Ser Phe Arg Val Ala Ile Ala Gln Glu Asn
        195                 200                 205

Ile Met Thr Lys Arg Leu Val Phe Asp Arg Glu Lys Leu Glu Lys Leu
    210                 215                 220

Arg Lys Arg Ile Ala Ala Ser Ser Asp Gly Val Arg Asp Pro Ser Arg
225                 230                 235                 240

Val Glu Ala Val Ser Val Phe Ile Trp Lys Ser Leu Ile Glu Ala His
                245                 250                 255

Lys Ala Glu Ser His Met Thr Glu Thr Pro Ala Val Ser Ile Ala Ser
            260                 265                 270

His Ala Val Asn Leu Arg Pro Arg Thr Val Pro Gln Met Asp Gln Thr
        275                 280                 285

Phe Gly Asn Cys Tyr Ala Pro Ala Ser Ala Val Ser Trp Asp Glu
    290                 295                 300

Asp Tyr Val His His Ser Arg Leu Arg Ala Ala Leu Arg Glu Ile Asp
305                 310                 315                 320

Asp Asp Tyr Ile Asn Lys Val Leu Lys Ala Asp Asn Asn Tyr Leu Thr
```

```
                        325                 330                 335
Gln Asp Gln Ile Gly Asp Leu Phe Lys Pro Glu Asn Ser Val Leu Ser
                340                 345                 350

Ser Trp Trp Arg Phe Pro Val Tyr Lys Val Asp Phe Gly Trp Gly Lys
            355                 360                 365

Pro Val Trp Val Ser Thr Thr Thr Ile Gln Tyr Met Asn Leu Ile Ile
        370                 375                 380

Phe Thr Ser Thr Pro Ser Glu Asp Gly Ile Glu Ala Trp Val Thr Thr
385                 390                 395                 400

Thr His Asn Phe Phe Gln Val Leu Gln Ala Asn Tyr Asn Lys Leu Asp
                405                 410                 415

Thr

<210> SEQ ID NO 16
<211> LENGTH: 1485
<212> TYPE: DNA
<213> ORGANISM: Artificial Sequence
<220> FEATURE:
<223> OTHER INFORMATION: FgaAT codon optimized for its expression in S.
      cerevisiae
<220> FEATURE:
<221> NAME/KEY: CDS
<222> LOCATION: (1)..(1485)

<400> SEQUENCE: 16 atg aag aag cag gtc act ttt aaa cct ttc aga ttg tca cca gtc gat      48
Met Lys Lys Gln Val Thr Phe Lys Pro Phe Arg Leu Ser Pro Val Asp
1               5                   10                  15 cat agt tta cct aag gtt tac atc ttc aag tct cta tat ttc aga ggg      96
His Ser Leu Pro Lys Val Tyr Ile Phe Lys Ser Leu Tyr Phe Arg Gly
            20                  25                  30 gta gat gac act ggt tct ctt agt aga cta cag gat ggc att gat cgt     144
Val Asp Asp Thr Gly Ser Leu Ser Arg Leu Gln Asp Gly Ile Asp Arg
        35                  40                  45 ttg ata tct tgt ctg cct ttc ctg tca ggc gag gtg gtt cca tgt gca     192
Leu Ile Ser Cys Leu Pro Phe Leu Ser Gly Glu Val Val Pro Cys Ala
    50                  55                  60 gac ata cca gat aag gtc ggt gta ctt caa gtt cag atg cct tgc cct     240
Asp Ile Pro Asp Lys Val Gly Val Leu Gln Val Gln Met Pro Cys Pro
65                  70                  75                  80 tcc ttg caa gaa att cca atg ctg cta gtc aaa agt tat cca aac cat     288
Ser Leu Gln Glu Ile Pro Met Leu Leu Val Lys Ser Tyr Pro Asn His
                85                  90                  95 aca tgg cca gca gct tct acc tcg gaa aga tgg aga aac acc gct ttg     336
Thr Trp Pro Ala Ala Ser Thr Ser Glu Arg Trp Arg Asn Thr Ala Leu
            100                 105                 110 cta gat cag tcg tat agg cca ttg ccg gat ttt ata ccc cca tca aag     384
Leu Asp Gln Ser Tyr Arg Pro Leu Pro Asp Phe Ile Pro Pro Ser Lys
        115                 120                 125 cct aga cct gtt ttg aga ttt cag gcg aac ttc ctg gct gat ggt tta     432
Pro Arg Pro Val Leu Arg Phe Gln Ala Asn Phe Leu Ala Asp Gly Leu
    130                 135                 140 atg cta tgt atg gga tat aat cat tct gta ttc gac gga aca ggt gcg     480
Met Leu Cys Met Gly Tyr Asn His Ser Val Phe Asp Gly Thr Gly Ala
145                 150                 155                 160 ggg aac att ctg gaa atg ttg gct gat tgt tgt aga gct aat cca aac     528
Gly Asn Ile Leu Glu Met Leu Ala Asp Cys Cys Arg Ala Asn Pro Asn
                165                 170                 175 tcc atc tta gca ctg cca aca aac ggt gac ata gag agc gag ttg aga     576
Ser Ile Leu Ala Leu Pro Thr Asn Gly Asp Ile Glu Ser Glu Leu Arg
```

```
            180                 185                 190
ggt tta ctg tcc agt cca ggt gta gca gtt gca aat gcc tct cag gaa       624
Gly Leu Leu Ser Ser Pro Gly Val Ala Val Ala Asn Ala Ser Gln Glu
        195                 200                 205 gcc tac gca att aat tgt gca cac acg gaa gta gaa ccc gaa ccc agt       672
Ala Tyr Ala Ile Asn Cys Ala His Thr Glu Val Glu Pro Glu Pro Ser
    210                 215                 220 tca gct atg ctt tac tgt tgg cct ttc ttg ctg agt tct gag aag att       720
Ser Ala Met Leu Tyr Cys Trp Pro Phe Leu Leu Ser Ser Glu Lys Ile
225                 230                 235                 240 gaa tgt tta cag gaa gca tgt aat agt tta cta cca cat atc gtt cgt       768
Glu Cys Leu Gln Glu Ala Cys Asn Ser Leu Leu Pro His Ile Val Arg
                245                 250                 255 ttg tac tct ggt acg cag agt tcg ctt ata aac caa gat acg aac tgg       816
Leu Tyr Ser Gly Thr Gln Ser Ser Leu Ile Asn Gln Asp Thr Asn Trp
            260                 265                 270 cca cat att ctt tca tca aac gac gtg cta acc gct ctt tta gct gtt       864
Pro His Ile Leu Ser Ser Asn Asp Val Leu Thr Ala Leu Leu Ala Val
        275                 280                 285 tca att gaa aag gct agg gaa gca aca ggt gcc ctt ggt cat atg agc       912
Ser Ile Glu Lys Ala Arg Glu Ala Thr Gly Ala Leu Gly His Met Ser
    290                 295                 300 aga tca ttg gct atg gct gtt aac cta cgt gag cgt tta aag cct atg       960
Arg Ser Leu Ala Met Ala Val Asn Leu Arg Glu Arg Leu Lys Pro Met
305                 310                 315                 320 cca aga cac tat ttg ggt aac cta gtt acc act gtg tgg gta tca cat      1008
Pro Arg His Tyr Leu Gly Asn Leu Val Thr Thr Val Trp Val Ser His
                325                 330                 335 cac cgt cct gcc gtt aag gac ctt gaa aca atg gtt tta cca gtg cca      1056
His Arg Pro Ala Val Lys Asp Leu Glu Thr Met Val Leu Pro Val Pro
            340                 345                 350 gca tgc aat agg cac gaa ata gac aga gac gac ttg ttg tgg ata acc      1104
Ala Cys Asn Arg His Glu Ile Asp Arg Asp Asp Leu Leu Trp Ile Thr
        355                 360                 365 cac gtg gca ttc cgt att aga tta ggg ctg aac gca ata aac gaa gaa      1152
His Val Ala Phe Arg Ile Arg Leu Gly Leu Asn Ala Ile Asn Glu Glu
    370                 375                 380 cat att aga ggt ctg atc cac tac ttg cat tcc caa gac gat tgg gaa      1200
His Ile Arg Gly Leu Ile His Tyr Leu His Ser Gln Asp Asp Trp Glu
385                 390                 395                 400 cag att gga ata cat ttc acc gat cca att ttc att tct tcc tgg cgt      1248
Gln Ile Gly Ile His Phe Thr Asp Pro Ile Phe Ile Ser Ser Trp Arg
                405                 410                 415 cac ctt aag gtc tat gaa cta gac ttc gga cct act atc ggt cat gct      1296
His Leu Lys Val Tyr Glu Leu Asp Phe Gly Pro Thr Ile Gly His Ala
            420                 425                 430 gaa cac ttt gag atg gat gtc ggc acc acc gat ggt gtg tgt gtt gtt      1344
Glu His Phe Glu Met Asp Val Gly Thr Thr Asp Gly Val Cys Val Val
        435                 440                 445 atg cct gct aac acc aga gcc gtc ggc aag act aag aag gct cct tgg      1392
Met Pro Ala Asn Thr Arg Ala Val Gly Lys Thr Lys Lys Ala Pro Trp
    450                 455                 460 gac att aga atc gtg tta aac ccc gaa gtg tta cag gca cta ata gct      1440
Asp Ile Arg Ile Val Leu Asn Pro Glu Val Leu Gln Ala Leu Ile Ala
465                 470                 475                 480 agt gcc atc ttt ggt tgg gct atg gtc aag gac gct tcg aca taa         1485
Ser Ala Ile Phe Gly Trp Ala Met Val Lys Asp Ala Ser Thr
                485                 490
```

<210> SEQ ID NO 17
<211> LENGTH: 494
<212> TYPE: PRT
<213> ORGANISM: Artificial Sequence
<220> FEATURE:
<223> OTHER INFORMATION: Synthetic Construct

<400> SEQUENCE: 17

```
Met Lys Lys Gln Val Thr Phe Lys Pro Phe Arg Leu Ser Pro Val Asp
1               5                   10                  15

His Ser Leu Pro Lys Val Tyr Ile Phe Lys Ser Leu Tyr Phe Arg Gly
            20                  25                  30

Val Asp Asp Thr Gly Ser Leu Ser Arg Leu Gln Asp Gly Ile Asp Arg
        35                  40                  45

Leu Ile Ser Cys Leu Pro Phe Leu Ser Gly Glu Val Pro Cys Ala
    50                  55                  60

Asp Ile Pro Asp Lys Val Gly Val Leu Gln Val Gln Met Pro Cys Pro
65                  70                  75                  80

Ser Leu Gln Glu Ile Pro Met Leu Leu Val Lys Ser Tyr Pro Asn His
                85                  90                  95

Thr Trp Pro Ala Ala Ser Thr Ser Glu Arg Trp Arg Asn Thr Ala Leu
            100                 105                 110

Leu Asp Gln Ser Tyr Arg Pro Leu Pro Asp Phe Ile Pro Pro Ser Lys
        115                 120                 125

Pro Arg Pro Val Leu Arg Phe Gln Ala Asn Phe Leu Ala Asp Gly Leu
130                 135                 140

Met Leu Cys Met Gly Tyr Asn His Ser Val Phe Asp Gly Thr Gly Ala
145                 150                 155                 160

Gly Asn Ile Leu Glu Met Leu Ala Asp Cys Cys Arg Ala Asn Pro Asn
                165                 170                 175

Ser Ile Leu Ala Leu Pro Thr Asn Gly Asp Ile Glu Ser Glu Leu Arg
            180                 185                 190

Gly Leu Leu Ser Ser Pro Gly Val Ala Val Ala Asn Ala Ser Gln Glu
        195                 200                 205

Ala Tyr Ala Ile Asn Cys Ala His Thr Glu Val Glu Pro Glu Pro Ser
210                 215                 220

Ser Ala Met Leu Tyr Cys Trp Pro Phe Leu Leu Ser Ser Glu Lys Ile
225                 230                 235                 240

Glu Cys Leu Gln Glu Ala Cys Asn Ser Leu Leu Pro His Ile Val Arg
                245                 250                 255

Leu Tyr Ser Gly Thr Gln Ser Ser Leu Ile Asn Gln Asp Thr Asn Trp
            260                 265                 270

Pro His Ile Leu Ser Ser Asn Asp Val Leu Thr Ala Leu Leu Ala Val
        275                 280                 285

Ser Ile Glu Lys Ala Arg Glu Ala Thr Gly Ala Leu Gly His Met Ser
290                 295                 300

Arg Ser Leu Ala Met Ala Val Asn Leu Arg Glu Arg Leu Lys Pro Met
305                 310                 315                 320

Pro Arg His Tyr Leu Gly Asn Leu Val Thr Thr Val Trp Val Ser His
                325                 330                 335

His Arg Pro Ala Val Lys Asp Leu Glu Thr Met Val Leu Pro Val Pro
            340                 345                 350

Ala Cys Asn Arg His Glu Ile Asp Arg Asp Leu Leu Trp Ile Thr
        355                 360                 365

His Val Ala Phe Arg Ile Arg Leu Gly Leu Asn Ala Ile Asn Glu Glu
```

```
                   370                 375                 380
His Ile Arg Gly Leu Ile His Tyr Leu His Ser Gln Asp Asp Trp Glu
385                 390                 395                 400

Gln Ile Gly Ile His Phe Thr Asp Pro Ile Phe Ile Ser Ser Trp Arg
                405                 410                 415

His Leu Lys Val Tyr Glu Leu Asp Phe Gly Pro Thr Ile Gly His Ala
                420                 425                 430

Glu His Phe Glu Met Asp Val Gly Thr Thr Asp Gly Val Cys Val Val
            435                 440                 445

Met Pro Ala Asn Thr Arg Ala Val Gly Lys Thr Lys Lys Ala Pro Trp
            450                 455                 460

Asp Ile Arg Ile Val Leu Asn Pro Glu Val Leu Gln Ala Leu Ile Ala
465                 470                 475                 480

Ser Ala Ile Phe Gly Trp Ala Met Val Lys Asp Ala Ser Thr
                485                 490

<210> SEQ ID NO 18
<211> LENGTH: 1548
<212> TYPE: DNA
<213> ORGANISM: Artificial Sequence
<220> FEATURE:
<223> OTHER INFORMATION: GAO81666.1 codon optimized for its expression
      in S. cerevisiae
<220> FEATURE:
<221> NAME/KEY: CDS
<222> LOCATION: (1)..(1548)

<400> SEQUENCE: 18 atg gaa gaa cat acc aga tcc ttt gag cca ttt gac ctg gcc tgc tta       48
Met Glu Glu His Thr Arg Ser Phe Glu Pro Phe Asp Leu Ala Cys Leu
1               5                   10                  15 gat cat act gtg ggg ccg gtt ttc atg aat ttc ttc tta agt ttc aag       96
Asp His Thr Val Gly Pro Val Phe Met Asn Phe Phe Leu Ser Phe Lys
                20                  25                  30 cct gcc aag atc gaa gag agt ctt atc tca att gaa gaa ggt gta act      144
Pro Ala Lys Ile Glu Glu Ser Leu Ile Ser Ile Glu Glu Gly Val Thr
            35                  40                  45 agg tta gtc aac aga ctg cca ttc ctg gcc ggt gac gtt gtt aat tct      192
Arg Leu Val Asn Arg Leu Pro Phe Leu Ala Gly Asp Val Val Asn Ser
        50                  55                  60 gaa aac gta gac ggt cgt gtt aat gta atg agg att cag cca agc tcg      240
Glu Asn Val Asp Gly Arg Val Asn Val Met Arg Ile Gln Pro Ser Ser
65                  70                  75                  80 aca ttg att aga gag att ccc atg cta cac aca aag cac cat cct cat      288
Thr Leu Ile Arg Glu Ile Pro Met Leu His Thr Lys His His Pro His
                85                  90                  95 cat att ttg ccg aat aca cct aga cag att aac cca ggg tcc gac cag      336
His Ile Leu Pro Asn Thr Pro Arg Gln Ile Asn Pro Gly Ser Asp Gln
                100                 105                 110 gat caa agg ttt gct ccc ttg gac gat tcg tac gta cca cca gtg tct      384
Asp Gln Arg Phe Ala Pro Leu Asp Asp Ser Tyr Val Pro Pro Val Ser
            115                 120                 125 tta tta cct ctt gct ccg ggc cca agg ccc gta gta aga ttc caa act      432
Leu Leu Pro Leu Ala Pro Gly Pro Arg Pro Val Val Arg Phe Gln Thr
        130                 135                 140 aat gtt gta att gac ggg att gtg ctt gca ctt ggg ttc cac cac tca      480
Asn Val Val Ile Asp Gly Ile Val Leu Ala Leu Gly Phe His His Ser
145                 150                 155                 160 gta ttt gat gct acc gga gtg ggt ttg ttg atc gaa atg ttg gcc aca      528
Val Phe Asp Ala Thr Gly Val Gly Leu Leu Ile Glu Met Leu Ala Thr
```

-continued

```
                       165                 170                 175
tgt tgt tca agc gat tgt cct gcc cta tca tcc cat att gaa ctg gaa      576
Cys Cys Ser Ser Asp Cys Pro Ala Leu Ser Ser His Ile Glu Leu Glu
            180                 185                 190 gaa gaa ata agg cta agg cgt tct gtg gac aag ata ggt aac ggc gct      624
Glu Glu Ile Arg Leu Arg Arg Ser Val Asp Lys Ile Gly Asn Gly Ala
        195                 200                 205 act gat tta gca tcc caa aga gat gaa gtt cag gac cca aat ggc agt      672
Thr Asp Leu Ala Ser Gln Arg Asp Glu Val Gln Asp Pro Asn Gly Ser
    210                 215                 220 atc act gag tcc cca gct cat gtg cct atg ggt gac agt agc tgg gta      720
Ile Thr Glu Ser Pro Ala His Val Pro Met Gly Asp Ser Ser Trp Val
225                 230                 235                 240 ccc cct aaa cta tct gtt tac tcc ttt aat tta tcg gct gcc ggt ttg      768
Pro Pro Lys Leu Ser Val Tyr Ser Phe Asn Leu Ser Ala Ala Gly Leu
                245                 250                 255 gct cat ttg aag aca gcc tgt aac aag tta ttg ccc gct atc cat gcg      816
Ala His Leu Lys Thr Ala Cys Asn Lys Leu Leu Pro Ala Ile His Ala
            260                 265                 270 agt caa aat ggt tca cca caa agt gcg gaa tca gaa ggt gag aaa tta      864
Ser Gln Asn Gly Ser Pro Gln Ser Ala Glu Ser Glu Gly Glu Lys Leu
        275                 280                 285 cag caa gaa ttc gtt tcg acg aat gat gtt cta acg gct ttg ttg gct      912
Gln Gln Glu Phe Val Ser Thr Asn Asp Val Leu Thr Ala Leu Leu Ala
    290                 295                 300 act tcc att cac caa gcg agg tct aga gtt act gaa acg gaa tta gtt      960
Thr Ser Ile His Gln Ala Arg Ser Arg Val Thr Glu Thr Glu Leu Val
305                 310                 315                 320 ccg aca aaa gcg aaa ctt gcg atg gcc gtt aat ttg agg gaa agg gcc     1008
Pro Thr Lys Ala Lys Leu Ala Met Ala Val Asn Leu Arg Glu Arg Ala
                325                 330                 335 agt tcg tta ccc aag act tat ttg ggg aac tcg cta aca gtt aca gaa     1056
Ser Ser Leu Pro Lys Thr Tyr Leu Gly Asn Ser Leu Thr Val Thr Glu
            340                 345                 350 gct ttt gtg tat tct tta gct gct acc gac ggt ttc gat ggt gtc ccc     1104
Ala Phe Val Tyr Ser Leu Ala Ala Thr Asp Gly Phe Asp Gly Val Pro
        355                 360                 365 gag aga cat tat cat cct gac ttg cgt aac gcc ttg cta tta gaa att     1152
Glu Arg His Tyr His Pro Asp Leu Arg Asn Ala Leu Leu Leu Glu Ile
    370                 375                 380 gct aga gtt gca ttg caa ttg aga aaa ggg ctg gca gcg ata gat gac     1200
Ala Arg Val Ala Leu Gln Leu Arg Lys Gly Leu Ala Ala Ile Asp Asp
385                 390                 395                 400 gcg tat ttt agg caa ttt gtg tct aga ttg agg gct aat cta gac tgg     1248
Ala Tyr Phe Arg Gln Phe Val Ser Arg Leu Arg Ala Asn Leu Asp Trp
                405                 410                 415 tca cag tta ggt gca aac ctg cct gac act atg gtg tca agc tgg aga     1296
Ser Gln Leu Gly Ala Asn Leu Pro Asp Thr Met Val Ser Ser Trp Arg
            420                 425                 430 cat ttg aaa gta tat cgt tta gac ttc ggt gct aga ttg ggg aga gtt     1344
His Leu Lys Val Tyr Arg Leu Asp Phe Gly Ala Arg Leu Gly Arg Val
        435                 440                 445 gta gag ttc cat cca caa acc gct ttg gtt gac ggt att tgt atc atc     1392
Val Glu Phe His Pro Gln Thr Ala Leu Val Asp Gly Ile Cys Ile Ile
    450                 455                 460 caa cct gaa agg ata gcc cat gag gat gat tca gct gat atg gct cca     1440
Gln Pro Glu Arg Ile Ala His Glu Asp Asp Ser Ala Asp Met Ala Pro
465                 470                 475                 480 gaa tct ggg tgg gaa gtt tgt gta aca tta caa agc gat gcc atg gag     1488
Glu Ser Gly Trp Glu Val Cys Val Thr Leu Gln Ser Asp Ala Met Glu
```

```
Glu Ser Gly Trp Glu Val Cys Val Thr Leu Gln Ser Asp Ala Met Glu
                485                 490                 495 tgc ttc tta aga ggt ggg ttg ttc aca agt ctt tct caa ggt gca att    1536
Cys Phe Leu Arg Gly Gly Leu Phe Thr Ser Leu Ser Gln Gly Ala Ile
            500                 505                 510 aga aga gtt taa                                                    1548
Arg Arg Val
        515

<210> SEQ ID NO 19
<211> LENGTH: 515
<212> TYPE: PRT
<213> ORGANISM: Artificial Sequence
<220> FEATURE:
<223> OTHER INFORMATION: Synthetic Construct

<400> SEQUENCE: 19

Met Glu Glu His Thr Arg Ser Phe Glu Pro Phe Asp Leu Ala Cys Leu
1               5                   10                  15

Asp His Thr Val Gly Pro Val Phe Met Asn Phe Leu Ser Phe Lys
            20                  25                  30

Pro Ala Lys Ile Glu Glu Ser Leu Ile Ser Ile Glu Glu Gly Val Thr
        35                  40                  45

Arg Leu Val Asn Arg Leu Pro Phe Leu Ala Gly Asp Val Val Asn Ser
    50                  55                  60

Glu Asn Val Asp Gly Arg Val Asn Val Met Arg Ile Gln Pro Ser Ser
65                  70                  75                  80

Thr Leu Ile Arg Glu Ile Pro Met Leu His Thr Lys His His Pro His
                85                  90                  95

His Ile Leu Pro Asn Thr Pro Arg Gln Ile Asn Pro Gly Ser Asp Gln
            100                 105                 110

Asp Gln Arg Phe Ala Pro Leu Asp Asp Ser Tyr Val Pro Pro Val Ser
        115                 120                 125

Leu Leu Pro Leu Ala Pro Gly Pro Arg Pro Val Val Arg Phe Gln Thr
    130                 135                 140

Asn Val Val Ile Asp Gly Ile Val Leu Ala Leu Gly Phe His His Ser
145                 150                 155                 160

Val Phe Asp Ala Thr Gly Val Gly Leu Leu Ile Glu Met Leu Ala Thr
                165                 170                 175

Cys Cys Ser Ser Asp Cys Pro Ala Leu Ser Ser His Ile Glu Leu Glu
            180                 185                 190

Glu Glu Ile Arg Leu Arg Arg Ser Val Asp Lys Ile Gly Asn Gly Ala
        195                 200                 205

Thr Asp Leu Ala Ser Gln Arg Asp Glu Val Gln Asp Pro Asn Gly Ser
    210                 215                 220

Ile Thr Glu Ser Pro Ala His Val Pro Met Gly Asp Ser Ser Trp Val
225                 230                 235                 240

Pro Pro Lys Leu Ser Val Tyr Ser Phe Asn Leu Ser Ala Ala Gly Leu
                245                 250                 255

Ala His Leu Lys Thr Ala Cys Asn Lys Leu Leu Pro Ala Ile His Ala
            260                 265                 270

Ser Gln Asn Gly Ser Pro Gln Ser Ala Glu Ser Glu Gly Glu Lys Leu
        275                 280                 285

Gln Gln Glu Phe Val Ser Thr Asn Asp Val Leu Thr Ala Leu Leu Ala
    290                 295                 300

Thr Ser Ile His Gln Ala Arg Ser Arg Val Thr Glu Thr Glu Leu Val
```

```
                    305                 310                 315                 320
        Pro Thr Lys Ala Lys Leu Ala Met Ala Val Asn Leu Arg Glu Arg Ala
                        325                 330                 335

Ser Ser Leu Pro Lys Thr Tyr Leu Gly Asn Ser Leu Thr Val Thr Glu
                        340                 345                 350

Ala Phe Val Tyr Ser Leu Ala Ala Thr Asp Gly Phe Asp Gly Val Pro
                        355                 360                 365

Glu Arg His Tyr His Pro Asp Leu Arg Asn Ala Leu Leu Leu Glu Ile
                        370                 375                 380

Ala Arg Val Ala Leu Gln Leu Arg Lys Gly Leu Ala Ala Ile Asp Asp
        385                 390                 395                 400

Ala Tyr Phe Arg Gln Phe Val Ser Arg Leu Arg Ala Asn Leu Asp Trp
                        405                 410                 415

Ser Gln Leu Gly Ala Asn Leu Pro Asp Thr Met Val Ser Ser Trp Arg
                        420                 425                 430

His Leu Lys Val Tyr Arg Leu Asp Phe Gly Ala Arg Leu Gly Arg Val
                        435                 440                 445

Val Glu Phe His Pro Gln Thr Ala Leu Val Asp Gly Ile Cys Ile Ile
                        450                 455                 460

Gln Pro Glu Arg Ile Ala His Glu Asp Asp Ser Ala Asp Met Ala Pro
        465                 470                 475                 480

Glu Ser Gly Trp Glu Val Cys Val Thr Leu Gln Ser Asp Ala Met Glu
                        485                 490                 495

Cys Phe Leu Arg Gly Gly Leu Phe Thr Ser Leu Ser Gln Gly Ala Ile
                        500                 505                 510

Arg Arg Val
                515

<210> SEQ ID NO 20
<211> LENGTH: 1284
<212> TYPE: DNA
<213> ORGANISM: Artificial Sequence
<220> FEATURE:
<223> OTHER INFORMATION: CfACT1-6 DNA sequence codon optimized for its
      expression in S. cerevisiae
<220> FEATURE:
<221> NAME/KEY: CDS
<222> LOCATION: (1)..(1284)

<400> SEQUENCE: 20 atg aag gta gaa cgt ttc tca aga aag ttg ata aaa ccc cac acg cct        48
Met Lys Val Glu Arg Phe Ser Arg Lys Leu Ile Lys Pro His Thr Pro
1               5                   10                  15 act ccc gag aac tta aag aaa tat aaa ttg tct cta ttg gac aaa tgc        96
Thr Pro Glu Asn Leu Lys Lys Tyr Lys Leu Ser Leu Leu Asp Lys Cys
            20                  25                  30 ctt gga cac gac aac ttc gcg atc gtg ttg ttt tac gaa tct aaa cca       144
Leu Gly His Asp Asn Phe Ala Ile Val Leu Phe Tyr Glu Ser Lys Pro
        35                  40                  45 aga aat aag agt gag ctt gag gaa tcg tta gag aag gtc ttg gta gac       192
Arg Asn Lys Ser Glu Leu Glu Glu Ser Leu Glu Lys Val Leu Val Asp
    50                  55                  60 ttt tat ccc ttg gct ggg cgt cac acg atg aac gac cat att gtc gac       240
Phe Tyr Pro Leu Ala Gly Arg His Thr Met Asn Asp His Ile Val Asp
65                  70                  75                  80 tgc tcg gat gtc ggc gct gtc ttt gta gaa gcc gag gct tta gat gta       288
Cys Ser Asp Val Gly Ala Val Phe Val Glu Ala Glu Ala Leu Asp Val
                85                  90                  95
```

-continued

| | | |
|---|---|---|
| gag ttg act atg gat gag tta gtc aag aac atg gaa gct caa act ata<br>Glu Leu Thr Met Asp Glu Leu Val Lys Asn Met Glu Ala Gln Thr Ile<br>100          105              110 | 336 |
| cac cac ttg ttg cca aat cag tac ttc agt gca gat gct ccg aac ccg<br>His His Leu Leu Pro Asn Gln Tyr Phe Ser Ala Asp Ala Pro Asn Pro<br>        115              120              125 | 384 |
| ctg ctt tcc atc caa gtt acg cac ttt cct tcc ggt ggt ttg gct atc<br>Leu Leu Ser Ile Gln Val Thr His Phe Pro Ser Gly Gly Leu Ala Ile<br>130              135              140 | 432 |
| gga atc gca gtc tcg cac gct gta ttt gat ggt ttc tct ttg ggc gtg<br>Gly Ile Ala Val Ser His Ala Val Phe Asp Gly Phe Ser Leu Gly Val<br>145              150              155              160 | 480 |
| ttc gta gca gca tgg tca aag gcg acc atg aac ccg gat agg aaa atc<br>Phe Val Ala Ala Trp Ser Lys Ala Thr Met Asn Pro Asp Arg Lys Ile<br>            165              170              175 | 528 |
| aaa ata aca ccg tca ttc gac tta cca tca ctt ctg ccc tac aaa gac<br>Lys Ile Thr Pro Ser Phe Asp Leu Pro Ser Leu Leu Pro Tyr Lys Asp<br>        180              185              190 | 576 |
| gac aac ttt ggt ttg act gct gct gaa att gtc agc cag agc gag gac<br>Asp Asn Phe Gly Leu Thr Ala Ala Glu Ile Val Ser Gln Ser Glu Asp<br>    195              200              205 | 624 |
| atc gta gtt aag aga ttt atc ttc ggc aag gaa gcc atc acg agg ttg<br>Ile Val Val Lys Arg Phe Ile Phe Gly Lys Glu Ala Ile Thr Arg Leu<br>210              215              220 | 672 |
| aga agt aag ctt agt cca aat agg aac ggg aag aaa ata tcc agg gtt<br>Arg Ser Lys Leu Ser Pro Asn Arg Asn Gly Lys Lys Ile Ser Arg Val<br>225              230              235              240 | 720 |
| agg gtc gtt tgt gca gtc att gta aag gcc ttg atg gga ttg gag cgt<br>Arg Val Val Cys Ala Val Ile Val Lys Ala Leu Met Gly Leu Glu Arg<br>            245              250              255 | 768 |
| gcc aaa cac ggt aag acg cgt gat ttc tta att act caa tca att aac<br>Ala Lys His Gly Lys Thr Arg Asp Phe Leu Ile Thr Gln Ser Ile Asn<br>        260              265              270 | 816 |
| atg agg gag aga act aag gcg ccg ctg cag aaa cac gcc tgc ggc aac<br>Met Arg Glu Arg Thr Lys Ala Pro Leu Gln Lys His Ala Cys Gly Asn<br>    275              280              285 | 864 |
| tta gca gtc ttg agt tgc acg aga aga gta gag gcc gag gag atg atg<br>Leu Ala Val Leu Ser Cys Thr Arg Arg Val Glu Ala Glu Glu Met Met<br>290              295              300 | 912 |
| gag tta cag aac cta gtt aat ttg atc ggc gac agt acc gaa aag gac<br>Glu Leu Gln Asn Leu Val Asn Leu Ile Gly Asp Ser Thr Glu Lys Asp<br>305              310              315              320 | 960 |
| atc gcc gac ttt gca gaa tta tta tca cca gat caa gtg ggc aga gac<br>Ile Ala Asp Phe Ala Glu Leu Leu Ser Pro Asp Gln Val Gly Arg Asp<br>            325              330              335 | 1008 |
| att ata atc aag atg atg aag tca ttc atg cag ttc ttg gac aat gac<br>Ile Ile Ile Lys Met Met Lys Ser Phe Met Gln Phe Leu Asp Asn Asp<br>        340              345              350 | 1056 |
| att tac agc gtg tgc ttt acc gat tgg tca aag ttt gaa ttt tac gaa<br>Ile Tyr Ser Val Cys Phe Thr Asp Trp Ser Lys Phe Glu Phe Tyr Glu<br>    355              360              365 | 1104 |
| gcg gac ttc ggc ttc ggg aag ccg gtt tgg atg gca gca ggc cca cag<br>Ala Asp Phe Gly Phe Gly Lys Pro Val Trp Met Ala Ala Gly Pro Gln<br>370              375              380 | 1152 |
| aga ccc att atc tct act gca ata ttg atg tca gac agg gaa ggc gac<br>Arg Pro Ile Ile Ser Thr Ala Ile Leu Met Ser Asp Arg Glu Gly Asp<br>385              390              395              400 | 1200 |
| ggt atc gag gct tgg tta cat ttg aat aag aac gac atg ttg att ttc<br>Gly Ile Glu Ala Trp Leu His Leu Asn Lys Asn Asp Met Leu Ile Phe<br>            405              410              415 | 1248 |

```
         gaa caa gac gag gaa atc aag tta ttc act aca taa              1284
         Glu Gln Asp Glu Glu Ile Lys Leu Phe Thr Thr
                     420                 425

<210> SEQ ID NO 21
<211> LENGTH: 427
<212> TYPE: PRT
<213> ORGANISM: Artificial Sequence
<220> FEATURE:
<223> OTHER INFORMATION: Synthetic Construct

<400> SEQUENCE: 21

Met Lys Val Glu Arg Phe Ser Arg Lys Leu Ile Lys Pro His Thr Pro
1               5                   10                  15

Thr Pro Glu Asn Leu Lys Lys Tyr Lys Leu Ser Leu Leu Asp Lys Cys
            20                  25                  30

Leu Gly His Asp Asn Phe Ala Ile Val Leu Phe Tyr Glu Ser Lys Pro
        35                  40                  45

Arg Asn Lys Ser Glu Leu Glu Ser Leu Glu Lys Val Leu Val Asp
    50                  55                  60

Phe Tyr Pro Leu Ala Gly Arg His Thr Met Asn Asp His Ile Val Asp
65                  70                  75                  80

Cys Ser Asp Val Gly Ala Val Phe Val Glu Ala Glu Ala Leu Asp Val
                85                  90                  95

Glu Leu Thr Met Asp Glu Leu Val Lys Asn Met Glu Ala Gln Thr Ile
            100                 105                 110

His His Leu Leu Pro Asn Gln Tyr Phe Ser Ala Asp Ala Pro Asn Pro
        115                 120                 125

Leu Leu Ser Ile Gln Val Thr His Phe Pro Ser Gly Gly Leu Ala Ile
    130                 135                 140

Gly Ile Ala Val Ser His Ala Val Phe Asp Gly Phe Ser Leu Gly Val
145                 150                 155                 160

Phe Val Ala Ala Trp Ser Lys Ala Thr Met Asn Pro Asp Arg Lys Ile
                165                 170                 175

Lys Ile Thr Pro Ser Phe Asp Leu Pro Ser Leu Leu Pro Tyr Lys Asp
            180                 185                 190

Asp Asn Phe Gly Leu Thr Ala Ala Glu Ile Val Ser Gln Ser Glu Asp
        195                 200                 205

Ile Val Val Lys Arg Phe Ile Phe Gly Lys Glu Ala Ile Thr Arg Leu
    210                 215                 220

Arg Ser Lys Leu Ser Pro Asn Arg Asn Gly Lys Lys Ile Ser Arg Val
225                 230                 235                 240

Arg Val Val Cys Ala Val Ile Val Lys Ala Leu Met Gly Leu Glu Arg
                245                 250                 255

Ala Lys His Gly Lys Thr Arg Asp Phe Leu Ile Thr Gln Ser Ile Asn
            260                 265                 270

Met Arg Glu Arg Thr Lys Ala Pro Leu Gln Lys His Ala Cys Gly Asn
        275                 280                 285

Leu Ala Val Leu Ser Cys Thr Arg Arg Val Glu Ala Glu Met Met
    290                 295                 300

Glu Leu Gln Asn Leu Val Asn Leu Ile Gly Asp Ser Thr Glu Lys Asp
305                 310                 315                 320

Ile Ala Asp Phe Ala Glu Leu Leu Ser Pro Asp Gln Val Gly Arg Asp
                325                 330                 335

Ile Ile Ile Lys Met Met Lys Ser Phe Met Gln Phe Leu Asp Asn Asp
```

```
                    340                 345                 350
Ile Tyr Ser Val Cys Phe Thr Asp Trp Ser Lys Phe Glu Phe Tyr Glu
                355                 360                 365

Ala Asp Phe Gly Phe Gly Lys Pro Val Trp Met Ala Ala Gly Pro Gln
            370                 375                 380

Arg Pro Ile Ile Ser Thr Ala Ile Leu Met Ser Asp Arg Glu Gly Asp
385                 390                 395                 400

Gly Ile Glu Ala Trp Leu His Leu Asn Lys Asn Asp Met Leu Ile Phe
                405                 410                 415

Glu Gln Asp Glu Glu Ile Lys Leu Phe Thr Thr
            420                 425

<210> SEQ ID NO 22
<211> LENGTH: 1272
<212> TYPE: DNA
<213> ORGANISM: Artificial Sequence
<220> FEATURE:
<223> OTHER INFORMATION: CfACT1-8 codon optimized for its expression in
      S. cerevisiae
<220> FEATURE:
<221> NAME/KEY: CDS
<222> LOCATION: (1)..(1272)

<400> SEQUENCE: 22 atg aaa gtc gaa agg att tca cgt aaa ttc atc aag cca tat aca cct      48
Met Lys Val Glu Arg Ile Ser Arg Lys Phe Ile Lys Pro Tyr Thr Pro
1               5                   10                  15 aca cca cag aac ctt aag aag tac aag cta tcc ttg ctg gat aaa tgc      96
Thr Pro Gln Asn Leu Lys Lys Tyr Lys Leu Ser Leu Leu Asp Lys Cys
                20                  25                  30 atg gga cac atg gac ttc gct gta gta ttg ttt tac gaa tca aag cca     144
Met Gly His Met Asp Phe Ala Val Val Leu Phe Tyr Glu Ser Lys Pro
            35                  40                  45 aga aac aag aat gag ctg gaa gaa tca cta gag aaa gtg tta gtc gat     192
Arg Asn Lys Asn Glu Leu Glu Glu Ser Leu Glu Lys Val Leu Val Asp
        50                  55                  60 ttc tat cca ttg gca ggc agg tat acc atg aac gac cac att gtc gat     240
Phe Tyr Pro Leu Ala Gly Arg Tyr Thr Met Asn Asp His Ile Val Asp
65                  70                  75                  80 tgc agc gat gag ggc gcc gtt ttc gtt gag gca gag gcc cct aat gtt     288
Cys Ser Asp Glu Gly Ala Val Phe Val Glu Ala Glu Ala Pro Asn Val
                85                  90                  95 gag ctt aca gtg gac cag ttg gtt aag aac atg gaa gcc cag aca atc     336
Glu Leu Thr Val Asp Gln Leu Val Lys Asn Met Glu Ala Gln Thr Ile
            100                 105                 110 cac gac ttc tta cca gac caa tat ttt cct gct gac gca cca aat ccg     384
His Asp Phe Leu Pro Asp Gln Tyr Phe Pro Ala Asp Ala Pro Asn Pro
        115                 120                 125 ttg cta agt att caa gta acg cac ttc cct tgt ggt ggt tta gct atc     432
Leu Leu Ser Ile Gln Val Thr His Phe Pro Cys Gly Gly Leu Ala Ile
    130                 135                 140 ggg att gtt gtt agt cac gcg gtc ttt gat gga ttc tca ttg ggc gta     480
Gly Ile Val Val Ser His Ala Val Phe Asp Gly Phe Ser Leu Gly Val
145                 150                 155                 160 ttc tta gcc gcc tgg agc aaa gct acc atg aac cct gag agg aag atc     528
Phe Leu Ala Ala Trp Ser Lys Ala Thr Met Asn Pro Glu Arg Lys Ile
                165                 170                 175 gaa atc acc cct tcc ttc gat ttg cct agt ctt ctg ccc tac aag gat     576
Glu Ile Thr Pro Ser Phe Asp Leu Pro Ser Leu Leu Pro Tyr Lys Asp
            180                 185                 190
```

```
gaa tct ttc ggt tta aat ttt agc gaa att gtc aaa gct gag aat atc    624
Glu Ser Phe Gly Leu Asn Phe Ser Glu Ile Val Lys Ala Glu Asn Ile
        195                 200                 205 gta gtt aaa cgt ttg aat ttc ggg aaa gag gct att acg cgt ttg agg    672
Val Val Lys Arg Leu Asn Phe Gly Lys Glu Ala Ile Thr Arg Leu Arg
    210                 215                 220 tcc aag ctg tct cct aac cag aat ggt aaa acc att tcc aga gtg agg    720
Ser Lys Leu Ser Pro Asn Gln Asn Gly Lys Thr Ile Ser Arg Val Arg
225                 230                 235                 240 gta gtc tgc gcg gtg ata gtt aag gcg ttg atg gga ctg gag aga gca    768
Val Val Cys Ala Val Ile Val Lys Ala Leu Met Gly Leu Glu Arg Ala
                245                 250                 255 aag act aga gac ttt atg ata tgt cag ggg atc aac atg aga gag agg    816
Lys Thr Arg Asp Phe Met Ile Cys Gln Gly Ile Asn Met Arg Glu Arg
            260                 265                 270 acg aag gcg ccc ctg cag aag cat gcg tgt ggc aac cta gca gtt tcg    864
Thr Lys Ala Pro Leu Gln Lys His Ala Cys Gly Asn Leu Ala Val Ser
        275                 280                 285 tct tac act aga agg gta gcg gca gcg gaa gca gaa gaa ctg cag tcc    912
Ser Tyr Thr Arg Arg Val Ala Ala Ala Glu Ala Glu Glu Leu Gln Ser
    290                 295                 300 tta gtg aat ttg atc ggg gac tct atc gaa aag tca atc gca gac tac    960
Leu Val Asn Leu Ile Gly Asp Ser Ile Glu Lys Ser Ile Ala Asp Tyr
305                 310                 315                 320 gct gat ata ctt tcg agt gat caa gat ggg aga cac atc att tcc act   1008
Ala Asp Ile Leu Ser Ser Asp Gln Asp Gly Arg His Ile Ile Ser Thr
                325                 330                 335 atg atg aag agc ttt atg cag ttt gct gca cct gat ata aaa gcc att   1056
Met Met Lys Ser Phe Met Gln Phe Ala Ala Pro Asp Ile Lys Ala Ile
            340                 345                 350 tca ttt acc gac tgg tca aag ttc ggc ttt tac caa gta gat ttt ggt   1104
Ser Phe Thr Asp Trp Ser Lys Phe Gly Phe Tyr Gln Val Asp Phe Gly
        355                 360                 365 ttt ggt aaa cca gtt tgg acc ggc gtc cgt cca gaa cgt cca atc ttc   1152
Phe Gly Lys Pro Val Trp Thr Gly Val Arg Pro Glu Arg Pro Ile Phe
    370                 375                 380 tca gcc gcg ata ttg atg agt aac agg gaa ggc gat ggc atc gag gct   1200
Ser Ala Ala Ile Leu Met Ser Asn Arg Glu Gly Asp Gly Ile Glu Ala
385                 390                 395                 400 tgg ctt cat ttg gac aag aac gat atg cta ata ttt gag caa gac gaa   1248
Trp Leu His Leu Asp Lys Asn Asp Met Leu Ile Phe Glu Gln Asp Glu
                405                 410                 415 gaa att aag ttg ttg ata acg taa                                   1272
Glu Ile Lys Leu Leu Ile Thr
            420

<210> SEQ ID NO 23
<211> LENGTH: 423
<212> TYPE: PRT
<213> ORGANISM: Artificial Sequence
<220> FEATURE:
<223> OTHER INFORMATION: Synthetic Construct

<400> SEQUENCE: 23

Met Lys Val Glu Arg Ile Ser Arg Lys Phe Ile Lys Pro Tyr Thr Pro
1               5                   10                  15

Thr Pro Gln Asn Leu Lys Lys Tyr Lys Leu Ser Leu Leu Asp Lys Cys
            20                  25                  30

Met Gly His Met Asp Phe Ala Val Val Leu Phe Tyr Glu Ser Lys Pro
        35                  40                  45
```

Arg Asn Lys Asn Glu Leu Glu Ser Leu Glu Lys Val Leu Val Asp
50                  55                  60

Phe Tyr Pro Leu Ala Gly Arg Tyr Thr Met Asn Asp His Ile Val Asp
65                  70                  75                  80

Cys Ser Asp Glu Gly Ala Val Phe Val Glu Ala Glu Ala Pro Asn Val
                85                  90                  95

Glu Leu Thr Val Asp Gln Leu Val Lys Asn Met Glu Ala Gln Thr Ile
            100                 105                 110

His Asp Phe Leu Pro Asp Gln Tyr Phe Pro Ala Asp Ala Pro Asn Pro
            115                 120                 125

Leu Leu Ser Ile Gln Val Thr His Phe Pro Cys Gly Gly Leu Ala Ile
130                 135                 140

Gly Ile Val Val Ser His Ala Val Phe Asp Gly Phe Ser Leu Gly Val
145                 150                 155                 160

Phe Leu Ala Ala Trp Ser Lys Ala Thr Met Asn Pro Glu Arg Lys Ile
                165                 170                 175

Glu Ile Thr Pro Ser Phe Asp Leu Pro Ser Leu Leu Pro Tyr Lys Asp
            180                 185                 190

Glu Ser Phe Gly Leu Asn Phe Ser Glu Ile Val Lys Ala Glu Asn Ile
            195                 200                 205

Val Val Lys Arg Leu Asn Phe Gly Lys Glu Ala Ile Thr Arg Leu Arg
210                 215                 220

Ser Lys Leu Ser Pro Asn Gln Asn Gly Lys Thr Ile Ser Arg Val Arg
225                 230                 235                 240

Val Val Cys Ala Val Ile Val Lys Ala Leu Met Gly Leu Glu Arg Ala
                245                 250                 255

Lys Thr Arg Asp Phe Met Ile Cys Gln Gly Ile Asn Met Arg Glu Arg
            260                 265                 270

Thr Lys Ala Pro Leu Gln Lys His Ala Cys Gly Asn Leu Ala Val Ser
            275                 280                 285

Ser Tyr Thr Arg Arg Val Ala Ala Glu Ala Glu Leu Gln Ser
290                 295                 300

Leu Val Asn Leu Ile Gly Asp Ser Ile Glu Lys Ser Ile Ala Asp Tyr
305                 310                 315                 320

Ala Asp Ile Leu Ser Ser Asp Gln Asp Gly Arg His Ile Ile Ser Thr
                325                 330                 335

Met Met Lys Ser Phe Met Gln Phe Ala Ala Pro Asp Ile Lys Ala Ile
            340                 345                 350

Ser Phe Thr Asp Trp Ser Lys Phe Gly Phe Tyr Gln Val Asp Phe Gly
            355                 360                 365

Phe Gly Lys Pro Val Trp Thr Gly Val Arg Pro Glu Arg Pro Ile Phe
370                 375                 380

Ser Ala Ala Ile Leu Met Ser Asn Arg Glu Gly Asp Gly Ile Glu Ala
385                 390                 395                 400

Trp Leu His Leu Asp Lys Asn Asp Met Leu Ile Phe Glu Gln Asp Glu
                405                 410                 415

Glu Ile Lys Leu Leu Ile Thr
            420

<210> SEQ ID NO 24
<211> LENGTH: 654
<212> TYPE: DNA
<213> ORGANISM: Artificial Sequence
<220> FEATURE:
<223> OTHER INFORMATION: OAH94415.1 codon optimized for its expression in S. cerevisiae
<220> FEATURE:
<221> NAME/KEY: CDS
<222> LOCATION: (1)..(654)

<400> SEQUENCE: 24

```
atg gat acc aag agg gtc ggt tat aca gtc gtt gat ttg agt cag tgg      48
Met Asp Thr Lys Arg Val Gly Tyr Thr Val Val Asp Leu Ser Gln Trp
1               5                   10                  15 ggc aga aaa gaa cac ttc gaa gca ttc cag agc ttc gcc cag tgc acc      96
Gly Arg Lys Glu His Phe Glu Ala Phe Gln Ser Phe Ala Gln Cys Thr
                20                  25                  30 ttt tcc cag act gtt caa tta gac ata act tcc ctg ctg aag act gtc     144
Phe Ser Gln Thr Val Gln Leu Asp Ile Thr Ser Leu Leu Lys Thr Val
            35                  40                  45 aag cag aac gga tat aaa ttc tac ccg acc ttt atc tac ata ata agc     192
Lys Gln Asn Gly Tyr Lys Phe Tyr Pro Thr Phe Ile Tyr Ile Ile Ser
        50                  55                  60 cgt tta gtg aac aag cat gcc gaa ttc cgt atg gcc atg aag gat ggt     240
Arg Leu Val Asn Lys His Ala Glu Phe Arg Met Ala Met Lys Asp Gly
65                  70                  75                  80 gaa ctg gta att tgg gac tcc gta aac cct ggt tac aca atc ttt cac     288
Glu Leu Val Ile Trp Asp Ser Val Asn Pro Gly Tyr Thr Ile Phe His
                85                  90                  95 gaa cag acc gaa aca ttt tca tct ctg tgg agc tat tac cac aag gac     336
Glu Gln Thr Glu Thr Phe Ser Ser Leu Trp Ser Tyr Tyr His Lys Asp
                100                 105                 110 atc aat cag ttt ctt aaa acg tat tct gaa gac atc gct cag tac ggg     384
Ile Asn Gln Phe Leu Lys Thr Tyr Ser Glu Asp Ile Ala Gln Tyr Gly
            115                 120                 125 gac gat ctg gcg tac ttc ccc aag gag ttt att gaa aat atg ttc ttc     432
Asp Asp Leu Ala Tyr Phe Pro Lys Glu Phe Ile Glu Asn Met Phe Phe
        130                 135                 140 gtg tca gcg aac cca tgg gtg agc ttc aca agt ttc aac tta aac gtg     480
Val Ser Ala Asn Pro Trp Val Ser Phe Thr Ser Phe Asn Leu Asn Val
145                 150                 155                 160 gcc aat att aat aac ttc ttc gca ccg gtc ttt aca atc ggt aaa tac     528
Ala Asn Ile Asn Asn Phe Phe Ala Pro Val Phe Thr Ile Gly Lys Tyr
                165                 170                 175 tac acg cag ggc gac aag gtg ttg atg ccg tta gct att cag gtc cat     576
Tyr Thr Gln Gly Asp Lys Val Leu Met Pro Leu Ala Ile Gln Val His
                180                 185                 190 cat gca gtc tgc gac ggg ttt cat gtc ggc agg tta ttg aac gaa att     624
His Ala Val Cys Asp Gly Phe His Val Gly Arg Leu Leu Asn Glu Ile
            195                 200                 205 cag cag tac tgc gat gag gga tgc aag taa                             654
Gln Gln Tyr Cys Asp Glu Gly Cys Lys
        210                 215
```

<210> SEQ ID NO 25
<211> LENGTH: 217
<212> TYPE: PRT
<213> ORGANISM: Artificial Sequence
<220> FEATURE:
<223> OTHER INFORMATION: Synthetic Construct

<400> SEQUENCE: 25

```
Met Asp Thr Lys Arg Val Gly Tyr Thr Val Val Asp Leu Ser Gln Trp
1               5                   10                  15

Gly Arg Lys Glu His Phe Glu Ala Phe Gln Ser Phe Ala Gln Cys Thr
                20                  25                  30
```

```
Phe Ser Gln Thr Val Gln Leu Asp Ile Thr Ser Leu Leu Lys Thr Val
         35                  40                  45

Lys Gln Asn Gly Tyr Lys Phe Tyr Pro Thr Phe Ile Tyr Ile Ile Ser
 50                  55                  60

Arg Leu Val Asn Lys His Ala Glu Phe Arg Met Ala Met Lys Asp Gly
 65                  70                  75                  80

Glu Leu Val Ile Trp Asp Ser Val Asn Pro Gly Tyr Thr Ile Phe His
                 85                  90                  95

Glu Gln Thr Glu Thr Phe Ser Ser Leu Trp Ser Tyr Tyr His Lys Asp
            100                 105                 110

Ile Asn Gln Phe Leu Lys Thr Tyr Ser Glu Asp Ile Ala Gln Tyr Gly
        115                 120                 125

Asp Asp Leu Ala Tyr Phe Pro Lys Glu Phe Ile Glu Asn Met Phe Phe
130                 135                 140

Val Ser Ala Asn Pro Trp Val Ser Phe Thr Ser Phe Asn Leu Asn Val
145                 150                 155                 160

Ala Asn Ile Asn Asn Phe Phe Ala Pro Val Phe Thr Ile Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Leu Leu Asn Glu Ile
        195                 200                 205

Gln Gln Tyr Cys Asp Glu Gly Cys Lys
    210                 215

<210> SEQ ID NO 26
<211> LENGTH: 1755
<212> TYPE: DNA
<213> ORGANISM: Dryopteris fragrans
<220> FEATURE:
<221> NAME/KEY: CDS
<222> LOCATION: (1)..(1755)

<400> SEQUENCE: 26 atg gag ttc tct gcc tct gct cct cct cct agg cta gcc agt gtc ata      48
Met Glu Phe Ser Ala Ser Ala Pro Pro Pro Arg Leu Ala Ser Val Ile
 1               5                  10                  15 ata ttg gag cct ctc ggc ttc ctc ctc aca cca cac tac tcc tct cag      96
Ile Leu Glu Pro Leu Gly Phe Leu Leu Thr Pro His Tyr Ser Ser Gln
             20                  25                  30 ctt ccc aaa aag ctg ctc cgt cgc ctg ttg tgc act aga atc tgg cac     144
Leu Pro Lys Lys Leu Leu Arg Arg Leu Leu Cys Thr Arg Ile Trp His
         35                  40                  45 agg tat cag cga ggc cgc ctt cgc ctg cgt gac gct gct atg ctg ctc     192
Arg Tyr Gln Arg Gly Arg Leu Arg Leu Arg Asp Ala Ala Met Leu Leu
 50                  55                  60 gcc cag ctc cca ttc cta gct gtg tct gat cac ccc tgg gct ctg gac     240
Ala Gln Leu Pro Phe Leu Ala Val Ser Asp His Pro Trp Ala Leu Asp
 65                  70                  75                  80 aat ctc gca agc ctg ctc cgc ccc aca gct gtg cgt gcg gtg cca tgg     288
Asn Leu Ala Ser Leu Leu Arg Pro Thr Ala Val Arg Ala Val Pro Trp
                 85                  90                  95 atg ctg ctg ctc gac ttc cta cga gac gag ctc cat ctg aag gta         336
Met Leu Leu Leu Asp Phe Leu Arg Asp Glu Leu His Leu Lys Val
            100                 105                 110 gtc tgc gcg acc aac tcc tcc cca gaa gag ctg caa gag ctg cgc cac     384
Val Cys Ala Thr Asn Ser Ser Pro Glu Glu Leu Gln Glu Leu Arg His
        115                 120                 125
```

```
cag ttt ccg gcc ctc ttt gcc aag gtc gat gcc acc gtt tct tca ggc       432
Gln Phe Pro Ala Leu Phe Ala Lys Val Asp Ala Thr Val Ser Ser Gly
    130             135                 140 gag gag ggc gtg ggc aag ccg tcc gtg cgc ttc ctg cag gct gcg ttg       480
Glu Glu Gly Val Gly Lys Pro Ser Val Arg Phe Leu Gln Ala Ala Leu
145                 150                 155                 160 gac aaa gcc ggt gtc cac gcg cag caa acc ttg tat ctt gac tct ttt       528
Asp Lys Ala Gly Val His Ala Gln Gln Thr Leu Tyr Leu Asp Ser Phe
                165                 170                 175 gac agc ttg gag acc atc atg gct gca cgc tct ctt ggc atg cat gca       576
Asp Ser Leu Glu Thr Ile Met Ala Ala Arg Ser Leu Gly Met His Ala
            180                 185                 190 cta tct gta gag cca tgc cac att gat gag ctc acc gcc agg gcc tct       624
Leu Ser Val Glu Pro Cys His Ile Asp Glu Leu Thr Ala Arg Ala Ser
        195                 200                 205 tcc ggc cag cta aga gat gca cag ctt ata agg cgt att gtg tgc gcc       672
Ser Gly Gln Leu Arg Asp Ala Gln Leu Ile Arg Arg Ile Val Cys Ala
210                 215                 220 atg cac ggg cca gca gta tct gca gtt gtg tcg ggc agt atc aca tcg       720
Met His Gly Pro Ala Val Ser Ala Val Val Ser Gly Ser Ile Thr Ser
225                 230                 235                 240 tcc ggc cca cag aca gca aag atc gag gaa ttg cca aca gct gct gat       768
Ser Gly Pro Gln Thr Ala Lys Ile Glu Glu Leu Pro Thr Ala Ala Asp
                245                 250                 255 agt cat ctc cgc agc gca gct ctc act tct gct cag cag ttt ttc ctc       816
Ser His Leu Arg Ser Ala Ala Leu Thr Ser Ala Gln Gln Phe Phe Leu
            260                 265                 270 aaa gtt att gct cca cat cgt cct gag aag cca ttc gtc cag ctt cca       864
Lys Val Ile Ala Pro His Arg Pro Glu Lys Pro Phe Val Gln Leu Pro
        275                 280                 285 tct ctc acc tcg gag ggc atc cga ata tac gac acc ttt gca cag ttt       912
Ser Leu Thr Ser Glu Gly Ile Arg Ile Tyr Asp Thr Phe Ala Gln Phe
290                 295                 300 gtc ata gcc gac ctg ctc gac gac acc cgc ttc cta ccc atg caa tct       960
Val Ile Ala Asp Leu Leu Asp Asp Thr Arg Phe Leu Pro Met Gln Ser
305                 310                 315                 320 cct cct ccc aat ggg ctc atc acc ttt gtt aac cca agc gcg tac ctt      1008
Pro Pro Pro Asn Gly Leu Ile Thr Phe Val Asn Pro Ser Ala Tyr Leu
                325                 330                 335 gct gat gat ata aag aat ggc aac agc cat att gtc ccg ggt gtg caa      1056
Ala Asp Asp Ile Lys Asn Gly Asn Ser His Ile Val Pro Gly Val Gln
            340                 345                 350 ttt tac gca tcc gat gcg tgc act ctc atc gac atc cca cat gac cta      1104
Phe Tyr Ala Ser Asp Ala Cys Thr Leu Ile Asp Ile Pro His Asp Leu
        355                 360                 365 gac acc acc tcc gtt ggc ttg tca gta ctg cac aag ttt gga aag gtg      1152
Asp Thr Thr Ser Val Gly Leu Ser Val Leu His Lys Phe Gly Lys Val
370                 375                 380 gac aag gac aca ctc aac aaa gtg cta gac aga atg ctc gag caa gtg      1200
Asp Lys Asp Thr Leu Asn Lys Val Leu Asp Arg Met Leu Glu Gln Val
385                 390                 395                 400 agt gaa gac gac ggc att ctg cag gtg tat ttt gat gtg gag cgt ccg      1248
Ser Glu Asp Asp Gly Ile Leu Gln Val Tyr Phe Asp Val Glu Arg Pro
                405                 410                 415 cgc atc gat cca gtt gtg gtg gca aac acg gtg ttt ctg ttc cac ttg      1296
Arg Ile Asp Pro Val Val Val Ala Asn Thr Val Phe Leu Phe His Leu
            420                 425                 430 gga aag aga ggg cat gag gtg gcg agg agt gag aag ttt gtg gag agt      1344
Gly Lys Arg Gly His Glu Val Ala Arg Ser Glu Lys Phe Val Glu Ser
        435                 440                 445
```

```
gtg ctg ctg cag agg gca tac gaa gaa ggg acg ttg tat tac aac ctg   1392
Val Leu Leu Gln Arg Ala Tyr Glu Glu Gly Thr Leu Tyr Tyr Asn Leu
    450                 455                 460 ggg gaa gca ttt ttg gtg agt gtg gcg agg ctg gtg cac gag ttt aag   1440
Gly Glu Ala Phe Leu Val Ser Val Ala Arg Leu Val His Glu Phe Lys
465                 470                 475                 480 gag cac ttt aca agg agc ggc atg agg agg gca ctg gag gag agg cta   1488
Glu His Phe Thr Arg Ser Gly Met Arg Arg Ala Leu Glu Glu Arg Leu
                485                 490                 495 aga gag cgg gca agg gcg ggc atg caa gag agg gat gat gcg ctg gcg   1536
Arg Glu Arg Ala Arg Ala Gly Met Gln Glu Arg Asp Asp Ala Leu Ala
            500                 505                 510 cta gcc atg cgc att cgt gca tgc gct ttg tgt ggc ctg gcc gga gag   1584
Leu Ala Met Arg Ile Arg Ala Cys Ala Leu Cys Gly Leu Ala Gly Glu
        515                 520                 525 ggc ctc aca aaa gca gca gag cag gag ctt ttg cgc ctg cag tgc aag   1632
Gly Leu Thr Lys Ala Ala Glu Gln Glu Leu Leu Arg Leu Gln Cys Lys
    530                 535                 540 tcc aag ggc tgt tgg ggg tgc cac cct ttc tat cgc aat ggc agt aat   1680
Ser Lys Gly Cys Trp Gly Cys His Pro Phe Tyr Arg Asn Gly Ser Asn
545                 550                 555                 560 gtg ctc agc tgg atc ggc agt gag gcc ctt acc act gct tac gct att   1728
Val Leu Ser Trp Ile Gly Ser Glu Ala Leu Thr Thr Ala Tyr Ala Ile
                565                 570                 575 gct gcg cta cag ccc att gat att taa                               1755
Ala Ala Leu Gln Pro Ile Asp Ile
            580

<210> SEQ ID NO 27
<211> LENGTH: 584
<212> TYPE: PRT
<213> ORGANISM: Dryopteris fragrans
<220> FEATURE:
<223> OTHER INFORMATION: DfHAD_Dryopteris fragrans

<400> SEQUENCE: 27

Met Glu Phe Ser Ala Ser Ala Pro Pro Arg Leu Ala Ser Val Ile
1               5                   10                  15

Ile Leu Glu Pro Leu Gly Phe Leu Leu Thr Pro His Tyr Ser Ser Gln
                20                  25                  30

Leu Pro Lys Lys Leu Leu Arg Arg Leu Cys Thr Arg Ile Trp His
            35                  40                  45

Arg Tyr Gln Arg Gly Arg Leu Arg Leu Arg Asp Ala Ala Met Leu Leu
        50                  55                  60

Ala Gln Leu Pro Phe Leu Ala Val Ser Asp His Pro Trp Ala Leu Asp
65                  70                  75                  80

Asn Leu Ala Ser Leu Arg Pro Thr Ala Val Arg Ala Val Pro Trp
                85                  90                  95

Met Leu Leu Leu Leu Asp Phe Leu Arg Asp Glu Leu His Leu Lys Val
                100                 105                 110

Val Cys Ala Thr Asn Ser Ser Pro Glu Glu Leu Gln Glu Leu Arg His
            115                 120                 125

Gln Phe Pro Ala Leu Phe Ala Lys Val Asp Ala Thr Val Ser Ser Gly
        130                 135                 140

Glu Glu Gly Val Gly Lys Pro Ser Val Arg Phe Leu Gln Ala Ala Leu
145                 150                 155                 160

Asp Lys Ala Gly Val His Ala Gln Gln Thr Leu Tyr Leu Asp Ser Phe
                165                 170                 175
```

```
Asp Ser Leu Glu Thr Ile Met Ala Ala Arg Ser Leu Gly Met His Ala
            180                 185                 190

Leu Ser Val Glu Pro Cys His Ile Asp Glu Leu Thr Ala Arg Ala Ser
            195                 200                 205

Ser Gly Gln Leu Arg Asp Ala Gln Leu Ile Arg Arg Ile Val Cys Ala
    210                 215                 220

Met His Gly Pro Ala Val Ser Ala Val Val Ser Gly Ser Ile Thr Ser
225                 230                 235                 240

Ser Gly Pro Gln Thr Ala Lys Ile Glu Glu Leu Pro Thr Ala Ala Asp
                245                 250                 255

Ser His Leu Arg Ser Ala Ala Leu Thr Ser Ala Gln Gln Phe Leu
            260                 265                 270

Lys Val Ile Ala Pro His Arg Pro Glu Lys Pro Phe Val Gln Leu Pro
            275                 280                 285

Ser Leu Thr Ser Glu Gly Ile Arg Ile Tyr Asp Thr Phe Ala Gln Phe
    290                 295                 300

Val Ile Ala Asp Leu Leu Asp Asp Thr Arg Phe Leu Pro Met Gln Ser
305                 310                 315                 320

Pro Pro Pro Asn Gly Leu Ile Thr Phe Val Asn Pro Ser Ala Tyr Leu
                325                 330                 335

Ala Asp Asp Ile Lys Asn Gly Asn Ser His Ile Val Pro Gly Val Gln
                340                 345                 350

Phe Tyr Ala Ser Asp Ala Cys Thr Leu Ile Asp Ile Pro His Asp Leu
            355                 360                 365

Asp Thr Thr Ser Val Gly Leu Ser Val Leu His Lys Phe Gly Lys Val
    370                 375                 380

Asp Lys Asp Thr Leu Asn Lys Val Leu Asp Arg Met Leu Glu Gln Val
385                 390                 395                 400

Ser Glu Asp Asp Gly Ile Leu Gln Val Tyr Phe Asp Val Glu Arg Pro
                405                 410                 415

Arg Ile Asp Pro Val Val Ala Asn Thr Val Phe Leu Phe His Leu
            420                 425                 430

Gly Lys Arg Gly His Glu Val Ala Arg Ser Lys Phe Val Glu Ser
            435                 440                 445

Val Leu Leu Gln Arg Ala Tyr Glu Glu Gly Thr Leu Tyr Tyr Asn Leu
    450                 455                 460

Gly Glu Ala Phe Leu Val Ser Val Ala Arg Leu Val His Glu Phe Lys
465                 470                 475                 480

Glu His Phe Thr Arg Ser Gly Met Arg Arg Ala Leu Glu Glu Arg Leu
                485                 490                 495

Arg Glu Arg Ala Arg Ala Gly Met Gln Glu Arg Asp Asp Ala Leu Ala
            500                 505                 510

Leu Ala Met Arg Ile Arg Ala Cys Ala Leu Cys Gly Leu Ala Gly Glu
            515                 520                 525

Gly Leu Thr Lys Ala Ala Glu Gln Glu Leu Leu Arg Leu Gln Cys Lys
    530                 535                 540

Ser Lys Gly Cys Trp Gly Cys His Pro Phe Tyr Arg Asn Gly Ser Asn
545                 550                 555                 560

Val Leu Ser Trp Ile Gly Ser Glu Ala Leu Thr Thr Ala Tyr Ala Ile
                565                 570                 575

Ala Ala Leu Gln Pro Ile Asp Ile
            580
```

<210> SEQ ID NO 28
<211> LENGTH: 1755
<212> TYPE: DNA
<213> ORGANISM: Dryopteris fragrans
<220> FEATURE:
<221> NAME/KEY: CDS
<222> LOCATION: (1)..(1755)

<400> SEQUENCE: 28

```
atg gag ttc tct gcc tct gct cct cct cct agg cta gcc agt gtc ata      48
Met Glu Phe Ser Ala Ser Ala Pro Pro Pro Arg Leu Ala Ser Val Ile
1               5                   10                  15 ata ttg gag cct ctc ggc ttc ctc ctc aca cca cac tac tcc tct cag      96
Ile Leu Glu Pro Leu Gly Phe Leu Leu Thr Pro His Tyr Ser Ser Gln
            20                  25                  30 ctt ccc aaa aag ctg ctc cgt cgc ctg ttg tgc act aga atc tgg cac     144
Leu Pro Lys Lys Leu Leu Arg Arg Leu Leu Cys Thr Arg Ile Trp His
        35                  40                  45 agg tat cag cga ggc cgc ctt cgc ctg cgt gac gct gct atg ctg ctc     192
Arg Tyr Gln Arg Gly Arg Leu Arg Leu Arg Asp Ala Ala Met Leu Leu
    50                  55                  60 gcc cag ctc cca ttc cta gct gtg tct gat cac ccc tgg gct ctg gac     240
Ala Gln Leu Pro Phe Leu Ala Val Ser Asp His Pro Trp Ala Leu Asp
65                  70                  75                  80 aat ctc gca agc ctg ctc cgc ccc aca gct gtg cgt gcg gtg cca tgg     288
Asn Leu Ala Ser Leu Leu Arg Pro Thr Ala Val Arg Ala Val Pro Trp
                85                  90                  95 atg ctg ctg ctg ctc gac ttc cta cga gac gag ctc cat ctg aag gta     336
Met Leu Leu Leu Leu Asp Phe Leu Arg Asp Glu Leu His Leu Lys Val
            100                 105                 110 gtc tgc gcg acc aac tcc tcc cca gaa gag ctg caa gag ctg cgc cac     384
Val Cys Ala Thr Asn Ser Ser Pro Glu Glu Leu Gln Glu Leu Arg His
        115                 120                 125 cag ttt ccg gcc ctc ttt gcc aag gtc gat gcc acc gtt tct tca ggc     432
Gln Phe Pro Ala Leu Phe Ala Lys Val Asp Ala Thr Val Ser Ser Gly
    130                 135                 140 gag gag ggc gtg ggc aag ccg tcc gtg cgc ttc ctg cag gct gcg ttg     480
Glu Glu Gly Val Gly Lys Pro Ser Val Arg Phe Leu Gln Ala Ala Leu
145                 150                 155                 160 gac aaa gcc ggt gtc cac gcg cag caa acc ttg tat ctt gac tct ttt     528
Asp Lys Ala Gly Val His Ala Gln Gln Thr Leu Tyr Leu Asp Ser Phe
                165                 170                 175 gac agc ttg gag acc atc atg gct gca cgc tct ctt ggc atg cat gca     576
Asp Ser Leu Glu Thr Ile Met Ala Ala Arg Ser Leu Gly Met His Ala
            180                 185                 190 cta tct gta gag cca tgc cac att gat gag ctc acc gcc agg gcc tct     624
Leu Ser Val Glu Pro Cys His Ile Asp Glu Leu Thr Ala Arg Ala Ser
        195                 200                 205 tcc ggc cag cta aga gat gca cag ctt ata agg cgt att gtg tgc gcc     672
Ser Gly Gln Leu Arg Asp Ala Gln Leu Ile Arg Arg Ile Val Cys Ala
    210                 215                 220 atg cac ggg cca gca gta tct gca gtt gtg tcg ggc agt atc aca tcg     720
Met His Gly Pro Ala Val Ser Ala Val Val Ser Gly Ser Ile Thr Ser
225                 230                 235                 240 tcc ggc cca cag aca gca aag atc gag gaa ttg cca aca gct gct gat     768
Ser Gly Pro Gln Thr Ala Lys Ile Glu Glu Leu Pro Thr Ala Ala Asp
                245                 250                 255 agt cat ctc cgc agc gca gct ctc act tct gct cag cag ttt ttc ctc     816
Ser His Leu Arg Ser Ala Ala Leu Thr Ser Ala Gln Gln Phe Phe Leu
            260                 265                 270
```

```
                                                               -continued aaa gtt att gct cca cat cgt cct gag aag cca ttc gtc cag ctt cca      864
Lys Val Ile Ala Pro His Arg Pro Glu Lys Pro Phe Val Gln Leu Pro
        275                 280                 285 tct ctc acc tcg gag ggc atc cga ata tac gac acc ttt gca cag ttt      912
Ser Leu Thr Ser Glu Gly Ile Arg Ile Tyr Asp Thr Phe Ala Gln Phe
    290                 295                 300 gtc ata gcc gac ctg ctc gac gac acc cgc ttc cta ccc atg caa tct      960
Val Ile Ala Asp Leu Leu Asp Asp Thr Arg Phe Leu Pro Met Gln Ser
305                 310                 315                 320 cct cct ccc aat ggg ctc atc acc ttt gtt aac cca agc gcg tac ctt     1008
Pro Pro Pro Asn Gly Leu Ile Thr Phe Val Asn Pro Ser Ala Tyr Leu
                325                 330                 335 gct gat gat ata aag aat ggc aac agc cat att gtc ccg ggt gtg caa     1056
Ala Asp Asp Ile Lys Asn Gly Asn Ser His Ile Val Pro Gly Val Gln
            340                 345                 350 ttt tac gca tcc gat gcg tgc act ctc atc gac atc cca cat gac cta     1104
Phe Tyr Ala Ser Asp Ala Cys Thr Leu Ile Asp Ile Pro His Asp Leu
        355                 360                 365 gac acc acc tcc gtt ggc ttg tca gta ctg cac aag ttt gga aag gtg     1152
Asp Thr Thr Ser Val Gly Leu Ser Val Leu His Lys Phe Gly Lys Val
    370                 375                 380 gac aag gac aca ctc aac aaa gtg cta gac aga atg ctc gag caa gtg     1200
Asp Lys Asp Thr Leu Asn Lys Val Leu Asp Arg Met Leu Glu Gln Val
385                 390                 395                 400 agt gaa gac gac ggc att ctg cag gtg tat ttt gat gtg gag cgt ccg     1248
Ser Glu Asp Asp Gly Ile Leu Gln Val Tyr Phe Asp Val Glu Arg Pro
                405                 410                 415 cgc atc gat cca gtt gtg gtg gca aac acg gtg ttt ctg ttc cac ttg     1296
Arg Ile Asp Pro Val Val Val Ala Asn Thr Val Phe Leu Phe His Leu
            420                 425                 430 gga aag aga ggg cat gag gtg gcg agg agt gag aag ttt gtg gag agt     1344
Gly Lys Arg Gly His Glu Val Ala Arg Ser Glu Lys Phe Val Glu Ser
        435                 440                 445 gtg ctg ctg cag agg gca tac gaa gaa ggg acg ttg tat tac aac ctg     1392
Val Leu Leu Gln Arg Ala Tyr Glu Glu Gly Thr Leu Tyr Tyr Asn Leu
    450                 455                 460 ggg gaa gca ttt ttg gtg agt gtg gcg agg ctg gtg cac gag ttt aag     1440
Gly Glu Ala Phe Leu Val Ser Val Ala Arg Leu Val His Glu Phe Lys
465                 470                 475                 480 gag cac ttt aca agg agc ggc atg agg agg gca ctg gag gag agg cta     1488
Glu His Phe Thr Arg Ser Gly Met Arg Arg Ala Leu Glu Glu Arg Leu
                485                 490                 495 aga gag cgg gca agg gcg ggc atg caa gag agg gat gat gcg ctg gcg     1536
Arg Glu Arg Ala Arg Ala Gly Met Gln Glu Arg Asp Asp Ala Leu Ala
            500                 505                 510 ctg gcc atg cgc att cgt gca tgc gct ttg tgt ggc ctg gcc gga gag     1584
Leu Ala Met Arg Ile Arg Ala Cys Ala Leu Cys Gly Leu Ala Gly Glu
        515                 520                 525 ggc ctc aca aga gca gca gag cag gag cta ctg cgc ctg cag tgc aag     1632
Gly Leu Thr Arg Ala Ala Glu Gln Glu Leu Leu Arg Leu Gln Cys Lys
    530                 535                 540 tcc aag ggc tgt tgg ggg tgc cac cct ttc tat cgc aat ggc agt aat     1680
Ser Lys Gly Cys Trp Gly Cys His Pro Phe Tyr Arg Asn Gly Ser Asn
545                 550                 555                 560 gtg ctc agc tgg atc ggc agt gag gcc ctt acc act gct tac gct att     1728
Val Leu Ser Trp Ile Gly Ser Glu Ala Leu Thr Thr Ala Tyr Ala Ile
                565                 570                 575 gct gcg cta cag ccc att gat att taa                                 1755
Ala Ala Leu Gln Pro Ile Asp Ile
            580
```

<210> SEQ ID NO 29
<211> LENGTH: 584
<212> TYPE: PRT
<213> ORGANISM: Dryopteris fragrans
<220> FEATURE:
<223> OTHER INFORMATION: DfHAD-8(K532R)_Dryopteris fragrans

<400> SEQUENCE: 29

```
Met Glu Phe Ser Ala Ser Ala Pro Pro Arg Leu Ala Ser Val Ile
1               5                  10                  15

Ile Leu Glu Pro Leu Gly Phe Leu Leu Thr Pro His Tyr Ser Ser Gln
            20                  25                  30

Leu Pro Lys Lys Leu Leu Arg Arg Leu Leu Cys Thr Arg Ile Trp His
            35                  40                  45

Arg Tyr Gln Arg Gly Arg Leu Arg Leu Arg Asp Ala Ala Met Leu Leu
50                  55                  60

Ala Gln Leu Pro Phe Leu Ala Val Ser Asp His Pro Trp Ala Leu Asp
65                  70                  75                  80

Asn Leu Ala Ser Leu Leu Arg Pro Thr Ala Val Arg Ala Val Pro Trp
                85                  90                  95

Met Leu Leu Leu Leu Asp Phe Leu Arg Asp Glu Leu His Leu Lys Val
            100                 105                 110

Val Cys Ala Thr Asn Ser Ser Pro Glu Glu Leu Gln Glu Leu Arg His
            115                 120                 125

Gln Phe Pro Ala Leu Phe Ala Lys Val Asp Ala Thr Val Ser Ser Gly
130                 135                 140

Glu Glu Gly Val Gly Lys Pro Ser Val Arg Phe Leu Gln Ala Ala Leu
145                 150                 155                 160

Asp Lys Ala Gly Val His Ala Gln Gln Thr Leu Tyr Leu Asp Ser Phe
                165                 170                 175

Asp Ser Leu Glu Thr Ile Met Ala Ala Arg Ser Leu Gly Met His Ala
            180                 185                 190

Leu Ser Val Glu Pro Cys His Ile Asp Glu Leu Thr Ala Arg Ala Ser
            195                 200                 205

Ser Gly Gln Leu Arg Asp Ala Gln Leu Ile Arg Arg Ile Val Cys Ala
210                 215                 220

Met His Gly Pro Ala Val Ser Ala Val Val Ser Gly Ser Ile Thr Ser
225                 230                 235                 240

Ser Gly Pro Gln Thr Ala Lys Ile Glu Glu Leu Pro Thr Ala Ala Asp
                245                 250                 255

Ser His Leu Arg Ser Ala Ala Leu Thr Ser Ala Gln Gln Phe Phe Leu
            260                 265                 270

Lys Val Ile Ala Pro His Arg Pro Glu Lys Pro Phe Val Gln Leu Pro
            275                 280                 285

Ser Leu Thr Ser Glu Gly Ile Arg Ile Tyr Asp Thr Phe Ala Gln Phe
290                 295                 300

Val Ile Ala Asp Leu Leu Asp Thr Arg Phe Leu Pro Met Gln Ser
305                 310                 315                 320

Pro Pro Pro Asn Gly Leu Ile Thr Phe Val Asn Pro Ser Ala Tyr Leu
                325                 330                 335

Ala Asp Asp Ile Lys Asn Gly Asn Ser His Ile Val Pro Gly Val Gln
            340                 345                 350

Phe Tyr Ala Ser Asp Ala Cys Thr Leu Ile Asp Ile Pro His Asp Leu
            355                 360                 365
```

```
Asp Thr Thr Ser Val Gly Leu Ser Val Leu His Lys Phe Gly Lys Val
    370                 375                 380

Asp Lys Asp Thr Leu Asn Lys Val Leu Asp Arg Met Leu Glu Gln Val
385                 390                 395                 400

Ser Glu Asp Asp Gly Ile Leu Gln Val Tyr Phe Asp Val Glu Arg Pro
            405                 410                 415

Arg Ile Asp Pro Val Val Val Ala Asn Thr Val Phe Leu Phe His Leu
            420                 425                 430

Gly Lys Arg Gly His Glu Val Ala Arg Ser Glu Lys Phe Val Glu Ser
        435                 440                 445

Val Leu Leu Gln Arg Ala Tyr Glu Glu Gly Thr Leu Tyr Tyr Asn Leu
    450                 455                 460

Gly Glu Ala Phe Leu Val Ser Val Ala Arg Leu Val His Glu Phe Lys
465                 470                 475                 480

Glu His Phe Thr Arg Ser Gly Met Arg Arg Ala Leu Glu Glu Arg Leu
            485                 490                 495

Arg Glu Arg Ala Arg Ala Gly Met Gln Glu Arg Asp Asp Ala Leu Ala
            500                 505                 510

Leu Ala Met Arg Ile Arg Ala Cys Ala Leu Cys Gly Leu Ala Gly Glu
        515                 520                 525

Gly Leu Thr Arg Ala Ala Glu Gln Glu Leu Leu Arg Leu Gln Cys Lys
530                 535                 540

Ser Lys Gly Cys Trp Gly Cys His Pro Phe Tyr Arg Asn Gly Ser Asn
545                 550                 555                 560

Val Leu Ser Trp Ile Gly Ser Glu Ala Leu Thr Thr Ala Tyr Ala Ile
            565                 570                 575

Ala Ala Leu Gln Pro Ile Asp Ile
            580

<210> SEQ ID NO 30
<211> LENGTH: 1755
<212> TYPE: DNA
<213> ORGANISM: Dryopteris fragrans
<220> FEATURE:
<221> NAME/KEY: CDS
<222> LOCATION: (1)..(1755)

<400> SEQUENCE: 30 atg gag ttc tct gcc tct gct cct cct cct agg cta gcc agt gtc ata      48
Met Glu Phe Ser Ala Ser Ala Pro Pro Pro Arg Leu Ala Ser Val Ile
1               5                   10                  15 ata ttg gag cct ctc ggc ttc ctc ctc aca cca cac tac tcc tct cag      96
Ile Leu Glu Pro Leu Gly Phe Leu Leu Thr Pro His Tyr Ser Ser Gln
            20                  25                  30 ctt ccc aaa aag ctg ctc cgt cgc ctg ttg tgc act aga atc tgg cac     144
Leu Pro Lys Lys Leu Leu Arg Arg Leu Leu Cys Thr Arg Ile Trp His
        35                  40                  45 agg tat cag cga ggc cgc ctt cgc ctg cgt gac gct gct atg ctg ctc     192
Arg Tyr Gln Arg Gly Arg Leu Arg Leu Arg Asp Ala Ala Met Leu Leu
    50                  55                  60 gcc cag ctc cca ttc cta gct gtg tct gat cac ccc tgg gct ctg gac     240
Ala Gln Leu Pro Phe Leu Ala Val Ser Asp His Pro Trp Ala Leu Asp
65                  70                  75                  80 aat ctc gca agc ctg ctc cgc ccc aca gct gtg cgt gcg gtg cca tgg     288
Asn Leu Ala Ser Leu Leu Arg Pro Thr Ala Val Arg Ala Val Pro Trp
                85                  90                  95 atg ctg ctg ctg ctc gac ttc cta cga gac gag ctc cat ctg aag gta     336
```

```
              Met Leu Leu Leu Leu Asp Phe Leu Arg Asp Glu Leu His Leu Lys Val
                          100                 105                 110 gtc tgc gcg acc aac tcc tcc cca gaa gag ctg caa gag ctg cgc cac          384
Val Cys Ala Thr Asn Ser Ser Pro Glu Glu Leu Gln Glu Leu Arg His
            115                 120                 125 cag ttt ccg gcc ctc ttt gcc aag gtc gat gcc acc gtt tct tca ggc          432
Gln Phe Pro Ala Leu Phe Ala Lys Val Asp Ala Thr Val Ser Ser Gly
        130                 135                 140 gag gag ggc gtg ggc aag ccg tcc gtg cgc ttc ctg cag gct gcg ttg          480
Glu Glu Gly Val Gly Lys Pro Ser Val Arg Phe Leu Gln Ala Ala Leu
145                 150                 155                 160 gac aaa gcc ggt gtc cac gcg cag caa acc ttg tat ctt gac tct ttt          528
Asp Lys Ala Gly Val His Ala Gln Gln Thr Leu Tyr Leu Asp Ser Phe
                165                 170                 175 gac agc ttg gag acc atc atg gct gca cgc tct ctt ggc atg cat gca          576
Asp Ser Leu Glu Thr Ile Met Ala Ala Arg Ser Leu Gly Met His Ala
            180                 185                 190 cta tct gta gag cca tgc cac att gat gag ctc acc gcc agg gcc tct          624
Leu Ser Val Glu Pro Cys His Ile Asp Glu Leu Thr Ala Arg Ala Ser
        195                 200                 205 tcc ggc cag cta aga gat gca cag ctt ata agg cgt att gtg tgc gcc          672
Ser Gly Gln Leu Arg Asp Ala Gln Leu Ile Arg Arg Ile Val Cys Ala
210                 215                 220 atg cac ggg cca gca gta tct gca gtt gtg tcg ggc agt atc aca tcg          720
Met His Gly Pro Ala Val Ser Ala Val Val Ser Gly Ser Ile Thr Ser
225                 230                 235                 240 tcc ggc cca cag aca gca aag atc gag gaa ttg cca aca gct gct gat          768
Ser Gly Pro Gln Thr Ala Lys Ile Glu Glu Leu Pro Thr Ala Ala Asp
                245                 250                 255 agt cat ctc cgc agc gca gct ctc act tct gct cag cag ttt ttc ctc          816
Ser His Leu Arg Ser Ala Ala Leu Thr Ser Ala Gln Gln Phe Phe Leu
            260                 265                 270 aaa gct att gct cca cat cgt cct gag aag cca ttc gtc cag ctt cca          864
Lys Ala Ile Ala Pro His Arg Pro Glu Lys Pro Phe Val Gln Leu Pro
        275                 280                 285 tct ctc acc tcg gag ggc atc cga ata tac gac acc ttt gca cag ttt          912
Ser Leu Thr Ser Glu Gly Ile Arg Ile Tyr Asp Thr Phe Ala Gln Phe
290                 295                 300 gtc ata gcc gac ctg ctc gac gac acc cgc ttc cta ccc atg caa tct          960
Val Ile Ala Asp Leu Leu Asp Asp Thr Arg Phe Leu Pro Met Gln Ser
305                 310                 315                 320 cct cct ccc aat ggg ctc atc acc ttt gtt aac cca agc gcg tac ctt         1008
Pro Pro Pro Asn Gly Leu Ile Thr Phe Val Asn Pro Ser Ala Tyr Leu
                325                 330                 335 gct gat gat ata aag aat ggc aac agc cat att gtc ccg ggt gtg caa         1056
Ala Asp Asp Ile Lys Asn Gly Asn Ser His Ile Val Pro Gly Val Gln
            340                 345                 350 ttt tac gca tct gat gcg tgc act ctc atc gac atc cca cat gac cta         1104
Phe Tyr Ala Ser Asp Ala Cys Thr Leu Ile Asp Ile Pro His Asp Leu
        355                 360                 365 gac acc acc tcc gtt ggc ttg tca gta ctg cac aag ttt gga aag gtg         1152
Asp Thr Thr Ser Val Gly Leu Ser Val Leu His Lys Phe Gly Lys Val
370                 375                 380 gac aag gac aca ctc aac aaa gtg cta gac aga atg ctg gag caa gtg         1200
Asp Lys Asp Thr Leu Asn Lys Val Leu Asp Arg Met Leu Glu Gln Val
385                 390                 395                 400 agt gaa gac gac ggc att ctc cag gtg tat ttt gat gtg gag cgt ccg         1248
Ser Glu Asp Asp Gly Ile Leu Gln Val Tyr Phe Asp Val Glu Arg Pro
                405                 410                 415
```

| | | |
|---|---|---|
| cgc atc gat cca gtt gtg gtg gca aac acg gtg ttt ctg ttc cac ttg<br>Arg Ile Asp Pro Val Val Val Ala Asn Thr Val Phe Leu Phe His Leu<br>420 425 430 | | 1296 |
| gga aag aga ggg cat gag gtg gcg agg agt gag aag ttt gtg gag agt<br>Gly Lys Arg Gly His Glu Val Ala Arg Ser Glu Lys Phe Val Glu Ser<br>435 440 445 | | 1344 |
| gtg ctg ctg cag agg gca tac gaa gaa ggg acg ttg tat tac aac ctg<br>Val Leu Leu Gln Arg Ala Tyr Glu Glu Gly Thr Leu Tyr Tyr Asn Leu<br>450 455 460 | | 1392 |
| ggg gaa gca ttt ttg gtg agt gtg gcg agg ctg gtg cac gag ttt aag<br>Gly Glu Ala Phe Leu Val Ser Val Ala Arg Leu Val His Glu Phe Lys<br>465 470 475 480 | | 1440 |
| gag cac ttt aca agg agc ggc atg agg agg gca ctg gag gag agg cta<br>Glu His Phe Thr Arg Ser Gly Met Arg Arg Ala Leu Glu Glu Arg Leu<br>485 490 495 | | 1488 |
| aga gag cgg gca agg gcg ggc atg caa gag agg gat gat gcg ctg gcg<br>Arg Glu Arg Ala Arg Ala Gly Met Gln Glu Arg Asp Asp Ala Leu Ala<br>500 505 510 | | 1536 |
| ctg gcc atg cgc att cgt gca tgc gct ttg tgt ggc ctg gcc gga gag<br>Leu Ala Met Arg Ile Arg Ala Cys Ala Leu Cys Gly Leu Ala Gly Glu<br>515 520 525 | | 1584 |
| ggc ctc aca aaa gca gca gag cag gag cta ctc gcc ctg cag tgc aag<br>Gly Leu Thr Lys Ala Ala Glu Gln Glu Leu Leu Arg Leu Gln Cys Lys<br>530 535 540 | | 1632 |
| tcc aag ggc tgt tgg ggg tgc cac cct ttc tat cgc aat ggc agt aat<br>Ser Lys Gly Cys Trp Gly Cys His Pro Phe Tyr Arg Asn Gly Ser Asn<br>545 550 555 560 | | 1680 |
| gtg ctc agc tgg atc ggc agt gag gcc ctt acc act gct tac gct att<br>Val Leu Ser Trp Ile Gly Ser Glu Ala Leu Thr Thr Ala Tyr Ala Ile<br>565 570 575 | | 1728 |
| gct gcg cta cag ccc att gat att taa<br>Ala Ala Leu Gln Pro Ile Asp Ile<br>580 | | 1755 |

```
<210> SEQ ID NO 31
<211> LENGTH: 584
<212> TYPE: PRT
<213> ORGANISM: Dryopteris fragrans
<220> FEATURE:
<223> OTHER INFORMATION: DfHAD-9(V274A)_Dryopteris fragrans

<400> SEQUENCE: 31
```

Met Glu Phe Ser Ala Ser Ala Pro Pro Arg Leu Ala Ser Val Ile
1               5                   10                  15

Ile Leu Glu Pro Leu Gly Phe Leu Leu Thr Pro His Tyr Ser Ser Gln
            20                  25                  30

Leu Pro Lys Lys Leu Leu Arg Arg Leu Leu Cys Thr Arg Ile Trp His
        35                  40                  45

Arg Tyr Gln Arg Gly Arg Leu Arg Leu Arg Asp Ala Ala Met Leu Leu
    50                  55                  60

Ala Gln Leu Pro Phe Leu Ala Val Ser Asp His Pro Trp Ala Leu Asp
65                  70                  75                  80

Asn Leu Ala Ser Leu Leu Arg Pro Thr Ala Val Arg Ala Val Pro Trp
                85                  90                  95

Met Leu Leu Leu Leu Asp Phe Leu Arg Asp Glu Leu His Leu Lys Val
            100                 105                 110

Val Cys Ala Thr Asn Ser Ser Pro Glu Glu Leu Gln Glu Leu Arg His
        115                 120                 125

Gln Phe Pro Ala Leu Phe Ala Lys Val Asp Ala Thr Val Ser Ser Gly

```
                130             135             140
Glu Glu Gly Val Gly Lys Pro Ser Val Arg Phe Leu Gln Ala Ala Leu
145                 150                 155                 160

Asp Lys Ala Gly Val His Ala Gln Gln Thr Leu Tyr Leu Asp Ser Phe
                165                 170                 175

Asp Ser Leu Glu Thr Ile Met Ala Ala Arg Ser Leu Gly Met His Ala
            180                 185                 190

Leu Ser Val Glu Pro Cys His Ile Asp Glu Leu Thr Ala Arg Ala Ser
            195                 200                 205

Ser Gly Gln Leu Arg Asp Ala Gln Leu Ile Arg Arg Ile Val Cys Ala
        210                 215                 220

Met His Gly Pro Ala Val Ser Ala Val Val Ser Gly Ser Ile Thr Ser
225                 230                 235                 240

Ser Gly Pro Gln Thr Ala Lys Ile Glu Glu Leu Pro Thr Ala Ala Asp
                245                 250                 255

Ser His Leu Arg Ser Ala Ala Leu Thr Ser Ala Gln Gln Phe Phe Leu
                260                 265                 270

Lys Ala Ile Ala Pro His Arg Pro Glu Lys Pro Phe Val Gln Leu Pro
            275                 280                 285

Ser Leu Thr Ser Glu Gly Ile Arg Ile Tyr Asp Thr Phe Ala Gln Phe
        290                 295                 300

Val Ile Ala Asp Leu Leu Asp Asp Thr Arg Phe Leu Pro Met Gln Ser
305                 310                 315                 320

Pro Pro Pro Asn Gly Leu Ile Thr Phe Val Asn Pro Ser Ala Tyr Leu
                325                 330                 335

Ala Asp Asp Ile Lys Asn Gly Asn Ser His Ile Val Pro Gly Val Gln
                340                 345                 350

Phe Tyr Ala Ser Asp Ala Cys Thr Leu Ile Asp Ile Pro His Asp Leu
            355                 360                 365

Asp Thr Thr Ser Val Gly Leu Ser Val Leu His Lys Phe Gly Lys Val
        370                 375                 380

Asp Lys Asp Thr Leu Asn Lys Val Leu Asp Arg Met Leu Glu Gln Val
385                 390                 395                 400

Ser Glu Asp Asp Gly Ile Leu Gln Val Tyr Phe Asp Val Glu Arg Pro
                405                 410                 415

Arg Ile Asp Pro Val Val Ala Asn Thr Val Phe Leu Phe His Leu
                420                 425                 430

Gly Lys Arg Gly His Glu Val Ala Arg Ser Glu Lys Phe Val Glu Ser
            435                 440                 445

Val Leu Leu Gln Arg Ala Tyr Glu Glu Gly Thr Leu Tyr Tyr Asn Leu
        450                 455                 460

Gly Glu Ala Phe Leu Val Ser Val Ala Arg Leu Val His Glu Phe Lys
465                 470                 475                 480

Glu His Phe Thr Arg Ser Gly Met Arg Arg Ala Leu Glu Glu Arg Leu
                485                 490                 495

Arg Glu Arg Ala Arg Ala Gly Met Gln Glu Arg Asp Asp Ala Leu Ala
                500                 505                 510

Leu Ala Met Arg Ile Arg Ala Cys Ala Leu Cys Gly Leu Ala Gly Glu
            515                 520                 525

Gly Leu Thr Lys Ala Ala Glu Gln Glu Leu Leu Arg Leu Gln Cys Lys
        530                 535                 540

Ser Lys Gly Cys Trp Gly Cys His Pro Phe Tyr Arg Asn Gly Ser Asn
545                 550                 555                 560
```

Val Leu Ser Trp Ile Gly Ser Glu Ala Leu Thr Thr Ala Tyr Ala Ile
            565                 570                 575

Ala Ala Leu Gln Pro Ile Asp Ile
            580

<210> SEQ ID NO 32
<211> LENGTH: 1755
<212> TYPE: DNA
<213> ORGANISM: Artificial Sequence
<220> FEATURE:
<223> OTHER INFORMATION: Codon-optimized sequence of DfHAD by Genscript
      genetic codon frequency of E. coli

<400> SEQUENCE: 32

| | | |
|---|---|---|
| atggagttca gcgcgagcgc tccgccgccg cgtctggcga gcgtgatcat tctggaaccg | 60 |
| ctgggttttc tgctgacccc gcactacagc agccagctgc gaagaaaact gctgcgtcgt | 120 |
| ctgctgtgca cccgtatctg gcaccgttat cagcgtggcc gtctgcgtct cgtgacgcg | 180 |
| gcgatgctgc tggcgcaact gccgttcctg gcggttagca ccacccgtg ggcgctggat | 240 |
| aacctggcga gcctgctgcg tccgaccgcg gttcgtgcgg tgccgtggat gctgctgctg | 300 |
| ctggactttc tgcgtgatga gctgcacctg aaagtggttt gcgcgaccaa cagcagcccg | 360 |
| gaggaactgc aggaactgcg tcaccaattc ccggcgctgt tgcgaaggt tgacgcgacc | 420 |
| gtgagcagcg gcgaggaagg tgttggcaaa ccgagcgtgc gtttcctgca gcggcgctg | 480 |
| gataaggcgg gcgtgcacgc gcagcaaacc ctgtacctgg acagctttga tagcctggag | 540 |
| accatcatgg cggcgcgtag cctgggtatg cacgcgctga gcgttgagcc gtgccacatt | 600 |
| gacgaactga ccgcgcgtgc gagcagcggt cagctgcgtg atgcgcaact gatccgtcgt | 660 |
| attgtttgcg cgatgcacgg tccggctgtg agcgcggtgg ttagcggtag catcaccagc | 720 |
| agcggtccgc agaccgcgaa aattgaggaa ctgccgaccg cggcggacag ccacctgcgt | 780 |
| agcgcggcgc tgaccagcgc gcagcaattc tttctgaaag tgattgcgcc gcaccgtccg | 840 |
| gagaagccgt tcgttcaact gccgagcctg accagcgaag gtatccgtat ttatgacacc | 900 |
| ttcgcgcagt ttgtgatcgc ggatctgctg gacgataccc gtttcctgcc gatgcaaagc | 960 |
| ccgccgccga acggcctgat tacctttgtt aacccgagcg cgtacctggc ggacgatatc | 1020 |
| aaaaacggta cagccacat tgttccgggc gtgcagttct atgcgagcga cgcgtgcacc | 1080 |
| ctgatcgata ttccgcacga cctggatacc accagcgttg gtctgagcgt gctgcacaag | 1140 |
| tttggcaaag ttgacaagga tacectgaac aaggtgctgg atcgtatgct ggagcaagtt | 1200 |
| agcgaagacg atggtatcct gcaagtttac tttgacgtgg agcgtccgcg tattgatccg | 1260 |
| gtggttgtgg cgaacaccgt gttcctgttt cacctgggta acgtggcca cgaagttgcg | 1320 |
| cgtagcgaga agttcgttga aagcgtgctg ctgcagcgtg cgtacgagga aggcaccctg | 1380 |
| tactataacc tgggcgaagc gtttctggtt agcgtggcgc gtctggtgca cgagttcaaa | 1440 |
| gaacactta cccgtagcgg tatgcgtcgt gcgctggagg aacgtctgcg tgagcgtgcg | 1500 |
| cgtgcgggta tgcaagaacg tgacgatgcg ctggcgctgg cgatgcgtat ccgtgcgtgc | 1560 |
| gcgctgtgcg gtctggcggg cgagggtctg accaaggcgg cggagcagga actgctgcgt | 1620 |
| ctgcaatgca agagcaaagg ttgctggggc tgccacccgt tctaccgtaa cggtagcaac | 1680 |
| gttctgagct ggatcggcag cgaagcgctg accaccgcgt atgcgattgc ggcgctgcag | 1740 |
| ccgatcgaca tttaa | 1755 |

<210> SEQ ID NO 33
<211> LENGTH: 1755
<212> TYPE: DNA
<213> ORGANISM: Artificial Sequence
<220> FEATURE:
<223> OTHER INFORMATION: Codon-optimized sequence of DfHAD by Genscript genetic codon frequency of tobacco

<400> SEQUENCE: 33

```
atggaatttt ctgcttcagc tccacctcca agacttgctt cagttattat tcttgagcct      60
ttgggatttc ttttgactcc acattactct tcacaattgc taagaaaact tttgagaagg     120
cttttgtgta caagaatttg gcataggtac caaaggggta ggcttagatt gagggatgct     180
gctatgcttt tggctcaact tccattttg gctgtttcag atcatccttg gctcttgat      240
aatttggctt ctcttttgag accaactgct gttaggctg ttccttggat gcttttgctt     300
ttggattttc ttagagatga acttcatttg aaggttgttt gcgctactaa ttcttcacca     360
gaagagcttc aagagttgag gcatcaattt cctgctttgt ttgctaaggt tgatgctaca     420
gtttcttcag gagaagaggg agttggtaaa ccatctgtta gatttcttca agctgctttg     480
gataaggctg gtgttcatgc tcaacaaact ctttatttgg attctttcga ttcacttgaa     540
acaattatgg ctgctaggtc attgggaatg catgctcttt ctgttgaacc atgtcatatt     600
gatgagttga ctgctagagc ttcttcagga caattgaggg atgctcaact tattagaagg     660
attgtttgcg ctatgcatgg tcctgctgtt tcagctgttg tttctggatc aattacttct     720
tcaggtccac aaacagctaa aattgaagag cttcctactg ctgctgattc tcatttgaga     780
tcagctgctc ttacatctgc tcaacaattt tccttaaag ttattgctcc acatagacct     840
gaaaagccat tgttcaact tccttctttg acttcagagg gaatcaggat ctatgataca     900
ttcgctcaat tcgttatcgc tgatcttttg gatgatacta ggttttgcc aatgcaatca     960
cctccaccta atggtcttat cacattcgtt aacccttctg cttatttggc tgatgatatt    1020
aaaaatggta actcacatat tgttccaggt gttcaatttt acgcttctga tgcttgtact    1080
ttgattgata ttcctcatga tcttgatact acatctgttg gactttcagt tttgcataag    1140
ttcggtaaag ttgataagga tacacttaat aaggttttgg atagaatgct tgaacaagtt    1200
tcagaggatg atggaatcct tcaagtttac ttcgatgttg aaagacctag gattgatcca    1260
gttgttgttg ctaacactgt tttctttttc catttgggaa aaagaggtca tgaggttgct    1320
agatcagaaa agtttgttga gtctgttctt ttgcaaagag cttacgaaga gggaactttg    1380
tattacaatc ttggtgaagc ttttcttgtt tctgttgcta gacttgttca tgagtttaag    1440
gagcatttta caaggtctgg aatgagaagg gctttggaag agagacttag ggaaagagct    1500
agggctggta tgcaagagag agatgatgct cttgctttgg ctatgagaat tagggcttgt    1560
gctctttgcg gtttggctgg agaaggtctt acaaaggctg ctgaacaaga gcttttgaga    1620
ttgcaatgca gtctaaagg atgttgggg tgccatccat tctacaggaa tggttctaac    1680
gttttgtcat ggattggttc tgaggctctt actacagctt acgctattgc tgctcttcaa    1740
cctattgata tttga                                                     1755
```

<210> SEQ ID NO 34
<211> LENGTH: 1755
<212> TYPE: DNA
<213> ORGANISM: Artificial Sequence
<220> FEATURE:
<223> OTHER INFORMATION: Codon-optimized sequence of DfHAD-8(K532R) by Genscript genetic codon frequency of E. coli

<400> SEQUENCE: 34

```
atggagttca gcgcgagcgc tccgccgccg cgtctggcga gcgtgatcat tctggaaccg      60
ctgggttttc tgctgacccc gcactacagc agccagctgc gaagaaact gctgcgtcgt     120
ctgctgtgca cccgtatctg gcaccgttat cagcgtggcc gtctgcgtct gcgtgacgcg    180
gcgatgctgc tggcgcaact gccgttcctg gcggttagcg accaccgtg ggcgctggat     240
aacctggcga gcctgctgcg tccgaccgcg gttcgtgcgg tgccgtggat gctgctgctg    300
ctggactttc tgcgtgatga gctgcacctg aaagtggttt gcgcgaccaa cagcagcccg    360
gaggaactgc aggaactgcg tcaccaattc ccggcgctgt ttgcgaaggt tgacgcgacc    420
gtgagcagcg gcgaggaagg tgttggcaaa ccgagcgtgc gtttcctgca gcggcgctg    480
gataaggcgg gcgtgcacgc gcagcaaacc ctgtacctgg acagctttga tagcctggag   540
accatcatgg cggcgcgtag cctgggtatg cacgcgctga gcgttgagcc gtgccacatt   600
gacgaactga ccgcgcgtgc gagcagcggt cagctgcgtg atgcgcaact gatccgtcgt   660
attgtttgcg cgatgcacgg tccggctgtg agcgcggtg ttagcggtag catcaccagc    720
agcggtccgc agaccgcgaa aattgaggaa ctgccgaccg cggcggacag ccacctgcgt   780
agcgcggcgc tgaccagcgc gcagcaattc tttctgaaag tgattgcgcc gcaccgtccg   840
gagaagccgt tcgttcaact gccgagcctg accagcgaag gtatccgtat ttatgacacc   900
ttcgcgcagt ttgtgatcgc ggatctgctg acgataccc gttcctgcc gatgcaaagc     960
ccgccgccga acggcctgat tacctttgtt aacccgagcg cgtacctggc ggacgatatc   1020
aaaaacggta cagccacat tgttccgggc gtgcagttct atgcgagcga cgcgtgcacc   1080
ctgatcgata ttccgcacga cctggatacc accagcgttg gtctgagcgt gctgcacaag   1140
tttggcaaag ttgacaagga taccctgaac aaggtgctgg atcgtatgct ggagcaagtt   1200
agcgaagacg atggtatcct gcaagtttac tttgacgtgg agcgtccgcg tattgatccg   1260
gtggttgtgg cgaacaccgt gttcctgtt cacctgggta acgtggcca cgaagttgcg    1320
cgtagcgaga agttcgttga aagcgtgctg ctgcagcgtg cgtacgagga aggcaccctg   1380
tactataacc tgggcgaagc gtttctggtt agcgtggcgc gtctggtgca cgagttcaaa   1440
gaacacttta cccgtagcgg tatgcgtcgt gcgctggagg aacgtctgcg tgagcgtgcg   1500
cgtgcgggta tgcaagaacg tgacgatgcg ctggcgctgg cgatgcgtat ccgtgcgtgc   1560
gcgctgtgcg gtctggcggg cgagggtctg acccgggcgg cggagcagga actgctgcgt   1620
ctgcaatgca agagcaaagg ttgctggggc tgccacccgt tctaccgtaa cggtagcaac   1680
gttctgagct ggatcggcag cgaagcgctg accaccgcgt atgcgattgc ggcgctgcag   1740
ccgatcgaca tttaa                                                    1755
```

<210> SEQ ID NO 35  
<211> LENGTH: 1755  
<212> TYPE: DNA  
<213> ORGANISM: Artificial Sequence  
<220> FEATURE:  
<223> OTHER INFORMATION: Codon-optimized sequence of DfHAD-9(V274A) by Genscript genetic codon frequency of E. coli

<400> SEQUENCE: 35

```
atggagttca gcgcgagcgc tccgccgccg cgtctggcga gcgtgatcat tctggaaccg      60
ctgggttttc tgctgacccc gcactacagc agccagctgc gaagaaact gctgcgtcgt     120
ctgctgtgca cccgtatctg gcaccgttat cagcgtggcc gtctgcgtct gcgtgacgcg    180
```

-continued

```
gcgatgctgc tggcgcaact gccgttcctg gcggttagcg accacccgtg ggcgctggat        240
aacctggcga gcctgctgcg tccgaccgcg gttcgtgcgg tgccgtggat gctgctgctg        300
ctggactttc tgcgtgatga gctgcacctg aaagtggttt gcgcgaccaa cagcagcccg        360
gaggaactgc aggaactgcg tcaccaattc ccggcgctgt ttgcgaaggt tgacgcgacc        420
gtgagcagcg gcgaggaagg tgttggcaaa ccgagcgtgc gtttcctgca agcggcgctg        480
gataaggcgg gcgtgcacgc gcagcaaacc ctgtacctgg acagctttga tagcctggag        540
accatcatgg cggcgcgtag cctgggtatg cacgcgctga gcgttgagcc gtgccacatt        600
gacgaactga ccgcgcgtgc gagcagcggt cagctgcgtg atgcgcaact gatccgtcgt        660
attgtttgcg cgatgcacgg tccggctgtg agcgcggtgg ttagcggtag catcaccagc        720
agcggtccgc agaccgcgaa aattgaggaa ctgccgaccg cggcggacag ccacctgcgt        780
agcgcggcgc tgaccagcgc gcagcaattc tttctgaaag cgattgcgcc gcaccgtccg        840
gagaagccgt tcgttcaact gccgagcctg accagcgaag gtatccgtat ttatgacacc        900
ttcgcgcagt ttgtgatcgc ggatctgctg gacgataccc gtttcctgcc gatgcaaagc        960
ccgccgccga acggcctgat taccttttgtt aacccgagcg cgtacctggc ggacgatatc       1020
aaaaacggta cagccacat tgttccgggc gtgcagttct atgcgagcga cgcgtgcacc        1080
ctgatcgata ttccgcacga cctggatacc accagcgttg gtctgagcgt gctgcacaag       1140
tttggcaaag ttgacaagga taccctgaac aaggtgctgg atcgtatgct ggagcaagtt       1200
agcgaagacg atggtatcct gcaagtttac tttgacgtgg agcgtccgcg tattgatccg       1260
gtggttgtgg cgaacaccgt gttcctgttt cacctgggta acgtggcca cgaagttgcg        1320 cgtagcgaga agttcgttga aagcgtgctg ctgcagcgtg cgtacgagga aggcacccctg      1380 tactataacc tgggcgaagc gtttctggtt agcgtggcgc gtctggtgca cgagttcaaa       1440
gaacacttta cccgtagcgg tatgcgtcgt gcgctggagg aacgtctgcg tgagcgtgcg       1500
cgtgcgggta tgcaagaacg tgacgatgcg ctggcgctgg cgatgcgtat ccgtgcgtgc       1560
gcgctgtgcg gtctggcggg cgagggtctg accaaggcgg cggagcagga actgctgcgt       1620
ctgcaatgca agagcaaagg ttgctggggc tgccacccgt tctaccgtaa cggtagcaac       1680
gttctgagct ggatcggcag cgaagcgctg accaccgcgt atgcgattgc ggcgctgcag       1740
ccgatcgaca tttaa                                                         1755
```

<210> SEQ ID NO 36
<211> LENGTH: 2496
<212> TYPE: DNA
<213> ORGANISM: Artificial Sequence
<220> FEATURE:
<223> OTHER INFORMATION: Codon-optimized sequence of DfHAD-6His-GST by Genscript genetic codon frequency of E. coli
<220> FEATURE:
<221> NAME/KEY: CDS
<222> LOCATION: (1)..(2496)

<400> SEQUENCE: 36

```
atg tct ggt tct cat cat cat cat cat cat agc agc ggt atg tcc cct         48
Met Ser Gly Ser His His His His His His Ser Ser Gly Met Ser Pro
1               5                   10                  15 ata cta ggt tat tgg aaa att aag ggc ctt gtg caa ccc act cga ctt         96
Ile Leu Gly Tyr Trp Lys Ile Lys Gly Leu Val Gln Pro Thr Arg Leu
            20                  25                  30 ctt ttg gaa tat ctt gaa gaa aaa tat gaa gag cat ttg tat gag cgc        144
Leu Leu Glu Tyr Leu Glu Glu Lys Tyr Glu Glu His Leu Tyr Glu Arg
        35                  40                  45
```

```
gat gaa ggt gat aaa tgg cga aac aaa aag ttt gaa ttg ggt ttg gag     192
Asp Glu Gly Asp Lys Trp Arg Asn Lys Lys Phe Glu Leu Gly Leu Glu
     50              55                  60 ttt ccc aat ctt cct tat tat att gat ggt gat gtt aaa tta aca cag     240
Phe Pro Asn Leu Pro Tyr Tyr Ile Asp Gly Asp Val Lys Leu Thr Gln
65              70                  75                  80 tct atg gcc atc ata cgt tat ata gct gac aag cac aac atg ttg ggt     288
Ser Met Ala Ile Ile Arg Tyr Ile Ala Asp Lys His Asn Met Leu Gly
                85                  90                  95 ggt tgt cca aaa gag cgt gca gag att tca atg ctt gaa gga gcg gtt     336
Gly Cys Pro Lys Glu Arg Ala Glu Ile Ser Met Leu Glu Gly Ala Val
            100                 105                 110 ttg gat att aga tac ggt gtt tcg aga att gca tat agt aaa gac ttt     384
Leu Asp Ile Arg Tyr Gly Val Ser Arg Ile Ala Tyr Ser Lys Asp Phe
        115                 120                 125 gaa act ctc aaa gtt gat ttt ctt agc aag cta cct gaa atg ctg aaa     432
Glu Thr Leu Lys Val Asp Phe Leu Ser Lys Leu Pro Glu Met Leu Lys
130                 135                 140 atg ttc gaa gat cgt tta tgt cat aaa aca tat tta aat ggt gat cat     480
Met Phe Glu Asp Arg Leu Cys His Lys Thr Tyr Leu Asn Gly Asp His
145                 150                 155                 160 gta acc cat cct gac ttc atg ttg tat gac gct ctt gat gtt gtt tta     528
Val Thr His Pro Asp Phe Met Leu Tyr Asp Ala Leu Asp Val Val Leu
                165                 170                 175 tac atg gac cca atg tgc ctg gat gcg ttc cca aaa tta gtt tgt ttt     576
Tyr Met Asp Pro Met Cys Leu Asp Ala Phe Pro Lys Leu Val Cys Phe
            180                 185                 190 aaa aaa cgt att gaa gct atc cca caa att gat aag tac ttg aaa tcc     624
Lys Lys Arg Ile Glu Ala Ile Pro Gln Ile Asp Lys Tyr Leu Lys Ser
        195                 200                 205 agc aag tat ata gca tgg cct ttg cag ggc tgg caa gcc acg ttt ggt     672
Ser Lys Tyr Ile Ala Trp Pro Leu Gln Gly Trp Gln Ala Thr Phe Gly
210                 215                 220 ggt ggc gac cat cct cca aaa tcg gat ctg ggc cac aca ggc cat aga     720
Gly Gly Asp His Pro Pro Lys Ser Asp Leu Gly His Thr Gly His Arg
225                 230                 235                 240 tct gac gac gac gac aag cat atg gag ttc agc gcg agc gct ccg ccg     768
Ser Asp Asp Asp Asp Lys His Met Glu Phe Ser Ala Ser Ala Pro Pro
                245                 250                 255 ccg cgt ctg gcg agc gtg atc att ctg gaa ccg ctg ggt ttt ctg ctg     816
Pro Arg Leu Ala Ser Val Ile Ile Leu Glu Pro Leu Gly Phe Leu Leu
            260                 265                 270 acc ccg cac tac agc agc cag ctg ccg aag aaa ctg ctg cgt cgt ctg     864
Thr Pro His Tyr Ser Ser Gln Leu Pro Lys Lys Leu Leu Arg Arg Leu
        275                 280                 285 ctg tgc acc cgt atc tgg cac cgt tat cag cgt ggc cgt ctg cgt ctg     912
Leu Cys Thr Arg Ile Trp His Arg Tyr Gln Arg Gly Arg Leu Arg Leu
290                 295                 300 cgt gac gcg gcg atg ctg ctg gcg caa ctg ccg ttc ctg gcg gtt agc     960
Arg Asp Ala Ala Met Leu Leu Ala Gln Leu Pro Phe Leu Ala Val Ser
305                 310                 315                 320 gac cac ccg tgg gcg ctg gat aac ctg gcg agc ctg ctg cgt ccg acc    1008
Asp His Pro Trp Ala Leu Asp Asn Leu Ala Ser Leu Leu Arg Pro Thr
                325                 330                 335 gcg gtt cgt gcg gtg ccg tgg atg ctg ctg ctg gac ttt ctg cgt        1056
Ala Val Arg Ala Val Pro Trp Met Leu Leu Leu Asp Phe Leu Arg
            340                 345                 350 gat gag ctg cac ctg aaa gtg gtt tgc gcg acc aac agc agc ccg gag    1104
Asp Glu Leu His Leu Lys Val Val Cys Ala Thr Asn Ser Ser Pro Glu
```

```
                  355                 360                 365
gaa ctg cag gaa ctg cgt cac caa ttc ccg gcg ctg ttt gcg aag gtt        1152
Glu Leu Gln Glu Leu Arg His Gln Phe Pro Ala Leu Phe Ala Lys Val
    370                 375                 380 gac gcg acc gtg agc agc ggc gag gaa ggt gtt ggc aaa ccg agc gtg        1200
Asp Ala Thr Val Ser Ser Gly Glu Glu Gly Val Gly Lys Pro Ser Val
385                 390                 395                 400 cgt ttc ctg caa gcg gcg ctg gat aag gcg ggc gtg cac gcg cag caa        1248
Arg Phe Leu Gln Ala Ala Leu Asp Lys Ala Gly Val His Ala Gln Gln
                405                 410                 415 acc ctg tac ctg gac agc ttt gat agc ctg gag acc atc atg gcg gcg        1296
Thr Leu Tyr Leu Asp Ser Phe Asp Ser Leu Glu Thr Ile Met Ala Ala
            420                 425                 430 cgt agc ctg ggt atg cac gcg ctg agc gtt gag ccg tgc cac att gac        1344
Arg Ser Leu Gly Met His Ala Leu Ser Val Glu Pro Cys His Ile Asp
        435                 440                 445 gaa ctg acc gcg cgt gcg agc agc ggt cag ctg cgt gat gcg caa ctg        1392
Glu Leu Thr Ala Arg Ala Ser Ser Gly Gln Leu Arg Asp Ala Gln Leu
    450                 455                 460 atc cgt cgt att gtt tgc gcg atg cac ggt ccg gct gtg agc gcg gtg        1440
Ile Arg Arg Ile Val Cys Ala Met His Gly Pro Ala Val Ser Ala Val
465                 470                 475                 480 gtt agc ggt agc atc acc agc agc ggt ccg cag acc gcg aaa att gag        1488
Val Ser Gly Ser Ile Thr Ser Ser Gly Pro Gln Thr Ala Lys Ile Glu
                485                 490                 495 gaa ctg ccg acc gcg gcg gac agc cac ctg cgt agc gcg gcg ctg acc        1536
Glu Leu Pro Thr Ala Ala Asp Ser His Leu Arg Ser Ala Ala Leu Thr
            500                 505                 510 agc gcg cag caa ttc ttt ctg aaa gtg att gcg ccg cac cgt ccg gag        1584
Ser Ala Gln Gln Phe Phe Leu Lys Val Ile Ala Pro His Arg Pro Glu
        515                 520                 525 aag ccg ttc gtt caa ctg ccg agc ctg acc agc gaa ggt atc cgt att        1632
Lys Pro Phe Val Gln Leu Pro Ser Leu Thr Ser Glu Gly Ile Arg Ile
    530                 535                 540 tat gac acc ttc gcg cag ttt gtg atc gcg gat ctg ctg gac gat acc        1680
Tyr Asp Thr Phe Ala Gln Phe Val Ile Ala Asp Leu Leu Asp Asp Thr
545                 550                 555                 560 cgt ttc ctg ccg atg caa agc ccg ccg ccg aac ggc ctg att acc ttt        1728
Arg Phe Leu Pro Met Gln Ser Pro Pro Pro Asn Gly Leu Ile Thr Phe
                565                 570                 575 gtt aac ccg agc gcg tac ctg gcg gac gat atc aaa aac ggt aac agc        1776
Val Asn Pro Ser Ala Tyr Leu Ala Asp Asp Ile Lys Asn Gly Asn Ser
            580                 585                 590 cac att gtt ccg ggc gtg cag ttc tat gcg agc gac gcg tgc acc ctg        1824
His Ile Val Pro Gly Val Gln Phe Tyr Ala Ser Asp Ala Cys Thr Leu
        595                 600                 605 atc gat att ccg cac gac ctg gat acc acc agc gtt ggt ctg agc gtg        1872
Ile Asp Ile Pro His Asp Leu Asp Thr Thr Ser Val Gly Leu Ser Val
    610                 615                 620 ctg cac aag ttt ggc aaa gtt gac aag gat acc ctg aac aag gtg ctg        1920
Leu His Lys Phe Gly Lys Val Asp Lys Asp Thr Leu Asn Lys Val Leu
625                 630                 635                 640 gat cgt atg ctg gag caa gtt agc gaa gac gat ggt atc ctg caa gtt        1968
Asp Arg Met Leu Glu Gln Val Ser Glu Asp Asp Gly Ile Leu Gln Val
                645                 650                 655 tac ttt gac gtg gag cgt ccg cgt att gat ccg gtg gtt gtg gcg aac        2016
Tyr Phe Asp Val Glu Arg Pro Arg Ile Asp Pro Val Val Val Ala Asn
            660                 665                 670 acc gtg ttc ctg ttt cac ctg ggt aaa cgt ggc cac gaa gtt gcg cgt        2064
```

```
Thr Val Phe Leu Phe His Leu Gly Lys Arg Gly His Glu Val Ala Arg
            675                 680                 685 agc gag aag ttc gtt gaa agc gtg ctg ctg cag cgt gcg tac gag gaa      2112
Ser Glu Lys Phe Val Glu Ser Val Leu Leu Gln Arg Ala Tyr Glu Glu
        690                 695                 700 ggc acc ctg tac tat aac ctg ggc gaa gcg ttt ctg gtt agc gtg gcg      2160
Gly Thr Leu Tyr Tyr Asn Leu Gly Glu Ala Phe Leu Val Ser Val Ala
705                 710                 715                 720 cgt ctg gtg cac gag ttc aaa gaa cac ttt acc cgt agc ggt atg cgt      2208
Arg Leu Val His Glu Phe Lys Glu His Phe Thr Arg Ser Gly Met Arg
                725                 730                 735 cgt gcg ctg gag gaa cgt ctg cgt gag cgt gcg cgt gcg ggt atg caa      2256
Arg Ala Leu Glu Glu Arg Leu Arg Glu Arg Ala Arg Ala Gly Met Gln
            740                 745                 750 gaa cgt gac gat gcg ctg gcg ctg gcg atg cgt atc cgt gcg tgc gcg      2304
Glu Arg Asp Asp Ala Leu Ala Leu Ala Met Arg Ile Arg Ala Cys Ala
        755                 760                 765 ctg tgc ggt ctg gcg ggc gag ggt ctg acc aag gcg gcg gag cag gaa      2352
Leu Cys Gly Leu Ala Gly Glu Gly Leu Thr Lys Ala Ala Glu Gln Glu
770                 775                 780 ctg ctg cgt ctg caa tgc aag agc aaa ggt tgc tgg ggc tgc cac ccg      2400
Leu Leu Arg Leu Gln Cys Lys Ser Lys Gly Cys Trp Gly Cys His Pro
785                 790                 795                 800 ttc tac cgt aac ggt agc aac gtt ctg agc tgg atc ggc agc gaa gcg      2448
Phe Tyr Arg Asn Gly Ser Asn Val Leu Ser Trp Ile Gly Ser Glu Ala
                805                 810                 815 ctg acc acc gcg tat gcg att gcg gcg ctg cag ccg atc gac att taa      2496
Leu Thr Thr Ala Tyr Ala Ile Ala Ala Leu Gln Pro Ile Asp Ile
            820                 825                 830

<210> SEQ ID NO 37
<211> LENGTH: 831
<212> TYPE: PRT
<213> ORGANISM: Artificial Sequence
<220> FEATURE:
<223> OTHER INFORMATION: Synthetic Construct

<400> SEQUENCE: 37

Met Ser Gly Ser His His His His His His Ser Ser Gly Met Ser Pro
1               5                   10                  15

Ile Leu Gly Tyr Trp Lys Ile Lys Gly Leu Val Gln Pro Thr Arg Leu
            20                  25                  30

Leu Leu Glu Tyr Leu Glu Glu Lys Tyr Glu Glu His Leu Tyr Glu Arg
        35                  40                  45

Asp Glu Gly Asp Lys Trp Arg Asn Lys Lys Phe Glu Leu Gly Leu Glu
    50                  55                  60

Phe Pro Asn Leu Pro Tyr Tyr Ile Asp Gly Asp Val Lys Leu Thr Gln
65                  70                  75                  80

Ser Met Ala Ile Ile Arg Tyr Ile Ala Asp Lys His Asn Met Leu Gly
                85                  90                  95

Gly Cys Pro Lys Glu Arg Ala Glu Ile Ser Met Leu Glu Gly Ala Val
            100                 105                 110

Leu Asp Ile Arg Tyr Gly Val Ser Arg Ile Ala Tyr Ser Lys Asp Phe
        115                 120                 125

Glu Thr Leu Lys Val Asp Phe Leu Ser Lys Leu Pro Glu Met Leu Lys
    130                 135                 140

Met Phe Glu Asp Arg Leu Cys His Lys Thr Tyr Leu Asn Gly Asp His
145                 150                 155                 160
```

```
Val Thr His Pro Asp Phe Met Leu Tyr Asp Ala Leu Asp Val Val Leu
            165                 170                 175

Tyr Met Asp Pro Met Cys Leu Asp Ala Phe Pro Lys Leu Val Cys Phe
        180                 185                 190

Lys Lys Arg Ile Glu Ala Ile Pro Gln Ile Asp Lys Tyr Leu Lys Ser
    195                 200                 205

Ser Lys Tyr Ile Ala Trp Pro Leu Gln Gly Trp Gln Ala Thr Phe Gly
    210                 215                 220

Gly Gly Asp His Pro Pro Lys Ser Asp Leu Gly His Thr Gly His Arg
225                 230                 235                 240

Ser Asp Asp Asp Lys His Met Glu Phe Ser Ala Ser Ala Pro Pro
            245                 250                 255

Pro Arg Leu Ala Ser Val Ile Ile Leu Glu Pro Leu Gly Phe Leu Leu
        260                 265                 270

Thr Pro His Tyr Ser Ser Gln Leu Pro Lys Lys Leu Leu Arg Arg Leu
        275                 280                 285

Leu Cys Thr Arg Ile Trp His Arg Tyr Gln Arg Gly Arg Leu Arg Leu
        290                 295                 300

Arg Asp Ala Ala Met Leu Leu Ala Gln Leu Pro Phe Leu Ala Val Ser
305                 310                 315                 320

Asp His Pro Trp Ala Leu Asp Asn Leu Ala Ser Leu Leu Arg Pro Thr
            325                 330                 335

Ala Val Arg Ala Val Pro Trp Met Leu Leu Leu Asp Phe Leu Arg
        340                 345                 350

Asp Glu Leu His Leu Lys Val Val Cys Ala Thr Asn Ser Ser Pro Glu
        355                 360                 365

Glu Leu Gln Glu Leu Arg His Gln Phe Pro Ala Leu Phe Ala Lys Val
    370                 375                 380

Asp Ala Thr Val Ser Ser Gly Glu Glu Gly Val Gly Lys Pro Ser Val
385                 390                 395                 400

Arg Phe Leu Gln Ala Ala Leu Asp Lys Ala Gly Val His Ala Gln Gln
            405                 410                 415

Thr Leu Tyr Leu Asp Ser Phe Asp Ser Leu Glu Thr Ile Met Ala Ala
        420                 425                 430

Arg Ser Leu Gly Met His Ala Leu Ser Val Glu Pro Cys His Ile Asp
    435                 440                 445

Glu Leu Thr Ala Arg Ala Ser Ser Gly Gln Leu Arg Asp Ala Gln Leu
    450                 455                 460

Ile Arg Arg Ile Val Cys Ala Met His Gly Pro Ala Val Ser Ala Val
465                 470                 475                 480

Val Ser Gly Ser Ile Thr Ser Ser Gly Pro Gln Thr Ala Lys Ile Glu
            485                 490                 495

Glu Leu Pro Thr Ala Ala Asp Ser His Leu Arg Ser Ala Ala Leu Thr
        500                 505                 510

Ser Ala Gln Gln Phe Leu Lys Val Ile Ala Pro His Arg Pro Glu
    515                 520                 525

Lys Pro Phe Val Gln Leu Pro Ser Leu Thr Ser Glu Gly Ile Arg Ile
    530                 535                 540

Tyr Asp Thr Phe Ala Gln Phe Val Ile Ala Asp Leu Leu Asp Asp Thr
545                 550                 555                 560

Arg Phe Leu Pro Met Gln Ser Pro Pro Asn Gly Leu Ile Thr Phe
            565                 570                 575

Val Asn Pro Ser Ala Tyr Leu Ala Asp Asp Ile Lys Asn Gly Asn Ser
```

His Ile Val Pro Gly Val Gln Phe Tyr Ala Ser Asp Ala Cys Thr Leu
            580                 585                 590

Ile Asp Ile Pro His Asp Leu Asp Thr Thr Ser Val Gly Leu Ser Val
            595                 600                 605

Leu His Lys Phe Gly Lys Val Asp Lys Asp Thr Leu Asn Lys Val Leu
610                 615                 620

Asp Arg Met Leu Glu Gln Val Ser Glu Asp Asp Gly Ile Leu Gln Val
625                 630                 635                 640

Tyr Phe Asp Val Glu Arg Pro Arg Ile Asp Pro Val Val Ala Asn
            645                 650                 655

Thr Val Phe Leu Phe His Leu Gly Lys Arg Gly His Glu Val Ala Arg
            660                 665                 670

Ser Glu Lys Phe Val Glu Ser Val Leu Leu Gln Arg Ala Tyr Glu Glu
675                 680                 685

Gly Thr Leu Tyr Tyr Asn Leu Gly Glu Ala Phe Leu Val Ser Val Ala
            690                 695                 700

Arg Leu Val His Glu Phe Lys Glu His Phe Thr Arg Ser Gly Met Arg
705                 710                 715                 720

Arg Ala Leu Glu Arg Leu Arg Glu Arg Ala Arg Ala Gly Met Gln
            725                 730                 735

Glu Arg Asp Asp Ala Leu Ala Leu Ala Met Arg Ile Arg Ala Cys Ala
            740                 745                 750

Leu Cys Gly Leu Ala Gly Glu Gly Leu Thr Lys Ala Ala Glu Gln Glu
755                 760                 765

Leu Leu Arg Leu Gln Cys Lys Ser Lys Gly Cys Trp Gly Cys His Pro
            770                 775                 780

Phe Tyr Arg Asn Gly Ser Asn Val Leu Ser Trp Ile Gly Ser Glu Ala
785                 790                 795                 800

Leu Thr Thr Ala Tyr Ala Ile Ala Ala Leu Gln Pro Ile Asp Ile
            805                 810                 815

820                 825                 830

<210> SEQ ID NO 38
<211> LENGTH: 526
<212> TYPE: PRT
<213> ORGANISM: Cryptoporus volvatus
<220> FEATURE:
<221> NAME/KEY: MISC_FEATURE
<222> LOCATION: (1)..(526)
<223> OTHER INFORMATION: CvTps1 protein

<400> SEQUENCE: 38

Met Thr Thr Ile His Arg Arg His Thr Thr Leu Ile Leu Asp Leu Gly
1               5                   10                  15

Asp Val Leu Phe Arg Trp Ser Pro Lys Thr Glu Thr Ala Ile Pro Pro
            20                  25                  30

Arg Gln Leu Lys Glu Ile Leu Thr Ser Val Thr Trp Phe Glu Tyr Glu
        35                  40                  45

Arg Gly Gln Ile Ser Gln Thr Glu Cys Tyr Glu Arg Cys Ala Ala Glu
    50                  55                  60

Phe Lys Val Asp Pro Leu Val Ile Ala Glu Ala Phe Lys Gln Ala Arg
65                  70                  75                  80

Glu Ser Leu Arg Pro Asn Lys Ala Phe Ile Ala Leu Ile Arg Glu Leu
                85                  90                  95

Arg His Gln Met His Gly Asp Leu Thr Val Leu Ala Leu Ser Asn Ile
            100                 105                 110

```
Ser Leu Pro Asp Tyr Glu Tyr Ile Met Ser Leu Ser Ser Asp Trp Ala
            115                 120                 125

Thr Val Phe Asn Arg Val Phe Pro Ser Ala Leu Val Gly Glu Arg Lys
        130                 135                 140

Pro His Leu Gly Cys Tyr Arg Lys Val Ile Ser Glu Met Ser Leu Glu
145                 150                 155                 160

Pro Gln Thr Thr Val Phe Val Asp Asp Lys Leu Asp Asn Val Ala Ser
                165                 170                 175

Ala Arg Ser Leu Gly Met His Gly Ile Val Phe Asp Asn Glu Ala Asn
            180                 185                 190

Val Phe Arg Gln Leu Arg Asn Ile Phe Gly Asn Pro Val Ser Arg Gly
        195                 200                 205

Gln Gly Tyr Leu Arg Lys His Ala Gly Lys Leu Glu Ser Ser Thr Asp
    210                 215                 220

Asn Gly Leu Thr Phe Glu Glu Asn Phe Thr Gln Leu Ile Ile Tyr Glu
225                 230                 235                 240

Val Thr Gln Asp Arg Ser Leu Ile Thr Leu Ser Glu Cys Pro Arg Thr
                245                 250                 255

Trp Asn Phe Phe Arg Gly Gln Pro Leu Phe Ser Glu Ser Phe Pro Asp
            260                 265                 270

Asp Val Asp Thr Thr Ser Val Ala Leu Thr Val Leu Gln Pro Asp Arg
        275                 280                 285

Ala Leu Val Asp Ser Ile Leu Asp Gln Met Leu Glu Tyr Val Asp Ala
    290                 295                 300

Asp Gly Ile Met Gln Thr Tyr Phe Asp Ser Ser Arg Pro Arg Ile Asp
305                 310                 315                 320

Pro Phe Val Cys Val Asn Val Leu Ser Leu Phe Tyr Ala Asn Gly Arg
                325                 330                 335

Gly Arg Glu Leu Pro His Thr Leu Glu Trp Val Tyr Glu Val Leu Leu
            340                 345                 350

His Arg Ala Tyr His Gly Gly Ser Arg Tyr Tyr Leu Ser Pro Asp Cys
        355                 360                 365

Phe Leu Phe Phe Met Ser Arg Leu Leu Lys Arg Ala Asn Asp Ser Ala
    370                 375                 380

Leu Gln Ala Arg Phe Arg Pro Leu Phe Met Glu Arg Val Lys Glu Arg
385                 390                 395                 400

Val Gly Ala Ala Gly Asp Ser Met Asp Leu Ala Phe Arg Ile Leu Ala
                405                 410                 415

Ala Ala Thr Ile Gly Val His Cys Pro Gln Asp Leu Glu Arg Leu Ala
            420                 425                 430

Ala Ala Gln Cys Glu Asp Gly Gly Trp Asp Met Cys Trp Phe Tyr Ala
        435                 440                 445

Phe Gly Ser Thr Gly Ile Lys Ala Gly Asn Arg Gly Leu Thr Thr Ala
    450                 455                 460

Leu Ala Val Ala Ala Ile Arg Thr Ala Leu Gly Arg Pro Pro Ser Pro
465                 470                 475                 480

Ser Pro Ser Asn Ile Ser Ser Ser Lys Leu Asp Ala Pro Asn Ser
                485                 490                 495

Phe Leu Gly Ile Pro Arg Pro Thr Ser Pro Ile Arg Phe Gly Glu Leu
            500                 505                 510

Phe Arg Ser Trp Arg Lys Asn Lys Pro Thr Ala Lys Ser Gln
        515                 520                 525
```

<210> SEQ ID NO 39
<211> LENGTH: 1956
<212> TYPE: DNA
<213> ORGANISM: Cryptoporus volvatus
<220> FEATURE:
<221> NAME/KEY: misc_feature
<222> LOCATION: (1)..(1956)
<223> OTHER INFORMATION: CvTps1 transcript (including non-coding sequences)

<400> SEQUENCE: 39

| | | |
|---|---|---|
| catcccgcct tttgagcatg gcacacaaac agcctttaag gagctccttg gttgcctagt | 60 |
| catgcctcca cctgccccct cctcactcat cccctcgcat cctaaaacat gaccacgatt | 120 |
| caccgtcggc acaccactct catcttggac ctcggcgacg tcctcttccg ctggtcacca | 180 |
| aagaccgaga ccgccatccc ccctcggcag cttaaggaga tacttacctc cgtcacctgg | 240 |
| ttcgagtacg aacgaggcca gatatcccaa acagaatgtt acgaacgatg cgctgcagaa | 300 |
| ttcaaagtcg acccccttagt gatcgctgaa gccttcaagc aagctcgcga gtcattacgg | 360 |
| cccaacaaag cgttcatcgc cttgattcgc gaacttcgcc atcaaatgca tggagacctc | 420 |
| acggtcctcg cccttttccaa catttccctc cccgattacg aatatatcat gtctctgagc | 480 |
| tcggattggg caaccgtctt caatcgcgta ttcccttctg cacttgttgg cgagcgaaaa | 540 |
| ccccatctgg ggtgctaccg caaggtcatt tcggagatga gcttggaacc ccagacaacc | 600 |
| gtatttgtcg atgataagct agacaacgtc gcctctgctc gctcacttgg catgcacggc | 660 |
| atcgtattcg acaacgaagc caatgtcttc cggcaactgc gcaatatctt cgggaatccg | 720 |
| gttagccgcg gtcaaggcta tcttcgcaag catgccggaa agcttgagtc ttctaccgac | 780 |
| aatggcttga cctttgagga gaacttcacc cagctcatca tctacgaggt gacacaagac | 840 |
| aggagtctca tcacgctctc agaatgtccc cgtacctgga atttctttcg aggtcaaccg | 900 |
| ctcttctcgg agtctttccc ggatgatgtg gacacaacat ccgtggcatt gacagtacta | 960 |
| caacccgata gagcgctcgt tgattctatt ctagaccaaa tgcttgaata tgttgacgcc | 1020 |
| gacggcatca tgcagacata cttcgacagc tcgcgaccac gcatagaccc ttttgtttgc | 1080 |
| gtcaatgtgc tttctctgtt ctacgcaaac ggccggggtc gggagctccc tcacacactg | 1140 |
| gagtgggtct atgaagtact cctgcatcgc gcctaccatg gaggctcacg ttactaccta | 1200 |
| tcaccggact gcttttttatt cttcatgagc cgcttgctca agcgcgccaa cgactcggcc | 1260 |
| ctccaggctc ggttccgccc actgttcatg gagagagtga agaacgagt aggggcagcc | 1320 |
| ggagactcaa tggacctggc cttccgcatc ctcgccgcgg ctaccattgg cgtccattgc | 1380 |
| ccccaagatc tagaaagatt ggccgccgcg caatgcgagg acggtggatg ggacatgtgc | 1440 |
| tggttctacg cgttcgggtc gacaggtatc aaggcgggca accgcggcct caccacggcc | 1500 |
| cttgccgtcg cagctatacg aaccgccctc gggcgccccc cctctcccag cccctccaac | 1560 |
| atctcgtcgt cgtcgaagct cgacgctccc aacagcttct tgggcatccc cgcccaacc | 1620 |
| agccccattc gctttggcga acttttccgt tcctggcgaa agaacaaacc gaccgcaaaa | 1680 |
| tctcaatgaa tctcaggttc tcgtgctctc gtgctatctt cgtacttatg ctactcgaca | 1740 |
| ttacccgtcg ctgtctacaa tgatacgggt actttgatga aactgtagat gtatttgtat | 1800 |
| catattgacc tccatccata gtcacctagc tactgttcgt gttatcacct gttgctgtta | 1860 |
| tatgatacaa gatgcccaaa cgagaatgta gaaatgttcc gtacacttgt gtacctgtga | 1920 |
| tgaagctaca taggccttca atcgatcact tggtcc | 1956 |

<210> SEQ ID NO 40
<211> LENGTH: 1581
<212> TYPE: DNA
<213> ORGANISM: Cryptoporus volvatus
<220> FEATURE:
<221> NAME/KEY: misc_feature
<223> OTHER INFORMATION: cDNA

<400> SEQUENCE: 40

| | | | | | |
|---|---|---|---|---|---|
| atgaccacga | ttcaccgtcg | gcacaccact | ctcatcttgg | acctcggcga | cgtcctcttc | 60 |
| cgctggtcac | caaagaccga | gaccgccatc | cccctcggc | agcttaagga | gatacttacc | 120 |
| tccgtcacct | ggttcgagta | cgaacgaggc | cagatatccc | aaacagaatg | ttacgaacga | 180 |
| tgcgctgcag | aattcaaagt | cgacccctta | gtgatcgctg | aagccttcaa | gcaagctcgc | 240 |
| gagtcattac | ggcccaacaa | agcgttcatc | gccttgattc | gcgaacttcg | ccatcaaatg | 300 |
| catggagacc | tcacggtcct | cgccctttcc | aacatttccc | tccccgatta | cgaatatatc | 360 |
| atgtctctga | gctcggattg | ggcaaccgtc | ttcaatcgcg | tattcccttc | tgcacttgtt | 420 |
| ggcgagcgaa | accccatct | ggggtgctac | cgcaaggtca | tttcggagat | gagcttggaa | 480 |
| ccccagacaa | ccgtatttgt | cgatgataag | ctagacaacg | tcgcctctgc | tcgctcactt | 540 |
| ggcatgcacg | gcatcgtatt | cgacaacgaa | gccaatgtct | tccggcaact | gcgcaatatc | 600 |
| ttcgggaatc | cggttagccg | cggtcaaggc | tatcttcgca | agcatgccgg | aaagcttgag | 660 |
| tcttctaccg | acaatggctt | gacctttgag | gagaacttca | cccagctcat | catctacgag | 720 |
| gtgacacaag | acaggagtct | catcacgctc | tcagaatgtc | cccgtacctg | gaatttcttt | 780 |
| cgaggtcaac | cgctcttctc | ggagtctttc | ccggatgatg | tggacacaac | atccgtggca | 840 |
| ttgacagtac | tacaacccga | tagagcgctc | gttgattcta | ttctagacca | aatgcttgaa | 900 |
| tatgttgacg | ccgacggcat | catgcagaca | tacttcgaca | gctcgcgacc | acgcatagac | 960 |
| cctttgtt | gcgtcaatgt | gcttctctg | ttctacgcaa | acggccgggg | tcgggagctc | 1020 |
| cctcacacac | tggagtgggt | ctatgaagta | ctcctgcatc | gcgcctacca | tggaggctca | 1080 |
| cgttactacc | tatcaccgga | ctgctttta | ttcttcatga | gccgcttgct | caagcgcgcc | 1140 |
| aacgactcgg | ccctccaggc | tcggttccgc | ccactgttca | tggagagagt | gaaagaacga | 1200 |
| gtaggggcag | ccggagactc | aatggacctg | gccttccgca | tcctcgccgc | ggctaccatt | 1260 |
| ggcgtccatt | gccccaaga | tctagaaaga | ttggccgccg | cgcaatgcga | ggacggtgga | 1320 |
| tgggacatgt | gctggttcta | cgcgttcggg | tcgacaggta | tcaaggcggg | caaccgcggc | 1380 |
| ctcaccacgg | cccttgccgt | cgcagctata | cgaaccgccc | tcgggcgccc | ccctctccc | 1440 |
| agcccctcca | acatctcgtc | gtcgtcgaag | ctcgacgctc | ccaacagctt | cttgggcatc | 1500 |
| ccgcgcccaa | ccagccccat | tcgctttggc | gaacttttcc | gttcctggcg | aaagaacaaa | 1560 |
| ccgaccgcaa | aatctcaatg | a | | | | 1581 |

<210> SEQ ID NO 41
<211> LENGTH: 1581
<212> TYPE: DNA
<213> ORGANISM: Artificial Sequence
<220> FEATURE:
<223> OTHER INFORMATION: codon optimized cDNA

<400> SEQUENCE: 41

| | | | | | |
|---|---|---|---|---|---|
| atgactacga | tccaccgccg | ccatactacg | ctgatcctgg | acctgggtga | tgttctgttc | 60 |
| cgctggtccc | cgaaaaccga | aaccgcaatt | ccgcctcgtc | agctgaaaga | aatcttgacc | 120 |

```
agcgttacct ggttcgagta tgagcgtggc caaattagcc agaccgaatg ctacgagcgt    180
tgtgctgccg agtttaaagt tgatccgctg gttattgccg aagcgtttaa acaagcgcgt    240
gaaagcctgc gtccgaacaa agcgtttatc gcgttgatcc gtgagttgcg ccaccagatg    300
catggtgacc tgacggtcct ggcactgagc aacattagcc tgcctgatta tgagtacatt    360
atgtcgctga gctccgattg ggcgacggtc tttaatcgcg tgtttccgag cgcactggtg    420
ggtgagcgta agccacacct gggttgctac cgcaaggtca tcagcgagat gtctctggag    480
ccgcagacca cggttttcgt cgatgacaaa ctggacaatg tcgcaagcgc tcgtagcctg    540
ggcatgcatg gcatcgtgtt cgacaacgaa gcgaacgttt ttcgtcagct gcgtaatatc    600
ttcggtaacc cggttagccg cggtcaaggt tacttgcgta acacgccgg taaactggaa    660 tctagcacgg ataatggtct gaccttcgaa gagaacttca ctcaattaat tatttacgaa    720
gtcacgcaag accgcagcct gatcaccctg agcgagtgcc cgcgtacctg gaacttcttc    780
cgcggtcaac cactgttttc tgagagcttt ccggacgacg tggacaccac ctctgtggcg    840
ttgaccgttc tgcagccgga tcgtgcgttg gtggatagca tcctggacca gatgttggaa    900
tatgttgacg cggatggtat tatgcaaacc tactttgatt catcccgtcc gcgcattgac    960
ccgttcgtgt gcgtgaatgt cctgagcctg ttctacgcca atggcagagg ccgcgagctg   1020
ccacacacgc tggaatgggt ctatgaagtt ctgctgcacc gtgcgtacca cggcggtagc   1080
cgttattacc tgagcccgga ctgtttcctg ttctttatga gccgtctgct gaagcgcgcg   1140
aatgactcgg cgctgcaggc ccgttttcgc ccgcttttca tggaacgtgt gaaagagcgt   1200
gtgggcgcag ccggcgatag catggacctg gcgttccgca ttctggccgc tgcaaccatc   1260
ggcgttcatt gcccacaaga tctggagcgt ctggcagcag cgcagtgcga agatggtggc   1320
tgggatatgt gttggtttta tgcgtttggc agcacgggta tcaaggctgg caaccgcggt   1380
ctgaccaccg cgttggctgt cgccgcaatt cgtaccgcgc tgggtcgtcc gccttccccg   1440
agcccgagca atatttctag ctccagcaaa ctggacgcgc cgaactcctt cctgggcatc   1500
ccgcgtccga ccagcccgat ccgtttcggt gaactgtttc gtagctggcg taagaacaag   1560
ccgaccgcga aaagccagta a                                              1581
```

<210> SEQ ID NO 42
<211> LENGTH: 521
<212> TYPE: PRT
<213> ORGANISM: Laricifomes officinalis
<220> FEATURE:
<221> NAME/KEY: MISC_FEATURE
<222> LOCATION: (1)..(521)
<223> OTHER INFORMATION: LoTps1 protein

<400> SEQUENCE: 42

```
Met Tyr Thr Ala Leu Ile Leu Asp Leu Gly Asp Val Leu Phe Ser Trp
1               5                   10                  15

Ser Ser Thr Thr Asn Thr Thr Ile Pro Pro Arg Gln Leu Lys Glu Ile
            20                  25                  30

Leu Ser Ser Pro Ala Trp Phe Glu Tyr Glu Arg Gly Arg Ile Thr Gln
        35                  40                  45

Ala Glu Cys Tyr Glu Arg Val Ser Ala Glu Phe Ser Leu Asp Ala Thr
    50                  55                  60

Ala Val Ala Glu Ala Phe Arg Gln Ala Arg Asp Ser Leu Arg Pro Asn
65                  70                  75                  80

Asp Lys Phe Leu Thr Leu Ile Arg Glu Leu Arg Gln Gln Ser His Gly
                85                  90                  95
```

```
Glu Leu Thr Val Leu Ala Leu Ser Asn Ile Ser Leu Pro Asp Tyr Glu
            100                 105                 110

Phe Ile Met Ala Leu Asp Ser Lys Trp Thr Ser Val Phe Asp Arg Val
            115                 120                 125

Phe Pro Ser Ala Leu Val Gly Glu Arg Lys Pro His Leu Gly Ala Phe
            130                 135                 140

Arg Gln Val Leu Ser Glu Met Asn Leu Asp Pro His Thr Thr Val Phe
145                 150                 155                 160

Val Asp Asp Lys Leu Asp Asn Val Val Ser Ala Arg Ser Leu Gly Met
                165                 170                 175

His Gly Val Val Phe Asp Ser Gln Asp Asn Val Phe Arg Met Leu Arg
            180                 185                 190

Asn Ile Phe Gly Asp Pro Ile His Arg Gly Arg Asp Tyr Leu Arg Gln
            195                 200                 205

His Ala Gly Arg Leu Glu Thr Ser Thr Asp Ala Gly Val Val Phe Glu
            210                 215                 220

Glu Asn Phe Thr Gln Leu Ile Ile Tyr Glu Leu Thr Asn Asp Lys Ser
225                 230                 235                 240

Leu Ile Thr Thr Ser Asn Cys Ala Arg Thr Trp Asn Phe Phe Arg Gly
                245                 250                 255

Lys Pro Leu Phe Ser Ala Ser Phe Pro Asp Asp Met Asp Thr Thr Ser
            260                 265                 270

Val Ala Leu Thr Val Leu Arg Leu Asp His Ala Leu Val Asn Ser Val
            275                 280                 285

Leu Asp Glu Met Leu Lys Tyr Val Asp Ala Asp Gly Ile Met Gln Thr
            290                 295                 300

Tyr Phe Asp His Thr Arg Pro Arg Met Asp Pro Phe Val Cys Val Asn
305                 310                 315                 320

Val Leu Ser Leu Phe His Glu Gln Gly Arg Gly His Glu Leu Pro Asn
                325                 330                 335

Thr Leu Glu Trp Val His Glu Val Leu Leu His Arg Ala Tyr Ile Gly
            340                 345                 350

Gly Ser Arg Tyr Tyr Leu Ser Ala Asp Cys Phe Leu Phe Phe Met Ser
            355                 360                 365

Arg Leu Leu Gln Arg Ile Thr Asp Pro Ser Val Leu Gly Arg Phe Arg
            370                 375                 380

Pro Leu Phe Ile Glu Arg Val Arg Glu Arg Val Gly Ala Thr Gly Asp
385                 390                 395                 400

Ser Ile Asp Leu Ala Phe Arg Ile Ile Ala Ala Ser Thr Val Gly Ile
                405                 410                 415

Gln Cys Pro Arg Asp Leu Glu Ser Leu Leu Ala Ala Gln Cys Glu Asp
            420                 425                 430

Gly Gly Trp Asp Leu Cys Trp Phe Tyr Gln Tyr Gly Ser Thr Gly Val
            435                 440                 445

Lys Ala Gly Asn Arg Gly Leu Thr Thr Ala Leu Ala Ile Lys Ala Ile
            450                 455                 460

Asp Ser Ala Ile Ala Arg Pro Pro Ser Pro Ala Leu Ser Val Ala Ser
465                 470                 475                 480

Ser Ser Lys Ser Glu Ile Pro Lys Pro Ile Gln Arg Ser Leu Arg Pro
                485                 490                 495

Leu Ser Pro Arg Arg Phe Gly Gly Phe Leu Met Pro Trp Arg Arg Ser
            500                 505                 510
```

Gln Arg Asn Gly Val Ala Val Ser Ser
        515                 520

<210> SEQ ID NO 43
<211> LENGTH: 2291
<212> TYPE: DNA
<213> ORGANISM: Laricifomes officinalis
<220> FEATURE:
<221> NAME/KEY: misc_feature
<222> LOCATION: (1)..(2291)
<223> OTHER INFORMATION: LoTps1 transcript (including non-coding
      sequence)

<400> SEQUENCE: 43

| | | | | |
|---|---|---|---|---|
| gcgtctgctg | cggtctctca | ccgcgccgag | cgacgggaag | cggaggcttt ttgatgcagc | 60 |
| cagctcagcg | ccatcctctc | acgcaggggg | tttgatccag | atctgatcgc ctccgggttc | 120 |
| tcatctagaa | cgcacggcgg | ctcccaggaa | gttctatcga | ccctctgcgc gctggtcggc | 180 |
| ggcacgatgt | ggctacacca | gtcccaatca | tatctcacac | ccagcaccat catctcgggc | 240 |
| ctcttcgtca | tgtaaccctc | ccaagcctat | ttttcagggc | gttcccctc accggcgcgc | 300 |
| ttcttaaaga | atcccgaaat | gtatacggct | cttatccttg | acctcggcga cgttctgttc | 360 |
| tcttggtcgt | cgacgaccaa | cacgactatt | cccctcggc | agctaaagga gatcctctca | 420 |
| tctcctgcct | ggtttgagta | cgagcgtggt | cgcataacgc | aagccgaatg ctacgagcgt | 480 |
| gtcagcgccg | agttcagcct | agacgccacc | gccgtcgcgg | aagcattccg gcaagctcgc | 540 |
| gactccttgc | gcccgaacga | caagttcctc | acgttaattc | gcgagcttcg acaacaatct | 600 |
| catggggagc | tcacggtgct | tgcgctgtcc | aacatatccc | ttcccgacta tgaattcatc | 660 |
| atggccctcg | actcgaagtg | gacttctgtc | tttgaccgcg | tcttcccttc tgccctcgtg | 720 |
| ggcgaacgga | agccacacct | tggagcgttt | cgccaggttc | tgtccgagat gaatcttgac | 780 |
| ccgcacacaa | ctgtgttcgt | cgatgacaag | ctggacaatg | tcgtctccgc acggtccctc | 840 |
| gggatgcacg | cgtcgtgtt | cgactcccaa | gacaatgtct | tcggatgct gagaaacatc | 900 |
| tttggcgatc | ccattcatcg | gggacgtgac | tatctccgac | agcacgccgg acgtctggag | 960 |
| acctccacgg | atgccggtgt | ggtcttcgaa | gagaatttca | cgcaactcat catctacgaa | 1020 |
| ctgacgaatg | acaagtctct | catcacgaca | tcaaactgtg | ctcgtacttg gaatttcttt | 1080 |
| cgtgggaagc | ctttgttctc | agcatcgttc | cctgacgaca | tggacacgac ctcggttgcc | 1140 |
| ttgactgtat | tacgtttaga | ccacgccctc | gtgaactcgg | ttttggacga gatgctaaag | 1200 |
| tatgtcgacg | cagacggcat | catgcagacc | tacttcgacc | atacacgccc acgcatggat | 1260 |
| ccatttgtct | gcgtcaatgt | gctctcgttg | tttcacgaac | aaggtcgtgg ccacgagctt | 1320 |
| ccgaacaccc | tcgaatgggt | ccatgaggtc | ctcctccacc | gcgcgtacat cggggctcg | 1380 |
| cggtactacc | tctccgcgga | ctgcttcctc | tttttcatga | gccgcctcct gcagcgcatc | 1440 |
| accgacccgt | ccgtccttgg | ccgcttccgt | ccactattca | tagagcgcgt tcgggagcgt | 1500 |
| gtaggtgcga | ccggggactc | catcgatctc | gcattccgca | tcatcgccgc gtccacagta | 1560 |
| ggcatccagt | gtccacgcga | cttggaaagt | ctcctcgccg | cacagtgtga agacggtggc | 1620 |
| tgggacctgt | gctggttcta | ccagtacgga | tcgaccggtg | tcaaggcggg caaccgcggg | 1680 |
| ctcaccaccg | ctctggcgat | caaagctatt | gactccgcca | ttgcgaggcc accttcgcct | 1740 |
| gccctctcag | tcgcttcgtc | gtccaaatcg | gagataccga | aaccatacaa acggtccctt | 1800 |
| aggcccctta | gccccgccg | gtttggcggt | tcctgatgc | cgtggcgcag gtcacagcgc | 1860 |
| aatggcgtgg | cggtctctag | ttgaacactt | gacccttgac | acttcgcttt gcactgcctg | 1920 |

```
ctcccctgcc aatcctcccc tacgatcgta tcatccctct cttgccctcg cctcccccctc    1980 gtaccccctc tcatggggtg ccatttgtag atatgtacgt agcgtgatgt agcggtactc    2040
ggatcgttct cgtactcgtc ttgctctgcc gtcgcttcca gcccgtgctg ttctctcgtt    2100
caggctattc gttggttacg cgtatatcgt aatagaccgc cccggttcct cgcctacaga    2160
cactcgcccg tctcgccacg gactcggcta cggattcaga ctacatgagt ggcagttatc    2220
acacgcagat ccctccttgg tcgttctgta gtacccacat atgtaattgt accagtccac    2280
tgttgcagat c                                                          2291
```

<210> SEQ ID NO 44
<211> LENGTH: 1566
<212> TYPE: DNA
<213> ORGANISM: Laricifomes officinalis
<220> FEATURE:
<221> NAME/KEY: misc_feature
<223> OTHER INFORMATION: cDNA

<400> SEQUENCE: 44

```
atgtatacgg ctcttatcct tgacctcggc gacgttctgt tctcttggtc gtcgacgacc      60
aacacgacta ttccccctcg gcagctaaag gagatcctct catctcctgc ctggtttgag     120
tacgagcgtg gtcgcataac gcaagccgaa tgctacgagc gtgtcagcgc cgagttcagc     180
ctagacgcca ccgccgtcgc ggaagcattc cggcaagctc gcgactcctt cgcccgaac     240 gacaagttcc tcacgttaat tcgcgagctt cgacaacaat ctcatgggga gctcacggtg     300
cttgcgctgt ccaacatatc ccttcccgac tatgaattca tcatggccct cgactcgaag     360
tggacttctg tctttgaccg cgtcttccct tctgccctcg tgggcgaacg gaagccacac     420
cttggagcgt ttcgccaggt tctgtccgag atgaatcttg acccgcacac aactgtgttc     480
gtcgatgaca agctggacaa tgtcgtctcc gcacggtccc tcgggatgca cggcgtcgtg     540
ttcgactccc aagacaatgt ctttcggatg ctgagaaaca tctttggcga tcccattcat     600
cggggacgtg actatctccg acagcacgcc ggacgtctgg agacctccac ggatgccggt     660
gtggtcttcg aagagaattt cacgcaactc atcatctacg aactgacgaa tgacaagtct     720
ctcatcacga catcaaactg tgctcgtact tggaatttct ttcgtgggaa gcctttgttc     780
tcagcatcgt tccctgacga catggacacg acctcggttg ccttgactgt attacgttta     840
gaccacgccc tcgtgaactc ggttttggac gagatgctaa agtatgtcga cgcagacggc     900
atcatgcaga cctacttcga ccatacacgc ccacgcatgg atccatttgt ctgcgtcaat     960
gtgctctcgt tgtttcacga acaaggtcgt ggccacgagc ttccgaacac cctcgaatgg    1020
gtccatgagg tcctcctcca ccgcgcgtac atcgggggct cgcggtacta cctctccgcg    1080
gactgcttcc tcttttttcat gagccgcctc ctgcagcgca tcaccgaccc gtccgtcctt    1140
ggccgcttcc gtccactatt catagagcgc gttcggagc gtgtaggtgc gaccggggac    1200
tccatcgatc tcgcattccg catcatcgcc gcgtccacag taggcatcca gtgtccacgc    1260
gacttggaaa gtctcctcgc cgcacagtgt gaagacggtg gctgggacct gtgctggttc    1320
taccagtacg gatcgaccgg tgtcaaggcg ggcaaccgcg ggctcaccac cgctctggcg    1380
atcaaagcta ttgactccgc cattgcgagg ccaccttcgc ctgccctctc agtcgcttcg    1440
tcgtccaaat cggagatacc gaaacccata caacggtccc ttaggcccct tagccccgc    1500 cggtttggcg gtttcctgat gccgtggcgc aggtcacagc gcaatggcgt ggcggtctct    1560
agttga                                                                 1566
```

<210> SEQ ID NO 45
<211> LENGTH: 1566
<212> TYPE: DNA
<213> ORGANISM: Artificial Sequence
<220> FEATURE:
<223> OTHER INFORMATION: codon optimized cDNA

<400> SEQUENCE: 45

```
atgtacacgg cgctgatttt ggatttgggt gatgttctgt ttagctggag ctcaacgact      60
aacaccacca ttccgccgcg tcagctgaaa gaaatcttga gctccccggc gtggttcgag     120
tacgagcgtg gccgtatcac ccaggcagag tgttatgagc gtgtcagcgc agagtttagc     180
ctggatgcga cggccgtggc tgaggctttt cgtcaggcac gtgatagcct gcgtccgaac     240
gacaaatttc tgaccctgat ccgtgagctg cgtcaacaga gccacggtga attgaccgtt     300
ctggccttgt ctaacatcag cctgccggat tacgaattta ttatggcact ggactcgaag     360
tggaccagcg tgtttgatcg tgtgttcccg agcgccctgg tgggcgaacg caagccgcac     420
ctgggcgcgt tccgccaagt cctgtccgag atgaatttgg acccgcatac caccgttttt     480
gtggacgaca aactggacaa tgttgtcagc gcacgcagcc tgggtatgca cggtgtcgtg     540
ttcgacagcc aagacaatgt ttttcgtatg ctgcgtaaca ttttcggtga cccaattcac     600
cgcggtcgtg actatctgcg ccagcacgct ggtcgtcttg aaacgtccac cgatgcgggc     660
gttgtgttcg aagagaactt cacccaactg atcatttacg aactgaccaa cgataagagc     720
ctgatcacca cctctaattg cgcccgcacc tggaacttct ccgcggcaa acctctgttc     780
tccgcgagct ttccggacga tatggacact acgtcggtag cgctgaccgt gctgcgtctg     840
gaccatgcgc tggtgaatag cgttctggat gaaatgctga atacgtcga tgctgacggt     900
attatgcaga cctactttga tcatacgcgt cctcgtatgg acccgttcgt ttgcgtcaat     960
gtgctgagcc tgtttcacga gcaaggtcgc ggtcatgaac tgccgaatac gctggaatgg    1020
gtgcatgaag tcctgctgca ccgtgcgtat atcggtggca gccgctatta tctgagcgcg    1080
gattgtttcc tgttctttat gagccgtctg ttgcaacgta ttaccgaccc gagcgtttta    1140
ggtagatttc gcccgctgtt catcgagcgt gttcgcgagc gcgttggcgc gactggcgac    1200
agcatcgacc tggcattccg tatcatcgcg gccagcacgg tcggcattca atgcccgcgt    1260
gacctggagt ctctgctggc agcacagtgc gaagatggtg gctgggatct gtgttggttt    1320
taccagtacg gcagcacggg tgttaaggcc ggtaaccgtg gtctgaccac ggcgttggcg    1380
atcaaagcga ttgacagcgc catcgcgcgt ccgccaagcc cggccctgtc cgttgcaagc    1440
tccagcaaga gcgagattcc gaagccgatt cagcgtagcc tccgcccgtt gagcccgcgt    1500
cgcttcggtg gcttcctgat gccgtggcgt cgtagccaac gcaatggtgt cgcggtgagc    1560
tcttaa                                                              1566
```

<210> SEQ ID NO 46
<211> LENGTH: 527
<212> TYPE: PRT
<213> ORGANISM: Obba rivulosa
<220> FEATURE:
<221> NAME/KEY: MISC_FEATURE
<222> LOCATION: (1)..(527)
<223> OTHER INFORMATION: OCH93767.1 protein

<400> SEQUENCE: 46

Met Ser Ala Ala Val Arg Tyr Thr Thr Leu Ile Leu Asp Leu Gly Asp
1               5                   10                  15

```
Val Leu Phe Thr Trp Ser Pro Lys Thr Lys Thr Ser Ile Ser Pro Arg
             20                  25                  30

Ile Leu Lys Glu Ile Leu Asn Ser Ala Thr Trp Tyr Glu Tyr Glu Arg
         35                  40                  45

Gly Ser Ile Thr Gln His Glu Cys Tyr Glu Arg Val Gly Val Glu Phe
     50                  55                  60

Gly Ile Ala Pro Ser Glu Ile His Asn Ala Phe Lys Gln Ala Arg Asp
 65                  70                  75                  80

Ser Met Glu Ser Asn Asp Glu Leu Ile Ala Leu Val Arg Glu Leu Lys
                 85                  90                  95

Glu Gln Ser Asp Gly Glu Leu Leu Val Phe Ala Leu Ser Asn Ile Ser
             100                 105                 110

Leu Pro Asp Tyr Glu Tyr Val Leu Thr Lys Pro Ala Asp Trp Ser Ile
         115                 120                 125

Phe Asp Lys Val Phe Pro Ser Ala Leu Val Gly Glu Arg Lys Pro His
     130                 135                 140

Leu Gly Ile Tyr Lys His Val Ile Ala Glu Thr Gly Val Asp Pro Arg
145                 150                 155                 160

Thr Thr Val Phe Val Asp Asp Lys Ile Asp Asn Val Leu Ser Ala Arg
                 165                 170                 175

Ser Leu Gly Met His Gly Ile Val Phe Asp Lys His Glu Asp Val Met
             180                 185                 190

Arg Ala Leu Arg Asn Ile Phe Gly Asp Pro Val Arg Arg Gly Arg Glu
         195                 200                 205

Tyr Leu Arg Arg Asn Ala Arg Lys Leu Glu Ser Ile Thr Asp His Gly
     210                 215                 220

Val Ala Phe Gly Glu Asn Phe Thr Gln Leu Leu Ile Leu Glu Leu Thr
225                 230                 235                 240

Ser Asp Ala Ser Leu Val Thr Leu Pro Asp Arg Pro Arg Thr Trp Asn
                 245                 250                 255

Phe Phe Arg Gly Lys Pro Leu Phe Ser Glu Ala Phe Pro Asp Asp Leu
             260                 265                 270

Asp Thr Thr Ser Leu Ala Leu Thr Val Leu Lys Arg Asp Ala Ala Thr
         275                 280                 285

Val Ser Ser Val Met Asp Glu Met Leu Lys Tyr Arg Asp Ala Asp Gly
     290                 295                 300

Ile Met Gln Thr Tyr Phe Asp Asn Gly Arg Gln Arg Leu Asp Pro Phe
305                 310                 315                 320

Val Asn Ala Asn Val Leu Thr Leu Phe Tyr Ala Asn Gly Arg Gly His
                 325                 330                 335

Glu Leu Asp Gln Ser Leu Ser Trp Val Arg Glu Val Leu Leu Tyr Arg
             340                 345                 350

Ala Tyr Leu Gly Gly Ser Arg Tyr Tyr Pro Ser Ala Asp Cys Phe Leu
         355                 360                 365

Tyr Phe Ile Ser Arg Leu Phe Ala Cys Thr Ser Asp Pro Val Leu His
     370                 375                 380

His Gln Leu Lys Pro Leu Phe Val Glu Arg Val His Glu Arg Ile Gly
385                 390                 395                 400

Val Gln Gly Asp Ala Leu Glu Leu Ala Phe Arg Leu Leu Val Cys Ala
                 405                 410                 415

Ser Phe Asn Ile Ser Asn Gln Pro Asp Met Arg Lys Leu Leu Glu Met
             420                 425                 430
```

```
Gln Cys Gln Asp Gly Gly Trp Asp Gly Gly Asn Leu Tyr Arg Phe Gly
            435                 440                 445

Thr Thr Gly Leu Lys Val Thr Asn Arg Gly Leu Thr Thr Ala Ala Ala
    450                 455                 460

Val Gln Ala Ile Glu Ala Thr Gln Leu Arg Pro Pro Ser Pro Ala Phe
465             470                 475                 480

Ser Val Glu Ser Pro Lys Ser Pro Val Thr Pro Val Thr Pro Met Leu
                485                 490                 495

Glu Ile Pro Ala Leu Gly Leu Ser Ile Ser Arg Pro Ser Ser Pro Leu
            500                 505                 510

Leu Gly Tyr Phe Lys Leu Pro Trp Lys Lys Ser Ala Glu Val His
            515                 520                 525
```

<210> SEQ ID NO 47
<211> LENGTH: 1584
<212> TYPE: DNA
<213> ORGANISM: Obba rivulosa
<220> FEATURE:
<221> NAME/KEY: misc_feature
<223> OTHER INFORMATION: cDNA

<400> SEQUENCE: 47

```
atgtccgcag cagttcggta cacgaccctc atcctcgacc ttggcgacgt cttgttcact      60
tggtcaccga agacgaagac cagcatctcg cctcgtattc tgaaggagat cctgaattcc     120
gcgacctggt atgagtacga gcgcggtagt atcactcagc acgaatgtta cgaacgcgtt     180
ggcgtggagt tcggtattgc gccgagcgag atccacaacg cgttcaagca ggctcgggac     240
tctatggagt cgaatgacga gctgatcgcc cttgttcggg aactgaagga gcagtcagat     300
ggagagcttc tcgtcttcgc attatcgaac atctcactgc cggactacga atacgtcctg     360
acgaagcccg cggactggtc catcttcgac aaagtctttc cttccgctct cgtcggcgag     420
cgcaagcccc atctcggcat ctacaaaacg gtcatcgcag agacgggcgt tgatccgcga     480
acaaccgtct tcgtggacga caagatcgac aatgtgcttt cggcgcggtc gctcggtatg     540
cacggcattg tcttcgacaa acacgaagac gtaatgcgcg ctctgcgaaa cattttcggt     600
gaccccgtgc gaagaggacg agaatatttg cgtcgaaatg caaggaaatt ggaatccatc     660
acagatcacg gcgtcgcctt cggggagaac ttcacccagc ttctgatcct cgaacttact     720
agtgatgcgt ccctcgttac tctccctgat cgtcctcgga catggaattt tttccgaggg     780
aagccgctct tttcggaggc cttccccgat gaccttgata ctacttcctt ggcactcact     840
gtcctgaaaa gagatgccgc cactgtatcg tccgtgatgg acgagatgct gaaatacagg     900
gacgcggacg gcatcatgca gacatacttc gacaacggtc ggcaacgact cgatccgttc     960
gtcaacgcca acgttttgac cctcttctac gccaacggtc gcggacacga gctggatcag    1020
agcctcagct gggttcgcga agtcttgctc taccgcgctt acctcggcgg ttcccgctac    1080
taccctccg ccgactgctt cctatatttc atcagccgcc tcttcgcctg caccagcgac    1140
ccggtcctcc atcatcaact taagcccctc tttgttgagc gtgtgcacga gcggatagga    1200
gtgcagggcg acgcgctgga gctcgccttc cgcctgcttg tatgcgcgag cttcaacatc    1260
tcgaaccagc ctgacatgcg caagctgctc gagatgcagt gccaggacgg aggctgggat    1320
ggcggaaacc tgtatcgttt cggcaccacg ggcctcaagg tcacgaaccg gggtctgacc    1380
accgcagcag ccgtgcaagc catcgaggcg acgcagctgc gtccaccatc accggcgttc    1440
tctgtcgagt cgcctaagag cccggtgacg ccggtgacgc ccatgctgga gattccagcg    1500
```
ctgggtctca gcatctcgcg gccctccagt cctctgttgg ggtatttcaa gctcccgtgg 1560
aagaagtcag ccgaggttca ttga 1584

<210> SEQ ID NO 48
<211> LENGTH: 1584
<212> TYPE: DNA
<213> ORGANISM: Artificial Sequence
<220> FEATURE:
<223> OTHER INFORMATION: codon optimized cDNA

<400> SEQUENCE: 48
atgtctgcag ctgttcgtta tactactctg atcctggatt tgggcgatgt tctgttcacc 60
tggtccccga aaccaagac ctctatcagc ccacgtatcc tgaaagaaat cctgaacagc 120
gcgacctggt acgagtatga gcgtggcagc atcacccagc acgagtgcta cgagcgtgtt 180
ggcgtcgaat ttggtattgc gccgagcgag attcacaacg cgttcaaaca gcccgcgac 240 agcatggaat ccaacgacga actgattgct ctggtgcgtg agctgaaaga cagagcgat 300 ggtgagctgc tggtctttgc cctgagcaat atctctctgc cggattacga atacgttctg 360
accaaaccag cggactggtc aatcttcgat aaagtctttc cgagcgcttt ggtcggtgag 420
cgtaaaccgc atctgggtat ttacaaacac gttattgcgg aaaccggtgt tgaccccgaga 480 acgaccgttt tgttgacga taagattgac aacgtcctga gcgcacgcag cctgggtatg 540
catggtattg tctttgataa acacgaagat gtgatgcgtg ctctgcgcaa tatctttggc 600
gacccggtgc gtcgcggtcg tgagtatttg cgccgcaacg cgcgcaaatt ggagtccatt 660
accgatcatg gtgtcgcatt tggtgagaat ttcacccagc tcctgattct ggaactgacc 720
agcgacgcgt ccctggtgac gctgccggat cgtccgcgta cgtggaactt cttccgcggc 780
aagccgctgt ttagcgaagc gttccccggat gacctggaca ccacgagcct ggcactgacg 840
gtgctgaaac gcgatgcagc aactgtgagc tccgtcatgg acgaaatgct gaagtaccgc 900
gacgcggatg gcatcatgca gacgtatttc gacaacggtc gtcagcgtct ggacccgttt 960
gtcaacgcca atgttctgac gctgtttttac gcgaatggcc gtggtcatga actggaccag 1020
agcttatcat gggtgcgtga agtgctgctg tatcgcgcct atctgggtgg cagccgctac 1080
tatccgagcg cggactgttt tctgtacttc attagccgct tgttcgcctg caccagcgat 1140
ccggttctgc atcaccaact gaagccattg ttcgtcgagc gtgtgcacga gcgtattggt 1200
gttcagggcg acgcactgga actggcgttc cgtctgttgg tgtgtgcgag cttcaacatt 1260
agcaatcagc cggatatgcg taagctgctg gaaatgcaat gccaagatgg cggctgggac 1320
ggtggtaatc tgtaccgttt tggcaccacc ggtttaaaag tgacgaatcg tggtttgacc 1380
accgctgcgg ccgttcaagc aattgaagca acgcaactgc gtccgccgag cccagcattt 1440
agcgtagagt cgcctaagag cccggttacg ccggtgacgc cgatgctgga aatcccggcg 1500
ctgggtctgt ctatcagccg tccgtcgagc ccgctgctgg gctatttcaa gttgccgtgg 1560
aagaaaagcg ccgaagtgca ctaa 1584

<210> SEQ ID NO 49
<211> LENGTH: 533
<212> TYPE: PRT
<213> ORGANISM: Gelatoporia subvermispora
<220> FEATURE:
<221> NAME/KEY: MISC_FEATURE
<222> LOCATION: (1)..(533)
<223> OTHER INFORMATION: EMD37666.1 protein

<400> SEQUENCE: 49

```
Met Ser Ala Ala Ala Gln Tyr Thr Thr Leu Ile Leu Asp Leu Gly Asp
1               5                   10                  15
Val Leu Phe Thr Trp Ser Pro Lys Thr Lys Thr Ser Ile Pro Pro Arg
            20                  25                  30
Thr Leu Lys Glu Ile Leu Asn Ser Ala Thr Trp Tyr Glu Tyr Glu Arg
            35                  40                  45
Gly Arg Ile Ser Gln Asp Glu Cys Tyr Glu Arg Val Gly Thr Glu Phe
50                  55                  60
Gly Ile Ala Pro Ser Glu Ile Asp Asn Ala Phe Lys Gln Ala Arg Asp
65                  70                  75                  80
Ser Met Glu Ser Asn Asp Glu Leu Ile Ala Leu Val Arg Glu Leu Lys
                85                  90                  95
Thr Gln Leu Asp Gly Glu Leu Leu Val Phe Ala Leu Ser Asn Ile Ser
            100                 105                 110
Leu Pro Asp Tyr Glu Tyr Val Leu Thr Lys Pro Ala Asp Trp Ser Ile
            115                 120                 125
Phe Asp Lys Val Phe Pro Ser Ala Leu Val Gly Glu Arg Lys Pro His
130                 135                 140
Leu Gly Val Tyr Lys His Val Ile Ala Glu Thr Gly Ile Asp Pro Arg
145                 150                 155                 160
Thr Thr Val Phe Val Asp Asp Lys Ile Asp Asn Val Leu Ser Ala Arg
                165                 170                 175
Ser Val Gly Met His Gly Ile Val Phe Glu Lys Gln Glu Asp Val Met
            180                 185                 190
Arg Ala Leu Arg Asn Ile Phe Gly Asp Pro Val Arg Gly Arg Glu
            195                 200                 205
Tyr Leu Arg Arg Asn Ala Met Arg Leu Glu Ser Val Thr Asp His Gly
210                 215                 220
Val Ala Phe Gly Glu Asn Phe Thr Gln Leu Leu Ile Leu Glu Leu Thr
225                 230                 235                 240
Asn Asp Pro Ser Leu Val Thr Leu Pro Asp Arg Pro Arg Thr Trp Asn
            245                 250                 255
Phe Phe Arg Gly Asn Gly Gly Arg Pro Ser Lys Pro Leu Phe Ser Glu
            260                 265                 270
Ala Phe Pro Asp Asp Leu Asp Thr Thr Ser Leu Ala Leu Thr Val Leu
            275                 280                 285
Gln Arg Asp Pro Gly Val Ile Ser Ser Val Met Asp Glu Met Leu Asn
            290                 295                 300
Tyr Arg Asp Pro Asp Gly Ile Met Gln Thr Tyr Phe Asp Asp Gly Arg
305                 310                 315                 320
Gln Arg Leu Asp Pro Phe Val Asn Val Asn Val Leu Thr Phe Phe Tyr
            325                 330                 335
Thr Asn Gly Arg Gly His Glu Leu Asp Gln Cys Leu Thr Trp Val Arg
            340                 345                 350
Glu Val Leu Leu Tyr Arg Ala Tyr Leu Gly Gly Ser Arg Tyr Tyr Pro
            355                 360                 365
Ser Ala Asp Cys Phe Leu Tyr Phe Ile Ser Arg Leu Phe Ala Cys Thr
            370                 375                 380
Asn Asp Pro Val Leu His His Gln Leu Lys Pro Leu Phe Val Glu Arg
385                 390                 395                 400
Val Gln Glu Gln Ile Gly Val Glu Gly Asp Ala Leu Glu Leu Ala Phe
                405                 410                 415
```

Arg Leu Leu Val Cys Ala Ser Leu Asp Val Gln Asn Ala Ile Asp Met
          420                 425                 430

Arg Arg Leu Leu Glu Met Gln Cys Glu Asp Gly Gly Trp Glu Gly Gly
            435                 440                 445

Asn Leu Tyr Arg Phe Gly Thr Thr Gly Leu Lys Val Thr Asn Arg Gly
        450                 455                 460

Leu Thr Thr Ala Ala Ala Val Gln Ala Ile Glu Ala Ser Gln Arg Arg
465                 470                 475                 480

Pro Pro Ser Pro Ser Pro Ser Val Glu Ser Thr Lys Ser Pro Ile Thr
                485                 490                 495

Pro Val Thr Pro Met Leu Glu Val Pro Ser Leu Gly Leu Ser Ile Ser
            500                 505                 510

Arg Pro Ser Ser Pro Leu Leu Gly Tyr Phe Arg Leu Pro Trp Lys Lys
        515                 520                 525

Ser Ala Glu Val His
    530

<210> SEQ ID NO 50
<211> LENGTH: 1602
<212> TYPE: DNA
<213> ORGANISM: Gelatoporia subvermispora
<220> FEATURE:
<221> NAME/KEY: misc_feature
<223> OTHER INFORMATION: cDNA

<400> SEQUENCE: 50

```
atgtccgcgg cagctcaata cacgaccctc attctcgacc ttggcgacgt cctgttcacc      60
tggtcaccga aaaccaagac gagcatcccc cctcggactc tgaaggagat tctcaattcc     120
gcgacatggt atgagtatga gcgcggccgc atctctcagg acgaatgtta cgaacgcgtt     180
ggcacggagt tcggaatcgc gcctagcgaa atcgacaacg cgttcaagca agctcgggat     240
tccatggaat ccaacgacga actgatcgcc cttgttcggg aactcaagac gcagttggac     300
ggcgaactcc ttgtcttcgc actctcaaat atctcgttgc ctgactacga gtacgtcctc     360
acgaaaccgg ccgactggtc catcttcgac aaggtcttcc cttccgccct cgtgggcgag     420
cgcaagccgc acctcggcgt ttacaagcac gtcattgcag aaacgggcat tgatccgcga     480
accaccgttt tcgtggacga caagatcgac aacgtgctct cagcgcggtc tgtaggtatg     540
catgggatcg ttttcgagaa gcaggaagac gtaatgcgcg ctctccgaaa catcttcgga     600
gacccggttc ggcgagggcg cgagtacttg cgccgtaatg ccatgaggct tgaatcggtt     660
acagaccatg tgtggcgtt tggcgagaac ttcacacaac tccttatcct cgaactaacg     720
aacgatccct ccctcgttac gctccctgat cgtcctcgaa catggaattt cttccgaggt     780
aacgggggac gaccaagcaa accattattc tcggaggcct tccccgatga cttggacact     840
acttcactag cgttgactgt cctccaaaga gatcccggcg tcatctcttc tgtgatggac     900
gaaatgttga actacaggga tccggacggc attatgcaga catacttcga cgatggtcgg     960
caaagactcg atccatttgt caatgtcaat gtcttaacgt tcttctacac caacggacgt    1020
ggtcatgaac tggaccaatg ccttacatgg gtccgcgaag ttttgctcta tcgcgcctat    1080
ctcggcggct cacgttatta ccctccgcc gactgctttc tctacttcat cagccgcctt    1140
ttcgcatgca cgaatgaccc cgtgctacac caccaactca aaccgctctt cgtcgagcgc    1200
gtgcaggagc aaatcggcgt ggagggcgat gcgctcgagt tggcgttccg attgctcgtc    1260
tgtgcaagcc tggacgtcca aaacgcgatc gacatgcgca ggctgctcga gatgcaatgc    1320
```

```
gaagatggcg gctgggaggg cgggaacctt tataggtttg gcacgaccgg gctcaaggtg      1380
actaaccggg gcctgacgac tgcagcggcc gtacaggcca tcgaggcgtc ccaacggcgc      1440
ccaccatcac cgtcccctc cgtcgaatct acaaagagcc caataacccc tgtgacgccc       1500
atgctggagg tccctcgct cggcctgagc atctcgaggc cgtccagccc tttactcggc       1560
tacttcaggc tcccgtggaa gaagtcggcc gaagtacact ga                          1602
```

<210> SEQ ID NO 51
<211> LENGTH: 1602
<212> TYPE: DNA
<213> ORGANISM: Artificial Sequence
<220> FEATURE:
<223> OTHER INFORMATION: codon optimized cDNA

<400> SEQUENCE: 51

```
atgtctgcgg cggctcaata cacgactttg attctggatc tgggtgatgt tctgttcact      60
tggtccccga aaaccaagac cagcatccct ccgcgtaccc tgaaagaaat cctgaatagc      120
gctacctggt atgagtacga gcgtggtcgc atttcccaag acgagtgtta cgaacgtgtg      180
ggcaccgagt tcggcattgc gccgagcgag attgacaacg cgttcaaaca agcgcgcgat      240
tcgatggaaa gcaatgatga actgatcgca ctggtccgtg agctgaaaac gcagctggac      300
ggtgagctgc tggttttcgc actgtccaat attagcctgc cggattacga atacgtcttg      360
accaaaccgg cggactggag catctttgac aaagtgttcc ctagcgcctt ggtgggcgag      420
cgtaagccgc atctgggcgt ttataaacac gttattgcgg aaacgggcat tgatccgcgc      480
acgacggttt tcgtggacga caagattgac aatgtgttaa gcgcacgcag cgtcggtatg      540
catggtatcg tgtttgagaa acaagaagat gtcatgcgtg cactgcgtaa catctttggt      600
gatccggtcc gtcgtggtcg tgagtatctg cgtagaaacg caatgcgtct ggagtccgtg      660
accgaccacg gcgtggcgtt tggtgagaac tttacccagt tgctgattct ggaattgacg      720
aacgacccga gcctggtcac cctgcctgat cgtccgcgta cctggaactt ttttcgcggc      780
aatggtggcc gcccgagcaa gccgctgttc agcgaagcgt tcccggatga tctggatacc      840
acgagcctgg cgctgaccgt gctgcagcgc gacccgggtg ttatcagcag cgttatggac      900
gaaatgctga attaccgtga cccggacggt atcatgcaga cttatttcga tgacggtcgc      960
caacgcttgg acccatttgt gaacgtcaat gttctgacct ttttctatac gaacggccgt      1020
ggtcacgaac tggaccagtg tctgacgtgg gtgcgtgaag tcctcttgta tcgtgcgtac      1080
cttggtggct cacgctacta cccatcggcg gattgcttcc tgtacttcat ctctcgtctg      1140
tttgcgtgta ccaatgaccc ggtgctgcac catcagctga agccactgtt tgttgagcgt      1200
gtccaagagc aaaattggtgt cgagggtgat gcactggaac tggcttttcg tctgctggtc      1260
tgcgccagcc tggatgtcca gaatgccatc gacatgcgcc gtctgctgga aatgcagtgc      1320
gaagatggcg gttgggaggg tggtaacctc taccgcttcg gcaccacggg cctgaaagtt      1380
accaaccgcg gtctgacgac cgcagccgcc gttcaagcga tcgaagcgag ccaacgcgt      1440 ccgccgagcc cgagcccgtc tgtagagagc acgaaaagcc cgattacccc ggtgaccccg      1500
atgctggaag ttccaagcct gggcttatct atcagccgtc cgtccagccc gctgctgggt      1560
tatttccgtt tgccgtggaa gaaaagcgca gaagtgcact aa                          1602
```

<210> SEQ ID NO 52
<211> LENGTH: 527
<212> TYPE: PRT
<213> ORGANISM: Gelatoporia subvermispora

```
<220> FEATURE:
<221> NAME/KEY: MISC_FEATURE
<222> LOCATION: (1)..(527)
<223> OTHER INFORMATION: EMD37666-B protein

<400> SEQUENCE: 52
```

| | | | | | | | | | | | | | | |
|---|---|---|---|---|---|---|---|---|---|---|---|---|---|---|
| Met | Ser | Ala | Ala | Ala | Gln | Tyr | Thr | Thr | Leu | Ile | Leu | Asp | Leu | Gly | Asp |
| 1 | | | | 5 | | | | | 10 | | | | | 15 | |

Val Leu Phe Thr Trp Ser Pro Lys Thr Lys Thr Ser Ile Pro Pro Arg
              20                  25                  30

Thr Leu Lys Glu Ile Leu Asn Ser Ala Thr Trp Tyr Glu Tyr Glu Arg
         35                  40                  45

Gly Arg Ile Ser Gln Asp Glu Cys Tyr Glu Arg Val Gly Thr Glu Phe
     50                  55                  60

Gly Ile Ala Pro Ser Glu Ile Asp Asn Ala Phe Lys Gln Ala Arg Asp
65                  70                  75                  80

Ser Met Glu Ser Asn Asp Glu Leu Ile Ala Leu Val Arg Glu Leu Lys
                 85                  90                  95

Thr Gln Leu Asp Gly Glu Leu Leu Val Phe Ala Leu Ser Asn Ile Ser
             100                 105                 110

Leu Pro Asp Tyr Glu Tyr Val Leu Thr Lys Pro Ala Asp Trp Ser Ile
             115                 120                 125

Phe Asp Lys Val Phe Pro Ser Ala Leu Val Gly Glu Arg Lys Pro His
130                 135                 140

Leu Gly Val Tyr Lys His Val Ile Ala Glu Thr Gly Ile Asp Pro Arg
145                 150                 155                 160

Thr Thr Val Phe Val Asp Asp Lys Ile Asp Asn Val Leu Ser Ala Arg
                165                 170                 175

Ser Val Gly Met His Gly Ile Val Phe Glu Lys Gln Glu Asp Val Met
             180                 185                 190

Arg Ala Leu Arg Asn Ile Phe Gly Asp Pro Val Arg Arg Gly Arg Glu
         195                 200                 205

Tyr Leu Arg Arg Asn Ala Met Arg Leu Glu Ser Val Thr Asp His Gly
     210                 215                 220

Val Ala Phe Gly Glu Asn Phe Thr Gln Leu Leu Ile Leu Glu Leu Thr
225                 230                 235                 240

Asn Asp Pro Ser Leu Val Thr Leu Pro Asp Arg Pro Arg Thr Trp Asn
                245                 250                 255

Phe Phe Arg Gly Lys Pro Leu Phe Ser Glu Ala Phe Pro Asp Asp Leu
             260                 265                 270

Asp Thr Thr Ser Leu Ala Leu Thr Val Leu Gln Arg Asp Pro Gly Val
         275                 280                 285

Ile Ser Ser Val Met Asp Glu Met Leu Asn Tyr Arg Asp Pro Asp Gly
     290                 295                 300

Ile Met Gln Thr Tyr Phe Asp Asp Gly Arg Gln Arg Leu Asp Pro Phe
305                 310                 315                 320

Val Asn Val Asn Val Leu Thr Phe Phe Tyr Thr Asn Gly Arg Gly His
                325                 330                 335

Glu Leu Asp Gln Cys Leu Thr Trp Val Arg Glu Val Leu Leu Tyr Arg
             340                 345                 350

Ala Tyr Leu Gly Gly Ser Arg Tyr Tyr Pro Ser Ala Asp Cys Phe Leu
         355                 360                 365

Tyr Phe Ile Ser Arg Leu Phe Ala Cys Thr Asn Asp Pro Val Leu His
     370                 375                 380

His Gln Leu Lys Pro Leu Phe Val Glu Arg Val Gln Glu Gln Ile Gly
385                 390                 395                 400

Val Glu Gly Asp Ala Leu Glu Leu Ala Phe Arg Leu Leu Val Cys Ala
            405                 410                 415

Ser Leu Asp Val Gln Asn Ala Ile Asp Met Arg Arg Leu Leu Glu Met
            420                 425                 430

Gln Cys Glu Asp Gly Gly Trp Glu Gly Asn Leu Tyr Arg Phe Gly
        435                 440                 445

Thr Thr Gly Leu Lys Val Thr Asn Arg Gly Leu Thr Ala Ala Ala
    450                 455                 460

Val Gln Ala Ile Glu Ala Ser Gln Arg Arg Pro Pro Ser Pro Ser Pro
465                 470                 475                 480

Ser Val Glu Ser Thr Lys Ser Pro Ile Thr Pro Val Thr Pro Met Leu
            485                 490                 495

Glu Val Pro Ser Leu Gly Leu Ser Ile Ser Arg Pro Ser Ser Pro Leu
            500                 505                 510

Leu Gly Tyr Phe Arg Leu Pro Trp Lys Lys Ser Ala Glu Val His
        515                 520                 525

<210> SEQ ID NO 53
<211> LENGTH: 1584
<212> TYPE: DNA
<213> ORGANISM: Artificial Sequence
<220> FEATURE:
<223> OTHER INFORMATION: codon optimized cDNA

<400> SEQUENCE: 53
atgtctgcgg ctgctcaata tactactttg attctggatc tgggcgacgt tctgttcacg      60
tggagcccga aaaccaagac cagcattcca ccgcgtaccc tgaaggagat cctcaatagc     120
gcgacttggt acgagtatga gcgtggccgc atcagccaag acgagtgcta cgaacgcgtc     180
ggtacggaat ttggcattgc accaagcgag attgacaatg cgtttaaaca agcgcgtgac     240
agcatggaaa gcaatgacga actgatcgcg ctggtccgtg agctgaaaac ccagctggat     300
ggtgagctgt tggtgtttgc gctgtcgaac atctctctgc cggactacga gtatgttctg     360
accaaaccgg cggattggag cattttttgat aaagtgtttc cgagcgcgct ggttggtgag     420
cgcaagccgc acctgggtgt gtacaaacac gttattgcag agactggcat cgacccgcgt     480
acgacggttt tcgttgacga caagatcgat aacgttctga cgcacgtag cgtcggtatg     540 cacggtattg ttttcgaaaa acaagaagat gttatgcgcg cactgcgtaa tatcttcggc     600
gatccggtca gacgtggccg tgagtatctg cgccgcaatg cgatgcgtct ggaatcggtg     660
accgatcatg gtgtcgcctt ggcgagaat tcaccccagc tgctgatttt agagctgacc     720
aatgatccta gctggtgac gctgccggat cgtccgcgta cctggaactt tttccgcggc     780
aagccgttgt ctccgaagc cttcccggac gacctggaca cgaccagcct ggcgctgacc     840
gtgctgcaac gtgatccggg tgtgatctct tccgtaatgg acgaaatgct gaactaccgt     900 gaccccggacg gtatcatgca gacctatttt gacgacggtc gtcagcgtct ggacccgttt     960
gtgaacgtga atgtcctgac gttcttttac accaatggtc gcggtcacga actggatcag    1020
tgtctgacct gggtccgcga agtgctgctg tatcgtgcat acctgggtgg cagccgttat    1080
tacccgagcg ccgattgctt tctgtacttt atcagccgtc tgttcgcgtg cacgaacgat    1140
ccggttctgc atcaccagct gaagccgtta tttgttgagc gcgttcagga acaaattggt    1200
gtcgagggtg atgcgctgga attggcattc cgcctgttgg tctgcgccag ccttgatgtc    1260

-continued

```
cagaacgcca ttgacatgcg tcgcttgctc gaaatgcagt gtgaggacgg cggttgggag      1320
ggtggcaacc tgtaccgttt cggtacgacc ggcctgaaag tcacgaaccg tggtctgacg      1380
acggcagctg cggtgcaagc aattgaagcc agccaacgtc gtccgccatc cccgtcaccg      1440
agcgttgagt ccaccaagag cccgattacc cctgtgaccc cgatgcttga agttccgagc      1500
ctgggtctga gcatctcccg tcctagcagc ccgctgttgg gttacttccg cctgccgtgg      1560
aagaaaagcg ctgaggtgca ttaa                                             1584
```

<210> SEQ ID NO 54
<211> LENGTH: 486
<212> TYPE: PRT
<213> ORGANISM: Aspergillus terreus
<220> FEATURE:
<221> NAME/KEY: MISC_FEATURE
<222> LOCATION: (1)..(486)
<223> OTHER INFORMATION: Protein

<400> SEQUENCE: 54

Met Ala Ile Thr Lys Gly Pro Val Lys Ala Leu Ile Leu Asp Phe Ser
1               5                   10                  15

Asn Val Leu Cys Ser Trp Lys Pro Ser Asn Val Ala Val Pro Pro
            20                  25                  30

Gln Ile Leu Lys Met Ile Met Ser Ser Asp Ile Trp His Asp Tyr Glu
        35                  40                  45

Cys Gly Arg Tyr Ser Arg Glu Asp Cys Tyr Ala Arg Val Ala Asp Arg
    50                  55                  60

Phe His Ile Ser Ala Ala Asp Met Glu Asp Thr Leu Lys Gln Ala Arg
65                  70                  75                  80

Lys Ser Leu Gln Val His His Glu Thr Leu Leu Phe Ile Gln Gln Val
                85                  90                  95

Lys Lys Asp Ala Gly Gly Glu Leu Met Val Cys Gly Met Thr Asn Thr
            100                 105                 110

Pro Arg Pro Glu Gln Asp Val Met His Ser Ile Asn Ala Glu Tyr Pro
        115                 120                 125

Val Phe Asp Arg Ile Tyr Ile Ser Gly Leu Met Gly Met Arg Lys Pro
    130                 135                 140

Ser Ile Cys Phe Tyr Gln Arg Val Met Glu Glu Ile Gly Leu Ser Gly
145                 150                 155                 160

Asp Ala Ile Met Phe Ile Asp Asp Lys Leu Glu Asn Val Ile Ala Ala
                165                 170                 175

Gln Ser Val Gly Ile Arg Gly Val Leu Phe Gln Ser Gln Gln Asp Leu
            180                 185                 190

Arg Arg Val Val Leu Asn Phe Leu Gly Asp Pro Val His Arg Gly Leu
        195                 200                 205

Gln Phe Leu Ala Ala Asn Ala Lys Lys Met Asp Ser Val Thr Asn Thr
    210                 215                 220

Gly Asp Thr Ile Gln Asp Asn Phe Ala Gln Leu Leu Ile Leu Glu Leu
225                 230                 235                 240

Ala Gln Asp Arg Glu Leu Val Lys Leu Gln Ala Gly Lys Arg Thr Trp
                245                 250                 255

Asn Tyr Phe Ile Gly Pro Pro Lys Leu Thr Thr Ala Thr Phe Pro Asp
            260                 265                 270

Asp Met Asp Thr Thr Ser Met Ala Leu Ser Val Leu Pro Val Ala Glu
        275                 280                 285

Asp Val Val Ser Ser Val Leu Asp Glu Met Leu Lys Phe Val Thr Asp

```
                    290                 295                 300
Asp Gly Ile Phe Met Thr Tyr Phe Asp Ser Ser Arg Pro Arg Val Asp
305                 310                 315                 320

Pro Val Val Cys Ile Asn Val Leu Gly Val Phe Cys Arg His Asn Arg
                325                 330                 335

Glu Arg Asp Val Leu Pro Thr Phe His Trp Ile Arg Asp Ile Leu Ile
            340                 345                 350

Asn Arg Ala Tyr Leu Ser Gly Thr Arg Tyr Tyr Pro Ser Pro Asp Leu
        355                 360                 365

Phe Leu Phe Phe Leu Ala Arg Leu Cys Leu Ala Val Arg Asn Gln Ser
    370                 375                 380

Leu Arg Glu Gln Leu Val Leu Pro Leu Val Asp Arg Leu Arg Glu Arg
385                 390                 395                 400

Val Gly Ala Pro Gly Glu Ala Val Ser Leu Ala Ala Arg Ile Leu Ala
                405                 410                 415

Cys Arg Ser Phe Gly Ile Asp Ser Ala Arg Asp Met Asp Ser Leu Arg
            420                 425                 430

Gly Lys Gln Cys Glu Asp Gly Gly Trp Pro Val Glu Trp Val Tyr Arg
        435                 440                 445

Phe Ala Ser Phe Gly Leu Asn Val Gly Asn Arg Gly Leu Ala Thr Ala
    450                 455                 460

Phe Ala Val Arg Ala Leu Glu Ser Pro Tyr Gly Glu Ser Ala Val Lys
465                 470                 475                 480

Val Met Arg Arg Ile Val
                485

<210> SEQ ID NO 55
<211> LENGTH: 1461
<212> TYPE: DNA
<213> ORGANISM: Aspergillus terreus
<220> FEATURE:
<221> NAME/KEY: misc_feature
<223> OTHER INFORMATION: cDNA

<400> SEQUENCE: 55
atggctatca ccaagggtcc agttaaggcg cttattcttg acttttccaa tgttctctgc      60
tcgtggaagc ctcccagcaa tgttgcggtg ccgccccaga tactcaaaat gatcatgtcc     120
tctgacatat ggcatgacta cgagtgcgga cggtactcga gagaggactg ctatgccaga     180
gtggcagacc gttttcatat cagcgccgcg gacatggaag acacgctgaa acaggcgcgc     240
aagagcctgc aggttcacca tgagacactg ttgtttatcc agcaagtcaa gaaggatgcc     300
gggggcgagt tgatggtgtg tgggatgacc aacacgcccc ggccagagca agacgtaatg     360
cattcaatca acgcggagta tcctgtgttt gataggatat atatatccgg tctcatgggc     420
atgaggaagc cgagcatctg cttctaccag cgggtgatgg aggagattgg cctatcaggc     480
gatgcgatca tgtttataga tgacaagttg gagaatgtca tcgccgccca gtcggtaggg     540
atccgaggcg ttctatttca gagtcagcaa gatctccgtc gggttgtatt aaatttcttg     600
ggcgatccgg tccatcgcgg cctgcagttc tagcggcca atgcgaaaaa gatggatagt     660
gtgaccaaca ccggcgatac tatccaagat aattttgctc agctcctcat cttggagctg     720
gcccaggaca gggaattggt gaagcttcag gctggaaaaa ggacttggaa ttacttcata     780
gggcctccca agctcacaac agccacgttc cccgatgaca tggacaccac atctatggct     840
ctctcggtcc ttcctgtggc cgaggatgtg gtctcttctg tcctggatga gatgcttaaa     900
```

```
ttcgtcaccg atgacggtat ctttatgact tacttcgatt cctcgcgccc tcgagtcgac    960
ccagtcgtat gtatcaacgt cttgggtgtt ttctgcaggc ataaccgaga gcagacgtc    1020 cttccaacgt tccattggat tcgagacatc ctgatcaacc gggcatatct ctcgggcacc   1080
cgatactacc catcgcccga tttgttttg ttttccttg cacgcctctg cctggcagtc     1140
cggaatcaga gcctacggga acaacttgtc ttgcctctgg tagaccgact gcgtgagcgg   1200
gtgggcgcac ctggagaagc ggtctcattg gcagcgcgga tccttgcctg ccgtagcttt   1260
ggtatcgaca gtgcgagaga catggacagc ttgaggggaa acaatgcga ggatggcggc    1320 tggccagtgg agtgggttta ccggtttgcc tctttcggcc tgaacgtagg caatcggggt   1380
cttgctactg ccttcgcggt cagggcgctc gaaagcccct atggtgagtc ggcggtgaag   1440
gttatgagac gcatcgtctg a                                             1461
```

<210> SEQ ID NO 56
<211> LENGTH: 1461
<212> TYPE: DNA
<213> ORGANISM: Artificial Sequence
<220> FEATURE:
<223> OTHER INFORMATION: codon optimized cDNA

<400> SEQUENCE: 56

```
atggcaatca ctaagggccc agttaaagcg ctgattcttg atttttctaa cgttctgtgt    60
agctggaagc cgccgagcaa tgttgcggtc ccgcctcaaa ttctgaagat gattatgtcg   120
agcgacatct ggcatgatta tgagtgtggc cgttacagcc gtgaggactg ctacgcccgt   180
gttgctgacc gttttcatat cagcgcagcg gacatggaag tacccctgaa acaggcacgt   240
aagtccctgc aagtgcacca cgaaacgctg ctgttcatcc aacaggtgaa gaaagacgcg   300
ggtggtgagc tgatggtttg cggcatgacc aacacgccgc gtccggaaca agacgtgatg   360
cattccatca atgctgagta tccggtgttc gaccgtattt acattagcgg cctgatgggc   420
atgcgtaaac cgagcatttg tttctaccaa cgcgtaatgg aagagattgg tctgagcggt   480
gacgccatca tgttcattga cgataaactg gaaaatgtga ttgccgcaca gagcgtgggt   540
atccgcggtg tgctgttcca aagccagcaa gatctgcgtc gtgtcgtgct gaactttctg   600
ggcgatccgg tccaccgtgg tctgcagttc ttggcggcga acgcaaagaa aatggacagc   660
gtcacgaata ccggcgacac tatccaagac aatttcgcac agctgttgat cttagagctg   720
gcgcaggatc gcgaattggt gaaattgcag gccggtaaac gtacctggaa ctactttatt   780
ggtccgccga agctgaccac ggcgacgttt ccggatgata tggacacgac cagcatggcg   840
ctgtcggtgc tgcctgtcgc ggaagatgtc gtgagctctg ttctggacga gatgctgaag   900
ttcgtgaccg atgatggtat ctttatgacc tatttcgact ctagccgtcc gcgtgtcgat   960
ccggttgtct gcattaatgt gttgggtgtt ttctgccgcc acaatcgtga gcgcgacgtg   1020
ttgccgacct ttcactggat tcgtgatatt ctgatcaacc gcgcatatct gagcggcacg   1080
cgctattacc cgtccccgga tctgtttctg ttttttcctgg ctcgtctgtg cctggccgtt   1140
cgcaaccaga gcctgcgcga acaactggtt ctcccgctgg ttgatcgtct gcgcgagcgt   1200
gttggtgctc cgggtgaggc tgtgagcctg cggcacgta tcctggcgtg ccgtagcttc    1260
ggtatcgact cagcccgcga catggactcc ttgcgtggca acagtgtga agatggtggt   1320 tggccggtcg aatgggtcta tcgcttcgcg agctttggtc tgaacgttgg caaccgtggt   1380
ttggccaccg cgtttgcggt tagagcgctg gagtccccat acggcgagag cgcagttaag   1440
gttatgcgcc gtatcgtgta a                                             1461
```

<210> SEQ ID NO 57
<211> LENGTH: 483
<212> TYPE: PRT
<213> ORGANISM: Aspergillus aculeatus

<400> SEQUENCE: 57

Met Pro Ser Val Lys Ala Leu Val Leu Asp Phe Ala Gly Val Leu Cys
1               5                   10                  15

Ser Trp Thr Pro Pro Ala Glu Ser Pro Leu Ser Pro Ala Gln Leu Lys
            20                  25                  30

Gln Leu Met Ser Ser Glu Ile Trp Phe Glu Tyr Glu Arg Gly Arg Tyr
        35                  40                  45

Ser Glu Glu Glu Cys Tyr Ala Lys Leu Val Glu Arg Phe Ser Ile Ser
    50                  55                  60

Ala Ala Asp Met Ala Ser Thr Met Glu Gln Ala Arg Gln Ser Leu Glu
65                  70                  75                  80

Leu Asn His Ala Val Leu Gln Leu Val Ser Glu Ile Arg Lys Arg Asn
                85                  90                  95

Pro Gly Leu Lys Val Tyr Gly Met Thr Asn Thr Pro His Ala Glu Gln
            100                 105                 110

Asp Cys Val Asn Arg Ile Val Asn Ser Tyr Pro Val Phe Asp His Val
        115                 120                 125

Tyr Leu Ser Gly Leu Val Gly Met Arg Lys Pro Asp Leu Gly Phe Tyr
    130                 135                 140

Arg Phe Val Leu Ala Glu Thr Gly Leu Arg Pro Asp Glu Val Val Phe
145                 150                 155                 160

Val Asp Asp Lys Thr Glu Asn Val Leu Val Ala Gln Ser Val Gly Met
                165                 170                 175

His Gly Val Val Phe Gln Asn Val Thr Asp Phe Lys Gln Gln Ile Ile
            180                 185                 190

Asn Val Thr Gly Asp Pro Val Ser Arg Gly Leu Arg Tyr Leu Arg Ser
        195                 200                 205

Asn Ala Lys Ser Leu Leu Thr Val Thr Ser Asn Asn Ser Val Ile His
    210                 215                 220

Glu Asn Phe Ala Gln Leu Leu Ile Leu Glu Leu Thr Gly Asp Arg Asp
225                 230                 235                 240

Leu Ile Glu Leu Glu Pro Trp Asp Arg Thr Trp Asn Tyr Phe Ile Gly
                245                 250                 255

Val Pro Gln Ser Pro Thr Ser Thr Phe Pro Asn Asp Leu Asp Thr Thr
            260                 265                 270

Ser Ile Ala Leu Ser Val Leu Pro Ile His Lys Asp Val Val Ala Asp
        275                 280                 285

Val Met Asp Glu Ile Met Leu Leu Leu Asp Asn Asp Gly Ile Val Pro
    290                 295                 300

Thr Tyr Phe Asp Pro Thr Arg Pro Arg Val Asp Pro Val Val Cys Val
305                 310                 315                 320

Asn Val Leu Ser Leu Phe Ala Gln Asn Gly Arg Glu Ser Glu Leu Leu
                325                 330                 335

Ala Thr Phe Asn Trp Val Leu Asp Val Leu Arg His Arg Ala Tyr Leu
            340                 345                 350

Gln Gly Thr Arg Tyr Tyr Ile Ser Pro Asp Ala Phe Leu Tyr Phe Leu
        355                 360                 365

Ala Arg Leu Ser Val Phe Leu Arg Met Ser Pro Leu Arg Ala Arg Leu

```
              370                 375                 380
Met Pro Leu Leu Glu Glu Arg Val Tyr Glu Arg Ile Gly Ala His Gly
385                 390                 395                 400

Asp Ala Ile Ser Leu Ala Met Arg Ile Tyr Thr Cys Lys Leu Leu Gly
            405                 410                 415

Met Ser Asn Met Leu Asp Glu Arg Ala Leu Arg Asp Met Gln Cys Glu
                420                 425                 430

Asp Gly Gly Phe Pro Thr Ser Trp Val Tyr Arg Phe Gly Ser Thr Gly
            435                 440                 445

Val Lys Ile Gly Asn Arg Gly Leu Thr Thr Ala Leu Ala Ile Lys Ala
        450                 455                 460

Ile Glu Met Pro Leu Ala Ser Leu Trp Lys Ser Trp Gly Leu Thr Thr
465                 470                 475                 480

Asp Ile Arg

<210> SEQ ID NO 58
<211> LENGTH: 1452
<212> TYPE: DNA
<213> ORGANISM: Aspergillus aculeatus
<220> FEATURE:
<221> NAME/KEY: misc_feature
<223> OTHER INFORMATION: cDNA

<400> SEQUENCE: 58
```

| | | | | | |
|---|---|---|---|---|---|
| atgccctccg | tcaaagcact | ggtcctggac | ttcgccggag | ttctatgctc | atggaccccg | 60 |
| ccagccgaga | gcccgctctc | cccagcccag | ctcaaacaac | tcatgtcctc | cgagatatgg | 120 |
| ttcgaatacg | agcgcgggag | atattccgaa | gaagaatgtt | atgcgaagct | cgtcgaacgg | 180 |
| ttctccatca | gcgctgcgga | catggcttcc | accatggaac | aggcccgtca | gagcctggaa | 240 |
| ctgaaccacg | ccgtacttca | gcttgtcagc | gagataagga | agcggaaccc | cgggctcaaa | 300 |
| gtttatggca | tgacgaacac | gccccatgcg | gaacaggatt | gtgtgaatcg | catcgtgaac | 360 |
| agctatcctg | ttttcgacca | tgtgtatctc | tccgggctcg | ttgggatgcg | caaaccagat | 420 |
| cttggattct | atcggtttgt | tctcgcagag | accgggttga | ggcctgacga | ggtcgtgttc | 480 |
| gtcgacgaca | aaacggagaa | tgtgttggtc | gcgcagtccg | tggggatgca | cggcgtggtg | 540 |
| ttccagaacg | ttacggattt | caagcagcag | atcataaacg | tgacgggaga | ccctgtctct | 600 |
| cggggcttga | ggtatctccg | ctcgaatgca | agagcctcc | tcactgtgac | tagcaataac | 660 |
| tccgtgatcc | acgaaaactt | gcgcagttg | ctgattctgg | agctgacggg | cgaccgagac | 720 |
| ttgatcgaac | tcgagccttg | ggatcgaaca | tggaactact | catcgggt | tcctcagtcg | 780 |
| ccgacgagca | ccttccccaa | cgacctggac | accacctcta | tcgcgctctc | ggtccttccc | 840 |
| attcataagg | acgtcgttgc | cgatgtgatg | acgagatta | tgcttctcct | agacaacgac | 900 |
| gggatagtcc | caacatattt | tgatcccact | cgccctcgag | tcgacccagt | cgtgtgtgtg | 960 |
| aatgtactca | gcctgtttgc | ccaaaacggc | cgagaatccg | agttactcgc | caccttcaac | 1020 |
| tgggtgctgg | acgtgctgcg | acatagagcc | tacctgcagg | gcacgagata | ttacatcagt | 1080 |
| ccggacgcct | tcttgtactt | tctagccaga | ctctcggtct | ttctgaggat | gagtccactc | 1140 |
| cgcgctcggc | taatgcctct | cctggaagaa | agagtgtatg | agcgaattgg | tgcccatggc | 1200 |
| gacgccattt | cgctggctat | gcggatctat | acgtgtaagc | tgctcgggat | gtcgaatatg | 1260 |
| ctcgatgaaa | gagcattgcg | ggacatgcag | tgtgaggatg | gcggcttccc | tacaagttgg | 1320 |
| gtctatagat | ttggatcgac | cggagtgaag | attgggaaca | gggggttgac | tactgcactt | 1380 |

-continued

| gcaataaagg ccattgagat gcctctcgct tcgctttgga agtcgtgggg attgacgact | 1440 |
| gacattcgat aa | 1452 |

<210> SEQ ID NO 59
<211> LENGTH: 1452
<212> TYPE: DNA
<213> ORGANISM: Artificial Sequence
<220> FEATURE:
<223> OTHER INFORMATION: codon optimized cDNA

<400> SEQUENCE: 59

| atgccgtcgg ttaaagcgtt ggttctggat tttgcgggtg tgttgtgttc ttggactcca | 60 |
| ccggcggaaa gcccgttgtc cccagcgcag ctgaagcagc tgatgagcag cgagatctgg | 120 |
| tttgagtatg agcgtggccg ctatagcgaa gaagagtgtt atgcaaaatt ggtggagcgt | 180 |
| ttctctatct cggccgcaga tatggcgagc acgatggaac aggcccgtca atcgctggag | 240 |
| ttgaaccacg ccgtgctgca attagtttcc gagattcgta acgtaatcc gggcttaaag | 300 |
| gtttacggta tgactaatac cccgcatgca gagcaagatt gtgtgaaccg tattgtcaat | 360 |
| agctatccgg ttttgatca tgtctacctg agcggtctgg tgggtatgcg caaaccggat | 420 |
| ctgggcttt accgtttcgt tctggcagag actggtctgc cccggatga agtcgtgttc | 480 |
| gttgacgaca agaccgaaaa tgtcctggtg gctcaatccg ttggcatgca tggtgtggtg | 540 |
| ttccaaaatg taaccgactt caaacaacag attatcaatg tcacgggtga tcctgtcagc | 600 |
| cgtggtttgc gctacttgcg ttccaacgcg aagtctctgc tcactgttac cagcaataac | 660 |
| agcgttatcc atgagaattt cgcgcagctg ctgatcctgg aactgacggg cgaccgtgac | 720 |
| ctgattgaac tggaaccgtg ggaccgtacg tggaactact ttatcggcgt gccgcaaagc | 780 |
| ccgaccagca cctttccgaa cgacctggat acgaccagca ttgccctgag cgttctgccg | 840 |
| attcacaaag atgtggttgc ggacgtgatg gatgagatta tgctgctgct ggacaatgac | 900 |
| ggtattgtcc cgacctactt cgatccaacc cgtccgcgtg ttgatcctgt tgtgtgcgtc | 960 |
| aacgttctga gcctgttcgc acagaacggt cgcgagtccg aattgctggc gacgttcaac | 1020 |
| tgggttttgg acgttctgag acaccgtgcg tatttgcagg gtacgcgcta ttatatcagc | 1080 |
| ccggatgcct ttctgtattt tctggcgcgc ctgtctgtgt ttctgcgtat gtctccgttg | 1140 |
| cgcgctcgtc tgatgccgct gctggaagaa cgcgtttatg agcgtatcgg cgcacacggc | 1200 |
| gatgctatta gcctggcgat gcgcatttac acctgtaagc tgctgggcat gagcaatatg | 1260 |
| ctggacgagc gtgcactgcg tgacatgcag tgtgaagatg gtggtttccc aaccagctgg | 1320 |
| gtgtaccgtt ttggtagcac gggcgtgaaa attggtaacc gtggcttgac gaccgcactg | 1380 |
| gccattaagg ccatcgaaat gccgctggcc agcctttgga aaagctgggg cctgaccacc | 1440 |
| gatattcgct aa | 1452 |

<210> SEQ ID NO 60
<211> LENGTH: 485
<212> TYPE: PRT
<213> ORGANISM: Aspergillus udagawae

<400> SEQUENCE: 60

Met Thr Arg Gln Lys Ser Pro Gln Tyr Lys Ala Ile Ile Phe Asp Leu
1               5                   10                  15

Gly Asp Val Phe Phe Thr Trp Asp Ala Pro Lys Asp Thr Ala Val Leu
                20                  25                  30

Pro Asn Leu Phe Lys Lys Met Leu Thr Ser Pro Thr Trp Ser Asp Tyr

```
                35                  40                  45
Glu Arg Gly Lys Leu Ser Glu Glu Ser Cys Tyr Glu Arg Leu Ala Glu
 50                  55                  60
Gln Phe Asp Val Asp Ser Ser Glu Ile Ala Arg Ser Leu Arg Lys Ala
 65                  70                  75                  80
Gln Gln Ser Leu Thr Thr Asp Ala Ala Ile Val Ser Leu Ile Ser Glu
                 85                  90                  95
Ile Arg Ala Leu Ala Gly His Ile Ala Ile Tyr Ala Met Ser Asn Ile
                100                 105                 110
Ser Ala Pro Ala Tyr Ala Ala Val Leu Gln Thr Gln Pro Glu Met Gly
                115                 120                 125
Ile Phe Asp Gly Val Phe Pro Ser Gly Cys Tyr Gly Thr Arg Lys Pro
                130                 135                 140
Glu Leu Leu Phe Tyr Lys Lys Val Leu Gln Ile Ala Val Pro Pro
145                 150                 155                 160
Asn Gln Ile Ile Phe Ile Asp Asp Gln Leu Glu Asn Val Val Ser Ala
                165                 170                 175
Gln Ser Thr Gly Met His Gly Ile Val Tyr Thr Gly Ala Gly Glu Leu
                180                 185                 190
Ser Arg Gln Leu Arg Asn Leu Val Leu Asp Pro Val Gln Arg Gly Arg
                195                 200                 205
Glu Phe Leu Arg Arg Asn Ala Gly Ala Leu Tyr Ser Ile Cys Glu Thr
                210                 215                 220
Gly Gln Val Ile Arg Glu Asn Phe Ser Gln Leu Leu Ile Leu Glu Ala
225                 230                 235                 240
Thr Gly Asp Arg Ser Leu Val Asn Leu Glu Tyr Gln Gln Arg Ser Trp
                245                 250                 255
Asn Phe Phe Gln Gly Gly Pro Pro Ser Thr Ser Glu Thr Phe Pro Asp
                260                 265                 270
Asp Val Asp Thr Thr Ser Ile Ala Leu Met Ile Leu Pro Ala Asp Asp
                275                 280                 285
Asn Thr Val Asn Ser Val Leu Gly Glu Ile Ser Glu Val Ala Asn Asp
                290                 295                 300
Glu Gly Ile Val Asn Thr Tyr Phe Asp Gln Thr Arg Gln Arg Ile Asp
305                 310                 315                 320
Pro Ala Val Cys Val Asn Val Leu Arg Leu Phe Tyr Thr Tyr Gly Arg
                325                 330                 335
Gly Ala Thr Leu Pro Leu Thr Leu Gln Trp Val Ser Asp Val Leu Glu
                340                 345                 350
His Arg Ala His Leu His Gly Thr Arg Tyr Tyr Pro Ser Pro Glu Val
                355                 360                 365
Phe Leu Tyr Phe Val Ser Gln Leu Cys Arg Phe Ser Lys Arg Glu Pro
                370                 375                 380
Thr Leu Gln Leu Leu Glu Thr Leu Leu Thr Asp Arg Leu Lys Glu Arg
385                 390                 395                 400
Ile Gln Val Lys Ala Asp Thr Leu Ser Leu Ala Met Arg Ile Leu Ala
                405                 410                 415
Cys Leu Ser Val Gly Ile Ser Gln Val Glu Val Asp Val Arg Glu Leu
                420                 425                 430
Leu Ala Leu Gln Cys Lys Asp Gly Ser Trp Glu Pro Gly Ser Phe Tyr
                435                 440                 445
Arg Phe Gly Ser Ser Lys Met Asn Val Gly Asn Arg Gly Leu Thr Thr
450                 455                 460
```

Ala Leu Ala Thr Arg Ala Val Glu Leu Tyr Gln Gly Thr Arg Ile Arg
465                 470                 475                 480

Ser Lys Gly Thr Glu
            485

<210> SEQ ID NO 61
<211> LENGTH: 1458
<212> TYPE: DNA
<213> ORGANISM: Aspergillus udagawae
<220> FEATURE:
<221> NAME/KEY: misc_feature
<223> OTHER INFORMATION: cDNA

<400> SEQUENCE: 61

| | | | | | | |
|---|---|---|---|---|---|---|
| atgacccgac | agaaatcgcc | tcaatacaaa | gcaatcatct | ttgacctagg | ggatgtcttt | 60 |
| ttcacctggg | acgccccaa | agacactgct | gtcttgccca | acctcttcaa | gaaaatgctt | 120 |
| acctcgccaa | cctggtcaga | ttacgagcgc | ggcaagttga | gcgaagaaag | ctgctacgag | 180 |
| agactggccg | aacagtttga | cgttgactcg | tcggaaatcc | cgcgcagctt | aaggaaagca | 240 |
| cagcagtctc | ttaccacaga | cgcagcaatc | gtgagcctga | tatcagagat | cagagcgttg | 300 |
| gccggacata | ttgccatcta | cgccatgtcc | aacatttccg | ccccagctta | tgcagctgtg | 360 |
| ctccagactc | agcccgaaat | gggcatcttt | gacggagtgt | tcccgtctgg | atgctatggg | 420 |
| acgaggaagc | cggagctgtt | gttctataag | aaagtcttgc | aggagattgc | agtgccgcca | 480 |
| aatcagatca | tctttattga | tgatcagcta | gagaatgtag | tttctgcgca | gtcaacaggt | 540 |
| atgcacggca | ttgtctacac | cggtgcgggt | gagctcagtc | gacagctcag | aaatctggtg | 600 |
| ttggaccctg | tacaaagggg | tcgagagttt | ctacggcgca | atgctggggc | attgtatagt | 660 |
| atctgcgaga | ctggtcaagt | catccgggaa | aacttctcgc | agctgctcat | cctagaggcg | 720 |
| acgggtgata | gaagcctggt | caaccttgaa | tatcagcagc | ggagctggaa | tttcttcaa | 780 |
| ggaggtcccc | cttctacgtc | ggaaacattc | ccagatgatg | tcgacacaac | atccattgcc | 840 |
| ttgatgattc | tccctgccga | tgataacaca | gtcaactcgg | ttctcggcga | gatttccgag | 900 |
| gtagctaatg | acgagggcat | tgtaaatacg | tactttgacc | agacccgaca | gcgaatcgac | 960 |
| ccagcagtct | gcgtcaatgt | cctccgtctc | ttttatacct | acggccgggg | cgccactctc | 1020 |
| ccattgaccc | tccagtgggt | gtccgacgtt | cttgagcatc | gtgcgcactt | acatggtacg | 1080 |
| cgatactacc | ccagcccgga | ggttttcctc | tactttgtca | gtcaactctg | ccggttctcc | 1140 |
| aagagggaac | cgacgctgca | gctgctggag | acgttgctca | cggatcgcct | caaggagcgc | 1200 |
| attcaggtca | aggcagacac | tctgtcactg | gctatgcgga | tcctggcatg | cttgtctgtg | 1260 |
| ggtatatcac | aagttgaagt | ggatgtccga | gagctgctcg | ccttgcaatg | caaggatgga | 1320 |
| tcgtgggaac | ccggctcgtt | ttaccggttt | gggtcgtcca | agatgaacgt | tggtaatcga | 1380 |
| ggtcttacga | ctgcgttggc | gactagggcg | gttgagttgt | accaggggac | tagaatacgc | 1440 |
| tctaagggca | ccgagtag | | | | | 1458 |

<210> SEQ ID NO 62
<211> LENGTH: 1458
<212> TYPE: DNA
<213> ORGANISM: Artificial Sequence
<220> FEATURE:
<223> OTHER INFORMATION: codon optimized cDNA

<400> SEQUENCE: 62

| | | | | | | |
|---|---|---|---|---|---|---|
| atgactcgcc | aaaaagcccc | tcaatacaaa | gcaattatct | tcgatctggg | tgacgttttc | 60 |

```
ttcacctggg atgcgccgaa agatacggcc gtactgccga acctgttcaa gaaaatgctg    120
acctcgccga cctggagcga ctatgagcgt ggtaagctgt ctgaggaaag ctgttacgaa    180
cgcttggccg agcaatttga cgtggacagc agcgagatcg cgcgtagcct ccgtaaagcg    240
cagcaaagcc tgacgaccga cgcagccatc gtgagcctga tcagcgagat ccgcgcattg    300
gcgggtcaca ttgctatcta tgctatgtct aacatttctg cgccagcata cgcagcggtg    360
ttacagaccc agccggaaat gggtatcttt gatggtgttt ttccgagcgg ctgctatggt    420
acgcgtaaac cggaactgct gttttacaaa aaagtgcttc aagaaattgc ggttccgccg    480
aatcagatta tcttcattga cgatcagctg gaaaacgtcg tcagcgcaca gtccacgggc    540
atgcatggca ttgtttacac cggtgccggt gagctgagcc gtcaactgcg taatctggtc    600
ctggacccgg tgcagcgtgg tcgtgagttc ctgcgccgta atgctggcgc cctgtacagc    660
atttgtgaga ctggccaagt tatccgtgag aacttcagcc agctgctgat tctggaagca    720
accggcgatc gttcgctggt gaacctggag tatcaacaac gttcctggaa cttcttcag    780 ggtggccctc catccacgag cgaaactttt ccggatgatg ttgacacgac ctcaatcgcg    840
ctgatgattt taccggcgga cgataatacc gtcaatagcg tcctgggtga atcagcgaa    900 gtcgcgaatg acgagggcat tgtgaatacc tatttcgatc agacccgcca acgtatcgat    960
ccggccgtgt gtgtcaacgt gttgcgcctg ttttacacct atggtcgtgg cgctacgctg    1020
ccgttgaccc tgcaatgggt tagcgacgtg ctggagcacc gtgcgcatct gcacggcacc    1080
cgctactatc cgtccccaga ggttttcctg tactttgtct ctcagctgtg ccgttttttcc    1140 aagcgcgaac cgaccctgca gctgctggaa acgctgttga ccgacagact gaaggaacgc    1200
atccaagtta aggcagatac gctgagcttg caatgcgta tttttggcgtg cctgagcgtg    1260 ggcatcagcc aggttgaggt tgacgtccgc gaactgctgg cgctgcagtg caaggacggt    1320
agctgggagc cgggtagctt ctaccgtttc ggtagcagca agatgaatgt cggtaaccgc    1380
ggtctgacga ccgctttggc gacccgtgcg gttgagctgt accagggtac gcgtattcgt    1440
agcaagggca ccgagtaa                                                  1458
```

<210> SEQ ID NO 63
<211> LENGTH: 524
<212> TYPE: PRT
<213> ORGANISM: Trametes versicolor

<400> SEQUENCE: 63

Met Ala Ser Pro His Arg Arg Tyr Thr Thr Leu Ile Leu Asp Leu Gly
1               5                   10                  15

Asp Val Leu Phe Ser Trp Ser Ser Lys Thr Asn Thr Pro Ile Pro Pro
            20                  25                  30

Lys Lys Leu Lys Glu Ile Leu Ser Ser Leu Thr Trp Phe Glu Tyr Glu
        35                  40                  45

Arg Gly Arg Ile Ser Gln Ala Glu Cys Tyr Asp Arg Val Ser Ser Glu
    50                  55                  60

Phe Ser Leu Asp Ala Ala Thr Ile Ala Glu Ala Phe Gln Gln Ala Arg
65                  70                  75                  80

Asp Ser Leu Arg Pro Asn Glu Glu Phe Leu Ala Leu Ile Arg Glu Leu
                85                  90                  95

Arg Gln Gln Thr His Gly Gln Leu Thr Val Leu Ala Leu Ser Asn Ile
            100                 105                 110

Ser Leu Pro Asp Tyr Glu Tyr Ile Met Ala Leu Asp Ser Asp Trp Thr

```
            115                 120                 125
Ser Val Phe Asp Arg Val Phe Pro Ser Ala Leu Val Gly Glu Arg Lys
    130                 135                 140

Pro His Leu Gly Ala Tyr Arg Val Ile Ser Glu Met His Leu Asp
145                 150                 155                 160

Pro Glu Thr Thr Val Phe Val Asp Asp Lys Leu Asp Asn Val Val Ser
                    165                 170                 175

Ala Arg Ser Leu Gly Met His Gly Val Val Phe Asp Ser Gln Glu Asn
                180                 185                 190

Val Phe Gln Thr Leu Arg Asn Ile Phe Gly Asp Pro Ile His Arg Gly
            195                 200                 205

Arg Asp Tyr Leu Arg Arg His Ala Gly Arg Leu Glu Thr Ser Thr Asp
        210                 215                 220

Ala Gly Val Val Phe Glu Glu Asn Phe Thr Gln Leu Ile Ile Tyr Glu
225                 230                 235                 240

Leu Thr Asn Asp Lys Ser Leu Ile Thr Thr Ser Asp Cys Pro Arg Thr
                    245                 250                 255

Trp Asn Phe Phe Arg Gly Lys Pro Leu Phe Ser Ala Ser Phe Pro Asp
                260                 265                 270

Asp Val Asp Thr Thr Ser Val Ala Leu Thr Val Leu Arg Pro Pro Arg
            275                 280                 285

Thr Leu Val Asn Ser Ile Leu Asp Glu Met Leu Glu Tyr Val Asp Ala
        290                 295                 300

Asp Gly Ile Met Gln Thr Tyr Phe Asp His Ser Arg Pro Arg Met Asp
305                 310                 315                 320

Pro Phe Val Cys Val Asn Val Leu Ser Leu Phe Tyr Glu Tyr Gly Arg
                    325                 330                 335

Gly Gln Asp Leu Pro Lys Thr Leu Glu Trp Val Tyr Glu Val Leu Leu
                340                 345                 350

His Arg Ala Tyr Ile Gly Gly Ser Arg Tyr Tyr Met Ser Ala Asp Cys
            355                 360                 365

Phe Leu Phe Phe Met Ser Arg Leu Leu Gln Arg Ile Thr Asp Pro Ala
        370                 375                 380

Val Leu Asn Arg Leu Arg Pro Leu Phe Val Glu Arg Met His Glu Arg
385                 390                 395                 400

Val Ser Ala Pro Gly Asp Ser Met Glu Leu Ala Phe Arg Ile Leu Ala
                    405                 410                 415

Gly Ser Ser Val Gly Ile Gln Phe Pro Arg Asp Leu Glu Lys Leu Leu
                420                 425                 430

Ala Ala Gln Cys Ala Asp Gly Gly Trp Asp Leu Cys Trp Phe Tyr Gln
            435                 440                 445

Tyr Gly Ser Thr Gly Val Lys Ala Gly Asn Arg Gly Leu Thr Thr Ala
        450                 455                 460

Leu Ala Ile Lys Ala Ile Glu Ser Ala Ile Ala Arg Pro Pro Ser Pro
465                 470                 475                 480

Ala Leu Ser Ala Val Ser Ser Lys Leu Glu Val Pro Lys Pro Ile
                    485                 490                 495

Leu Gln Arg Pro Leu Ser Pro Arg Leu Gly Asp Phe Leu Met Pro
                500                 505                 510

Trp Arg Arg Ala Gln Arg Glu Val Ala Val Ser Ser
        515                 520

<210> SEQ ID NO 64
```

-continued

```
<211> LENGTH: 1575
<212> TYPE: DNA
<213> ORGANISM: Trametes versicolor
<220> FEATURE:
<221> NAME/KEY: misc_feature
<223> OTHER INFORMATION: cDNA

<400> SEQUENCE: 64
atggcttcac ctcaccgcag gtatacgaca ctcatcctag acctgggcga cgtcctcttc      60
tcttggtcat ccaagaccaa cacacctatc cctcccaaga agctgaagga gatcctctcg     120
tccctgacct ggttcgagta cgagcgcggt cggatatcac aggccgagtg ctatgaccgg     180
gtcagctccg agttcagtct tgacgctgcc accatcgcag aagcgttcca gcaggctcgc     240
gactctctgc gaccgaacga agagttcctg gcgttgattc gcgaactccg ccaacaaacg     300
catggtcagc ttaccgtcct cgcgctctcg aacatctcac tccccgacta tgaatacatc     360
atggctctcg actcggactg gacgtcggtc ttcgaccgcg tcttcccttc tgccctcgtc     420
ggcgagcgca agccacatct gggggcgtac cgccgtgtca tctctgagat gcacctagac     480
ccagaaacga ccgtctttgt ggacgacaag ctggacaacg tggtgtccgc gcgatcgctc     540
gggatgcacg gcgtggtctt cgactcccag gagaacgtct tccagacgct gaggaatatc     600
ttcggcgacc cgatacatcg cggacgtgac tatctccgca ggcatgccgg tcgtctggag     660
acatctacgg acgccggcgt tgtcttcgag gaaaacttta cgcagctcat catctacgaa     720
ctaacaaatg acaaatccct catcacgaca tcagactgtc cccgcacttg gaacttcttc     780
cgcgggaagc ccttgttctc ggcctcgttt cccgacgatg tggacacgac gtcggttgcc     840
ctgacagtgt tgcgcccacc ccgcacgctt gtcaactcga tcttggacga gatgctagag     900
tatgtcgacg ccgacggcat catgcagacc tacttcgacc actcgcgccc gcggatggat     960
ccgttcgtct gtgtcaacgt cctgtcgctg ttctacgagt acggccgggg acaggacctc    1020
ccgaagaccc tcgaatgggt atacgaggtt ctgctgcacc gcgcctacat cggcggctcg    1080
cggtactaca tgtccgcgga ctgcttcctc ttcttcatga gccgccttct ccaacgtatc    1140
accgacccag ccgtcctgaa ccgcctccgc ccgttgttcg tcgagcgcat gcacgaacgt    1200
gtcagcgcac cgggcgactc catggagctc gcgttccgca tcctcgctgg ctcgtccgtc    1260
ggcatccagt tcccacgtga cctggagaag ctcctcgccg cgcagtgcgc cgacggcggc    1320
tgggacctgt gctggttcta ccagtatggg tccaccggcg tgaaggcagg caaccgcggg    1380
ctcaccaccg cgctcgccat caaggctatc gagagcgcta tcgcgcgccc tccgtccccc    1440
gctctatcag ctgtatcgtc gtcgaaactg gaagtgccga aaccaattct ccagcgtccc    1500
ctcagcccgc gccggcttgg cgacttcctg atgccctgga ggagagcaca gcgcgaggtc    1560
gcggtttcca gctag                                                    1575

<210> SEQ ID NO 65
<211> LENGTH: 1575
<212> TYPE: DNA
<213> ORGANISM: Artificial Sequence
<220> FEATURE:
<223> OTHER INFORMATION: codon optimized cDNA

<400> SEQUENCE: 65
atggctagcc cgcaccgtcg ctatactact ctgattctgg atttgggtga tgttttgttt      60
agctggagca gcaaaaccaa tacgcctatt ccgcccgaaaa agctgaaaga aatcctgtct     120
agcctgacct ggttcgagta cgagcgcggt cgcatttctc aagccgagtg ctatgaccgt     180
```

```
gtgagctctg agtttagcct ggacgcagcg accattgcag aggcattcca acaggctcgt    240
gactcgctgc gcccgaacga agaatttctg gcgttgattc gtgagctgcg ccagcagacc    300
cacggccaac tcaccgttct ggcactgagc aacatctccc tgccggatta cgagtacatc    360
atggctctgg atagcgattg gaccagcgtc tttgatagag ttttcccgag cgcgctggtt    420
ggtgagcgta agccgcatct gggtgcttac cgtcgtgtca ttagcgagat gcatctggac    480
ccggagacta cggtgtttgt ggacgacaaa ctggacaacg ttgtctccgc gcgcagcctg    540
ggtatgcacg cgtcgttttt tgactcacaa gaaaatgttt tccagacgct gcgtaacatt    600
ttcggtgacc ctatccaccg tggccgcgac tatttgcgtc gtcatgccgg tcgtttggaa    660
accagcaccg acgcgggcgt tgtttttgaa gaaaacttca cccagctgat catctacgaa    720
ctgacgaatg acaagagcct gatcaccacg agcgattgtc cgcgcacctg gaacttcttc    780
cgtggtaagc cgctgtttag cgcgtccttc ccagacgatg tcgatacgac ttcggtggcc    840
ctgaccgttc tgcgcccacc gcgcaccctg gtaaacagca tcctggacga aatgttagaa    900
tacgtcgatg cggatggtat tatgcagacc tatttcgacc acagccgtcc gcgcatggac    960
ccgtttgtgt gtgtgaatgt gttgagcctg ttctatgagt acggccgtgg tcaagatctg   1020
ccaaaaaccc tggaatgggt ctacgaagtc cttctgcatc gtgcctacat cggtggctcc   1080
cgttattaca tgagcgcaga ttgcttttttg ttctttatgt ctcgtctgct gcagcgcatc   1140
acggaccctg ccgtgctgaa tcgtctgcgt ccgctgttcg tggagcgtat gcacgagcgc   1200
gtgtctgccc cgggtgacag catggaactg gcgttccgta tcctggcggg cagcagcgtg   1260
ggtattcaat ttccgcgtga tttggagaaa ctgctggctg cgcagtgtgc ggacggtggc   1320
tgggatctgt gctggtttta tcaatacggt agcaccggcg ttaaggccgg caatcgtggc   1380
ctgacgacgg cactggcaat taaggccatt gagtccgcga ttgcgcgtcc gccgagcccg   1440
gcattgagcg cggtcagcag cagcaaactg gaagtgccga agccgatctt gcagcgtcca   1500
ctgagcccgc gtcgtctggg tgacttcctg atgccgtggc gccgtgcgca acgcgaagtc   1560
gcggttagct cctaa                                                   1575
```

<210> SEQ ID NO 66
<211> LENGTH: 527
<212> TYPE: PRT
<213> ORGANISM: Dichomitus squalens

<400> SEQUENCE: 66

```
Met Ala Ser Ile His Arg Arg Tyr Thr Thr Leu Ile Leu Asp Leu Gly
1               5                   10                  15

Asp Val Leu Phe Arg Trp Ser Pro Lys Thr Glu Thr Ala Ile Pro Pro
            20                  25                  30

Gln Gln Leu Lys Asp Ile Leu Ser Val Thr Trp Phe Glu Tyr Glu
        35                  40                  45

Arg Gly Arg Leu Ser Gln Glu Ala Cys Tyr Glu Arg Cys Ala Glu Glu
    50                  55                  60

Phe Lys Ile Glu Ala Ser Val Ile Ala Glu Ala Phe Lys Gln Ala Arg
65                  70                  75                  80

Gly Ser Leu Arg Pro Asn Glu Glu Phe Ile Ala Leu Ile Arg Asp Leu
                85                  90                  95

Arg Arg Glu Met His Gly Asp Leu Thr Val Leu Ala Leu Ser Asn Ile
            100                 105                 110

Ser Leu Pro Asp Tyr Glu Tyr Ile Met Ser Leu Ser Ser Asp Trp Thr
        115                 120                 125
```

Thr Val Phe Asp Arg Val Phe Pro Ser Ala Leu Val Gly Glu Arg Lys
    130                 135                 140

Pro His Leu Gly Cys Tyr Arg Lys Val Ile Ser Glu Met Asn Leu Glu
145                 150                 155                 160

Pro Gln Thr Thr Val Phe Val Asp Asp Lys Leu Asp Asn Val Ala Ser
                165                 170                 175

Ala Arg Ser Leu Gly Met His Gly Ile Val Phe Asp Asn Gln Ala Asn
            180                 185                 190

Val Phe Arg Gln Leu Arg Asn Ile Phe Gly Asp Pro Ile Arg Arg Gly
        195                 200                 205

Gln Glu Tyr Leu Arg Gly His Ala Gly Lys Leu Glu Ser Ser Thr Asp
    210                 215                 220

Asn Gly Leu Ile Phe Glu Glu Asn Phe Thr Gln Leu Ile Ile Tyr Glu
225                 230                 235                 240

Leu Thr Gln Asp Arg Thr Leu Ile Ser Leu Ser Glu Cys Pro Arg Thr
                245                 250                 255

Trp Asn Phe Phe Arg Gly Glu Pro Leu Phe Ser Glu Thr Phe Pro Asp
            260                 265                 270

Asp Val Asp Thr Thr Ser Val Ala Leu Thr Val Leu Gln Pro Asp Arg
        275                 280                 285

Ala Leu Val Asn Ser Val Leu Asp Glu Met Leu Glu Tyr Val Asp Ala
    290                 295                 300

Asp Gly Ile Met Gln Thr Tyr Phe Asp Arg Ser Arg Pro Arg Met Asp
305                 310                 315                 320

Pro Phe Val Cys Val Asn Val Leu Ser Leu Phe Tyr Glu Asn Gly Arg
                325                 330                 335

Gly His Glu Leu Pro Arg Thr Leu Asp Trp Val Tyr Gly Val Leu Leu
            340                 345                 350

His Arg Ala Tyr His Gly Gly Ser Arg Tyr Tyr Leu Ser Pro Asp Cys
        355                 360                 365

Phe Leu Phe Phe Met Ser Arg Leu Leu Lys Arg Ala Asp Asp Pro Ala
    370                 375                 380

Val Gln Ala Arg Leu Arg Pro Leu Phe Val Glu Arg Val Asn Glu Arg
385                 390                 395                 400

Val Gly Ala Ala Gly Asp Ser Met Asp Leu Ala Phe Arg Ile Leu Ala
                405                 410                 415

Ala Ala Ser Val Gly Val Gln Cys Pro Arg Asp Leu Glu Arg Leu Thr
            420                 425                 430

Ala Gly Gln Cys Asp Asp Gly Gly Trp Asp Leu Cys Trp Phe Tyr Val
        435                 440                 445

Phe Gly Ser Thr Gly Val Lys Ala Gly Asn Arg Gly Leu Thr Thr Ala
    450                 455                 460

Leu Ala Val Thr Ala Ile Gln Thr Ala Ile Gly Arg Pro Pro Ser Pro
465                 470                 475                 480

Ser Pro Ser Ala Ala Ser Ser Phe Arg Pro Ser Pro Tyr Lys
                485                 490                 495

Phe Leu Gly Ile Ser Arg Pro Ala Ser Pro Ile Arg Phe Gly Asp Leu
            500                 505                 510

Leu Arg Pro Trp Arg Lys Met Ser Arg Ser Asn Leu Lys Ser Gln
        515                 520                 525

<210> SEQ ID NO 67
<211> LENGTH: 1584

```
<212> TYPE: DNA
<213> ORGANISM: Dichomitus squalens
<220> FEATURE:
<221> NAME/KEY: misc_feature
<223> OTHER INFORMATION: cDNA

<400> SEQUENCE: 67
atggcctcaa tccaccgtcg atacactact ctcatcctcg acctcggcga cgtactcttt      60
cgttggtctc caaagactga daccgccatt ccacctcaac aactcaagga tatcctctcc     120
tctgtcacct ggtttgagta cgaacgcggc agactatccc aggaagcatg ctacgagcgc     180
tgcgccgagg agttcaagat agaggcctcg gtcattgcag aagcctttaa gcaggctcgc     240
gggtcactgc ggcccaacga ggagttcatc gccttgatcc gtgacctccg ccgtgagatg     300
cacggtgacc ttaccgttct tgccctctcc aacatctccc tccccgacta cgaatacatc     360
atgtcgctaa gctcagattg gacgaccgtc ttcgatcgcg tattcccctc tgcactcgtt     420
ggcgagcgca agcctcatct gggatgctat cgcaaggtca tctcggagat gaacctagaa     480
cctcagacga ctgtgttcgt ggatgacaag cttgacaacg tcgcgtctgc tcgctcactt     540
ggtatgcacg gcatcgtgtt tgacaaccaa gccaacgtct tccgccaact ccgcaatatc     600
ttcggagacc ccatccgccg tggccaagag tatctccgtg ggcatgctgg caaactcgag     660
tcttcgaccg acaacgggtt gatcttcgag gagaacttca cacagctgat catctacgag     720
ttgacgcaag acaggactct catctcgctt tcagaatgtc ctcgtacttg gaatttcttc     780
cgaggcgaac cgctattctc ggagaccttc ccggatgatg tcgacacaac atctgtggcg     840
ttgacggtat tgcaaccgga cagagcactg gtcaactccg ttctagacga gatgctggag     900
tatgtcgacg ccgatggcat catgcagaca tacttcgatc gttcacgacc acgcatggac     960
ccttcgtct gcgtgaacgt actctccctg ttctacgaga acgtcgtgg tcacgagctc      1020
cctcgcacat tggactgggt ctacgaggtg ctcctccatc gcgcgtacca cggcggttcg    1080
cgttattacc tgtcgcccga ctgctttcta ttcttcatga ccgcctact caagcgcgca     1140
gacgatccag cagtccaggc tcggctccgc ccgctcttcg tcgagcgggt gaacgagcga    1200
gtaggcgccg ctggcgactc gatggacctc gccttccgca tcctcgccgc agcgtctgtt    1260
ggcgtccagt gccccgcga tctggaaagg ttgactgccg ggcaatgcga cgacggtgga    1320
tgggacctct gctggttcta cgtgttcggc tcgacgggcg tgaaggcggg caaccgcggc    1380
ctcacaacgg ccctcgctgt cacggccata cagacggcca tcggacgccc ccttcgccc    1440
agtccctccg cggcctcctc gtctttcaga cctagttccc cttacaaatt cctaggcatt    1500
tcgcgcccag ctagccccat tcgctttggc gacttacttc gcccatggcg aagatgagc    1560
aggtcgaact tgaagtctca atga                                          1584

<210> SEQ ID NO 68
<211> LENGTH: 1584
<212> TYPE: DNA
<213> ORGANISM: Artificial Sequence
<220> FEATURE:
<223> OTHER INFORMATION: codon optimized cDNA

<400> SEQUENCE: 68
atggcaagca ttcatcgtcg ctatactacg ctgattctgg acctgggtga tgttttgttc      60
cgctggagcc cgaaaaccga gactgcgatt cctccgcaac aactgaaaga catcctgagc     120
agcgtcacct ggttcgagta cgagcgtggc cgtctgagcc aagaggcttg ctacgagcgt     180
tgcgccgaag agttcaagat tgaagccagc gtgattgcgg aagcgttcaa acaagcgcgt     240
```

```
ggtagcctgc gtccgaacga agaatttatc gcactgatcc gtgatctgcg tcgcgagatg    300
catggtgacc tgaccgttct ggctctgagc aatatctcgt tgccggatta cgagtatatt    360
atgtctctga gcagcgactg gacgacggtc tttgatcgtg tgttcccgtc agctctggtg    420
ggcgagcgta aaccgcactt gggttgctat cgcaaggtca tcagcgagat gaacctggaa    480
cctcagacca cggtctttgt ggacgataaa ctggataatg tcgcaagcgc gcgtagcctg    540
ggtatgcacg gtatcgtgtt tgataatcaa gcgaatgtgt tcgccagct gcgtaatatt     600
ttcggtgatc caatccgtcg cggtcaagag tatctgcgtg gccatgccgg taaattggag    660
agcagcacgg acaatggttt gatctttgaa gagaacttca cccagctgat catttatgaa    720
ctgacccagg accgcacgtt gatcagcctg tcggagtgtc gcgtacctg gaacttcttc     780
cgtggcgagc gttgttttc tgaaaccttc ccggacgacg tggacaccac gtccgttgca    840
ctgacggttc tgcaaccgga tcgcgcactg gttaacagcg tgctggacga aatgctggaa    900
tatgtcgatg cggatggcat catgcagacg tatttcgacc gctcgcgtcc gcgtatggac    960
ccgtttgttt gcgtcaacgt actgagcctg ttttacgaga acggtcgtgg tcacgaactg   1020
ccgcgcactc tggattgggt gtacgaagtc ctgctccacc gcgcctacca cggtggttcc   1080
cgttactacc tgagcccgga ctgtttcttg tttttatga gccgtctgct gaaacgtgca    1140
gacgacccag cggttcaggc gagattgcgt ccgctgtttg tggaacgcgt taacgaacgt   1200
gttggcgcgg ccggtgatag catggacctg gcgtttcgca ttctggccgc agcgagcgtg   1260
ggtgtgcagt gtccgcgcga cctggagcgt ctgaccgctg gtcaatgcga tgatggcggc   1320
tgggatctgt gttggttcta cgttttcggc agcaccggcg ttaaggccgg taatcgtggt   1380
ctgaccacgg cgctggcagt caccgcgatc cagaccgcca tcggccgtcc gcctagcccg   1440
agcccgtccg cggcaagctc cagcttccgc ccgagcagcc cgtacaagtt tctgggtatt   1500
agccgtccgg cgtccccaat tcgcttcggt gaccttctgc gtccgtggcg taaaatgtct   1560
cgctctaacc tgaagtccca gtaa                                          1584
```

<210> SEQ ID NO 69
<211> LENGTH: 495
<212> TYPE: PRT
<213> ORGANISM: Antrodia cinnamomea

<400> SEQUENCE: 69

Met Arg Arg Asn Val Leu Asn Lys Ala Thr His Ser Gln Ser Pro Leu
1               5                   10                  15

Lys Pro Asn Ile Thr Thr Leu Ile Phe Asp Leu Gly Asp Val Leu Leu
            20                  25                  30

Thr Trp Ser Asp Ser Thr Pro Lys Ser Pro Leu Pro Pro Lys Ile Val
        35                  40                  45

Lys Gly Ile Leu Arg Ser Leu Thr Trp Phe Glu Tyr Glu Lys Gly Asn
    50                  55                  60

Leu Thr Glu Ser Gln Thr Tyr Gly Gln Val Ala Gln Glu Phe Gly Val
65                  70                  75                  80

Asp Ala Ser Glu Val Lys Ala Ser Phe Glu Ala Ala Arg Asp Ser Leu
                85                  90                  95

Lys Ser Asn Pro Met Leu Leu Gln Leu Ile Arg Ser Leu Lys Asp Ser
            100                 105                 110

Gly His Val Ile Tyr Ala Met Ser Asn Ile Ser Ala Pro Asp Trp Glu
        115                 120                 125

```
Phe Leu Lys Thr Arg Ala Asp Leu Ser Asp Trp Ala Leu Phe Asp Arg
    130                 135                 140
Val Phe Pro Ser Ala Glu Ala His Asp Arg Lys Pro Asn Ile Gly Phe
145                 150                 155                 160
Tyr Gln His Val Ile Asn Glu Thr Gly Leu Asn Pro Ser Asn Thr Val
                165                 170                 175
Phe Val Asp Asp Arg Ile Glu Asn Val Val Ser Ala Arg Ser Ala Gly
            180                 185                 190
Met His Gly Ile Val Phe Asp Ile Asn Asn Val Ile Arg Gln Leu
        195                 200                 205
Lys Asn Leu Cys Glu Asp Pro Ile His Arg Ala Arg Ser Phe Leu Tyr
    210                 215                 220
Ala Asn Lys Lys Cys Leu Asn Thr Val Ser Thr Asp Gly Thr Ile Val
225                 230                 235                 240
Ser Glu Asn Phe Ser Gln Leu Leu Ile Leu Glu Ala Ile Gly Asp Glu
                245                 250                 255
Ser Leu Val Asp Phe Val Arg His Glu Gly Arg Phe Asn Phe Gln
            260                 265                 270
Gly Glu Ala Lys Leu Ile Met Thr Asn His Tyr Pro Asp Asp Phe Asp
        275                 280                 285
Thr Thr Ser Ile Gly Leu Thr Val Val Pro Tyr Ile Asp Asp Lys Thr
    290                 295                 300
Arg Asn Arg Val Met Asp Glu Ile Leu Ala Tyr Gln Ser Glu Asp Gly
305                 310                 315                 320
Ile Val Leu Val Tyr Phe Asp His Lys Arg Pro Arg Ile Asp Pro Val
                325                 330                 335
Val Cys Val Asn Val Leu Thr Leu Phe Tyr Arg Tyr Gly Arg Gly His
            340                 345                 350
Gln Leu Gln Lys Thr Leu Asp Trp Val Glu Gln Val Leu Ile Asn Arg
        355                 360                 365
Ala Cys Ala Ser Gly Thr Phe Tyr Tyr Ala Thr Glu Glu Gln Phe Leu
    370                 375                 380
Phe Phe Leu Ser Arg Leu Ile Gln Ser Ser Pro Asp Val Arg Gln Arg
385                 390                 395                 400
Leu Glu Gly Val Phe Lys Arg Val Val Glu Arg Phe Gly Ala Asp
                405                 410                 415
Gly Asp Ala Leu Ala Met Ala Met Arg Ile His Thr Ala Ala Ser Val
            420                 425                 430
Gly Leu Val Asp His Val Asp Leu Asp Lys Leu Phe Ala Leu Gln Gln
        435                 440                 445
Asn Asp Gly Ser Trp Arg Asp Ser Ala Phe Tyr Arg Phe Pro Ser Ala
    450                 455                 460
Arg Gln Leu Ala Ser Asn Asp Gly Leu Thr Thr Ala Ile Ala Ile Gln
465                 470                 475                 480
Ala Ile Gln Ala Ala Glu Arg Leu Arg Glu Asp Gly Asn Val Leu
                485                 490                 495

<210> SEQ ID NO 70
<211> LENGTH: 1488
<212> TYPE: DNA
<213> ORGANISM: Antrodia cinnamomea
<220> FEATURE:
<221> NAME/KEY: misc_feature
<223> OTHER INFORMATION: cDNA

<400> SEQUENCE: 70
```

| | | |
|---|---|---|
| atgaggcgaa acgtactcaa caaagcaaca cattctcagt caccattgaa gcccaacatc | 60 | |
| acgacgctca tatttgactt gggcgacgta cttctcacgt ggtccgactc aacacctaaa | 120 | |
| tctccactgc ccccaaaaat tgtcaaggga atactacgtt cactgacctg gtttgagtac | 180 | |
| gagaaaggga acttgacaga gtcccagacc tacgggcaag ttgctcagga atttggagtg | 240 | |
| gatgcttccg aagtcaaagc ttccttcgaa gcagctcgcg actcgctcaa gagcaaccca | 300 | |
| atgcttctcc agttgatccg tagcctcaaa gactctggcc acgtcattta cgcaatgtct | 360 | |
| aacatatctg ctcccgactg ggaattttg aagacgcggg cagacctctc agattgggct | 420 | |
| cttttgaca gagtcttccc ttctgccgaa gcgcatgacc gcaagccgaa cattggtttc | 480 | |
| tatcagcacg tcataaacga gactggtctg aacccgtcca acactgtctt tgtcgatgac | 540 | |
| aggatcgaga tgttgtatc cgcacgctca gcaggaatgc acgggatcgt gtttgacgac | 600 | |
| ataaataatg tgatccgaca gttgaaaaac ctctgcgagg atccgattca ccgcgcacga | 660 | |
| tcttttcttt atgcaaataa gaagtgtttg aatacggtta gcacagatgg cacaattgtg | 720 | |
| agcgagaact tctcgcaatt gttgatcctt gaggccattg gcgacgaaag cctagtcgac | 780 | |
| tttgtgaggc atgagggccg attcaacttc ttccagggg aggccaaact catcatgacg | 840 | |
| aatcactacc ccgatgattt cgatactaca tccataggtt taaccgttgt tccatatatt | 900 | |
| gacgacaaga ctagaaatag agttatggat gagatcctgg cctaccaaag cgaagacggc | 960 | |
| attgtgctgg tatactttga ccacaagcgc cccaggattg atcctgttgt ctgtgtcaat | 1020 | |
| gtcctcaccc tcttctatag gtatggccgt gggcaccagc ttcaaaagac actggattgg | 1080 | |
| gtcgaacagg tcctgatcaa ccgtgcgtgt gcgtccggca cgttctatta cgcaacagag | 1140 | |
| gaacaattcc tcttttttcct ctcccgcctg atccaaagct ctccggacgt acgacagcgg | 1200 | |
| ttggaagggg tcttaaaag aagagtagtc gagcggtttg gtgcagacgg cgacgctctc | 1260 | |
| gctatgcgga tgcgcattca caccgcgcg agcgtgggcc tcgttgacca tgtcgatctt | 1320 | |
| gacaagctgt tcgcattgca gcaaaatgac ggttcttgga gagacagcgc tttctacaga | 1380 | |
| tttccgtcgg ccaggcaact ggctagtaac gacggcttga cgactgcaat cgctattcag | 1440 | |
| gccattcaag ctgcggagag gctcaggag gatgggaacg tgctttga | 1488 | |

<210> SEQ ID NO 71
<211> LENGTH: 1488
<212> TYPE: DNA
<213> ORGANISM: Artificial Sequence
<220> FEATURE:
<223> OTHER INFORMATION: codon optimized cDNA

<400> SEQUENCE: 71

| | | |
|---|---|---|
| atgcgccgta atgtcctgaa caaagcaacc catagccagt caccgttgaa accgaatatc | 60 | |
| accacgctga tttttgactt gggcgatgtc ctgctgacct ggagcgacag cactccgaaa | 120 | |
| tctccgttgc cgccgaagat cgtcaagggc atcctgcgta gcctgacttg gttcgagtac | 180 | |
| gaaaagggca atttgaccga agccaaacg tatggtcagg tcgcgcaaga atttggtgtg | 240 | |
| gatgcctctg aagtgaaggc cagctttgag gctgcgcgtg atagcttgaa atcgaatccg | 300 | |
| atgctgctgc agctgattcg cagcctgaaa gattccggtc acgtgatcta cgccatgagc | 360 | |
| aacatcagcg cgcctgattg ggaatttctg aaaacccgcg ctgacctgtc tgactgggcc | 420 | |
| ctgtttgacc gcgtgttccc gtctgccgag gcacatgacc gcaaaccgaa cattggctt | 480 | |
| taccaacacg tgatcaatga aacgggtctg aatccatcca ataccgtgtt cgttgacgac | 540 | |

```
cgtattgaaa acgttgttag cgcacgtagc gctggtatgc acggtatcgt tttcgatgac    600
attaacaacg tcattcgcca gctgaagaat ctgtgcgagg acccaattca ccgtgcacgt    660
tccttttgt atgcgaacaa aaagtgcctg aataccgtga gcaccgatgg tacgatcgtc     720
agcgagaact ttagccagct tctgattctg gaagccattg gtgacgagtc cctggtagac    780
ttcgtccgcc atgagggccg ttttaacttc ttccagggtg aggcaaagct gatcatgacc    840
aatcactacc cggacgattt cgataccacg agcattggtc tgaccgttgt cccgtatatc    900
gatgacaaaa cgcgtaatcg tgtgatggat gaaatcctgg cgtatcagtc cgaggatggt    960
atcgttctgg tgtacttcga tcacaagcgt ccgcgcattg acccggtcgt ttgtgtgaac   1020
gttctgacgc tgttctaccg ctatggtcgt ggccatcaac tgcagaaaac cctggactgg   1080
gttgagcaag tcctgattaa tcgtgcgtgt gcgagcggca cgttctacta cgcgaccgaa   1140
gaacagttcc tgttttttcct gagccgtctg attcagtcga ccctgacgt gcgccaacgt   1200
ctggaaggcg tgttcaagcg tcgtgtcgtt gagcgctttg gtgcgacgg tgatgccctg   1260
gcaatggcga tgcgtatcca taccgcagcg agcgttggcc tggtgaccca cgtggatctg   1320
gataagctgt tcgcgctgca acagaacgac ggtagctggc gcgatagcgc gttttatcgt   1380
tttccgagcg cgcgtcaact cgcgagcaac gacggcttga ccacggcaat tgctattcag   1440
gccatccaag cggctgagag attacgtgag gatggtaacg ttctgtaa               1488
```

<210> SEQ ID NO 72
<211> LENGTH: 543
<212> TYPE: PRT
<213> ORGANISM: Aspergillus ustus

<400> SEQUENCE: 72

```
Met Val Arg Ala Leu Ile Leu Asp Leu Gly Asp Val Leu Phe Asn Trp
1               5                   10                  15

Asp Ala Pro Lys Ser Thr Pro Val Ser Arg Lys Thr Leu Ser Gln Met
                20                  25                  30

Leu His Ser Asp Ile Trp Gly Glu Tyr Glu Cys Gly Gln Leu Thr Glu
            35                  40                  45

Pro Glu Ser Tyr Lys Ala Leu Ala Ser Arg Tyr Ser Cys Gln Ala Gln
        50                  55                  60

Asp Val Ala Asp Thr Phe Tyr Leu Ala Arg Glu Ser Leu Arg Leu Asp
65                  70                  75                  80

Ala Thr Phe Lys Thr Phe Leu Gln Asp Leu Lys Gln Arg Ala Asn Gly
                85                  90                  95

Ser Leu Arg Val Tyr Gly Met Ser Asn Ile Ser Gln Pro Asp Tyr Glu
            100                 105                 110

Val Leu Leu Ser Lys Ala Asp Asp Leu Ser Leu Phe Asp Lys Ile Phe
        115                 120                 125

Pro Ser Gly His Val Gly Met Arg Lys Pro Asp Leu Ala Phe Phe Arg
    130                 135                 140

His Val Leu Arg Glu Ile Ser Thr Ala Ser Glu Asp Ile Val Phe Val
145                 150                 155                 160

Asp Asp Asn Leu Glu Asn Val Thr Ser Ala Arg Ser Leu Gly Met Gln
                165                 170                 175

Gly Ile Val Phe Arg Asp Lys Glu Asp Val Gln Arg Gln Leu Arg Asn
            180                 185                 190

Leu Phe Gly Ser Pro Ala Glu Arg Gly Arg Glu Tyr Leu Ser Ile Asn
        195                 200                 205
```

```
Lys Thr Lys Leu Gln Ser Val Thr Thr Asn Ile Pro Ile Leu Asp
210                 215                 220
Asn Phe Gly Gln Leu Leu Ile Leu Glu Ala Thr Arg Asp Pro Asp Leu
225                 230                 235                 240
Val Ser Met His Pro Gly Gln Arg Thr Trp Asn Phe Phe Ile Gly Ser
            245                 250                 255
Pro Thr Leu Thr Thr Asp Ala Phe Pro Asp Asp Met Asp Thr Thr Ser
        260                 265                 270
Leu Gly Leu Ser Ile Ile Pro Pro Ser Pro Glu Ile Ala Ala Ser Val
    275                 280                 285
Met Asp Glu Ile Val Thr Arg Leu Asn Lys Asp Gly Ile Val Pro Thr
290                 295                 300
Tyr Phe Asp Ser Thr Arg Pro Arg Val Asp Pro Ile Val Cys Val Asn
305                 310                 315                 320
Val Leu Thr Leu Phe Ala Lys Tyr Gly Arg Glu Asp Glu Leu Ser Gly
            325                 330                 335
Thr Ile Ala Trp Val Arg Asp Val Leu Tyr His Arg Ala Tyr Leu Ala
        340                 345                 350
Gly Thr Arg Tyr Tyr Ala Ser Pro Glu Ala Phe Leu Phe Phe Phe Thr
    355                 360                 365
Arg Phe Thr Arg Asn Leu Arg Pro Gly Pro Arg Lys Gln Glu Leu Thr
370                 375                 380
Ala Leu Leu Ser Gln Arg Leu Gln Glu Arg Asn Lys Thr Pro Val Asp
385                 390                 395                 400
Ala Leu Ala Leu Ser Met Arg Ile Ile Ala Cys Leu Thr Leu Gly Ile
            405                 410                 415
Glu Ser Pro Ala Asp Asp Val Ala Thr Leu Thr Gly Met Gln Cys Gly
        420                 425                 430
Asp Gly Gly Trp Pro Ala Cys Val Ile Tyr Lys Tyr Gly Ala Gly Gly
    435                 440                 445
Leu Gly Ile Thr Asn Arg Gly Val Ser Thr Ala Phe Ala Val Lys Ala
    450                 455                 460
Ile Thr Thr Thr Pro Leu Ala Val Gln Pro Glu Val Ser Val Ser Ala
465                 470                 475                 480
Gly Ala Gly Gly Ser Ser Arg Pro Val Gly Ala Asp Ala Ala Val
            485                 490                 495
Ser Leu Arg Pro Arg Trp Arg Ala Val Val Gln Ser Leu His Pro Leu
        500                 505                 510
Ser Arg Val Gly Gly Leu Val Ala Val Ile Phe Ala Ala Leu His Phe
    515                 520                 525
Asn Leu Ala Trp Leu Tyr Asn Val Ser Leu Ala Ser Arg Ile Val
530                 535                 540

<210> SEQ ID NO 73
<211> LENGTH: 1632
<212> TYPE: DNA
<213> ORGANISM: Aspergillus ustus
<220> FEATURE:
<221> NAME/KEY: misc_feature
<223> OTHER INFORMATION: cDNA

<400> SEQUENCE: 73
atggtccgcg cactgattct cgatctcggc gacgtcctct tcaactggga cgccccaaag      60
tcaacccccg tttcccgcaa gacactcagc cagatgctgc atagcgacat ctggggcgaa     120
tacgaatgtg gccaactgac agagccggaa agctacaagg cgcttgccag ccgctattct     180
```
tgccaggctc aagatgttgc agataccttc tatctagccc gcgaatcgct gaggctcgat      240
gcgaccttca agaccttcct gcaggacttg aagcagaggg ccaacggctc acttcgcgta      300
tatgggatgt ccaacatctc ccagcccgat tatgaggtcc tgctgtccaa ggcggatgac      360
ttgagcctgt tgacaagat cttcccatcc ggccacgtcg gatgcgtaa gcctgacctt        420 gcgttttttc gacatgtcct gcgtgagatc tcgacggcca gcgaggatat tgtgtttgtt      480
gacgacaacc tggagaacgt gacatctgcc cggtctctgg gcatgcaggg gattgtcttt      540
cgcgacaagg aggatgtaca gagacagctg cggaacctct ttggcagtcc tgctgaacgt      600
ggaagggagt atttgtccat caacaagaca aagctccaga gcgtcacgac gaccaatatc      660
cccattctcg acaactttgg ccagctcctt atcctcgaag ccaccagaga cccagacctg      720
gtgtccatgc atcctggaca gaggacctgg aacttttttca tcggatctcc aactctgaca      780
acggacgcct tcccagacga tatggacacc acctcacttg gcctttctat tatacccca       840 agtcccgaga ttgcagcgtc cgtgatggat gagattgtga cccgcctgaa caaggacggc      900
attgtcccaa catattttga cagcaccaga ccccgcgtcg acccgatcgt ctgcgtcaac      960
gttctcaccc tcttcgctaa atacggccgc gaagacgagc tgtccgggac atagcctgg      1020 gtgcgcgatg tgctgtatca cagggcctac cttgcaggga ccagatacta cgcatcccca     1080
gaagcattcc ttttcttctt cacgcgcttc acccgaaacc tgcgcccggg ccgcgcaag      1140 caggagctca cggcgctgct gtcccagcgc ctgcaggagc gcaacaagac gcccgttgac      1200
gcacttgcgc tctcgatgcg gattattgcg tgcctcacgc tgggtattga atcccccgct     1260
gacgacgtgg ctaccctcac gggcatgcag tgtggggatg gcggtggcc ggcctgtgtc      1320 atctacaagt acggcgccgg tgggctgggg atcacgaaca gggggtctc gaccgcgttt      1380 gctgtcaagg caatcactac tactcctttg gcggtgcagc ctgaagttag tgtcagcgca     1440
ggtgcaggag gcagcagtcg ccctgtgggt gccgatgctg ctgcagtctc gctccgcccg     1500
agatggcgag ctgttgtgca gagtctccat ccgctctctc gggttggtgg gttggtggcc     1560 gtcattttg ctgcactgca tttcaacttg gcctggcttt ataatgtgtc ccttgctagt     1620
aggatcgttt ag                                                          1632

<210> SEQ ID NO 74
<211> LENGTH: 1632
<212> TYPE: DNA
<213> ORGANISM: Artificial Sequence
<220> FEATURE:
<223> OTHER INFORMATION: codon optimized cDNA

<400> SEQUENCE: 74
atggttcgtg cattgatttt ggatttgggt gatgtgttgt ttaactggga tgcgcctaag       60
agcaccccgg tttccgcaa gactctgagc caaatgctgc actcggatat tggggcgag      120 tacgagtgtg tcaactgac tgagccggag tcctataaag ccctggcgag ccgctatagc      180
tgccaggcgc aagatgtcgc tgacaccttt tacctggcgc gtgagagcct gcgtctggac      240
gcaacgttta agaccttcct gcaagatctg aagcaacgcg ccaacggttc tctgcgtgtc      300
tatggtatga gcaatatcag ccagccggat tacgaagtcc tgctgagcaa agctgacgat      360
ctcagcctgt tgacaaaat cttttccgtcg ggtcacgttg gtatgagaaa gcctgacctg      420 gcgttttttcc gtcacgttct gcgtgagatc agcacggcta gcgaagatat tgtgtttgtt      480
gacgacaatt tggaaaacgt cacgtctgca cgctcccctgg gtatgcaagg catcgtcttt      540

```
cgtgataagg aagatgtcca gcgccagctg cgcaatctgt tcggttcccc ggcagagcgc      600
ggtcgtgagt atctgagcat taataagacc aaactgcaga gcgtgaccac caccaatatc     660
ccgattctgg acaacttcgg tcagttgctg atcctggaag ctacccgtga cccggattta     720
gtcagcatgc atccaggcca acgtacgtgg aacttcttca ttggcagccc gaccttgacg     780
accgacgcgt ttccggacga tatggacacg acttctctgg gcctgagcat catcccgccg     840
agcccggaaa ttgcagcaag cgttatggac gaaatcgtca cccgtctgaa taaagatggt     900
attgtgccga cctacttcga cagcacgcgt ccacgtgtgg acccgatcgt ctgcgttaac     960
gtcctgacct tgtttgcgaa atatggtcgt gaagatgaac tgagcggcac gattgcgtgg    1020
gtccgcgacg ttctgtatca tcgcgcatac ctggcgggca cgcgctacta cgcgtcccca    1080
gaggccttcc tgttcttctt tacgcgtttc acccgcaatc tgcgtccggg tccgcgtaaa    1140
caagaactta cggcgctgct gagccagcgt ctgcaggaac gcaacaagac gccggttgac    1200
gctctggccc tgagcatgcg tatcatcgcc tgtctgaccc tgggcattga gagcccggca    1260
gacgacgtgg ccaccctgac cggtatgcag tgtggtgatg gtggctggcc ggcgtgcgtg    1320
atctacaaat atggtgcggg tggcttgggt atcacgaatc gtggcgttag cactgccttc    1380
gcggtgaaag cgattacgac caccccgctg gcagtgcagc cagaagtcag cgtcagcgct    1440
ggtgccggcg gctccagccg cccggttggt gcggatgcgg cagcggttag cttgcgtccg    1500
cgttggcgtg cggttgtgca gagcctgcat ccgctgagcc gcgtgggtgg cctggttgcc    1560
gtgatcttcg cggcactgca ctttaacctg gcgtggctgt acaacgtaag cctggctagc    1620
cgtattgtgt aa                                                          1632

<210> SEQ ID NO 75
<211> LENGTH: 477
<212> TYPE: PRT
<213> ORGANISM: Aspergillus oryzae

<400> SEQUENCE: 75

Met Thr Arg Trp Lys Ser Ser Gln Tyr Gln Ala Ile Ile Phe Asp Leu
1               5                   10                  15

Gly Gly Val Ile Leu Thr Trp Asp Leu Pro Glu Asp Thr Val Ile Ser
            20                  25                  30

Ala Gln Ile Phe Lys Arg Met Leu Thr Ser Gln Thr Trp Ser Asp Tyr
        35                  40                  45

Glu Arg Gly Asn Leu Ser Glu Asn Gly Cys Tyr Gln Arg Leu Ala Glu
    50                  55                  60

Asp Phe Gly Ile Asp Ser Ala Asp Ile Ala His Thr Val Arg Gln Ala
65                  70                  75                  80

Arg Glu Ser Leu Val Thr Asp Thr Ala Ile Met Asn Ile Ile Ser Glu
                85                  90                  95

Ile Arg Ala Gly Ala Asn His Ile Ala Ile Phe Ala Met Ser Asn Ile
            100                 105                 110

Ser Gln Pro Asp Tyr Ala Ala Leu Leu Asp His Arg Gly Met Cys
        115                 120                 125

Ser Phe Asp Arg Val Phe Pro Ser Gly Cys Tyr Gly Thr Arg Lys Pro
    130                 135                 140

Glu Leu Ser Phe Tyr Asn Lys Val Leu Arg Glu Ile Asp Thr Pro Pro
145                 150                 155                 160

Glu Asn Val Ile Phe Val Asp Asp Gln Leu Glu Asn Val Ile Ser Ala
                165                 170                 175
```

```
Gln Ser Ile Gly Ile His Gly Ile Ala Tyr Thr Asn Ala Ala Glu Leu
            180                 185                 190

Gly Arg Gln Leu Arg Asn Leu Ile Phe Asp Pro Val Glu Arg Gly Arg
        195                 200                 205

Glu Phe Leu Arg Arg Asn Ala Gly Glu Phe His Ser Ile Thr Glu Thr
    210                 215                 220

Asp Gln Ile Val Arg Glu Asn Phe Ser Gln Leu Leu Ile Leu Glu Ala
225                 230                 235                 240

Thr Gly Asp Lys Ser Leu Val Ser Leu Glu Tyr His Gln Lys Ser Trp
                245                 250                 255

Asn Phe Phe Gln Gly Asn Pro Ile Leu Thr Thr Glu Thr Phe Pro Asp
            260                 265                 270

Asp Val Asp Thr Thr Ser Leu Ala Leu Met Thr Leu Pro Thr Asp Thr
        275                 280                 285

Lys Thr Ala Asn Leu Leu Asp Gln Ile Leu Gly Leu Val Asn Ala
    290                 295                 300

Asp Glu Ile Val Thr Thr Tyr Phe Asp Gln Thr Arg Glu Arg Ile Asp
305                 310                 315                 320

Pro Val Val Cys Val Asn Val Leu Arg Leu Phe Cys Thr Tyr Gly Arg
                325                 330                 335

Gly Ile Ala Leu Pro Leu Thr Leu Gln Trp Val Tyr Asp Val Leu Ala
            340                 345                 350

His Arg Ala Tyr Ile Asn Gly Thr Arg Tyr Tyr Thr Ser Pro Glu Ser
        355                 360                 365

Phe Leu Tyr Phe Val Gly Gln Leu Cys Arg Phe Ser Thr Gly Val Leu
    370                 375                 380

Ala Leu Arg Pro Leu Glu Thr Leu Leu Ile Asp Arg Leu Lys Glu Arg
385                 390                 395                 400

Leu Gln Val Lys Ala Asp Pro Leu Ser Leu Ala Met Arg Ile Leu Thr
                405                 410                 415

Cys Leu Ser Val Gly Val Ser Gln Val Glu Val Asp Leu Arg Glu Leu
            420                 425                 430

Leu Ser Met Gln Cys Glu Asp Gly Ser Trp Glu His Cys Pro Phe Thr
        435                 440                 445

Arg Tyr Gly Leu Ser Lys Val Ser Ile Gly Asn Arg Gly Leu Thr Thr
    450                 455                 460

Ala Phe Val Val Lys Ala Val Glu Met Cys Arg Gly Ser
465                 470                 475

<210> SEQ ID NO 76
<211> LENGTH: 1434
<212> TYPE: DNA
<213> ORGANISM: Aspergillus oryzae
<220> FEATURE:
<221> NAME/KEY: misc_feature
<223> OTHER INFORMATION: cDNA

<400> SEQUENCE: 76
atgactcgat ggaaatcgtc ccaataccaa gcaattatct ttgacctagg cggtgtcatt    60
ttaacatggg acctcccgga agacactgtg atatcggccc agatctttaa gagaatgctc   120
acatcgcaga catggtcaga ttatgagcgc ggaaatctca gcgaaaatgg ttgctaccag   180
aggttggccg aggattttgg cattgactct gccgacattg cacataccgt tagacaagca   240
cgggaatccc ttgtcactga taccgctatc atgaacatta tatctgagat cagagctggg   300
gctaaccata ttgctatctt cgctatgtcg aacatctccc aaccagatta tgcggctctg   360
```

```
ctccttgatc atcgcgggat gtgcagtttt gaccgggtgt tcccatctgg atgctacggg      420
acaaggaaac cagagctctc attctataac aaagtcttgc gggagattga cacgccaccg      480
gaaaacgtca tctttgtcga tgatcagctg aaaatgtga tctctgcgca gtccattggc       540
atacacggga ttgcctatac gaatgctgct gaactcggtc gacagcttag gaacctaata      600
tttgaccctg tagagagggg tagggaattc ttacggcgca atgctggaga gttccatagc      660
atcactgaaa ccgatcaaat tgttcgggaa aatttctcac agttgctcat tctagaagcg      720
actggtgata agagtctggt atctcttgaa tatcaccaga gagctggaa tttcttccaa       780 ggaaacccta ttctcacgac agagacattc ccagatgatg ttgacacaac atctcttgcc      840
ttgatgactc tacctacaga cacaaaaact gcaaatttgt tactcgacca gattttgggg     900
ctagtcaacg ctgatgaaat cgtaacaaca tactttgacc agacccgaga acggatcgat     960
ccagtagtct gcgtcaatgt ccttcgtctc ttttgcacct acggccgggg cattgcgctc     1020
cctttgactc ttcagtgggt gtacgacgtc ctcgctcatc gggcatatat aaacggtaca     1080
cgttactaca caagtcccga aagcttccta tacttcgtcg gtcaactttg tcgattctca     1140 acagggtac tggcacttcg ccgctggaa acgttgctta tagatcgtct caaggaacgt       1200
cttcaggtca aagcagatcc tctatcactc gctatgcgga tcttgacctg tttgtccgtt     1260
ggtgtgtctc aagttgaagt cgatctccga gagttgctct cgatgcagtg tgaagatggc     1320
tcgtgggaac attgtccatt cacccggtat ggtttgtcca aagtgagcat tggcaatcgg     1380
ggccttacaa ctgcttttgt ggtcaaggcg gttgaaatgt gtcgaggcag ttag           1434

<210> SEQ ID NO 77
<211> LENGTH: 1434
<212> TYPE: DNA
<213> ORGANISM: Artificial Sequence
<220> FEATURE:
<223> OTHER INFORMATION: codon optimized cDNA

<400> SEQUENCE: 77
atgactcgtt ggaaaagctc tcaatatcag gcaatcattt tcgatctggg cggtgttatt      60
ctgacctggg acttgccgga agatacggtt atctccgcgc aaatctttaa gcgtatgctg     120
accagccaga cctggtccga ttatgagcgc ggtaatctga gcgagaacgg ctgctatcaa     180
cgtttggcgg aagatttcgg catcgatagc gccgatattg cccacaccgt ccgtcaggca     240
cgtgagtccc tggtgaccga caccgccatc atgaatatca tctccgagat ccgtgcaggc     300
gcgaaccaca tcgcaatttt cgcgatgagc aacatctcac agccggatta cgctcgcctg     360
ctgctggacc atcgcggtat gtgcagcttt gaccgcgtct ttccgagcgg ttgttacggc     420
acccgtaagc ctgagctgag cttctacaat aaagtgctgc gtgaaattga cacccgccg     480 gaaaatgtta ttttcgttga cgatcaattg aaaatgtga ttagcgcgca aagcattggt     540
attcatggca ttgcgtatac gaatgccgcg gaactgggcc gccagctgag aaacctgatc     600
ttcgatccgg tggagcgcgg tcgtgagttc ctgcgtcgta acgctggtga gtttcactct     660
attacggaaa cggaccagat tgtgcgcgag aacttcagcc agctgctgat tctggaagcg     720
accggtgaca aaagcctggt tagcctggaa taccaccaaa agtcgtggaa cttcttccaa     780
ggtaacccaa tcctgacgac ggaaaccttc ccggacgatg ttgacactac tagcctggct     840
ctgatgacgc tgccgacgga caccaagacc gcgaatctgt tgctggacca gattctgggt     900
ttggttaatg ccgatgaaat tgtgactacg tacttcgacc agacccgtga gcgtatcgat     960
```

-continued

```
ccagtggtct gtgtgaatgt cctgcgcctg ttctgtacgt acggccgcgg catcgcgctg    1020
ccgctgaccc tgcaatgggt ctacgatgtg ctggcgcacc gcgcatacat taacggtacg    1080
cgttattaca ccagcccgga gagctttctg tattttgtcg gtcagctctg tcgttttagc    1140
accggtgtgc tggcactgcg tccgctggag actctgctga ttgatcgtct gaaagagcgc    1200
ctgcaagtta agctgacccc gctgagcctg gcaatgcgca tccttacgtg cttatctgtc    1260
ggtgtcagcc aggttgaagt ggacttgcgt gagttgttga gcatgcagtg cgaggacggt    1320
agctgggagc attgcccgtt cacccgctac ggcctgagca aggtttccat cggtaaccgt    1380
ggcctgacca cggcgtttgt ggttaaagcc gtcgagatgt gccgtggcag ctaa          1434
```

<210> SEQ ID NO 78
<211> LENGTH: 528
<212> TYPE: PRT
<213> ORGANISM: Aspergillus calidoustus

<400> SEQUENCE: 78

```
Met Val Arg Ala Leu Ile Leu Asp Leu Gly Asp Val Leu Phe Asn Trp
1               5                   10                  15

Asp Ala Pro Ala Ser Thr Pro Ile Ser Arg Lys Thr Leu Gly Gln Met
            20                  25                  30

Leu His Ser Glu Ile Trp Gly Glu Tyr Glu Arg Gly His Leu Thr Glu
        35                  40                  45

Asp Glu Ala Tyr Asn Ala Leu Ala Lys Arg Tyr Ser Cys Glu Ala Lys
    50                  55                  60

Asp Val Ala His Thr Phe Val Leu Ala Arg Glu Ser Leu Arg Leu Asp
65                  70                  75                  80

Thr Lys Phe Lys Thr Phe Leu Gln Thr Leu Lys Gln Asn Ala Asn Gly
                85                  90                  95

Ser Leu Arg Val Tyr Gly Met Ser Asn Ile Ser Lys Pro Asp Phe Glu
            100                 105                 110

Val Leu Leu Gly Lys Ala Asp Asp Trp Thr Leu Phe Asp Lys Ile Phe
        115                 120                 125

Pro Ser Gly His Val Gly Met Arg Lys Pro Asp Leu Ala Phe Phe Arg
    130                 135                 140

Tyr Val Leu Lys Asp Ile Ser Thr Pro Val Glu Asp Val Phe Val
145                 150                 155                 160

Asp Asp Asn Leu Asp Asn Val Thr Ser Ala Arg Ser Leu Gly Met Arg
                165                 170                 175

Ser Val Leu Phe His Lys Lys Asp Glu Val Gln Arg Gln Leu Thr Asn
            180                 185                 190

Ile Phe Gly Ser Pro Ala Glu Arg Gly Leu Glu Tyr Leu Ser Ala Asn
        195                 200                 205

Lys Thr Asn Leu Gln Ser Ala Thr Thr Asp Ile Pro Ile Gln Asp
    210                 215                 220

Asn Phe Gly Gln Leu Leu Ile Leu Glu Ala Thr Glu Asp Pro Ser Leu
225                 230                 235                 240

Val Arg Met Glu Pro Gly Lys Arg Thr Trp Asn Phe Ile Gly Ser
                245                 250                 255

Pro Ser Leu Thr Thr Asp Thr Phe Pro Asp Asp Leu Asp Thr Ser
            260                 265                 270

Leu Ala Leu Ser Ile Val Pro Thr Ser Pro Asp Val Val Asn Ser Val
        275                 280                 285

Ile Asp Glu Ile Ile Ser Arg Arg Asp Lys Asp Gly Ile Val Pro Thr
```

| | | | | | | | | | | |
|---|---|---|---|---|---|---|---|---|---|---|
| | | 290 | | | 295 | | | 300 | | |
| Tyr | Phe | Asp | Asn | Thr | Arg | Pro | Arg | Val | Asp | Pro | Ile | Val | Cys | Val | Asn |
| 305 | | | | 310 | | | | 315 | | | | 320 |

Tyr Phe Asp Asn Thr Arg Pro Arg Val Asp Pro Ile Val Cys Val Asn
305                 310                 315                 320

Val Leu Ser Met Phe Ala Lys Tyr Gly Arg Glu His Asp Leu Pro Ala
                325                 330                 335

Thr Val Ala Trp Val Arg Asp Val Leu Tyr His Arg Ala Tyr Leu Gly
            340                 345                 350

Gly Thr Arg Tyr Tyr Gly Ser Ala Glu Ala Phe Leu Phe Phe Phe Thr
        355                 360                 365

Arg Phe Val Arg Asn Leu Arg Pro Gly Thr Leu Lys Gln Asp Leu His
    370                 375                 380

Ala Leu Leu Ser Glu Arg Val Arg Glu Arg Leu Asn Thr Pro Val Asp
385                 390                 395                 400

Ala Leu Ala Leu Ser Met Arg Ile Gln Ala Cys His Ala Leu Gly Phe
                405                 410                 415

Asp Ala Pro Ala Asp Ile Ala Thr Leu Ile Thr Met Gln Asp Glu Asp
            420                 425                 430

Gly Gly Trp Pro Ala Ala Val Ile Tyr Lys Tyr Gly Ala Gly Gly Leu
        435                 440                 445

Gly Ile Thr Asn Arg Gly Val Ser Thr Ala Phe Ala Val Lys Ala Ile
    450                 455                 460

Thr Gly Ser Pro Val Lys Thr Glu Thr Asn Ile Gly Gly Asp Gly Ala
465                 470                 475                 480

Arg Ala Val Ser Ala Met Ser Ser Leu Glu Ala Arg Arg Leu Gln Pro
                485                 490                 495

Ile Ser Ser Val Gly Asp Trp Val Arg Phe Ile Ile Ala Ser Leu His
            500                 505                 510

Val His Leu Ala Trp Leu Trp Asn Val Leu Leu Leu Ser Lys Val Val
        515                 520                 525

<210> SEQ ID NO 79
<211> LENGTH: 1587
<212> TYPE: DNA
<213> ORGANISM: Aspergillus calidoustus
<220> FEATURE:
<221> NAME/KEY: misc_feature
<223> OTHER INFORMATION: cDNA

<400> SEQUENCE: 79

```
atggtccgcg cactcatcct cgatctcggc gatgtcctct tcaactggga cgcgcctgcg    60
tccaccccca tttcacgcaa gaccctcggc cagatgctgc atagtgagat ctggggtgag   120
tatgaacgtg ccatttgac agaagacgag gcatacaacg cactcgcgaa gcggtattcc   180
tgcgaggcca aggatgtcgc acatacccttt gtcctggcac gagaatcgct gcggctcgac   240
acgaaattca aaacgtttct gcagactcta aagcagaatg ccaacggctc ccttcgtgtc   300
tatggcatgt cgaatatatc gaaaccggat ttcgaagtcc tgctgggcaa ggccgatgac   360
tggactctgt ttgacaagat cttcccctct ggccatgtcg gtatgcgcaa gccagatctt   420
gccttcttcc gctatgtgct caaggacatt tcaacgcctg tcgaggatgt ggtgtttgtt   480
gacgataacc tggacaacgt gacgagtgct cggtctctgg catgcgcag cgtcctcttt   540
cataagaaag acgaggtcca gcgacagctc accaacatct ttggcagccc tgctgagcgg   600
ggcttggagt atctctccgc caacaagacg aatctgcaga gtgctaccac gacagatatc   660
ccaatccagg ataactttgg ccaacttctg attctcgagg ccactgaaga cccatcgctg   720
```

```
gtccgcatgg agcccggtaa gcgaacctgg aatttcttca tcggttctcc atccctcaca    780
accgacacct tccccgacga tctcgacacc acatcccttg ccctctccat cgtacccaca    840
agccccgacg tcgtcaactc ggtcatcgac gagattatca gccgtcgcga caaggacggt    900
atcgtcccga cttacttcga caacaccgcc cccgcgtgg acccaatcgt ctgcgtaaac     960
gtcctctcca tgttcgcaaa gtacggccgc gagcacgacc tccccgcaac agttgcgtgg   1020
gtccgcgacg tcttgtatca tcgagcatac ctcggcggaa cacggtacta cgggtcagct   1080
gaggccttcc tcttcttctt cactcgcttc gttcgcaacc tccgaccggg aactctcaag   1140
caggatctac acgcattgct atcagagcgc gtgcgcgagc gactcaatac ccccgtcgac   1200
gcactcgccc tgtcaatgcg catccaggcc tgtcatgcgc tgggctttga cgccccgca    1260
gacattgcga cgctcatcac aatgcaggac gaggacggcg gtggccggc agccgtcatc    1320
tacaagtacg gggccggggg gttggggatc acgaaccggg gtgtttcgac tgcgttttgcc  1380
gtaaaggcga ttacagggtc gcccgtgaag actgaaacca acataggcgg cgatggagct   1440
cgcgctgtct cggccatgtc ctccttggag gcgaggaggc tacagccgat ctcgtcggtt   1500
ggggactggg tgcggtttat cattgcgtcg ttgcatgtcc atctggcttg gctttggaat   1560
gttttgcttt tgagcaaggt tgtttga                                       1587

<210> SEQ ID NO 80
<211> LENGTH: 1587
<212> TYPE: DNA
<213> ORGANISM: Artificial Sequence
<220> FEATURE:
<223> OTHER INFORMATION: codon optimized cDNA

<400> SEQUENCE: 80
atggttcgtg cgttgatttt ggatttgggt gatgtgttgt ttaattggga cgcccctgca     60
agcactccga tcagccgtaa gaccctgggc cagatgctgc attccgagat tggggtgag    120
tatgagcgtg tcacctgac cgaagatgaa gcgtacaacg cgctggcaaa gcgctacagc    180
tgcgaggcaa aagacgtggc gcatactttt gttttggcgc gtgaaagcct gcgcctggat   240
accaagttta agactttct gcagaccctg aaacagaacg cgaacggctc gctgcgtgtt    300
tatggtatgt ccaatatcag caaaccggat tttgaagtgc tgctgggtaa agctgacgac   360
tggaccttgt tcgacaagat cttcccgagc ggtcatgtcg gtatgcgcaa accgacctg   420
gctttctttc gttacgtgct gaaagacatc agcaccccgg ttgaggatgt tgtgtttgtt   480
gacgataacc tggataatgt gacgtctgcc cgttccctgg gtatgcgtag cgtcctgttc   540
cacaaaaaag acgaagtcca acgtcagctg accaacattt tcggtagccc tgctgagcgc   600
ggtctggagt atctgtccgc gaacaagacc aatctgcaaa gcgcaaccac caccgacatc   660
cctatccaag acaactttgg tcaattactg attctggaag ccaccgaaga tccgagcctg   720
gtacgcatgg aaccgggcaa gcgtacctgg aatttcttca ttggctctcc gagcctgacg   780
acggataacct tcccggatga cctggacacg acgagcctcg cactgtccat cgtgccgacc   840
agcccagatg ttgttaatag cgtgatcgat gagatcatca gccgtcgcga caaggacggt   900
attgtgccga cgtactttga taacacgcgc ccgcgtgtgg acccgattgt ttgtgttaac   960
gttctgtcta tgttcgcgaa atatggccgt gagcacgatc tgccggcgac ggtcgcgtgg  1020
gtccgcgacg tcctctatca tcgcgcatac ctgggtggca ccagatacta cggtagcgcg  1080
gaagccttcc tttcttctt tacgcgcttt gtgcgtaatc tgcgtccggg cacgctgaaa  1140
caagatctgc acgcgttgct gagcgagcgt gtccgtgagc gcctgaatac cccggtggat  1200
```

-continued

```
gcgctggcgc tgagcatgcg cattcaggct tgccacgcac tgggctttga cgccccagct    1260
gacatcgcga cgctgattac catgcaagat gaagatggtg gctggccggc ggcagttatc    1320
tacaaatatg gtgcgggtgg cctgggcatt acgaaccgtg gtgtgtccac ggcattcgcg    1380
gtgaaggcaa tcacgggtag cccggttaaa accgaaacca acatcggcgg cgacggtgcc    1440
cgtgcagtgt cggccatgag cagcctggaa gcccgtcgtt tgcagccgat ttctagcgtc    1500
ggcgactggg tccgtttcat catcgcatca ctgcacgtcc acctggcgtg gctgtggaat    1560
gtcctgctgc tgagcaaagt cgtttaa                                        1587
```

<210> SEQ ID NO 81
<211> LENGTH: 531
<212> TYPE: PRT
<213> ORGANISM: Heterobasidion irregulare

<400> SEQUENCE: 81

```
Met Ser Met Ile Pro Arg Cys Ser Asn Leu Ile Leu Asp Ile Gly Asp
1               5                   10                  15

Val Leu Phe Thr Trp Ser Pro Lys Thr Ser Thr Ser Ile Ser Pro Arg
            20                  25                  30

Thr Met Lys Ser Ile Leu Ser Ser Thr Thr Trp His Gln Tyr Glu Thr
        35                  40                  45

Gly His Ile Ser Gln Gly Asp Cys Tyr Arg Leu Ile Gly Asn Gln Phe
    50                  55                  60

Ser Ile Asp Pro Gln Glu Val Gly Leu Ala Phe Gln Gln Ala Arg Asp
65                  70                  75                  80

Ser Leu Gln Pro Asn Val Asp Phe Ile His Phe Ile Arg Ala Leu Lys
                85                  90                  95

Ala Glu Ser His Gly Thr Leu Arg Val Phe Ala Met Ser Asn Ile Ser
            100                 105                 110

Gln Pro Asp Tyr Ala Val Leu Arg Thr Lys Asp Ala Asp Trp Ala Val
        115                 120                 125

Phe Asp Asp Ile Phe Thr Ser Ala Asp Ala Gly Val Arg Lys Pro His
    130                 135                 140

Leu Gly Phe Tyr Lys Leu Val Leu Gly Lys Ile Gly Ala Asp Pro Asn
145                 150                 155                 160

Asp Thr Val Phe Val Asp Asp Lys Gly Asp Asn Val Leu Ser Ala Arg
                165                 170                 175

Ser Leu Gly Leu His Gly Ile Val Phe Asp Ser Met Asp Asn Val Lys
            180                 185                 190

Arg Ala Leu Arg Tyr Leu Ile Ser Asp Pro Ile Arg Arg Gly Arg Glu
        195                 200                 205

Phe Leu Gln Ala Arg Ala Gly His Leu Glu Ser Glu Thr Asn Thr Gly
    210                 215                 220

Ile Glu Ile Gly Asp Asn Phe Ala Gln Leu Leu Ile Leu Glu Ala Thr
225                 230                 235                 240

Lys Asp Arg Thr Leu Val Asn Tyr Met Asp His Pro Asn Lys Trp Asn
                245                 250                 255

Phe Phe Arg Asp Gln Pro Leu Thr Thr Glu Glu Phe Pro Phe Asp
            260                 265                 270

Leu Asp Thr Thr Ser Ile Gly Thr Leu Ala Thr Gln Arg Asp Asp Gly
        275                 280                 285

Thr Ala Asn Leu Val Met Asp Glu Met Leu Gln Tyr Arg Asp Glu Asp
    290                 295                 300
```

```
Gly Ile Ile Gln Thr Tyr Phe Asp His Glu Arg Pro Arg Ile Asp Pro
305                 310                 315                 320

Ile Val Cys Val Asn Val Leu Ser Leu Phe Tyr Ser Arg Gly Arg Gly
            325                 330                 335

Ser Glu Leu Ala Pro Thr Leu Glu Trp Val Arg Gly Val Leu Lys His
        340                 345                 350

Arg Ala Tyr Leu Asp Gly Thr Arg Tyr Tyr Glu Thr Gly Glu Cys Phe
    355                 360                 365

Leu Phe Phe Leu Ser Arg Leu Leu Gln Ser Thr Lys Asp Ala Ala Leu
370                 375                 380

His Ala Ser Leu Lys Ser Leu Phe Ala Glu Arg Val Lys Glu Arg Ile
385                 390                 395                 400

Gly Ala Pro Gly Asp Ala Leu Ala Leu Ala Met Arg Ile Leu Ala Cys
                405                 410                 415

Ala Ala Val Gly Val Arg Asp Glu Ile Asp Leu Arg Ser Leu Leu Pro
            420                 425                 430

Leu Gln Cys Glu Asp Gly Gly Trp Glu Ala Gly Trp Val Tyr Lys Tyr
        435                 440                 445

Gly Ser Ser Gly Val Lys Ile Gly Asn Arg Gly Leu Thr Thr Ala Leu
    450                 455                 460

Ala Leu Asn Ala Ile Glu Ala Val Glu Gly Arg Arg Thr Arg Pro Lys
465                 470                 475                 480

Ser Gly Lys Ile Ser Arg Val Ser Arg His Ser Glu Val Ala Ala Ala
                485                 490                 495

Pro Arg Ser Ser Thr Ser Ser His Arg Ser Asn Arg Ser Ile Ser Arg
            500                 505                 510

Thr Phe Gln Ala Tyr Phe Lys Ala Ser Trp Thr Ser Met Lys Gln Val
        515                 520                 525

Ala Val Ala
    530
```

<210> SEQ ID NO 82
<211> LENGTH: 1596
<212> TYPE: DNA
<213> ORGANISM: Heterobasidion irregulare
<220> FEATURE:
<221> NAME/KEY: misc_feature
<223> OTHER INFORMATION: cDNA

<400> SEQUENCE: 82

```
atgtccatga tacccagatg ctcgaatctc atcctcgaca tcggggatgt tctcttcaca      60
tggtctccga agacgtccac ttcgatctcc ccccgcacca tgaagagcat actgtcatcg     120
acgacctggc accaatacga gaccgggcac atttcacagg cgactgctac ccgcctcata     180
ggcaaccagt tctccatcga tcctcaggaa gtcggacttg cattccaaca agctcgggac     240
tcattgcagc ctaatgttga cttcattcac ttcatccgcg ccctcaaggc ggaatcacac     300
gggacgctgc gcgtcttcgc tatgtccaac atctctcagc ccgattacgc agttcttcgg     360
actaaggacg ccgactgggc cgttttttgac gatatattca cgtctgcaga tgctgggggtt     420 cgaaagccac accttgggtt ctacaagttg gtactcggaa agatcggcgc cgatccaaac     480
gataccgtct tcgtcgatga caaggggggac aatgtcctct ctgcacggtc tctcggcctt     540
catggaatcg tctttgacag tatggacaac gtcaagcgag ccctgcgcta cttgatcagc     600
gaccccatac ggcgaggacg agagtttctc caagcgcgag ccggccattt ggagtcggag     660
```

```
accaatacgg gcatcgaaat cggtgataat tttgcccagc tccttattct cgaggccacg    720
aaggatagga cactcgtcaa ttatatggac catccgaaca aatggaattt cttccgagat    780
caaccgctcc tcacaacgga ggagttccct ttcgatctcg atacgacatc tattggaacg    840
cttgcgacgc agcgcgatga tgggactgcc aatctagtaa tggatgagat gcttcagtac    900
cgtgatgagg atggcataat acaaacatat ttcgatcatg aacgaccgag gatagatccc    960
atcgtctgtg tcaacgtctt gagccttttc tactcccggg gtcgtggttc ggagctagca   1020
ccgacactag agtgggtgcg tggtgtcctc aagcaccgcg cgtatctcga tggaacgcga   1080
tactacgaga caggcgaatg cttccttttc ttcctcagcc ggctcttgca atcaaccaag   1140
gacgccgcct tgcacgcatc gttgaaatct ttgttcgccg aacgggtcaa ggagcgcata   1200
ggggcaccag gggacgcgct ggcgctggcg atgcgtatac tggcatgcgc agcagtgggc   1260
gtgcgggacg agatcgatct tcgatcacta ttacctctgc agtgcgagga tgggggggtgg   1320 gaggcaggct gggtgtacaa gtatgggtct tcgggagtca agatcggcaa tcgtggcctc   1380
acgactgcgc ttgcgctcaa tgccatcgag gctgtggagg gacgtcgcac gaggccgaag   1440
tcgggtaaga tcagccgagt cagccgtcat tctgaggtcg cagcagcgcc acggtcttcc   1500
accagcagtc atcgttctaa tcgctcgatc tcaaggacat tccaggcgta cttcaaggcg   1560
tcgtggacat cgatgaaaca ggtggccgtg gcgtga                             1596
```

<210> SEQ ID NO 83
<211> LENGTH: 1596
<212> TYPE: DNA
<213> ORGANISM: Artificial Sequence
<220> FEATURE:
<223> OTHER INFORMATION: codon optimized cDNA

<400> SEQUENCE: 83

```
atgagcatga ttccacgttg tagcaatctg attctcgaca tcggtgatgt gttgtttacg     60
tggagcccga aaaccagcac cagcattagc ccgcgtacca tgaaatctat cctgagctct    120
accacctggc atcaatatga gactggccac atcagccagg gtgattgcta ccgcctgatc    180
ggtaatcagt tctccatcga cccgcaagag gtcggtttgg ccttccagca agccagagac    240
agcctgcaac cgaatgttga tttcatccat ttcattcgtg ccctgaaagc tgagtcgcac    300
ggcaccctgc gcgttttttgc gatgagcaat atcagccaac tgactatgc agtcctgcgt    360 acgaaagacg cggactgggc tgttttttgat gatatcttca cgagcgcgga tgctggtgtt    420
cgtaaaccgc acctgggttt ttataaactg gtcttaggca agattggcgc ggaccctaac    480
gacaccgttt ttgtggatga taagggtgac aacgtcctct ctgcacgttc cctgggtctg    540
cacggtatcg tttttgattc aatggacaac gtgaagcgcg cactgcgcta cctgattagc    600
gacccgatcc gccgcggccg tgaatttctg caggcccgtg cgggtcacct ggagtccgaa    660
acgaacacgg gtattgagat tggtgataat tcgcgcaat tgctgatcct ggaagcgacc    720
aaagatcgta ctctggtgaa ctacatggac cacccgaaca agtggaactt cttccgtgac    780
cagccgctgc tgaccaccga gaatttccg ttcgacctgg acacgaccag cattggcacg    840
ctggccaccc aacgtgacga tggtacggcg aatctggtaa tggacgaaat gttgcagtat    900
cgtgacgaag atggcatcat tcagacctat ttcgatcatg agcgcccgcg tattgatccg    960
attgtttgtg tgaatgtgct gtctctgttc tacagccgtg gccgtggctc tgagttggcg   1020
ccgacgctga atgggtgcg cggtgtgttg aaacatcgtg cgtacctgga tggtacgcgt   1080
tattacgaga ctggtgagtg tttcctgttt ttcctgagcc gtctgctgca gagcaccaaa   1140
```

```
gacgcagccc tgcacgcgag cctgaagtcc ctgtttgcag agcgtgttaa agagcgcatc      1200
ggtgcgccgg gcgatgctct ggcgctggct atgcgcatcc tggcgtgcgc cgctgttggt      1260
gtgcgcgatg aaattgattt gcgtagcctg ctgccgctgc aatgcgaaga tggcggctgg      1320
gaagcgggct gggtctacaa atacggcagc agcggtgtga agattggcaa tcgcggtctt      1380
accacggcgc tggcattgaa tgctatcgaa gccgttgagg ccgtcgcac  ccgcccaaag      1440 tccggtaaga tcagccgtgt tagccgtcat agcgaagtcg cagcggcacc gcgttcctcg      1500
acgagcagcc accgtagcaa ccgtagcatt agccgcacct tccaggcata ttttaaagcg      1560
agctggacca gcatgaaaca agtcgcagtg gcgtaa                                1596
```

<210> SEQ ID NO 84
<211> LENGTH: 518
<212> TYPE: PRT
<213> ORGANISM: Schizopora paradoxa

<400> SEQUENCE: 84

```
Met Ser Ile His Gly Ser Ser Met Ser Ser Tyr Ser Ser Thr Val Pro
1               5                   10                  15

Ser Met Thr Ser Ser Pro Ala Ser Thr Ser Thr Pro Ser Ser Pro Ala
            20                  25                  30

Ser Ser Ile His Glu Ile Gly Pro Val Pro Glu Ala Arg Arg Lys Gly
        35                  40                  45

Gln Cys Asn Ala Leu Ile Phe Asp Leu Gly Asp Val Leu Phe Thr Trp
    50                  55                  60

Ser Ala Glu Thr Lys Thr Thr Ile Ser Pro Lys Leu Leu Lys Lys Ile
65                  70                  75                  80

Leu Asn Ser Leu Thr Trp Phe Glu Tyr Glu Lys Gly Asn Ile Gly Glu
                85                  90                  95

Gln Glu Ala Tyr Asp Ala Val Ala Lys Glu Phe Gly Val Pro Ser Ser
            100                 105                 110

Glu Val Gly Ala Ala Phe Gln Cys Ala Arg Asp Ser Leu Gln Ser Asn
        115                 120                 125

Pro Arg Leu Val Ser Leu Ile Arg Glu Leu Lys Ser Gln Tyr Asp Leu
    130                 135                 140

Lys Val Tyr Ala Met Ser Asn Ile Ser Ala Pro Asp Trp Glu Val Leu
145                 150                 155                 160

Arg Thr Lys Ala Thr Pro Glu Glu Trp Ala Met Phe Asp Arg Val Phe
                165                 170                 175

Thr Ser Ala Ala Ala Arg Glu Arg Lys Pro Asn Leu Gly Phe Tyr Arg
            180                 185                 190

Gln Val Val Glu Ala Thr Gly Val Asp Pro Ala Arg Ser Val Phe Val
        195                 200                 205

Asp Asp Lys Leu Asp Asn Val Ile Ser Ala Arg Ser Val Gly Leu Asn
    210                 215                 220

Ala Ile Ile Phe Asp Ser Phe Glu Asn Val Ala Arg Gln Leu Lys Asn
225                 230                 235                 240

Tyr Val Ala Asp Pro Ile Gly Arg Ala Glu Ala Trp Leu Arg Asp Asn
                245                 250                 255

Ala Lys Lys Met Leu Ser Ile Thr Asp Ala Gly Val Val Tyr Glu
            260                 265                 270

Asn Phe Gly Gln Met Leu Ile Leu Glu Ala Thr Gly Asp Arg Ser Leu
        275                 280                 285
```

```
Val Asp Tyr Val Glu Tyr Pro Arg Leu Phe Asn Phe Phe Gln Gly Asn
    290                 295                 300

Gly Val Phe Thr Thr Glu Ser Phe Pro Cys Asp Leu Asp Ser Thr Ser
305                 310                 315                 320

Ile Gly Leu Thr Val Thr Asn His Val Asp Glu Lys Thr Arg His Ser
                325                 330                 335

Val Met Asp Glu Met Leu Thr Tyr Lys Asn Glu Asp Gly Ile Ile Ala
                340                 345                 350

Thr Tyr Phe Asp Ala Thr Arg Pro Arg Ile Asp Pro Val Val Cys Ala
                355                 360                 365

Asn Val Leu Thr Phe Phe Tyr Lys Asn Gly Arg Gly Glu Glu Leu Asn
370                 375                 380

Glu Thr Leu Asp Trp Val Tyr Asp Ile Leu Leu His Arg Ala Tyr Leu
385                 390                 395                 400

Asp Gly Thr Arg Tyr Tyr Phe Gly Ser Asp Thr Phe Leu Phe Phe Leu
                405                 410                 415

Ser Arg Leu Leu Ser Glu Ser Pro Ser Val Tyr Ala Arg Phe Ala Pro
                420                 425                 430

Val Phe Gln Glu Arg Val Lys Glu Arg Met Gly Ala Thr Gly Asp Ala
                435                 440                 445

Met Ser Leu Ala Met Arg Ile Ile Ala Ala Ala Thr Val Lys Ile Gln
450                 455                 460

Asp Arg Val Asp Cys Asp Ala Leu Leu Gln Thr Gln Glu Asp Asp Gly
465                 470                 475                 480

Gly Phe Pro Ile Gly Trp Met Tyr Lys Tyr Gly Ala Thr Gly Met Leu
                485                 490                 495

Leu Gly Asn Lys Gly Leu Ser Thr Ala Leu Ala Ile Gln Ala Ile Lys
                500                 505                 510

Ala Val Glu Ser Phe Pro
                515

<210> SEQ ID NO 85
<211> LENGTH: 1557
<212> TYPE: DNA
<213> ORGANISM: Schizopora paradoxa
<220> FEATURE:
<221> NAME/KEY: misc_feature
<223> OTHER INFORMATION: cDNA

<400> SEQUENCE: 85
atgtcgattc acggttcttc tatgtcctcc tattcctcga ctgtgccgtc aatgacttcc      60
tctcccgcgt ccacttctac tccgtcgtct cctgcatcgt cgatccatga gattggtcct     120 gtccagaag ctcgacgaaa gggacagtgc aacgcgctga tcttcgacct cggagacgtc      180
ctcttcacct ggtcggcaga gactaagacc accatttccc cgaaactcct gaaaaagatc     240
cttaactcct taacatggtt cgaatacgag aagggaaaca tcggggagca ggaggcgtat     300
gacgcagtcg caaggagtt tggcgtcccg tcgtccgagg tcggggccgc tttccagtgc      360
gcgcgcgatt cgctacagag caatccccgc ctcgtctcgc tcatccgtga gctgaagtcg     420
caatatgatc tcaaggtgta cgccatgtcc aacatctctg cgccggactg ggaagtccta     480
aggacgaagg cgaccctga ggagtgggca atgtttgacc gcgtcttcac gagcgcggcc      540
gcgcgcgagc gtaagccaaa cctcggattc tacagacagg ttgttgaggc gaccggcgtc     600
gaccccgctc gctccgtgtt cgtcgacgat aaactcgaca atgtcatctc tgcgcgttca     660
gtcggattaa atgcgatcat cttcgactca tttgagaacg tcgcccggca gctcaaaaac     720
```

```
tatgtcgctg atcctatcgg acgggcggag gcgtggttgc gcgataacgc aaagaagatg      780
ttgtcaatta cggatgccgg ggtggtcgta tacgagaatt tcggccagat gctgatcttg      840
gaggcaacag gcgataggtc gcttgtggac tacgtcgagt accctcgtct cttcaacttc      900
ttccaaggca atggcgtctt tacgaccgag tcattccctt cgaccttgat tcgacttcc      960 atcggcttaa ccgtcacgaa ccacgtcgat gagaaaacaa ggcacagcgt catggatgag     1020
atgctgacct acaaaaatga ggatggtatc attgcgactt actttgatgc cacgcgtccc     1080
cgaattgacc ccgtcgtctg cgccaatgtc ttgacgttct tctacaagaa cggccgaggg     1140
gaggagctca atgaaacact tgactgggtc tacgacatcc tccttcatcg cgcgtacctc     1200
gatggcacac gctattattt cggctcagac accttcctct tcttcctttc tcgacttctc     1260
tccgaatcgc catccgttta cgcccgtttc gctccggtgt tccaggagag agtcaaggag     1320
cgcatggggg cgacgggaga tgcgatgtcc cttgcgatgc gcatcatcgc ggccgcaact     1380
gtcaagatcc aagaccgagt cgactgcgac gctctgctgc agacgcagga agacgacggt     1440
ggattcccga taggttggat gtacaagtac ggggcgaccg ggatgcttct gggtaacaag     1500
ggcttgtcga cagctctggc aatccaagct atcaaagcgg tcgaatcttt cccttga       1557

<210> SEQ ID NO 86
<211> LENGTH: 1557
<212> TYPE: DNA
<213> ORGANISM: Artificial Sequence
<220> FEATURE:
<223> OTHER INFORMATION: codon optimized cDNA

<400> SEQUENCE: 86
atgtcgattc acggtagcag catgtcgtct tatagcagca cggttccatc tatgactagc       60
agcccggctt ccacgagcac gccgtccagc ccggccagca gcatccacga aatcggcccg      120
gtccctgagg cgcgtcgcaa gggccaatgc aatgcactga tcttcgaccct gggtgatgtt      180 ctgtttacct ggagcgcaga aaccaagacc acgatcagcc cgaagctgct gaaaaagatt      240
ctgaacagct tgacctggtt tgagtatgag aaaggcaaca tcggtgaaca agaagcctat      300
gacgccgttg cgaaagagtt cggtgtgccg agctctgagg ttggcgctgc gtttcaatgt      360
gcgcgtgact ccctgcaaag caatccgcgt ttggttagcc tgattcgtga gctgaagtcc      420
cagtacgacc tgaaagtgta cgctatgagc aatattagcg cgccagactg ggaagtgctg      480
cgtactaaag cgaccccgga agagtgggca atgttcgatc gtgtctttac ttctgcggcg      540
gcgcgtgagc gtaagccgaa cttgggcttt taccgccaag tcgtggaagc aaccggtgtc      600
gatccggcgc gtagcgtttt cgtcgatgat aaactggaca atgtgatcag cgcgcgctct      660
gtcggtctga acgctattat cttcgactcc ttcgaaaacg tcgcccgtca gctgaagaat      720
tacgtcgcag acccgattgg tcgcgctgag gcgtggctgc gcgacaacgc aaagaaaatg      780
ctgagcatca ccgatgcggg tgttgtggtt tacgagaatt ttggccagat gctgatcctg      840
gaagctaccg gtgaccgtag cctggtggac tatgtggagt atccgcgcct cttTaacttc      900
ttccagggta acggcgtttt tacgaccgag agctttccat gcgatctgga cagcaccagc      960
atcggtctga ctgtgaccaa tcatgtggac gaaaagactc gccacagcgt catggacgaa     1020
atgctgacct acaaaaatga agatggtatt attgcgacgt actttgacgc gacgcgcccg     1080
cgcattgacc ctgttgtctg tgccaatgtt ctgaccttct tctacaaaaa cggtcgtggt     1140
gaagaattga acgaaaccct ggattgggtg tacgacattc tgctgcatcg cgcgtatctg     1200
```

```
gacggtacgc gttattattt cggctccgat acgttcctgt ttttcctgag ccgtctgctg    1260
agcgagtctc cgagcgttta cgcgcgtttt gccccggtgt ttcaagagcg cgtgaaagag    1320
cgtatgggcg cgaccggtga tgcgatgagc ctggccatgc gtatcattgc agcagcaacc    1380
gtaaagatcc aggatcgtgt ggattgcgac gcactgttgc agacccaaga agatgatggc    1440
ggtttcccga ttggttggat gtacaaatat ggtgcgaccg gtatgttgct gggcaacaaa    1500
ggcctgagca cggccctggc gatccaggca attaaagccg tcgagtcgtt cccgtaa      1557
```

<210> SEQ ID NO 87
<211> LENGTH: 507
<212> TYPE: PRT
<213> ORGANISM: Aspergillus versicolor

<400> SEQUENCE: 87

```
Met Gly Ser Thr Lys Ala Leu Val Val Asp Phe Gly Asn Val Leu Cys
1               5                   10                  15

Thr Trp Thr Pro Pro Arg Glu Leu Ser Ile Pro Lys Lys Leu Lys
            20                  25                  30

Gln Ile Met Ser Ser Asp Ile Trp Leu Asp Tyr Glu Arg Gly Ile Tyr
        35                  40                  45

Lys Ser Glu Asp Glu Cys Tyr Leu Ala Val Ala Thr Arg Phe Gly Val
    50                  55                  60

Ser Pro Ser Asp Leu Ser Ser Val Met Lys Lys Ala Arg Glu Ser Leu
65                  70                  75                  80

Gln Pro Asn Thr Ala Thr Leu Asn His Leu Ser His Leu Lys Lys Thr
                85                  90                  95

Gln Pro Gly Leu Arg Ile Tyr Gly Leu Thr Asn Thr Pro Leu Pro Glu
            100                 105                 110

Gln Ser Ser Val Arg Ser Ile Ala Gln Glu Trp Pro Ile Phe Asp His
        115                 120                 125

Ile Tyr Ile Ser Gly Ile Leu Gly Met Arg Lys Pro Asp Ile Gly Cys
    130                 135                 140

Tyr Arg Leu Val Leu Arg Lys Ile Gly Leu Pro Ala Glu Ser Val Val
145                 150                 155                 160

Phe Ile Asp Asp Ser Pro Glu Asn Ile Leu Ala Ala Gln Ser Leu Gly
                165                 170                 175

Val His Ser Ile Leu Phe Gln Ser His Asp Gln Leu Ser Arg Gln Leu
            180                 185                 190

Gly Asn Val Leu Gly Asp Pro Ile Gln Arg Gly His Asn Phe Leu Leu
        195                 200                 205

Ser Asn Ala Lys Gln Met Asn Ser Thr Thr Asp Lys Gly Val Ile Ile
    210                 215                 220

Arg Asp Asn Phe Ala Gln Leu Leu Ile Ile Glu Leu Thr Gln Asn Pro
225                 230                 235                 240

Asp Leu Val Ala Leu Glu Thr Trp Asp Arg Thr Trp Asn Phe Ile
                245                 250                 255

Gly Pro Pro Gln Leu Thr Thr Glu Ser Phe Pro Asn Asp Leu Asp Thr
            260                 265                 270

Thr Ser Ile Ala Leu Ser Val Leu Pro Val Asp Lys Glu Val Val Trp
        275                 280                 285

Ser Val Met Asp Glu Met Leu Thr Phe Thr Asn Ala Asp Gly Ile Phe
    290                 295                 300

Met Thr Tyr Phe Asp Arg Ser Arg Pro Arg Val Asp Pro Val Val Cys
305                 310                 315                 320
```

```
Thr Asn Val Leu Asn Leu Phe Cys Met His Gly Arg Glu Ser Glu Val
                325                 330                 335

Ala Ala Thr Phe Asp Trp Val Leu Asp Val Leu Arg Asn Ser Ala Tyr
            340                 345                 350

Leu Ser Gly Ser Arg Tyr Tyr Ser Ser Pro Asp Cys Phe Leu Tyr Phe
        355                 360                 365

Leu Ser Arg Leu Ser Cys Val Val Arg Asp Gly Thr Arg Arg Arg Glu
    370                 375                 380

Leu Lys Ser Leu Leu Lys Gln Gln Val Ser Gln Arg Ile Gly Ala Asp
385                 390                 395                 400

Gly Asp Ser Val Ser Leu Ala Thr Arg Leu Leu Ala Ser Asn Ile Leu
                405                 410                 415

Gly Ile Thr Asn Gly Arg Asp Arg Ser Arg Leu Leu Ala Leu Gln Glu
            420                 425                 430

Thr Asp Gly Gly Trp Pro Ala Gly Trp Val Tyr Lys Phe Gly Ser Ser
        435                 440                 445

Gly Val Gln Ile Gly Asn Arg Gly Leu Ser Thr Ala Leu Ala Leu Lys
    450                 455                 460

Ser Ile Glu Arg Gln Lys Gly Pro Val Glu Ala Ile Ser Ser Glu Pro
465                 470                 475                 480

Glu Ala Trp Trp Pro Ser Leu Arg Leu Asp Arg Leu Leu Asn Val Trp
                485                 490                 495

Pro Phe Ile Asp Trp Lys Gly Tyr Ser Pro Ser
                500                 505

<210> SEQ ID NO 88
<211> LENGTH: 1524
<212> TYPE: DNA
<213> ORGANISM: Aspergillus versicolor
<220> FEATURE:
<221> NAME/KEY: misc_feature
<223> OTHER INFORMATION: cDNA

<400> SEQUENCE: 88
atgggttcca ccaaggctct tgttgttgac tttgggaatg ttttgtgtac ctggacacca      60
cccagggagt tatccatccc gcccaagaag ctgaaacaaa tcatgtcttc tgacatttgg     120
ctcgactatg aacggggtat ctataagtcg gaggacgagt gctacttggc ggttgcaact     180
cgcttcggcg tctctcccag cgacctctcc tcggtgatga aaaaggcccg cgagagcctg     240
caaccaaaca ccgcaaccct gaatcatctg tctcatctca aaagaccca gcctggcctc     300 aggatatacg gtttgaccaa caccctctc ccagaacaaa gcagtgtacg atccatcgcc     360
caggaatggc ctatcttcga ccatatctac atatcaggca tcctcggaat gcgcaagccg     420
gacattggct gctacaggct ggtgctgcga aagattgggc ttccagcgga gtccgtggtc     480
ttcattgatg attcacccga gaacatcctg gccgcgcagt cactgggagt acacagcata     540
ctgttccaaa gccacgacca gctctctcgt cagcttggca atgtgctggg tgatccaatc     600
cagcggggcc ataacttcct actctcgaac gcaaagcaaa tgaatagtac gaccgacaag     660
ggagttatta tccgggacaa ctttgcgcaa ctgctgatca tcgagctgac gcagaaccca     720
gaccttgtgg cgttagaaac atgggaccgt acctggaatt ttttattgg acctccacaa     780 ttgacaactg aaagctttcc caatgatctt gacactacct ccatcgctct ctcggttctt     840
ccggttgaca agaagtggt atggtctgtg atggacgaga tgctaacgtt taccaatgcg     900
gatgggattt ttatgaccta tttcgaccga tcacgccctc gagttgatcc ggtagttttgc    960
```

| | |
|---|---|
| accaatgtcc tgaatctttt ctgcatgcat ggacgggaaa gcgaagttgc agccacattt | 1020 |
| gactgggtgc tggacgttct tcgaaattcg gcctatttat caggatccag atactattct | 1080 |
| tcgcctgatt gctttctata ctttctttca cggctgagct gtgtggtccg agacggcacg | 1140 |
| cgacgcaggg agctcaagtc actgttgaaa caacaagtga gccagcgtat ggcgctgat | 1200 |
| ggtgattccg tctctctcgc cactaggcta cttgcatcga acattttagg aatcacaaat | 1260 |
| ggccgtgatc gctccaggct tcttgctctg caggaaactg acggtggatg gcctgctggg | 1320 |
| tgggtttata aattcggaag ctcgggggta cagattggca atcggggct cagtacagcc | 1380 |
| ttggcgttaa atcaattga gcgtcagaag gggcctgttg aggcgatatc cagtgagcca | 1440 |
| gaagcgtggt ggccatccct caggcttgac cgacttctca acgtttggcc tttcatcgac | 1500 |
| tggaagggat attcgccgag ttga | 1524 |

<210> SEQ ID NO 89
<211> LENGTH: 1524
<212> TYPE: DNA
<213> ORGANISM: Artificial Sequence
<220> FEATURE:
<223> OTHER INFORMATION: codon optimized cDNA

<400> SEQUENCE: 89

| | |
|---|---|
| atgggttcta cgaaagcgtt ggttgttgat tttggtaatg ttctgtgcac ttggacgcca | 60 |
| ccacgtgaat tgtccatccc gccgaagaaa ctgaagcaaa tcatgagcag cgacatttgg | 120 |
| ctggactatg agcgtggtat ctacaaatcg gaagatgagt gctacctggc agttgcgacg | 180 |
| cgctttggtg tcagcccgtc cgacctgagc tccgttatga aaaagcccg tgagagcctg | 240 |
| cagccgaata ccgcaacgct gaaccacttg agccatctga gaaaaccca gcctggcctt | 300 |
| cgtatctacg gcctgacgaa caccccgttg ccggaacaga gctcagtccg tagcattgcg | 360 |
| caggaatggc cgattttga ccacatctac attagcggca tcttgggtat gcgcaaaccg | 420 |
| gatattggtt gttaccgtct ggttctgcgt aagatcggtc tgccagcgga gtccgtcgta | 480 |
| ttcatcgacg acagcccgga gaacattctg gcagctcaat cgttgggtgt ccatagcatc | 540 |
| ctgttccagt cccacgatca gctgagccgt cagctgggca atgtgctggg tgatccgatt | 600 |
| cagcgcggtc acaacttcct cctgtccaac gcgaagcaaa tgaacagcac accgataag | 660 |
| ggtgtgatta ccgcgacaa cttcgcccag ctgctgatta ttgagctgac ccaaaatccg | 720 |
| gatctggttg cgctggagac ttgggaccgt acgtggaatt tctttattgg tccgccgcaa | 780 |
| ctgaccaccg agagctttcc gaacgacctg acaccacga gcattgccct gagcgtgttg | 840 |
| ccggtggata agaagtcgt ttggtctgtg atggatgaga tgctgacctt caccaacgca | 900 |
| gacggcatct tcatgaccta tttcgatcgt agccgtccgc gtgttgaccc ggtcgtttgt | 960 |
| accaatgtcc tgaatctgtt ttgcatgcat ggtcgcgaga gcgaagtggc cgcgacgttc | 1020 |
| gactgggtgc tggacgtgct gcgcaacagc gcgtacctga gcggttcccg ttattacagc | 1080 |
| agcccggatt gttttctgta ttttcctgtct cgtctgagct gcgtcgtccg tgatggcacg | 1140 |
| cgtcgtcgtg aactgaaaag cctgctgaag caacaagttt ctcaacgtat cggcgctgac | 1200 |
| ggtgattccg tcagcctggc cacccgtttg ctggcgagca catcctggg cattactaac | 1260 |
| ggtcgtgacc gcagccgtct gctggcattg caagaaaccg atggtggctg gcctgcaggc | 1320 |
| tgggtctata gtttggtag cagcggcgtg caaattggca atcgcggtct gagcaccgcg | 1380 |
| ctggctctga agtctatcga gcgccagaaa ggtccggtgg aagcaatcag cagcgagccg | 1440 |

```
gaagcgtggt ggcctagctt acgcttggac cgcttgctga atgtttggcc atttatcgac    1500
tggaagggct actccccgag ctaa                                           1524
```

<210> SEQ ID NO 90
<211> LENGTH: 540
<212> TYPE: PRT
<213> ORGANISM: Agaricus bisporus

<400> SEQUENCE: 90

```
Met Ala Pro Pro Gln Arg Pro Phe Thr Ala Ile Val Phe Asp Ile Gly
1               5                   10                  15

Asp Val Leu Phe Gln Trp Ser Ala Thr Thr Lys Thr Ser Ile Ser Pro
            20                  25                  30

Lys Thr Leu Arg Ser Ile Leu Asn Cys Pro Thr Trp Phe Asp Tyr Glu
        35                  40                  45

Arg Gly Arg Leu Ala Glu Asn Ala Cys Tyr Ala Ala Ile Ser Gln Glu
    50                  55                  60

Phe Asn Val Asn Pro Asp Glu Val Arg Asp Ala Phe Ser Gln Ala Arg
65                  70                  75                  80

Asp Ser Leu Gln Ala Asn His Asp Phe Ile Ser Leu Ile Arg Glu Leu
                85                  90                  95

Lys Ala Gln Ala Asn Gly Arg Leu Arg Val Tyr Ala Met Ser Asn Ile
            100                 105                 110

Ser Leu Pro Asp Trp Glu Val Leu Arg Met Lys Pro Ala Asp Trp Asp
        115                 120                 125

Ile Phe Asp His Val Phe Thr Ser Gly Ala Val Gly Glu Arg Lys Pro
    130                 135                 140

Asn Leu Ala Phe Tyr Arg His Val Ile Ala Ala Thr Asp Leu Gln Pro
145                 150                 155                 160

His Gln Thr Ile Phe Val Asp Asp Lys Leu Glu Asn Val Leu Ser Ala
                165                 170                 175

Arg Ser Leu Gly Phe Thr Gly Ile Val Phe Asp Glu Pro Ser Glu Val
            180                 185                 190

Lys Arg Ala Leu Arg Asn Leu Ile Gly Asp Pro Val Gln Arg Gly Gly
        195                 200                 205

Glu Phe Leu Val Arg Asn Ala Gly Lys Leu Gly Ser Ile Thr Arg Thr
    210                 215                 220

Thr Ala Lys His Glu Ser Ile Pro Leu Asp Glu Asn Phe Ala Gln Leu
225                 230                 235                 240

Leu Ile Leu Glu Ile Thr Gly Asn Arg Ala Leu Val Asn Leu Val Glu
                245                 250                 255

His Pro Gln Thr Trp Asn Phe Phe Gln Gly Lys Gly Gln Leu Thr Thr
            260                 265                 270

Glu Glu Phe Pro Phe Asp Leu Asp Thr Thr Ser Leu Gly Leu Thr Ile
        275                 280                 285

Leu Lys Arg Ser Arg Glu Ile Ala Asp Ser Val Met Asp Glu Met Leu
    290                 295                 300

Glu Tyr Val Asp Pro Asp Gly Ile Ile Gln Thr Tyr Phe Asp His Arg
305                 310                 315                 320

Arg Pro Arg Phe Asp Pro Val Val Cys Val Asn Ala Leu Ser Leu Phe
                325                 330                 335

Tyr Ala Tyr Gly Arg Gly Glu Gln Leu Arg Ser Thr Leu Thr Trp Val
            340                 345                 350

His Glu Val Leu Leu Asn Arg Ala Tyr Leu Asp Gly Thr Arg Tyr Tyr
```

```
                355                 360                 365
Glu Thr Ala Glu Cys Phe Leu Tyr Phe Met Ser Arg Leu Leu Ala Thr
            370                 375                 380

Ser Gly Asp Pro Asp Leu His Ser Leu Leu Lys Pro Leu Leu Lys Glu
385                 390                 395                 400

Arg Val Gln Glu Arg Ile Gly Ala Asp Gly Asp Ser Leu Ala Leu Ala
                405                 410                 415

Met Arg Ile Leu Ala Cys Asp Phe Val Gly Ile Arg Asp Glu Val Asp
            420                 425                 430

Leu Arg Thr Leu Leu Thr Leu Gln Cys Glu Asp Gly Gly Trp Glu Val
                435                 440                 445

Gly Trp Met Tyr Lys Tyr Gly Ser Ser Gly Ile Ser Ile Gly Asn Arg
            450                 455                 460

Gly Leu Ala Thr Ala Leu Ala Ile Lys Ala Val Asp Thr Met Phe Gln
465                 470                 475                 480

Pro Gln Ile Arg Phe Ser Glu Ser Pro Thr Asp Thr Leu Val Glu Asn
                485                 490                 495

Ala Ile His Lys Arg Arg Pro Ser Phe Ser Glu Lys Phe Leu Gly Lys
            500                 505                 510

Arg Pro Arg Ser Gly Ser Phe Arg Lys Pro Leu Gln Trp Ile Leu Gln
                515                 520                 525

Gly Ser Lys Leu Arg Lys Ser Val Glu Ile Gly Ser
530                 535                 540

<210> SEQ ID NO 91
<211> LENGTH: 1808
<212> TYPE: DNA
<213> ORGANISM: Agaricus bisporus
<220> FEATURE:
<221> NAME/KEY: misc_feature
<222> LOCATION: (1)..(1808)
<223> OTHER INFORMATION: cDNA

<400> SEQUENCE: 91
atggctccgc ctcagcgacc ctttactgcg attgtctttg acatcgggga tgttctattc      60
caatggtctg caaccaccaa aacctctatc tcaccaaaga cactccgctc tattctcaac     120
tgtccgacat ggttgactga tgaacgtgga cgcctggcag aaaacgcttg ttatgccgct     180
atctcacaag aattcaacgt caacccagac gaagttcgcg acgctttcag ccaagcgcgc     240
gactctctcc aagcaaacca cgacttcatc agtctcatcc gtgagctgaa ggcacaagca     300
aatggtcgtt acgtgtgta cgccatgtcg aacatatctc ttcctgattg ggaagtgctg     360
cggatgaaac ctgctgattg ggatattttc gaccacgtct tcacatccgg tgcggttggg     420
gaacgcaagc ccaatctcgc cttttatcgc catgttatcg cggccaccga tctgcagcct     480
catcagacaa tatttgttga cgataagctg gagaatgttc tctcagcacg ttccctcggg     540
ttcacaggca tcgtgtttga cgagccctcc gaggtcaaac gtgcgcttcg taacctcatt     600
ggggatcctg ttcaacgagg aggtgaattc ttggttcgga atgccggaaa gcttggctct     660
atcacaagga ctactgcaaa gcacgagtca atcccctcg acgagaattt tgctcagctt     720
cttattctcg agataacggg gaacaggtgc gttagcttct tgtagggtct tctgtcgtaa     780
tactaaattt tttctggtgt taggctttt ggtcaacctc gttgagcatc ctcaaacgtg     840
gaatttcttc caaggtgcgc tgctaaaata aacatccagt tgcgtttcga agctcattgt     900
gggcgtcccg tcacaggcaa gggccagctg acaacagaag aatttccatt cgatctcgat     960
```

```
acaacttctc ttggtctcac gatcctcaag cgaagcaggg aaatcgccga ttcagtcatg    1020
gatgaaatgc tggagtatgt cgatcctgat ggtatcattc aggcaagttt catttatcgg    1080
cttgagaaaa taaagacaaa aacgttctga tgggggatg tttctagacg tatttcgatc     1140
atcggagacc acgttttgat ccagtcgtgt gtgtcaatgc attaagcctc ttctatgctt    1200
acggccgcgg ggagcaactg cggtcgactt tgacatgggt acatgaagtc cttctcaatc    1260
gagcctactt ggatggcaca cggtactacg aaacagccga atgcttcctc tatttcatga    1320
gccgacttct cgccacttca ggcgaccctg accttcactc ccttcttaaa cctcttctca    1380
aagaacgggt gcaagaacgc attggagctg atggagactc tcttgcactc gcaatgcgta    1440
ttctcgcctg tgatttcgtc ggaatcagag atgaagtgga tttacgcaca cttctgactt    1500
tgcaatgtga agatggaggt tgggaagtgg gttggatgta caagtatgga tcttccggta    1560
tcagtatcgg aaatcgtgga ctggccaccg cgctcgctat caaggccgtc gacacgatgt    1620
ttcaacccca aattcggttc tctgaatcac ccacagatac tttggttgaa aacgctatcc    1680
acaaacgccg tccctcattt tccgaaaaat tcctcggcaa acgtcctcgc agcggatcgt    1740
tcaggaaacc tttacagtgg atactgcaag gttccaagct tcgcaaatct gtcgaaatag    1800
gaagctaa                                                             1808

<210> SEQ ID NO 92
<211> LENGTH: 1623
<212> TYPE: DNA
<213> ORGANISM: Agaricus bisporus
<220> FEATURE:
<221> NAME/KEY: misc_feature
<222> LOCATION: (1)..(1623)
<223> OTHER INFORMATION: optimized cDNA

<400> SEQUENCE: 92
atggcaccac cgcaacgtcc gttcactgca attgttttcg atattggcga tgttttgttc      60
caatggtctg cgaccacgaa aaccagcatt agcccgaaaa ccctgcgcag cattctgaat     120
tgtccgacct ggtttgatta tgagcgcggc cgtctggcgg aaaatgcgtg ttacgctgcg     180
atcagccaag aatttaacgt caacccggac gaagttcgcg acgccttcag ccaagcgcgc     240
gacagcctgc aggcgaatca cgacttcatc agcctgattc gtgagctgaa agctcaggcg     300
aacggtcgtc tgcgtgtcta cgccatgtct aatatcagcc tgccggattg ggaagtcctg     360
cgtatgaagc cagccgattg ggacatcttt gaccatgtat ttaccagcgg tgcggtgggt     420
gagcgcaagc cgaacctggc ctttttatcgt cacgtcatcg cggccacgga tctgcagccg     480
caccagacga tcttcgtgga tgacaaactg gaaaacgtgc tgtctgcgcg ctcgctgggc     540
ttcacgggta tcgtgttcga cgagccaagc gaagtcaaac gtgcgctgcg taatctgatc     600
ggcgacccgg tgcagcgtgg tggcgagttc ctggttcgta tgctggcaa actgggttct     660 atcacccgta cgaccgcaaa acatgagagc atcccgctgg atgagaattt gcacaactg     720 ttgattctgg aaattactgg taaccgcgca ctggtcaatc tggttgagca cccgcagacg    780
tggaacttct tccagggtaa gggccagctg acgaccgaag aatttccttt tgacctggat    840
acgacgagcc tgggtctgac gatcctgaag cgtagccgcg agattgccga ctccgtcatg    900
gacgaaatgt tggaatacgt ggaccctgac ggcatcattc agacctactt cgatcatcgt    960
cgcccgcgct ttgacccggt tgtttgcgtt aatgccctga gcctgttcta tgcatacggc    1020
cgtggtgagc aactgcgttc caccttgacc tgggtgcacg aagttctgtt gaaccgtgcg    1080
tatttggatg gtacgcgtta ctatgaaacg gccgagtgct ttctgtattt catgtcccgt    1140
```

```
ctgctggcaa ccagcggtga cccggatctg cattccctgc tgaagccgtt gctgaaggaa    1200
cgcgtgcaag agcgcatcgg cgctgacggt gacagcctgg cgctggcgat gcgcattttg    1260
gcatgtgatt ttgttggcat ccgtgatgaa gtggatctgc gtaccctgct gaccttacag    1320
tgcgaggatg gcggttggga agtgggctgg atgtacaaat acggtagcag cggtattagc    1380
attggtaacc gtggtctggc aaccgcattg gcgatcaaag ctgttgacac catgtttcaa    1440
ccgcaaatcc gtttcagcga gagcccgacc gacactctgg tggagaacgc gattcacaag    1500
cgccgcccga gcttttcaga gaaattttta ggtaagcgtc cgcgttccgg ttcgttccgt    1560
aaaccgctgc aatggattct gcagggcagc aagctgcgca agagcgtcga gatcggtagc    1620
taa                                                                  1623
```

<210> SEQ ID NO 93
<211> LENGTH: 1584
<212> TYPE: DNA
<213> ORGANISM: Artificial Sequence
<220> FEATURE:
<223> OTHER INFORMATION: XP_007369631.1 optimized cDNA for S. cerevisiae
      expression

<400> SEQUENCE: 93

```
atggcttcta tccacagaag atacactact tgatcttgg  acttgggtga cgttttgttc     60
agatggtctc caaagactga aactgctatc ccaccacaac aattgaagga catcttgtct    120
tctgttactt ggttcgaata cgaaagaggt agattgtctc aagaagcttg ttacgaaaga    180
tgtgctgaag aattcaagat cgaagcttct gttatcgctg aagctttcaa gcaagctaga    240
ggttctttga gaccaaacga gaattcatcg ctttgatca gagacttgag aagagaaatg    300
cacggtgact tgactgtttt ggctttgtct aacatctctt tgccagacta cgaatacatc    360
atgtctttgt cttctgactg gactactgtt tcgacagag ttttcccatc tgctttggtt    420
ggtgaaagaa agccacactt gggttgttac agaaaggtta tctctgaaat gaacttggaa    480
ccacaaacta ctgttttcgt tgacgacaag ttggacaacg ttgcttctgc tagatctttg    540
ggtatgcacg gtatcgtttt cgacaaccaa gctaacgttt tcagacaatt gagaaacatc    600
ttcggtgacc caatcagaag aggtcaagaa tacttgagag gtcacgctgg taagttggaa    660
tcttctactg acaacggttt gatcttcgaa gaaaacttca ctcaattgat catctacgaa    720
ttgactcaag acagaacttt gatctctttg tctgaatgtc caagaacttg gaacttcttc    780
agaggtgaac cattgttctc tgaaactttc ccagacgacg ttgacactac ttctgttgct    840
ttgactgttt tgcaaccaga cagagctttg gttaactctg ttttggacga atgttggaa    900 tacgttgacg ctgacggtat catgcaaact tacttcgaca gatctagacc aagaatggac    960
ccattcgttt gtgttaacgt tttgtctttg ttctacgaaa acggtagagg tcacgaattg   1020
ccaagaactt tggactgggt ttacgaagtt tgttgcaca  gagcttacca cggtggttct   1080
agatactact tgtctccaga ctgtttcttg ttcttcatgt ctagattgtt gaagagagct   1140
gacgacccag ctgttcaagc tagattgaga ccattgttcg ttgaaagagt aacgaaaga   1200 gttggtgctg ctggtgactc tatggacttg gctttcagaa tcttggctgc tgcttctgtt   1260
ggtgttcaat gtccaagaga cttggaaaga ttgactgctg gtcaatgtga cgacggtggt   1320
tgggacttgt gttggttcta cgttttcggt tctactggtg ttaaggctgg taacagaggt   1380
ttgactactg ctttggctgt tactgctatc caaactgcta tcggtagacc accatctcca   1440
tctccatctg ctgcttcttc ttctttcaga ccatcttctc catacaagtt cttgggtatc   1500
```

```
tctagaccag cttctccaat cagattcggt gacttgttga gaccatggag aaagatgtct    1560
agatctaact tgaagtctca ataa                                          1584

<210> SEQ ID NO 94
<211> LENGTH: 1623
<212> TYPE: DNA
<213> ORGANISM: Artificial Sequence
<220> FEATURE:
<223> OTHER INFORMATION: XP_006461126 optimized cDNA for S. cerevisiae
      expression

<400> SEQUENCE: 94
atggctccac acaaagacc attcactgct atcgttttcg acatcggtga cgttttgttc      60
caatggtctg ctactactaa gacttctatc tctccaaaga ctttgagatc tatcttgaac    120
tgtccaactt ggttcgacta cgaaagaggt agattggctg aaaacgcttg ttacgctgct    180
atctctcaag aattcaacgt taacccagac gaagttagag acgctttctc tcaagctaga    240
gactctttgc aagctaacca cgacttcatc tctttgatca gagaattgaa ggctcaagct    300
aacggtagat tgagagttta cgctatgtct aacatctctt tgccagactg gaagttttg    360 agaatgaagc cagctgactg gacatcttc gaccacgttt tcacttctgg tgctgttggt    420
gaaagaaagc caaacttggc tttctacaga cacgttatcg ctgctactga cttgcaacca    480
caccaaacta tcttcgttga cgacaagttg aaaacgtttg tgtctgctag atctttgggt    540
ttcactggta tcgttttcga cgaaccatct gaagttaaga gagctttgag aaacttgatc    600
ggtgacccag ttcaaagagg tggtgaattc ttggttagaa acgctggtaa gttgggttct    660
atcactagaa ctactgctaa gcacgaatct atcccattgg acgaaaactt cgctcaattg    720
ttgatcttgg aaatcactgg taacagagct ttggttaact tggttgaaca cccacaaact    780
tggaacttct ccaaggtaa gggtcaattg actactgaag aattcccatt cgacttggac    840
actacttctt tgggttttgac tatcttgaag agatctagag aaatcgctga ctctgttatg    900
gacgaaatgt tggaatacgt tgacccagac ggtatcatcc aaacttactt cgaccacaga    960
agaccaagat cgacccagt tgtttgtgtt aacgctttgt ctttgttcta cgcttacggt    1020
agaggtgaac aattgagatc tactttgact tgggttcacg aagttttgtt gaacagagct    1080
tacttggacg gtactagata ctacgaaact gctgaatgtt tcttgtactt catgtctaga    1140
ttgttggcta cttctggtga cccagacttg cactcttgtg tgaagccatt gttgaaggaa    1200
agagttcaag aaagaatcgg tgctgacggt gactctttgg cttggctat gagaatcttg    1260 gcttgtgact tcgttggtat cagagacgaa gttgacttga gaactttgtt gactttgcaa    1320
tgtgaagacg gtggttggga gttggttgg atgtacaagt acggttcttc tggtatctct    1380
atcggtaaca gaggtttggc tactgctttg gctatcaagg ctgttgacac tatgttccaa    1440 ccacaaaatca gattctctga atctccaact gacactttgg ttgaaaacgc tatccacaag    1500
agaagaccat ctttctctga aaagttcttg ggtaagagac aagatctgg ttctttcaga    1560 aagccattgc aatggatctt gcaaggttct aagttgagaa agtctgttga atcggttct    1620 taa                                                                 1623

<210> SEQ ID NO 95
<211> LENGTH: 1566
<212> TYPE: DNA
<213> ORGANISM: Artificial Sequence
<220> FEATURE:
<223> OTHER INFORMATION: LoTps1 Optimized cDNA for S. cerevisiae
``` expression

<400> SEQUENCE: 95

| | |
|---|---|
| atgtacactg ctttgatctt ggacttgggt gacgttttgt tctcttggtc ttctactact | 60 |
| aacactacta tcccaccaag acaattgaag gaaatcttgt cttctccagc ttggttcgaa | 120 |
| tacgaaagag gtagaatcac tcaagctgaa tgttacgaaa gagtttctgc tgaattctct | 180 |
| ttggacgcta ctgctgttgc tgaagctttc agacaagcta gagactcttt gagaccaaac | 240 |
| gacaagttct tgactttgat cagagaattg agacaacaat ctcacggtga attgactgtt | 300 |
| ttggctttgt ctaacatctc tttgccagac tacgaattca tcatggcttt ggactctaag | 360 |
| tggacttctg ttttcgacag agttttccca tctgctttgg ttggtgaaag aaagccacac | 420 |
| ttgggtgctt tcagacaagt tttgtctgaa atgaacttgg acccacacac tactgttttc | 480 |
| gttgacgaca agttggacaa cgttgtttct gctagatctt tgggtatgca cggtgttgtt | 540 |
| ttcgactctc aagacaacgt tttcagaatg ttgagaaaca tcttcggtga cccaatccac | 600 |
| agaggtagag actacttgag acaacacgct ggtagattgg aaacttctac tgacgctggt | 660 |
| gttgttttcg aagaaaactt cactcaattg atcatctacg aattgactaa cgacaagtct | 720 |
| ttgatcacta cttctaactg tgctagaact tggaacttct tcagaggtaa gccattgttc | 780 |
| tctgcttctt tcccagacga catggacact acttctgttg ctttgactgt tttgagattg | 840 |
| gaccacgctt tggttaactc tgttttggac gaaatgttga agtacgttga cgctgacggt | 900 |
| atcatgcaaa cttacttcga ccacactaga ccaagaatgg acccattcgt tgtgttaac | 960 |
| gttttgtctt tgttccacga acaaggtaga ggtcacgaat tgccaaacac tttggaatgg | 1020 |
| gttcacgaag ttttgttgca cagagcttac atcggtggtt ctagatacta cttgtctgct | 1080 |
| gactgtttct tgttcttcat gtctagattg ttgcaaagaa tcactgaccc atctgttttg | 1140 |
| ggtagattca gaccattgtt catcgaaaga gttagagaaa gagttggtgc tactggtgac | 1200 |
| tctatcgact tggcttttcag aatcatcgct gcttctactg ttggtatcca atgtccaaga | 1260 |
| gacttggaat ctttgttggc tgctcaatgt gaagacggtg gttgggactt gtgttggttc | 1320 |
| taccaatacg gttctactgg tgttaaggct ggtaacagag gtttgactac tgctttggct | 1380 |
| atcaaggcta tcgactctgc tatcgctaga ccaccatctc cagctttgtc tgttgcttct | 1440 |
| tcttctaagt ctgaaatccc aaagccaatc caaagatctt tgagaccatt gtctccaaga | 1500 |
| agattcggtg gtttcttgat gccatggaga agatctcaaa gaaacggtgt tgctgttttct | 1560 |
| tcttaa | 1566 |

<210> SEQ ID NO 96
<211> LENGTH: 1602
<212> TYPE: DNA
<213> ORGANISM: Artificial Sequence
<220> FEATURE:
<223> OTHER INFORMATION: EMD37666.1 optimized cDNA for S. cerevisiae expression

<400> SEQUENCE: 96

| | |
|---|---|
| atgtctgctg ctgctcaata cactactttg atcttggact gggtgacgt tttgttcact | 60 |
| tggtctccaa agactaagac ttctatccca ccaagaactt tgaaggaaat cttgaactct | 120 |
| gctacttggt acgaatacga aagaggtaga atctctcaag acgaatgtta cgaaagagtt | 180 |
| ggtactgaat tcggtatcgc tccatctgaa atcgacaacg ctttcaagca agctagagac | 240 |
| tctatggaat ctaacgacga attgatcgct ttggttagag aattgaagac tcaattggac | 300 |

| | |
|---|---|
| ggtgaattgt tggttttcgc tttgtctaac atctctttgc cagactacga atacgttttg | 360 |
| actaagccag ctgactggtc tatcttcgac aaggttttcc catctgcttt ggttggtgaa | 420 |
| agaaagccac acttgggtgt ttacaagcac gttatcgctg aaactggtat cgacccaaga | 480 |
| actactgttt tcgttgacga caagatcgac aacgttttgt ctgctagatc tgttggtatg | 540 |
| cacggtatcg ttttcgaaaa gcaagaagac gttatgagag ctttgagaaa catcttcggt | 600 |
| gacccagtta agagaggtag agaatacttg agaagaaacg ctatgagatt ggaatctgtt | 660 |
| actgaccacg tgttgctttt cggtgaaaac ttcactcaat tgttgatctt ggaattgact | 720 |
| aacgacccat ctttggttac tttgccagac agaccaagaa cttggaactt cttcagaggt | 780 |
| aacggtggta gaccatctaa gccattgttc tctgaagctt ccccagacga cttggacact | 840 |
| acttctttgg ctttgactgt tttgcaaaga gacccaggtg ttatctcttc tgttatggac | 900 |
| gaaatgttga actacagaga cccagacggt atcatgcaaa cttacttcga cgacggtaga | 960 |
| caaagattgg acccattcgt taacgttaac gttttgactt tcttctacac taacggtaga | 1020 |
| ggtcacgaat tggaccaatg tttgacttgg gttagagaag ttttgttgta cagagcttac | 1080 |
| ttgggtggtt ctagatacta cccatctgct gactgtttct tgtacttcat ctctagattg | 1140 |
| ttcgcttgta ctaacgaccc agttttgcac caccaattga agccattgtt cgttgaaaga | 1200 |
| gttcaagaac aaatcggtgt tgaaggtgac gctttggaat tggctttcag attgttggtt | 1260 |
| tgtgcttctt tggacgttca aaacgctatc gacatgagaa gattgttgga atgcaatgt | 1320 |
| gaagacggtg gttgggaagg tggtaacttg tacagattcg gtactactgg tttgaaggtt | 1380 |
| actaacagag gtttgactac tgctgctgct gttcaagcta tcgaagcttc tcaaagaaga | 1440 |
| ccaccatctc catctccatc tgttgaatct actaagtctc caatcactcc agttactcca | 1500 |
| atgttggaag ttccatcttt ggtttgtct atctctagac catcttctcc attgttgggt | 1560 |
| tacttcagat tgccatggaa gaagtctgct gaagttcact aa | 1602 |

<210> SEQ ID NO 97
<211> LENGTH: 1461
<212> TYPE: DNA
<213> ORGANISM: Artificial Sequence
<220> FEATURE:
<223> OTHER INFORMATION: XP_001217376.1 optimized cDNA for S. cerevisiae expression

<400> SEQUENCE: 97

| | |
|---|---|
| atggctatca ctaagggtcc agttaaggct ttgatcttgg acttctctaa cgttttgtgt | 60 |
| tcttggaagc caccatctaa cgttgctgtt ccaccacaaa tcttgaagat gatcatgtct | 120 |
| tctgacatct ggcacgacta cgaatgtggt agatactcta gaagaagactg ttacgctaga | 180 |
| gttgctgaca gattccacat ctctgctgct gacatggaag acactttgaa gcaagctaga | 240 |
| aagtctttgc aagttcacca cgaaactttg ttgttcatcc aacaagttaa gaaggacgct | 300 |
| ggtggtgaat tgatggttttg tggtatgact aacactccaa gaccagaaca agacgttatg | 360 |
| cactctatca acgctgaata cccagttttc gacagaatct acatctctgg tttgatgggt | 420 |
| atgagaaagc catctatctg tttctaccaa agagttatgg aagaaatcgg tttgtctggt | 480 |
| gacgctatca tgttcatcga cgacaagttg gaaaacgtta tcgctgctca atctgttggt | 540 |
| atcagaggtg ttttgttcca atctcaacaa gacttgagaa gagttgtttt gaacttcttg | 600 |
| ggtgacccag ttcacagagg tttgcaattc ttggctgcta cgctaagaa gatggactct | 660 |
| gttactaaca ctggtgacac tatccaagac aacttcgctc aattgttgat cttggaattg | 720 |

```
gctcaagaca gagaattggt taagttgcaa gctggtaaga gaacttggaa ctacttcatc      780
ggtccaccaa agttgactac tgctactttc ccagacgaca tggacactac ttctatggct      840
ttgtctgttt tgccagttgc tgaagacgtt gtttcttctg ttttggacga aatgttgaag      900
ttcgttactg acgacggtat cttcatgact tacttcgact cttctagacc aagagttgac      960
ccagttgttt gtatcaacgt tttgggtgtt ttctgtagac acaacagaga aagagacgtt     1020
ttgccaactt tccactggat cagagacatc ttgatcaaca gagcttactt gtctggtact     1080
agatactacc catctccaga cttgttcttg ttcttcttgg ctagattgtg tttggctgtt     1140
agaaaccaat ctttgagaga acaattggtt ttgccattgg ttgacagatt gagagaaaga     1200
gttggtgctc caggtgaagc tgtttctttg gctgctagaa tcttggcttg tagatctttc     1260
ggtatcgact ctgctagaga catggactct ttgagaggta agcaatgtga agacggtggt     1320
tggccagttg aatgggttta cagattcgct tctttcggtt tgaacgttgg taacagaggt     1380
ttggctactg ctttcgctgt tagagctttg gaatctccat acggtgaatc tgctgttaag     1440
gttatgagaa gaatcgttta a                                                1461
```

<210> SEQ ID NO 98
<211> LENGTH: 1680
<212> TYPE: DNA
<213> ORGANISM: Drimys lanceolata
<220> FEATURE:
<221> NAME/KEY: misc_feature
<222> LOCATION: (1)..(1680)
<223> OTHER INFORMATION: DlTps589 wild type DNA sequence

<400> SEQUENCE: 98

```
atggatctta ttaatccctc cccagcggct tccacccctcc ctctcccagt tgatggagat       60
tcagaagttg ttaggcgatc tgccgggttt catccgacta tctggggcga tcacttcctc      120
tcctacaagc ccgatccaaa gaaaatagat gcatggaata aagggttga agagctgaag       180 gaagaagtga agaagatatt aagcaatgca aagggacgg tggaagagct gaatttgatt      240
gatgatctcg tacaccttgg gattagttat catttgaga aggagattga tgatgctcta       300
caacacatct tgatacccca tcttgatgat tttcctaagg atgatctata tgtcgccgct       360
ctccgatttg gcgtcttaag gaaacagggg caccgtgttt ctccagatgt attcaaaaaa      420
ttcaaagatg agcaggggaa tttcaaggca gagttgagca ccgatgcgaa aggtttgcta      480
tgtttaaatg atgtggctta tctcagcaca agagggaag atatcttgga tgaagccatt      540
cctttcactg aggagcacct taggtcttgt attagccatg tagattctca tatggcagca      600
aaaattgaac attctctcga gcttcccctt catcatcgca taccaaggct agagaacagg     660
cactacatct cagtctatga aggagacaag gaaaggaacg aagttgtcct tgagcttgcc     720
aatttagatt tcaatctgat tcaaatcttg caccaaagag agctgagaga catcacaatg     780
tggtggaagg agattgacct tgcagcaaag ctgccttta ttagggatag gttggtggag      840
tgctactact ggatcatggg ggtctatttt gaaccaatat actcgagggc tagggttttt    900
tccaccaaaa tgacaatgtt ggtctcagtt gtggacgaca tatatgatgt gtatgctacc     960
gaggatgagc ttcaactatt cactgatgcc atctataggt gggatgctga tgacattgat    1020
cagctgcctc agtacttgaa agatgctttt atggtactct acaacactgt gaagactcta    1080
gaagaagaac ttgaaccaga aggaaactct tatcgtggat tctatgtaaa agatgcaatg    1140
aaggttttgg caagggatta ctttgtggag cacaaatggt ataacagaaa aattgtgcca    1200
tccgtagagg aatacttgaa aatttcttgc atcagtgtgg ccgttcatat ggctacagtt    1260
```

-continued

```
cactgtattg ctgggatgta tgaaattgca accaaagagg cattcgaatg gttgatgact    1320
gagcccaaac ttgttattga tgcatctctg attggtcgtc tccttgatga catgcagtcc    1380
acctcgtttg agcaacagag aggccacgtg tcatcagcag tacagtgtta catggctgaa    1440
tatggtgtaa cagcggaaga agcatgtgaa aagctccgag atatggctgc aattgcttgg    1500
aaagatgtga acgaggcatg ccttaggccc acggttttcc ctatgcctat cctttttgcct    1560 tctatcaact ggcacgtgt ggcagaagtc atctacctac gtggagatgg atacacgcac    1620
gctgggggtg agaccaagaa acacatcacg gccatgcttg ttaagccaat tgaagtctga    1680
```

<210> SEQ ID NO 99
<211> LENGTH: 559
<212> TYPE: PRT
<213> ORGANISM: Drimys lanceolata

<400> SEQUENCE: 99

```
Met Asp Leu Ile Asn Pro Ser Pro Ala Ala Ser Thr Leu Pro Leu Pro
1               5                   10                  15

Val Asp Gly Asp Ser Glu Val Val Arg Arg Ser Ala Gly Phe His Pro
            20                  25                  30

Thr Ile Trp Gly Asp His Phe Leu Ser Tyr Lys Pro Asp Pro Lys Lys
        35                  40                  45

Ile Asp Ala Trp Asn Lys Arg Val Glu Glu Leu Lys Glu Val Lys
    50                  55                  60

Lys Ile Leu Ser Asn Ala Lys Gly Thr Val Glu Glu Leu Asn Leu Ile
65                  70                  75                  80

Asp Asp Leu Val His Leu Gly Ile Ser Tyr His Phe Glu Lys Glu Ile
                85                  90                  95

Asp Asp Ala Leu Gln His Ile Phe Asp Thr His Leu Asp Asp Phe Pro
            100                 105                 110

Lys Asp Asp Leu Tyr Val Ala Ala Leu Arg Phe Gly Val Leu Arg Lys
        115                 120                 125

Gln Gly His Arg Val Ser Pro Asp Val Phe Lys Lys Phe Lys Asp Glu
    130                 135                 140

Gln Gly Asn Phe Lys Ala Glu Leu Ser Thr Asp Ala Lys Gly Leu Leu
145                 150                 155                 160

Cys Leu Asn Asp Val Ala Tyr Leu Ser Thr Arg Gly Glu Asp Ile Leu
                165                 170                 175

Asp Glu Ala Ile Pro Phe Thr Glu Glu His Leu Arg Ser Cys Ile Ser
            180                 185                 190

His Val Asp Ser His Met Ala Ala Lys Ile Glu His Ser Leu Glu Leu
        195                 200                 205

Pro Leu His His Arg Ile Pro Arg Leu Glu Asn Arg His Tyr Ile Ser
    210                 215                 220

Val Tyr Glu Gly Asp Lys Glu Arg Asn Glu Val Val Leu Glu Leu Ala
225                 230                 235                 240

Asn Leu Asp Phe Asn Leu Ile Gln Ile Leu His Gln Arg Glu Leu Arg
                245                 250                 255

Asp Ile Thr Met Trp Trp Lys Glu Ile Asp Leu Ala Ala Lys Leu Pro
            260                 265                 270

Phe Ile Arg Asp Arg Leu Val Glu Cys Tyr Tyr Trp Ile Met Gly Val
        275                 280                 285

Tyr Phe Glu Pro Ile Tyr Ser Arg Ala Arg Val Phe Ser Thr Lys Met
    290                 295                 300
```

Thr Met Leu Val Ser Val Val Asp Asp Ile Tyr Asp Val Tyr Ala Thr
305                 310                 315                 320

Glu Asp Glu Leu Gln Leu Phe Thr Asp Ala Ile Tyr Arg Trp Asp Ala
            325                 330                 335

Asp Asp Ile Asp Gln Leu Pro Gln Tyr Leu Lys Asp Ala Phe Met Val
        340                 345                 350

Leu Tyr Asn Thr Val Lys Thr Leu Glu Glu Glu Leu Glu Pro Glu Gly
    355                 360                 365

Asn Ser Tyr Arg Gly Phe Tyr Val Lys Asp Ala Met Lys Val Leu Ala
370                 375                 380

Arg Asp Tyr Phe Val Glu His Lys Trp Tyr Asn Arg Lys Ile Val Pro
385                 390                 395                 400

Ser Val Glu Glu Tyr Leu Lys Ile Ser Cys Ile Ser Val Ala Val His
                405                 410                 415

Met Ala Thr Val His Cys Ile Ala Gly Met Tyr Glu Ile Ala Thr Lys
            420                 425                 430

Glu Ala Phe Glu Trp Leu Met Thr Glu Pro Lys Leu Val Ile Asp Ala
        435                 440                 445

Ser Leu Ile Gly Arg Leu Leu Asp Asp Met Gln Ser Thr Ser Phe Glu
    450                 455                 460

Gln Gln Arg Gly His Val Ser Ser Ala Val Gln Cys Tyr Met Ala Glu
465                 470                 475                 480

Tyr Gly Val Thr Ala Glu Glu Ala Cys Glu Lys Leu Arg Asp Met Ala
                485                 490                 495

Ala Ile Ala Trp Lys Asp Val Asn Glu Ala Cys Leu Arg Pro Thr Val
            500                 505                 510

Phe Pro Met Pro Ile Leu Leu Pro Ser Ile Asn Leu Ala Arg Val Ala
        515                 520                 525

Glu Val Ile Tyr Leu Arg Gly Asp Gly Tyr Thr His Ala Gly Gly Glu
    530                 535                 540

Thr Lys Lys His Ile Thr Ala Met Leu Val Lys Pro Ile Glu Val
545                 550                 555

<210> SEQ ID NO 100
<211> LENGTH: 1680
<212> TYPE: DNA
<213> ORGANISM: Artificial Sequence
<220> FEATURE:
<223> OTHER INFORMATION: Codon optimized DNA sequence of DlTps589 from
      D. lanceolata

<400> SEQUENCE: 100
atggacctga ttaacccgag ccctgctgca tccaccctgc cactgccagt cgatggtgat     60
agcgaagttg tgcgccgtag cgcgggtttc catccgacca tctggggtga ccactttctg    120
tcttataagc cggaccccga aaagattgat gcgtggaaca gcgtgttgag gaactgaaa    180 gaagaggtca aaagatttt gagcaatgcg aaaggcacgg ttgaggaact gaatttgatt    240
gacgacctgg tacacctggg tattagctat cactttgaga agaaatcga cgacgcgctg    300 cagcatatct tcgatacgca cctggatgat ttcccgaaag atgacctcta cgtggctgcg    360
ctgcgttttg gcgtcctgcg taagcaaggc atcgtgtca gcccggacgt ctttaagaaa    420
ttcaaagacg agcaaggcaa cttcaaagcg gagctgtcaa ccgatgcaaa gggcctgttg    480
tgcctgaacg atgtggcgta cctgagcacc cgtggtgagg atatcctgga cgaagcgatc    540
ccgttcacgg aagaacattt gcgctcgtgc attagccacg ttgatagcca catggcagcg    600

```
aagattgagc actctctgga gctgccgctg caccatcgca ttccgcgttt agagaatcgc    660
cattacatct ccgtgtacga gggtgacaaa gagcgtaatg aagtcgttct ggagttggct    720
aacttggact ttaatcttat ccagatcctg caccagcgcg agctgcgcga catcacgatg    780
tggtggaaag aaattgatct ggccgcaaag ctgccgttta ttcgtgaccg tctggtggag    840
tgttactatt ggattatggg cgtgtacttc gagccgatct acagccgtgc gcgcgtgttt    900
agcaccaaga tgaccatgct ggttagcgtg gtggatgaca tctatgatgt ctacgctacg    960
gaagatgagt tgcagctgtt taccgacgcc atttacagat gggacgccga tgacattgat   1020
caactgccgc aatatctgaa agacgccttt atggttctgt acaacaccgt caaaaccctg   1080
gaagaagaac tggagccgga aggtaactct tatcgtggtt tctacgttaa agatgcgatg   1140
aaagttctgg cgcgtgacta tttcgttgag cataagtggt acaatcgtaa gatcgtcccg   1200
tccgttgaag agtacttgaa gattagctgt atcagcgtcg cagtccacat ggcgaccgtg   1260
cactgtatcg ccggcatgta tgagatcgcc acgaaagaag cattcgagtg gctgatgacc   1320
gagccgaaac tggtgattga cgcaagcctg attggtcgcc tgctggacga tatgcagagc   1380
acgagctttg agcagcagcg cggtcatgtt agctccgcag ttcaatgcta catggctgag   1440
tacggtgtga ctgccgaaga agcatgcgag aagctgcgtg atatggcggc cattgcgtgg   1500
aaagatgtga atgaagcatg cctgcgcccg accgttttcc cgatgccgat tttactgcct   1560
agcatcaacc tggcacgtgt ggcggaagtt atctatctgc gtggcgacgg ttatacgcac   1620
gcgggtggtg agactaagaa gcacatcacc gcgatgctgg tcaagccgat cgaagtgtaa   1680
```

<210> SEQ ID NO 101
<211> LENGTH: 1656
<212> TYPE: DNA
<213> ORGANISM: Drimys winteri
<220> FEATURE:
<221> NAME/KEY: misc_feature
<222> LOCATION: (1)..(1656)
<223> OTHER INFORMATION: SCH51_3228_9 wild type DNA sequence

<400> SEQUENCE: 101

```
atggcttcca ccctccctct cccagcttat ggagattcag aagttgttag gcgatctgcc     60
gggtttcatc cgacgatctg gggcgatcac ttcctctcct acaagcctga tccaacgaaa    120
atagatgaat ggaataaaag ggttgaagag ctgaaggaag aagtgaagaa gatattaagc    180
aatgcaaaag ggacagtgga agagctgaat ttgcttgatg atctcgtaca ccttgggatt    240
agttatcatt ttgagaagga gattgatgat gctttacaac aaatctttga tacccatctt    300
gatgtttttc ctaaggatga tctatatgcc accgctctcc gatttggcgt cttaaggaaa    360
caggggcacc gtgtttctcc agatgtattc aaaaaattca agatgagca ggggaatttc    420 aaggcagagt tgagcaccga tgcgaagggt ttgctatgtt tatatgatgt ggcttatctc    480
agcacaagag gggaagatat cttggatgaa gccattcctt tcactaagga gcaccttagg    540
tcttgtatta gccatgtcga ttctcatatg gcagcaaaaa ttgagcattc tctagagctt    600 cccctteate atcgcatacc aaggctagag aacaggcact acatctcagt ctatgaagga    660
gacaaggaaa ggaatgaagt tgtccttgag cttgccaaat tagatttcaa tctgattcaa    720
atcttgcacc aaagagagct gagggacatc acaacgtggt ggaaggagat tgaccttgca    780
gcaaagctac cttttattag ggataggttg gtggagtgct actattggat catgggagtc    840
tattttgaac caatatactc aagggctaga gttttttcga ccaaaatgac aatcttggtc    900
```

-continued

```
tcagttgtgg acgacatata tgatgtatat gctacagagg atgagctcca acttttcact      960
gatgcaatct ataggtggga tgctgaggac attgagcagc ttccacagta cttgaaagat     1020
gcttttcttg tactctataa cactgtgaag gacctagaag aggaattgga accagaagga     1080
aactcttatc gtggatacta tgtaaaagat gcgatgaagg ttttggcaag ggattacttt     1140
gtggagcaca atggtataa cagaaaaatt gtgccatcag tagaggacta cctgcgaatt     1200
tcttgcatta gtgttgccgt tcatatggcc acagttcatt gtattgctgg gatgtatgaa     1260
attgcaacca agaggcatt cgaatggttg aagacggaac ctaaacttgt tatagatgca     1320
tcactgattg ggcgtctcct cgatgacatg cagtccacct cgtttgagca acagagaggt     1380
catgtgtcat cagcggtaca gtgttacatg atccaatatg gggtatcaca cgaagaagcg     1440
tgtgagaagt tgcgagaaat ggctgcaatt gcgtggaaag atgtaaacca agcatgcctt     1500
aggcccactg ttttccctat gcctattctt ctgccctcca tcaaccttgc acgtgtggca     1560
gaagtgattt acctacgcgg agatggatat acacatgcgg tggtgagac caaaaaacat     1620
atcacggcca tgcttgttga tccaatcaaa gtctga                                1656
```

<210> SEQ ID NO 102
<211> LENGTH: 551
<212> TYPE: PRT
<213> ORGANISM: Drimys winteri

<400> SEQUENCE: 102

```
Met Ala Ser Thr Leu Pro Leu Pro Ala Tyr Gly Asp Ser Glu Val Val
1               5                   10                  15

Arg Arg Ser Ala Gly Phe His Pro Thr Ile Trp Gly Asp His Phe Leu
            20                  25                  30

Ser Tyr Lys Pro Asp Pro Thr Lys Ile Asp Glu Trp Asn Lys Arg Val
        35                  40                  45

Glu Glu Leu Lys Glu Glu Val Lys Lys Ile Leu Ser Asn Ala Lys Gly
    50                  55                  60

Thr Val Glu Glu Leu Asn Leu Leu Asp Asp Leu Val His Leu Gly Ile
65                  70                  75                  80

Ser Tyr His Phe Glu Lys Glu Ile Asp Asp Ala Leu Gln Gln Ile Phe
                85                  90                  95

Asp Thr His Leu Asp Val Phe Pro Lys Asp Asp Leu Tyr Ala Thr Ala
            100                 105                 110

Leu Arg Phe Gly Val Leu Arg Lys Gln Gly His Arg Val Ser Pro Asp
        115                 120                 125

Val Phe Lys Lys Phe Lys Asp Glu Gln Gly Asn Phe Lys Ala Glu Leu
    130                 135                 140

Ser Thr Asp Ala Lys Gly Leu Leu Cys Leu Tyr Asp Val Ala Tyr Leu
145                 150                 155                 160

Ser Thr Arg Gly Glu Asp Ile Leu Asp Glu Ala Ile Pro Phe Thr Lys
                165                 170                 175

Glu His Leu Arg Ser Cys Ile Ser His Val Asp Ser His Met Ala Ala
            180                 185                 190

Lys Ile Glu His Ser Leu Glu Leu Pro Leu His Arg Ile Pro Arg
        195                 200                 205

Leu Glu Asn Arg His Tyr Ile Ser Val Tyr Glu Gly Asp Lys Glu Arg
    210                 215                 220

Asn Glu Val Val Leu Glu Leu Ala Lys Leu Asp Phe Asn Leu Ile Gln
225                 230                 235                 240
```

```
Ile Leu His Gln Arg Glu Leu Arg Asp Ile Thr Thr Trp Trp Lys Glu
                245                 250                 255

Ile Asp Leu Ala Ala Lys Leu Pro Phe Ile Arg Asp Arg Leu Val Glu
            260                 265                 270

Cys Tyr Tyr Trp Ile Met Gly Val Tyr Phe Glu Pro Ile Tyr Ser Arg
        275                 280                 285

Ala Arg Val Phe Ser Thr Lys Met Thr Ile Leu Val Ser Val Val Asp
    290                 295                 300

Asp Ile Tyr Asp Val Tyr Ala Thr Glu Asp Glu Leu Gln Leu Phe Thr
305                 310                 315                 320

Asp Ala Ile Tyr Arg Trp Asp Ala Glu Asp Ile Glu Gln Leu Pro Gln
                325                 330                 335

Tyr Leu Lys Asp Ala Phe Leu Val Leu Tyr Asn Thr Val Lys Asp Leu
            340                 345                 350

Glu Glu Glu Leu Glu Pro Glu Gly Asn Ser Tyr Arg Gly Tyr Tyr Val
        355                 360                 365

Lys Asp Ala Met Lys Val Leu Ala Arg Asp Tyr Phe Val Glu His Lys
    370                 375                 380

Trp Tyr Asn Arg Lys Ile Val Pro Ser Val Glu Asp Tyr Leu Arg Ile
385                 390                 395                 400

Ser Cys Ile Ser Val Ala Val His Met Ala Thr Val His Cys Cys Ala
                405                 410                 415

Gly Met Asp Glu Ile Ala Thr Lys Glu Ala Phe Glu Trp Leu Lys Thr
            420                 425                 430

Glu Pro Lys Leu Val Ile Asp Ala Ser Leu Ile Gly Arg Leu Leu Asp
        435                 440                 445

Asp Met Gln Ser Thr Ser Phe Glu Gln Gln Arg Gly His Val Ser Ser
    450                 455                 460

Ala Val Gln Cys Tyr Met Ile Gln Tyr Gly Val Ser His Glu Glu Ala
465                 470                 475                 480

Cys Glu Lys Leu Arg Glu Met Ala Ala Ile Ala Trp Lys Asp Val Asn
                485                 490                 495

Gln Ala Cys Leu Arg Pro Thr Val Phe Pro Met Pro Ile Leu Leu Pro
            500                 505                 510

Ser Ile Asn Leu Ala Arg Val Ala Glu Val Ile Tyr Leu Arg Gly Asp
        515                 520                 525

Gly Tyr Thr His Ala Gly Gly Glu Thr Lys Lys His Ile Thr Ala Met
    530                 535                 540

Leu Val Asp Pro Ile Lys Val
545                 550
```

<210> SEQ ID NO 103
<211> LENGTH: 1656
<212> TYPE: DNA
<213> ORGANISM: Artificial Sequence
<220> FEATURE:
<223> OTHER INFORMATION: Codon optimized DNA sequence of SCH51-3228-9

<400> SEQUENCE: 103

```
atggcaagca ccctgccgct gcctgcctat ggtgatagcg aagttgttcg tcgtagcgca     60
ggttttcatc cgaccatttg gggtgatcat tttctgagct ataaaccgga tccgaccaaa    120
attgatgaat ggaataaacg tgtcgaagaa ctgaaagaag aagtgaaaaa aatcctgagc    180
aatgccaaag gcaccgttga ggaactgaat ctgctggatg atctggttca tctgggtatc    240
agctatcact ttgagaaaga aatcgatgat gcactgcagc agatttttga tacccatctg    300
```

```
gatgttttcc cgaaagatga tctgtatgca accgcactgc gttttggtgt tctgcgtaaa    360
cagggtcatc gtgttagtcc ggatgtgttc aaaaaattca agatgaaaca gggcaacttc    420
aaagcagaac tgagcaccga tgcaaaaggt ctgctgtgtc tgtatgatgt tgcatatctg    480
agcacccgtg gtgaagatat tctggatgaa gcaattccgt ttaccaaaga acatctgcgt    540
agctgtatta gccatgttga tagccacatg gcagcgaaaa ttgaacatag cctggaactg    600
cctctgcatc accgtattcc gcgtctggaa aatcgtcact atattagcgt ttatgagggc    660
gataaagaac gcaatgaagt tgtgctggaa ctggcaaaac tggattttaa cctgattcag    720
attctgcatc agcgtgaact gcgtgatatt accacctggt ggaaagaaat tgatctggca    780
gcaaaactgc cgtttattcg tgatcgtctg gttgaatgct attattggat tatgggcgtg    840
tatttcgaac cgatttatag ccgtgcacgt gttttagca ccaaaatgac cattctggtt    900
agcgtggtgg atgatatcta tgatgtttat gccaccgaag atgaactgca gctgtttacc    960
gatgccattt atcgttggga tgcagaagat attgaacagc tgccgcagta tctgaaagat   1020
gcatttctgg ttctgtacaa caccgtgaaa gatctggaag aagaactgga accggaaggt   1080
aatagctatc gtggttatta tgttaaagat gccatgaaag ttctggcacg cgattatttt   1140
gttgagcaca atggtataa ccgcaaaatt gttccgagcg tggaagatta tctgcgtatt   1200
agctgcatta gcgttgcagt tcacatggca accgttcatt gttgtgcagg tatggatgaa   1260
attgcaacca agaagcatt tgagtggctg aaaaccgaac cgaaactggt tattgatgca   1320
agcctgattg gtcgtctgct ggacgatatg cagagcacca gctttgaaca gcagcgtggt   1380
catgttagca gcgcagttca gtgttatatg attcagtatg gtgttagcca tgaagaagca   1440
tgcgaaaaac tgcgcgaaat ggcagcaatt gcatggaaag atgttaatca ggcatgtctg   1500
cgtccgaccg ttttccgat gccgattctg ctgccgagca ttaatctggc acgtgttgcc   1560
gaagttatct atctgcgtgg tgatggttat acccatgccg gtggtgaaac caaaaaacat   1620
attaccgcaa tgctggtcga tccgattaaa gtttaa                             1656
```

<210> SEQ ID NO 104
<211> LENGTH: 1656
<212> TYPE: DNA
<213> ORGANISM: Drimys winteri
<220> FEATURE:
<221> NAME/KEY: misc_feature
<222> LOCATION: (1)..(1656)
<223> OTHER INFORMATION: SCH51_3228_11 wild type DNA sequence

<400> SEQUENCE: 104

```
atggcttcca ccctcctct cccagcttat ggagattcag aagttgttag gcgatctgcc      60
gggtttcatc cgacgatctg gggcgatcac ttcctctcct acaagcctga tccaacgaaa    120
atagatgaat ggaataaaag ggttgaagag ctgaggaag aagtgaagaa gatattaagc    180
aatgcaaaag gacagtgga agagctgaat ttgcttgatg atctcgtaca ccttgggatt    240
agttatcatt ttgagaagga gattgatgat gctttacaac aaatctttga tacccatctt    300 gatgttttc ctaaggatga tctatatgcc accgctctcc gatttggcgt cttaaggaaa    360
caggggcacc gtgtttctcc agatgtattc aaaaaattca agatgagca ggggaatttc    420 aaggcagagt tgagcaccga tgcgaagggt ttgctatgtt tatatgatgt ggcttatctc    480
agcacaagag gggaagatat cttggatgaa gccattcctt tcactaagga gcacttagg    540 tcttgtatta gccatgtcga ttctcatatg gcagcaaaaa ttgagcattc tctagagctt    600
```

```
ccccttcatc atcgcatacc aaggctagag aacaggcact acatctcagt ctatgaagga    660
gacaaggaaa ggaatgaagt tgtccttgag cttgccaaat tagatttcaa tctgattcaa    720
atcttgcacc aaagagagct gagggacatc acaatgtggt ggaaggagat tgaccttgca    780
gcaaagctac cttttattag agataggttg gtggagtgct actactggat catgggggtc    840 tatttttgaac caatatactc cagggctagg gttttttcca ctaaaatgac aatcttggtc    900
tcagttgtgg acgacatata tgatgtctat gctacggagg atgagcttca actattcact    960
gatgcaatct ataggtggga tgctgatgac attgatcagc tgcctcagta cttgaaagat   1020
gcttttatgg tactctataa cactgtgaag actctagaag aagaacttga accagaagga   1080
aactcttatc gtggatacta cgtaaaagat gcaatgaagg ttttggcaag agattacttt   1140
gtggaacaca atggtataa cagacaaatt gtgccatccg tagaggaata cttgaaaatt   1200
tcttgcatta gtgtggctgt tcatatggct acagttcatt gtattgctgg gatgtatgaa   1260
attgctacca agaggcatt cgaatggttg aagactgaac ccaaacttgt tatcgatgca   1320
tctctgatcg gtcgtcttct tgatgacatg cagtctacct cgtttgagca acaagagggg   1380
cacgtgtcat cagcagtaca gtgttacatg gcccaatatg gagtaacagc agaagaagca   1440
tgtgaaaagc tacgagaaat ggctgcaatt gcttggaaag atgtgaatga agcatgcctt   1500
aggcccacgg tattccctat gcctatcctc ttgccttcta tcaacttggc acgtgtggca   1560
gaagtgatct acctacgtgg agatggatac acgcacgctg ggggtgagac caaaaaacac   1620
atcacggcca tgcttgttaa gccaattgaa gtctga                             1656
```

<210> SEQ ID NO 105
<211> LENGTH: 551
<212> TYPE: PRT
<213> ORGANISM: Drimys winteri

<400> SEQUENCE: 105

```
Met Ala Ser Thr Leu Pro Leu Pro Ala Tyr Gly Asp Ser Glu Val Val
1               5                   10                  15

Arg Arg Ser Ala Gly Phe His Pro Thr Ile Trp Gly Asp His Phe Leu
            20                  25                  30

Ser Tyr Lys Pro Asp Pro Thr Lys Ile Asp Glu Trp Asn Lys Arg Val
        35                  40                  45

Glu Glu Leu Lys Glu Glu Val Lys Lys Ile Leu Ser Asn Ala Lys Gly
    50                  55                  60

Thr Val Glu Glu Leu Asn Leu Leu Asp Asp Leu Val His Leu Gly Ile
65                  70                  75                  80

Ser Tyr His Phe Glu Lys Glu Ile Asp Asp Ala Leu Gln Gln Ile Phe
                85                  90                  95

Asp Thr His Leu Asp Val Phe Pro Lys Asp Leu Tyr Ala Thr Ala
            100                 105                 110

Leu Arg Phe Gly Val Leu Arg Lys Gln Gly His Arg Val Ser Pro Asp
        115                 120                 125

Val Phe Lys Lys Phe Lys Asp Glu Gln Gly Asn Phe Lys Ala Glu Leu
    130                 135                 140

Ser Thr Asp Ala Lys Gly Leu Leu Cys Leu Tyr Asp Val Ala Tyr Leu
145                 150                 155                 160

Ser Thr Arg Gly Glu Asp Ile Leu Asp Glu Ala Ile Pro Phe Thr Lys
                165                 170                 175

Glu His Leu Arg Ser Cys Ile Ser His Val Asp Ser His Met Ala Ala
            180                 185                 190
```

Lys Ile Glu His Ser Leu Glu Leu Pro Leu His His Arg Ile Pro Arg
          195                 200                 205

Leu Glu Asn Arg His Tyr Ile Ser Val Tyr Glu Gly Asp Lys Glu Arg
          210                 215                 220

Asn Glu Val Val Leu Glu Leu Ala Lys Leu Asp Phe Asn Leu Ile Gln
225                 230                 235                 240

Ile Leu His Gln Arg Glu Leu Arg Asp Ile Thr Met Trp Trp Lys Glu
                245                 250                 255

Ile Asp Leu Ala Ala Lys Leu Pro Phe Ile Arg Asp Arg Leu Val Glu
                260                 265                 270

Cys Tyr Tyr Trp Ile Met Gly Val Tyr Phe Glu Pro Ile Tyr Ser Arg
                275                 280                 285

Ala Arg Val Phe Ser Thr Lys Met Thr Ile Leu Val Ser Val Val Asp
                290                 295                 300

Asp Ile Tyr Asp Val Tyr Ala Thr Glu Asp Glu Leu Gln Leu Phe Thr
305                 310                 315                 320

Asp Ala Ile Tyr Arg Trp Asp Ala Asp Ile Asp Gln Leu Pro Gln
                325                 330                 335

Tyr Leu Lys Asp Ala Phe Met Val Leu Tyr Asn Thr Val Lys Thr Leu
                340                 345                 350

Glu Glu Glu Leu Glu Pro Glu Gly Asn Ser Tyr Arg Gly Tyr Tyr Val
                355                 360                 365

Lys Asp Ala Met Lys Val Leu Ala Arg Asp Tyr Phe Val Glu His Lys
                370                 375                 380

Trp Tyr Asn Arg Gln Ile Val Pro Ser Val Glu Tyr Leu Lys Ile
385                 390                 395                 400

Ser Cys Ile Ser Val Ala Val His Met Ala Thr Val His Cys Ile Ala
                405                 410                 415

Gly Met Tyr Glu Ile Ala Thr Lys Glu Ala Phe Glu Trp Leu Lys Thr
                420                 425                 430

Glu Pro Lys Leu Val Ile Asp Ala Ser Leu Ile Gly Arg Leu Leu Asp
                435                 440                 445

Asp Met Gln Ser Thr Ser Phe Glu Gln Gln Arg Gly His Val Ser Ser
                450                 455                 460

Ala Val Gln Cys Tyr Met Ala Gln Tyr Gly Val Thr Ala Glu Ala
465                 470                 475                 480

Cys Glu Lys Leu Arg Glu Met Ala Ala Ile Ala Trp Lys Asp Val Asn
                485                 490                 495

Glu Ala Cys Leu Arg Pro Thr Val Phe Pro Met Pro Ile Leu Leu Pro
                500                 505                 510

Ser Ile Asn Leu Ala Arg Val Ala Glu Val Ile Tyr Leu Arg Gly Asp
                515                 520                 525

Gly Tyr Thr His Ala Gly Gly Glu Thr Lys Lys His Ile Thr Ala Met
                530                 535                 540

Leu Val Lys Pro Ile Glu Val
545                 550

<210> SEQ ID NO 106
<211> LENGTH: 1656
<212> TYPE: DNA
<213> ORGANISM: Artificial Sequence
<220> FEATURE:
<223> OTHER INFORMATION: Codon optimized DNA sequence of SCH51-3228-11

<400> SEQUENCE:

```
atggcatcta ctcttccact gccggcttat ggtgattctg aggttgttcg tcgttccgcg      60
ggttttcacc ctaccatctg gggcgatcac tttctgtcct ataagccaga cccgaccaag     120
attgacgagt ggaataagcg tgtcgaggaa ctgaaagaag aagtgaaaaa gatcctgtcc     180
aacgcaaaag gtactgtcga ggagctgaat ctgctggatg acctggtgca tctgggcatc     240
agctatcact tcgaaaagga aattgacgac gctttgcagc aaattttga tacgcacctg      300 gacgtctttc cgaaagatga cctgtatgcg accgcgctgc gctttggtgt gctgcgtaaa     360
cagggtcatc gcgtgtctcc tgatgtgttc aagaaattta agatgaaca gggcaatttc      420 aaggccgagt tgagcacgga cgccaaaggt ttgctctgcc tgtacgacgt tgcatatctg     480
agcacccgtg gtgaagatat cctggacgaa gcgattccgt tcaccaagga acatctgcgc     540
tcgtgcattt cccatgtaga tagccacatg gcggccaaga tcgagcacag cctggagctg     600
cctttgcacc atcgtattcc gcgcctggag aatcgccatt acattagcgt ctatgagggt     660
gacaaagagc gcaacgaagt cgtgttagag ctggcgaagc tggacttcaa cctgattcaa     720
attctgcatc aacgcgagct gcgcgacatt accatgtggt ggaaagagat tgatctggca     780
gcgaagctgc cgttcatccg cgatcgtctg gttgagtgct actactggat catgggcgtc     840
tacttcgagc cgatctacag ccgcgctcgt gtgttttcga cgaagatgac catcctggtt     900
agcgttgttg atgacattta tgacgtttac gcgaccgaag atgaactgca gctgtttacg     960
gacgcaatct accgttggga cgcggatgat atcgaccagc tgccgcaata cttgaaagat    1020
gcgttcatgg ttttgtacaa caccgtcaaa acgctggaag aagaactgga gccggaaggc    1080
aacagctacc gtggttacta tgttaaagat gcgatgaaag ttctggcgcg cgactacttc    1140
gtcgagcaca gtggtataaa ccgtcagatt gtgccgagcg tcgaggaata cctgaagatt    1200
agctgtatca gcgttgccgt tcacatggca acggtgcact gcatcgccgg tatgtacgag    1260
attgcgacga aagaagcctt cgaatggttg aaaaccgagc cgaagctggt tatcgacgcc    1320
agcctgatcg gtcgtttgct ggacgacatg caaagcacga gcttcgagca gcagcgcggc    1380
catgtgagca gcgctgttca gtgttatatg gcgcaatatg gcgtgaccgc agaagaagcg    1440
tgcgagaagc tgcgtgagat ggcagcaatt gcgtggaaag atgtgaatga agcctgtctg    1500
cgtccgactg tgtttccgat gccgatcctg ctgccgagca ttaacctggc gcgtgtggca    1560
gaggtcatct atctgcgtgg tgacggttac acccacgcgg tggcgaaaac caagaaacat    1620
atcaccgcaa tgctggttaa gccgattgaa gtgtaa                              1656
```

<210> SEQ ID NO 107
<211> LENGTH: 1677
<212> TYPE: DNA
<213> ORGANISM: Drimys winteri
<220> FEATURE:
<221> NAME/KEY: misc_feature
<222> LOCATION: (1)..(1677)
<223> OTHER INFORMATION: SCH51_998_28 wild type DNA sequence

<400> SEQUENCE: 107

```
atggatctta gtacttcacc tgttctttct tcctcccccc ttccggtgga agacggaaaa      60
aatccggccg ttcgccgttc agctggattt caccccagta tttggggtga tcatttcctc    120
tcctacactg aagatcacaa gaagctggat gcatggagcg aaaggactca agtgttgaag    180
gaagaggtga ggagaatttt aatcaatgcc aaggggtcac tagaagagtt ggatttgttg    240
gatgcaatcc aacgccttgg ggtgaaatat cactttgaga aagagattga gaggcatta    300
```

```
caccatattt atgttgcaga aactcatgtt tctactgatg acttatattc cgtttctctc    360
cggtttcgac ttcttagaca acaagggtac aatgtatctg ctgatgtatt taaaaagttc    420
aaagatgaga ggggcaactt caaggcaagc ttaagtactg atgccagggg gttgctaagc    480
ttgtatgaag ctgcatttct cagcatacga ggagatgata tcttagatga agccataact    540
ttcacaagag agcagcttaa gtcttctatg acccatgttg atgcccctct tgccaaacaa    600
atagcccatg ccttagaggt accagcgcac aagcgcatac aaagactaga gaacattcgc    660
tacctcacaa tctaccaaga agagaaagga aggaatgatg tgttgcttga gcttgccaag    720
ttggatttca atatcttaca acaattgcat aagaaagaac tgagagacct tacaaagtgg    780
tggaaggaca cagacgttgc aggaaagcta cctttcatca gagataggtt ggtggaatgc    840
tattattgga tcttgggtgt gtattatgag ccagaatact ccagagctag aattttttct    900
accaaaatga caatcatggt ctcagttgtt gatgacatat atgacgtata tgctactgaa    960
gatgagctcc aactattcac tgatgcaatc tataggtggg atctggaggg cctagatcaa   1020
ctcccacagt tcttgaaaga ctgttttctt gtactctatg acaccgtcaa ggaattagaa   1080
gacgaactag aaccggaagg aaaatcctat cgtggatact atgtaaagga tgcgatgaag   1140
gttttggcta gagattactt cgttgagcac aaatggtata cagaaacat agtgccaagt   1200
gtagaagaat atctccgtgt ttcttgcatc agtgttgcag tccatatggc taacgtccat   1260
tgctgtgctg ggatgggaga tgtaatgagc aaagaggcat cgaatggtt gaagagtgaa   1320
ccaaaggttg taatggatgc atcactaatt ggccgactgc tcgatgacat gcagtccacc   1380
gagtttgagc aaaagagagg ccatgttgca tcggctgtcc aatgttacat gaatgagtat   1440
ggagtgactt acaaagaagc gtgtgaaaag ctgcatgaaa tggctgccct tgcatggaaa   1500
gacgtaaacc aggcttgcct taaaccaact gttttccctc tccctgtatt tatgcctgca   1560
atcaaccttg cgcgagtggc tgaagtcatc taccttcgtg gagatgggta tactcattca   1620
ggaggagaga ctaaagaaaa tatcacgttg atgcttgtca atccaatctc tgtgtga     1677
```

<210> SEQ ID NO 108
<211> LENGTH: 558
<212> TYPE: PRT
<213> ORGANISM: Drimys winteri

<400> SEQUENCE: 108

```
Met Asp Leu Ser Thr Ser Pro Val Leu Ser Ser Pro Leu Pro Val
1               5                   10                  15

Glu Asp Gly Lys Asn Pro Ala Val Arg Arg Ser Ala Gly Phe His Pro
            20                  25                  30

Ser Ile Trp Gly Asp His Phe Leu Ser Tyr Thr Glu Asp His Lys Lys
        35                  40                  45

Leu Asp Ala Trp Ser Glu Arg Thr Gln Val Leu Lys Glu Glu Val Arg
    50                  55                  60

Arg Ile Leu Ile Asn Ala Lys Gly Ser Leu Glu Leu Asp Leu Leu
65                  70                  75                  80

Asp Ala Ile Gln Arg Leu Gly Val Lys Tyr His Phe Glu Lys Glu Ile
                85                  90                  95

Glu Glu Ala Leu His His Ile Tyr Val Ala Glu Thr His Val Ser Thr
            100                 105                 110

Asp Asp Leu Tyr Ser Val Ser Leu Arg Phe Arg Leu Leu Arg Gln Gln
        115                 120                 125

Gly Tyr Asn Val Ser Ala Asp Val Phe Lys Lys Phe Lys Asp Glu Arg
```

```
            130                 135                 140
Gly Asn Phe Lys Ala Ser Leu Ser Thr Asp Ala Arg Gly Leu Leu Ser
145                 150                 155                 160

Leu Tyr Glu Ala Ala Phe Leu Ser Ile Arg Gly Asp Asp Ile Leu Asp
                165                 170                 175

Glu Ala Ile Thr Phe Thr Arg Glu Gln Leu Lys Ser Ser Met Thr His
            180                 185                 190

Val Asp Ala Pro Leu Ala Lys Gln Ile Ala His Ala Leu Glu Val Pro
        195                 200                 205

Ala His Lys Arg Ile Gln Arg Leu Glu Asn Ile Arg Tyr Leu Thr Ile
    210                 215                 220

Tyr Gln Glu Glu Lys Gly Arg Asn Asp Val Leu Leu Glu Leu Ala Lys
225                 230                 235                 240

Leu Asp Phe Asn Ile Leu Gln Gln Leu His Lys Lys Glu Leu Arg Asp
                245                 250                 255

Leu Thr Lys Trp Trp Lys Asp Thr Asp Val Ala Gly Lys Leu Pro Phe
            260                 265                 270

Ile Arg Asp Arg Leu Val Glu Cys Tyr Tyr Trp Ile Leu Gly Val Tyr
        275                 280                 285

Tyr Glu Pro Glu Tyr Ser Arg Ala Arg Ile Phe Ser Thr Lys Met Thr
    290                 295                 300

Ile Met Val Ser Val Val Asp Asp Ile Tyr Asp Val Tyr Ala Thr Glu
305                 310                 315                 320

Asp Glu Leu Gln Leu Phe Thr Asp Ala Ile Tyr Arg Trp Asp Leu Glu
                325                 330                 335

Gly Leu Asp Gln Leu Pro Gln Phe Leu Lys Asp Cys Phe Leu Val Leu
            340                 345                 350

Tyr Asp Thr Val Lys Glu Leu Glu Asp Glu Leu Glu Pro Glu Gly Lys
        355                 360                 365

Ser Tyr Arg Gly Tyr Tyr Val Lys Asp Ala Met Lys Val Leu Ala Arg
    370                 375                 380

Asp Tyr Phe Val Glu His Lys Trp Tyr Asn Arg Asn Ile Val Pro Ser
385                 390                 395                 400

Val Glu Glu Tyr Leu Arg Val Ser Cys Ile Ser Val Ala Val His Met
                405                 410                 415

Ala Asn Val His Cys Cys Ala Gly Met Gly Asp Val Met Ser Lys Glu
            420                 425                 430

Ala Phe Glu Trp Leu Lys Ser Glu Pro Lys Val Val Met Asp Ala Ser
        435                 440                 445

Leu Ile Gly Arg Leu Leu Asp Asp Met Gln Ser Thr Glu Phe Glu Gln
    450                 455                 460

Lys Arg Gly His Val Ala Ser Ala Val Gln Cys Tyr Met Asn Glu Tyr
465                 470                 475                 480

Gly Val Thr Tyr Lys Glu Ala Cys Glu Lys Leu His Glu Met Ala Ala
                485                 490                 495

Leu Ala Trp Lys Asp Val Asn Gln Ala Cys Leu Lys Pro Thr Val Phe
            500                 505                 510

Pro Leu Pro Val Phe Met Pro Ala Ile Asn Leu Ala Arg Val Ala Glu
        515                 520                 525

Val Ile Tyr Leu Arg Gly Asp Gly Tyr Thr His Ser Gly Gly Glu Thr
    530                 535                 540

Lys Glu Asn Ile Thr Leu Met Leu Val Asn Pro Ile Ser Val
545                 550                 555
```

<210> SEQ ID NO 109
<211> LENGTH: 1677
<212> TYPE: DNA
<213> ORGANISM: Artificial Sequence
<220> FEATURE:
<223> OTHER INFORMATION: Codon optimized DNA sequence of SCH51-998-28

<400> SEQUENCE: 109

```
atggatctga gcaccagtcc ggttctgagc agctcaccgc tgccggttga agatggtaaa      60
aatccggcag ttcgtcgtag cgcaggtttt catccgagca tttggggtga tcattttctg     120
agctataccg aggatcacaa aaaactggat gcatggtcag aacgtaccca ggttctgaaa     180
gaagaagtgc gtcgtattct gattaatgca aaaggtagcc tggaagaact ggatctgctg     240
gatgcaattc agcgtctggg tgttaaatat cactttgaga agaaatcga agaagccctg     300
catcatattt atgttgcaga aacccatgtg tcaaccgatg atctgtatag cgttagcctg     360
cgttttcgtc tgctgcgtca gcagggttat aatgttagcg cagatgtgtt caaaaaattc     420
aaagatgaac gcggtaactt caaagcaagc ctgagcaccg atgcacgtgg tctgctgagc     480
ctgtatgaag cagcatttct gagcattcgt ggtgatgata ttctggatga agcaattacc     540
tttacccgtg aacagctgaa agcagcatg acccatgttg atgcaccgct ggcaaaacaa     600
attgcacatg cactggaagt tccggcacat aaacgtattc agcgcctgga aaatattcgc     660
tatctgacca tttaccaaga agagaaaggt cgtaacgatg ttctgctgga actggccaaa     720
ctggatttta acattctgca gcagctgcat aaaaaagaac tgcgtgatct gaccaaatgg     780
tggaaagata ccgatgttgc aggtaaactg ccgtttattc gtgatcgtct ggttgaatgc     840
tattattgga ttctgggcgt ttattatgag ccggaatata gccgtgcacg tatttttagc     900
accaaaatga ccattatggt tagcgtggtg atgacatct atgatgttta tgcaaccgaa     960
gatgaactgc agctgtttac cgatgcaatt tatcgttggg atctggaagg tctggatcag    1020
ctgccgcagt tcctgaaaga ttgttttctg gttctgtatg ataccgtgaa agaactggaa    1080
gatgagctgg aaccggaagg taaaagctat cgtggttatt atgttaaaga tgccatgaaa    1140
gttctggcac gcgattattt tgttgagcac aaatggtata ccgcaatat tgttccgagc    1200
gtggaagaat atctgcgtgt tagctgtatt agcgttgcag ttcacatggc aaatgttcat    1260
tgttgtgcag gtatgggtga tgtgatgagc aagaagcat ttgaatggct gaaaagtgaa    1320
ccgaaagttg ttatggatgc cagcctgatt ggtcgcctgc tggacgatat gcagagcacc    1380
gaatttgaac agaaacgtgg tcatgttgca agcgcagttc agtgtatat gaatgaatat    1440
ggcgtgacct ataaagaggc atgcgaaaaa ctgcatgaaa tggcagcact ggcatggaaa    1500
gatgttaatc aggcatgtct gaaaccgacc gttttccgc tgcctgtttt tatgcctgca    1560
attaatctgg cacgtgttgc cgaagttatt acctgcgtg gggatggtta tcccatagc    1620
ggtggtgaaa ccaaagaaaa cattaccctg atgctggtta atccgattag cgtttaa      1677
```

<210> SEQ ID NO 110
<211> LENGTH: 1680
<212> TYPE: DNA
<213> ORGANISM: Drimys lanceolata

<400> SEQUENCE: 110

```
atggatgttc taattccctc ccctgtggct tccactctcc ctctgcccga agatggaaac      60
ttggacgtcg ttcgcagatc cgccgggttt catccgacgg tctggggcga tcacttcctc     120
```

-continued

| | |
|---|---|
| gcttactcgc cgatccaac caaaatagat gcttggacta aaagagttga agagctgaag | 180 |
| caagaagtga agaggattct aagcaatgtg aaagggtcac tggaagagct gaacttgctt | 240 |
| gatgctatcc aacaccttgg gattggttat cattttgaga aagagattga tgatgcttta | 300 |
| caactaatct tgattccca tattgatgct tttcctactg atgatctata tgtggctgcc | 360 |
| ctccgattta gcctactaag gcgacaaggg cactgtgttt cttcagatgt attcaaaaaa | 420 |
| ttcaaagatg agcaggggaa tttcaaggca gagctgagca ccgatgcgaa aggtttgctg | 480 |
| agtctctatg acgcggcgta tctcagtgta agaggggaag atatattgga tgaggccatt | 540 |
| cctttcacta gggagcacct taggacttgt attagccatg tagattctca tttggcagca | 600 |
| aaaattgagc attctctaga gcttccctg catcatcgca taccaaggct agagaacagg | 660 |
| cactacatct cagtgtacga aggagagaag gaaggaatg aagttgtact agagcttgcc | 720 |
| aaattagatt tcaatctgat tcaaatcttg caccaaagag agctgaggga catcacaacg | 780 |
| tggtggaatg agattgacct cgcagcaaag ctaccattta ttagggatag gttggtggag | 840 |
| tgctactatt ggatcatggg tgtctatttt gaaccaatat tctcaagggc tagagttttt | 900 |
| tcgaccaaaa tgacaatttt ggtctcagtt gtcgacgaca tatgatgt ctacgctaca | 960 |
| gaggatgagc tccaactttt cactgacgca atctataggt gggatgccga ggacattgag | 1020 |
| cagcttccac agtacttgaa agattctttt cttgtactct ataacaccgt gaaggactta | 1080 |
| gaagaggagc tgaaaccaga aggaaactca tatcgtggag actatgtaaa agatgcgatg | 1140 |
| aaggttttgg caagagatta ctttgtggag cacaaatggt ataacagaaa aattgtaccg | 1200 |
| tcagtagagg actacctacg aatttcttgc attagtgttg ccgttcatat ggctacagtt | 1260 |
| cattgttgtg ctgggatgga tgaaattgca accaaagagg cattcgaatg gttgaagacc | 1320 |
| gaacctaaac ttgttataga tgcatcactg attgggcgtc tcctcgatga catgcagtcc | 1380 |
| acctcgtttg agcaacagag aggtcatgtg tcatcggcgg tacagtgtta catgatccaa | 1440 |
| tatggcgtat cacacgaaga agcgtgtgag aagttgacag aaatggctgc aattgcatgg | 1500 |
| aaagatgtaa accaagcatg ccttaggccc actgttttcc caatgcctat tcttctgcct | 1560 |
| tcaatcaacc ttgcacgtgt ggcagaagtc atctacctgc gcggagatgg atatacacat | 1620 |
| gctggtggtg agaccaaaaa acatatcacg gccatgcttg ttgaaccaat ccaagtctga | 1680 |

<210> SEQ ID NO 111
<211> LENGTH: 559
<212> TYPE: PRT
<213> ORGANISM: Drimys lanceolata

<400> SEQUENCE: 111

Met Asp Val Leu Ile Pro Ser Pro Val Ala Ser Thr Leu Pro Leu Pro
1               5                   10                  15

Glu Asp Gly Asn Leu Asp Val Val Arg Arg Ser Ala Gly Phe His Pro
                20                  25                  30

Thr Val Trp Gly Asp His Phe Leu Ala Tyr Ser Pro Asp Pro Thr Lys
            35                  40                  45

Ile Asp Ala Trp Thr Lys Arg Val Glu Glu Leu Lys Gln Glu Val Lys
        50                  55                  60

Arg Ile Leu Ser Asn Val Lys Gly Ser Leu Glu Leu Asn Leu Leu
65                  70                  75                  80

Asp Ala Ile Gln His Leu Gly Ile Gly Tyr His Phe Glu Lys Glu Ile
                85                  90                  95

Asp Asp Ala Leu Gln Leu Ile Phe Asp Ser His Ile Asp Ala Phe Pro

-continued

```
                100             105             110
Thr Asp Asp Leu Tyr Val Ala Ala Leu Arg Phe Ser Leu Leu Arg Arg
            115                 120             125
Gln Gly His Cys Val Ser Ser Asp Val Phe Lys Lys Phe Lys Asp Glu
        130                 135             140
Gln Gly Asn Phe Lys Ala Glu Leu Ser Thr Asp Ala Lys Gly Leu Leu
145                 150             155                 160
Ser Leu Tyr Asp Ala Ala Tyr Leu Ser Val Arg Gly Glu Asp Ile Leu
            165             170                 175
Asp Glu Ala Ile Pro Phe Thr Arg Glu His Leu Arg Thr Cys Ile Ser
            180             185                 190
His Val Asp Ser His Leu Ala Ala Lys Ile Glu His Ser Leu Glu Leu
        195             200             205
Pro Leu His His Arg Ile Pro Arg Leu Glu Asn Arg His Tyr Ile Ser
        210             215                 220
Val Tyr Glu Gly Glu Lys Glu Arg Asn Glu Val Val Leu Glu Leu Ala
225             230             235                 240
Lys Leu Asp Phe Asn Leu Ile Gln Ile Leu His Gln Arg Glu Leu Arg
            245             250                 255
Asp Ile Thr Thr Trp Trp Asn Glu Ile Asp Leu Ala Ala Lys Leu Pro
            260             265                 270
Phe Ile Arg Asp Arg Leu Val Glu Cys Tyr Tyr Trp Ile Met Gly Val
            275             280             285
Tyr Phe Glu Pro Ile Phe Ser Arg Ala Arg Val Phe Ser Thr Lys Met
        290             295             300
Thr Ile Leu Val Ser Val Val Asp Ile Tyr Asp Val Tyr Ala Thr
305             310             315                 320
Glu Asp Glu Leu Gln Leu Phe Thr Asp Ala Ile Tyr Arg Trp Asp Ala
            325             330                 335
Glu Asp Ile Glu Gln Leu Pro Gln Tyr Leu Lys Asp Ser Phe Leu Val
            340             345             350
Leu Tyr Asn Thr Val Lys Asp Leu Glu Glu Glu Leu Lys Pro Glu Gly
            355             360             365
Asn Ser Tyr Arg Gly Asp Tyr Val Lys Asp Ala Met Lys Val Leu Ala
        370             375             380
Arg Asp Tyr Phe Val Glu His Lys Trp Tyr Asn Arg Lys Ile Val Pro
385             390             395                 400
Ser Val Glu Asp Tyr Leu Arg Ile Ser Cys Ile Ser Val Ala Val His
            405             410                 415
Met Ala Thr Val His Cys Cys Ala Gly Met Asp Glu Ile Ala Thr Lys
            420             425             430
Glu Ala Phe Glu Trp Leu Lys Thr Glu Pro Lys Leu Val Ile Asp Ala
            435             440             445
Ser Leu Ile Gly Arg Leu Leu Asp Asp Met Gln Ser Thr Ser Phe Glu
            450             455             460
Gln Gln Arg Gly His Val Ser Ser Ala Val Gln Cys Tyr Met Ile Gln
465             470             475                 480
Tyr Gly Val Ser His Glu Glu Ala Cys Glu Lys Leu Thr Glu Met Ala
            485             490                 495
Ala Ile Ala Trp Lys Asp Val Asn Gln Ala Cys Leu Arg Pro Thr Val
            500             505                 510
Phe Pro Met Pro Ile Leu Leu Pro Ser Ile Asn Leu Ala Arg Val Ala
            515             520                 525
```

```
Glu Val Ile Tyr Leu Arg Gly Asp Gly Tyr Thr His Ala Gly Gly Glu
    530                 535                 540

Thr Lys Lys His Ile Thr Ala Met Leu Val Glu Pro Ile Gln Val
545                 550                 555
```

<210> SEQ ID NO 112
<211> LENGTH: 1680
<212> TYPE: DNA
<213> ORGANISM: Artificial Sequence
<220> FEATURE:
<223> OTHER INFORMATION: Codon optimized DNA sequence of SCH51-13163-6

<400> SEQUENCE: 112

```
atggatgttc tgattccgag tccggttgca agcaccctgc cgctgccgga gatggtaat      60
ctggatgttg ttcgtcgtag cgcaggtttt catccgaccg tttggggtga tcattttctg    120
gcatatagtc cggatccgac caaaattgat gcatggacca aacgtgttga ggaactgaaa    180
caagaagtga aacgtattct gagcaatgtg aaaggtagcc tggaagaact gaatctgctg    240
gatgcaattc agcatctggg tattggttat cacttcgaga agaaattga tgatgcactg     300
cagctgatct tgatagcca tattgatgcc tttccgaccg atgatctgta tgttgcagca    360
ctgcgtttta gcctgctgcg tcgtcagggt cattgtgtta gcagtgatgt tttcaaaaaa    420
ttcaaagacg agcagggcaa cttttaaagca gaactgagca ccgatgcaaa aggtctgctg    480
agcctgtatg atgccgcata tctgagcgtt cgtggtgaag atattctgga tgaagcaatt    540
ccgtttaccc gtgaacatct gcgtacctgt attagccatg tggatagcca tctggcagca    600
aaaattgaac atagtctgga actgcctctg catcatcgta ttccgcgtct ggaaaatcgt    660
cactatatta gcgtttatga aggcgaaaaa gaacgcaatg aagttgtgct ggaactggca    720
aaactggatt ttaacctgat tcagattctg catcagcgtg aactgcgtga tattaccacc    780
tggtggaatg aaattgacct ggcagccaaa ctgccgttta ttcgtgatcg tctggttgaa    840
tgctattatt ggattatggg cgtgtatttt gaaccgattt ttagccgtgc acgtgtgttt    900
agcaccaaaa tgaccattct ggttagcgtg gtggatgata tctatgatgt ttatgcaacc    960
gaagatgagc tgcaactgtt taccgatgcc atttatcgtt gggatgcaga agatattgaa   1020
cagctgcctc agtatctgaa agatagcttt ctggttctgt acaacaccgt gaaagatctg   1080
gaagaagaac tgaaaccgga aggtaatagc tatcgtggtg attatgttaa agacgccatg   1140
aaagttctgg cacgcgatta ttttgttgag cacaaatggt ataaccgcaa aattgttccg   1200
agcgtggaag attatctgcg tattagctgc attagcgttg cagttcacat ggcaaccgtt   1260
cattgttgtg caggtatgga tgaaattgca accaaagaag catttgagtg gctgaaaacc   1320
gaaccgaaac tggttattga tgcaagcctg attggtcgtc tgctggacga tatgcagtca   1380
accagctttg aacagcagcg tggtcatgtt agcagcgcag ttcagtgtta tatgattcag   1440
tatggtgtta gccatgaaga agcatgcgaa aaactgaccg aaatggcagc aattgcatgg   1500
aaagatgtta tcaggcatg tctgcgtccg accgtgtttc ctatgccgat tctgctgccg   1560
agcattaatc tggcacgtgt tgccgaagtt atctatctgc gtggtgatgg ttataccat    1620
gccggtggtg aaaccaaaaa acatattacc gcaatgctgg tagaaccgat tcaggtttaa   1680
```

<210> SEQ ID NO 113
<211> LENGTH: 1671
<212> TYPE: DNA
<213> ORGANISM: Valeriana amurensis

<400> SEQUENCE: 113

```
atgtctactg cattaaacag tgagcatgaa actgttcgtc cattagcaag ttttaaaccg      60
agtacatggg gcgatctttt catctcttat tctgaagata gccagcttaa ggaagtatat     120
ggtaaagagc acgaatgtct gaaacaacaa gtgaaaacaa tgttgttgga tctgacaaat     180
tatagaattt cggagaaaat cgctttcata aatacgttgg agagattagg ggtatctcat     240
gagtttgaga atgagattga agggctgctt catcaaatgt ttgatgctca ttctaaattc     300
caagatggca ttcaacactt tgatttgttc acattgggga tttactttag gattctcagg     360
caacatggct atagaatctc ttgtgatgtt tcaacaagt tgaaagatag caacaatgaa     420
ttcaagaagg aacttaaaga ggacgctatt ggtttgctaa gttgtacga agcgacacaa     480
gtaagagcac acgctgaaga aattttagac gaagccctca ttttcacaaa ggctcaactt     540
gaatccatag ccgcaacctc gagcttaagc ccatttgtcg agaagcaaat tactcatgct     600
ttggtccaag ctctccacaa aggaatccca agagtcgaat cgcgccattt catctctgtt     660
tatgaagaag atcctgacaa aatgatttg ttgttgaggt tctcaaagat tgattacaat     720
cttgtacaaa tgcttcacaa gcaagaattg tgccatatct caaagtggtg gagagattcg     780
gagctcgaaa caaaactaac ttatgtgagg aatagagtgg cggaatgctt tttatggact     840
ctttgtgtgt accacgaacc aaagtactct ccggctcggc ttctgttagg caaactcata     900
aatatcatat cttgcactga tgacacatat gatgcgtatg gtacattaga ggaagttcag     960
atctttacag atgtcataca aaggttggat aggagttcta tggagcagct gccggattac    1020
atgaaaatcc tctacaaagc tgtccttgat cttttttgacg aagtagaagt tcagctatcg    1080
aaccatgaaa ctaataatac ttatcgtatg gcttatgcga aggaagagtt aaaagctatc    1140
gccaagtgct acgaaaagga gcacatatgg ttcagaaaat gtcacgtgcc cccattcgaa    1200
gaatatctag agaatgcggt agtgtcaatc ggtaatcgtt tggccgtacc tttttctttt    1260
ctgggaatgg atcaagtagc aggtgttgaa gcgttcgagt gggccaaaac tgatcccaaa    1320
atggtaaaat cgtgcggtaa agtcttacga cttgttgacg atgtaatgag ccacgaggag    1380
gaagatgtaa gaggacacgt ggcaacggga gtcgaatgct acatgaaaga acacggagtg    1440
agtagggaag aggccatcgt ggagttctac aagagggtcg agtacgcgtg gaaggatgtg    1500
aacgaggaat ttataacgcc gaaccatctg catatcgacc tcctcaaccg cgttcttaac    1560
cttacaagaa ttgcagacgt tgtttacaag tttgaagacg gctacacgca tcccgagaag    1620
actctgaaac atcatatcat ggcgttgttc gtcgaccccg tccccatata g              1671
```

<210> SEQ ID NO 114
<211> LENGTH: 556
<212> TYPE: PRT
<213> ORGANISM: Valeriana amurensis

<400> SEQUENCE: 114

```
Met Ser Thr Ala Leu Asn Ser Glu His Glu Thr Val Arg Pro Leu Ala
1               5                   10                  15

Ser Phe Lys Pro Ser Thr Trp Gly Asp Leu Phe Ile Ser Tyr Ser Glu
            20                  25                  30

Asp Ser Gln Leu Lys Glu Val Tyr Gly Lys Glu His Glu Cys Leu Lys
        35                  40                  45

Gln Gln Val Lys Thr Met Leu Leu Asp Leu Thr Asn Tyr Arg Ile Ser
    50                  55                  60

Glu Lys Ile Ala Phe Ile Asn Thr Leu Glu Arg Leu Gly Val Ser His
```

```
            65                  70                  75                  80
Glu Phe Glu Asn Glu Ile Glu Gly Leu Leu His Gln Met Phe Asp Ala
                85                  90                  95

His Ser Lys Phe Gln Asp Gly Ile Gln His Phe Asp Leu Phe Thr Leu
            100                 105                 110

Gly Ile Tyr Phe Arg Ile Leu Arg Gln His Gly Tyr Arg Ile Ser Cys
            115                 120                 125

Asp Val Phe Asn Lys Leu Lys Asp Ser Asn Glu Phe Lys Lys Glu
        130                 135                 140

Leu Lys Glu Asp Ala Ile Gly Leu Leu Ser Leu Tyr Glu Ala Thr Gln
145                 150                 155                 160

Val Arg Ala His Ala Glu Glu Ile Leu Asp Glu Ala Leu Ile Phe Thr
                165                 170                 175

Lys Ala Gln Leu Glu Ser Ile Ala Ala Thr Ser Ser Leu Ser Pro Phe
            180                 185                 190

Val Glu Lys Gln Ile Thr His Ala Leu Val Gln Ala Leu His Lys Gly
            195                 200                 205

Ile Pro Arg Val Glu Ser Arg His Phe Ile Ser Val Tyr Glu Glu Asp
        210                 215                 220

Pro Asp Lys Asn Asp Leu Leu Arg Phe Ser Lys Ile Asp Tyr Asn
225                 230                 235                 240

Leu Val Gln Met Leu His Lys Gln Glu Leu Cys His Ile Ser Lys Trp
                245                 250                 255

Trp Arg Asp Ser Glu Leu Glu Thr Lys Leu Thr Tyr Val Arg Asn Arg
            260                 265                 270

Val Ala Glu Cys Phe Leu Trp Thr Leu Cys Val Tyr His Glu Pro Lys
            275                 280                 285

Tyr Ser Pro Ala Arg Leu Leu Gly Lys Leu Ile Asn Ile Ile Ser
        290                 295                 300

Cys Thr Asp Asp Thr Tyr Asp Ala Tyr Gly Thr Leu Glu Glu Val Gln
305                 310                 315                 320

Ile Phe Thr Asp Val Ile Gln Arg Leu Asp Arg Ser Ser Met Glu Gln
                325                 330                 335

Leu Pro Asp Tyr Met Lys Ile Leu Tyr Lys Ala Val Leu Asp Leu Phe
            340                 345                 350

Asp Glu Val Glu Val Gln Leu Ser Asn His Glu Thr Asn Asn Thr Tyr
            355                 360                 365

Arg Met Ala Tyr Ala Lys Glu Glu Leu Lys Ala Ile Ala Lys Cys Tyr
        370                 375                 380

Glu Lys Glu His Ile Trp Phe Arg Lys Cys His Val Pro Pro Phe Glu
385                 390                 395                 400

Glu Tyr Leu Glu Asn Ala Val Val Ser Ile Gly Asn Arg Leu Ala Val
                405                 410                 415

Pro Phe Ser Phe Leu Gly Met Asp Gln Val Ala Gly Val Glu Ala Phe
            420                 425                 430

Glu Trp Ala Lys Thr Asp Pro Lys Met Val Lys Ser Cys Gly Lys Val
            435                 440                 445

Leu Arg Leu Val Asp Asp Val Met Ser His Glu Glu Asp Val Arg
        450                 455                 460

Gly His Val Ala Thr Gly Val Glu Cys Tyr Met Lys Glu His Gly Val
465                 470                 475                 480

Ser Arg Glu Glu Ala Ile Val Glu Phe Tyr Lys Arg Val Glu Tyr Ala
                485                 490                 495
```

Trp Lys Asp Val Asn Glu Glu Phe Ile Thr Pro Asn His Leu His Ile
            500                 505                 510

Asp Leu Leu Asn Arg Val Leu Asn Leu Thr Arg Ile Ala Asp Val Val
        515                 520                 525

Tyr Lys Phe Glu Asp Gly Tyr Thr His Pro Glu Lys Thr Leu Lys His
    530                 535                 540

His Ile Met Ala Leu Phe Val Asp Pro Val Pro Ile
545                 550                 555

<210> SEQ ID NO 115
<211> LENGTH: 1671
<212> TYPE: DNA
<213> ORGANISM: Artificial Sequence
<220> FEATURE:
<223> OTHER INFORMATION: Codon optimised sequence

<400> SEQUENCE: 115

```
atgagcaccg cgttgaactc cgagcatgaa accgtccgtc cgctggctag ctttaaaccg      60
agcacgtggg gtgacctgtt catcagctac agcgaggaca gccagctgaa agaagtgtat     120
ggtaaagagc atgaatgtct taagcaacaa gttaagacca tgctgctgga cctgacgaat     180
taccgtatca gcgagaagat tgccttcatc aatacgctgg agcgcctggg tgtttctcac     240
gagttcgaga tgaaatcga aggcctcctg catcagatgt tcgacgcgca ctccaagttt      300
caagatggca ttcagcactt tgacctgttt accctgggca tttacttccg tattttgcgc     360
cagcacggtt atcgtatctc gtgcgatgtg tttaacaagc tgaaggactc taataacgaa     420
ttcaagaaag aactgaaaga gatgcaatt ggtctgctgt ctctgtatga agcgacccaa      480
gtgcgtgccc atgcagaaga gatttttggac gaagcgctga tcttcaccaa ggctcagctg     540
gagagcatcg cggcgacgag cagcctgagc ccgtttgtcg agaaacagat acccacgcc      600
ttggtgcaag cgttgcataa aggcatccca cgcgtggaga ccgccacctt cattagcgtg     660
tacgaagagg acccggacaa gaacgatttg ctgctgcgtt tttccaagat tgactacaat     720
ttagttcaaa tgctgcacaa caagagttg tgtcatatta gcaaatggtg gcgtgactcc      780
gagctggaga ctaaactgac ctacgtccgt aatcgcgtgg cagagtgttt tctgtggacc     840
ctgtgtgttt accacgagcc gaagtatagc ccggcacgtc tgctgctggg taaactgatc     900
aacatcattt cttgcacgga cgacacctat gatgcatacg gtacgctgga agaagtccaa     960
atctttaccg acgtgatcca gcgtttggac cgtagctcga tggagcagct gccggattac    1020
atgaagattc tgtataaagc tgttctggat ctgttcgatg aagttgaggt tcagctgagc    1080
aaccatgaga ctaacaatac ctaccgcatg gcgtacgcaa agaagaact gaaggctatt     1140
gcgaaatgct acgagaaaga gcacatctgg tttcgcaagt gtcatgttcc accgttcgaa    1200
gagtatctgg agaacgccgt ggtgagcatc ggtaatcgtc tggcggtccc gttcagcttc    1260
ttgggtatgg accaggttgc gggcgtcgag gcctttgagt gggcaaagac cgatcctaaa    1320
atggttaaaa gctgcggtaa ggttctgcgc ctggtcgatg atgtcatgag ccatgaagaa    1380
gaagatgtgc gtggtcacgt ggcgacgggc gttgagtgct acatgaaaga gcacggtgtc    1440
agccgtgaag aggcgatcgt tgaattctat aagcgtgtcg agtatgcatg gaaagacgtc    1500
aacgaagagt tcattactcc gaatcacttg cacattgatc tgctgaaccg tgttctgaac    1560
ttaacccgca ttgccgatgt cgtatacaag tttgaagatg gctatccca cccgaaaaag    1620
acgctgaaac accatatcat ggcgctgttc gtggacccgg tgccgatcta a             1671
```

<210> SEQ ID NO 116
<211> LENGTH: 1332
<212> TYPE: DNA
<213> ORGANISM: Dryopteris fragrans
<220> FEATURE:
<221> NAME/KEY: misc_feature
<222> LOCATION: (1)..(1332)
<223> OTHER INFORMATION: DfACT13 native nucleotide sequence

<400> SEQUENCE: 116

```
atggcctgtg gaggcggcgt gaggaatatt gaggtgaagg cgcaggagcc cgttttggtg      60
cagcctttat ctacagcaca aagctctgcc tataatcttc ttacaaaact ggaccagacg     120
ctcgcacaat tggtggtgca gattgtcttt gtcttcgatg tgaaaaaccc cgtaacccgc     180
cgacccacg atggcgccga tcctgccaag cttctgaagg aggctctgag gaaggtcctt      240
gtgcccttct acccgctcgc tgggcgtctt tgcctctcgc ccgatgacgg cagtctgttc     300
attgactgca atgctcaggg ggtttccttt gttgaggcca atgccgacgc ggatatctcc     360
gaactcggcg acttctcgca gcccgatttc gcgactctgg ctcccttgt cttcccctta     420
cctcctatag cttcggatga tggtcctctt ctatctgcgc aggtgaccag attcaagtgt     480
ggaggatttg tgctgggctt cgtattccat cattgtttat ttgatggatt cgcactttcg     540
gaattcctaa atgcgtgggc ggagactgca tgcggcgtgc ctctttctac acctcctgtc     600
ctcgacagaa cttttccgag ggcgcgttct cccttgcaaa tcaagtatcc cacaccgag      660
ttcctggaag tcgaagatgt ctcttttgact caaaatatct ctaacgatgc catcaaccgg     720
tctttctgct ttacttcggc aagtctagag atactcaaga agaaagcctt ggaggatggg     780
gtgctatcaa aatgcactac ttttgaagct ttatctgggc tgatatggag ggcccgaact     840
agagccctgt ggagcgatta cccggagcac aaactaaagg tgctcattgt cgtcgacccg     900
agagcacgtt ttgagcctcg tgtggtgcca aagggtatg tgggcaatgc ggtgcttttt      960
acatgtgctt cgcaagcgc aagggagctg aagaaaaatc ccttgtcaca tgcagtgaag    1020
catgtgcaac atgccatcgg gcgtatgacg gaggagtaca tgttgtcgca aatcgactac    1080
atggagcatc agaaggtatg gtgccccaccg ctaggagcta gtacatcttt catgaccaaa    1140
tggtctaggt tggccttcaa tattctagac tttgggtggg gcaggccgaa gtatgtgggg    1200
ccggccacgt cgctgtcgat ggagacgact acttttgtat cttatggaaa gggcatgagt    1260
gtggtgttgg ctcttcctcc agaagcaatg cgcaaatttg aaaaaatcgt acatccctac    1320
ctcaatccat ga                                                        1332
```

<210> SEQ ID NO 117
<211> LENGTH: 1332
<212> TYPE: DNA
<213> ORGANISM: Artificial Sequence
<220> FEATURE:
<223> OTHER INFORMATION: DfACT13_codon optimized for its expression in
    S. cerevisiae
<220> FEATURE:
<221> NAME/KEY: CDS
<222> LOCATION: (1)..(1332)

<400> SEQUENCE: 117

```
atg gca tgt ggc ggt ggg gtc agg aat atc gaa gtg aag gct caa gag    48
Met Ala Cys Gly Gly Gly Val Arg Asn Ile Glu Val Lys Ala Gln Glu
1               5                   10                  15 cca gtc ttg gtg caa ccg tta agc act gct caa tcg tca gcc tac aat    96
Pro Val Leu Val Gln Pro Leu Ser Thr Ala Gln Ser Ser Ala Tyr Asn
            20                  25                  30
```

```
ttg tta aca aag tta gac cag act ttg gcg caa ttg gtt gtc caa ata    144
Leu Leu Thr Lys Leu Asp Gln Thr Leu Ala Gln Leu Val Val Gln Ile
         35                  40                  45 gtg ttt gtt ttc gat gtg aag aac cct gtg aca aga agg cct cat gat    192
Val Phe Val Phe Asp Val Lys Asn Pro Val Thr Arg Arg Pro His Asp
 50                  55                  60 gga gcc gat cca gct aag tta ttg aaa gag gcc tta agg aaa gta cta    240
Gly Ala Asp Pro Ala Lys Leu Leu Lys Glu Ala Leu Arg Lys Val Leu
 65                  70                  75                  80 gta cca ttc tat ccc ctt gcc gga aga cta tgt ctt tcc cca gac gat    288
Val Pro Phe Tyr Pro Leu Ala Gly Arg Leu Cys Leu Ser Pro Asp Asp
                 85                  90                  95 ggt agt cta ttc ata gac tgc aac gct caa ggt gtt tca ttt gtc gaa    336
Gly Ser Leu Phe Ile Asp Cys Asn Ala Gln Gly Val Ser Phe Val Glu
            100                 105                 110 gca aac gct gat gcc gac atc agt gag tta ggt gat ttc tcc caa ccg    384
Ala Asn Ala Asp Ala Asp Ile Ser Glu Leu Gly Asp Phe Ser Gln Pro
        115                 120                 125 gat ttt gcg acc tta ggt tct tta gtc ttc cct ctt cca cca att gcg    432
Asp Phe Ala Thr Leu Gly Ser Leu Val Phe Pro Leu Pro Pro Ile Ala
    130                 135                 140 tct gac gat gga cca ttg tta agt gct caa gtc aca aga ttc aaa tgt    480
Ser Asp Asp Gly Pro Leu Leu Ser Ala Gln Val Thr Arg Phe Lys Cys
145                 150                 155                 160 ggt ggc ttc gtt cta ggt ttc gtc ttc cat cac tgt cta ttt gat ggt    528
Gly Gly Phe Val Leu Gly Phe Val Phe His His Cys Leu Phe Asp Gly
                165                 170                 175 ttt gcc tta tct gaa ttt ctt aat gca tgg gct gag aca gcg tgt gga    576
Phe Ala Leu Ser Glu Phe Leu Asn Ala Trp Ala Glu Thr Ala Cys Gly
            180                 185                 190 gtc ccg tta tca acc cca cct gtt tta gat aga aca ttt cct cgt gct    624
Val Pro Leu Ser Thr Pro Pro Val Leu Asp Arg Thr Phe Pro Arg Ala
        195                 200                 205 aga tct ccc ctg caa ata aag tac cca cat aca gag ttc cta gag gta    672
Arg Ser Pro Leu Gln Ile Lys Tyr Pro His Thr Glu Phe Leu Glu Val
    210                 215                 220 gaa gat gtt tca tta act cag aac atc tct aac gat gct atc aac aga    720
Glu Asp Val Ser Leu Thr Gln Asn Ile Ser Asn Asp Ala Ile Asn Arg
225                 230                 235                 240 tcc ttc tgt ttt aca tca gcc tct ttg gaa att ttg aag aag aag gcg    768
Ser Phe Cys Phe Thr Ser Ala Ser Leu Glu Ile Leu Lys Lys Lys Ala
                245                 250                 255 cta gaa gac ggg gtg tta agc aaa tgt acg acc ttc gaa gct cta tct    816
Leu Glu Asp Gly Val Leu Ser Lys Cys Thr Thr Phe Glu Ala Leu Ser
            260                 265                 270 ggc tta ata tgg aga gca cgt acc aga gcc tta tgg agc gac tac ccc    864
Gly Leu Ile Trp Arg Ala Arg Thr Arg Ala Leu Trp Ser Asp Tyr Pro
        275                 280                 285 gag cac aag tta aag gtc ctg att gtc gtg gac cct cgt gcc aga ttt    912
Glu His Lys Leu Lys Val Leu Ile Val Val Asp Pro Arg Ala Arg Phe
    290                 295                 300 gaa ccg aga gtg gtg cca aaa ggc tac gta ggg aat gca gtc ttg ttt    960
Glu Pro Arg Val Val Pro Lys Gly Tyr Val Gly Asn Ala Val Leu Phe
305                 310                 315                 320 act tgt gca ttt gct tca gcc aga gaa cta gaa gaa aat cca tta tct   1008
Thr Cys Ala Phe Ala Ser Ala Arg Glu Leu Glu Glu Asn Pro Leu Ser
                325                 330                 335 cat gct gtt aaa cac gta cag cac gcg atc ggc cgt atg act gag gaa   1056
His Ala Val Lys His Val Gln His Ala Ile Gly Arg Met Thr Glu Glu
```

```
                340                 345                 350
tat atg cta tca caa att gat tac atg gag cac cag aag gtt tgg tgt    1104
Tyr Met Leu Ser Gln Ile Asp Tyr Met Glu His Gln Lys Val Trp Cys
        355                 360                 365 ccc cca cta ggt gcg tcg act tct ttt atg act aag tgg tca agg ctt    1152
Pro Pro Leu Gly Ala Ser Thr Ser Phe Met Thr Lys Trp Ser Arg Leu
370                 375                 380 gcc ttt aac atc tta gat ttt ggt tgg ggt aga cct aag tat gtt ggt    1200
Ala Phe Asn Ile Leu Asp Phe Gly Trp Gly Arg Pro Lys Tyr Val Gly
385                 390                 395                 400 ccg gct act tca ttg tct atg gaa aca act aca ttc gtc tcc tat gga    1248
Pro Ala Thr Ser Leu Ser Met Glu Thr Thr Thr Phe Val Ser Tyr Gly
        405                 410                 415 aag ggt atg agc gtg gtg tta gcc cta ccc cca gag gca atg aga aag    1296
Lys Gly Met Ser Val Val Leu Ala Leu Pro Pro Glu Ala Met Arg Lys
        420                 425                 430 ttc gaa aag att gta cac cct tat ttg aac cct taa                    1332
Phe Glu Lys Ile Val His Pro Tyr Leu Asn Pro
        435                 440

<210> SEQ ID NO 118
<211> LENGTH: 443
<212> TYPE: PRT
<213> ORGANISM: Artificial Sequence
<220> FEATURE:
<223> OTHER INFORMATION: Synthetic Construct

<400> SEQUENCE: 118

Met Ala Cys Gly Gly Gly Val Arg Asn Ile Glu Val Lys Ala Gln Glu
1               5                   10                  15

Pro Val Leu Val Gln Pro Leu Ser Thr Ala Gln Ser Ser Ala Tyr Asn
            20                  25                  30

Leu Leu Thr Lys Leu Asp Gln Thr Leu Ala Gln Leu Val Val Gln Ile
        35                  40                  45

Val Phe Val Phe Asp Val Lys Asn Pro Val Thr Arg Arg Pro His Asp
    50                  55                  60

Gly Ala Asp Pro Ala Lys Leu Leu Lys Glu Ala Leu Arg Lys Val Leu
65                  70                  75                  80

Val Pro Phe Tyr Pro Leu Ala Gly Arg Leu Cys Leu Ser Pro Asp Asp
                85                  90                  95

Gly Ser Leu Phe Ile Asp Cys Asn Ala Gln Gly Val Ser Phe Val Glu
            100                 105                 110

Ala Asn Ala Asp Ala Asp Ile Ser Glu Leu Gly Asp Phe Ser Gln Pro
        115                 120                 125

Asp Phe Ala Thr Leu Gly Ser Leu Val Phe Pro Leu Pro Pro Ile Ala
    130                 135                 140

Ser Asp Asp Gly Pro Leu Leu Ser Ala Gln Val Thr Arg Phe Lys Cys
145                 150                 155                 160

Gly Gly Phe Val Leu Gly Phe Val Phe His His Cys Leu Phe Asp Gly
                165                 170                 175

Phe Ala Leu Ser Glu Phe Leu Asn Ala Trp Ala Glu Thr Ala Cys Gly
            180                 185                 190

Val Pro Leu Ser Thr Pro Pro Val Leu Asp Arg Thr Phe Pro Arg Ala
        195                 200                 205

Arg Ser Pro Leu Gln Ile Lys Tyr Pro His Thr Glu Phe Leu Glu Val
    210                 215                 220

Glu Asp Val Ser Leu Thr Gln Asn Ile Ser Asn Asp Ala Ile Asn Arg
```

```
                225                 230                 235                 240
Ser Phe Cys Phe Thr Ser Ala Ser Leu Glu Ile Leu Lys Lys Ala
                    245                 250                 255
Leu Glu Asp Gly Val Leu Ser Lys Cys Thr Thr Phe Glu Ala Leu Ser
                260                 265                 270
Gly Leu Ile Trp Arg Ala Arg Thr Arg Ala Leu Trp Ser Asp Tyr Pro
                275                 280                 285
Glu His Lys Leu Lys Val Leu Ile Val Val Asp Pro Arg Ala Arg Phe
            290                 295                 300
Glu Pro Arg Val Val Pro Lys Gly Tyr Val Gly Asn Ala Val Leu Phe
305                 310                 315                 320
Thr Cys Ala Phe Ala Ser Ala Arg Glu Leu Glu Asn Pro Leu Ser
                    325                 330                 335
His Ala Val Lys His Val Gln His Ala Ile Gly Arg Met Thr Glu Glu
                340                 345                 350
Tyr Met Leu Ser Gln Ile Asp Tyr Met Glu His Gln Lys Val Trp Cys
                355                 360                 365
Pro Pro Leu Gly Ala Ser Thr Ser Phe Met Thr Lys Trp Ser Arg Leu
        370                 375                 380
Ala Phe Asn Ile Leu Asp Phe Gly Trp Gly Arg Pro Lys Tyr Val Gly
385                 390                 395                 400
Pro Ala Thr Ser Leu Ser Met Glu Thr Thr Thr Phe Val Ser Tyr Gly
                    405                 410                 415
Lys Gly Met Ser Val Val Leu Ala Leu Pro Pro Glu Ala Met Arg Lys
                420                 425                 430
Phe Glu Lys Ile Val His Pro Tyr Leu Asn Pro
            435                 440

<210> SEQ ID NO 119
<211> LENGTH: 1440
<212> TYPE: DNA
<213> ORGANISM: Aspergillus sclerotiicarbonarius
<220> FEATURE:
<221> NAME/KEY: misc_feature
<222> LOCATION: (1)..(1440)
<223> OTHER INFORMATION: PYI04555.1 native nucleotide sequence

<400> SEQUENCE: 119
atgggtgcca gcgtctcttt ccagcccttt gtgccactc ccctggacca tgctatgccc      60
ccaatttacg tgtctcaatt tctatgcttt cctaccacaa ctccgcaatc cgctattcaa    120
agtctccaag tgggaatcga gagattattc gaacgcctgc cattcctggc gggagagatt    180
ctcatcaatg aacacaccgg agccatcaaa gtccaggctc ccagtgcttt gatccgggaa    240
attccctaca tggccctccg agcccatcct gatctttacc ttccagctaa gcaatgtgca    300
accacaccaa tcgagagaca gttgaagacc aacagccttg atgaatccta ccatccactc    360
ccggcggcac ttccactctc caaccccag ccgtcatcc gattccaagc aaacacccte     420 gcagacggca ttctctttgc agtcagctat catcattgca tattcgatgg cactggatgc    480
ggacagattc tggaaatgtt ggctcagtgc tgttcggcct ccgacgataa gatctccctg    540
ccgactgatt gccacaccga tgtgctcctc cgcgaataca tctccaatct aagccctact    600
accaacatcc ccacgattta cacgcaagcg tatagcacta cggtgcaacc ggaccccgat    660
gcctcagacc cagacgtc cccgccata cctcctcac tctacacaga agcattcacc        720
tttccctccc aacaaatcac cactctccgt gatgcatgca accacctctt gcccaaatta    780
```

```
cccagcacca gcaacgcaca tccccacaaa ccaacaccga atccccctatc atcaaatgac    840 gtcctcaccg cactaatagc cctatgcatc acacgcgcca ccaacaccac cacccccaccc    900 ctccaaccca acaatcacag tctctcaatg ccgtcaacc tccgaacccg catccagccc      960
caagtaccag atcactttct gggaaacttc gccacgctac tcccaataca ctttaccagt   1020
ccagtccaca cccaacagtc tgatctcctc ctcaccacag aaccccccga cccgccctc    1080 atccacctaa ccaccctcgc ctcccaaatc cggtccagcc tatccacagt caacaccgat   1140
tacatctgcg gtctcatgac ggatctccga acccggcgca atgcaggaga aaacagcagt   1200
cttctaattg aaggcattaa gatttccagt tggagacatc tatccgtcta caagccggac   1260
tttggccctg ggttggggaa aatagcgggg tttgagttcc aggcggggct tatggataat   1320
ttggtggtga ttttgccttg gagaaatggg gattgggatg tgcgtgttac gttgttggag   1380
agggatatgc gcgggtttag ggaggatcgg ttggttaggt gggcgttggg gtctgggtag   1440
```

<210> SEQ ID NO 120
<211> LENGTH: 1470
<212> TYPE: DNA
<213> ORGANISM: Artificial Sequence
<220> FEATURE:
<223> OTHER INFORMATION: PYI04555.1_codon optimized for its expression
      in S. cerevisiae_C-terminally extended
<220> FEATURE:
<221> NAME/KEY: CDS
<222> LOCATION: (1)..(1470)

<400> SEQUENCE: 120

```
atg ggt gcg tca gtt agt ttt caa cct ttc gtt cct acc ccc ttg gat       48
Met Gly Ala Ser Val Ser Phe Gln Pro Phe Val Pro Thr Pro Leu Asp
1               5                   10                  15 cac gcc atg cca ccg ata tac gtg tca cag ttc ttg tgt ttc cct act       96
His Ala Met Pro Pro Ile Tyr Val Ser Gln Phe Leu Cys Phe Pro Thr
                20                  25                  30 acg acg ccg cag tca gca ata caa tcc cta cag gtc ggt att gag cgt      144
Thr Thr Pro Gln Ser Ala Ile Gln Ser Leu Gln Val Gly Ile Glu Arg
            35                  40                  45 ttg ttt gaa aga cta cct ttt cta gcc ggg gaa att ctg ata aat gag      192
Leu Phe Glu Arg Leu Pro Phe Leu Ala Gly Glu Ile Leu Ile Asn Glu
        50                  55                  60 cac aca ggt gca ata aaa gtt caa gct ccc tct gct ctg att aga gaa      240
His Thr Gly Ala Ile Lys Val Gln Ala Pro Ser Ala Leu Ile Arg Glu
65                  70                  75                  80 att ccg tac atg gcc tta agg gct cat ccg gat ttg tat ctg cct gct      288
Ile Pro Tyr Met Ala Leu Arg Ala His Pro Asp Leu Tyr Leu Pro Ala
                85                  90                  95 aag caa tgt gca act act cca ata gag agg cag ttg aaa act aac agc      336
Lys Gln Cys Ala Thr Thr Pro Ile Glu Arg Gln Leu Lys Thr Asn Ser
            100                 105                 110 ctt gat gag tct tat cat cca tta cct gcg gca cta cca ttg tct caa      384
Leu Asp Glu Ser Tyr His Pro Leu Pro Ala Ala Leu Pro Leu Ser Gln
        115                 120                 125 cca caa cca gtc atc aga ttc caa gct aat aca ctt gct gac gga ata      432
Pro Gln Pro Val Ile Arg Phe Gln Ala Asn Thr Leu Ala Asp Gly Ile
    130                 135                 140 ctt ttc gct gtc agt tac cac cat tgt ata ttt gat gga acg ggc tgc      480
Leu Phe Ala Val Ser Tyr His His Cys Ile Phe Asp Gly Thr Gly Cys
145                 150                 155                 160 gga cag atc ctt gaa atg tta gcc cag tgt tgt tcg gcc tca gac gat      528
Gly Gln Ile Leu Glu Met Leu Ala Gln Cys Cys Ser Ala Ser Asp Asp
                165                 170                 175
```

```
aag atc agc ttg cct acg gac tgt cat aca gat gta ttg ttg aga gaa    576
Lys Ile Ser Leu Pro Thr Asp Cys His Thr Asp Val Leu Leu Arg Glu
            180                 185                 190 tat att tcg aat cta tct cca acc acg aat atc ccg cat gac tac act    624
Tyr Ile Ser Asn Leu Ser Pro Thr Thr Asn Ile Pro His Asp Tyr Thr
        195                 200                 205 caa gct tat tct act aca gtt caa cca gat cct gac gca tcc gat cct    672
Gln Ala Tyr Ser Thr Thr Val Gln Pro Asp Pro Asp Ala Ser Asp Pro
    210                 215                 220 gat act agc cca gcc att ccg agt tcg ctg tac act gaa gca ttt acg    720
Asp Thr Ser Pro Ala Ile Pro Ser Ser Leu Tyr Thr Glu Ala Phe Thr
225                 230                 235                 240 ttt cct tca caa cag att acc aca cta aga gat gcg tgc aac cat tta    768
Phe Pro Ser Gln Gln Ile Thr Thr Leu Arg Asp Ala Cys Asn His Leu
                245                 250                 255 ttg cct aaa tta cca tct act tca aac gca cat ccc cac aaa cca aca    816
Leu Pro Lys Leu Pro Ser Thr Ser Asn Ala His Pro His Lys Pro Thr
            260                 265                 270 cca aac ccg tta tcc tca aat gac gtt ttg acg gca ctg atc gca ttg    864
Pro Asn Pro Leu Ser Ser Asn Asp Val Leu Thr Ala Leu Ile Ala Leu
        275                 280                 285 tgc atc acc aga gct act aat acg acg aca ccc cca tta caa cca aac    912
Cys Ile Thr Arg Ala Thr Asn Thr Thr Thr Pro Pro Leu Gln Pro Asn
    290                 295                 300 aac cat tct ctt agc atg gcc gtc aat cta agg act cgt att caa ccc    960
Asn His Ser Leu Ser Met Ala Val Asn Leu Arg Thr Arg Ile Gln Pro
305                 310                 315                 320 caa gtc ccg gac cac ttt ctt ggt aat ttt gcc acc ttg cta cct att   1008
Gln Val Pro Asp His Phe Leu Gly Asn Phe Ala Thr Leu Leu Pro Ile
                325                 330                 335 cac ttc aca agt cca gtc cat acg cag caa tca gat tta tta ttg act   1056
His Phe Thr Ser Pro Val His Thr Gln Gln Ser Asp Leu Leu Leu Thr
            340                 345                 350 act gag ccg cca gac cca gca ttg atc cac ctt aca acc ctt gca tcg   1104
Thr Glu Pro Pro Asp Pro Ala Leu Ile His Leu Thr Thr Leu Ala Ser
        355                 360                 365 caa att agg tct agt tta tcg acc gtt aac acc gat tac ata tgt ggc   1152
Gln Ile Arg Ser Ser Leu Ser Thr Val Asn Thr Asp Tyr Ile Cys Gly
    370                 375                 380 ttg atg aca gat ctg agg act agg aga aac gcc ggt gag aat tcc tct   1200
Leu Met Thr Asp Leu Arg Thr Arg Arg Asn Ala Gly Glu Asn Ser Ser
385                 390                 395                 400 ttg tta ata gaa ggt att aag att tct tca tgg aga cat ctt agc gtt   1248
Leu Leu Ile Glu Gly Ile Lys Ile Ser Ser Trp Arg His Leu Ser Val
                405                 410                 415 tac aag cca gat ttc gga cct gga tta ggg aag att gca gga ttt gag   1296
Tyr Lys Pro Asp Phe Gly Pro Gly Leu Gly Lys Ile Ala Gly Phe Glu
            420                 425                 430 ttt caa gct ggt tta atg gac aac ctt gtt gtg ata ttg cct tgg aga   1344
Phe Gln Ala Gly Leu Met Asp Asn Leu Val Val Ile Leu Pro Trp Arg
        435                 440                 445 aac ggt gat tgg gac gtg cgt gta act ctt ctg gag aga gat atg agg   1392
Asn Gly Asp Trp Asp Val Arg Val Thr Leu Leu Glu Arg Asp Met Arg
    450                 455                 460 ggt ttt agg gaa gac aga tta gtc aga tgg gca tta ggt agc gga aca   1440
Gly Phe Arg Glu Asp Arg Leu Val Arg Trp Ala Leu Gly Ser Gly Thr
465                 470                 475                 480 ggc ccc ttt tcc ttt gtc gat atc atg taa                           1470
Gly Pro Phe Ser Phe Val Asp Ile Met
```

-continued

485

<210> SEQ ID NO 121
<211> LENGTH: 489
<212> TYPE: PRT
<213> ORGANISM: Artificial Sequence
<220> FEATURE:
<223> OTHER INFORMATION: Synthetic Construct

<400> SEQUENCE: 121

Met Gly Ala Ser Val Ser Phe Gln Pro Phe Val Thr Pro Leu Asp
1               5                   10                  15

His Ala Met Pro Pro Ile Tyr Val Ser Gln Phe Leu Cys Phe Pro Thr
            20                  25                  30

Thr Thr Pro Gln Ser Ala Ile Gln Ser Leu Gln Val Gly Ile Glu Arg
        35                  40                  45

Leu Phe Glu Arg Leu Pro Phe Leu Ala Gly Glu Ile Leu Ile Asn Glu
50                  55                  60

His Thr Gly Ala Ile Lys Val Gln Ala Pro Ser Ala Leu Ile Arg Glu
65                  70                  75                  80

Ile Pro Tyr Met Ala Leu Arg Ala His Pro Asp Leu Tyr Leu Pro Ala
                85                  90                  95

Lys Gln Cys Ala Thr Thr Pro Ile Glu Arg Gln Leu Lys Thr Asn Ser
            100                 105                 110

Leu Asp Glu Ser Tyr His Pro Leu Pro Ala Ala Leu Pro Leu Ser Gln
        115                 120                 125

Pro Gln Pro Val Ile Arg Phe Gln Ala Asn Thr Leu Ala Asp Gly Ile
130                 135                 140

Leu Phe Ala Val Ser Tyr His His Cys Ile Phe Asp Gly Thr Gly Cys
145                 150                 155                 160

Gly Gln Ile Leu Glu Met Leu Ala Gln Cys Cys Ser Ala Ser Asp Asp
                165                 170                 175

Lys Ile Ser Leu Pro Thr Asp Cys His Thr Asp Val Leu Leu Arg Glu
            180                 185                 190

Tyr Ile Ser Asn Leu Ser Pro Thr Thr Asn Ile Pro His Asp Tyr Thr
        195                 200                 205

Gln Ala Tyr Ser Thr Thr Val Gln Pro Asp Pro Asp Ala Ser Asp Pro
210                 215                 220

Asp Thr Ser Pro Ala Ile Pro Ser Ser Leu Tyr Thr Glu Ala Phe Thr
225                 230                 235                 240

Phe Pro Ser Gln Gln Ile Thr Thr Leu Arg Asp Ala Cys Asn His Leu
                245                 250                 255

Leu Pro Lys Leu Pro Ser Thr Ser Asn Ala His Pro His Lys Pro Thr
            260                 265                 270

Pro Asn Pro Leu Ser Ser Asn Asp Val Leu Thr Ala Leu Ile Ala Leu
        275                 280                 285

Cys Ile Thr Arg Ala Thr Asn Thr Thr Pro Pro Leu Gln Pro Asn
290                 295                 300

Asn His Ser Leu Ser Met Ala Val Asn Leu Arg Thr Arg Ile Gln Pro
305                 310                 315                 320

Gln Val Pro Asp His Phe Leu Gly Asn Phe Ala Thr Leu Leu Pro Ile
                325                 330                 335

His Phe Thr Ser Pro Val His Thr Gln Gln Ser Asp Leu Leu Leu Thr
            340                 345                 350

Thr Glu Pro Pro Asp Pro Ala Leu Ile His Leu Thr Thr Leu Ala Ser

|  | 355 |  |  |  | 360 |  |  |  | 365 |  |  |
|---|---|---|---|---|---|---|---|---|---|---|---|

Gln Ile Arg Ser Ser Leu Ser Thr Val Asn Thr Asp Tyr Ile Cys Gly
370 375 380

Leu Met Thr Asp Leu Arg Thr Arg Arg Asn Ala Gly Glu Asn Ser Ser
385 390 395 400

Leu Leu Ile Glu Gly Ile Lys Ile Ser Ser Trp Arg His Leu Ser Val
405 410 415

Tyr Lys Pro Asp Phe Gly Pro Gly Leu Gly Lys Ile Ala Gly Phe Glu
420 425 430

Phe Gln Ala Gly Leu Met Asp Asn Leu Val Val Ile Leu Pro Trp Arg
435 440 445

Asn Gly Asp Trp Asp Val Arg Val Thr Leu Leu Glu Arg Asp Met Arg
450 455 460

Gly Phe Arg Glu Asp Arg Leu Val Arg Trp Ala Leu Gly Ser Gly Thr
465 470 475 480

Gly Pro Phe Ser Phe Val Asp Ile Met
485

<210> SEQ ID NO 122
<211> LENGTH: 1425
<212> TYPE: DNA
<213> ORGANISM: Bazzania trilobata
<220> FEATURE:
<221> NAME/KEY: misc_feature
<222> LOCATION: (1)..(1425)
<223> OTHER INFORMATION: ERR364415-1_contig_8546 native nucleotide sequence

<400> SEQUENCE: 122

```
atggcccggg caccaccacc tccgcctcct ggtctcagaa tgagagacac agtgctcagc    60
atcgtgaagc cgatacggaa gacacagcat ttggagacga tcgacgcaac gttcgtcgat   120
ttgatgagaa tggacagctt tatacccgtg atttcgcct acaggcctgc ggacaagtcc    180
gaggccgcgt actcgcgtct cgtgaatcgc atcaaggagt cgctccagaa ggttttggtc   240
ccctttttcg ggttcgcggg ccgctggggtt ccaagcagtg cgggagcag gcggctcttg   300
tgcaacgatg agggcgttcc cttcattgaa gcgtttgtgg acgaagagtt ggactcggtg   360
gtgaaggctt ccgccgcatt ccagccggtt acggagctga atggcttggg cgtcctcgga   420
atggacatga cttcatacga tcaaaggatg ccaccggaag gtgggcaacc ttgcgtcgtt   480
gctcaagtca cacggttcaa atgtggggga gtggttctgg gggtggcttt caatcacact   540
cacactgacg gccagggatt ctacaccttc atgcgagcat ggtccgactt ctctcgaacc   600
aacggaacgg caatcaaggt ggaccacaac cgggccctgc cagaactggc ttccctctca   660
cagttcttca tcaaacagca cgaccgaata ggaggcaaaa cttctaccga tcgagtcaac   720
gatcattgtt ctaaagttcc ggaacggctg gctttgaaag cttcgaggt cgtgcgtct    780
aagatcaaag ccgcaaagct agcagccgaa gatggagggg ttgggtatgt cagcacggta   840
gattgcattg tggctcactt atggaaaact cttgccagat gccgcccgt cgtgttggat    900
gggagggaga ttacggtctt ctcgcctgtg gaggggagga acagattctt ggacccgcca   960
agacccaata tgtgtggaaa ttgttttgca gcaatggtga ccccaaaat cccaacccag   1020
gagttgctgg agatgcctct cgctgcaatt gcaggcaagc aacgggagaa attatccaca   1080
acccgaaggg aggaatggtt tggacagcaa agctttaggg agctggcctc cgcgatgaac   1140
accagcaaat ctgctctact tattgtgacc tcgtggttca actttccat gtatgagatc   1200
```

```
gactttggag ctggcaaacc atttttttgca tccactacga acatgatttc tcctatcaac   1260
ggcgtgtgtt gtggagtcat tgcaccccca actcctggga gctgctcctc cattgccact   1320
ctgtacattt tgtgccttcc cgcggtacta gaggctcttg aaaatgttcc agatttccta   1380
tccttcttcg ttcctcaccc aaatcacaaa gataactcgc aatag                    1425
```

<210> SEQ ID NO 123
<211> LENGTH: 1455
<212> TYPE: DNA
<213> ORGANISM: Artificial Sequence
<220> FEATURE:
<223> OTHER INFORMATION: ERR364415-1_contig_8546_codon optimized for its
      expression in S. cerevisiae_C-terminally extended
<220> FEATURE:
<221> NAME/KEY: CDS
<222> LOCATION: (1)..(1455)

<400> SEQUENCE: 123

```
atg gcc agg gct cca ccc cca cca ccg ggc ttg cgt atg aga gat         48
Met Ala Arg Ala Pro Pro Pro Pro Pro Gly Leu Arg Met Arg Asp
1               5                   10                  15 acg gtc cta tca atc gtc aaa cct ata aga aag act caa cac cta gag     96
Thr Val Leu Ser Ile Val Lys Pro Ile Arg Lys Thr Gln His Leu Glu
            20                  25                  30 aca att gat gca aca ttc gta gat tta atg aga atg gac tca ttt atc    144
Thr Ile Asp Ala Thr Phe Val Asp Leu Met Arg Met Asp Ser Phe Ile
        35                  40                  45 cct gtg atc ttc gct tat aga cct gca gat aag agc gag gct gcg tac    192
Pro Val Ile Phe Ala Tyr Arg Pro Ala Asp Lys Ser Glu Ala Ala Tyr
    50                  55                  60 tct aga tta gtt aat agg ata aaa gaa agc tta cag aaa gta cta gta    240
Ser Arg Leu Val Asn Arg Ile Lys Glu Ser Leu Gln Lys Val Leu Val
65                  70                  75                  80 cca ttc ttt gga ttt gct gga agg tgg gtg cct tct tcc ggt ggc tca    288
Pro Phe Phe Gly Phe Ala Gly Arg Trp Val Pro Ser Ser Gly Gly Ser
                85                  90                  95 agg cgt ctg cta tgc aat gac gaa ggt gtc cct ttt att gag gcg ttt    336
Arg Arg Leu Leu Cys Asn Asp Glu Gly Val Pro Phe Ile Glu Ala Phe
            100                 105                 110 gta gac gaa gaa ctg gac tct gtc gtt aag gct tca gct gcc ttc caa    384
Val Asp Glu Glu Leu Asp Ser Val Val Lys Ala Ser Ala Ala Phe Gln
        115                 120                 125 cct gta act gaa ctt aat ggt cta ggt gtg ttg ggt atg gat atg act    432
Pro Val Thr Glu Leu Asn Gly Leu Gly Val Leu Gly Met Asp Met Thr
    130                 135                 140 agt tat gat caa aga atg ccc cct gaa ggc ggt caa ccg tgc gtc gta    480
Ser Tyr Asp Gln Arg Met Pro Pro Glu Gly Gly Gln Pro Cys Val Val
145                 150                 155                 160 gct cag gta acg aga ttt aaa tgc ggc ggt gtg gta ttg ggt gta gca    528
Ala Gln Val Thr Arg Phe Lys Cys Gly Gly Val Val Leu Gly Val Ala
                165                 170                 175 ttc aac cat acc cat act gac ggg cag ggc ttt tat act ttt atg cgt    576
Phe Asn His Thr His Thr Asp Gly Gln Gly Phe Tyr Thr Phe Met Arg
            180                 185                 190 gca tgg tcg gat ttc agt aga acg aat ggt acc gca att aaa gtc gat    624
Ala Trp Ser Asp Phe Ser Arg Thr Asn Gly Thr Ala Ile Lys Val Asp
        195                 200                 205 cac aac agg gca cta ccc gaa tta gca tct ttg agt cag ttc ttt att    672
His Asn Arg Ala Leu Pro Glu Leu Ala Ser Leu Ser Gln Phe Phe Ile
    210                 215                 220 aag cag cat gat aga att ggt ggg aaa act tcc acc gat aga gtc aat    720
```

```
                    Lys Gln His Asp Arg Ile Gly Gly Lys Thr Ser Thr Asp Arg Val Asn
                    225                 230                 235                 240 gac cac tgt agc aaa gtc cct gaa aga cta gca cta aag gct ttt gaa        768
Asp His Cys Ser Lys Val Pro Glu Arg Leu Ala Leu Lys Ala Phe Glu
                245                 250                 255 gtt agg gcg tcc aaa atc aag gca gca aaa cta gcc gca gaa gat ggt        816
Val Arg Ala Ser Lys Ile Lys Ala Ala Lys Leu Ala Ala Glu Asp Gly
                260                 265                 270 ggt gta ggc tac gtc tcg acg gtg gat tgt att gtt gct cat cta tgg        864
Gly Val Gly Tyr Val Ser Thr Val Asp Cys Ile Val Ala His Leu Trp
            275                 280                 285 aag aca cta gct cgt ttg cca cca gtt gtg tta gac ggt cgt gag atc        912
Lys Thr Leu Ala Arg Leu Pro Pro Val Val Leu Asp Gly Arg Glu Ile
        290                 295                 300 act gtg ttt agc cca gta gaa ggc aga aat agg ttt ctt gat ccg ccc        960
Thr Val Phe Ser Pro Val Glu Gly Arg Asn Arg Phe Leu Asp Pro Pro
305                 310                 315                 320 cgt ccg aac atg tgt ggt aat tgt ttc gct gca atg gta acc cct aaa       1008
Arg Pro Asn Met Cys Gly Asn Cys Phe Ala Ala Met Val Thr Pro Lys
                325                 330                 335 atc cca aca caa gaa ttg tta gag atg cca tta gcc gcc att gcc ggc       1056
Ile Pro Thr Gln Glu Leu Leu Glu Met Pro Leu Ala Ala Ile Ala Gly
                340                 345                 350 aag cag aga gag aaa cta tct acc acg aga cgt gaa gag tgg ttc gga       1104
Lys Gln Arg Glu Lys Leu Ser Thr Thr Arg Arg Glu Glu Trp Phe Gly
            355                 360                 365 cag caa tca ttc agg gag ttg gct tca gct atg aat act tct aaa tca       1152
Gln Gln Ser Phe Arg Glu Leu Ala Ser Ala Met Asn Thr Ser Lys Ser
        370                 375                 380 gct ttg tta atc gtg aca tct tgg ttt aac ttc ccg atg tat gaa atc       1200
Ala Leu Leu Ile Val Thr Ser Trp Phe Asn Phe Pro Met Tyr Glu Ile
385                 390                 395                 400 gat ttt ggt gcc ggt aag ccg ttc ttc gct agt acg act aat atg att       1248
Asp Phe Gly Ala Gly Lys Pro Phe Phe Ala Ser Thr Thr Asn Met Ile
                405                 410                 415 tct cct ata aat gga gtt tgt tgt ggt gtc ata gcc ccg ccc acc ccc       1296
Ser Pro Ile Asn Gly Val Cys Cys Gly Val Ile Ala Pro Pro Thr Pro
                420                 425                 430 ggt tcc tgt tca tcc ata gcg aca tta tac att tta tgt tta cca gcc       1344
Gly Ser Cys Ser Ser Ile Ala Thr Leu Tyr Ile Leu Cys Leu Pro Ala
            435                 440                 445 gtg tta gaa gct ctt gaa aat gtc cca gat ttc ctt tcg ttc ttc gta       1392
Val Leu Glu Ala Leu Glu Asn Val Pro Asp Phe Leu Ser Phe Phe Val
        450                 455                 460 ccg cat cca aac cat aaa gac aac agc caa aca ggc ccc ttt tcc ttt       1440
Pro His Pro Asn His Lys Asp Asn Ser Gln Thr Gly Pro Phe Ser Phe
465                 470                 475                 480 gtc gat atc atg taa                                                    1455
Val Asp Ile Met <210> SEQ ID NO 124
<211> LENGTH: 484
<212> TYPE: PRT
<213> ORGANISM: Artificial Sequence
<220> FEATURE:
<223> OTHER INFORMATION: Synthetic Construct

<400> SEQUENCE: 124

Met Ala Arg Ala Pro Pro Pro Pro Pro Gly Leu Arg Met Arg Asp
1               5                   10                  15
```

-continued

```
Thr Val Leu Ser Ile Val Lys Pro Ile Arg Lys Thr Gln His Leu Glu
            20                  25                  30
Thr Ile Asp Ala Thr Phe Val Asp Leu Met Arg Met Asp Ser Phe Ile
        35                  40                  45
Pro Val Ile Phe Ala Tyr Arg Pro Ala Asp Lys Ser Glu Ala Ala Tyr
    50                  55                  60
Ser Arg Leu Val Asn Arg Ile Lys Glu Ser Leu Gln Lys Val Leu Val
65                  70                  75                  80
Pro Phe Phe Gly Phe Ala Gly Arg Trp Val Pro Ser Ser Gly Gly Ser
                85                  90                  95
Arg Arg Leu Leu Cys Asn Asp Glu Gly Val Pro Phe Ile Glu Ala Phe
            100                 105                 110
Val Asp Glu Glu Leu Asp Ser Val Val Lys Ala Ser Ala Ala Phe Gln
        115                 120                 125
Pro Val Thr Glu Leu Asn Gly Leu Gly Val Leu Gly Met Asp Met Thr
    130                 135                 140
Ser Tyr Asp Gln Arg Met Pro Pro Glu Gly Gly Gln Pro Cys Val Val
145                 150                 155                 160
Ala Gln Val Thr Arg Phe Lys Cys Gly Gly Val Val Leu Gly Val Ala
            165                 170                 175
Phe Asn His Thr His Thr Asp Gly Gln Gly Phe Tyr Thr Phe Met Arg
        180                 185                 190
Ala Trp Ser Asp Phe Ser Arg Thr Asn Gly Thr Ala Ile Lys Val Asp
            195                 200                 205
His Asn Arg Ala Leu Pro Glu Leu Ala Ser Leu Ser Gln Phe Phe Ile
        210                 215                 220
Lys Gln His Asp Arg Ile Gly Gly Lys Thr Ser Thr Asp Arg Val Asn
225                 230                 235                 240
Asp His Cys Ser Lys Val Pro Glu Arg Leu Ala Leu Lys Ala Phe Glu
            245                 250                 255
Val Arg Ala Ser Lys Ile Lys Ala Lys Leu Ala Ala Glu Asp Gly
        260                 265                 270
Gly Val Gly Tyr Val Ser Thr Val Asp Cys Ile Val Ala His Leu Trp
    275                 280                 285
Lys Thr Leu Ala Arg Leu Pro Pro Val Val Leu Asp Gly Arg Glu Ile
290                 295                 300
Thr Val Phe Ser Pro Val Glu Gly Arg Asn Arg Phe Leu Asp Pro Pro
305                 310                 315                 320
Arg Pro Asn Met Cys Gly Asn Cys Phe Ala Ala Met Val Thr Pro Lys
            325                 330                 335
Ile Pro Thr Gln Glu Leu Leu Glu Met Pro Leu Ala Ala Ile Ala Gly
        340                 345                 350
Lys Gln Arg Glu Lys Leu Ser Thr Thr Arg Arg Glu Glu Trp Phe Gly
    355                 360                 365
Gln Gln Ser Phe Arg Glu Leu Ala Ser Ala Met Asn Thr Ser Lys Ser
370                 375                 380
Ala Leu Leu Ile Val Thr Ser Trp Phe Asn Phe Pro Met Tyr Glu Ile
385                 390                 395                 400
Asp Phe Gly Ala Gly Lys Pro Phe Phe Ala Ser Thr Thr Asn Met Ile
            405                 410                 415
Ser Pro Ile Asn Gly Val Cys Cys Gly Val Ile Ala Pro Thr Pro
        420                 425                 430
Gly Ser Cys Ser Ser Ile Ala Thr Leu Tyr Ile Leu Cys Leu Pro Ala
```

Val Leu Glu Ala Leu Glu Asn Val Pro Asp Phe Leu Ser Phe Phe Val
        450                 455                 460

Pro His Pro Asn His Lys Asp Asn Ser Gln Thr Gly Pro Phe Ser Phe
465                 470                 475                 480

Val Asp Ile Met

<210> SEQ ID NO 125
<211> LENGTH: 1530
<212> TYPE: DNA
<213> ORGANISM: Aspergillus fischeri
<220> FEATURE:
<221> NAME/KEY: misc_feature
<222> LOCATION: (1)..(1530)
<223> OTHER INFORMATION: XP_001258079 native nucleotide sequence

<400> SEQUENCE: 125

```
atgaccgtga ccatcagttt cgagccatat gtgggctcct ctgtcgatgc tctaagcatc      60
cctctctatc ttcgatgtca actcgtcttc aaactttcta agccacttgc tgcggtgcct     120
ctgcttgagt ctggagttaa tcgtcttgta caagcgttac ccttcctctc gggcgagttc     180
acggccgtgc cagcatccga cggtgggaaa gaaattcttc tcgttcgccc tgtgctcaac     240
ttcgagctca gccgtatact caagatcaag taccatgaaa catccctacg acatgtatgc     300
aaacagatga acaggccaag cagccagggt ggtgaccttc gcatgagcc atacatgccc      360
tacccacgac ttccagatcc ttcacgccct caacccatcg tcgggttcca agtcaacgtt     420
cacacggatg catcattct ctccgttgct acgcatcact gttcctttga cgcaacaggg      480
atgggatcaa tcgtccaaaa cctcgcggct tgttgccgtt ctcctccgag cgacgagcct     540
gacttgacca cgtcgccagc caggaagca gaagcaagaa aagtcctctc gcaagtccgc      600
gagacgcctt ttgatccaaa gatgttcccg gagtacagac ccttggacag tatgctgtcc     660
tattacaaag gcgtccagtc agcgctccag ggtcgtcaaa ccactatcgt caatcgatgt     720
ttcacaatcg ccgccgacaa gatcaacgcg ctcaaaaggc gctgcaatca actgataccg     780
gaaatggtga agaagtatgg gctttcaact gaggatgcca ttgggagcgc ctgggtctcg     840
agtaatgatg ttgttgctgc cctcttgtgg acatgtatca atcgagcgcg atatcccgaa     900
atccgcgagc gcagcgttca ccagctccca ccagacctcc tacatgcgac atctagcctg     960
ggtgtgccag tgaacgttcg ctctcgactg tcgccgccct acccaaaatc gactttaggt    1020
aacgccgtgt gtcttctccg ggagaaggtc ccgctgcaat ttttcgcttt gcctagtcat    1080
gccaacatgg aggccacttc tagcgtttgc gcagaccatt ccggagacga cgaatgggcc    1140
ttgtccttct gtcgagtcgc ctacggactc agagcgaagc tgaacgcaat tgatgacgac    1200
tatatccgcg actatatctc ctacgtgcaa aagtctccgt gccatctgtc agtgacactg    1260
gatacagaga acctgtacct cagtaactgg cgcgagatcg gtgtgtatga tgctgatttt    1320
ggaggcatgc tgggcaagcc gctacggatg agagctccgg atggatacac cgatggcctg    1380
atttttgtga tggcgcagcg gagcgaagat aagtctgcac cgtgggagtt taatatctcg    1440
ctggaggcat cgacaatgaa gcgtattgtg catgatcccc tctggtgcaa gtatgttgag    1500
ctggatgcgt tctggcatgg agaagaatga                                    1530
```

<210> SEQ ID NO 126
<211> LENGTH: 1530
<212> TYPE: DNA
<213> ORGANISM: Artificial Sequence

```
<220> FEATURE:
<223> OTHER INFORMATION: XP_001258079_codon optimized for its expression
      in S. cerevisiae
<220> FEATURE:
<221> NAME/KEY: CDS
<222> LOCATION: (1)..(1530)

<400> SEQUENCE: 126 atg acc gtc acg att tca ttc gaa cca tat gtg gga tct agc gtg gac         48
Met Thr Val Thr Ile Ser Phe Glu Pro Tyr Val Gly Ser Ser Val Asp
1               5                  10                  15 gcg ctg tcc ata ccc ttg tat cta agg tgc caa ctg gtg ttc aaa tta         96
Ala Leu Ser Ile Pro Leu Tyr Leu Arg Cys Gln Leu Val Phe Lys Leu
            20                  25                  30 tcc aag cct ctt gca gcc gtg ccc ctg cta gaa tct ggg gta aac cgt        144
Ser Lys Pro Leu Ala Ala Val Pro Leu Leu Glu Ser Gly Val Asn Arg
        35                  40                  45 cta gta caa gca tta cca ttc ttg tct ggt gaa ttt act gct gtc cct        192
Leu Val Gln Ala Leu Pro Phe Leu Ser Gly Glu Phe Thr Ala Val Pro
    50                  55                  60 gca agc gat ggt ggg aag gaa atc tta ctt gtt aga cca gtc tta aat        240
Ala Ser Asp Gly Gly Lys Glu Ile Leu Leu Val Arg Pro Val Leu Asn
65                  70                  75                  80 ttc gaa cta agt cgt ata ctg aag atc aaa tac cac gaa aca tcc tta        288
Phe Glu Leu Ser Arg Ile Leu Lys Ile Lys Tyr His Glu Thr Ser Leu
                85                  90                  95 aga cac gta tgc aag cag atg aac aga cca tcc tcg caa ggt ggt gac        336
Arg His Val Cys Lys Gln Met Asn Arg Pro Ser Ser Gln Gly Gly Asp
            100                 105                 110 ttg cca cac gaa ccg tat atg cca tac ccc agg tta cca gat cca tct        384
Leu Pro His Glu Pro Tyr Met Pro Tyr Pro Arg Leu Pro Asp Pro Ser
        115                 120                 125 agg cct caa cca atc gtg ggt ttt caa gtc aat gtc cac act gac ggt        432
Arg Pro Gln Pro Ile Val Gly Phe Gln Val Asn Val His Thr Asp Gly
    130                 135                 140 ata atc ctg agt gta gca act cac cat tgc agt ttt gac gcc acg ggg        480
Ile Ile Leu Ser Val Ala Thr His His Cys Ser Phe Asp Ala Thr Gly
145                 150                 155                 160 atg gga agt att gta cag aac ttg gcc gca tgc tgt aga tct ccg cca        528
Met Gly Ser Ile Val Gln Asn Leu Ala Ala Cys Cys Arg Ser Pro Pro
                165                 170                 175 tcg gac gag cca gat tta act aca agc cct gct caa gaa gca gaa gct        576
Ser Asp Glu Pro Asp Leu Thr Thr Ser Pro Ala Gln Glu Ala Glu Ala
            180                 185                 190 agg aag gtc ctg agc caa gtt aga gaa aca cca ttc gac cca aag atg        624
Arg Lys Val Leu Ser Gln Val Arg Glu Thr Pro Phe Asp Pro Lys Met
        195                 200                 205 ttt ccc gaa tat agg ccc tta gac tct atg tta tct tat tac aaa ggt        672
Phe Pro Glu Tyr Arg Pro Leu Asp Ser Met Leu Ser Tyr Tyr Lys Gly
    210                 215                 220 gtc cag tct gct ttg cag ggt cgt caa act act atc gtt aac aga tgt        720
Val Gln Ser Ala Leu Gln Gly Arg Gln Thr Thr Ile Val Asn Arg Cys
225                 230                 235                 240 ttc act atc gct gct gat aag ata aac gcc tta aag agg aga tgt aac        768
Phe Thr Ile Ala Ala Asp Lys Ile Asn Ala Leu Lys Arg Arg Cys Asn
                245                 250                 255 caa ctt att ccg gaa atg gta aag aaa tac gga ttg agt aca gaa gat        816
Gln Leu Ile Pro Glu Met Val Lys Lys Tyr Gly Leu Ser Thr Glu Asp
            260                 265                 270 gct atc ggt tct gca tgg gtc tct tct aat gac gtg gtt gcc gca ctt        864
Ala Ile Gly Ser Ala Trp Val Ser Ser Asn Asp Val Val Ala Ala Leu
```

| | | | | | | | | | | | | | | | |
|---|---|---|---|---|---|---|---|---|---|---|---|---|---|---|---|
| | | 275 | | | | | 280 | | | | | 285 | | | |
| ttg | tgg | acc | tgt | att | aat | cgt | gct | aga | tac | cca | gag | att | aga | gaa | aga | 912 |
| Leu | Trp | Thr | Cys | Ile | Asn | Arg | Ala | Arg | Tyr | Pro | Glu | Ile | Arg | Glu | Arg | |
| | 290 | | | | | 295 | | | | | 300 | | | | | |

```
ttg tgg acc tgt att aat cgt gct aga tac cca gag att aga gaa aga      912
Leu Trp Thr Cys Ile Asn Arg Ala Arg Tyr Pro Glu Ile Arg Glu Arg
    290                 295                 300 agt gta cat cag ctt cca cca gac ttg ttg cat gct aca tct tca ttg      960
Ser Val His Gln Leu Pro Pro Asp Leu Leu His Ala Thr Ser Ser Leu
305                 310                 315                 320 ggt gta cct gtt aat gtt aga tct aga ctt tca cca ccc tta ccc aaa     1008
Gly Val Pro Val Asn Val Arg Ser Arg Leu Ser Pro Pro Leu Pro Lys
                325                 330                 335 tcc act ctt ggg aat gcg gtc tgc ctg cta agg gag aag gta cct ttg     1056
Ser Thr Leu Gly Asn Ala Val Cys Leu Leu Arg Glu Lys Val Pro Leu
            340                 345                 350 caa ttc ttc gct ctt ccg agt cac gca aac atg gaa gca acc agt tca     1104
Gln Phe Phe Ala Leu Pro Ser His Ala Asn Met Glu Ala Thr Ser Ser
        355                 360                 365 gtt tgc gct gac cat tca ggg gat gat gaa tgg gcg ttg agc ttt tgt     1152
Val Cys Ala Asp His Ser Gly Asp Asp Glu Trp Ala Leu Ser Phe Cys
    370                 375                 380 agg gta gct tat ggt ctg cgt gca aaa ttg aac gcg atc gat gat gat     1200
Arg Val Ala Tyr Gly Leu Arg Ala Lys Leu Asn Ala Ile Asp Asp Asp
385                 390                 395                 400 tac ata agg gat tac att agt tat gta cag aag tcg ccc tgt cat ctt     1248
Tyr Ile Arg Asp Tyr Ile Ser Tyr Val Gln Lys Ser Pro Cys His Leu
                405                 410                 415 tca gtt aca cta gat act gag aac tta tac ctg tct aat tgg aga gaa     1296
Ser Val Thr Leu Asp Thr Glu Asn Leu Tyr Leu Ser Asn Trp Arg Glu
            420                 425                 430 ata ggc gtc tac gat gca gac ttc ggt ggt atg cta ggg aaa cca ttg     1344
Ile Gly Val Tyr Asp Ala Asp Phe Gly Gly Met Leu Gly Lys Pro Leu
        435                 440                 445 cgt atg aga gct ccg gat ggc tac act gac ggt ttg att ttc gtt atg     1392
Arg Met Arg Ala Pro Asp Gly Tyr Thr Asp Gly Leu Ile Phe Val Met
    450                 455                 460 gcc caa aga tct gaa gac aag tca gct ccg tgg gaa ttc aac ata tcc     1440
Ala Gln Arg Ser Glu Asp Lys Ser Ala Pro Trp Glu Phe Asn Ile Ser
465                 470                 475                 480 ctt gag gct tct aca atg aaa agg att gta cat gat ccg ctg tgg tgt     1488
Leu Glu Ala Ser Thr Met Lys Arg Ile Val His Asp Pro Leu Trp Cys
                485                 490                 495 aaa tat gtt gaa ttg gat gcc ttt tgg cat ggg gaa gag taa             1530
Lys Tyr Val Glu Leu Asp Ala Phe Trp His Gly Glu Glu
            500                 505

<210> SEQ ID NO 127
<211> LENGTH: 509
<212> TYPE: PRT
<213> ORGANISM: Artificial Sequence
<220> FEATURE:
<223> OTHER INFORMATION: Synthetic Construct

<400> SEQUENCE: 127

Met Thr Val Thr Ile Ser Phe Glu Pro Tyr Val Gly Ser Ser Val Asp
1               5                   10                  15

Ala Leu Ser Ile Pro Leu Tyr Leu Arg Cys Gln Leu Val Phe Lys Leu
            20                  25                  30

Ser Lys Pro Leu Ala Ala Val Pro Leu Leu Glu Ser Gly Val Asn Arg
        35                  40                  45

Leu Val Gln Ala Leu Pro Phe Leu Ser Gly Glu Phe Thr Ala Val Pro
    50                  55                  60
```

-continued

```
Ala Ser Asp Gly Gly Lys Glu Ile Leu Leu Val Arg Pro Val Leu Asn
 65                  70                  75                  80

Phe Glu Leu Ser Arg Ile Leu Lys Ile Lys Tyr His Glu Thr Ser Leu
                 85                  90                  95

Arg His Val Cys Lys Gln Met Asn Arg Pro Ser Ser Gln Gly Gly Asp
            100                 105                 110

Leu Pro His Glu Pro Tyr Met Pro Tyr Pro Arg Leu Pro Asp Pro Ser
        115                 120                 125

Arg Pro Gln Pro Ile Val Gly Phe Gln Val Asn Val His Thr Asp Gly
    130                 135                 140

Ile Ile Leu Ser Val Ala Thr His His Cys Ser Phe Asp Ala Thr Gly
145                 150                 155                 160

Met Gly Ser Ile Val Gln Asn Leu Ala Ala Cys Cys Arg Ser Pro Pro
                165                 170                 175

Ser Asp Glu Pro Asp Leu Thr Thr Ser Pro Ala Gln Glu Ala Glu Ala
            180                 185                 190

Arg Lys Val Leu Ser Gln Val Arg Glu Thr Pro Phe Asp Pro Lys Met
        195                 200                 205

Phe Pro Glu Tyr Arg Pro Leu Asp Ser Met Leu Ser Tyr Tyr Lys Gly
    210                 215                 220

Val Gln Ser Ala Leu Gln Gly Arg Gln Thr Thr Ile Val Asn Arg Cys
225                 230                 235                 240

Phe Thr Ile Ala Ala Asp Lys Ile Asn Ala Leu Lys Arg Arg Cys Asn
                245                 250                 255

Gln Leu Ile Pro Glu Met Val Lys Lys Tyr Gly Leu Ser Thr Glu Asp
            260                 265                 270

Ala Ile Gly Ser Ala Trp Val Ser Ser Asn Asp Val Val Ala Ala Leu
        275                 280                 285

Leu Trp Thr Cys Ile Asn Arg Ala Arg Tyr Pro Glu Ile Arg Glu Arg
    290                 295                 300

Ser Val His Gln Leu Pro Pro Asp Leu Leu His Ala Thr Ser Ser Leu
305                 310                 315                 320

Gly Val Pro Val Asn Val Arg Ser Arg Leu Ser Pro Pro Leu Pro Lys
                325                 330                 335

Ser Thr Leu Gly Asn Ala Val Cys Leu Leu Arg Glu Lys Val Pro Leu
            340                 345                 350

Gln Phe Phe Ala Leu Pro Ser His Ala Asn Met Glu Ala Thr Ser Ser
        355                 360                 365

Val Cys Ala Asp His Ser Gly Asp Asp Glu Trp Ala Leu Ser Phe Cys
    370                 375                 380

Arg Val Ala Tyr Gly Leu Arg Ala Lys Leu Asn Ala Ile Asp Asp Asp
385                 390                 395                 400

Tyr Ile Arg Asp Tyr Ile Ser Tyr Val Gln Lys Ser Pro Cys His Leu
                405                 410                 415

Ser Val Thr Leu Asp Thr Glu Asn Leu Tyr Leu Ser Asn Trp Arg Glu
            420                 425                 430

Ile Gly Val Tyr Asp Ala Asp Phe Gly Gly Met Leu Gly Lys Pro Leu
        435                 440                 445

Arg Met Arg Ala Pro Asp Gly Tyr Thr Asp Gly Leu Ile Phe Val Met
    450                 455                 460

Ala Gln Arg Ser Glu Asp Lys Ser Ala Pro Trp Glu Phe Asn Ile Ser
465                 470                 475                 480
```

Leu Glu Ala Ser Thr Met Lys Arg Ile Val His Asp Pro Leu Trp Cys
            485                 490                 495

Lys Tyr Val Glu Leu Asp Ala Phe Trp His Gly Glu Glu
            500                 505

<210> SEQ ID NO 128
<211> LENGTH: 1323
<212> TYPE: DNA
<213> ORGANISM: Aspergillus terreus
<220> FEATURE:
<221> NAME/KEY: misc_feature
<222> LOCATION: (1)..(1323)
<223> OTHER INFORMATION: XP_001217250 native nucleotide sequence

<400> SEQUENCE: 128

| | | |
|---|---|---|
| atggcaacct tcgaccatat cgaggatgtc atcggccagc tacctatgct gaagagctac | 60 |
| acccatatct tgctgtgctt tcccctcgct gagagccaac tcaatgaagc catcgagagc | 120 |
| cttgaatctg ctgtacgtca ggttataaaa accttttcgt tcttggctgg caaagtagtc | 180 |
| aacgaaggca agggacccaa cagctcgggt actttcaggg tcgctccctg tgagacgtgg | 240 |
| gagtccccag atcatcaatt tgtgcgagtc gttgatcgct ctttcatgct ggcctcctac | 300 |
| gatgagatcc gcggagcaca ggcacctgct tccatgctcc caggaagtca actcgggtat | 360 |
| cgggtggctt ttccagcgca ttatcacgag acagaggacg atcccgcgcc ggtcctggac | 420 |
| attcagtgca atttgatacg gggcggactg ctacttgaca tcgctgccca acacaacatt | 480 |
| atcgatgcga gcggtatctt tcaaattgcc agcttgatcg ctctttccat gcgaggcgag | 540 |
| tcaattcctg aggatgtcat caaggaaggg aaccgtgatc gacgcaatat cattccacta | 600 |
| ctagaggcag atgagcctct tcttgatcac agcgagctca agccagcag cgcggtgcaa | 660 |
| aatccgccgc ccgtcaactt cctccagggg tataaatggc aaatcttcaa gctctctgcc | 720 |
| gaggtgttaa ctcgaattac cgctgaagga cgacgacagc cacaggagtt tgtcccctcc | 780 |
| gtcacatttg tctcggcaaa cgattgcttg acagcctttc tgtggcaacg ggtgatagcc | 840 |
| atgcgcctga gcggctcca tacgcccgag gccgtatcca aactgagccg tgctgttgat | 900 |
| cttcggcggg cgatgggcat taccccagca tacatgggcc atatgattcg tgtcgcaaat | 960 |
| actagtctca cttttcaaga aattgtggca tgctctttat ccaggcttgc atctctgctc | 1020 |
| cgcaagagca tcatcgatgt cagccagccg tatgcgattc ggagctacgt gacctttatt | 1080 |
| gcaaatgaga cggataaatc aaagattgcg tatgcgggtg ctttcaatcc ttgcaccgac | 1140 |
| atgtcgtgct cgtccattgc acacatcact gctcctgaat tcggtcgttt gggagcgcct | 1200 |
| gactttataa ggaggcctac ctacgggcct ctgccgtgct gcacctatgt cgctcccgat | 1260 |
| aagaacgatg gagctttgga tcaaaaccag gcatggtcag acgttgtgaa gcgcatcggt | 1320 |
| tga | 1323 |

<210> SEQ ID NO 129
<211> LENGTH: 1323
<212> TYPE: DNA
<213> ORGANISM: Artificial Sequence
<220> FEATURE:
<223> OTHER INFORMATION: XP_001217250_codon optimized for its expression in S. cerevisiae
<220> FEATURE:
<221> NAME/KEY: CDS
<222> LOCATION: (1)..(1323)

<400> SEQUENCE: 129 atg gcc acc ttc gac cac att gag gac gtg ata gga caa ttg ccc atg    48

```
     Met Ala Thr Phe Asp His Ile Glu Asp Val Ile Gly Gln Leu Pro Met
     1               5                   10                  15 cta aag agc tac aca cat att tta ctt tgc ttt ccg ttg gca gaa tct        96
Leu Lys Ser Tyr Thr His Ile Leu Leu Cys Phe Pro Leu Ala Glu Ser
            20                  25                  30 caa ctg aac gag gcg att gaa tct ttg gag tca gca gtc aga caa gta       144
Gln Leu Asn Glu Ala Ile Glu Ser Leu Glu Ser Ala Val Arg Gln Val
                35                  40                  45 att aag acg ttt tca ttc ctt gca ggt aag gtt gtt aat gaa ggc aaa       192
Ile Lys Thr Phe Ser Phe Leu Ala Gly Lys Val Val Asn Glu Gly Lys
    50                  55                  60 ggt ccg aat tcc tct ggt acg ttc cgt gtt gct ccg tgt gaa act tgg       240
Gly Pro Asn Ser Ser Gly Thr Phe Arg Val Ala Pro Cys Glu Thr Trp
65                  70                  75                  80 gaa tct cct gat cat caa ttt gtt cgt gtt gta gat agg agc ttt atg       288
Glu Ser Pro Asp His Gln Phe Val Arg Val Val Asp Arg Ser Phe Met
                85                  90                  95 ttg gcc tcg tat gat gag atc cgt ggt gct caa gcc ccc gct tcc atg       336
Leu Ala Ser Tyr Asp Glu Ile Arg Gly Ala Gln Ala Pro Ala Ser Met
            100                 105                 110 tta cct ggg tca caa ctg ggg tat agg gta gca ttc cca gcc cat tat       384
Leu Pro Gly Ser Gln Leu Gly Tyr Arg Val Ala Phe Pro Ala His Tyr
                115                 120                 125 cat gaa act gaa gac gat cca gct cca gtt cta gat atc cag tgt aat       432
His Glu Thr Glu Asp Asp Pro Ala Pro Val Leu Asp Ile Gln Cys Asn
        130                 135                 140 ttg ata aga ggt ggt ctg ctt cta gat ata gcg gcc caa cac aac ata       480
Leu Ile Arg Gly Gly Leu Leu Leu Asp Ile Ala Ala Gln His Asn Ile
145                 150                 155                 160 att gat gct tcc ggg ata ttt caa atc gct agt ctg atc gcc tta agc       528
Ile Asp Ala Ser Gly Ile Phe Gln Ile Ala Ser Leu Ile Ala Leu Ser
                165                 170                 175 atg aga gga gaa agt atc cct gaa gat gtt atc aaa gaa gga aac aga       576
Met Arg Gly Glu Ser Ile Pro Glu Asp Val Ile Lys Glu Gly Asn Arg
            180                 185                 190 gat aga agg aat atc att ccg tta ttg gaa gcc gat gag cct tta tta       624
Asp Arg Arg Asn Ile Ile Pro Leu Leu Glu Ala Asp Glu Pro Leu Leu
        195                 200                 205 gac cat agt gaa ttg aag gca tcc agc gcc gtt cag aac ccg cca cca       672
Asp His Ser Glu Leu Lys Ala Ser Ser Ala Val Gln Asn Pro Pro Pro
    210                 215                 220 gtt aat ttc ttg caa ggt tat aaa tgg cag att ttc aaa ctg tcc gct       720
Val Asn Phe Leu Gln Gly Tyr Lys Trp Gln Ile Phe Lys Leu Ser Ala
225                 230                 235                 240 gag gta ttg acc cgt att act gcc gaa gga cgt aga caa cca caa gaa       768
Glu Val Leu Thr Arg Ile Thr Ala Glu Gly Arg Arg Gln Pro Gln Glu
                245                 250                 255 ttt gtg ccc tca gtg acc ttt gtg tcc gca aac gac tgc ttg act gct       816
Phe Val Pro Ser Val Thr Phe Val Ser Ala Asn Asp Cys Leu Thr Ala
            260                 265                 270 ttc ttg tgg cag cgt gtg ata gct atg agg cta aag aga ttg cat acc       864
Phe Leu Trp Gln Arg Val Ile Ala Met Arg Leu Lys Arg Leu His Thr
        275                 280                 285 ccc gag gcc gtt tcc aag cta tct aga gcc gtg gat tta aga agg gcc       912
Pro Glu Ala Val Ser Lys Leu Ser Arg Ala Val Asp Leu Arg Arg Ala
    290                 295                 300 atg ggt ata acc cct gca tac atg ggc cat atg ata aga gtc gca aac       960
Met Gly Ile Thr Pro Ala Tyr Met Gly His Met Ile Arg Val Ala Asn
305                 310                 315                 320
```

| | | |
|---|---|---|
| aca tcc tta acc ttt caa gaa att gtc gca tgt agt tta tca cgt ctt<br>Thr Ser Leu Thr Phe Gln Glu Ile Val Ala Cys Ser Leu Ser Arg Leu<br>                        325                    330                    335 | 1008 |
| gcg agc tta ctt aga aaa tct atc att gat gtg tcc caa cca tat gcg<br>Ala Ser Leu Leu Arg Lys Ser Ile Ile Asp Val Ser Gln Pro Tyr Ala<br>                    340                    345                    350 | 1056 |
| atc aga tca tac gtc acc ttc ata gca aac gaa aca gac aaa tct aag<br>Ile Arg Ser Tyr Val Thr Phe Ile Ala Asn Glu Thr Asp Lys Ser Lys<br>                355                    360                    365 | 1104 |
| ata gcc tat gcc ggg gca ttt aac ccg tgt act gat atg tca tgt tca<br>Ile Ala Tyr Ala Gly Ala Phe Asn Pro Cys Thr Asp Met Ser Cys Ser<br>           370                    375                    380 | 1152 |
| tcc ata gct cat att acg gca ccg gag ttt ggt agg tta ggg gcg cct<br>Ser Ile Ala His Ile Thr Ala Pro Glu Phe Gly Arg Leu Gly Ala Pro<br>385                    390                    395                    400 | 1200 |
| gac ttc att agg aga ccc act tat ggc cca cta cct tgc tgt act tac<br>Asp Phe Ile Arg Arg Pro Thr Tyr Gly Pro Leu Pro Cys Cys Thr Tyr<br>                    405                    410                    415 | 1248 |
| gta gct cct gac aag aat gac ggt gca ttg gat cag aat caa gca tgg<br>Val Ala Pro Asp Lys Asn Asp Gly Ala Leu Asp Gln Asn Gln Ala Trp<br>           420                    425                    430 | 1296 |
| tca gat gtc gta aag agg ata ggt taa<br>Ser Asp Val Val Lys Arg Ile Gly<br>          435                    440 | 1323 |

<210> SEQ ID NO 130
<211> LENGTH: 440
<212> TYPE: PRT
<213> ORGANISM: Artificial Sequence
<220> FEATURE:
<223> OTHER INFORMATION: Synthetic Construct

<400> SEQUENCE: 130

Met Ala Thr Phe Asp His Ile Glu Asp Val Ile Gly Gln Leu Pro Met
1               5                   10                  15

Leu Lys Ser Tyr Thr His Ile Leu Leu Cys Phe Pro Leu Ala Glu Ser
            20                  25                  30

Gln Leu Asn Glu Ala Ile Glu Ser Leu Glu Ser Ala Val Arg Gln Val
        35                  40                  45

Ile Lys Thr Phe Ser Phe Leu Ala Gly Lys Val Val Asn Glu Gly Lys
    50                  55                  60

Gly Pro Asn Ser Ser Gly Thr Phe Arg Val Ala Pro Cys Glu Thr Trp
65                  70                  75                  80

Glu Ser Pro Asp His Gln Phe Val Arg Val Asp Arg Ser Phe Met
            85                  90                  95

Leu Ala Ser Tyr Asp Glu Ile Arg Gly Ala Gln Ala Pro Ala Ser Met
            100                 105                 110

Leu Pro Gly Ser Gln Leu Gly Tyr Arg Val Ala Phe Pro Ala His Tyr
        115                 120                 125

His Glu Thr Glu Asp Asp Pro Ala Pro Val Leu Asp Ile Gln Cys Asn
    130                 135                 140

Leu Ile Arg Gly Gly Leu Leu Leu Asp Ile Ala Ala Gln His Asn Ile
145                 150                 155                 160

Ile Asp Ala Ser Gly Ile Phe Gln Ile Ala Ser Leu Ile Ala Leu Ser
                165                 170                 175

Met Arg Gly Glu Ser Ile Pro Glu Asp Val Ile Lys Glu Gly Asn Arg
            180                 185                 190

Asp Arg Arg Asn Ile Ile Pro Leu Leu Glu Ala Asp Glu Pro Leu Leu 195                 200                 205
Asp His Ser Glu Leu Lys Ala Ser Ser Ala Val Gln Asn Pro Pro
    210                 215                 220
Val Asn Phe Leu Gln Gly Tyr Lys Trp Gln Ile Phe Lys Leu Ser Ala
225                 230                 235                 240
Glu Val Leu Thr Arg Ile Thr Ala Glu Gly Arg Arg Gln Pro Gln Glu
                245                 250                 255
Phe Val Pro Ser Val Thr Phe Val Ser Ala Asn Asp Cys Leu Thr Ala
            260                 265                 270
Phe Leu Trp Gln Arg Val Ile Ala Met Arg Leu Lys Arg Leu His Thr
        275                 280                 285
Pro Glu Ala Val Ser Lys Leu Ser Arg Ala Val Asp Leu Arg Arg Ala
    290                 295                 300
Met Gly Ile Thr Pro Ala Tyr Met Gly His Met Ile Arg Val Ala Asn
305                 310                 315                 320
Thr Ser Leu Thr Phe Gln Glu Ile Val Ala Cys Ser Leu Ser Arg Leu
                325                 330                 335
Ala Ser Leu Leu Arg Lys Ser Ile Ile Asp Val Ser Gln Pro Tyr Ala
            340                 345                 350
Ile Arg Ser Tyr Val Thr Phe Ile Ala Asn Glu Thr Asp Lys Ser Lys
        355                 360                 365
Ile Ala Tyr Ala Gly Ala Phe Asn Pro Cys Thr Asp Met Ser Cys Ser
    370                 375                 380
Ser Ile Ala His Ile Thr Ala Pro Glu Phe Gly Arg Leu Gly Ala Pro
385                 390                 395                 400
Asp Phe Ile Arg Arg Pro Thr Tyr Gly Pro Leu Pro Cys Cys Thr Tyr
                405                 410                 415
Val Ala Pro Asp Lys Asn Asp Gly Ala Leu Asp Gln Asn Gln Ala Trp
            420                 425                 430
Ser Asp Val Val Lys Arg Ile Gly
        435                 440

<210> SEQ ID NO 131
<211> LENGTH: 1485
<212> TYPE: DNA
<213> ORGANISM: Penicillium simplicissimum
<220> FEATURE:
<221> NAME/KEY: misc_feature
<222> LOCATION: (1)..(1485)
<223> OTHER INFORMATION: Penicillium simplicissimum

<400> SEQUENCE: 131
atgtccaagc ccttattcga agcgtatcct ctcacagggc ttgatcatac gattcctcca      60
tgttatgttc gcttccttct aactttcccc gtgccggatg tggcattggc tgtcaatcag     120
ctgcaaaagg gagctgaaaa tttaatcgag aaacttcctt tcctggccgg atatttggct     180
tcatgcgaga ccccggcgt acgcccaggg cagctcgaga ttcgacctcc cgctggggaa     240
aggagacctg tctgcctcgt cgcacatcac tcgaactcct atctcgcaga ttccagtgcg     300
acgtcgacga cggaacagct gggcaccgcc aacgagaact atctccctgt cccgttcttc     360
ccggagctag acaagccggt gcccatcttc cgggttaagg tgaatgccat gacggacggc     420
atcattctgg gatttgcgtt ccaccatagc gtgatcgatg ccaccgggat gggcaccatt     480
gtccgggact ttgccagatg ctgccgtggc cctgatggcg gtccctgga aatcagtctg     540
gagtctcagc aggactctag agagaagctg agacactccg gaggacctcc cgatccgcgg     600

-continued

```
tttgaccaca atggggagta ccctctcgtg gcgtctctgc ccgccgacct cgaagccatg    660
aagcaggtct tgatccagac ggcccgtctc atgtcaacgc agtatttccg catccctgcc    720
agcctagtta acacgctaaa ggaatcctgc aatcggatgc ttcgggaatc accagcgctc    780
agggacgaag gggagaatcc atggatttcg agcaacgatc tggtggtgtc gctgttgtgg    840
ctgtgtctga atcgcgttcg gtatcctgaa gataatacca acgtcattcc tccttccgat    900
tcctcggtct gcatggccgt gaatatccga gggcgtttgc agtcgcccat tgatccagga    960
tacgttggca acgccatcgt ccttctccgg gagagcgttg gcatgaatgc tttctgcat   1020 aaaccgggcg acgatgatcc cctgggcgcc aatgttacg aaacagcgaa acggctaggc   1080
cgagaagcgt gggaagcagc cctggtgcgc atcgccctgg ccatccgccg caagctcaac   1140
accataaacg cgagttacgt gcgcagtgtt atatcctatc tggaggacgt gcccgacctg   1200
tccactgtgg cgtttggcca gacggactac cacatcagca gctggcggga tattggcgtc   1260
tacgaggctg attttggtgg ccacatgggc catcccagcg aaatgcgagt accagatggg   1320
atggtcgatg gcatgtttta catcttacct cgaaggcagg aacacaccc ttgctgggag   1380 atccatgtta ctatccacca ggacacaatg aagcgactca ttgcagaccc tgtgtgggca   1440
cgatatacag tgagaaagcc ttcatcactc tgccgggatg aatga                  1485
```

<210> SEQ ID NO 132
<211> LENGTH: 1485
<212> TYPE: DNA
<213> ORGANISM: Artificial Sequence
<220> FEATURE:
<223> OTHER INFORMATION: BAU61551_codon optimized for its expression in
      S. cerevisiae
<220> FEATURE:
<221> NAME/KEY: CDS
<222> LOCATION: (1)..(1485)

<400> SEQUENCE: 132

```
atg tca aag cct ctg ttt gaa gca tac ccc cta act ggt cta gat cat     48
Met Ser Lys Pro Leu Phe Glu Ala Tyr Pro Leu Thr Gly Leu Asp His
1               5                  10                  15 act ata ccc cct tgt tac gtc agg ttc tta tta act ttc cca gtt cca     96
Thr Ile Pro Pro Cys Tyr Val Arg Phe Leu Leu Thr Phe Pro Val Pro
            20                  25                  30 gat gta gcc ctt gct gtt aac caa tta cag aaa ggc gcc gaa aat tta    144
Asp Val Ala Leu Ala Val Asn Gln Leu Gln Lys Gly Ala Glu Asn Leu
        35                  40                  45 ata gag aaa ttg cct ttt ctt gca ggg tac cta gct agc tgt gaa aca    192
Ile Glu Lys Leu Pro Phe Leu Ala Gly Tyr Leu Ala Ser Cys Glu Thr
    50                  55                  60 cct ggc gta aga ccg ggg cag tta gaa atc agg cca cca gca ggt gaa    240
Pro Gly Val Arg Pro Gly Gln Leu Glu Ile Arg Pro Pro Ala Gly Glu
65                  70                  75                  80 aga aga cca gtg tgt ttg gtc gca cat cac agt aac tcg tac ctt gcg    288
Arg Arg Pro Val Cys Leu Val Ala His His Ser Asn Ser Tyr Leu Ala
                85                  90                  95 gat tct tct gca aca agt acg acg gag caa ttg gga aca gct aac gaa    336
Asp Ser Ser Ala Thr Ser Thr Thr Glu Gln Leu Gly Thr Ala Asn Glu
            100                 105                 110 aat tac ctt ccc gta cca ttc ttt cca gag ttg gac aaa cct gtt cca    384
Asn Tyr Leu Pro Val Pro Phe Phe Pro Glu Leu Asp Lys Pro Val Pro
        115                 120                 125 ata ttc cgt gtc aaa gtt aac gct atg aca gat ggg att atc ttg ggg    432
Ile Phe Arg Val Lys Val Asn Ala Met Thr Asp Gly Ile Ile Leu Gly
    130                 135                 140
```

```
ttc gct ttc cac cat agt gta ata gat gct acg gga atg ggt aca ata    480
Phe Ala Phe His His Ser Val Ile Asp Ala Thr Gly Met Gly Thr Ile
145                 150                 155                 160 gtt agg gac ttc gcc agg tgc tgc aga ggt cct gat ggt ggg ccc tta    528
Val Arg Asp Phe Ala Arg Cys Cys Arg Gly Pro Asp Gly Gly Pro Leu
                165                 170                 175 gag ata agt cta gaa agc caa caa gat tcg aga gaa aag ctg agg cac    576
Glu Ile Ser Leu Glu Ser Gln Gln Asp Ser Arg Glu Lys Leu Arg His
            180                 185                 190 tca ggc ggt ccg cca gat ccc aga ttc gat cat aac gga gaa tac cca    624
Ser Gly Gly Pro Pro Asp Pro Arg Phe Asp His Asn Gly Glu Tyr Pro
        195                 200                 205 ttg gtg gcc tca ctg cca gcg gac tta gaa gct atg aaa caa gtt tta    672
Leu Val Ala Ser Leu Pro Ala Asp Leu Glu Ala Met Lys Gln Val Leu
    210                 215                 220 atc caa aca gcg agg ctg atg agt aca caa tac ttt aga ata cct gct    720
Ile Gln Thr Ala Arg Leu Met Ser Thr Gln Tyr Phe Arg Ile Pro Ala
225                 230                 235                 240 agc ctt gtg aac act tta aaa gag tca tgt aat aga atg ctt cgt gaa    768
Ser Leu Val Asn Thr Leu Lys Glu Ser Cys Asn Arg Met Leu Arg Glu
                245                 250                 255 tcc cct gca ctg agg gat gaa ggt gaa aac ccg tgg att agt tct aac    816
Ser Pro Ala Leu Arg Asp Glu Gly Glu Asn Pro Trp Ile Ser Ser Asn
            260                 265                 270 gat tta gta gtg agt cta ctg tgg ctt tgt ttg aac agg gtg agg tac    864
Asp Leu Val Val Ser Leu Leu Trp Leu Cys Leu Asn Arg Val Arg Tyr
        275                 280                 285 ccc gaa gac aat aca aat gtg att cca ccc tct gac agt tct gtt tgc    912
Pro Glu Asp Asn Thr Asn Val Ile Pro Pro Ser Asp Ser Ser Val Cys
    290                 295                 300 atg gct gta aat ata aga ggg aga tta cag tcg ccg atc gat cca ggt    960
Met Ala Val Asn Ile Arg Gly Arg Leu Gln Ser Pro Ile Asp Pro Gly
305                 310                 315                 320 tat gtt ggt aat gct att gta tta tta aga gaa tct gtt gga atg aat   1008
Tyr Val Gly Asn Ala Ile Val Leu Leu Arg Glu Ser Val Gly Met Asn
                325                 330                 335 gcc ttt cta cat aaa cct ggt gat gac gac ccg ctt ggt gcc caa tgt   1056
Ala Phe Leu His Lys Pro Gly Asp Asp Asp Pro Leu Gly Ala Gln Cys
            340                 345                 350 tac gag aca gct aaa aga ctt gga aga gaa gca tgg gaa gca gca tta   1104
Tyr Glu Thr Ala Lys Arg Leu Gly Arg Glu Ala Trp Glu Ala Ala Leu
        355                 360                 365 gtc agg att gct ttg gca att agg cgt aag ttg aac act att aat gct   1152
Val Arg Ile Ala Leu Ala Ile Arg Arg Lys Leu Asn Thr Ile Asn Ala
    370                 375                 380 tcc tat gtc aga tca gtt att agc tac tta gag gat gtg ccc gat cta   1200
Ser Tyr Val Arg Ser Val Ile Ser Tyr Leu Glu Asp Val Pro Asp Leu
385                 390                 395                 400 tca acc gtt gcc ttc ggg caa act gat tat cat atc tcc agt tgg aga   1248
Ser Thr Val Ala Phe Gly Gln Thr Asp Tyr His Ile Ser Ser Trp Arg
                405                 410                 415 gac att gga gtt tac gag gct gac ttt ggt ggt cat atg ggc cat cca   1296
Asp Ile Gly Val Tyr Glu Ala Asp Phe Gly Gly His Met Gly His Pro
            420                 425                 430 tct gag atg aga gtc cct gac ggg atg gtc gat ggt atg ttt tac ata   1344
Ser Glu Met Arg Val Pro Asp Gly Met Val Asp Gly Met Phe Tyr Ile
        435                 440                 445 cta cct aga aga caa ggt act cac cca tgt tgg gaa att cat gtg act   1392
Leu Pro Arg Arg Gln Gly Thr His Pro Cys Trp Glu Ile His Val Thr
```

```
                    450                 455                 460
ata cac cag gat acc atg aaa aga ctg atc gct gat ccg gtt tgg gca      1440
Ile His Gln Asp Thr Met Lys Arg Leu Ile Ala Asp Pro Val Trp Ala
465                 470                 475                 480 aga tat acc gtt aga aag cct agt tct ttg tgc agg gac gag taa          1485
Arg Tyr Thr Val Arg Lys Pro Ser Ser Leu Cys Arg Asp Glu
                485                 490

<210> SEQ ID NO 133
<211> LENGTH: 494
<212> TYPE: PRT
<213> ORGANISM: Artificial Sequence
<220> FEATURE:
<223> OTHER INFORMATION: Synthetic Construct

<400> SEQUENCE: 133

Met Ser Lys Pro Leu Phe Glu Ala Tyr Pro Leu Thr Gly Leu Asp His
1               5                   10                  15

Thr Ile Pro Pro Cys Tyr Val Arg Phe Leu Leu Thr Phe Pro Val Pro
            20                  25                  30

Asp Val Ala Leu Ala Val Asn Gln Leu Gln Lys Gly Ala Glu Asn Leu
        35                  40                  45

Ile Glu Lys Leu Pro Phe Leu Ala Gly Tyr Leu Ala Ser Cys Glu Thr
    50                  55                  60

Pro Gly Val Arg Pro Gly Gln Leu Glu Ile Arg Pro Pro Ala Gly Glu
65                  70                  75                  80

Arg Arg Pro Val Cys Leu Val Ala His His Ser Asn Ser Tyr Leu Ala
                85                  90                  95

Asp Ser Ser Ala Thr Ser Thr Thr Glu Gln Leu Gly Thr Ala Asn Glu
            100                 105                 110

Asn Tyr Leu Pro Val Pro Phe Phe Pro Glu Leu Asp Lys Pro Val Pro
        115                 120                 125

Ile Phe Arg Val Lys Val Asn Ala Met Thr Asp Gly Ile Ile Leu Gly
    130                 135                 140

Phe Ala Phe His His Ser Val Ile Asp Ala Thr Gly Met Gly Thr Ile
145                 150                 155                 160

Val Arg Asp Phe Ala Arg Cys Cys Arg Gly Pro Asp Gly Gly Pro Leu
                165                 170                 175

Glu Ile Ser Leu Glu Ser Gln Gln Asp Ser Arg Glu Lys Leu Arg His
            180                 185                 190

Ser Gly Gly Pro Pro Asp Pro Arg Phe Asp His Asn Gly Glu Tyr Pro
        195                 200                 205

Leu Val Ala Ser Leu Pro Ala Asp Leu Glu Ala Met Lys Gln Val Leu
    210                 215                 220

Ile Gln Thr Ala Arg Leu Met Ser Thr Gln Tyr Phe Arg Ile Pro Ala
225                 230                 235                 240

Ser Leu Val Asn Thr Leu Lys Glu Ser Cys Asn Arg Met Leu Arg Glu
                245                 250                 255

Ser Pro Ala Leu Arg Asp Glu Gly Glu Asn Pro Trp Ile Ser Ser Asn
            260                 265                 270

Asp Leu Val Val Ser Leu Leu Trp Leu Cys Leu Asn Arg Val Arg Tyr
        275                 280                 285

Pro Glu Asp Asn Thr Asn Val Ile Pro Pro Ser Asp Ser Ser Val Cys
    290                 295                 300

Met Ala Val Asn Ile Arg Gly Arg Leu Gln Ser Pro Ile Asp Pro Gly
305                 310                 315                 320
```

Tyr Val Gly Asn Ala Ile Val Leu Leu Arg Glu Ser Val Gly Met Asn
            325                 330                 335

Ala Phe Leu His Lys Pro Gly Asp Asp Pro Leu Gly Ala Gln Cys
            340                 345                 350

Tyr Glu Thr Ala Lys Arg Leu Gly Arg Glu Ala Trp Glu Ala Ala Leu
            355                 360                 365

Val Arg Ile Ala Leu Ala Ile Arg Arg Lys Leu Asn Thr Ile Asn Ala
    370                 375                 380

Ser Tyr Val Arg Ser Val Ile Ser Tyr Leu Glu Asp Val Pro Asp Leu
385                 390                 395                 400

Ser Thr Val Ala Phe Gly Gln Thr Asp Tyr His Ile Ser Ser Trp Arg
            405                 410                 415

Asp Ile Gly Val Tyr Glu Ala Asp Phe Gly Gly His Met Gly His Pro
            420                 425                 430

Ser Glu Met Arg Val Pro Asp Gly Met Val Asp Gly Met Phe Tyr Ile
            435                 440                 445

Leu Pro Arg Arg Gln Gly Thr His Pro Cys Trp Glu Ile His Val Thr
    450                 455                 460

Ile His Gln Asp Thr Met Lys Arg Leu Ile Ala Asp Pro Val Trp Ala
465                 470                 475                 480

Arg Tyr Thr Val Arg Lys Pro Ser Ser Leu Cys Arg Asp Glu
            485                 490

<210> SEQ ID NO 134
<211> LENGTH: 1425
<212> TYPE: DNA
<213> ORGANISM: Papaver somniferum
<220> FEATURE:
<221> NAME/KEY: misc_feature
<222> LOCATION: (1)..(1425)
<223> OTHER INFORMATION: PsSalAT native nucleotide sequence

<400> SEQUENCE: 134

| | | | | | |
|---|---|---|---|---|---|
| atggcaacaa | tgtatagtgc | tgctgttgaa | gtgatctcta | aggaaaccat | taaacccaca | 60 |
| actccaaccc | catctcaact | taaaaacttc | aatctgtcac | ttctcgatca | atgttttcct | 120 |
| ttatattatt | atgttccaat | cattcttttc | tacccagcca | ccgccgctaa | tagtaccggt | 180 |
| agcagtaacc | atcatgatga | tcttgacttg | cttaagagtt | ctctttccaa | aacactagtt | 240 |
| cacttttatc | caatggctgg | taggatgata | gacaatattc | tggtcgactg | tcatgaccaa | 300 |
| gggattaact | tttacaaagt | taaaattaga | ggtaaaatgt | gtgagttcat | gtcgcaaccg | 360 |
| gatgtgccac | taagccagct | tcttccctct | gaagttgttt | ccgcgagtgt | ccctaaggaa | 420 |
| gcactggtga | tcgttcaagt | gaacatgttt | gactgtggtg | aacagccat | ttgttcgagt | 480 |
| gtatcacata | agattgccga | tgcagctaca | atgagtacgt | tcattcgtag | ttgggcaagc | 540 |
| accactaaaa | catctcgtag | tggggggttca | actgctgccg | ttacagatca | gaaattgatt | 600 |
| ccttctttcg | actcggcatc | tctattccca | cctagtgaac | gattgacatc | tccatcaggg | 660 |
| atgtcagaga | taccattttc | cagtaccccca | gaggatacag | aagatgataa | aactgtcagc | 720 |
| aagagatttg | tgttcgattt | tgcaaagata | acatctgtac | gtgaaaagtt | gcaagtattg | 780 |
| atgcatgata | actacaaaag | ccgcaggcaa | acaagggttg | aggtggttac | ttctctaata | 840 |
| tggaagtccg | tgatgaaatc | cactccagcc | ggttttttac | cagtggtaca | tcatgccgtg | 900 |
| aaccttagaa | agaaaatgga | cccaccatta | caagatgttt | cattcggaaa | tctatctgta | 960 |
| actgtttcgg | cgttcttacc | agcaacaaca | acgacaacaa | caaatgcggt | caacaagaca | 1020 |

```
atcaatagta cgagtagtga atcacaagtg gtacttcatg agttacatga ttttatagct   1080
cagatgagga gtgaaataga taaggtcaag ggtgataaag gtagcttgga gaaagtcatt   1140
caaaattttg cttctggtca tgatgcttca ataagaaaaa tcaatgatgt tgaagtgata   1200 aactttttgga taagtagctg gtgcaggatg ggattatacg agattgattt tggttgggga   1260
aagccaattt gggtaacagt tgatccaaat atcaagccga acaagaattg ttttttcatg   1320
aatgatacga aatgtggtga aggaataga gtttgggcga gctttcttga ggatgatatg   1380
gctaagttcg agcttcacct aagtgaaatc cttgaattga tttga                   1425
```

<210> SEQ ID NO 135
<211> LENGTH: 1425
<212> TYPE: DNA
<213> ORGANISM: Artificial Sequence
<220> FEATURE:
<223> OTHER INFORMATION: PsSalAT_codon optimized for its expression in S. cerevisiae
<220> FEATURE:
<221> NAME/KEY: CDS
<222> LOCATION: (1)..(1425)

<400> SEQUENCE: 135

```
atg gca aca atg tac tca gct gca gtt gag gtt ata tct aag gaa acg    48
Met Ala Thr Met Tyr Ser Ala Ala Val Glu Val Ile Ser Lys Glu Thr
1               5                   10                  15 ata aaa cca acc act cca acc cca agc caa ttg aag aat ttc aat tta    96
Ile Lys Pro Thr Thr Pro Thr Pro Ser Gln Leu Lys Asn Phe Asn Leu
            20                  25                  30 tct tta tta gac cag tgc ttt ccc ttg tac tac tat gtc ccc atc atc   144
Ser Leu Leu Asp Gln Cys Phe Pro Leu Tyr Tyr Tyr Val Pro Ile Ile
        35                  40                  45 ttg ttc tac cct gcg act gct gca aac tcc act ggt tcc tcg aac cac   192
Leu Phe Tyr Pro Ala Thr Ala Ala Asn Ser Thr Gly Ser Ser Asn His
50                  55                  60 cat gat gat cta gat ctt ctg aag agc tcc ctt agc aag aca ctt gtt   240
His Asp Asp Leu Asp Leu Leu Lys Ser Ser Leu Ser Lys Thr Leu Val
65                  70                  75                  80 cac ttc tac cct atg gcc ggt agg atg atc gat aac ata ttg gtt gac   288
His Phe Tyr Pro Met Ala Gly Arg Met Ile Asp Asn Ile Leu Val Asp
                85                  90                  95 tgc cac gat cag ggt atc aat ttc tat aaa gtt aaa atc agg ggc aag   336
Cys His Asp Gln Gly Ile Asn Phe Tyr Lys Val Lys Ile Arg Gly Lys
            100                 105                 110 atg tgt gaa ttc atg tct cag cct gat gtg cca ctg tcg cag ctg cta   384
Met Cys Glu Phe Met Ser Gln Pro Asp Val Pro Leu Ser Gln Leu Leu
        115                 120                 125 cct agt gaa gtg gta tcc gca tct gtc cca aaa gag gcc ttg gtc ata   432
Pro Ser Glu Val Val Ser Ala Ser Val Pro Lys Glu Ala Leu Val Ile
130                 135                 140 gtc caa gtt aat atg ttc gat tgc ggt ggg acg gcc atc tgc tcg tcg   480
Val Gln Val Asn Met Phe Asp Cys Gly Gly Thr Ala Ile Cys Ser Ser
145                 150                 155                 160 gtc agt cat aag atc gca gac gcc gca acc atg tca aca ttt att aga   528
Val Ser His Lys Ile Ala Asp Ala Ala Thr Met Ser Thr Phe Ile Arg
                165                 170                 175 tct tgg gcg agt acc acc aaa act tca agg tct ggg ggg tca acc gcc   576
Ser Trp Ala Ser Thr Thr Lys Thr Ser Arg Ser Gly Gly Ser Thr Ala
            180                 185                 190 gct gtt act gac cag aag ttg att cct agc ttt gat tcg gca agc tta   624
Ala Val Thr Asp Gln Lys Leu Ile Pro Ser Phe Asp Ser Ala Ser Leu
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 195 |     |     |     |     | 200 |     |     |     |     | 205 |     |     |     |      |
| ttc | cca | cct | tcc | gaa | agg | ttg | act | tca | cca | agc | ggg | atg | tct | gag | ata | 672  |
| Phe | Pro | Pro | Ser | Glu | Arg | Leu | Thr | Ser | Pro | Ser | Gly | Met | Ser | Glu | Ile |      |
| 210 |     |     |     |     | 215 |     |     |     |     | 220 |     |     |     |     |     |      |
| cca | ttt | tct | tca | acc | cct | gaa | gat | acc | gag | gac | gac | aaa | aca | gtt | agc | 720  |
| Pro | Phe | Ser | Ser | Thr | Pro | Glu | Asp | Thr | Glu | Asp | Asp | Lys | Thr | Val | Ser |      |
| 225 |     |     |     |     | 230 |     |     |     |     | 235 |     |     |     |     | 240 |      |
| aaa | aga | ttc | gtg | ttt | gac | ttt | gca | aag | ata | aca | tct | gtt | aga | gaa | aag | 768  |
| Lys | Arg | Phe | Val | Phe | Asp | Phe | Ala | Lys | Ile | Thr | Ser | Val | Arg | Glu | Lys |      |
|     |     |     |     | 245 |     |     |     |     | 250 |     |     |     |     | 255 |     |      |
| ctt | cag | gta | tta | atg | cac | gac | aac | tac | aaa | agc | agg | cgt | cag | acc | agg | 816  |
| Leu | Gln | Val | Leu | Met | His | Asp | Asn | Tyr | Lys | Ser | Arg | Arg | Gln | Thr | Arg |      |
|     |     |     | 260 |     |     |     |     | 265 |     |     |     |     | 270 |     |     |      |
| gtt | gag | gtc | gta | acg | agc | ctg | atc | tgg | aag | agt | gtc | atg | aag | tca | aca | 864  |
| Val | Glu | Val | Val | Thr | Ser | Leu | Ile | Trp | Lys | Ser | Val | Met | Lys | Ser | Thr |      |
|     |     | 275 |     |     |     |     | 280 |     |     |     |     | 285 |     |     |     |      |
| cca | gct | ggg | ttc | ctt | ccc | gtc | gtg | cat | cat | gcg | gta | aat | ttg | agg | aag | 912  |
| Pro | Ala | Gly | Phe | Leu | Pro | Val | Val | His | His | Ala | Val | Asn | Leu | Arg | Lys |      |
| 290 |     |     |     |     | 295 |     |     |     |     | 300 |     |     |     |     |     |      |
| aag | atg | gac | cca | cca | ttg | cag | gat | gtc | tcc | ttc | ggc | aac | ctg | agt | gtt | 960  |
| Lys | Met | Asp | Pro | Pro | Leu | Gln | Asp | Val | Ser | Phe | Gly | Asn | Leu | Ser | Val |      |
| 305 |     |     |     |     | 310 |     |     |     |     | 315 |     |     |     |     | 320 |      |
| act | gtc | tca | gca | ttc | ttg | ccc | gcc | aca | act | acc | acc | acc | aca | aat | gcc | 1008 |
| Thr | Val | Ser | Ala | Phe | Leu | Pro | Ala | Thr | Thr | Thr | Thr | Thr | Thr | Asn | Ala |      |
|     |     |     |     | 325 |     |     |     |     | 330 |     |     |     |     | 335 |     |      |
| gtt | aat | aag | aca | ata | aat | tca | act | tca | tcg | gag | agt | cag | gtg | gtg | cta | 1056 |
| Val | Asn | Lys | Thr | Ile | Asn | Ser | Thr | Ser | Ser | Glu | Ser | Gln | Val | Val | Leu |      |
|     |     |     | 340 |     |     |     |     | 345 |     |     |     |     | 350 |     |     |      |
| cat | gaa | ttg | cac | gat | ttt | atc | gca | caa | atg | aga | agt | gag | ata | gac | aaa | 1104 |
| His | Glu | Leu | His | Asp | Phe | Ile | Ala | Gln | Met | Arg | Ser | Glu | Ile | Asp | Lys |      |
|     |     | 355 |     |     |     |     | 360 |     |     |     |     | 365 |     |     |     |      |
| gtt | aaa | ggc | gat | aag | ggt | agc | cta | gaa | aag | gtg | att | cag | aac | ttt | gcc | 1152 |
| Val | Lys | Gly | Asp | Lys | Gly | Ser | Leu | Glu | Lys | Val | Ile | Gln | Asn | Phe | Ala |      |
| 370 |     |     |     |     | 375 |     |     |     |     | 380 |     |     |     |     |     |      |
| tct | ggt | cat | gac | gct | tca | ata | aag | aaa | ata | aat | gac | gta | gag | gtc | ata | 1200 |
| Ser | Gly | His | Asp | Ala | Ser | Ile | Lys | Lys | Ile | Asn | Asp | Val | Glu | Val | Ile |      |
| 385 |     |     |     |     | 390 |     |     |     |     | 395 |     |     |     |     | 400 |      |
| aat | ttc | tgg | ata | tct | tca | tgg | tgc | aga | atg | ggc | ttg | tat | gag | atc | gac | 1248 |
| Asn | Phe | Trp | Ile | Ser | Ser | Trp | Cys | Arg | Met | Gly | Leu | Tyr | Glu | Ile | Asp |      |
|     |     |     |     | 405 |     |     |     |     | 410 |     |     |     |     | 415 |     |      |
| ttc | ggc | tgg | ggc | aag | ccg | att | tgg | gtt | aca | gtt | gac | cct | aat | atc | aag | 1296 |
| Phe | Gly | Trp | Gly | Lys | Pro | Ile | Trp | Val | Thr | Val | Asp | Pro | Asn | Ile | Lys |      |
|     |     |     | 420 |     |     |     |     | 425 |     |     |     |     | 430 |     |     |      |
| cca | aat | aag | aat | tgc | ttc | ttt | atg | aac | gac | aca | aaa | tgc | gga | gaa | gga | 1344 |
| Pro | Asn | Lys | Asn | Cys | Phe | Phe | Met | Asn | Asp | Thr | Lys | Cys | Gly | Glu | Gly |      |
|     |     | 435 |     |     |     |     | 440 |     |     |     |     | 445 |     |     |     |      |
| ata | gag | gta | tgg | gca | agc | ttc | ctg | gaa | gac | gac | atg | gcc | aag | ttt | gaa | 1392 |
| Ile | Glu | Val | Trp | Ala | Ser | Phe | Leu | Glu | Asp | Asp | Met | Ala | Lys | Phe | Glu |      |
|     | 450 |     |     |     |     | 455 |     |     |     |     | 460 |     |     |     |     |      |
| ttg | cac | tta | tcg | gag | ata | ttg | gaa | ttg | atc | taa |     |     |     |     |     | 1425 |
| Leu | His | Leu | Ser | Glu | Ile | Leu | Glu | Leu | Ile |     |     |     |     |     |     |      |
| 465 |     |     |     | 470 |     |     |     |     |     |     |     |     |     |     |     |      |

<210> SEQ ID NO 136
<211> LENGTH: 474
<212> TYPE: PRT
<213> ORGANISM: Artificial Sequence
<220> FEATURE:
<223> OTHER INFORMATION: Synthetic Construct

<400> SEQUENCE: 136

-continued

```
Met Ala Thr Met Tyr Ser Ala Ala Val Glu Val Ile Ser Lys Glu Thr
1               5                   10                  15

Ile Lys Pro Thr Thr Pro Thr Pro Ser Gln Leu Lys Asn Phe Asn Leu
                20                  25                  30

Ser Leu Leu Asp Gln Cys Phe Pro Leu Tyr Tyr Val Pro Ile Ile
            35                  40                  45

Leu Phe Tyr Pro Ala Thr Ala Ala Asn Ser Thr Gly Ser Ser Asn His
    50                  55                  60

His Asp Asp Leu Asp Leu Leu Lys Ser Ser Leu Ser Lys Thr Leu Val
65                  70                  75                  80

His Phe Tyr Pro Met Ala Gly Arg Met Ile Asp Asn Ile Leu Val Asp
                85                  90                  95

Cys His Asp Gln Gly Ile Asn Phe Tyr Lys Val Lys Ile Arg Gly Lys
            100                 105                 110

Met Cys Glu Phe Met Ser Gln Pro Asp Val Pro Leu Ser Gln Leu Leu
            115                 120                 125

Pro Ser Glu Val Val Ser Ala Ser Val Pro Lys Glu Ala Leu Val Ile
    130                 135                 140

Val Gln Val Asn Met Phe Asp Cys Gly Gly Thr Ala Ile Cys Ser Ser
145                 150                 155                 160

Val Ser His Lys Ile Ala Asp Ala Ala Thr Met Ser Thr Phe Ile Arg
                165                 170                 175

Ser Trp Ala Ser Thr Thr Lys Thr Ser Arg Ser Gly Gly Ser Thr Ala
            180                 185                 190

Ala Val Thr Asp Gln Lys Leu Ile Pro Ser Phe Asp Ser Ala Ser Leu
            195                 200                 205

Phe Pro Pro Ser Glu Arg Leu Thr Ser Pro Ser Gly Met Ser Glu Ile
    210                 215                 220

Pro Phe Ser Ser Thr Pro Glu Asp Thr Glu Asp Lys Thr Val Ser
225                 230                 235                 240

Lys Arg Phe Val Phe Asp Phe Ala Lys Ile Thr Ser Val Arg Glu Lys
                245                 250                 255

Leu Gln Val Leu Met His Asp Asn Tyr Lys Ser Arg Arg Gln Thr Arg
            260                 265                 270

Val Glu Val Val Thr Ser Leu Ile Trp Lys Ser Val Met Lys Ser Thr
            275                 280                 285

Pro Ala Gly Phe Leu Pro Val Val His His Ala Val Asn Leu Arg Lys
    290                 295                 300

Lys Met Asp Pro Pro Leu Gln Asp Val Ser Phe Gly Asn Leu Ser Val
305                 310                 315                 320

Thr Val Ser Ala Phe Leu Pro Ala Thr Thr Thr Thr Thr Asn Ala
                325                 330                 335

Val Asn Lys Thr Ile Asn Ser Thr Ser Ser Glu Ser Gln Val Val Leu
            340                 345                 350

His Glu Leu His Asp Phe Ile Ala Gln Met Arg Ser Glu Ile Asp Lys
            355                 360                 365

Val Lys Gly Asp Lys Gly Ser Leu Glu Lys Val Ile Gln Asn Phe Ala
    370                 375                 380

Ser Gly His Asp Ala Ser Ile Lys Lys Ile Asn Asp Val Glu Val Ile
385                 390                 395                 400

Asn Phe Trp Ile Ser Ser Trp Cys Arg Met Gly Leu Tyr Glu Ile Asp
                405                 410                 415
```

```
Phe Gly Trp Gly Lys Pro Ile Trp Val Thr Val Asp Pro Asn Ile Lys
            420                 425                 430

Pro Asn Lys Asn Cys Phe Phe Met Asn Asp Thr Lys Cys Gly Glu Gly
        435                 440                 445

Ile Glu Val Trp Ala Ser Phe Leu Glu Asp Asp Met Ala Lys Phe Glu
    450                 455                 460

Leu His Leu Ser Glu Ile Leu Glu Leu Ile
465                 470

<210> SEQ ID NO 137
<211> LENGTH: 1443
<212> TYPE: DNA
<213> ORGANISM: Artificial Sequence
<220> FEATURE:
<223> OTHER INFORMATION: AstC_codon optimized for its expression in S.
      cerevisiae
<220> FEATURE:
<221> NAME/KEY: CDS
<222> LOCATION: (1)..(1443)

<400> SEQUENCE: 137 atg act aag atc aac cca tac aag ggt atc ttg gtt gaa ttg aag gac      48
Met Thr Lys Ile Asn Pro Tyr Lys Gly Ile Leu Val Glu Leu Lys Asp
1               5                   10                  15 atc gtt ttc act tct tct tct gac caa atc aag ttg cca atc aac act     96
Ile Val Phe Thr Ser Ser Ser Asp Gln Ile Lys Leu Pro Ile Asn Thr
                20                  25                  30 ttc aag tct atc ttg tgt tgt ggt gct act gct caa tac caa tgt ggt    144
Phe Lys Ser Ile Leu Cys Cys Gly Ala Thr Ala Gln Tyr Gln Cys Gly
            35                  40                  45 aag atc aac aga gct caa tac tac tct aga ttg gct aga gac ttc gct    192
Lys Ile Asn Arg Ala Gln Tyr Tyr Ser Arg Leu Ala Arg Asp Phe Ala
        50                  55                  60 ttg tct ttg gct gac gtt act gct ttg ttc gac act gtt caa gct act    240
Leu Ser Leu Ala Asp Val Thr Ala Leu Phe Asp Thr Val Gln Ala Thr
65                  70                  75                  80 atc aga cca gaa gaa tct ttc ttg gct ttc ttg gct gaa ttg aag tct    288
Ile Arg Pro Glu Glu Ser Phe Leu Ala Phe Leu Ala Glu Leu Lys Ser
                85                  90                  95 aga ttc ggt gaa caa ttg aag ttg tac gct gtt gct aac atg tct aga    336
Arg Phe Gly Glu Gln Leu Lys Leu Tyr Ala Val Ala Asn Met Ser Arg
            100                 105                 110 gaa gac tac gct atg ttg aag tct ttg cca atc gac tgg tct ttg ttc    384
Glu Asp Tyr Ala Met Leu Lys Ser Leu Pro Ile Asp Trp Ser Leu Phe
        115                 120                 125 gac ggt gtt ttc ttg tct gct gac ttg ggt atg aga aag cca gaa ttg    432
Asp Gly Val Phe Leu Ser Ala Asp Leu Gly Met Arg Lys Pro Glu Leu
    130                 135                 140 aga ttc ttc aga cac gtt ttg gaa tct atc tct atg aag cca gaa gac    480
Arg Phe Phe Arg His Val Leu Glu Ser Ile Ser Met Lys Pro Glu Asp
145                 150                 155                 160 act atc ttg gtt gac aac gac act gac aac atc ttg tgt gct ttg tct    528
Thr Ile Leu Val Asp Asn Asp Thr Asp Asn Ile Leu Cys Ala Leu Ser
                165                 170                 175 atg ggt ttg aag ggt atc ttg ttc ggt tct act tct gtt cca caa gct    576
Met Gly Leu Lys Gly Ile Leu Phe Gly Ser Thr Ser Val Pro Gln Ala
            180                 185                 190 ttg act aac ttg ttg gaa tac gac cac atc tct aga gct gaa caa ttc    624
Leu Thr Asn Leu Leu Glu Tyr Asp His Ile Ser Arg Ala Glu Gln Phe
        195                 200                 205 ttg aga tct cac gct aag tct ttg cac tct gtt act cac act ggt gtt    672
```

```
Leu Arg Ser His Ala Lys Ser Leu His Ser Val Thr His Gly Val
    210                 215                 220 act atc aga gaa aac ttc gct caa ttg ttg atc ttg gaa gct act ggt     720
Thr Ile Arg Glu Asn Phe Ala Gln Leu Leu Ile Leu Glu Ala Thr Gly
225                 230                 235                 240 gac atc gac ttg gtt gaa ttg gaa tac cac cca act act tgg aac tac     768
Asp Ile Asp Leu Val Glu Leu Glu Tyr His Pro Thr Thr Trp Asn Tyr
                245                 250                 255 ttc atc ggt act cca gtt ttg act caa act gaa ttc cca cac gac ttg     816
Phe Ile Gly Thr Pro Val Leu Thr Gln Thr Glu Phe Pro His Asp Leu
            260                 265                 270 gac act act tct ttg gct act act gtt ttg gac aga cca aag gac atc     864
Asp Thr Thr Ser Leu Ala Thr Thr Val Leu Asp Arg Pro Lys Asp Ile
        275                 280                 285 gct aac gaa atc atg gac gaa atg ttg aag tac aga tct gac gac gac     912
Ala Asn Glu Ile Met Asp Glu Met Leu Lys Tyr Arg Ser Asp Asp Asp
    290                 295                 300 ttg atg ttg act ttc ttc act gac ttc aag aac aga gtt gac cca gtt     960
Leu Met Leu Thr Phe Phe Thr Asp Phe Lys Asn Arg Val Asp Pro Val
305                 310                 315                 320 gtt tgt tgt aac gtt ttg tct ttg ttc tac aag tac ggt aga ggt cac    1008
Val Cys Cys Asn Val Leu Ser Leu Phe Tyr Lys Tyr Gly Arg Gly His
                325                 330                 335 gaa ttg cac cac act ttg gct tgg gtt aga caa gtt ttg atc aga aga    1056
Glu Leu His His Thr Leu Ala Trp Val Arg Gln Val Leu Ile Arg Arg
            340                 345                 350 gct tac atc aac ggt act gct ttc tac cca atg cca gaa gct ttc ttg    1104
Ala Tyr Ile Asn Gly Thr Ala Phe Tyr Pro Met Pro Glu Ala Phe Leu
        355                 360                 365 tac ttc ttc ttc aga ttc ttg caa cac atc act cac ttg cca caa ttg    1152
Tyr Phe Phe Phe Arg Phe Leu Gln His Ile Thr His Leu Pro Gln Leu
    370                 375                 380 tac gac ggt ttg aag gtt ttg ttg aag gaa aga ttg caa gaa aga gtt    1200
Tyr Asp Gly Leu Lys Val Leu Leu Lys Glu Arg Leu Gln Glu Arg Val
385                 390                 395                 400 ggt gtt cca gtt gac cca atc tct ttg tct atg aga ttg atc gct tgt    1248
Gly Val Pro Val Asp Pro Ile Ser Leu Ser Met Arg Leu Ile Ala Cys
                405                 410                 415 aac ggt gtt ggt atc cac gac aga atg ggt ttg aac gct ttg ttg tct    1296
Asn Gly Val Gly Ile His Asp Arg Met Gly Leu Asn Ala Leu Leu Ser
            420                 425                 430 atg caa aac cca gac ggt tct tgg gac ttg ggt act atg tac cac tac    1344
Met Gln Asn Pro Asp Gly Ser Trp Asp Leu Gly Thr Met Tyr His Tyr
        435                 440                 445 gct tct aag aga ttg cca atc ggt aac caa ggt gtt tct act gct atg    1392
Ala Ser Lys Arg Leu Pro Ile Gly Asn Gln Gly Val Ser Thr Ala Met
    450                 455                 460 gct atc aag gct atc aag caa tgt caa gct aac caa tgt gct ggt atc    1440
Ala Ile Lys Ala Ile Lys Gln Cys Gln Ala Asn Gln Cys Ala Gly Ile
465                 470                 475                 480 taa                                                                1443
```

<210> SEQ ID NO 138
<211> LENGTH: 480
<212> TYPE: PRT
<213> ORGANISM: Artificial Sequence
<220> FEATURE:
<223> OTHER INFORMATION: Synthetic Construct

<400> SEQUENCE: 138

```
Met Thr Lys Ile Asn Pro Tyr Lys Gly Ile Leu Val Glu Leu Lys Asp
1               5                   10                  15
Ile Val Phe Thr Ser Ser Asp Gln Ile Lys Leu Pro Ile Asn Thr
        20                  25                  30
Phe Lys Ser Ile Leu Cys Cys Gly Ala Thr Ala Gln Tyr Gln Cys Gly
            35                  40                  45
Lys Ile Asn Arg Ala Gln Tyr Tyr Ser Arg Leu Ala Arg Asp Phe Ala
50                  55                  60
Leu Ser Leu Ala Asp Val Thr Ala Leu Phe Asp Thr Val Gln Ala Thr
65                  70                  75                  80
Ile Arg Pro Glu Glu Ser Phe Leu Ala Phe Leu Ala Glu Leu Lys Ser
                85                  90                  95
Arg Phe Gly Glu Gln Leu Lys Leu Tyr Ala Val Ala Asn Met Ser Arg
            100                 105                 110
Glu Asp Tyr Ala Met Leu Lys Ser Leu Pro Ile Asp Trp Ser Leu Phe
            115                 120                 125
Asp Gly Val Phe Leu Ser Ala Asp Leu Gly Met Arg Lys Pro Glu Leu
        130                 135                 140
Arg Phe Phe Arg His Val Leu Glu Ser Ile Ser Met Lys Pro Glu Asp
145                 150                 155                 160
Thr Ile Leu Val Asp Asn Asp Thr Asp Asn Ile Leu Cys Ala Leu Ser
                165                 170                 175
Met Gly Leu Lys Gly Ile Leu Phe Gly Ser Thr Ser Val Pro Gln Ala
            180                 185                 190
Leu Thr Asn Leu Leu Glu Tyr Asp His Ile Ser Arg Ala Glu Gln Phe
        195                 200                 205
Leu Arg Ser His Ala Lys Ser Leu His Ser Val Thr His Thr Gly Val
210                 215                 220
Thr Ile Arg Glu Asn Phe Ala Gln Leu Leu Ile Leu Glu Ala Thr Gly
225                 230                 235                 240
Asp Ile Asp Leu Val Glu Leu Glu Tyr His Pro Thr Thr Trp Asn Tyr
                245                 250                 255
Phe Ile Gly Thr Pro Val Leu Thr Gln Thr Glu Phe Pro His Asp Leu
            260                 265                 270
Asp Thr Thr Ser Leu Ala Thr Thr Val Leu Asp Arg Pro Lys Asp Ile
        275                 280                 285
Ala Asn Glu Ile Met Asp Glu Met Leu Lys Tyr Arg Ser Asp Asp Asp
        290                 295                 300
Leu Met Leu Thr Phe Phe Thr Asp Phe Lys Asn Arg Val Asp Pro Val
305                 310                 315                 320
Val Cys Cys Asn Val Leu Ser Leu Phe Tyr Lys Tyr Gly Arg Gly His
                325                 330                 335
Glu Leu His His Thr Leu Ala Trp Val Arg Gln Val Leu Ile Arg Arg
            340                 345                 350
Ala Tyr Ile Asn Gly Thr Ala Phe Tyr Pro Met Pro Glu Ala Phe Leu
        355                 360                 365
Tyr Phe Phe Phe Arg Phe Leu Gln His Ile Thr His Leu Pro Gln Leu
370                 375                 380
Tyr Asp Gly Leu Lys Val Leu Leu Lys Glu Leu Gln Glu Arg Val
385                 390                 395                 400
Gly Val Pro Val Asp Pro Ile Ser Leu Ser Met Arg Leu Ile Ala Cys
                405                 410                 415
Asn Gly Val Gly Ile His Asp Arg Met Gly Leu Asn Ala Leu Leu Ser
```

-continued

```
                420             425             430
Met Gln Asn Pro Asp Gly Ser Trp Asp Leu Gly Thr Met Tyr His Tyr
            435                 440                 445

Ala Ser Lys Arg Leu Pro Ile Gly Asn Gln Gly Val Ser Thr Ala Met
        450                 455                 460

Ala Ile Lys Ala Ile Lys Gln Cys Gln Ala Asn Gln Cys Ala Gly Ile
465                 470                 475                 480
```

<210> SEQ ID NO 139
<211> LENGTH: 606
<212> TYPE: DNA
<213> ORGANISM: Artificial Sequence
<220> FEATURE:
<223> OTHER INFORMATION: AstI_codon optimized for its expression in S. cerevisiae
<220> FEATURE:
<221> NAME/KEY: CDS
<222> LOCATION: (1)..(606)

<400> SEQUENCE: 139

```
atg act aga caa tct cac tac caa gct atc atc ttg gac ttg ggt aac      48
Met Thr Arg Gln Ser His Tyr Gln Ala Ile Ile Leu Asp Leu Gly Asn
1               5                   10                  15 gtt gtt ttc gaa tgg gac act tct caa aac cca cca act gct gct cca      96
Val Val Phe Glu Trp Asp Thr Ser Gln Asn Pro Pro Thr Ala Ala Pro
            20                  25                  30 aac caa atc tct ttg ttg aga act tct atg aag tct cca gtt tac cac     144
Asn Gln Ile Ser Leu Leu Arg Thr Ser Met Lys Ser Pro Val Tyr His
        35                  40                  45 tct tac gaa aga ggt caa ttg tct act gaa gaa tgt cac aga ttg ttg     192
Ser Tyr Glu Arg Gly Gln Leu Ser Thr Glu Glu Cys His Arg Leu Leu
    50                  55                  60 ggt gaa tct ttg cac gtt gac cca ggt caa atc aag gaa gct ttc gac     240
Gly Glu Ser Leu His Val Asp Pro Gly Gln Ile Lys Glu Ala Phe Asp
65                  70                  75                  80 ttg gct aga caa tct ttg aga tct aac cca gct ttg ttg gac ttc atc     288
Leu Ala Arg Gln Ser Leu Arg Ser Asn Pro Ala Leu Leu Asp Phe Ile
                85                  90                  95 aga caa ttg aag caa act aga ggt gtt gct gtt tac gct atg tct aac     336
Arg Gln Leu Lys Gln Thr Arg Gly Val Ala Val Tyr Ala Met Ser Asn
            100                 105                 110 atc cca caa gct gaa atc gaa tac ttg aag gaa tct aga gct ggt gac     384
Ile Pro Gln Ala Glu Ile Glu Tyr Leu Lys Glu Ser Arg Ala Gly Asp
        115                 120                 125 atg gaa gtt ttc gac gaa gtt ttc gct tct ggt tac gtt ggt tct aga     432
Met Glu Val Phe Asp Glu Val Phe Ala Ser Gly Tyr Val Gly Ser Arg
    130                 135                 140 aag cca gaa act gaa ttc tac aga aga gtt atg ggt gaa atc ggt ttg     480
Lys Pro Glu Thr Glu Phe Tyr Arg Arg Val Met Gly Glu Ile Gly Leu
145                 150                 155                 160 aag gct gaa aga gtt gtt ttc gtt gac gac aag gaa gaa aac gtt gac     528
Lys Ala Glu Arg Val Val Phe Val Asp Asp Lys Glu Glu Asn Val Asp
                165                 170                 175 gtt gct aga ggt ttg ggt ttg tac ggt gtt tgt ttc ggt ggt gtt gaa     576
Val Ala Arg Gly Leu Gly Leu Tyr Gly Val Cys Phe Gly Gly Val Glu
            180                 185                 190 gaa ttg aga ggt cac ttg ttg ggt atc taa                             606
Glu Leu Arg Gly His Leu Leu Gly Ile
        195                 200
```

<210> SEQ ID NO 140

```
<211> LENGTH: 201
<212> TYPE: PRT
<213> ORGANISM: Artificial Sequence
<220> FEATURE:
<223> OTHER INFORMATION: Synthetic Construct

<400> SEQUENCE: 140

Met Thr Arg Gln Ser His Tyr Gln Ala Ile Ile Leu Asp Leu Gly Asn
1               5                   10                  15

Val Val Phe Glu Trp Asp Thr Ser Gln Asn Pro Pro Thr Ala Ala Pro
                20                  25                  30

Asn Gln Ile Ser Leu Leu Arg Thr Ser Met Lys Ser Pro Val Tyr His
            35                  40                  45

Ser Tyr Glu Arg Gly Gln Leu Ser Thr Glu Glu Cys His Arg Leu Leu
    50                  55                  60

Gly Glu Ser Leu His Val Asp Pro Gly Gln Ile Lys Glu Ala Phe Asp
65                  70                  75                  80

Leu Ala Arg Gln Ser Leu Arg Ser Asn Pro Ala Leu Leu Asp Phe Ile
                85                  90                  95

Arg Gln Leu Lys Gln Thr Arg Gly Val Ala Val Tyr Ala Met Ser Asn
            100                 105                 110

Ile Pro Gln Ala Glu Ile Glu Tyr Leu Lys Glu Ser Arg Ala Gly Asp
        115                 120                 125

Met Glu Val Phe Asp Glu Val Phe Ala Ser Gly Tyr Val Gly Ser Arg
    130                 135                 140

Lys Pro Glu Thr Glu Phe Tyr Arg Arg Val Met Gly Glu Ile Gly Leu
145                 150                 155                 160

Lys Ala Glu Arg Val Val Phe Val Asp Asp Lys Glu Glu Asn Val Asp
                165                 170                 175

Val Ala Arg Gly Leu Gly Leu Tyr Gly Val Cys Phe Gly Gly Val Glu
            180                 185                 190

Glu Leu Arg Gly His Leu Leu Gly Ile
        195                 200

<210> SEQ ID NO 141
<211> LENGTH: 591
<212> TYPE: DNA
<213> ORGANISM: Artificial Sequence
<220> FEATURE:
<223> OTHER INFORMATION: AstK_codon optimized for its expression in S.
      cerevisiae
<220> FEATURE:
<221> NAME/KEY: CDS
<222> LOCATION: (1)..(591)

<400> SEQUENCE: 141 atg tgt act act ttc aag gct gct atc ttc gac atg ggt ggt gtt ttg      48
Met Cys Thr Thr Phe Lys Ala Ala Ile Phe Asp Met Gly Gly Val Leu
1               5                   10                  15 ttc act tgg aac cca atc gtt gac act caa gtt tct ttg aag gac ttg      96
Phe Thr Trp Asn Pro Ile Val Asp Thr Gln Val Ser Leu Lys Asp Leu
                20                  25                  30 ggt act atc atc aac tct gaa act tgg gaa caa ttc gaa aga ggt aag     144
Gly Thr Ile Ile Asn Ser Glu Thr Trp Glu Gln Phe Glu Arg Gly Lys
            35                  40                  45 atc gaa cca gac gac tgt tac cac caa ttg ggt tct caa atc ggt ttg     192
Ile Glu Pro Asp Asp Cys Tyr His Gln Leu Gly Ser Gln Ile Gly Leu
        50                  55                  60 cca ggt tct gaa atc gct gct act ttc aga caa act act ggt tgt ttg     240
Pro Gly Ser Glu Ile Ala Ala Thr Phe Arg Gln Thr Thr Gly Cys Leu
```

|   |   |   |   |   |   |   |   |   |   |   |   |   |   |   |   |
|---|---|---|---|---|---|---|---|---|---|---|---|---|---|---|---|
| | | 65 | | | | 70 | | | | 75 | | | | 80 | |

```
aga cca gac gct aga atg act tct ttg ttg aga gaa ttg aag ggt caa      288
Arg Pro Asp Ala Arg Met Thr Ser Leu Leu Arg Glu Leu Lys Gly Gln
                85                  90                  95 ggt gtt gct gtt tac atg atg act aac atc cca gct cca gac ttc cac      336
Gly Val Ala Val Tyr Met Met Thr Asn Ile Pro Ala Pro Asp Phe His
            100                 105                 110 caa ttg aga gaa atg cac tac gaa tgg gac ttg ttc gac ggt atc ttc      384
Gln Leu Arg Glu Met His Tyr Glu Trp Asp Leu Phe Asp Gly Ile Phe
        115                 120                 125 gct tct gct ttg gaa ggt atg aga aag cca gac ttg gaa ttc tac gaa      432
Ala Ser Ala Leu Glu Gly Met Arg Lys Pro Asp Leu Glu Phe Tyr Glu
    130                 135                 140 cac gtt ttg aag caa atc gac act tct gct gct gaa act atc ttc gtt      480
His Val Leu Lys Gln Ile Asp Thr Ser Ala Ala Glu Thr Ile Phe Val
145                 150                 155                 160 gac gac aag ttg gaa aac gtt atc gct gct caa gct gtt ggt atg gtt      528
Asp Asp Lys Leu Glu Asn Val Ile Ala Ala Gln Ala Val Gly Met Val
                165                 170                 175 ggt ttg cac ttg act gac tct ttg gct act tgt atg gaa ttg aga caa      576
Gly Leu His Leu Thr Asp Ser Leu Ala Thr Cys Met Glu Leu Arg Gln
            180                 185                 190 ttg gtt ggt tgt taa                                                  591
Leu Val Gly Cys
        195
```

<210> SEQ ID NO 142
<211> LENGTH: 196
<212> TYPE: PRT
<213> ORGANISM: Artificial Sequence
<220> FEATURE:
<223> OTHER INFORMATION: Synthetic Construct

<400> SEQUENCE: 142

```
Met Cys Thr Thr Phe Lys Ala Ala Ile Phe Asp Met Gly Gly Val Leu
1               5                   10                  15

Phe Thr Trp Asn Pro Ile Val Asp Thr Gln Val Ser Leu Lys Asp Leu
                20                  25                  30

Gly Thr Ile Ile Asn Ser Glu Thr Trp Glu Gln Phe Glu Arg Gly Lys
            35                  40                  45

Ile Glu Pro Asp Asp Cys Tyr His Gln Leu Gly Ser Gln Ile Gly Leu
        50                  55                  60

Pro Gly Ser Glu Ile Ala Ala Thr Phe Arg Gln Thr Thr Gly Cys Leu
65                  70                  75                  80

Arg Pro Asp Ala Arg Met Thr Ser Leu Leu Arg Glu Leu Lys Gly Gln
                85                  90                  95

Gly Val Ala Val Tyr Met Met Thr Asn Ile Pro Ala Pro Asp Phe His
            100                 105                 110

Gln Leu Arg Glu Met His Tyr Glu Trp Asp Leu Phe Asp Gly Ile Phe
        115                 120                 125

Ala Ser Ala Leu Glu Gly Met Arg Lys Pro Asp Leu Glu Phe Tyr Glu
    130                 135                 140

His Val Leu Lys Gln Ile Asp Thr Ser Ala Ala Glu Thr Ile Phe Val
145                 150                 155                 160

Asp Asp Lys Leu Glu Asn Val Ile Ala Ala Gln Ala Val Gly Met Val
                165                 170                 175

Gly Leu His Leu Thr Asp Ser Leu Ala Thr Cys Met Glu Leu Arg Gln
            180                 185                 190
```

-continued

Leu Val Gly Cys
        195

<210> SEQ ID NO 143
<211> LENGTH: 479
<212> TYPE: PRT
<213> ORGANISM: Aspergillus sclerotiicarbonarius

<400> SEQUENCE: 143

Met Gly Ala Ser Val Ser Phe Gln Pro Phe Val Thr Pro Leu Asp
1               5                   10                  15

His Ala Met Pro Pro Ile Tyr Val Ser Gln Phe Leu Cys Phe Pro Thr
            20                  25                  30

Thr Thr Pro Gln Ser Ala Ile Gln Ser Leu Gln Val Gly Ile Glu Arg
        35                  40                  45

Leu Phe Glu Arg Leu Pro Phe Leu Ala Gly Glu Ile Leu Ile Asn Glu
    50                  55                  60

His Thr Gly Ala Ile Lys Val Gln Ala Pro Ser Ala Leu Ile Arg Glu
65                  70                  75                  80

Ile Pro Tyr Met Ala Leu Arg Ala His Pro Asp Leu Tyr Leu Pro Ala
                85                  90                  95

Lys Gln Cys Ala Thr Thr Pro Ile Glu Arg Gln Leu Lys Thr Asn Ser
            100                 105                 110

Leu Asp Glu Ser Tyr His Pro Leu Pro Ala Ala Leu Pro Leu Ser Gln
        115                 120                 125

Pro Gln Pro Val Ile Arg Phe Gln Ala Asn Thr Leu Ala Asp Gly Ile
    130                 135                 140

Leu Phe Ala Val Ser Tyr His His Cys Ile Phe Asp Gly Thr Gly Cys
145                 150                 155                 160

Gly Gln Ile Leu Glu Met Leu Ala Gln Cys Cys Ser Ala Ser Asp Asp
                165                 170                 175

Lys Ile Ser Leu Pro Thr Asp Cys His Thr Asp Val Leu Leu Arg Glu
            180                 185                 190

Tyr Ile Ser Asn Leu Ser Pro Thr Thr Asn Ile Pro His Asp Tyr Thr
        195                 200                 205

Gln Ala Tyr Ser Thr Thr Val Gln Pro Asp Pro Asp Ala Ser Asp Pro
    210                 215                 220

Asp Thr Ser Pro Ala Ile Pro Ser Ser Leu Tyr Thr Glu Ala Phe Thr
225                 230                 235                 240

Phe Pro Ser Gln Gln Ile Thr Thr Leu Arg Asp Ala Cys Asn His Leu
                245                 250                 255

Leu Pro Lys Leu Pro Ser Thr Ser Asn Ala His Pro His Lys Pro Thr
            260                 265                 270

Pro Asn Pro Leu Ser Ser Asn Asp Val Leu Thr Ala Leu Ile Ala Leu
        275                 280                 285

Cys Ile Thr Arg Ala Thr Asn Thr Thr Thr Pro Leu Gln Pro Asn
    290                 295                 300

Asn His Ser Leu Ser Met Ala Val Asn Leu Arg Thr Arg Ile Gln Pro
305                 310                 315                 320

Gln Val Pro Asp His Phe Leu Gly Asn Phe Ala Thr Leu Leu Pro Ile
                325                 330                 335

His Phe Thr Ser Pro Val His Thr Gln Gln Ser Asp Leu Leu Leu Thr
            340                 345                 350

Thr Glu Pro Pro Asp Pro Ala Leu Ile His Leu Thr Thr Leu Ala Ser

```
                355                 360                 365
Gln Ile Arg Ser Ser Leu Ser Thr Val Asn Thr Asp Tyr Ile Cys Gly
        370                 375                 380
Leu Met Thr Asp Leu Arg Thr Arg Arg Asn Ala Gly Glu Asn Ser Ser
385                 390                 395                 400
Leu Leu Ile Glu Gly Ile Lys Ile Ser Ser Trp Arg His Leu Ser Val
                405                 410                 415
Tyr Lys Pro Asp Phe Gly Pro Gly Leu Gly Lys Ile Ala Gly Phe Glu
            420                 425                 430
Phe Gln Ala Gly Leu Met Asp Asn Leu Val Val Ile Leu Pro Trp Arg
        435                 440                 445
Asn Gly Asp Trp Asp Val Arg Val Thr Leu Leu Glu Arg Asp Met Arg
    450                 455                 460
Gly Phe Arg Glu Asp Arg Leu Val Arg Trp Ala Leu Gly Ser Gly
465                 470                 475
```

<210> SEQ ID NO 144
<211> LENGTH: 474
<212> TYPE: PRT
<213> ORGANISM: Bazzania trilobata

<400> SEQUENCE: 144

```
Met Ala Arg Ala Pro Pro Pro Pro Gly Leu Arg Met Arg Asp
1               5                   10                  15
Thr Val Leu Ser Ile Val Lys Pro Ile Arg Lys Thr Gln His Leu Glu
                20                  25                  30
Thr Ile Asp Ala Thr Phe Val Asp Leu Met Arg Met Asp Ser Phe Ile
            35                  40                  45
Pro Val Ile Phe Ala Tyr Arg Pro Ala Asp Lys Ser Glu Ala Ala Tyr
        50                  55                  60
Ser Arg Leu Val Asn Arg Ile Lys Gly Ser Leu Gln Lys Val Leu Val
65                  70                  75                  80
Pro Phe Phe Gly Phe Ala Gly Arg Trp Val Pro Ser Ser Gly Gly Ser
                85                  90                  95
Arg Arg Leu Leu Cys Asn Asp Glu Gly Val Pro Phe Ile Glu Ala Phe
                100                 105                 110
Val Asp Glu Glu Leu Asp Ser Val Val Lys Ala Ser Ala Ala Phe Gln
            115                 120                 125
Pro Val Thr Glu Leu Asn Gly Leu Gly Val Leu Gly Met Asp Met Thr
        130                 135                 140
Ser Tyr Asp Gln Arg Met Pro Pro Glu Gly Gly Gln Pro Cys Val Val
145                 150                 155                 160
Ala Gln Val Thr Arg Phe Lys Cys Gly Gly Val Val Leu Gly Val Ala
                165                 170                 175
Phe Asn His Thr His Thr Asp Gly Gln Gly Phe Tyr Thr Phe Met Arg
            180                 185                 190
Ala Trp Ser Asp Phe Ser Arg Thr Asn Gly Thr Ala Ile Lys Val Asp
        195                 200                 205
His Asn Arg Ala Leu Pro Glu Leu Ala Ser Leu Ser Gln Phe Phe Ile
    210                 215                 220
Lys Gln His Asp Arg Ile Gly Gly Lys Thr Ser Thr Asp Arg Val Asn
225                 230                 235                 240
Asp His Cys Ser Lys Val Pro Glu Arg Leu Ala Leu Lys Ala Phe Glu
                245                 250                 255
```

```
Val Arg Ala Ser Lys Ile Lys Ala Ala Lys Leu Ala Ala Glu Asp Gly
            260             265             270
Gly Val Gly Tyr Val Ser Thr Val Asp Cys Ile Val Ala His Leu Trp
        275             280             285
Lys Thr Leu Ala Arg Leu Pro Pro Val Val Leu Asp Gly Arg Glu Ile
    290             295             300
Thr Val Phe Ser Pro Val Glu Gly Arg Asn Arg Phe Leu Asp Pro Pro
305             310             315             320
Arg Pro Asn Met Cys Gly Asn Cys Phe Ala Ala Met Val Thr Pro Lys
                325             330             335
Ile Pro Thr Gln Glu Leu Leu Glu Met Pro Leu Ala Ala Ile Ala Gly
            340             345             350
Lys Gln Arg Glu Lys Leu Ser Thr Thr Arg Arg Glu Glu Trp Phe Gly
        355             360             365
Gln Gln Ser Phe Arg Glu Leu Ala Ser Ala Met Asn Thr Ser Lys Ser
    370             375             380
Ala Leu Leu Ile Val Thr Ser Trp Phe Asn Phe Pro Met Tyr Glu Ile
385             390             395             400
Asp Phe Gly Ala Gly Lys Pro Phe Phe Ala Ser Thr Thr Asn Met Ile
                405             410             415
Ser Pro Ile Asn Gly Val Cys Cys Gly Val Ile Ala Pro Pro Thr Pro
            420             425             430
Gly Ser Cys Ser Ser Ile Ala Thr Leu Tyr Ile Leu Cys Leu Pro Ala
        435             440             445
Val Leu Glu Ala Leu Glu Asn Val Pro Asp Phe Leu Ser Phe Phe Val
    450             455             460
Pro His Pro Asn His Lys Asp Asn Ser Gln
465             470
```

METHOD FOR PRODUCING DRIMANYL ACETATE COMPOUNDS

CROSS-REFERENCE TO RELATED APPLICATIONS

This application is a U.S. National Phase Application of International Patent Application No. PCT/EP2019/077716, filed Oct. 14, 2019, which claims the benefit of priority to European Patent Application No. 18200539.7, filed Oct. 15, 2018, the entire contents of which are hereby incorporated by reference herein.

REFERENCE TO AN ELECTRONIC SEQUENCE LISTING

The contents of the electronic sequence listing 36803-282_sequence_listing.txt; Size: 549,736 bytes; and Date of Creation: Nov. 23, 2022) is herein incorporated by reference in its entirety.

TECHNICAL FIELD

The present invention provides novel methods for the acetyl transferase-catalyzed production of drimanyl-acetate compounds by the acetylation of the respective drimanyl alcohol sources performed in vitro or in vivo. The present invention also relates to the identification of enzymes having corresponding acetyl transferase activity from different microbial and plant sources. The present invention also relates to the provision of enzyme mutants derived from said newly identified enzymes. A further aspect of the present invention relates to the provision of corresponding coding sequences of such enzymes and mutants, recombinant vectors, and recombinant host cells suitable for the production of such acetyl transferases and mutants and for performing the novel production methods of drimanyl acetate compounds. Another aspect of the invention relates to the use of such drimanyl acetates, as obtained according to the present invention, as intermediates for the production of odorant, flavor or fragrance or insect/pest control ingredients.

BACKGROUND

Terpenes are found in most organisms (microorganisms, animals and plants). These compounds are made up of five carbon units called isoprene units and are classified by the number of these units present in their structure, which may comprise cyclic structural elements. Thus monoterpenes, sesquiterpenes and diterpenes are terpenes containing 10, 15 and 20 carbon atoms, respectively. Sesquiterpenes, for example, are widely found in the plant kingdom. Many sesquiterpene molecules are known for their flavor and fragrance properties and their cosmetic, medicinal and antimicrobial effects. Numerous sesquiterpene hydrocarbons and sesquiterpenoids have been identified. Chemical synthesis approaches have been developed but are still complex and not always cost-effective.

Biosynthetic production of terpenes involves enzymes called terpene synthases. There are numerous sesquiterpene synthases present in the plant kingdom, all using the same substrate (farnesyl diphosphate, FPP), but having different product profiles. Genes and cDNAs encoding sesquiterpene synthases have been cloned and the corresponding recombinant enzymes characterized.

Many of the main sources for sesquiterpenes, for example compounds with a drimane structure, like drimanyl alcohols, in particular albicanol or drimenol, are plants or microorganisms naturally containing the sesquiterpene; however, the content of sesquiterpenes in these natural sources can be low. Even if available, such drimanyl alcohols are difficult to handle during their further processing, mainly in view of the fact that they are solid at ambient temperature. Providing easier to handle derivatives would be an improved approach and simplify the further processing of drimanyl alcohols.

Akita, H. et al describe in Tetrahedron: Asymmetry 11 (2000). 1375-1388 the lipase catalyzed asymmetric synthesis of (+) albicanyl acetate. This prior art approach requires at least eight steps of chemical synthesis and two sequential reactions catalyzed by lipases to obtain an enantiomerically pure albicanyl acetate. In addition, the acetylation reactions occurred in the presence of diisopropyl ether and isopropenyl acetate at 33° C., conditions not compatible with the physiological conditions required for in a biosynthetic route. Moreover, under physiological conditions, lipases, to the best of our knowledge, are incapable to catalyze the required transesterification reaction. Although ester formation by lipases is possible, this activity is strongly dependent on the content of water present. Thus, in aqueous environments such as the in vivo setting of the present invention, lipases catalyse the hydrolysis of ester bonds rather than acetylation (Jaeger K. et al; *FEMS Microbiology Reviews*, 1994, 15:1 pp 29-63).

There still remains a need for the provision of novel methods of producing drimanyl acetate compounds, in particular methods which may be implemented into the fully biochemical synthesis of drimanyl acetates in an aqueous environment, as for example in a host cell-based process, which provides the drimanyl alcohol precursor by metabolization of sugar substrate.

SUMMARY

The above-mentioned problem could be solved by providing a new class of enzymes which show acetyl transferase activity and produce a drimanyl acetate, like albicanyl acetate or drimenyl acetate, from the respective drimane alcohol precursor, like albicanol or drimenol via acetylation and using acetyl-CoA as acetyl group donor. Due to their physicochemical properties, in particular as they are liquid at ambient temperature, acetylated derivatives of drimanyl alcohols could serve as more appropriate materials.

ABBREVIATIONS USED bp base pair
kb kilo base
CoA Coenzyme A
DNA deoxyribonucleic acid
cDNA complementary DNA
DTT dithiothreitol
FPP farnesyl diphosphate
GC gas chromatograph
MS mass spectrometer/mass spectrometry
MVA mevalonic acid
PCR polymerase chain reaction
RNA ribonucleic acid
mRNA messenger ribonucleic acid
miRNA micro RNA
siRNA small interfering RNA
rRNA ribosomal RNA
tRNA transfer RNA Definitions Unless otherwise stated the following definitions of technical terms shall apply:

An "acetyl transferase" or "polypeptide having acetyl transferase activity" or "polypeptide capable of transferring an acetyl group" for the purpose of this invention refers more generally to an enzyme of the class of acyl transferases E.C. 2.3.1, and in particular to an acetyl-CoA:alcohol O-acetyl transferase E.C. 2.3.1.84. It shows the capability of acetylating at least one drimanyl alcohol, selected from albicanol, drimenol and bicyclofarnesol with acetyl-CoA as the acetyl group donor. The drimanyl acetate(s) may be produced in the form of any of its stereoisomers or as a mixture thereof. Albicanyl acetate, drimenyl acetate or bicyclofarnesyl acetate may be the only product if the corresponding alcohol precursor is present as the single acetyl-group acceptor or may be part of a mixture of two or more drimanyl acetates if a mixture of two or more drimanyl alcohols is provided and the acetyl transferase is not substrate specific. In case of increased selectivity the acetyl transferase may predominantly form one single drimanyl acetate. Acetyl transferases as described herein may show identical or different preference or specificity to different drimanyl alcohols as substrate. For example, a first type of acetyl transferases may predominantly acetylate albicanol, a second type of acetyl transferases may predominantly acetylate drimenol and a third type of acetyl transferases may predominantly acetylate bicyclofarnesol. In such cases albicanol acetate, drimenol acetate or bicyclofarnesyl acetate would be formed as the respective main product, if a mixture of such drimanyl alcohols is used as substrate. In case of substrate specificity the acetyl transferase may selectively form one single drimanyl acetate, even if a mixture of such drimanyl alcohols would be used as substrate. In particular, the acetylation is performed under retention of the respective stereochemichal configuration of the drimanyl alcohol substrate.

An "acetyl group donor" refers to a chemical entity or molecule which acts as a source for an acetyl group to be enzymatically transferred from said donor to an acceptor molecule, like a molecule having a functional hydroxyl group, which in turn may react with said acetyl group to form the corresponding acetic acid ester. A particular acetyl group donor is acetyl-Coenzyme A (acetyl-CoA).

Figure 1A:
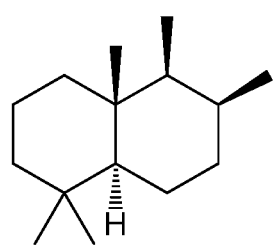
FIG. 1A: Structure of (+)-albicanol, (−)-drimenol and bicyclofarnesol, as well as of a drimane moiety more specific than the drimane structure of FIG. 1C.
Figure 1A:
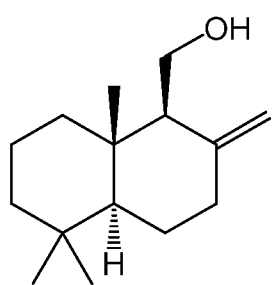
Figure 1A:
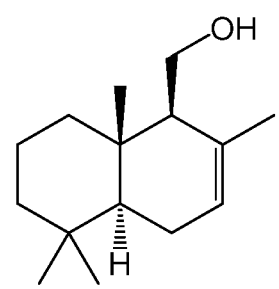
Figure 1A:
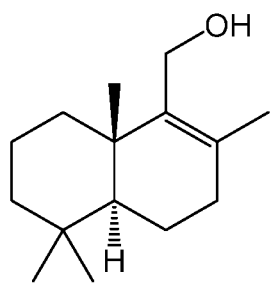
Figure 1B:
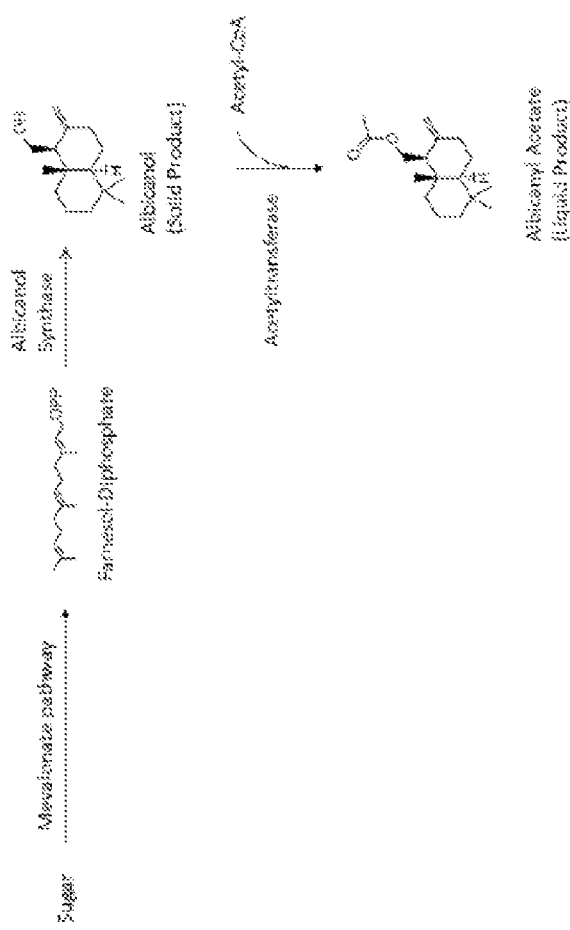
FIG. 1B: Reaction scheme illustrating the cellular biological production of albicanyl acetate via the acyclic sesquiterpene precursor FPP and albicanol.
Figure 1C:
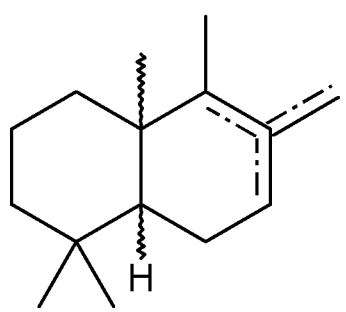
FIG. 1C: More generic "drimane structure", the potential positions of a C=C-double are indicated.
Figure 2A:
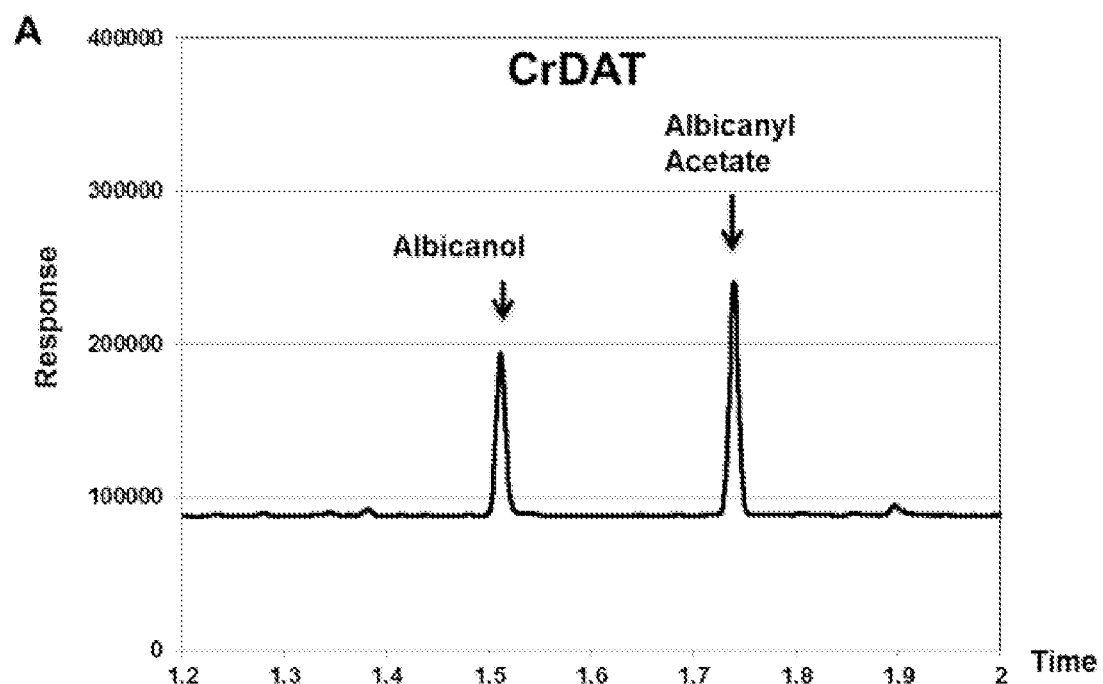
FIG. 2A: GC-FID analysis of albicanyl acetate produced using the modified *S. cerevisiae* strain YST069 co-expressing the albicanol synthase XP_007369631.1 with the acetyltransferase CrDAT.
Figure 2B:
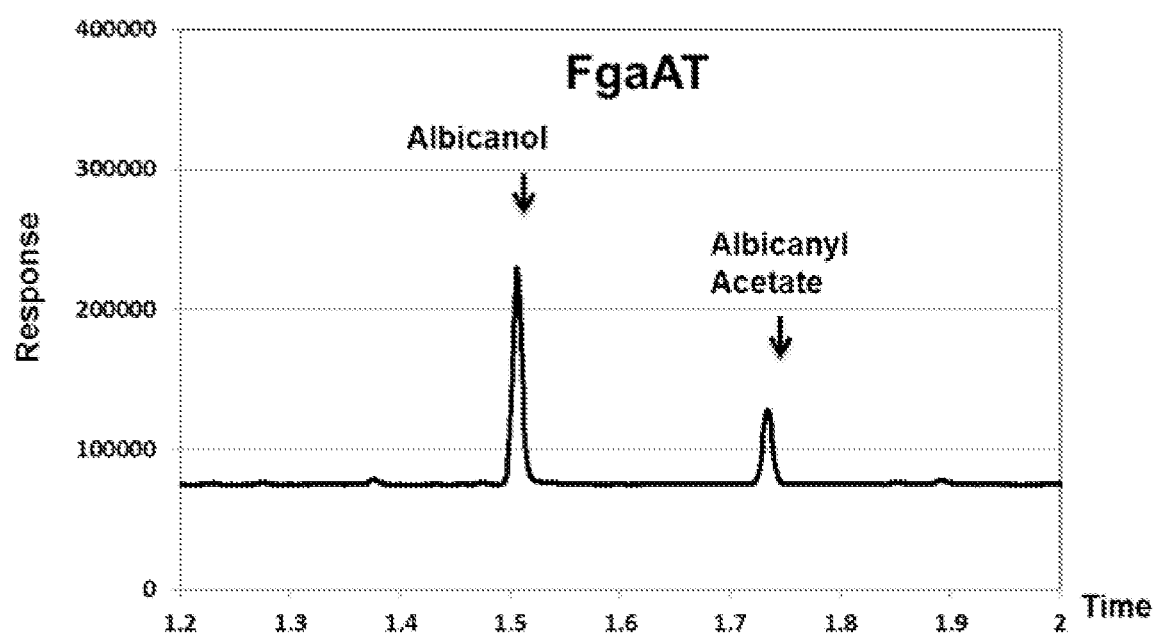
FIG. 2B: GC-FID analysis of albicanyl acetate produced using the modified *S. cerevisiae* strain YST069 co-expressing the albicanol synthase XP_007369631.1 with the acetyltransferase FgaAT.
Figure 2C:
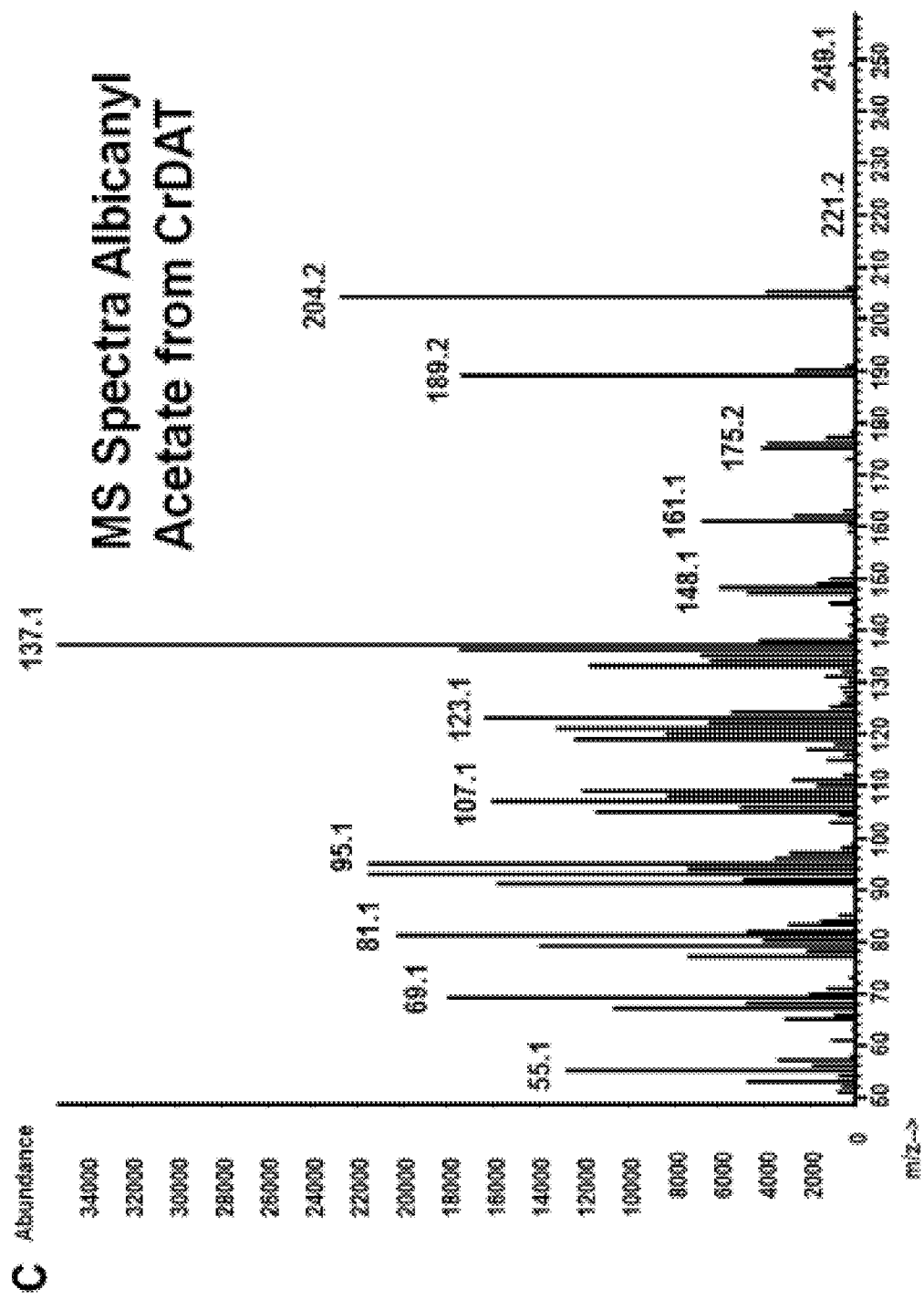
FIG. 2C: The MS spectra of the produced albicanyl acetate by the acetyltransferase CrDAT from FIG. 2A. It is identical to the MS spectra from an albicanyl acetate standard.
Figure 2D:
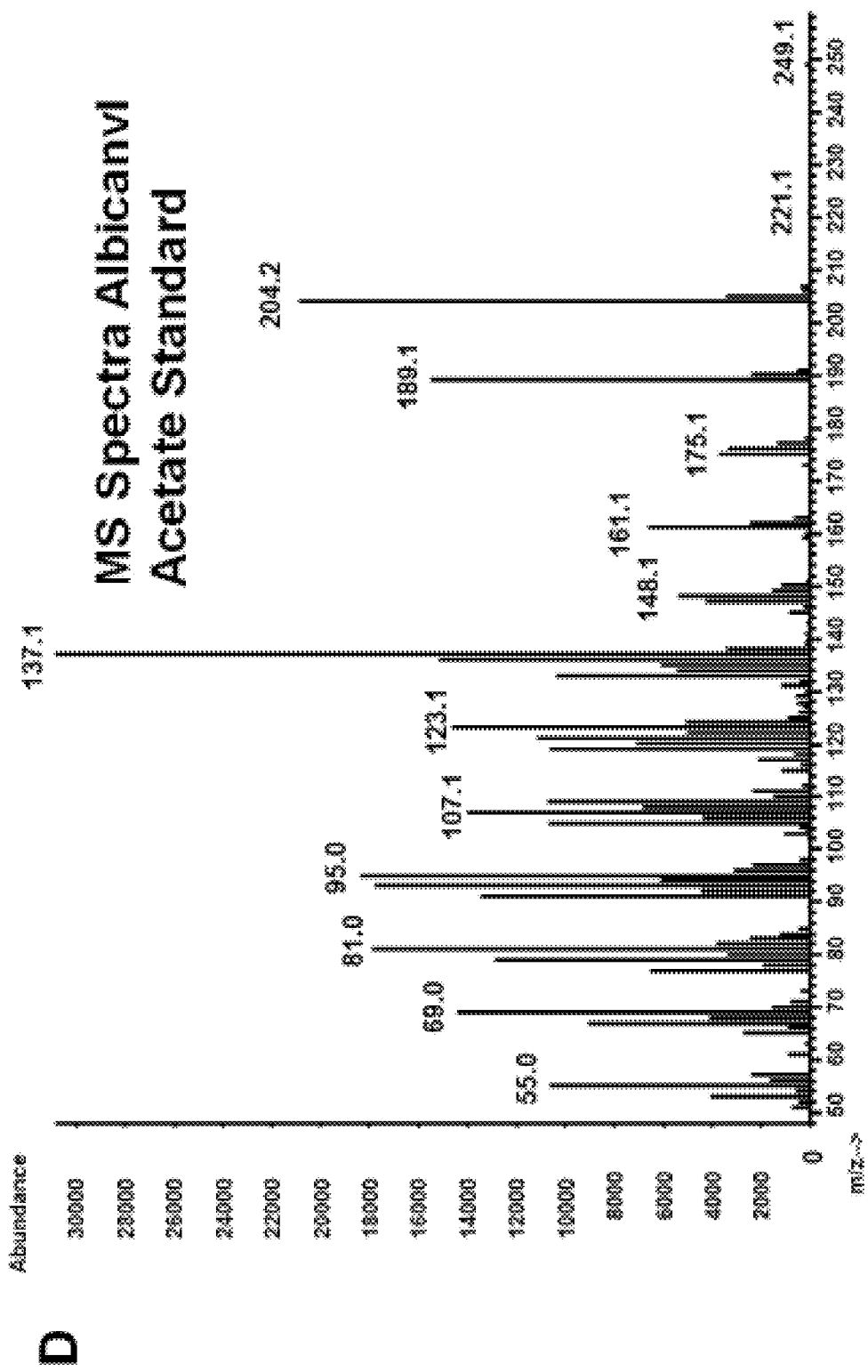
FIG. 2D: The MS spectra of an albicanyl acetate standard.

The term "drimane sesquiterpene" or "drimane" relates to a cyclic terpene having a drimane-like carbon skeleton structure as depicted in FIG. 1A, or more particularly to the more generic structure of FIG. 1C, wherein the potential positions of an optionally present C=C-double bond are marked with dotted lines.

The term "drimanyl alcohol" relates to hydroxylated derivative of a "drimane sesquiterpene" or "drimane". Examples thereof are albicanol, drimenol and bicyclofarnesol in any stereoisomeric form.

The term "drimanyl acetate" relates to the acetyl ester derivative of such drimanyl alcohol, like albicanyl acetate, drimenyl acetate, and bicyclofarnesyl acetate.

"Albicanol" for the purpose of this application particularly relates to (+)-albicanol (CAS: 54632-04-1).

"Drimenol" for purposes of this application particularly relates to (−)-drimenol (CAS: 468-68-8).

"Bicyclofarnesol" for purposes of this application particularly relates to (+)-bicyclofarnesol or [(4aS,8aS)-2,5,5,8a-Tetramethyl-3,4,4a,5,6,7,8,8a-octahydro-1-naphthalenyl]methanol (IUPAC Name)

"Farnesyl diphosphate" refers to (2E,6E)-3,7,11-trimethyldodeca-2,6,10-triene-1-pyrophosphate (FPP).

"Ambrox" for purposes of this application relates to IUPAC Name: (−)-(3aR,5aS,9aS,9bR)-3a,6,6,9a-tetramethyldodecahydronaphto[2,1-b]furan (CAS: 6790-58-5).

The terms "terpene synthase" or "sesquiterpene synthase" or "drimane sesquiterpene synthase" are used herein interchangeably.

The terms "bifunctional terpene synthase" or "polypeptide having bifunctional terpene synthase activity" relate to a polypeptide as further defined in PCT/EP2018/064344, filed May 31, 2018.

The terms "albicanyl diphosphate synthase" or "polypeptide having albicanyl diphosphate synthase activity" or "albicanyl diphosphate synthase protein" or "having the ability to produce albicanyl diphosphate" relate to a polypeptide capable of catalyzing the synthesis of albicanyl diphosphate, in the form of any of its stereoisomers or a mixture thereof, starting from an acyclic terpene pyrophosphate, particularly farnesyl diphosphate (FPP). Albicanyl diphosphate may be the only product or may be part of a mixture of sesquiterpenes. Said mixture may comprise albicanyl monophosphate and/or albicanol. Such polypeptides are described for example in PCT/CN2018/088902, filed May 29, 2018.

"Albicanyl diphosphate synthase activity" is determined under "standard conditions" as described in PCT/CN2018/088902.

The terms "albicanol synthase" or "polypeptide having albicanol synthase activity" or "albicanol synthase protein" relate to a polypeptide capable of catalyzing the synthesis of albicanol, in the form of any of its stereoisomers or a mixture thereof, starting from an acyclic terpene pyrophosphate, particularly farnesyl diphosphate (FPP). Albicanol may be the only product or may be part of a mixture of two or more sesquiterpenes.

The terms "drimenol synthase" or "polypeptide having a drimenol synthase activity" or "drimenol synthase protein" relate to a polypeptide capable of catalyzing the synthesis of drimenol, in the form of any of its stereoisomers or a mixture thereof, starting from an acyclic terpene pyrophosphate, particularly farnesyl diphosphate (FPP). Drimenol may be the only product or may be part of a mixture of two or more sesquiterpenes.

The "albicanol synthase activity" and the drimenol synthase activity are determined as described for example in PCT/EP2018/064344, WO2015/169871 or WO 2015/176959.

A "phosphatase" enzyme as used in the present invention has the ability to convert an orthophosphoric ester under consumption of water into the respective alcohol and orthophosphate. Herein encompassed are acidic phosphatases (EC.3.1.3.2 with acidic reaction optimum) and alkaline phosphatases (EC.3.1.3.1 with alkaline reaction optimum).

The terms "biological function," "function," "biological activity" or "activity" refer to the ability of the terpene synthase as described herein a) to catalyze the formation of albicanyl diphosphate and/or albicanol or a mixture of compounds comprising albicanyl diphosphate, and/or albicanyl monophosphate and/or albicanol and/or and one or more other terpenes, in particular albicanyl diphosphate; or b) to catalyze the formation of a drimanyl alcohol or a mixture of two or more drimanyl alcohols and optionally one or more other terpenes.

The terms "biological function", "function", "biological activity" or "activity" refer to the ability of an acetyl transferase as described herein, to catalyze the formation of a drimanyl acetate or a mixture of two or more drimanyl acetates and optionally one or more other acetylated compounds.

The terms "mixture of terpenes" or "mixture of sesquiterpenes" refer to a mixture of terpenes or of sesquiterpenes that comprises at least one of albicanol, drimenol and bicyclofarnesol, and may also comprise one or more additional terpenes and/or one or more additional sesquiterpenes.

The "mevalonate pathway" also known as the "isoprenoid pathway" or "HMG-CoA reductase pathway" is an essential metabolic pathway present in eukaryotes, archaea, and some bacteria. The mevalonate pathway begins with acetyl-CoA and produces two five-carbon building blocks called isopentenyl pyrophosphate (IPP) and dimethylallyl pyrophosphate (DMAPP). Key enzymes are acetoacetyl-CoA thiolase, HMG-CoA synthase, HMG-CoA reductase, mevalonate kinase, phosphomevalonate kinase, a mevalonate diphosphate decarboxylase, and an isopentenyl diphosphate isomerase. Combining the mevalonate pathway with enzyme activity to generate the terpene precursors GPP, FPP or GGPP, like in particular FPP synthase, allows the recombinant cellular production of terpenes.

As used herein, the term "host cell" or "transformed cell" refers to a cell (or organism) altered to harbor at least one nucleic acid molecule, for instance, a recombinant gene encoding a desired protein or nucleic acid sequence which upon transcription yields at least one functional polypeptide of the present invention required for performing a biocatalytic method or other recombinant method as described herein. In particular such host cells or transformed cells provide an acetyl transferase useful to prepare at least one drimanyl acetate from the corresponding drimanyl alcohol. They also may provide other enzymes like albicanyl diphosphate synthase protein useful to produce albicanyl diphosphate and/or albicanyl monophosphate and/or albicanol or corresponding mixtures of terpenes containing albicanyl diphosphate and/or albicanyl monophosphate and/or albicanol. They may also provide terpene synthases useful to prepare at least one drimanyl alcohol. The host cell is particularly a bacterial cell, a fungal cell or a plant cell or plants. The host cell may contain a recombinant gene which has been integrated into the nuclear or organelle genomes of the host cell. Alternatively, the host may contain the recombinant gene extra-chromosomally.

The term "organism" refers to any non-human multicellular or unicellular organisms such as a plant, or a micro-organism. Particularly, a micro-organism is a bacterium, a yeast, an algae or a fungus.

The term "plant" is used interchangeably to include plant cells including plant protoplasts, plant tissues, plant cell tissue cultures giving rise to regenerated plants, or parts of plants, or plant organs such as roots, stems, leaves, flowers, pollen, ovules, embryos, fruits and the like. Any plant can be used to carry out the methods of an embodiment herein.

A particular organism or cell is meant to be "capable of producing FPP" when it produces FPP naturally or when it does not produce FPP naturally but is transformed to produce FPP with a nucleic acid as described herein. Organisms or cells transformed to produce a higher amount of FPP than the naturally occurring organism or cell are also encompassed by the "organisms or cells capable of producing FPP".

A particular organism or cell is meant to be "capable of producing drimanyl acetate" when it produces a drimanyl acetate naturally or when it does not produce a drimanyl acetate naturally but is transformed to produce a drimanyl acetate with a nucleic acid as described herein. Organisms or cells transformed to produce a higher amount of a drimanyl acetate than the naturally occurring organism or cell are also encompassed by the "organisms or cells capable of producing a drimanyl acetate".

A particular organism or cell is meant to be "capable of producing a drimanyl alcohol" when it produces a drimanyl alcohol naturally or when it does not produce a drimanyl alcohol naturally but is transformed to produce drimanyl diphosphate, and optionally further transformed with a nucleic acid to produce enzyme activity converting drimanyl diphosphate to drimanyl alcohol. Organisms or cells transformed to produce a higher amount of a drimanyl alcohol than the naturally occurring organism or cell are also encompassed by the "organisms or cells capable of producing a drimanyl alcohol".

For the descriptions herein and the appended claims, the use of "or" means "and/or" unless stated otherwise. Similarly, "comprise", "comprises", "comprising", "include", "includes", and "including" are interchangeable and not intended to be limiting.

It is to be further understood that where descriptions of various embodiments use the term "comprising", those skilled in the art would understand that in some specific instances, an embodiment can be alternatively described using language "consisting essentially of" or "consisting of".

The terms "purified," "substantially purified", and "isolated" as used herein refer to the state of being free of other, dissimilar compounds with which a compound of the invention is normally associated in its natural state, so that the "purified", "substantially purified", and "isolated" subject comprises at least 0.5%, 1%, 5%, 10% or 20%, or at least 50% or 75% of the mass, by weight, of a given sample. In one embodiment, these terms refer to the compound of the invention comprising at least 95, 96, 97, 98, 99 or 100% of the mass, by weight, of a given sample. As used herein, the terms "purified", "substantially purified", and "isolated" when referring to a nucleic acid or protein, of nucleic acids or proteins, also refers to a state of purification or concentration different than that which occurs naturally, for example in an prokaryotic or eukaryotic environment, like, for example in a bacterial or fungal cell, or in the mammalian organism, especially human body. Any degree of purification or concentration greater than that which occurs naturally, including (1) the purification from other associated structures or compounds or (2) the association with structures or compounds to which it is not normally associated in said prokaryotic or eukaryotic environment, are within the meaning of "isolated". The nucleic acid or protein or classes of nucleic acids or proteins, described herein, may be isolated, or otherwise associated with structures or compounds to which they are not normally associated in nature, according to a variety of methods and processes known to those of skill in the art.

The term "about" indicates a potential variation of ±25% of the stated value, in particular ±15%, ±10%, more particularly ±5%, ±2% or ±1%.

The term "substantially" describes a range of values of from about 80 to 100%, such as, for example, 85-99.9%, in particular 90 to 99.9%, more particularly 95 to 99.9%, or 98 to 99.9% and especially 99 to 99.9%.

"Predominantly" refers to a proportion in the range of above 50%, as for example in the range of 51 to 100%, particularly in the range of 75 to 99.9%; more particularly 85 to 99.5%, like 95 to 99%.

A "main product" in the context of the present invention designates a single compound or a group of at least 2 compounds, like 2, 3, 4, 5 or more, particularly 2 or 3 compounds, which single compound or group of compounds is "predominantly" prepared by a reaction as described herein, and is contained in said reaction in a predominant proportion based on the total amount of the constituents of the product formed by said reaction. Said proportion may be a molar proportion, a weight proportion or, preferably based on chromatographic analytics, an area proportion calculated from the corresponding chromatogram of the reaction products.

A "side product" in the context of the present invention designates a single compound or a group of at least 2 compounds, like 2, 3, 4, 5 or more, particularly 2 or 3 compounds, which single compound or group of compounds is not "predominantly" prepared by a reaction as described herein.

Because of the reversibility of enzymatic reactions, the present invention relates, unless otherwise stated, to the enzymatic or biocatalytic reactions described herein in both directions of reaction.

"Functional mutants" of herein described polypeptides include the "functional equivalents" of such polypeptides as defined below.

The term "stereoisomers" includes in particular conformational isomers.

Included in general are, according to the invention, all "stereoisomeric forms" of the compounds described herein, such as constitutional isomers and, in particular, stereoisomers and mixtures thereof, e.g. optical isomers, or geometric isomers, such as E- and Z-isomers, and combinations thereof. If several asymmetric centers are present in one molecule, the invention encompasses all combinations of different conformations of these asymmetry centers, e.g. enantiomeric pairs "Stereoselectivity" describes the ability to produce a particular stereoisomer of a compound in a stereoisomerically pure form or to specifically convert a particular stereoisomer in an enzyme catalyzed method as described herein out of a plurality of stereoisomers. More specifically, this means that a product of the invention is enriched with respect to a specific stereoisomer, or an educt may be depleted with respect to a particular stereoisomer. This may be quantified via the purity % ee-parameter calculated according to the formula:

$$\% \ ee = [X_A - X_B]/[X_A + X_B] * 100,$$

wherein $X_A$ and $X_B$ represent the molar ratio (Molenbruch) of the stereoisomers A and B.

The terms "selectively converting" or "increasing the selectivity" in general means that a particular stereoisomeric form, as for example the E-form, of an unsaturated hydrocarbon, is converted in a higher proportion or amount (compared on a molar basis) than the corresponding other stereoisomeric form, as for example Z-form, either during the entire course of said reaction (i.e. between initiation and termination of the reaction), at a certain point of time of said reaction, or during an "interval" of said reaction. In particular, said selectivity may be observed during an "interval" corresponding 1 to 99%, 2 to 95%, 3 to 90%, 5 to 85%, 10 to 80%, 15 to 75%, 20 to 70%, 25 to 65%, 30 to 60%, or 40 to 50% conversion of the initial amount of the substrate. Said higher proportion or amount may, for example, be expressed in terms of:

a higher maximum yield of an isomer observed during the entire course of the reaction or said interval thereof;

a higher relative amount of an isomer at a defined % degree of conversion value of the substrate; and/or an identical relative amount of an isomer at a higher % degree of conversion value;

each of which preferably being observed relative to a reference method, said reference method being performed under otherwise identical condition with known chemical or biochemical means.

Generally also comprised in accordance with the invention are all "isomeric forms" of the compounds described herein, such as constitutional isomers and in particular stereoisomers and mixtures of these, such as, for example, optical isomers or geometric isomers, such as E- and Z-isomers, and combinations of these. If several centers of asymmetry are present in a molecule, then the invention comprises all combinations of different conformations of these centers of asymmetry, such as, for example, pairs of enantiomers, or any mixtures of stereoisomeric forms.

"Yield" and/or the "conversion rate" of a reaction according to the invention is determined over a defined period of, for example, 4, 6, 8, 10, 12, 16, 20, 24, 36 or 48 hours, in which the reaction takes place. In particular, the reaction is carried out under precisely defined conditions, for example at "standard conditions" as herein defined.

The different yield parameters ("Yield" or $Y_{P/S}$; "Specific Productivity Yield"; or Space-Time-Yield (STY)) are well known in the art and are determined as described in the literature.

"Yield" and "$Y_{P/S}$" (each expressed in mass of product produced/mass of material consumed) are herein used as synonyms.

The specific productivity-yield describes the amount of a product that is produced per h and L fermentation broth per g of biomass. The amount of wet cell weight stated as WCW describes the quantity of biologically active microorganism in a biochemical reaction. The value is given as g product per g WCW per h (i.e. g/gWCW$^{-1}$ h$^{-1}$). Alternatively, the quantity of biomass can also be expressed as the amount of dry cell weight stated as DCW. Furthermore, the biomass concentration can be more easily determined by measuring the optical density at 600 nm (OD$_{600}$) and by using an experimentally determined correlation factor for estimating the corresponding wet cell or dry cell weight, respectively.

The term "fermentative production" or "fermentation" refers to the ability of a microorganism (assisted by enzyme activity contained in or generated by said microorganism) to produce a chemical compound in cell culture utilizing at least one carbon source added to the incubation.

The term "fermentation broth" is understood to mean a liquid, particularly aqueous or aqueous/organic solution which is based on a fermentative process and has not been worked up or has been worked up, for example, as described herein.

An "enzymatically catalyzed" or "biocatalytic" method means that said method is performed under the catalytic action of an enzyme, including enzyme mutants, as herein defined. Thus the method can either be performed in the presence of said enzyme in isolated (purified, enriched) or crude form or in the presence of a cellular system, in particular, natural or recombinant microbial cells containing said enzyme in active form, and having the ability to catalyze the conversion reaction as disclosed herein.

If the present disclosure refers to features, parameters and ranges thereof of different degree of preference (including general, not explicitly preferred features, parameters and ranges thereof) then, unless otherwise stated, any combination of two or more of such features, parameters and ranges thereof, irrespective of their respective degree of preference, is encompassed by the disclosure of the present description.

DETAILED DESCRIPTION a. Particular Embodiments of the Invention

1. A biocatalytic method of producing at least one, in particular one, two or three, particularly one or two drimanyl acetate compounds comprising the steps of (1) contacting in the presence of an acetyl group donor at least one, in particular one drimanyl alcohol, in stereoisomerically pure form or in the form of a mixture of stereoisomers, with at least one, in particular one polypeptide having acetyl transferase activity capable of, in particular transferring an acetyl group from said acetyl group donor to said at least one, in particular one drimanyl alcohol to obtain at least one drimanyl acetate as main product, in particular one drimanyl acetate as main product; and (2) optionally isolating said at least one, in particular one drimanyl acetate compound from the reaction product of step (1).

If more than one drimanyl acetate is formed, the mixture may be further separated and individual acetates may be purified.

2. The method of embodiment 1, wherein said drimanyl acetate compound is selected from the group consisting of albicanyl acetate, drimenyl acetate, and bicyclofarnesyl acetate, each in stereoisomerically pure form or as a mixture of at least two stereoisomers thereof, or combinations thereof comprising at least two members of said group of acetates. In a particular embodiment merely one drimanyl alcohol is used as substrate and merely one drimanyl acetate is obtained as product in stereoisomerically pure form or as a mixture of at least two stereoisomers thereof, in particular in stereoisomerically pure form.

3. The method of embodiment 1 or 2, wherein said drimanyl alcohol is selected from the group consisting of albicanol, in particular (+)-albicanol, drimenol, in particular (−)-drimenol, and bicyclofarnesol, in particular (+)-bicyclofarnesol, each in stereoisomerically pure form or as a mixture of at least two stereoisomers thereof, or combinations thereof comprising at least two members of said group of alcohols. In a particular embodiment merely one drimanyl alcohol, in particular in stereoisomerically pure form is used as substrate.

4. The method of anyone of the preceding embodiments, wherein said acetyl group donor is acetyl-Coenzyme A (acetyl-CoA). Said donor may be exogenously added to the reaction mixture, for example in an in vitro process applying isolated, enriched or purified enzyme, or more particularly be endogenously present, for example in an in vivo process applying a host cell system producing acetyl-CoA as metabolite and expressing the required polypeptide or polypeptides for performing the intended acetylation or a more complex, multistep process encompassing said acetylation as one step.

5. The method of anyone of the preceding embodiments, wherein said acetyl transferase is selected from
a) polypeptides comprising an amino acid sequence selected from SEQ ID NO: 9, 11, 13, 15, 17, 19, 21, 23, 25, 118, 121, 124, 127, 130, 133, 136, 143 and 144 and
b) polypeptides having acetyl transferase activity and comprising an amino acid sequence showing an degree of sequence identity of at least 40%, 45%, 50%, 55%, 60%, 65%, 70%, 75%, 80%, 85%, 90%, 95%, 96%, 97%, 98%, or 99% to at least one of said amino acid sequences of SEQ ID NO: 9, 11, 13, 15, 17, 19, 21, 23, 25, 118, 121, 124, 127, 130, 133, 136, 143 and 144.

The ability of particular acetyl transferases of the invention to produce one or more drimane acetate compounds selected from the group consisting of albicanyl acetate, drimenyl acetate, and bicyclofarnesyl acetate is illustrated by the following listing:

| Acetyl tansferase | SEQ ID NO | Albicanyl acetate | Drimenyl acetate | Bicyclofarnesyl acetate |
|---|---|---|---|---|
| CrDAT | 9 | + | + | + |
| TcTAT | 11 | + | + | + |
| CrMAT | 13 | + |  | + |
| LiAAT-4 | 15 | + |  |  |
| FgaAT | 17 | + | + | + |
| GAO81666.1 | 19 | + | + | + |
| CfACT1-6 | 21 | + | + | + |
| CfACT1-8 | 23 | + | + | + |
| OAH94415.1 | 25 | + | + |  |
| DfACT13 | 118 | + | + | + |
| PYI04555.1 | 121 or 143 |  |  | + |
| ERR364415-1_contig_8546 | 124 or 144 | + | + | + |
| XP_001258079.1 | 127 | + |  |  |
| XP_001217250.1 | 130 |  |  | + |
| BAU61551.1 | 133 |  |  | + |
| PsSalAT | 136 |  |  | + |

6. The method of anyone of the preceding embodiments, further comprising, prior to step 1) the biocatalytic formation of said at least one, in particular one drimanyl alcohol compound.

7. The method of embodiment 6, wherein said drimanyl alcohol compound may endogenously be present in the reaction mixture, for example in an in vivo process applying a host cell system producing said drimanyl alcohol compound as metabolite and expressing the required polypeptide or polypeptides for performing the intended drimanyl alcohol synthesis or a more complex, multistep process encompassing said drimanyl alcohol synthesis as one step whereby said drimanyl alcohol is enzymatically synthesized from a non-cyclic sesquiterpene precursor.

Alternatively, said drimanyl alcohol compound is either chemically or enzymatically produced, and is exogenously added to the reaction mixture, for example in an in vitro process applying an isolated, enriched or purified synthase enzyme required for its formation as defined below.

8. The method of embodiment 7, wherein said non-cyclic sesquiterpene precursor is farnesyl pyrophosphate (FPP).

9. The method of anyone of the embodiments 7 to 8, wherein said enzymatic synthesis of the drimanyl alcohol is catalysed by one or more polypeptides having the ability to convert said non-cyclic sesquiterpene precursor to at least one drimanyl alcohol, in particular one drimanyl alcohol, in one or more enzymatic steps, in particular as main product.

10. The method of anyone of the embodiments 6 to 9, wherein said at least one drimanyl alcohol is produced in a single or more, in particular two enzymatic steps from FPP.

11. The method of embodiment 10, wherein said at least one drimanyl alcohol is produced by the enzymatic conversion of FPP, catalysed by
   a) a polypeptide having drimane sesquiterpene synthase activity forming said drimanyl alcohol (single step biosynthesis); or
   b) a combination of a polypeptide having drimanyl phosphate synthase activity forming at least one drimanyl phosphate intermediate, and a polypeptide having phosphatase activity converting said at least one drimanyl phosphate (monophosphate and/or diphosphate) intermediate to at least one drimanyl alcohol (two step biosynthesis).

12. The method of embodiment 11, wherein
   a) said polypeptide having drimane sesquiterpene synthase activity is selected from a polypeptide having albicanol synthase activity, drimenol synthase activity, bicyclofarnesol synthase activity or any combination of such activities, in particular showing one of said activities preferentially, and more particular, showing one of said activities specifically; and
   b) said combination of polypeptides comprises a drimanyl diphosphate synthase activity, in particular an albicanyl diphosphate synthase activity and a phosphatase enzyme, as for example a bacterial alkaline phosphatase.

13. The method of embodiment 12, wherein
   a) said polypeptide having drimane sesquiterpene synthase activity is selected from drimane synthases as described in PCT/EP2018/064344 (filed May 31, 2018) and drimenol synthases as described in published WO2015/169871 and WO 2015/176959;
   b) said polypeptide having drimanyl phosphate synthase activity is an albicanyl diphosphate synthase as described in PCT/CN2018/088902, filed on May 29, 2018, comprising the ability to produce an albicanyl phosphate derivative like a monophosphate and more particularly an albicanyl diphosphate from farnesyl diphosphate (FPP) as substrate.

Albicanyl diphosphate synthases as described in PCT/CN2018/088902 (filed May 29, 2018) are:

DfHAD, DfHAD-9 (V274A), DfHAD-His_GST, and DfHAD-8 (K532R) of *Dryopteris fragrans* and polypeptides derived therefrom having at least 40%, 45%, 50%, 55%, 60%, 65%, 70%, 75%, 80%, 85%, 90%, 95%, 96%, 97%, 98%, or 99% sequence identity thereto.

Drimane synthases (i.e. albicanol synthases or drimenol synthases) as described in PCT/EP2018/064344 (filed May 31, 2018) are

| Name or NCBI accession number | Source | Product |
|---|---|---|
| CvTps1 | *Cryptoporus volvatus* | Albicanol |
| LoTps1 | *Laricifomes officinalis* | Albicanol |
| OCH93767.1 | *Obba rivulosa* | Albicanol |
| EMD37666.1 | *Gelatoporia subvermispora* | Albicanol |
| EMD37666-B | *Gelatoporia subvermispora* | Albicanol |
| XP_001217376.1 | *Aspergillus terreus* | Albicanol |
| OJJ98394.1 | *Aspergillus aculeatus* | Albicanol |
| GAO87501.1 | *Aspergillus udagawae* | Albicanol |
| XP_008034151.1 | *Trametes versicolor* | Albicanol |
| XP_007369631.1 | *Dichomitus squalens* | Albicanol |
| ACg006372 | *Antrodia cinnamomea* | Albicanol |
| KIA75676.1 | *Aspergillus ustus* | Drimenol |
| XP_001820867.2 | *Aspergillus oryzae* | Drimenol |
| CEN60542.1 | *Aspergillus calidoustus* | Drimenol |
| XP_009547469.1 | *Heterobasidion irregulare* | Drimenol |
| KLO09124.1 | *Schizopora paradoxa* | Drimenol |
| OJI95797.1 | *Aspergillus versicolor* | Drimenol |
| XP_006461126 | *Agaricus bisporus* | Drimenol | and polypeptides derived therefrom having at least 40%, 45%, 50%, 55%, 60%, 65%, 70%, 75%, 80%, 85%, 90%, 95%, 96%, 97%, 98%, or 99% sequence identity thereto.

Drimenol synthases as described in WO2015/169871 are

| Name | Source |
| --- | --- |
| DlTps589 | *Drimys lanceolota* |
| SCH51_3228_11 | *Drimys winteri* |
| SCH51_3228_9 | *Drimys winteri* |
| SCH51_998_28 | *Drimys winteri* |
| SCH52_13163_6 | *Drimys lanceolota* | and polypeptides derived therefrom having at least 40%, 45%, 50%, 55%, 60%, 65%, 70%, 75%, 80%, 85%, 90%, 95%, 96%, 97%, 98%, or 99% sequence identity thereto.

Drimenol synthases as described in WO 2015/176959 are VaTPS3 of *Valeriana amurensis* and polypeptides derived therefrom having at least 40%, 45%, 50%, 55%, 60%, 65%, 70%, 75%, 80%, 85%, 90%, 95%, 96%, 97%, 98%, or 99% sequence identity thereto.

The SEQ ID NOs of respective amino acid and nucleotide sequences of the above-mentioned synthase enzymes are listed at the end of the current description. These polypeptides and nucleic acids as well as polypeptides and nucleic acids derived therefrom having at least 40%, 45%, 50%, 55%, 60%, 65%, 70%, 75%, 80%, 85%, 90%, 95%, 96%, 97%, 98%, or 99% sequence identity to at least one of these sequences are also part of the current disclosure.

14. The method of embodiment 13, wherein said drimane sesquiterpene synthase is selected from
   a) a polypeptide having (bifunctional) albicanol synthase activity and comprising an amino acid sequence of SEQ ID NO: 5 or a mutant or variant polypeptide having albicanol synthase activity and comprising an amino acid sequence having at least 40%, 45%, 50%, 55%, 60%, 65%, 70%, 75%, 80%, 85%, 90%, 95%, 96%, 97%, 98%, or 99% sequence identity to SEQ ID NO: 5 as described in PCT/EP2018/064344;
   b) a polypeptide having (bifunctional) drimenol synthase activity and comprising an amino acid sequence of SEQ ID NO: 7 or a mutant or variant polypeptide having drimenol synthase activity and comprising an amino acid sequence having at least 40%, 45%, 50%, 55%, 60%, 65%, 70%, 75%, 80%, 85%, 90%, 95%, 96%, 97%, 98%, or 99% sequence identity to SEQ ID NO: 7 as described in PCT/EP2018/064344.

15. The method of anyone of the preceding embodiments, performed in vivo in host cell culture or in vitro in a liquid reaction medium comprising a host cell lysate or enriched or isolated polypeptides required for producing at least one drimanyl acetate, each under conditions conducive to the production of at least one drimanyl acetate.

In particular, the reaction is performed in the presence of endogenously formed or exogenously added acetyl-CoA as acetyl group donor. In particular, the reaction is performed in the presence of endogenously formed or exogenously added FPP. Endogenously formed FPP in particular is the result of the metabolization of at least one carbon source, as for example a sugar substrate, bioconvertible to FPP. A cellular in vivo method is of particular interest, wherein FPP and acetyl-CoA are endogenously formed.

Some of these host cells or organisms do not produce FPP naturally. To be suitable to carry out the method of an embodiment as described herein, organisms or cells that do not produce an acyclic terpene pyrophosphate precursor, e.g. FPP, naturally are genetically modified to produce said precursor. They can be, for example, so transformed either before the modification with the nucleic acid described according to any of the above embodiments or simultaneously. Methods to transform organisms so that they produce an acyclic terpene pyrophosphate precursor, e.g. FPP, are already known in the art. For example, introducing enzyme activities of the mevalonate pathway, is a suitable strategy to make the organism produce FPP.

16. The method of embodiment 15 performed in a recombinant non-human host cell or a recombinant non-human host organism capable of functionally expressing,
   a) at least one acetyl transferase as defined in embodiment 5; optionally
   b) at least one polypeptide having the ability to convert the non-cyclic sesquiterpene precursor FPP to at least one drimanyl alcohol as defined in anyone of the embodiments 9 to 14; and optionally
   c) at least one enzyme selected from enzymes involved in the mevalonate pathway as defined above.
      In a particular embodiment enzymes a) and b) or enzymes a), b) and c) are functionally expressed by such cellular system as applied in an in vivo method of the invention.

17. The method of embodiment 16, wherein said non-human host cell or host organism is selected from a prokaryotic or eukaryotic microorganism, or a cell derived therefrom.

18. The method of embodiment 17, wherein said non-human host cell or host organism is selected from bacterial, fungal and plant cells or plants.

19. The method of embodiment 18, wherein said fungal cells are yeast cells, in particular selected from the genus *Saccharomyces, Pichia* or *Yarrowia*, in particular from the species *Saccharomyces cerevisiae, Pichia pastori* or *Yarrowia lipolytica.*

20. The method of embodiment 18 wherein said bacterial cells are selected from the genus *Rhodococcus, Pseudomonas, Bacillus* or *Escherichia*, in particular from the species *E. coli.*

21. The method of anyone of the preceding embodiments, further comprising as step (3) the processing of the at least one drimanyl acetate of step (1) or of step (2) to obtain a derivative using chemical or biocatalytic synthesis or a combination of both.

22. The method of embodiment 21, wherein the derivative is a hydrocarbon, alcohol, diol, triol, acetal, ketal, aldehyde, acid, ether, amide, ketone, lactone, epoxide, acetate, glycoside, ester and/or polycyclic compound.

23. The method of anyone of the preceding embodiments, wherein, the drimanyl acetate comprises albicanyl acetate, drimenyl acetate or bicyclofarnesyl acetate, in particular albicanyl acetate or drimenyl acetate, as main drimanyl alcohol product or, in particular as the single drimanyl alcohol product.

24. The method of any one of the preceding embodiments which comprises providing, in particular by transforming, a non-human host organism or host cell with
   a) at least one nucleic acid, expression construct or vector comprising a nucleic acid sequence encoding at least one polypeptide having acetyl transferase activity capable of transferring an acetyl group from an acetyl group donor to drimanyl alcohol, optionally stably integrated into the genome; optionally b) at least one nucleic acid, expression construct or vector comprising a nucleic acid sequence encoding at least one polypeptide having drimanyl alcohol synthase activity capable of producing a drimanyl alcohol from a non-cyclic sesquiterpene precursor, optionally stably integrated into the genome; and optionally c) at least one nucleic acid, expression construct or vector comprising a nucleic acid sequence encoding at least one polypeptide involved in the biosynthetic pathway for producing said non-cyclic sesquiterpene precursor, optionally stably integrated into the genome.

In a particular embodiment the non-human host organism or host cell is transformed with a) and b) or a), b) and c), and more particularly contains said nucleic acids stably integrated into the genome. The nucleic acids a), b) and/or c) may be located on the same or on two or more different vectors.

25. A polypeptide having acetyl transferase activity, capable of transferring an acetyl group from an acetyl group donor to drimanyl alcohol in order to produce a drimanyl acetate, which comprises an amino acid sequence having a sequence identity of 40%, 45%, 50%, 55%, 60%, 65%, 70%, 75%, 80%, 85%, 90%, 95%, 96%, 97%, 98%, or 99% to less than 100% to a least one amino acid sequence selected from SEQ ID NO: 9, 11, 13, 15, 17, 19, 21, 23, 25, 118, 121, 124, 127, 130, 133, 136, 143 and 144.

26. An isolated nucleic acid molecule
a) comprising a nucleotide sequence encoding the polypeptide of embodiment 5; or
b) comprising a nucleotide sequence having least 40%, 45%, 50%, 55%, 60%, 65%, 70%, 75%, 80%, 85%, 90%, 95%, 96%, 97%, 98%, or 99% and less than 100% sequence identity to a nucleotide sequence selected from SEQ ID NO:8, 10, 12, 14, 16, 18, 20, 22, 24, 116, 117, 119, 120, 122, 123, 125, 126, 128, 129, 131, 132, 134 and 135; or
c) comprising a nucleotide sequence comprising a sequence complementary to one of the sequences of a) or b); or
d) comprising a nucleotide sequence hybridizing under stringent conditions to a nucleotide sequence of a), b) or c).

27. An expression construct comprising at least one nucleic acid molecule of embodiment 26.

28. A vector comprising at least one nucleic acid molecule of embodiment 25 or at least one expression construct of embodiment 26.

29. The vector of embodiment 28, wherein the vector is a prokaryotic, viral or eukaryotic vector.

30. The vector of embodiment 28 or 29, wherein the vector is an expression vector.

31. The vector of anyone of the embodiments 28 to 30, which is a plasmid vector.

32. A recombinant host cell or a recombinant non-human host organism comprising
a) at least one isolated nucleic acid molecule of embodiment 26, optionally stably integrated into the genome; or
b) at least one expression construct of embodiment 27, optionally stably integrated into the genome; or
c) at least one vector of any one of embodiments 28 to 31.

In a particular embodiment the non-human host organism or host cell is transformed with a) and b) or a), b) and c), and more particularly contains said nucleic acids stably integrated into the genome.

33. The host cell or host organism of embodiment 32, selected from a prokaryotic or eukaryotic microorganism, or a cell derived therefrom.

34. The host cell or host organism of embodiment 33, selected from bacterial, fungal and plant cells or plants.

35. The host cell or host organism of embodiment 34, wherein said fungal cells are yeast cells.

36. The host cell or host organism of embodiment 35, wherein said bacterial cells are selected from the genus *Escherichia*, in particular from the species *E. coli* and said yeast cells are selected from the genus *Saccharomyces, Pichia* or *Yarrowia*, in particular from the species *Saccharomyces cerevisiae* or *Pichia pastoris*, or *Yarrowia lipolytica*.

37. A method for producing at least one catalytically active polypeptide according to embodiment 25 comprising:
a) culturing a non-human host organism or host cell of one of the embodiments 32 to 34 to express or over-express at least one polypeptide according to embodiment 25; and
b) optionally isolating the polypeptide from the non-human host cell or organism cultured in step a).

38. The method of embodiment 37, further comprising, prior to step a), providing, in particular transforming a non-human host organism or cell with at least one nucleic acid according to claim 26, or at least one construct of claim 27, or at least one vector of anyone of the claims 28 to 31 so that it expresses or over-expresses the polypeptide according to claim 25.

39. A method for preparing a mutant polypeptide comprising acetyl transferase activity, capable of transferring an acetyl group from an acetyl group donor to at least one, in particular one drimanyl alcohol in order to produce at least one, in particular one drimanyl acetate, which method comprises the steps of:
a) selecting a nucleic acid molecule encoding a polypeptide selected from SEQ ID NO: 9, 11, 13, 15, 17, 19, 21, 23, 25, 118, 121, 124, 127, 130, 133, 136, 143 and 144,
b) modifying the selected nucleic acid molecule to obtain at least one mutant nucleic acid molecule;
c) transforming host cells or unicellular host organisms with the mutant nucleic acid sequence to express a polypeptide encoded by the mutant nucleic acid sequence;
d) screening the expression product for at least one mutant comprising acetyl transferase activity; and,
e) optionally, if the polypeptide has no desired mutant activity, repeat the process steps a) to d) until a polypeptide with a desired mutant activity is obtained; and
f) optionally, if a polypeptide having a desired mutant activity was identified in step d), isolating the corresponding mutant nucleic acid obtained in step c).

40. The use of an acetyltransferase as defined in anyone of the preceding embodiments, for preparing odorants, flavours or fragrance ingredients or insect/pest control as for example for use in the preparation of a composition selected from body care, home care, or fragrance compositions.

b. Polypeptides Applicable According to the Invention

In this context the following definitions apply:

The generic terms "polypeptide" or "peptide", which may be used interchangeably, refer to a natural or synthetic linear chain or sequence of consecutive, peptidically linked amino acid residues, comprising about 10 up to more than 1.000 residues. Short chain polypeptides with up to 30 residues are also designated as "oligopeptides".

The term "protein" refers to a macromolecular structure consisting of one or more polypeptides. The amino acid sequence of its polypeptide(s) represents the "primary structure" of the protein. The amino acid sequence also predetermines the "secondary structure" of the protein by the formation of special structural elements, such as alpha-helical and beta-sheet structures formed within a polypeptide chain. The arrangement of a plurality of such secondary structural elements defines the "tertiary structure" or spatial arrangement of the protein. If a protein comprises more than one polypeptide chains said chains are spatially arranged forming the "quaternary structure" of the protein. A correct spacial arrangement or "folding" of the protein is prerequisite of protein function. Denaturation or unfolding destroys protein function. If such destruction is reversible, protein function may be restored by refolding.

A typical protein function referred to herein is an "enzyme function", i.e. the protein acts as biocatalyst on a substrate, for example a chemical compound, and catalyzes the conversion of said substrate to a product. An enzyme may show a high or low degree of substrate and/or product specificity.

A "polypeptide" referred to herein as having a particular "activity" thus implicitly refers to a correctly folded protein showing the indicated activity, as for example a specific enzyme activity.

Thus, unless otherwise indicated the term "polypeptide" also encompasses the terms "protein" and "enzyme".

Similarly, the term "polypeptide fragment" encompasses the terms "protein fragment" and "enzyme fragment".

The term "isolated polypeptide" refers to an amino acid sequence that is removed from its natural environment by any method or combination of methods known in the art and includes recombinant, biochemical and synthetic methods.

"Target peptide" refers to an amino acid sequence which targets a protein, or polypeptide to intracellular organelles, i.e., mitochondria, or plastids, or to the extracellular space (secretion signal peptide). A nucleic acid sequence encoding a target peptide may be fused to the nucleic acid sequence encoding the amino terminal end, e.g., N-terminal end, of the protein or polypeptide, or may be used to replace a native targeting polypeptide.

The present invention also relates to "functional equivalents" (also designated as "analogs" or "functional mutations") of the polypeptides specifically described herein.

For example, "functional equivalents" refer to polypeptides which, in a test used for determining enzymatic activity, display at least a 1 to 10%, or at least 20%, or at least 50%, or at least 75%, or at least 90% higher or lower enzymatic activity, as that of the polypeptide specifically described herein and serving as basis for said comparison.

"Functional equivalents", according to the invention, also cover particular mutants, which, in at least one sequence position of an amino acid sequences stated herein, have an amino acid that is different from that concretely stated one, but nevertheless possess one of the aforementioned biological activities, as for example enzyme activity. "Functional equivalents" thus comprise mutants obtainable by one or more, like 1 to 20, in particular 1 to 15 or 5 to 10 amino acid additions, substitutions, in particular conservative substitutions (i.e. as a result thereof the amino acid in question is replaced by an amino acid of the same charge, size, polarity and/or solubility), deletions and/or inversions, where the stated changes can occur in any sequence position, provided they lead to a mutant with the profile of properties according to the invention. Functional equivalence is in particular also provided if the activity patterns coincide qualitatively between the mutant and the unchanged polypeptide, i.e. if, for example, interaction with the same agonist or antagonist or substrate, however at a different rate, (i.e. expressed by a $EC_{50}$ or $IC_{50}$ value or any other parameter suitable in the present technical field) is observed. Examples of suitable (conservative) amino acid substitutions are shown in the following table:

| Original residue | Examples of substitution |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also "precursors" of the polypeptides described herein, as well as "functional derivatives" and "salts" of the polypeptides.

"Precursors" are in that case natural or synthetic precursors of the polypeptides with or without the desired biological activity.

The expression "salts" means salts of carboxyl groups as well as salts of acid addition of amino groups of the protein molecules according to the invention. Salts of carboxyl groups can be produced in a known way and comprise inorganic salts, for example sodium, calcium, ammonium, iron and zinc salts, and salts with organic bases, for example amines, such as triethanolamine, arginine, lysine, piperidine and the like. Salts of acid addition, for example salts with inorganic acids, such as hydrochloric acid or sulfuric acid and salts with organic acids, such as acetic acid and oxalic acid, are also covered by the invention.

"Functional derivatives" of polypeptides according to the invention can also be produced on functional amino acid side groups or at their N-terminal or C-terminal end using known techniques. Such derivatives comprise for example aliphatic esters of carboxylic acid groups, amides of carboxylic acid groups, obtainable by reaction with ammonia or with a primary or secondary amine; N-acyl derivatives of free amino groups, produced by reaction with acyl groups; or O-acyl derivatives of free hydroxyl groups, produced by reaction with acyl groups.

"Functional equivalents" naturally also comprise polypeptides that can be obtained from other organisms, as well as naturally occurring variants. For example, areas of homologous sequence regions can be established by sequence comparison, and equivalent polypeptides can be determined on the basis of the concrete parameters of the invention.

"Functional equivalents" also comprise "fragments", like individual domains or sequence motifs, of the polypeptides according to the invention, or N- and/or C-terminally truncated forms, which may or may not display the desired biological function. Preferably such "fragments" retain the desired biological function at least qualitatively.

"Functional equivalents" are, moreover, fusion proteins, which have one of the polypeptide sequences stated herein or functional equivalents derived therefrom and at least one further, functionally different, heterologous sequence in functional N-terminal or C-terminal association (i.e. without substantial mutual functional impairment of the fusion protein parts). Non-limiting examples of these heterologous sequences are e.g. signal peptides, histidine anchors or enzymes.

"Functional equivalents" which are also comprised in accordance with the invention are homologs to the specifically disclosed polypeptides. These have at least 60%, preferably at least 75%, in particular at least 80 or 85%, such as, for example, 90, 91, 92, 93, 94, 95, 96, 97, 98 or 99%, homology (or identity) to one of the specifically disclosed amino acid sequences, calculated by the algorithm of Pearson and Lipman, Proc. Natl. Acad, Sci. (USA) 85(8), 1988, 2444-2448. A homology or identity, expressed as a percentage, of a homologous polypeptide according to the invention means in particular an identity, expressed as a percentage, of the amino acid residues based on the total length of one of the amino acid sequences described specifically herein.

The identity data, expressed as a percentage, may also be determined with the aid of BLAST alignments, algorithm blastp (protein-protein BLAST), or by applying the Clustal settings specified herein below.

In the case of a possible protein glycosylation, "functional equivalents" according to the invention comprise polypeptides as described herein in deglycosylated or glycosylated form as well as modified forms that can be obtained by altering the glycosylation pattern.

Functional equivalents or homologues of the polypeptides according to the invention can be produced by mutagenesis, e.g. by point mutation, lengthening or shortening of the protein or as described in more detail below.

Functional equivalents or homologs of the polypeptides according to the invention can be identified by screening combinatorial databases of mutants, for example shortening mutants. For example, a variegated database of protein variants can be produced by combinatorial mutagenesis at the nucleic acid level, e.g. by enzymatic ligation of a mixture of synthetic oligonucleotides. There are a great many methods that can be used for the production of databases of potential homologues from a degenerated oligonucleotide sequence. Chemical synthesis of a degenerated gene sequence can be carried out in an automatic DNA synthesizer, and the synthetic gene can then be ligated in a suitable expression vector. The use of a degenerated genome makes it possible to supply all sequences in a mixture, which code for the desired set of potential protein sequences. Methods of synthesis of degenerated oligonucleotides are known to a person skilled in the art.

In the prior art, several techniques are known for the screening of gene products of combinatorial databases, which were produced by point mutations or shortening, and for the screening of cDNA libraries for gene products with a selected property. These techniques can be adapted for the rapid screening of the gene banks that were produced by combinatorial mutagenesis of homologues according to the invention. The techniques most frequently used for the screening of large gene banks, which are based on a high-throughput analysis, comprise cloning of the gene bank in expression vectors that can be replicated, transformation of the suitable cells with the resultant vector database and expression of the combinatorial genes in conditions in which detection of the desired activity facilitates isolation of the vector that codes for the gene whose product was detected. Recursive Ensemble Mutagenesis (REM), a technique that increases the frequency of functional mutants in the databases, can be used in combination with the screening tests, in order to identify homologues.

An embodiment provided herein provides orthologs and paralogs of polypeptides disclosed herein as well as methods for identifying and isolating such orthologs and paralogs. A definition of the terms "ortholog" and "paralog" is given below and applies to amino acid and nucleic acid sequences.

c. Coding Nucleic Acid Sequences Applicable According to the Invention

In this context the following definitions apply:

The terms "nucleic acid sequence," "nucleic acid," "nucleic acid molecule" and "polynucleotide" are used interchangeably meaning a sequence of nucleotides. A nucleic acid sequence may be a single-stranded or double-stranded deoxyribonucleotide, or ribonucleotide of any length, and include coding and non-coding sequences of a gene, exons, introns, sense and anti-sense complimentary sequences, genomic DNA, cDNA, miRNA, siRNA, mRNA, rRNA, tRNA, recombinant nucleic acid sequences, isolated and purified naturally occurring DNA and/or RNA sequences, synthetic DNA and RNA sequences, fragments, primers and nucleic acid probes. The skilled artisan is aware that the nucleic acid sequences of RNA are identical to the DNA sequences with the difference of thymine (T) being replaced by uracil (U). The term "nucleotide sequence" should also be understood as comprising a polynucleotide molecule or an oligonucleotide molecule in the form of a separate fragment or as a component of a larger nucleic acid.

An "isolated nucleic acid" or "isolated nucleic acid sequence" relates to a nucleic acid or nucleic acid sequence that is in an environment different from that in which the nucleic acid or nucleic acid sequence naturally occurs and can include those that are substantially free from contaminating endogenous material.

The term "naturally-occurring" as used herein as applied to a nucleic acid refers to a nucleic acid that is found in a cell of an organism in nature and which has not been intentionally modified by a human in the laboratory.

A "fragment" of a polynucleotide or nucleic acid sequence refers to contiguous nucleotides that is particularly at least 15 bp, at least 30 bp, at least 40 bp, at least 50 bp and/or at least 60 bp in length of the polynucleotide of an embodiment herein. Particularly the fragment of a polynucleotide comprises at least 25, more particularly at least 50, more particularly at least 75, more particularly at least 100, more particularly at least 150, more particularly at least 200, more particularly at least 300, more particularly at least 400, more particularly at least 500, more particularly at least 600, more particularly at least 700, more particularly at least 800, more particularly at least 900, more particularly at least 1000 contiguous nucleotides of the polynucleotide of an embodiment herein. Without being limited, the fragment of the polynucleotides herein may be used as a PCR primer, and/or as a probe, or for anti-sense gene silencing or RNAi.

As used herein, the term "hybridization" or hybridizes under certain conditions is intended to describe conditions for hybridization and washes under which nucleotide sequences that are significantly identical or homologous to each other remain bound to each other. The conditions may be such that sequences, which are at least about 70%, such as at least about 80%, and such as at least about 85%, 90%, or 95% identical, remain bound to each other. Definitions of low stringency, moderate, and high stringency hybridization conditions are provided herein below. Appropriate hybridization conditions can also be selected by those skilled in the art with minimal experimentation as exemplified in Ausubel et al. (1995, Current Protocols in Molecular Biology, John Wiley & Sons, sections 2, 4, and 6). Additionally, stringency conditions are described in Sambrook et al. (1989, Molecular Cloning: A Laboratory Manual, 2nd ed., Cold Spring Harbor Press, chapters 7, 9, and 11).

"Recombinant nucleic acid sequences" are nucleic acid sequences that result from the use of laboratory methods (for example, molecular cloning) to bring together genetic material from more than on source, creating or modifying a nucleic acid sequence that does not occur naturally and would not be otherwise found in biological organisms.

"Recombinant DNA technology" refers to molecular biology procedures to prepare a recombinant nucleic acid sequence as described, for instance, in Laboratory Manuals edited by Weigel and Glazebrook, 2002, Cold Spring Harbor Lab Press; and Sambrook et al., 1989, Cold Spring Harbor, NY, Cold Spring Harbor Laboratory Press.

The term "gene" means a DNA sequence comprising a region, which is transcribed into a RNA molecule, e.g., an mRNA in a cell, operably linked to suitable regulatory regions, e.g., a promoter. A gene may thus comprise several operably linked sequences, such as a promoter, a 5' leader sequence comprising, e.g., sequences involved in translation initiation, a coding region of cDNA or genomic DNA, introns, exons, and/or a 3'non-translated sequence comprising, e.g., transcription termination sites.

"Polycistronic" refers to nucleic acid molecules, in particular mRNAs, that can encode more than one polypeptide separately within the same nucleic acid molecule A "chimeric gene" refers to any gene which is not normally found in nature in a species, in particular, a gene in which one or more parts of the nucleic acid sequence are present that are not associated with each other in nature. For example the promoter is not associated in nature with part or all of the transcribed region or with another regulatory region. The term "chimeric gene" is understood to include expression constructs in which a promoter or transcription regulatory sequence is operably linked to one or more coding sequences or to an antisense, i.e., reverse complement of the sense strand, or inverted repeat sequence (sense and antisense, whereby the RNA transcript forms double stranded RNA upon transcription). The term "chimeric gene" also includes genes obtained through the combination of portions of one or more coding sequences to produce a new gene.

A "3' UTR" or "3' non-translated sequence" (also referred to as "3' untranslated region," or "3' end") refers to the nucleic acid sequence found downstream of the coding sequence of a gene, which comprises, for example, a transcription termination site and (in most, but not all eukaryotic mRNAs) a polyadenylation signal such as AAUAAA or variants thereof. After termination of transcription, the mRNA transcript may be cleaved downstream of the polyadenylation signal and a poly(A) tail may be added, which is involved in the transport of the mRNA to the site of translation, e.g., cytoplasm.

The term "primer" refers to a short nucleic acid sequence that is hybridized to a template nucleic acid sequence and is used for polymerization of a nucleic acid sequence complementary to the template.

The term "selectable marker" refers to any gene which upon expression may be used to select a cell or cells that include the selectable marker. Examples of selectable markers are described below. The skilled artisan will know that different antibiotic, fungicide, auxotrophic or herbicide selectable markers are applicable to different target species.

The invention also relates to nucleic acid sequences that code for polypeptides as defined herein.

In particular, the invention also relates to nucleic acid sequences (single-stranded and double-stranded DNA and RNA sequences, e.g. cDNA, genomic DNA and mRNA), coding for one of the above polypeptides and their functional equivalents, which can be obtained for example using artificial nucleotide analogs.

The invention relates both to isolated nucleic acid molecules, which code for polypeptides according to the invention or biologically active segments thereof, and to nucleic acid fragments, which can be used for example as hybridization probes or primers for identifying or amplifying coding nucleic acids according to the invention.

The present invention also relates to nucleic acids with a certain degree of "identity" to the sequences specifically disclosed herein. "Identity" between two nucleic acids means identity of the nucleotides, in each case over the entire length of the nucleic acid.

The "identity" between two nucleotide sequences (the same applies to peptide or amino acid sequences) is a function of the number of nucleotide residues (or amino acid residues) or that are identical in the two sequences when an alignment of these two sequences has been generated. Identical residues are defined as residues that are the same in the two sequences in a given position of the alignment. The percentage of sequence identity, as used herein, is calculated from the optimal alignment by taking the number of residues identical between two sequences dividing it by the total number of residues in the shortest sequence and multiplying by 100. The optimal alignment is the alignment in which the percentage of identity is the highest possible. Gaps may be introduced into one or both sequences in one or more positions of the alignment to obtain the optimal alignment. These gaps are then taken into account as non-identical residues for the calculation of the percentage of sequence identity. Alignment for the purpose of determining the percentage of amino acid or nucleic acid sequence identity can be achieved in various ways using computer programs and for instance publicly available computer programs available on the world wide web.

Particularly, the BLAST program (Tatiana et al, FEMS Microbiol Lett., 1999, 174:247-250, 1999) set to the default parameters, available from the National Center for Biotechnology Information (NCBI) website at ncbi.nlm.nih.gov/BLAST/bl2seq/wblast2.cgi, can be used to obtain an optimal alignment of protein or nucleic acid sequences and to calculate the percentage of sequence identity.

In another example the identity may be calculated by means of the Vector NTI Suite 7.1 program of the company Informax (USA) employing the Clustal Method (Higgins D G, Sharp P M. (1989)) with the following settings:

| Multiple alignment parameters: | |
| --- | --- |
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |

| Pairwise alignment parameter: | |
| --- | --- |
| FAST algorithm | on |
| K-tuple size | 1 |
| Gap penalty | 3 |
| Window size | 5 |
| Number of best diagonals | 5 |

Alternatively the identity may be determined according to Chenna, et al. (2003), the web page: http://www.ebi.ac.uk/Tools/clustalw/index.html# and the following settings

| | |
| --- | --- |
| DNA Gap Open Penalty | 15.0 |
| DNA Gap Extension Penalty | 6.66 |
| DNA Matrix | Identity |
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of individual overlapping, complementary nucleic acid building blocks of the double helix. Chemical synthesis of oligonucleotides can, for example, be performed in a known way, by the phosphoamidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

The nucleic acid molecules according to the invention can in addition contain non-translated sequences from the 3' and/or 5' end of the coding genetic region.

The invention further relates to the nucleic acid molecules that are complementary to the concretely described nucleotide sequences or a segment thereof.

The nucleotide sequences according to the invention make possible the production of probes and primers that can be used for the identification and/or cloning of homologous sequences in other cellular types and organisms. Such probes or primers generally comprise a nucleotide sequence region which hybridizes under "stringent" conditions (as defined herein elsewhere) on at least about 12, preferably at least about 25, for example about 40, 50 or 75 successive nucleotides of a sense strand of a nucleic acid sequence according to the invention or of a corresponding antisense strand.

"Homologous" sequences include orthologous or paralogous sequences. Methods of identifying orthologs or paralogs including phylogenetic methods, sequence similarity and hybridization methods are known in the art and are described herein.

"Paralogs" result from gene duplication that gives rise to two or more genes with similar sequences and similar functions. Paralogs typically cluster together and are formed by duplications of genes within related plant species. Paralogs are found in groups of similar genes using pair-wise Blast analysis or during phylogenetic analysis of gene families using programs such as CLUSTAL. In paralogs, consensus sequences can be identified characteristic to sequences within related genes and having similar functions of the genes.

"Orthologs", or orthologous sequences, are sequences similar to each other because they are found in species that descended from a common ancestor. For instance, plant species that have common ancestors are known to contain many enzymes that have similar sequences and functions. The skilled artisan can identify orthologous sequences and predict the functions of the orthologs, for example, by constructing a polygenic tree for a gene family of one species using CLUSTAL or BLAST programs. A method for identifying or confirming similar functions among homologous sequences is by comparing of the transcript profiles in host cells or organisms, such as plants or microorganisms, overexpressing or lacking (in knockouts/knockdowns) related polypeptides. The skilled person will understand that genes having similar transcript profiles, with greater than 50% regulated transcripts in common, or with greater than 70% regulated transcripts in common, or greater than 90% regulated transcripts in common will have similar functions. Homologs, paralogs, orthologs and any other variants of the sequences herein are expected to function in a similar manner by making the host cells, organism such as plants or microorganisms producing terpene synthase proteins.

The term "selectable marker" refers to any gene which upon expression may be used to select a cell or cells that include the selectable marker. Examples of selectable markers are described below. The skilled artisan will know that different antibiotic, fungicide, auxotrophic or herbicide selectable markers are applicable to different target species.

An "isolated" nucleic acid molecule is separated from other nucleic acid molecules that are present in the natural source of the nucleic acid and can moreover be substantially free from other cellular material or culture medium, if it is being produced by recombinant techniques, or can be free from chemical precursors or other chemicals, if it is being synthesized chemically.

A nucleic acid molecule according to the invention can be isolated by means of standard techniques of molecular biology and the sequence information supplied according to the invention. For example, cDNA can be isolated from a suitable cDNA library, using one of the concretely disclosed complete sequences or a segment thereof as hybridization probe and standard hybridization techniques (as described for example in Sambrook, (1989)).

In addition, a nucleic acid molecule comprising one of the disclosed sequences or a segment thereof, can be isolated by the polymerase chain reaction, using the oligonucleotide primers that were constructed on the basis of this sequence. The nucleic acid amplified in this way can be cloned in a suitable vector and can be characterized by DNA sequencing. The oligonucleotides according to the invention can also be produced by standard methods of synthesis, e.g. using an automatic DNA synthesizer.

Nucleic acid sequences according to the invention or derivatives thereof, homologues or parts of these sequences, can for example be isolated by usual hybridization techniques or the PCR technique from other bacteria, e.g. via genomic or cDNA libraries. These DNA sequences hybridize in standard conditions with the sequences ac-cording to the invention.

"Hybridize" means the ability of a polynucleotide or oligonucleotide to bind to an almost complementary sequence in standard conditions, whereas nonspecific binding does not occur between non-complementary partners in these conditions. For this, the sequences can be 90-100% complementary. The property of complementary sequences of being able to bind specifically to one another is utilized for example in Northern Blotting or Southern Blotting or in primer binding in PCR or RT-PCR.

Short oligonucleotides of the conserved regions are used advantageously for hybridization. However, it is also possible to use longer fragments of the nucleic acids according to the invention or the complete sequences for the hybridization. These "standard conditions" vary depending on the nucleic acid used (oligonucleotide, longer fragment or complete sequence) or depending on which type of nucleic acid—DNA or RNA—is used for hybridization. For example, the melting temperatures for DNA:DNA hybrids are approx. 10° C. lower than those of DNA:RNA hybrids of the same length.

For example, depending on the particular nucleic acid, standard conditions mean temperatures between 42 and 58° C. in an aqueous buffer solution with a concentration between 0.1 to 5×SSC (1×SSC=0.15 M NaCl, 15 mM sodium citrate, pH 7.2) or additionally in the presence of 50% formamide, for example 42° C. in 5×SSC, 50% formamide. Advantageously, the hybridization conditions for DNA:DNA hybrids are 0.1×SSC and temperatures between about 20° C. to 45° C., preferably between about 30° C. to 45° C. For DNA:RNA hybrids the hybridization conditions are advantageously 0.1×SSC and temperatures between about 30° C. to 55° C., preferably between about 45° C. to 55° C. These stated temperatures for hybridization are examples of calculated melting temperature values for a nucleic acid with a length of approx. 100 nucleotides and a G+C content of 50% in the absence of formamide. The experimental conditions for DNA hybridization are described in relevant genetics textbooks, for example Sambrook et al., 1989, and can be calculated using formulae that are known by a person skilled in the art, for example depending on the length of the nucleic acids, the type of hybrids or the G+C content. A person skilled in the art can obtain further information on hybridization from the following textbooks: Ausubel et al. (eds), (1985), Brown (ed) (1991).

"Hybridization" can in particular be carried out under stringent conditions. Such hybridization conditions are for example described in Sambrook (1989), or in Current Protocols in Molecular Biology, John Wiley & Sons, N.Y. (1989), 6.3.1-6.3.6.

As used herein, the term hybridization or hybridizes under certain conditions is intended to describe conditions for hybridization and washes under which nucleotide sequences that are significantly identical or homologous to each other remain bound to each other. The conditions may be such that sequences, which are at least about 70%, such as at least about 80%, and such as at least about 85%, 90%, or 95% identical, remain bound to each other. Definitions of low stringency, moderate, and high stringency hybridization conditions are provided herein.

Appropriate hybridization conditions can be selected by those skilled in the art with minimal experimentation as exemplified in Ausubel et al. (1995, Current Protocols in Molecular Biology, John Wiley & Sons, sections 2, 4, and 6). Additionally, stringency conditions are described in Sambrook et al. (1989, Molecular Cloning: A Laboratory Manual, 2nd ed., Cold Spring Harbor Press, chapters 7, 9, and 11).

As used herein, defined conditions of low stringency are as follows. Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×106 32P-labeled probe is used. Filters are incubated in hybridization mixture for 18-20 h at 40° C., and then washed for 1.5 h at 55° C. In a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography.

As used herein, defined conditions of moderate stringency are as follows. Filters containing DNA are pretreated for 7 h at 50° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×106 32P-labeled probe is used. Filters are incubated in hybridization mixture for 30 h at 50° C., and then washed for 1.5 h at 55° C. In a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography.

As used herein, defined conditions of high stringency are as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in the prehybridization mixture containing 100 µg/ml denatured salmon sperm DNA and 5-20×106 cpm of 32P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 minutes.

Other conditions of low, moderate, and high stringency well known in the art (e.g., as employed for cross-species hybridizations) may be used if the above conditions are inappropriate (e.g., as employed for cross-species hybridizations).

A detection kit for nucleic acid sequences encoding a polypeptide of the invention may include primers and/or probes specific for nucleic acid sequences encoding the polypeptide, and an associated protocol to use the primers and/or probes to detect nucleic acid sequences encoding the polypeptide in a sample. Such detection kits may be used to determine whether a plant, organism, microorganism or cell has been modified, i.e., transformed with a sequence encoding the polypeptide.

To test a function of variant DNA sequences according to an embodiment herein, the sequence of interest is operably linked to a selectable or screenable marker gene and expression of said reporter gene is tested in transient expression assays, for example, with microorganisms or with protoplasts or in stably transformed plants.

The invention also relates to derivatives of the concretely disclosed or derivable nucleic acid sequences.

Thus, further nucleic acid sequences according to the invention can be derived from the sequences specifically disclosed herein and can differ from it by one or more, like 1 to 20, in particular 1 to 15 or 5 to 10 additions, substitutions, insertions or deletions of one or several (like for example 1 to 10) nucleotides, and furthermore code for polypeptides with the desired profile of properties.

The invention also encompasses nucleic acid sequences that comprise so-called silent mutations or have been altered, in comparison with a concretely stated sequence, according to the codon usage of a special original or host organism.

According to a particular embodiment of the invention variant nucleic acids may be prepared in order to adapt its nucleotide sequence to a specific expression system. For example, bacterial expression systems are known to more efficiently express polypeptides if amino acids are encoded by particular codons. Due to the degeneracy of the genetic code, more than one codon may encode the same amino acid sequence, multiple nucleic acid sequences can code for the same protein or polypeptide, all these DNA sequences being encompassed by an embodiment herein. Where appropriate, the nucleic acid sequences encoding the polypeptides described herein may be optimized for increased expression in the host cell. For example, nucleic acids of an embodiment herein may be synthesized using codons particular to a host for improved expression.

The invention also encompasses naturally occurring variants, e.g. splicing variants or allelic variants, of the sequences described therein.

Allelic variants may have at least 60% homology at the level of the derived amino acid, preferably at least 80% homology, quite especially preferably at least 90% homology over the entire sequence range (regarding homology at the amino acid level, reference should be made to the details given above for the polypeptides). Advantageously, the homologies can be higher over partial regions of the sequences.

The invention also relates to sequences that can be obtained by conservative nucleotide substitutions (i.e. as a result thereof the amino acid in question is replaced by an amino acid of the same charge, size, polarity and/or solubility).

The invention also relates to the molecules derived from the concretely disclosed nucleic acids by sequence polymorphisms. Such genetic polymorphisms may exist in cells from different populations or within a population due to natural allelic variation. Allelic variants may also include functional equivalents. These natural variations usually produce a variance of 1 to 5% in the nucleotide sequence of a gene. Said polymorphisms may lead to changes in the amino acid sequence of the polypeptides disclosed herein. Allelic variants may also include functional equivalents.

Furthermore, derivatives are also to be understood to be homologs of the nucleic acid sequences according to the invention, for example animal, plant, fungal or bacterial homologs, shortened sequences, single-stranded DNA or RNA of the coding and noncoding DNA sequence. For example, homologs have, at the DNA level, a homology of at least 40%, preferably of at least 60%, especially preferably of at least 70%, quite especially preferably of at least 80% over the entire DNA region given in a sequence specifically disclosed herein.

Moreover, derivatives are to be understood to be, for example, fusions with promoters. The promoters that are added to the stated nucleotide sequences can be modified by at least one nucleotide exchange, at least one insertion, inversion and/or deletion, though without impairing the functionality or efficacy of the promoters. Moreover, the efficacy of the promoters can be increased by altering their sequence or can be exchanged completely with more effective promoters even of organisms of a different genus.

d. Generation of Functional Polypeptide Mutants

Moreover, a person skilled in the art is familiar with methods for generating functional mutants, that is to say nucleotide sequences which code for a polypeptide with at least 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% sequence identity to anyone of amino acid related SEQ ID NOs as disclosed herein and/or encoded by a nucleic acid molecule comprising a nucleotide sequence having at least 70% sequence identity to anyone of the nucleotide related SEQ ID NOs as disclosed herein.

Depending on the technique used, a person skilled in the art can introduce entirely random or else more directed mutations into genes or else noncoding nucleic acid regions (which are for example important for regulating expression) and subsequently generate genetic libraries. The methods of molecular biology required for this purpose are known to the skilled worker and for example described in Sambrook and Russell, Molecular Cloning. 3rd Edition, Cold Spring Harbor Laboratory Press 2001.

Methods for modifying genes and thus for modifying the polypeptide encoded by them have been known to the skilled worker for a long time, such as, for example site-specific mutagenesis, where individual or several nucleotides of a gene are replaced in a directed fashion (Trower M K (Ed.) 1996; In vitro mutagenesis protocols. Humana Press, New Jersey), saturation mutagenesis, in which a codon for any amino acid can be exchanged or added at any point of a gene (Kegler-Ebo D M, Docktor C M, DiMaio D (1994) Nucleic Acids Res 22:1593; Barettino D, Feigenbutz M, Valcarel R, Stunnenberg H G (1994) Nucleic Acids Res 22:541; Barik S (1995) Mol Biotechnol 3:1), error-prone polymerase chain reaction, where nucleotide sequences are mutated by error-prone DNA polymerases (Eckert K A, Kunkel T A (1990) Nucleic Acids Res 18:3739);

the SeSaM method (sequence saturation method), in which preferred exchanges are prevented by the polymerase. Schenk et al., Biospektrum, Vol. 3, 2006, 277-279 the passaging of genes in mutator strains, in which, for example owing to defective DNA repair mechanisms, there is an increased mutation rate of nucleotide sequences (Greener A, Callahan M, Jerpseth B (1996) An efficient random mutagenesis technique using an *E. coli* mutator strain. In: Trower M K (Ed.) In vitro mutagenesis protocols. Humana Press, New Jersey), or DNA shuffling, in which a pool of closely related genes is formed and digested and the fragments are used as templates for a polymerase chain reaction in which, by repeated strand separation and reassociation, full-length mosaic genes are ultimately generated (Stemmer W P C (1994) Nature 370:389; Stemmer W P C (1994) Proc Natl Acad Sci USA 91:10747).

Using so-called directed evolution (described, inter alia, in Reetz M T and Jaeger K-E (1999), Topics Curr Chem 200:31; Zhao H, Moore J C, Volkov A A, Arnold F H (1999), Methods for optimizing industrial polypeptides by directed evolution, In: Demain A L, Davies J E (Ed.) Manual of industrial microbiology and biotechnology. American Society for Microbiology), a skilled worker can produce functional mutants in a directed manner and on a large scale. To this end, in a first step, gene libraries of the respective polypeptides are first produced, for example using the methods given above. The gene libraries are expressed in a suitable way, for example by bacteria or by phage display systems.

The relevant genes of host organisms which express functional mutants with properties that largely correspond to the desired properties can be submitted to another mutation cycle. The steps of the mutation and selection or screening can be repeated iteratively until the present functional mutants have the desired properties to a sufficient extent. Using this iterative procedure, a limited number of mutations, for example 1, 2, 3, 4 or 5 mutations, can be performed in stages and assessed and selected for their influence on the activity in question. The selected mutant can then be submitted to a further mutation step in the same way. In this way, the number of individual mutants to be investigated can be reduced significantly.

The results according to the invention also provide important information relating to structure and sequence of the relevant polypeptides, which is required for generating, in a targeted fashion, further polypeptides with desired modified properties. In particular, it is possible to define so-called "hot spots", i.e. sequence segments that are potentially suitable for modifying a property by introducing targeted mutations.

Information can also be deduced regarding amino acid sequence positions, in the region of which mutations can be effected that should probably have little effect on the activity, and can be designated as potential "silent mutations".

e. Constructs for Expressing Polypeptides of the Invention

In this context the following definitions apply:

"Expression of a gene" encompasses "heterologous expression" and "over-expression" and involves transcription of the gene and translation of the mRNA into a protein. Overexpression refers to the production of the gene product as measured by levels of mRNA, polypeptide and/or enzyme activity in transgenic cells or organisms that exceeds levels of production in non-transformed cells or organisms of a similar genetic background.

"Expression vector" as used herein means a nucleic acid molecule engineered using molecular biology methods and recombinant DNA technology for delivery of foreign or exogenous DNA into a host cell. The expression vector typically includes sequences required for proper transcription of the nucleotide sequence. The coding region usually codes for a protein of interest but may also code for an RNA, e.g., an antisense RNA, siRNA and the like.

An "expression vector" as used herein includes any linear or circular recombinant vector including but not limited to viral vectors, bacteriophages and plasmids. The skilled person is capable of selecting a suitable vector according to the expression system. In one embodiment, the expression vector includes the nucleic acid of an embodiment herein operably linked to at least one "regulatory sequence", which controls transcription, translation, initiation and termination, such as a transcriptional promoter, operator or enhancer, or an mRNA ribosomal binding site and, optionally, including at least one selection marker. Nucleotide sequences are "operably linked" when the regulatory sequence functionally relates to the nucleic acid of an embodiment herein.

An "expression system" as used herein encompasses any combination of nucleic acid molecules required for the expression of one, or the co-expression of two or more polypeptides either in vivo of a given expression host, or in vitro. The respective coding sequences may either be located on a single nucleic acid molecule or vector, as for example a vector containing multiple cloning sites, or on a polycistronic nucleic acid, or may be distributed over two or more physically distinct vectors.

As used herein, the terms "amplifying" and "amplification" refer to the use of any suitable amplification methodology for generating or detecting recombinant of naturally expressed nucleic acid, as described in detail, below. For example, the invention provides methods and reagents (e.g., specific degenerate oligonucleotide primer pairs, oligo dT primer) for amplifying (e.g., by polymerase chain reaction, PCR) naturally expressed (e.g., genomic DNA or mRNA) or recombinant (e.g., cDNA) nucleic acids of the invention in vivo, ex vivo or in vitro.

"Regulatory sequence" refers to a nucleic acid sequence that determines expression level of the nucleic acid sequences of an embodiment herein and is capable of regulating the rate of transcription of the nucleic acid sequence operably linked to the regulatory sequence. Regulatory sequences comprise promoters, enhancers, transcription factors, promoter elements and the like.

A "promoter", a "nucleic acid with promoter activity" or a "promoter sequence" is understood as meaning, in accordance with the invention, a nucleic acid which, when functionally linked to a nucleic acid to be transcribed, regulates the transcription of said nucleic acid. "Promoter" in particular refers to a nucleic acid sequence that controls the expression of a coding sequence by providing a binding site for RNA polymerase and other factors required for proper transcription including without limitation transcription factor binding sites, repressor and activator protein binding sites. The meaning of the term promoter also includes the term "promoter regulatory sequence". Promoter regulatory sequences may include upstream and downstream elements that may influences transcription, RNA processing or stability of the associated coding nucleic acid sequence. Promoters include naturally-derived and synthetic sequences. The coding nucleic acid sequences is usually located downstream of the promoter with respect to the direction of the transcription starting at the transcription initiation site.

In this context, a "functional" or "operative" linkage is understood as meaning for example the sequential arrangement of one of the nucleic acids with a regulatory sequence. For example the sequence with promoter activity and of a nucleic acid sequence to be transcribed and optionally further regulatory elements, for example nucleic acid sequences which ensure the transcription of nucleic acids, and for example a terminator, are linked in such a way that each of the regulatory elements can perform its function upon transcription of the nucleic acid sequence. This does not necessarily require a direct linkage in the chemical sense. Genetic control sequences, for example enhancer sequences, can even exert their function on the target sequence from more remote positions or even from other DNA molecules. Preferred arrangements are those in which the nucleic acid sequence to be transcribed is positioned behind (i.e. at the 3'-end of) the promoter sequence so that the two sequences are joined together covalently. The distance between the promoter sequence and the nucleic acid sequence to be expressed recombinantly can be smaller than 200 base pairs, or smaller than 100 base pairs or smaller than 50 base pairs.

In addition to promoters and terminator, the following may be mentioned as examples of other regulatory elements: targeting sequences, enhancers, polyadenylation signals, selectable markers, amplification signals, replication origins and the like. Suitable regulatory sequences are described, for example, in Goeddel, Gene Expression Technology: Methods in Enzymology 185, Academic Press, San Diego, CA (1990).

The term "constitutive promoter" refers to an unregulated promoter that allows for continual transcription of the nucleic acid sequence it is operably linked to.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous. The nucleotide sequence associated with the promoter sequence may be of homologous or heterologous origin with respect to the plant to be transformed. The sequence also may be entirely or partially synthetic. Regardless of the origin, the nucleic acid sequence associated with the promoter sequence will be expressed or silenced in accordance with promoter properties to which it is linked after binding to the polypeptide of an embodiment herein. The associated nucleic acid may code for a protein that is desired to be expressed or suppressed throughout the organism at all times or, alternatively, at a specific time or in specific tissues, cells, or cell compartment. Such nucleotide sequences particularly encode proteins conferring desirable phenotypic traits to the host cells or organism altered or transformed therewith. More particularly, the associated nucleotide sequence leads to the production of the product or products of interest as herein defined in the cell or organism. Particularly, the nucleotide sequence encodes a polypeptide having an enzyme activity as herein defined.

The nucleotide sequence as described herein above may be part of an "expression cassette". The terms "expression cassette" and "expression construct" are used synonymously. The (preferably recombinant) expression construct contains a nucleotide sequence which encodes a polypeptide according to the invention and which is under genetic control of regulatory nucleic acid sequences.

In a process applied according to the invention, the expression cassette may be part of an "expression vector", in particular of a recombinant expression vector.

An "expression unit" is understood as meaning, in accordance with the invention, a nucleic acid with expression activity which comprises a promoter as defined herein and, after functional linkage with a nucleic acid to be expressed or a gene, regulates the expression, i.e. the transcription and the translation of said nucleic acid or said gene. It is therefore in this connection also referred to as a "regulatory nucleic acid sequence". In addition to the promoter, other regulatory elements, for example enhancers, can also be present.

An "expression cassette" or "expression construct" is understood as meaning, in accordance with the invention, an expression unit which is functionally linked to the nucleic acid to be expressed or the gene to be expressed. In contrast to an expression unit, an expression cassette therefore comprises not only nucleic acid sequences which regulate transcription and translation, but also the nucleic acid sequences that are to be expressed as protein as a result of transcription and translation.

The terms "expression" or "overexpression" describe, in the context of the invention, the production or increase in intracellular activity of one or more polypeptides in a microorganism, which are encoded by the corresponding DNA. To this end, it is possible for example to introduce a gene into an organism, replace an existing gene with another gene, increase the copy number of the gene(s), use a strong promoter or use a gene which encodes for a corresponding polypeptide with a high activity; optionally, these measures can be combined.

Preferably such constructs according to the invention comprise a promoter 5'-upstream of the respective coding sequence and a terminator sequence 3'-downstream and optionally other usual regulatory elements, in each case in operative linkage with the coding sequence.

Nucleic acid constructs according to the invention comprise in particular a sequence coding for a polypeptide for example derived from the amino acid related SEQ ID NOs as described therein or the reverse complement thereof, or derivatives and homologs thereof and which have been linked operatively or functionally with one or more regulatory signals, advantageously for controlling, for example increasing, gene expression.

In addition to these regulatory sequences, the natural regulation of these sequences may still be present before the actual structural genes and optionally may have been genetically modified so that the natural regulation has been switched off and expression of the genes has been enhanced. The nucleic acid construct may, however, also be of simpler construction, i.e. no additional regulatory signals have been inserted before the coding sequence and the natural promoter, with its regulation, has not been removed. Instead, the natural regulatory sequence is mutated such that regulation no longer takes place and the gene expression is increased.

A preferred nucleic acid construct advantageously also comprises one or more of the already mentioned "enhancer" sequences in functional linkage with the promoter, which sequences make possible an enhanced expression of the nucleic acid sequence. Additional advantageous sequences may also be inserted at the 3'-end of the DNA sequences, such as further regulatory elements or terminators. One or more copies of the nucleic acids according to the invention may be present in a construct. In the construct, other markers, such as genes which complement auxotrophisms or antibiotic resistances, may also optionally be present so as to select for the construct.

Examples of suitable regulatory sequences are present in promoters such as cos, tac, trp, tet, trp-tet, lpp, lac, lpp-lac, lacI$^q$, T7, T5, T3, gal, trc, ara, rhaP (rhaP$_{BAD}$)SP6, lambda-P$_R$ or in the lambda-P$_L$ promoter, and these are advantageously employed in Gram-negative bacteria. Further advantageous regulatory sequences are present for example in the Gram-positive promoters amy and SPO2, in the yeast or fungal promoters ADC1, MFalpha, AC, P-60, CYC1, GAPDH, TEF, rp28, ADH. Artificial promoters may also be used for regulation.

For expression in a host organism, the nucleic acid construct is inserted advantageously into a vector such as, for example, a plasmid or a phage, which makes possible optimal expression of the genes in the host. Vectors are also understood as meaning, in addition to plasmids and phages, all the other vectors which are known to the skilled worker, that is to say for example viruses such as SV40, CMV, baculovirus and adenovirus, transposons, IS elements, plasmids, cosmids and linear or circular DNA or artificial chromosomes. These vectors are capable of replicating autonomously in the host organism or else chromosomally. These vectors are a further development of the invention. Binary or cpo-integration vectors are also applicable.

Suitable plasmids are, for example, in *E. coli* pLG338, pACYC184, pBR322, pUC18, pUC19, pKC30, pRep4, pHS1, pKK223-3, pDHE19.2, pHS2, pPLc236, pMBL24, pLG200, pUR290, pIN-III$^{113}$-B1, λgt11 or pBdCI, in *Streptomyces* pIJ101, pIJ364, pIJ702 or pIJ361, in *Bacillus* pUB110, pC194 or pBD214, in *Corynebacterium* pSA77 or pAJ667, in fungi pALS1, pIL2 or pBB116, in yeasts 2alphaM, pAG-1, YEp6, YEp13 or pEMBLYe23 or in plants pLGV23, pGHlac$^+$, pBIN19, pAK2004 or pDH51. The abovementioned plasmids are a small selection of the plasmids which are possible. Further plasmids are well known to the skilled worker and can be found for example in the book Cloning Vectors (Eds. Pouwels P. H. et al. Elsevier, Amsterdam-New York-Oxford, 1985, ISBN 0 444 904018).

In a further development of the vector, the vector which comprises the nucleic acid construct according to the invention or the nucleic acid according to the invention can advantageously also be introduced into the microorganisms in the form of a linear DNA and integrated into the host organism's genome via heterologous or homologous recombination. This linear DNA can consist of a linearized vector such as a plasmid or only of the nucleic acid construct or the nucleic acid according to the invention.

For optimal expression of heterologous genes in organisms, it is advantageous to modify the nucleic acid sequences to match the specific "codon usage" used in the organism. The "codon usage" can be determined readily by computer evaluations of other, known genes of the organism in question.

An expression cassette according to the invention is generated by fusing a suitable promoter to a suitable coding nucleotide sequence and a terminator or polyadenylation signal. Customary recombination and cloning techniques are used for this purpose, as are described, for example, in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, NY (1984) and in Ausubel, F. M. et al., Current Protocols in Molecular Biology, Greene Publishing Assoc. and Wiley Interscience (1987).

For expression in a suitable host organism, the recombinant nucleic acid construct or gene construct is advantageously inserted into a host-specific vector which makes possible optimal expression of the genes in the host. Vectors are well known to the skilled worker and can be found for example in "cloning vectors" (Pouwels P. H. et al., Ed., Elsevier, Amsterdam-New York-Oxford, 1985).

An alternative embodiment of an embodiment herein provides a method to "alter gene expression" in a host cell. For instance, the polynucleotide of an embodiment herein may be enhanced or overexpressed or induced in certain contexts (e.g. upon exposure to certain temperatures or culture conditions) in a host cell or host organism.

Alteration of expression of a polynucleotide provided herein may also result in ectopic expression which is a different expression pattern in an altered and in a control or wild-type organism. Alteration of expression occurs from interactions of polypeptide of an embodiment herein with exogenous or endogenous modulators, or as a result of chemical modification of the polypeptide. The term also refers to an altered expression pattern of the polynucleotide of an embodiment herein which is altered below the detection level or completely suppressed activity.

One embodiment, provided herein is also an isolated, recombinant or synthetic polynucleotide encoding a polypeptide or variant polypeptide provided herein.

In one embodiment, several polypeptide encoding nucleic acid sequences are co-expressed in a single host, particularly under control of different promoters. In another embodiment, several polypeptide encoding nucleic acid sequences can be present on a single transformation vector or be co-transformed at the same time using separate vectors and selecting transformants comprising both chimeric genes. Similarly, one or polypeptide encoding genes may be expressed in a single plant, cell, microorganism or organism together with other chimeric genes.

f. Hosts to be Applied for the Present Invention

Depending on the context, the term "host" can mean the wild-type host or a genetically altered, recombinant host or both.

In principle, all prokaryotic or eukaryotic organisms may be considered as host or recombinant host organisms for the nucleic acids or the nucleic acid constructs according to the invention.

Using the vectors according to the invention, recombinant hosts can be produced, which are for example transformed with at least one vector according to the invention and can be used for producing the polypeptides according to the invention. Advantageously, the recombinant constructs according to the invention, described above, are introduced into a suitable host system and expressed. Preferably common cloning and transfection methods, known by a person skilled in the art, are used, for example co-precipitation, protoplast fusion, electroporation, retroviral transfection and the like, for expressing the stated nucleic acids in the respective expression system. Suitable systems are described for example in Current Protocols in Molecular Biology, F. Ausubel et al., Ed., Wiley Interscience, New York 1997, or Sambrook et al. Molecular Cloning: A Laboratory Manual. 2nd edition, Cold Spring Harbor Laboratory, Cold Spring Harbor Laboratory Press, Cold Spring Harbor, N.Y., 1989.

Advantageously, microorganisms such as bacteria, fungi or yeasts are used as host organisms. Advantageously, gram-positive or gram-negative bacteria are used, preferably bacteria of the families Enterobacteriaceae, Pseudomonadaceae, Rhizobiaceae, Streptomycetaceae, Streptococcaceae or Nocardiaceae, especially preferably bacteria of the genera *Escherichia, Pseudomonas, Streptomyces, Lactococcus, Nocardia, Burkholderia, Salmonella, Agrobacterium, Clostridium* or *Rhodococcus*. The genus and species *Escherichia coli* is quite especially preferred. Furthermore, other advantageous bacteria are to be found in the group of alpha-Proteobacteria, beta-Proteobacteria or gamma-Proteobacteria. Advantageously also yeasts of families like *Saccharomyces* or *Pichia* are suitable hosts.

Alternatively, entire plants or plant cells may serve as natural or recombinant host. As non-limiting examples the following plants or cells derived therefrom may be mentioned the genera *Nicotiana*, in particular *Nicotiana benthamiana* and *Nicotiana tabacum* (tobacco); as well as *Arabidopsis*, in particular *Arabidopsis thaliana*.

Depending on the host organism, the organisms used in the method according to the invention are grown or cultured in a manner known by a person skilled in the art. Culture can be batchwise, semi-batchwise or continuous. Nutrients can be present at the beginning of fermentation or can be supplied later, semicontinuously or continuously. This is also described in more detail below.

g. Recombinant Production of Polypeptides According to the Invention

The invention further relates to methods for recombinant production of polypeptides according to the invention or functional, biologically active fragments thereof, wherein a polypeptide-producing microorganism is cultured, optionally the expression of the polypeptides is induced by applying at least one inducer inducing gene expression and the expressed polypeptides are isolated from the culture. The polypeptides can also be produced in this way on an industrial scale, if desired.

The microorganisms produced according to the invention can be cultured continuously or discontinuously in the batch method or in the fed-batch method or repeated fed-batch method. A summary of known cultivation methods can be found in the textbook by Chmiel (Bioprozesstechnik 1. Einflihrung in die Bioverfahrenstechnik [Bioprocess technology 1. Introduction to bioprocess technology] (Gustav Fischer Verlag, Stuttgart, 1991)) or in the textbook by Storhas (Bioreaktoren and periphere Einrichtungen [Bioreactors and peripheral equipment] (Vieweg Verlag, Braunschweig/Wiesbaden, 1994)).

The culture medium to be used must suitably meet the requirements of the respective strains. Descriptions of culture media for various microorganisms are given in the manual "Manual of Methods for General Bacteriology" of the American Society for Bacteriology (Washington D. C., USA, 1981).

These media usable according to the invention usually comprise one or more carbon sources, nitrogen sources, inorganic salts, vitamins and/or trace elements.

Preferred carbon sources are sugars, such as mono-, di- or polysaccharides. Very good carbon sources are for example glucose, fructose, mannose, galactose, ribose, sorbose, ribulose, lactose, maltose, sucrose, raffinose, starch or cellulose. Sugars can also be added to the media via complex compounds, such as molasses, or other by-products of sugar refining. It can also be advantageous to add mixtures of different carbon sources. Other possible carbon sources are oils and fats, for example soybean oil, sunflower oil, peanut oil and coconut oil, fatty acids, for example palmitic acid, stearic acid or linoleic acid, alcohols, for example glycerol, methanol or ethanol and organic acids, for example acetic acid or lactic acid.

Nitrogen sources are usually organic or inorganic nitrogen compounds or materials that contain these compounds. Examples of nitrogen sources comprise ammonia gas or ammonium salts, such as ammonium sulfate, ammonium chloride, ammonium phosphate, ammonium carbonate or ammonium nitrate, nitrates, urea, amino acids or complex nitrogen sources, such as corn-steep liquor, soya flour, soya protein, yeast extract, meat extract and others. The nitrogen sources can be used alone or as a mixture.

Inorganic salt compounds that can be present in the media comprise the chloride, phosphorus or sulfate salts of calcium, magnesium, sodium, cobalt, molybdenum, potassium, manganese, zinc, copper and iron.

Inorganic sulfur-containing compounds, for example sulfates, sulfites, dithionites, tetrathionates, thiosulfates, sulfides, as well as organic sulfur compounds, such as mercaptans and thiols, can be used as the sulfur source.

Phosphoric acid, potassium dihydrogen phosphate or dipotassium hydrogen phosphate or the corresponding sodium-containing salts can be used as the phosphorus source.

Chelating agents can be added to the medium, in order to keep the metal ions in solution. Especially suitable chelating agents comprise dihydroxyphenols, such as catechol or protocatechuate, or organic acids, such as citric acid.

The fermentation media used according to the invention usually also contain other growth factors, such as vitamins or growth promoters, which include for example biotin, riboflavin, thiamine, folic acid, nicotinic acid, pantothenate and pyridoxine. Growth factors and salts often originate from the components of complex media, such as yeast extract, molasses, corn-steep liquor and the like. Moreover, suitable precursors can be added to the culture medium. The exact composition of the compounds in the medium is strongly dependent on the respective experiment and is decided for each specific case individually. Information on media optimization can be found in the textbook "Applied Microbiol. Physiology, A Practical Approach" (Ed. P. M. Rhodes, P. F. Stanbury, IRL Press (1997) p. 53-73, ISBN 0 19 963577 3). Growth media can also be obtained from commercial suppliers, such as Standard 1 (Merck) or BHI (brain heart infusion, DIFCO) and the like.

All components of the medium are sterilized, either by heat (20 min at 1.5 bar and 121° C.) or by sterile filtration. The components can either be sterilized together, or separately if necessary. All components of the medium can be present at the start of culture or can be added either continuously or batchwise.

The culture temperature is normally between 15° C. and 45° C., preferably 25° C. to 40° C. and can be varied or kept constant during the experiment. The pH of the medium should be in the range from 5 to 8.5, preferably around 7.0. The pH for growing can be controlled during growing by adding basic compounds such as sodium hydroxide, potassium hydroxide, ammonia or ammonia water or acid compounds such as phosphoric acid or sulfuric acid. Antifoaming agents, for example fatty acid polyglycol esters, can be used for controlling foaming. To maintain the stability of plasmids, suitable selective substances, for example antibiotics, can be added to the medium. To maintain aerobic conditions, oxygen or oxygen-containing gas mixtures, for example ambient air, are fed into the culture. The temperature of the culture is normally in the range from 20° C. to 45° C. The culture is continued until a maximum of the desired product has formed. This target is normally reached within 10 hours to 160 hours.

The fermentation broth is then processed further. Depending on requirements, the biomass can be removed from the fermentation broth completely or partially by separation techniques, for example centrifugation, filtration, decanting or a combination of these methods or can be left in it completely.

If the polypeptides are not secreted in the culture medium, the cells can also be lysed and the product can be obtained from the lysate by known methods for isolation of proteins. The cells can optionally be disrupted with high-frequency ultrasound, high pressure, for example in a French press, by osmolysis, by the action of detergents, lytic enzymes or organic solvents, by means of homogenizers or by a combination of several of the aforementioned methods.

The polypeptides can be purified by known chromatographic techniques, such as molecular sieve chromatography (gel filtration), such as Q-sepharose chromatography, ion exchange chromatography and hydrophobic chromatography, and with other usual techniques such as ultrafiltration, crystallization, salting-out, dialysis and native gel electrophoresis. Suitable methods are described for example in Cooper, T. G., Biochemische Arbeitsmethoden [Biochemical processes], Verlag Walter de Gruyter, Berlin, New York or in Scopes, R., Protein Purification, Springer Verlag, New York, Heidelberg, Berlin.

For isolating the recombinant protein, it can be advantageous to use vector systems or oligonucleotides, which lengthen the cDNA by defined nucleotide sequences and therefore code for altered polypeptides or fusion proteins, which for example serve for easier purification. Suitable modifications of this type are for example so-called "tags" functioning as anchors, for example the modification known as hexa-histidine anchor or epitopes that can be recognized as antigens of antibodies (described for example in Harlow, E. and Lane, D., 1988, Antibodies: A Laboratory Manual. Cold Spring Harbor (N.Y.) Press). These anchors can serve for attaching the proteins to a solid carrier, for example a polymer matrix, which can for example be used as packing in a chromatography column, or can be used on a microtiter plate or on some other carrier.

At the same time these anchors can also be used for recognition of the proteins. For recognition of the proteins, it is moreover also possible to use usual markers, such as fluorescent dyes, enzyme markers, which form a detectable reaction product after reaction with a substrate, or radioactive markers, alone or in combination with the anchors for derivatization of the proteins.

h. Polypeptide Immobilization

The enzymes or polypeptides according to the invention can be used free or immobilized in the method described herein. An immobilized enzyme is an enzyme that is fixed to an inert carrier. Suitable carrier materials and the enzymes immobilized thereon are known from EP-A-1149849, EP-A-1 069 183 and DE-OS 100193773 and from the references cited therein. Reference is made in this respect to the disclosure of these documents in their entirety. Suitable carrier materials include for example clays, clay minerals, such as kaolinite, diatomaceous earth, perlite, silica, aluminum oxide, sodium carbonate, calcium carbonate, cellulose powder, anion exchanger materials, synthetic polymers, such as polystyrene, acrylic resins, phenol formaldehyde resins, polyurethanes and polyolefins, such as polyethylene and polypropylene. For making the supported enzymes, the carrier materials are usually employed in a finely-divided, particulate form, porous forms being preferred. The particle size of the carrier material is usually not more than 5 mm, in particular not more than 2 mm (particle-size distribution curve). Similarly, when using dehydrogenase as whole-cell catalyst, a free or immobilized form can be selected. Carrier materials are e.g. Ca-alginate, and carrageenan. Enzymes as well as cells can also be crosslinked directly with glutaraldehyde (cross-linking to CLEAs). Corresponding and other immobilization techniques are described for example in J. Lalonde and A. Margolin "Immobilization of Enzymes" in K. Drauz and H. Waldmann, Enzyme Catalysis in Organic Synthesis 2002, Vol. III, 991-1032, Wiley-VCH, Weinheim. Further information on biotransformations and bioreactors for carrying out methods according to the invention are also given for example in Rehm et al. (Ed.) Biotechnology, 2nd Edn, Vol 3, Chapter 17, VCH, Weinheim.

i. Reaction Conditions for Biocatalytic Production Methods of the Invention

The reaction of the present invention may be performed under in vivo or in vitro conditions.

The at least one polypeptide/enzyme which is present during a method of the invention or an individual step of a multistep-method as defined herein above, can be present in living cells naturally or recombinantly producing the enzyme or enzymes, in harvested cells. i.e. under in vivo conditions, or, in dead cells, in permeabilized cells, in crude cell extracts, in purified extracts, or in essentially pure or completely pure form, i.e. under in vitro conditions. The at least one enzyme may be present in solution or as an enzyme immobilized on a carrier. One or several enzymes may simultaneously be present in soluble and/or immobilised form.

The methods according to the invention can be performed in common reactors, which are known to those skilled in the art, and in different ranges of scale, e.g. from a laboratory scale (few millilitres to dozens of litres of reaction volume) to an industrial scale (several litres to thousands of cubic meters of reaction volume). If the polypeptide is used in a form encapsulated by non-living, optionally permeabilized cells, in the form of a more or less purified cell extract or in purified form, a chemical reactor can be used. The chemical reactor usually allows controlling the amount of the at least one enzyme, the amount of the at least one substrate, the pH, the temperature and the circulation of the reaction medium. When the at least one polypeptide/enzyme is present in living cells, the process will be a fermentation. In this case the biocatalytic production will take place in a bioreactor (fermenter), where parameters necessary for suitable living conditions for the living cells (e.g. culture medium with nutrients, temperature, aeration, presence or absence of oxygen or other gases, antibiotics, and the like) can be controlled. Those skilled in the art are familiar with chemical reactors or bioreactors, e.g. with procedures for up-scaling chemical or biotechnological methods from laboratory scale to industrial scale, or for optimizing process parameters, which are also extensively described in the literature (for biotechnological methods see e.g. Crueger and Crueger, Biotechnologie—Lehrbuch der angewandten Mikrobiologie, 2. Ed., R. Oldenbourg Verlag, München, Wien, 1984).

Cells containing the at least one enzyme can be permeabilized by physical or mechanical means, such as ultrasound or radiofrequency pulses, French presses, or chemical means, such as hypotonic media, lytic enzymes and detergents present in the medium, or combination of such methods. Examples for detergents are digitonin, n-dodecylmaltoside, octylglycoside, Triton® X-100, Tween® 20, deoxycholate, CHAPS (3-[(3-Cholamidopropyl)dimethylammonio]-1-propansulfonate), Nonidet® P40 (Ethylphenolpoly(ethyleneglycolether), and the like.

Instead of living cells biomass of non-living cells containing the required biocatalyst(s) may be applied of the biotransformation reactions of the invention as well.

If the at least one enzyme is immobilised, it is attached to an inert carrier as described above.

The conversion reaction can be carried out batch wise, semi-batch wise or continuously. Reactants (and optionally nutrients) can be supplied at the start of reaction or can be supplied subsequently, either semi-continuously or continuously.

The reaction of the invention, depending on the particular reaction type, may be performed in an aqueous, aqueous-organic or non-aqueous reaction medium.

An aqueous or aqueous-organic medium may contain a suitable buffer in order to adjust the pH to a value in the range of 5 to 11, like 6 to 10.

In an aqueous-organic medium an organic solvent miscible, partly miscible or immiscible with water may be applied. Non-limiting examples of suitable organic solvents are listed below. Further examples are mono- or polyhydric, aromatic or aliphatic alcohols, in particular polyhydric aliphatic alcohols like glycerol.

The non-aqueous medium may contain is substantially free of water, i.e. will contain less that about 1 wt.-% or 0.5 wt.-% of water.

Biocatalytic methods may also be performed in an organic non-aqueous medium. As suitable organic solvents there may be mentioned aliphatic hydrocarbons having for example 5 to 8 carbon atoms, like pentane, cyclopentane, hexane, cyclohexane, heptane, octane or cyclooctane; aromatic carbohydrates, like benzene, toluene, xylenes, chlorobenzene or dichlorobenzene, aliphatic acyclic and ethers, like diethylether, methyl-tert.-butylether, ethyl-tert.-butylether, dipropylether, diisopropylether, dibutylether; or mixtures thereof.

The concentration of the reactants/substrates may be adapted to the optimum reaction conditions, which may depend on the specific enzyme applied. For example, the initial substrate concentration may be in the 0.1 to 0.5 M, as for example 10 to 100 mM.

The reaction temperature may be adapted to the optimum reaction conditions, which may depend on the specific enzyme applied. For example, the reaction may be performed at a temperature in a range of from 0 to 70° C., as for example 20 to 50 or 25 to 40° C. Examples for reaction temperatures are about 30° C., about 35° C., about 37° C., about 40° C., about 45° C., about 50° C., about 55° C. and about 60° C.

The process may proceed until equilibrium between the substrate and then product(s) is achieved, but may be stopped earlier. Usual process times are in the range from 1 minute to 25 hours, in particular 10 min to 6 hours, as for example in the range from 1 hour to 4 hours, in particular 1.5 hours to 3.5 hours. These parameters are non-limiting examples of suitable process conditions.

If the host is a transgenic plant, optimal growth conditions can be provided, such as optimal light, water and nutrient conditions, for example.

Particular reaction conditions for performing the preparation of drimanyl acetate compound are as follows. In an aqueous environment, incubated at 20 to 35° C. and a pH of 4 to 7, the acetyltransferase enzyme can be present as a purified polypeptide or in a whole-cell system. Substrate concentration might vary between 10 and 100 mM.

k. Product Isolation

The methodology of the present invention can further include a step of recovering an end or intermediate product, optionally in stereoisomerically or enantiomerically substantially pure form. The term "recovering" includes extracting, harvesting, isolating or purifying the compound from culture or reaction media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), distillation, dialysis, filtration, concentration, crystallization, recrystallization, pH adjustment, lyophilization and the like.

Identity and purity of the isolated product may be determined by known techniques, like High Performance Liquid Chromatography (HPLC), gas chromatography (GC), Spektroskopy (like IR, UV, NMR), Colouring methods, TLC, NIRS, enzymatic or microbial assays. (see for example: Patek et al. (1994) Appl. Environ. Microbiol. 60:133-140; Malakhova et al. (1996) Biotekhnologiya 11 27-32; und Schmidt et al. (1998) Bioprocess Engineer. 19:67-70. Ullmann's Encyclopedia of Industrial Chemistry (1996) Bd. A27, VCH: Weinheim, S. 89-90, S. 521-540, S. 540-547, S. 559-566, 575-581 und S. 581-587; Michal, G (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, Bd. 17.)

The cyclic terpene compound produced in any of the method described herein can be converted to derivatives such as, but not limited to hydrocarbons, esters, amides, glycosides, ethers, epoxides, aldehydes, ketons, alcohols, diols, acetals or ketals. The terpene compound derivatives can be obtained by a chemical method such as, but not limited to oxidation, reduction, alkylation, acylation and/or rearrangement. Alternatively, the terpene compound derivatives can be obtained using a biochemical method by contacting the terpene compound with an enzyme such as, but not limited to an oxidoreductase, a monooxygenase, a dioxygenase, a transferase. The biochemical conversion can be performed in-vitro using isolated enzymes, enzymes from lysed cells or in-vivo using whole cells.

l. Fermentative Production of a Drimenyl Acetate

The invention also relates to methods for the fermentative production of drimanyl acetate.

A fermentation as used according to the present invention can, for example, be performed in stirred fermenters, bubble columns and loop reactors. A comprehensive overview of the possible method types including stirrer types and geometric designs can be found in "Chmiel: Bioprozesstechnik: Einfuhrung in die Bioverfahrenstechnik, Band 1". In the process of the invention, typical variants available are the following variants known to those skilled in the art or explained, for example, in "Chmiel, Hammes and Bailey: Biochemical Engineering", such as batch, fed-batch, repeated fed-batch or else continuous fermentation with and without recycling of the biomass. Depending on the production strain, sparging with air, oxygen, carbon dioxide, hydrogen, nitrogen or appropriate gas mixtures may be effected in order to achieve good yield (YP/S).

The culture medium that is to be used must satisfy the requirements of the particular strains in an appropriate manner Descriptions of culture media for various microorganisms are given in the handbook "Manual of Methods for General Bacteriology" of the American Society for Bacteriology (Washington D. C., USA, 1981).

These media that can be used according to the invention may comprise one or more sources of carbon, sources of nitrogen, inorganic salts, vitamins and/or trace elements.

Preferred sources of carbon are sugars, such as mono-, di- or polysaccharides. Very good sources of carbon are for example glucose, fructose, mannose, galactose, ribose, sorbose, ribulose, lactose, maltose, sucrose, raffinose, starch or cellulose. Sugars can also be added to the media via complex compounds, such as molasses, or other by-products from sugar refining. It may also be advantageous to add mixtures of various sources of carbon. Other possible sources of carbon are oils and fats such as soybean oil, sunflower oil, peanut oil and coconut oil, fatty acids such as palmitic acid, stearic acid or linoleic acid, alcohols such as glycerol, methanol or ethanol and organic acids such as acetic acid or lactic acid.

Sources of nitrogen are usually organic or inorganic nitrogen compounds or materials containing these compounds. Examples of sources of nitrogen include ammonia gas or ammonium salts, such as ammonium sulfate, ammonium chloride, ammonium phosphate, ammonium carbonate or ammonium nitrate, nitrates, urea, amino acids or complex sources of nitrogen, such as corn-steep liquor, soybean flour, soy-bean protein, yeast extract, meat extract and others. The sources of nitrogen can be used separately or as a mixture.

Inorganic salt compounds that may be present in the media comprise the chloride, phosphate or sulfate salts of calcium, magnesium, sodium, cobalt, molybdenum, potassium, manganese, zinc, copper and iron.

Inorganic sulfur-containing compounds, for example sulfates, sulfites, di-thionites, tetrathionates, thiosulfates, sulfides, but also organic sulfur compounds, such as mercaptans and thiols, can be used as sources of sulfur.

Phosphoric acid, potassium dihydrogenphosphate or dipotassium hydrogenphosphate or the corresponding sodium-containing salts can be used as sources of phosphorus.

Chelating agents can be added to the medium, in order to keep the metal ions in solution. Especially suitable chelating agents comprise dihydroxyphenols, such as catechol or protocatechuate, or organic acids, such as citric acid.

The fermentation media used according to the invention may also contain other growth factors, such as vitamins or growth promoters, which include for example biotin, riboflavin, thiamine, folic acid, nicotinic acid, pantothenate and pyridoxine. Growth factors and salts often come from complex components of the media, such as yeast extract, molasses, corn-steep liquor and the like. In addition, suitable precursors can be added to the culture medium. The precise composition of the compounds in the medium is strongly dependent on the particular experiment and must be decided individually for each specific case. Information on media optimization can be found in the textbook "Applied Microbiol. Physiology, A Practical Approach" (1997) Growing media can also be obtained from commercial suppliers, such as Standard 1 (Merck) or BHI (Brain heart infusion, DIFCO) etc.

All components of the medium are sterilized, either by heating (20 min at 1.5 bar and 121° C.) or by sterile filtration. The components can be sterilized either together, or if necessary separately. All the components of the medium can be present at the start of growing, or optionally can be added continuously or by batch feed.

The temperature of the culture is normally between 15° C. and 45° C., preferably 25° C. to 40° C. and can be kept constant or can be varied during the experiment. The pH value of the medium should be in the range from 5 to 8.5, preferably around 7.0. The pH value for growing can be controlled during growing by adding basic compounds such as sodium hydroxide, potassium hydroxide, ammonia or ammonia water or acid compounds such as phosphoric acid or sulfuric acid. Antifoaming agents, e.g. fatty acid polyglycol esters, can be used for controlling foaming. To maintain the stability of plasmids, suitable substances with selective action, e.g. antibiotics, can be added to the medium. Oxygen or oxygen-containing gas mixtures, e.g. the ambient air, are fed into the culture in order to maintain aerobic conditions. The temperature of the culture is normally from 20° C. to 45° C. Culture is continued until a maximum of the desired product has formed. This is normally achieved within 1 hour to 160 hours.

The methodology of the present invention can further include a step of recovering said drimanyl acetate.

The term "recovering" includes extracting, harvesting, isolating or purifying the compound from culture media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), distillation, dialysis, filtration, concentration, crystallization, recrystallization, pH adjustment, lyophilization and the like.

Before the intended isolation the biomass of the broth can be removed. Processes for removing the biomass are known to those skilled in the art, for example filtration, sedimentation and flotation. Consequently, the biomass can be removed, for example, with centrifuges, separators, decanters, filters or in flotation apparatus. For maximum recovery of the product of value, washing of the biomass is often advisable, for example in the form of a diafiltration. The selection of the method is dependent upon the biomass content in the fermenter broth and the properties of the biomass, and also the interaction of the biomass with the product of value.

In one embodiment, the fermentation broth can be sterilized or pasteurized. In a further embodiment, the fermentation broth is concentrated. Depending on the requirement, this concentration can be done batch wise or continuously. The pressure and temperature range should be selected such that firstly no product damage occurs, and secondly minimal use of apparatus and energy is necessary. The skillful selection of pressure and temperature levels for a multistage evaporation in particular enables saving of energy.

The following examples are illustrative only and are not intended to limit the scope of the claims an embodiments described herein.

The numerous possible variations that will become immediately evident to a person skilled in the art after heaving considered the disclosure provided herein also fall within the scope of the invention.

EXPERIMENTAL PART

Materials:

Unless otherwise stated, all chemical and biochemical materials and microorganisms or cells employed herein are commercially available products.

Unless otherwise specified, recombinant proteins are cloned and expressed by standard methods, such as, for example, as described by Sambrook, J., Fritsch, E. F. and Maniatis, T., Molecular cloning: A Laboratory Manual, $2^{nd}$ Edition, Cold Spring Harbor Laboratory, Cold Spring Harbor Laboratory Press, Cold Spring Harbor, N.Y., 1989.

Gas Chromatography Mass Spectrometry (GC-MS)

Agilent Intuvo 9000 series GC system equipped with a DB-5MS UI column (10 m×0.25 mm×0.25 μm film thickness (custom column made by Agilent Technologies Inc, Santa Clara, CA). The GC was coupled to two detectors by a 1:1 Detector Splitter Chip (G4588-60502, Agilent Technologies Inc, Santa Clara, CA). The first detector was a Agilent 5977B series mass spectrometer, while the second detector was a standard Intuvo 9000 Flame ionization detector (FID). The carrier gas was helium at a constant flow of 2.5 ml/min. Injection was in split (1:100) mode with the injector temperature set at 240° C. The oven temperature was programmed from 150° C. (0.1 min hold) to 240° C. at 40° C./min, then to 325° C. at 180° C./min and held 0.5 min)

Example 1

Selection of Acetyltransferase Candidates for the Conversion of Drimane Sesquiterpenes into Drimanyl Acetylated Sesquiterpenes.

Acetyltransferases constitute a genetically diverse class of enzymes with more than 8,000 known representatives (PFAM database: PF02458 transferase family). Although the repertoire of molecules accepted as substrates by acetyltransferases is vast, none of them have been reported to accept sesquiterpene alcohols as substrates. In order to identify acetyltransferases capable to acetylate drimane-type sesquiterpene alcohols, fifty four (Table 1) out of the thousands known acetyltransferases originating from plants, fungi and bacteria were selected based on the following rationale:

Two out of five clades known from the plant acetyltransferase BAHD family, clades 3 and 5, have members identified for acetylation of alkaloids and terpenoids with acetyl-CoA as acyl donor (Curr Opin Plant Biol. 2006, 9(3):331-40). In addition, some substrates used by acetyltransferases from clades 3 and 5 are bulky, polycyclic and bear sterically hindered alcohol groups as acyl acceptors (BMC Genomics 2011, 12:236; Curr Opin Plant Biol. 2006, 9:331-40; Elife. 2017 Mar. 14; 6: e23001; Planta. 2015, 242:709-19). Based on this, twenty one candidates were selected from the plant BAHD family clades 3 and 5, these candidates include the identified acetyltransferases involved in the biosynthesis of the polycyclic diterpene paclitaxel (taxol) (Proc Natl Acad Sci USA. 2000, 18; 97(2): 583-587) and two acetyltransferases from Plectranthus barbatus involved in the biosynthesis of the bicyclic, labdane diterpene Forskolin (Elife 2017, 14; 6: e23001).

Similarly to the plant candidates, seven fungal acetyltransferases were selected based on their putative or experimentally confirmed ability to accept acetyl-CoA as acyl donor and the structural characteristics of their substrates: bulky, polycyclic compounds, bearing sterically hindered alcohol groups (FEMS Microbiol Lett. 2005, 251:193-201; Chembiochem. 2009, 10:2325-8; Biotechnol Biotechnol Equip. 2014, 28(5):818-826; Nat Chem. 2010, 2:858-64). Among these, the protein AstG (from Aspergillus oryzae, NCBI accession No XP_023091083.1) involved in the biosynthesis of the aryl acid esterified drimane-type sesquiterpene lactone, astellolide (Sci Rep. 2016, 6:32865) was selected.

In addition, twenty one putative fungal acetyltransferases from the NCBI protein database were retrieved based on their sequence similarity with AstG using a PSI Blast search (Trends Biochem Sci. 2002, 27:161-4.) (standard parameters & 2 iterations). The results were visualized on a phylogenetic tree using the NCBI Blast Tree View function to show homology between AstG and 500 PSI-Blast derived sequences. Candidates were selected by homology to the query sequence, which were derived from a single branch of the phylogenetic tree.

Finally, chloramphenicol acetyltransferases are known to be promiscuous enzymes and able to accommodate bulky, larger than chloramphenicol, substrates (Protein Sci. 2012, 21(4): 520-530). Thus, five bacterial chloramphenicol acetyltransferases from classes 1 to 3 were selected from the NCBI protein database as putative chloramphenicol acetyltransferase or were selected from literature (Biochem J. 1990, 272:505-10).

TABLE 1

Acetyltransferases selected for the conversion of drimane sesquiterpenes into drimanyl acetylate sesquiterpenes

| Name | Accession Number | Organism |
| --- | --- | --- |
| CrDAT | NCBI: AAC99311.1 | Catharanthus roseus |
| TcDBAT | NCBI: AAF27621.1 | Taxus cuspidate |
| TcTAT | NCBI: AAF34254.1 | Taxus cuspidate |
| FaSAAT | NCBI: AAG13130.1 | Fragaria x ananassa |
| PsSalAT | NCBI: AAK73661.1 | Papaver somniferum |
| AtCHAT | NCBI: AAN09797.1 | Arabidopsis thaliana |
| CrMAT | NCBI: AAO13736.1 | Catharanthus roseus |
| MdAAT2 | NCBI: AAS79797.1 | Malus domestica |
| RhAAT1 | NCBI: AAW31948.1 | Rosa x hybrid |
| AGZ20197.1 | NCBI: AGZ20197.1 | Penicillium crustosum |
| LiAAT-3 | NCBI: AIW81431.1 | Lavandula x intermedia |
| LiAAT-4 | NCBI: AIW81432.1 | Lavandula x intermedia |
| BAU61551.1 | NCBI: BAU61551.1 | Penicillium simplicissimum |
| tri3 | NCBI: BAX01959.1 | Fusarium asiaticum |
| FvVAAT | NCBI: CAC09062.1 | Fragaria vesca |
| RsVISY | NCBI: CAD89104.2 | Rauvolfia serpentine |
| CEL05746.1 | NCBI: CEL05746.1 | Aspergillus calidoustus |
| FgaAT | NCBI: EAL94101.1 | Aspergillus fumigatus |
| GAO81666.1 | NCBI: GAO81666.1 | Aspergillus udagawae |
| GAQ06029.1 | NCBI: GAQ06029.1 | Aspergillus lentulus |
| KIA75847.1 | NCBI: KIA75847.1 | Aspergillus ustus |
| CfACT1-6 | NCBI: KT382361.1 | C. forskohlii |
| CfACT1-8 | NCBI: KT382363.1 | C. forskohlii |
| CfACT2 | NCBI: KT382364.1 | C. forskohlii |
| CfACT3 | NCBI: KT382365.1 | C. forskohlii |
| CfACT4 | NCBI: KT382366.1 | C. forskohlii |
| CfACT5 | NCBI: KT382367.1 | C. forskohlii |
| CfACT6 | NCBI: KT382368.1 | C. forskohlii |
| CfACT8 | NCBI: KT382370.1 | C. forskohlii |
| KUM59602.1 | NCBI: KUM59602.1 | Penicillium freii |
| OAH94415.1 | NCBI: OAH94415.1 | Proteus mirabilis |
| OJJ08848.1 | NCBI: OJJ08848.1 | Aspergillus versicolor |
| OQD79314.1 | NCBI: OQD79314.1 | Penicillium antarcticum |
| OXN37635.1 | NCBI: OXN37635.1 | Aspergillus turcosus |
| P00484.1 | NCBI: P00484.1 | Escherichia coli |
| P22615.1 | NCBI: P22615.1 | Escherichia coli |
| PIG69200.1 | NCBI: PIG69200.1 | Aspergillus arachidicola |
| ppb8 | NCBI: FW308713.1; Nucleotides 23205-24773 | Penicillium coprobium |
| ppb9 | NCBI: FW308713.1; Nucleotides 25824 27178 | Penicillium coprobium |
| pyr8 | NCBI: Q4WLC8.1 | Aspergillus fumigatus |
| pyr7 | NCBI: Q4WLC9.1 | Aspergillus fumigatus |
| RAQ51407.1 | NCBI: RAQ51407.1 | Aspergillus flavus |
| WP_061323745.1 | NCBI: WP_061323745.1 | Clostridium botulinum |
| XP_001214750.1 | NCBI: XP_001214750.1 | Aspergillus terreus |
| XP_001217250.1 | NCBI: XP_001217250.1 | Aspergillus terreus |
| XP_001218652.1 | NCBI: XP_001218652.1 | Aspergillus terreus |
| XP_001258079.1 | NCBI: XP_001258079.1 | Aspergillus fischeri |
| XP_020058309.1 | NCBI: XP_020058309.1 | Aspergillus aculeatus |
| AstG | NCBI: XP_023091083.1 | Aspergillus oryzae |
| XP_024675087.1 | NCBI: XP_024675087.1 | Aspergillus candidus |
| XP_024675090.1 | NCBI: XP_024675090.1 | Aspergillus candidus |
| XP_024682561.1 | NCBI: XP_024682561.1 | Aspergillus novofumigatus |
| XP_024683987.1 | NCBI: XP_024683987.1 | Aspergillus novofumigatus |
| YP_006162226.1 | NCBI: YP_006162226.1 | Escherichia coli |

Example 2

In Vivo Albicanyl Acetate Production in Saccharomyces cerevisiae Co-Expressing an Albicanol Synthase and Different Acetyltransferase Candidates.

The enzyme candidates were each screened for the in vivo bioconversion of albicanol to albicanyl acetate. For the screening, acetyltransferase candidates were each co-expressed with the gene encoding for the albicanol synthase XP_007369631.1, NCBI accession No XP_007369631.1, from *Dichomitus squalens* in an engineered *Saccharomyces cerevisiae* strain with increased level of endogenous farnesyl-diphosphate (FPP).

To increase the level of endogenous FPP pool in *S. cerevisiae*, an extra copy of all the yeast endogenous genes involved in the mevalonate pathway, from ERG10 coding for acetyl-CoA C-acetyltransferase to ERG20 coding for FPP synthase, were integrated in the genome of the *S. cerevisiae* strain CEN.PK2-1C (Euroscarf, Frankfurt, Germany) under the control of galactose-inducible promoters, similarly as described in Paddon et al., *Nature*, 2013, 496: 528-532. Briefly, three cassettes were integrated in the LEU2, TRP1 and URA3 loci respectively. A first cassette containing the genes ERG20 and a truncated HMG1 (tHMG1 as described in Proc Natl Acad Sci USA, 1997, 109:E111-8) under the control of the bidirectional promoter of GAL10/GAL1 and the genes ERG19 and ERG13 also under the control of GAL10/GAL1 promoter, the cassette was flanked by two 100 nucleotides regions corresponding to the up- and down-stream sections of LEU2. A second cassette where the genes IDI1 and tHMG1 were under the control of the GAL10/GAL1 promoter and the gene ERG13 under the control of the promoter region of GALT, the cassette was flanked by two 100 nucleotides regions corresponding to the up- and down-stream sections of TRP1. A third cassette with the genes ERG10, ERG12, tHMG1 and ERGS, all under the control of GAL10/GAL1 promoters, the cassette was flanked by two 100 nucleotides regions corresponding to the up- and down-stream sections of URA3. All genes in the three cassettes included 200 nucleotides of their own terminator regions. Also, an extra copy of GAL4 under the control of a mutated version of its own promoter, as described in *Proc Natl Acad Sci USA*, 1991, 88:8597-8601, was integrated upstream the ERG9 promoter region. In addition, the expression of ERG9 was modified by promoter exchange. The GALT, GAL10 and GAL1 genes were deleted using a cassette containing the HIS3 gene with its own promoter and terminator. The resulting strain was mated with the strain CEN.PK2-1D (Euroscarf, Frankfurt, Germany) obtaining a diploid strain termed YST045 which was induced for sporulation according to Solis-Escalante et al, *FEMS Yeast Res*, 2015, 15:2. Spore separation was achieved by resuspension of asci in 200 µL 0.5M sorbitol with 2 µL zymolyase (1000 U mL-1, Zymo research, Irvine, CA) and incubated at 37° C. for 20 minutes. The mix then was plated on media containing 20 g/L peptone, 10 g/L yeast extract, 20 g/L glucose and 20 g/L agar, one germinated spore was isolated and termed YST069.

For expression of XP_007369631.1 and the evaluated acetyltransferases in YST069, plasmids were constructed in vivo using yeast endogenous homologous recombination as previously described in Kuijpers et al., *Microb Cell Fact.*, 2013, 12:47. The plasmids are composed of four DNA fragments which were used for *S. cerevisiae* co-transformation. The fragments were:

a) The plasmid pF167 (SEQ ID NO: 1) linearized by enzymatic restriction with BsmBI. pF167 was previously constructed by in vivo assembly in yeast, it contains the yeast marker LEU2 with its own promoter and terminator, the *Escherichia coli* marker AmpR, the 2µ yeast origin of replication, the *E. coli* pUC replication origin and the sequences 5'-GCACTTGCTA-CACTGTCAGGATAGCTTCCGTCACATGGTGGC-GATCACC GTACATCTGAG-3' (SEQ ID NO: 2) and 5'-AGGTGCAGTTCGCGTGCAAT-TATAACGTCGTGGCAACTGTTATCAGTCG TACCGCGCCAT-3' (SEQ ID NO: 3) for homologous recombination;

b) a fragment composed by the sequence 5'-GCACTTGC-TACACTGTCAGGATAGCTTCCGTCA-CATGGTGGCGATCACC GTACATCTGAG-3' (SEQ ID NO: 2), the terminator region of the yeast gene PGK1 and the sesquiterpene synthase XP_007369631.1 DNA sequence codon optimized for its expression in *S. cerevisiae* (SEQ ID NO: 4), this fragment was obtained by DNA synthesis (ATUM, Menlo Park, CA 94025). The bidirectional GAL1/GAL10 promoter region from yeast was added to this fragment by PCR overlap extension (Yolov and Shabarova., *Nucleic Acids Res.* 1990, 18(13):3983-6);

c) a fragment composed by 60 bp corresponding to the first nucleotides of the yeast GAL10 promoter region, one of the to be evaluated acetyltransferase DNA coding sequences (codon optimized for its expression in *S. cerevisiae*) and 60 bp of the yeast CYC1 terminator region, this fragment was obtained by DNA synthesis (ATUM, Menlo Park, CA 94025); and d) a fragment composed by the terminator region of the yeast gene CYC1 and the sequence 5'-AGGTGCAGTTCGCGTGCAAT-TATAACGTCGTGGCAACTGTTATCAGTCG TACCGCGCCAT-3' (SEQ ID NO: 3), this fragment was obtained by DNA synthesis (ATUM, Menlo Park, CA 94025).

YST069 was transformed with the fragments required for in vivo plasmid assembly. Yeast transformations were performed with the lithium acetate protocol as described in Gietz and Woods, Methods Enzymol., 2002, 350:87-96. The transformation mixtures were plated on SmLeu-media containing 6.7 g/L of Yeast Nitrogen Base without amino acids (BD Difco, New Jersey, USA), 1.6 g/L Dropout supplement without leucine (Sigma Aldrich, Missouri, USA), 20 g/L glucose and 20 g/L agar. Plates were incubated for 3-4 days at 30° C. Individual colonies were used to produce albicanol and albicanyl acetate in deep well plates containing 250 µL media as described in Westfall et al., Proc Natl Acad Sci USA, 2012, 109:E111-118 and 50 µL adipic acid diisodecyl ester (abcr GmbH, Germany) as organic overlay. The deep well plates were incubated for 3 days at 30° C. in a plate incubator. To extract albicanol and albicanyl acetate produced by the yeast cells, each well of the deep well plate was extracted with 700 µL of ethyl acetate containing an internal standard. The production of albicanol and albicanyl acetate was identified using GC-MS analysis and quantified by GC-FID using the above mentioned internal standard.

Under these experimental conditions, albicanyl acetate was detected for 9 combinations of albicanol synthase and acetyltransferases (Table 2). Remarkably, the two most active acetyltransferases (CrDAT and FgaAT) produced titers of albicanyl acetate of more than 150 mg/L under the non-optimized screening conditions. The GC-FID chromatograms are displayed in FIG. 2. Further, FIG. 2 shows that the MS spectrum of the yeast-derived albicanyl acetate is identical to a reference albicanyl acetate MS spectrum.

Interestingly, the most active acetyltransferases in our screening, CrDAT, a member of the plant BAHD-family Glade 3, is involved in the biosynthesis of plant alkaloids, however, other tested acetyltransferases from the same family and clade, PsSalAT and RsVISY, and involved in plant alkaloid biosynthesis (Thebaine and Vinorine, respectively) were not active when albicanol was presented as substrate. In addition, FgaAT from *Aspergillus fumigatus*, also involved in the biosynthesis of alkaloids (active on Fumigaclavine B), produced significant amounts of albicanyl acetate in our screening; whereas, surprisingly, the putative Fumigaclavine B O-acetyltransferase GA081666.1 produced one order of magnitude less albicanyl acetate than FgaAT.

It is worth to notice, that neither the acetyltransferase AstG nor any of the proteins selected base on its similarity with AstG (excluding GA081666.1, see above) produced the Drimanyl acetylated sesquiterpene albicanyl acetate, despite the fact that AstG is involved in the biosynthesis of the modified drimane-type sesquiterpene Astellolide.

The only identified acetyltransferases in diterpene biosynthesis are those involved in the production of Paclitaxel (Taxol) and Forskolin. From the eight acetyltransferases tested from C. forskohlii only CfACT1-6 and CfACT1-8 were able to acetylate albicanol. Although the genes TcTAT and TcDBAT are capable to acetylate structurally similar intermediates in the biosynthesis of Taxol (Taxa-4(20),11 (12)-dien-5a-yl acetate and Baccatin III, respectively), only TcTAT produced albicanyl acetate.

To add on the, now documented, complexity to identify an acetyltransferase capable to use albicanol as acyl acceptor, only one of the five tested substrate versatile Chloramphenicol acetyltransferases was able to convert albicanol to albicanyl acetate.

TABLE 2

Acetyltransferases found able to convert albicanol to albicanyl acetate in Saccharomyces cerevisiae

| Name | SEQ ID NO (amino acid sequence) | Accession Number | Organism | Titers Albicanyl Acetate [mg/L] |
|---|---|---|---|---|
| CrDAT | 9 | NCBI: AAC99311.1 | Catharanthus roseus | 400 |
| FgaAT | 17 | NCBI: EAL94101.1 | Aspergillus fumigatus Af293 | 176 |
| OAH94415.1 | 25 | NCBI: OAH94415.1 | Proteus mirabilis | 15 |
| TcTAT | 11 | NCBI: AAF34254.1 | Taxus cuspidata | 12 |
| CrMAT | 13 | NCBI: AAO13736.1 | Catharanthus roseus | 5 |
| LiAAT-4 | 15 | NCBI: AIW81432.1 | Lavandula x intermedia | 8 |
| GA081666.1 | 19 | NCBI: GA081666.1 | Aspergillus udagawae | 10 |
| CfACT1-6 | 21 | NCBI: KT382361.1 | Plectranthus barbatus | 50 |
| CfACT1-8 | 23 | NCBI: KT382363.1 | Plectranthus barbatus | 56 |

Example 3

In Vivo Drimenyl Acetate Production in Saccharomyces cerevisiae Co-Expressing a Drimenol Synthase and Selected Acetyltransferase Candidates.

For the production of drimenyl acetate in Saccharomyces cerevisiae the nine selected acetyltransferases (CrDAT, FgaAT, OAH94415.1, TcTAT, CrMAT, LiAAT-4, GA081666.1, CfACT1-6, CfACT1-8) capable to convert albicanol to albicanyl acetate, as shown in example 2, were used to evaluate the conversion of drimenol to drimenyl acetate. Drimenyl acetate was produced in vivo in the engineered S. cerevisiae strain YST069 with increased level of endogenous FPP (see Example 2) by the co-expression of each of the selected acetyltransferase enzyme candidates with the gene encoding for the drimenol synthase XP_006461126, NCBI accession No XP_006461126, from Agaricus bisporus.

For expression of XP_006461126 and the selected acetyltransferases (CrDAT, FgaAT, OAH94415.1, TcTAT, CrMAT, LiAAT-4, GA081666.1, CfACT1-6 and CfACT1-8) in YST069, plasmids were constructed in vivo using yeast endogenous homologous recombination as previously described in Kuijpers et al., Microb Cell Fact., 2013, 12:47. The plasmids are composed of four DNA fragments which were used for S. cerevisiae co-transformation. The fragments were:

a) The plasmid pF167 (SEQ ID NO: 1) linearized by enzymatic restriction with BsmBI. pF167 was previously constructed by in vivo assembly in yeast, it contains the yeast marker LEU2 with its own promoter and terminator, the Escherichia coli marker AmpR, the 2µ yeast origin of replication, the E. coli pUC replication origin and the sequences 5'-GCACTTGCTA-CACTGTCAGGATAGCTTCCGTCACATGGTGGC-GATCACC GTACATCTGAG-3' (SEQ ID NO: 2) and 5'-AGGTGCAGTTCGCGTGCAAT-TATAACGTCGTGGCAACTGTTATCAGTCG TACCGCGCCAT-3' (SEQ ID NO: 3) for homologous recombination;

b) a fragment composed by the sequence 5'-GCACTTGC-TACACTGTCAGGATAGCTTCCGTCA-CATGGTGGCGATCACC GTACATCTGAG-3' (SEQ ID NO: 2), the terminator region of the yeast gene PGK1 and the sesquiterpene synthase XP_006461126 DNA sequence codon optimized for its expression in S. cerevisiae (SEQ ID NO: 6), this fragment was obtained by DNA synthesis (ATUM, Menlo Park, CA 94025). The bidirectional GAL1/GAL10 promoter region from yeast was added to this fragment by PCR overlap extension (Yolov and Shabarova., Nucleic Acids Res. 1990, 18(13):3983-6);

c) a fragment composed by 60 bp corresponding to the first nucleotides of the yeast GAL10 promoter region, one of the evaluated acetyltransferases DNA coding sequence codon optimized for its expression in S. cerevisiae and 60 bp of the yeast CYC1 terminator region, this fragment was obtained by DNA synthesis (ATUM, Menlo Park, CA 94025); and d) a fragment composed by the terminator region of the yeast gene CYC1 and the sequence 5'-AGGTGCAGTTCGCGTGCAAT-TATAACGTCGTGGCAACTGTTATCAGTCG TACCGCGCCAT-3' (SEQ ID NO: 3), this fragment was obtained by DNA synthesis (ATUM, Menlo Park, CA 94025).

Yeast transformation, screening conditions and quantification of drimenol and drimenyl acetate were performed as described in example 2 for the production of albicanol and albicanyl Acetate.

Figure 3:
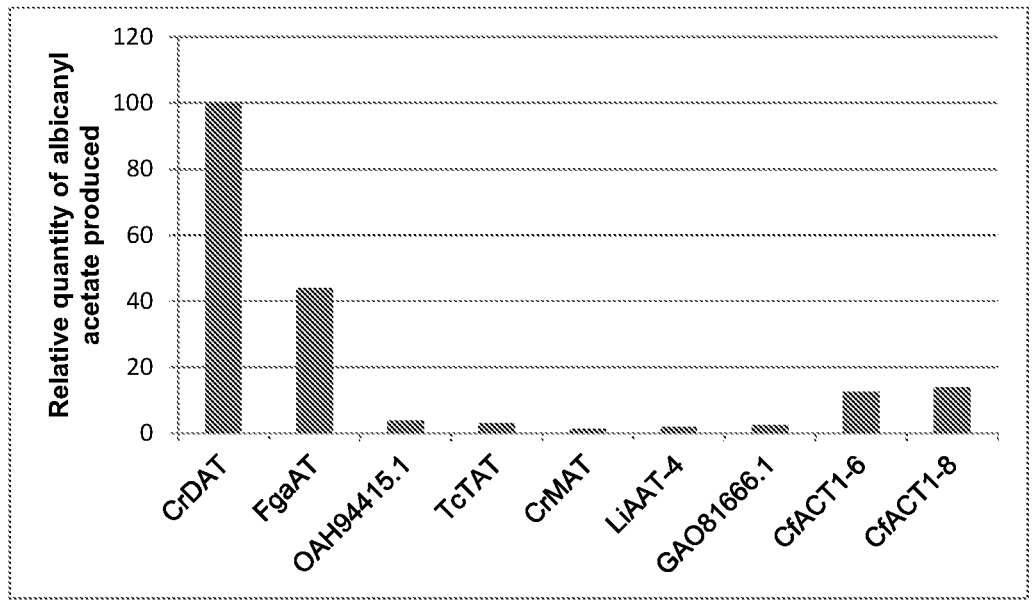
FIG. 3: Relative quantity of albicanyl acetate produced by the nine acetyltransferases (CrDAT, FgaAT, OAH94415.1, TcTAT, CrMAT, LiAAT-4, GAO81666.1, CfACT1-6 and CfACT1-8), which were found to be active on albicanol (as described in example 2).
Figure 4:
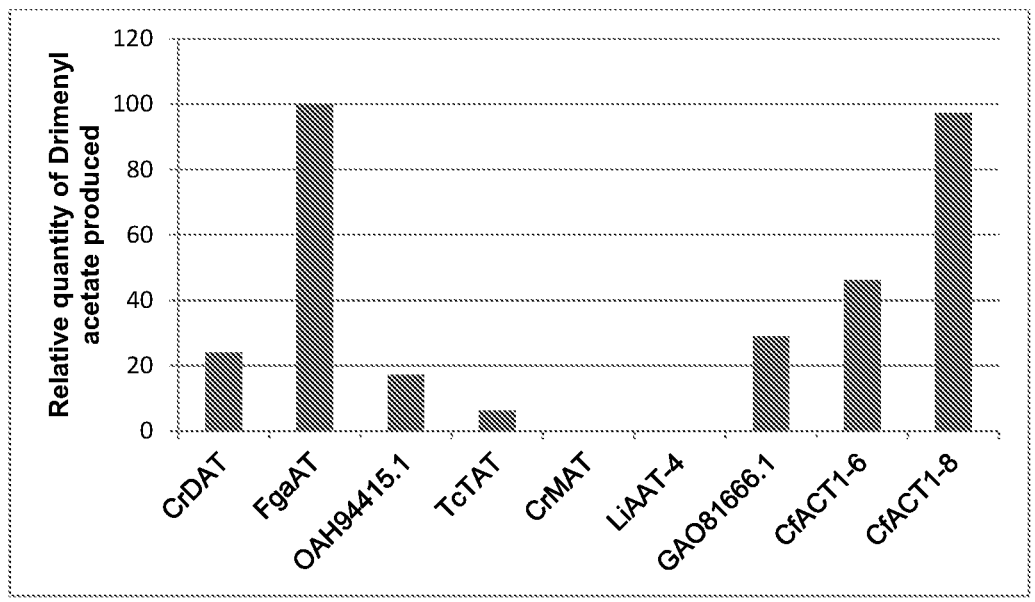
FIG. 4: Relative quantity of drimenyl acetate produced by the nine acetyltransferases (CrDAT, FgaAT, OAH94415.1, TcTAT, CrMAT, LiAAT-4, GAO81666.1, CfACT1-6 and CfACT1-8), which were found to be also active on albicanol (as described in example 2).

The relative quantities of albicanyl acetate (from Example 2) and drimenyl acetate are shown in FIG. 3 and FIG. 4, respectively. From the nine enzyme candidates tested, seven (CrDAT, FgaAT, OAH94415.1, TcTAT, GA081666.1, CfACT1-6 and CfACT1-8) produced drimenyl acetate. Due to the high structural similarity between albicanol and drimenol, it was expected to find similar relative conversion rates.

Unexpectedly, the conversion of drimenol to his corresponding acetate was found to be significantly altered. In particular, CrDAT, which was found to produce the highest relative quantity of albicanyl acetate, was found to be one of the lowest producers of drimenyl acetate. By contrast, FgaAT and CfACT1-8 were found to produce the highest relative amounts ofd acetate whereas they were poorly active on albicanol. These surprising findings demonstrate the difficulty in identifying suitable acetyltransferase enzyme candidates to accept non physiological substrates.

Example 4

Selection of Acetyltransferase Candidates for the Conversion of Drimane Sesquiterpenes into Acetylated Drimanyl Sesquiterpenes Based on Acetyltransferases Active on Drimenol and Albicanol.

a) Experiment 1

In order to identify further acetyltransferases capable to acetylate drimane-type sesquiterpene alcohols, the amino acid sequences from the acetyltransferases CrDAT and FgaAT (shown in Example 2 and 3), which were active on albicanol and drimenol, were used in a NCBI Protein Blast search to find close protein sequence homologs. The Protein Blast search was executed using default parameters (Tatiana et al, FEMS Microbiol Lett., 1999, 174:247-250, 1999).

The plant acetyltransferase XP_008340165.2 homolog to CrDAT and the 4 fungal acetyltransferases homologs (KEY80391, PYI04555.1, XP_001276734.1, XP_024709055.1) to FgaAT were retrieved from the Blast search. They are listed in Table 3.

Table 3: Acetyltransferases Selected for the Conversion of Drimane Sesquiterpenes into Drimanyl Acetylate Sesquiterpenes Based on Amino Acid Sequence Homology to Either CrDAT or FgaAT

| Name | Accession Number | Organism |
| --- | --- | --- |
| KEY80391.1 | KEY80391.1 | *Aspergillus fumigatus* |
| PYI04555.1 | PYI04555.1 | *Aspergillus sclerotiicarbonarius* |
| XP_001276734.1 | XP_001276734.1 | *Aspergillus clavatus* |
| XP_024709055.1 | XP_024709055.1 | *Aspergillus steynii* |
| XP_008340165.2 | XP_008340165.2 | *Malus domestica* | b) Experiment 2

Additionally, extra acetyltransferases candidates were retrieved from the transcriptomes from the liverwort *Bazzania trilobata* and from the fern *Dryopteris fragrans* The liverwort *Bazzania* is a rich source of terpenoids including drimane sesquiterpenes; moreover, albicanyl acetate and albicanyl caffeate were reported as natural products from liverwort of the genus *Bazzania* (Asakawa et al, Phytochemistry, Volume 30, Issue 9, 1991, Pages 3037-3040). Similarly, several different natural products including albicanyl acetate were reported in the genus *Dryopteris*. (Hideyuki Ito et al. Chem. Pharm. Bull. 48(8) 1190-1195 (2000); Froissard D et al. Nat Prod Commun. 2014 January; 9(1):137-40.)

The *Bazzania trilobata* (NCBI accession number ER364415) transcriptome was assembled using the CLC Genomic Workbench (Qiagen) resulting in a total of 22083 contigs with an average length of 1,225 base pairs. The CrDAT amino acid sequence was used to search for homologous sequences in the *Bazzania trilobata* transcriptome. For this search, the tBlastn algorithm was used (Altschul et al. 1990, J. Mol. Biol. 215, 403-410) with default parameters. Transcripts above an E-value of 0.001 were taken into account. 10 transcripts belonging to the plant acetyltransferase BAHD family with an amino acid sequence homology as low as 20% to CrDAT were selected.

Plant materials from *D. fragrans* were collected from Northern China. Fresh leaves of *D. fragrans* (sample ID PNLI20141074) were used for transcriptome analysis. Total RNA of *D. fragrans* was extracted using the RNeasy Plant Mini Kit (Cat N. 74904) from QIAGEN. The total RNA sample PNLI20141074 was processed using the NEBNext® Ultra™ RNA Library Prep Kit for Illumina (NEB, USA) and TruSeq PE Cluster Kit (Illumina, USA) and then sequenced on Illumina Miseq sequencer. An amount of 20.88 million of paired-end reads of 2×350 bp was generated. The reads were assembled using the Trinity (http://trinityrnaseq.sf.net/) software and 85753 contigs with an N50 of 1373 bp were obtained. The contigs were analysed using the EMBOSS software (http://emboss.sourceforge.net/) to get protein sequences. The amino acid sequence of the acetyltransferase ERR364415-1_contig_8546 (as obtained from the *Bazzania trilobata* (NCBI accession number ERR364415) transcriptome as described above) (SEQ ID NO: 144) was used to search for homologous sequences in the *D. fragrans* transcriptome. For this search the tBlastn algorithm was used (Altschul et al 1990, J. Mol. Biol. 215, 403-410) using standard parameters. This approach provided 20 transcripts belonging to the plant acetyltransferase BAHD family.

Example 5

In Vivo Drimanyl Acetate Production in *Saccharomyces cerevisiae* by Co-Expressing Enzymes for the Production of Either Albicanol, Dirmenol or Bicyclofarnesol Together with Selected Acetyltransferase Candidates.

An extended screening of acetyltransferases to convert albicanol, drimenol and bicyclofarnesol into their corresponding acetate derivatives was performed. A total of 89 acetyltransferases, described in Table 1 of Example 1 and in Example 4, were screened in vivo in engineered *Saccharomyces cerevisiae* cells. Screening data generated on a preliminary number of acetyltransferases as described in Example 2 and Example 3 was not repeated. Consequently, only new combinations of acetyltransferases with *Saccharomyces cerevisiae* cells producing either albicanol, drimenol or bicyclofarnesol that were not tested in in Example 2 and Example 3 were screened.

The engineered *S. cerevisiae* strain YST069 was used for the screening of the production of albicanyl acetate and drimenyl acetate as described above in Example 2 and Example 3.

Bicyclofarnesyl acetate was produced in vivo in the engineered *S. cerevisiae* strain YST069 by the co-expression of each of the selected acetyltransferase enzyme candidates together with the enzymes AstC (SEQ ID NO: 138), AstI (SEQ ID NO: 140) and AstK (SEQ ID NO: 142) responsible the production of bicyclofarnesol from the astellolide biosynthesis (Yasutomo Shinohara et. al. Sci Rep. 2016, 6:32865).

For the simultaneous expression of AstC and AstI, an expression cassette containing codon optimized for *S. cerevisiae* versions of the genes coding for AstC (SEQ ID NO: 138) and AstI (SEQ ID NO: 140) and the bidirectional GAL1/GAL10 promoter was constructed and integrated into the genome of YST069 resulting in the new strain termed YST216. The codon optimized DNA sequences of AstC and AstI were obtained by DNA synthesis (ATUM, Menlo Park, CA 94025). The bidirectional GAL1/GAL10 promoter region from yeast was added to these genes by PCR overlap extension (Yolov and Shabarova., Nucleic Acids Res. 1990, 18(13):3983-6).

For expression of AstK and the evaluated acetyltransferases in YST216, plasmids were constructed in vivo using yeast endogenous homologous recombination as previously described in Kuijpers et al., Microb Cell Fact., 2013, 12:47. The plasmids are composed of four DNA fragments which were used for *S. cerevisiae* co-transformation. The fragments were:
 a) The plasmid pF167 (SEQ ID NO: 1) linearized by enzymatic restriction with BsmBI.
 b) a fragment composed by the sequence 5'-GCACTTGCTACACTGTCAGGATAGCTTCCGTCA-CATGGTGGCGATCACCGTACAT CTGAG-3' (SEQ ID NO: 2), the terminator region of the yeast gene PGK1 and the AstK DNA sequence codon optimized for its expression in *S. cerevisiae* (SEQ ID NO: 141), this fragment was obtained by DNA synthesis (ATUM, Menlo Park, CA 94025). The bidirectional GAL1/GAL10 promoter region from yeast was added to this fragment by PCR overlap extension (Yolov and Shabarova., Nucleic Acids Res. 1990, 18(13):3983-6);
 c) a fragment composed by 60 bp corresponding to the first nucleotides of the yeast GAL10 promoter region, one of the evaluated acetyltransferases DNA coding sequence codon optimized for its expression in *S. cerevisiae* and 60 bp of the yeast CYC1 terminator region, this fragment was obtained by DNA synthesis (ATUM, Menlo Park, CA 94025); and
 d) a fragment composed by the terminator region of the yeast gene CYC1 and the sequence 5'-AGGTGCAGTTCGCGTGCAAT-TATAACGTCGTGGCAACTGTTATCAGT CGTACCGCGCCAT-3' (SEQ ID NO: 3), this fragment was obtained by DNA synthesis (ATUM, Menlo Park, CA 94025).

Figure 5:
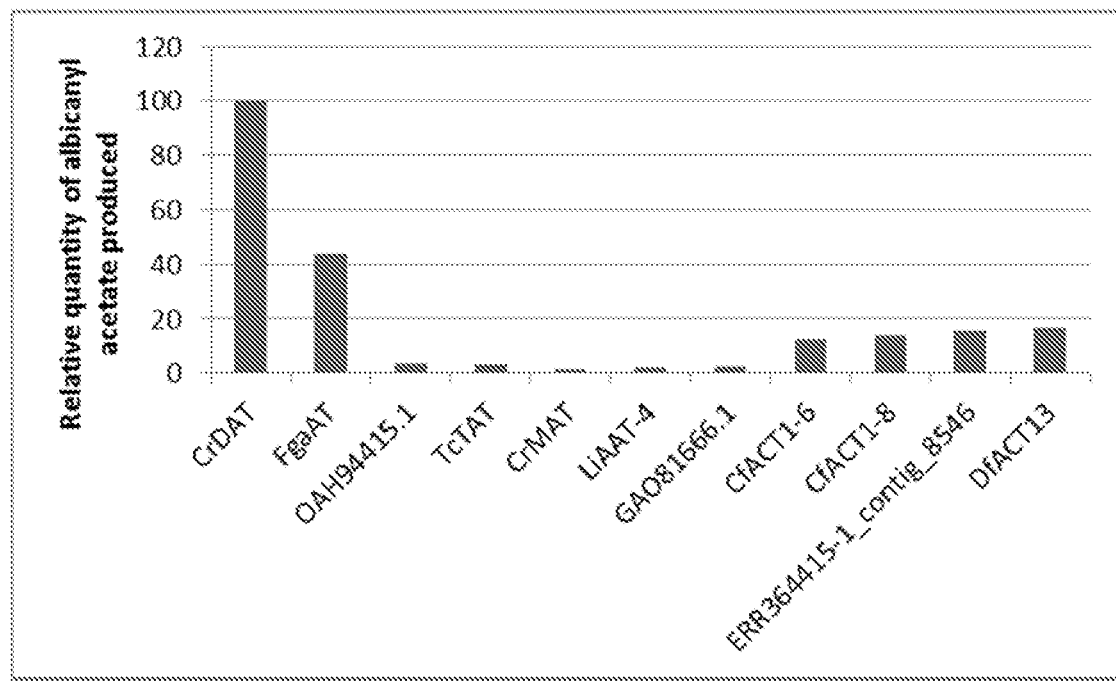
FIG. 5: Relative quantities of albicanyl acetate produced by *S. cerevisiae* cells expressing each of the acetyltransferases: CrDAT, FgaAT, OAH94415.1, TcTAT, CrMAT, LiAAT-4, GAO81666.1, CfACT1-6, CfACT1-8, ERR364415-1_contig_8546 and DfATC13.

YST216 was transformed with the fragments required for in vivo plasmid assembly. Yeast transformation was performed as described in example 2. Screening conditions and quantification of bicyclofarnesol and bicyclofarnesyl acetate were identical as described in example 2, with the exception of the use of 25 µL Mineral oil (2705-01, VWR International, LLC.) as organic overlay in the screening procedure.
Results:

In addition to the previously described nine enzymes active on albicanol (CrDAT, FgaAT, OAH94415.1, TcTAT, CrMAT, LiAAT-4, GA081666.1, CfACT1-6, CfACT1-8) (see Example 2), albicanyl acetate was detected, under these experimental conditions, when the acetyltransferases ERR364415-1_contig_8546 from *Bazzania trilobata* (SEQ ID NO: 124 or 144), and DfATC13 from *Dryopteris fragrans* (SEQ ID NO: 118), were used. However, their activity was lower compared to CrDAT and FgaAT. The relative quantities of albicanyl acetate are shown in FIG. 5.

Figure 6:
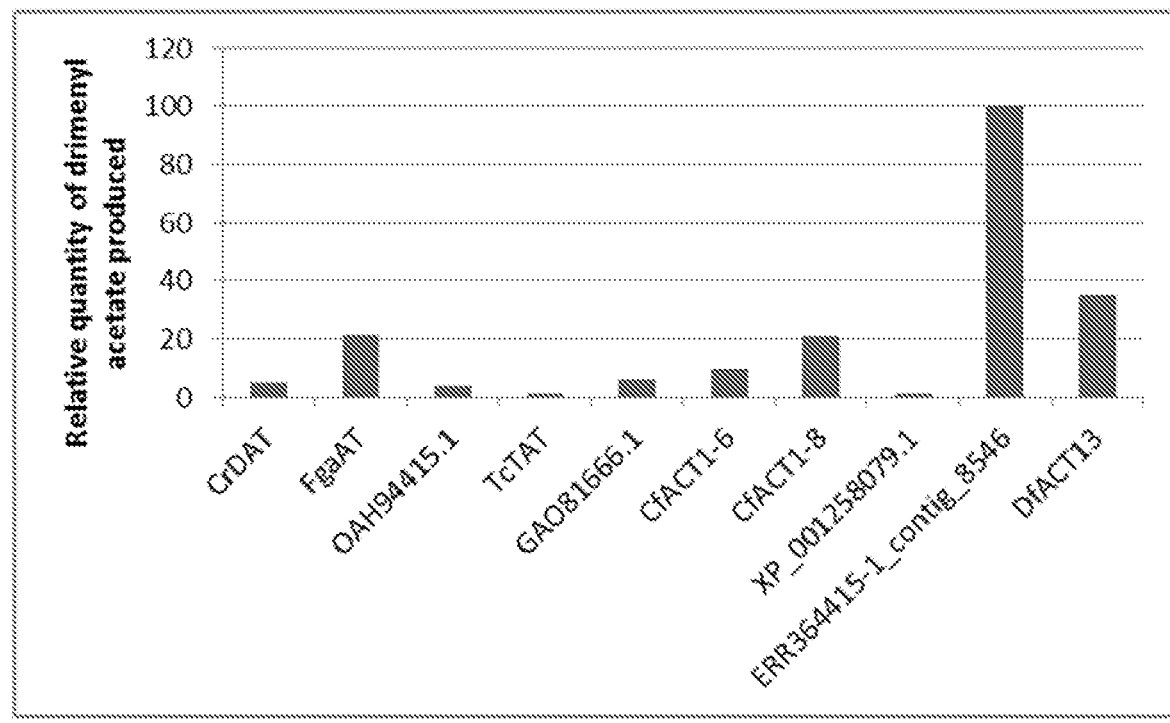
FIG. 6: Relative quantities of drimenyl acetate produced by *S. cerevisiae* cells expressing each of the acetyltransferases: CrDAT, FgaAT, OAH94415.1, TcTAT, GAO81666.1, CfACT1-6, CfACT1-8, XP_001258079.1, ERR364415-1_contig_8546 and DfATC13.
Figure 7A:
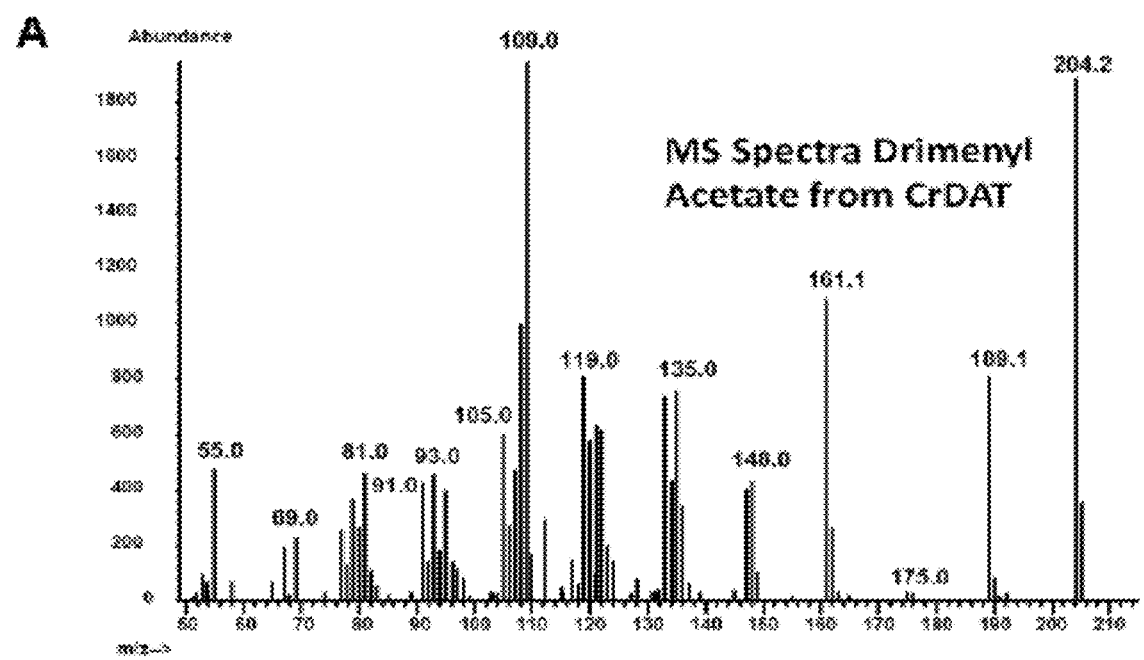
FIG. 7A: The MS spectra of the produced drimenyl acetate by the acetyltransferase CrDAT. It is identical to the MS spectra from a drimenyl acetate standard as shown in FIG. 7B.
Figure 7B:
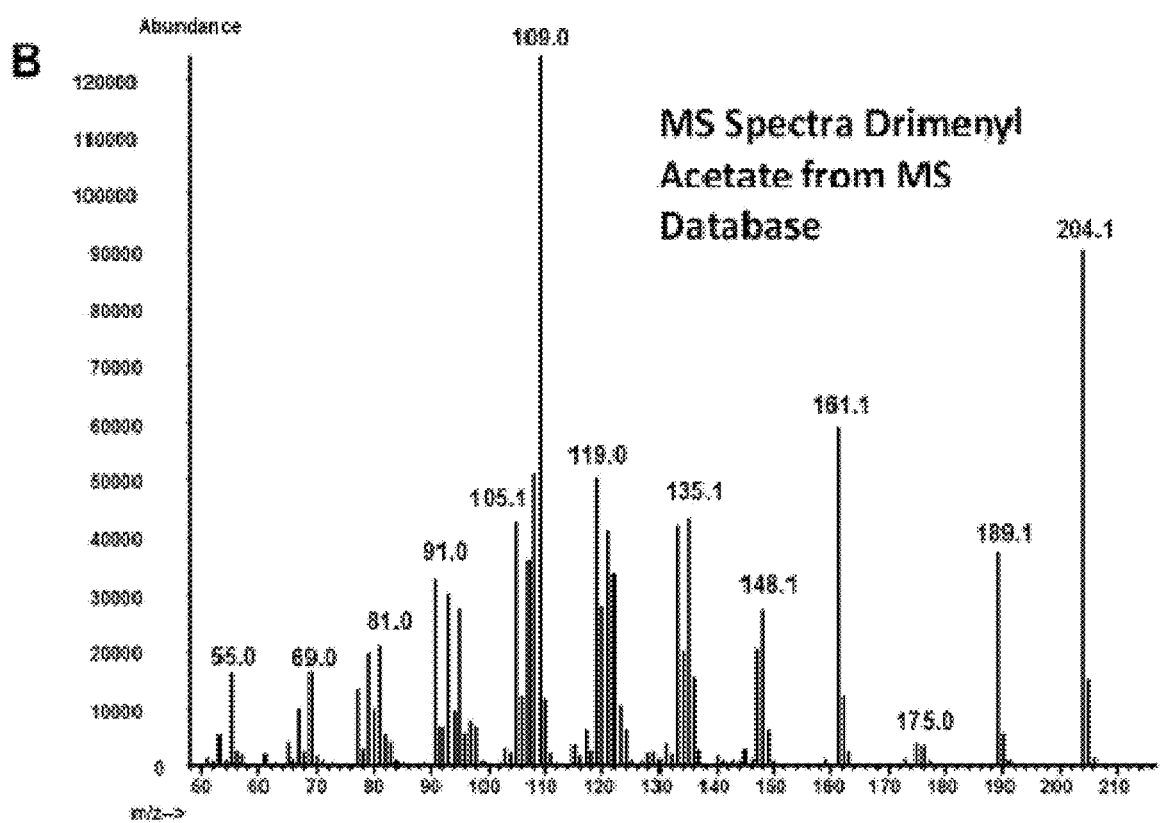
FIG. 7B: The MS spectra of a drimenyl acetate standard.

Besides the seven enzyme candidates (CrDAT, FgaAT, OAH94415.1, TcTAT, GA081666.1, CfACT1-6 and CfACT1-8) which could convert drimenol to drimenyl acetate (see Example 3), three extra acetyltransferases, XP_001258079.1 from *Aspergillus fischeri*, (SEQ ID NO: 127), ERR364415-1_contig_8546 from *Bazzania trilobata* (SEQ ID NO: 124 or 144), and DfATC13 from *Dryopteris fragrans* (SEQ ID NO: 118), were found to produce drimenyl acetate from drimenol in the expanded screening. The relative quantities of drimenyl acetate obtained are shown in FIG. 6. FIG. 7 shows that the MS spectrum of the yeast-derived drimenyl acetate is identical to a reference drimenyl acetate MS spectrum. Interestingly, under these experimental conditions, ERR364415-1_contig_8546 and DfATC13 showed the highest activity of all acetyltransferases tested.

Figure 8A:
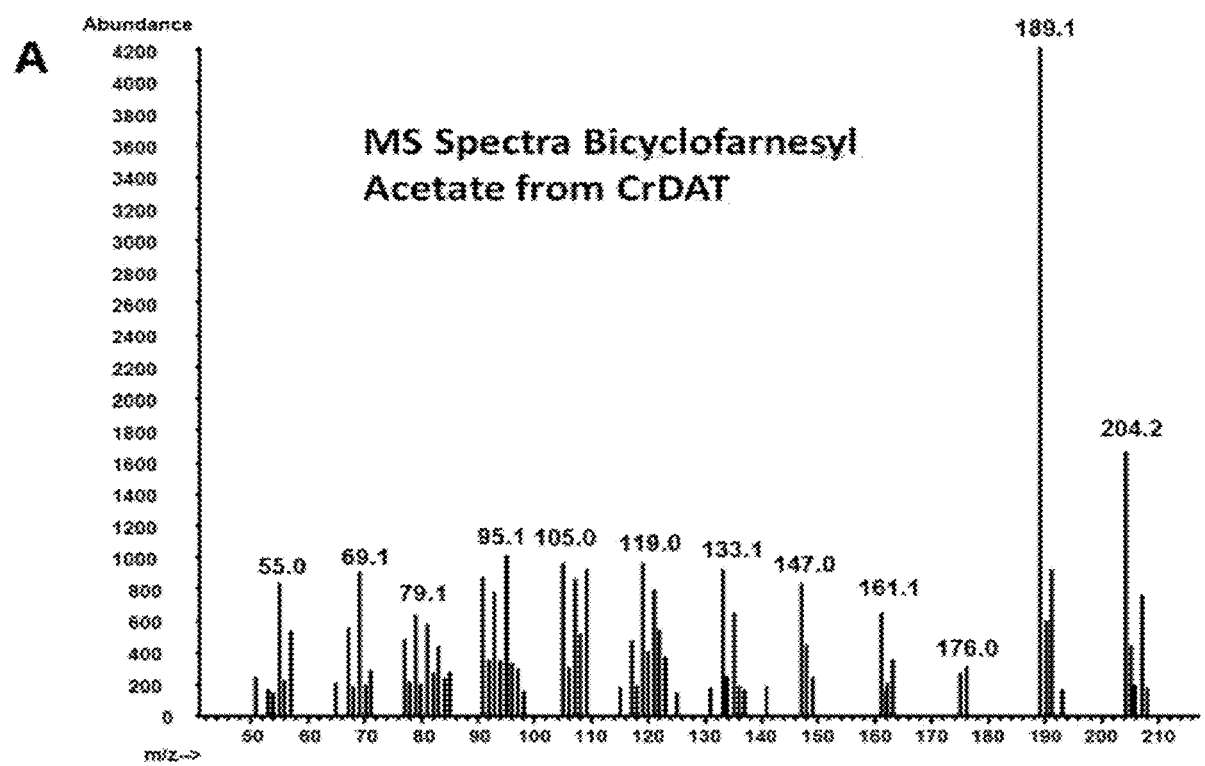
FIG. 8A: The MS spectra of the produced bicyclofarnesyl acetate by the acetyltransferase CrDAT. It is identical to the MS spectra from a bicyclofarnesyl acetate standard as shown in FIG. 8B.
Figure 8B:
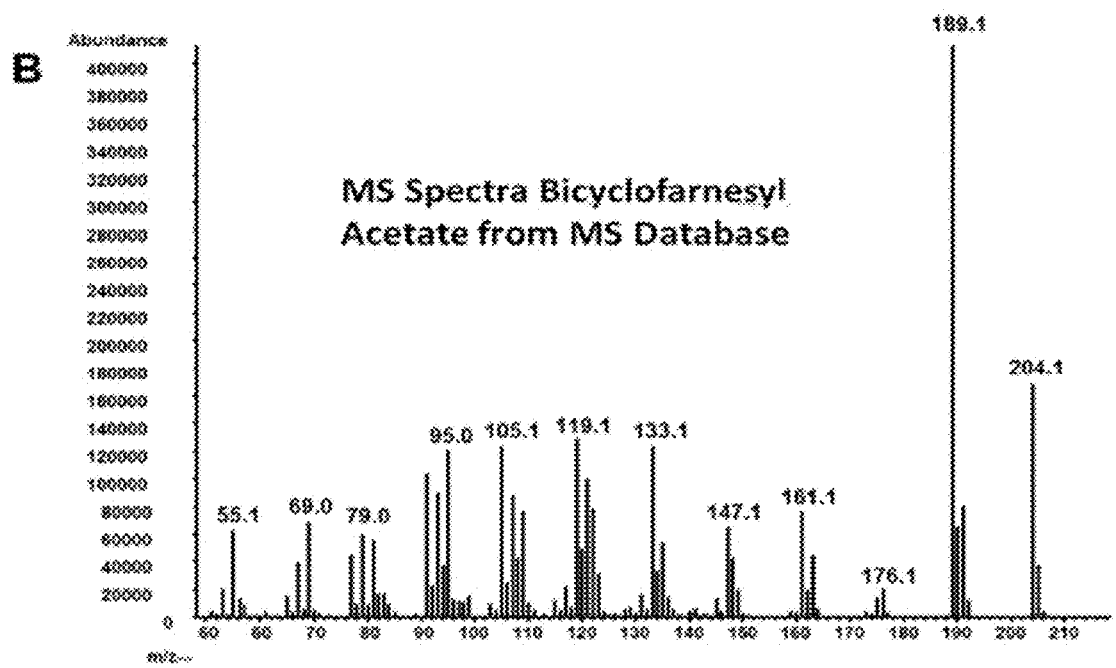
FIG. 8B: The MS spectra of a bicyclofarnesyl acetate standard.
Figure 9:
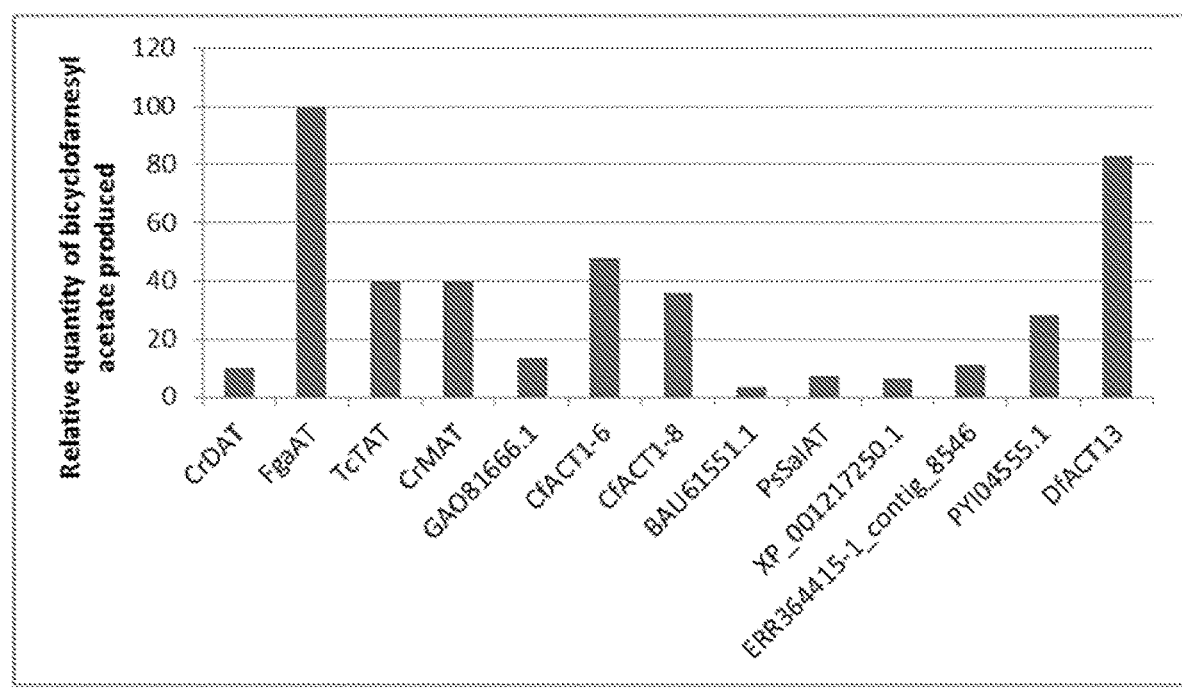
FIG. 9: Relative quantities of bicyclofarnesyl acetate produced by *S. cerevisiae* cells expressing each of the acetyltransferases: CrDAT, FgaAT, TcTAT, CrMAT, GAO81666.1, CfACT1-6, CfACT1-8, BAU61551.1, PsSalAT, XP_001217250.1, ERR364415-1_contig_8546, PYI04555.1 and DfACT13.

Bicyclofarnesyl acetate was detected for 13 combinations of AstC, AstI and AstK with the tested 89 acetyltransferases. FIG. 8 shows that the MS spectrum of the yeast-derived bicyclofarnesyl acetate is identical to a reference bicyclofarneyl acetate MS spectrum. The relative quantities of bicyclofarnesyl acetate are shown in FIG. 9. The acetyltransferase FgaAT from *Aspergillus fumigatus* and ERR364415-1_contig_8546 from *Bazzania trilobata* showed the highest acetylating activity with Bicyclofarnesol. Of these 13 discovered acetyltransferase, i.e. CrDAT, FgaAT, TcTAT, CrMAT, GA081666.1, CfACT1-6, CfACT1-8 as described above in Example 2, as well as BAU61551.1 (SEQ ID NO: 133), PsSalAT (SEQ ID NO:136), XP_001217250.1 (SEQ ID NO: 130), ERR364415-1_contig_8546 (SEQ ID NO: 124 or 144), PYI04555.1 (SEQ ID NO: 121 or 143), DfACT13 (SEQ ID NO: 118), which are active on bicyclofarnesol, nine i.e. CrDAT, FgaAT, TcTAT, CrMAT, GA081666.1, CfACT1-6, CfACT1-8, ERR364415-1_contig_8546, DfACT13 were also found to active on albicanol and drimenol. It is worth to notice that the acetyltransferase AstG involved in the biosynthesis of the aryl acid esterified drimane-type sesquiterpene lactone, astellolide (Sci Rep. 2016, 6:32865) was not active against any drimane-type sesquiterpene alcohols tested. This shows once more the unpredictability and complexity to identify an acetyltransferase that is capable to use albicanol, drimenol or bicyclofarnesol as acyl acceptor.

The content of the documents cross-referenced is incorporated by reference.

Sequences as herein referred to are:

| SEQ ID NO | Name | Source | Type |
|---|---|---|---|
| 1 | Plasmid pF167 | Artificial | NA |
| 2 | Sequence for homologous recombination | Artificial | NA |
| 3 | Sequence for homologous recombination | Artificial | NA |
| 4 | XP_007369631.1 DNA sequence codon optimized for its expression in *S. cerevisiae* | Artificial | NA |
| 5 | XP_007369631.1 Amino acid sequence of Albicanol synthase | *Dichomitus squalens* | AA |
| 6 | XP_006461126 Drimeol synthase DNA sequence codon optimized for its expression in *S. cerevisiae* | Artificial | NA |
| 7 | XP_006461126 Protein sequence of Drimenol synthase | *Agaricus bisporus* | AA |
| 8 | CrDAT DNA sequence codon optimized for its expression in *S. cerevisiae* | Artificial | NA |
| 9 | CrDAT Protein sequence | *Catharanthus roseus* | AA |
| 10 | TcTAT DNA sequence codon optimized for its expression in *S. cerevisiae* | Artificial | NA |
| 11 | TcTAT Protein sequence | *Taxus cuspidata* | AA |
| 12 | CrMAT DNA sequence codon optimized for its expression in *S. cerevisiae* | Artificial | NA |
| 13 | CrMAT Protein sequence | *Catharanthus roseus* | AA |
| 14 | LiAAT-4 DNA sequence codon optimized for its expression in *S. cerevisiae* | Artificial | NA |

| SEQ ID NO | Name | Source | Type |
|---|---|---|---|
| 15 | LiAAT-4 Protein sequence | *Lavandula x intermedia* | AA |
| 16 | FgaAT DNA sequence codon optimized for its expression in *S. cerevisiae* | Artificial | NA |
| 17 | FgaAT Protein sequence | *Aspergillus fumigatus* Af293 | AA |
| 18 | GAO81666.1 DNA sequence codon optimized for its expression in *S. cerevisiae* | Artificial | NA |
| 19 | GAO81666.1 Protein sequence | *Aspergillus udagawae* | AA |
| 20 | CfACT1-6 DNA sequence codon optimized for its expression in *S. cerevisiae* | Artificial | NA |
| 21 | CfACT1-6 Protein sequence | *Plectranthus barbatus* | AA |
| 22 | CfACT1-8 DNA sequence codon optimized for its expression in *S. cerevisiae* | Artificial | NA |
| 23 | CfACT1-8 Protein sequence | *Plectranthus barbatus* | AA |
| 24 | OAH94415.1 DNA sequence codon optimized for its expression in *S. cerevisiae* | Artificial | NA |
| 25 | OAH94415.1 Protein sequence | *Proteus mirabilis* | AA |
| 116 | DfACT13 nativeNucleotide sequence | *Dryopteris fragrans* | NA |
| 117 | DfACT13 Nucleotide sequence codon optimized for its expression in *S. cerevisiae*. | Artificial | NA |
| 118 | DfACT13 Protein sequence | *Dryopteris fragrans* | AA |
| 119 | PYI04555.1 native Nucleotide sequence | *Aspergillus sclerotiicarbonarius* | NA |
| 120 | PYI04555.1 Nucleotide sequence codon optimized for its expression in *S. cerevisiae*. | Artificial | NA |
| 121 | PYI04555.1 Protein C-terminally extended version of SEQ ID NO : 143 | *Aspergillus sclerotiicarbonarius* | AA |
| 122 | ERR364415-1_contig_8546 native Nucleotide sequence | *Bazzania trilobata* | NA |
| 123 | ERR364415-1_contig_8546 Nucleotide sequence codon optimized for its expression in *S. cerevisiae* | Artificial | NA |
| 124 | ERR364415-1_contig_8546 Protein sequence C-terminally extended version of SEQ ID NO : 144 | *Bazzania trilobata* | AA |
| 125 | XP_001258079.1 native Nucleotide sequence | *Aspergillus fischeri* | NA |
| 126 | XP_001258079.1 Nucleotide sequence codonm optimized for its expression in *S. cerevisiae* | Artificial | NA |
| 127 | XP_001258079.1 Protein sequence | *Aspergillus fischeri* | AA |
| 128 | XP_001217250.1 native Nucleotide sequence | *Aspergillus terreus* | NA |
| 129 | XP_001217250.1 Nucleotide sequence codon optimized for its expression in *S. cerevisiae* | Artificial | NA |
| 130 | XP_001217250.1 Protein sequence | *Aspergillus terreus* | AA |
| 131 | BAU61551.1 native Nucleotide sequence | *Penicillium simplicissimum* | NA |
| 132 | BAU61551.1 Nucleotide sequence codon optimized for its expression in *S. cerevisiae* | Artificial | NA |
| 133 | BAU61551.1 Protein sequence | *Penicillium simplicissimum* | AA |
| 134 | PsSalAT native Nucleotide sequence | *Papaver somniferum* | NA |
| 135 | PsSalAT Nucleotide sequence codon optimized for its expression in *S. cerevisiae*. | Artificial | NA |
| 136 | PsSalAT Protein sequence | *Papaver somniferum* | AA |
| 137 | AstC Nucleotide sequence codon optimized for its expression in *S. cerevisiae* | Artificial | NA |
| 138 | AstC Protein sequence | *Aspergillus oryzae* | AA |
| 139 | AstI Nucleotide sequence codon optimized for its expression in *S. cerevisiae* | Artificial | NA |
| 140 | AstI Protein sequence | *Aspergillus oryzae* | AA |
| 141 | AstK Nucleotide sequence codon optimized for its expression in *S. cerevisiae* | Artificial | NA |
| 142 | AstK Protein sequence | *Aspergillus oryzae* | AA |
| 143 | PYI04555.1 Protein sequence, | *Aspergillus sclerotiicarbonarius* | AA |
| 144 | ERR364415-1_contig_8546 Protein sequence | *Bazzania trilobata* | AA |

NA = Nucleic Acid
AA = Amino Acid

LISTING OF SEQUENCES

SEQ ID NO: 1
Plasmid pF167

TGGTCAGCAACAACGCCGAAGAATCACTCTCGTGTTGAGAATTGCACGCCTTGACCACGACA

CGTTAAGGGATTTTGGTCATGAGATTATCAAAAAGGATCTTCACCTAGATCCTTTTAAATTA

AAAATGAAGTTTTAAATCAATCTAAAGTATATATGAGTAAACTTGGTCTGACAGTTACCAAT

GCTTAATCAGTGAGGCACCTATCTCAGCGATCTGTCTATTTCGTTCATCCATAGTTGCCTGA

CTCCCCGTCGTGTAGATAACTACGATACGGGAGGGCTTACCATCTGGCCCCAGTGCTGCAAT

GATACCGCGAGACCCACGCTCACCGGCTCCAGATTTATCAGCAATAAACCAGCCAGCCGGAA

GGGCCGAGCGCAGAAGTGGTCCTGCAACTTTATCCGCCTCCATCCAGTCTATTAATTGTTGC

CGGGAAGCTAGAGTAAGTAGTTCGCCAGTTAATAGTTTGCGCAACGTTGTTGCCATTGCTAC

AGGCATCGTGGTGTCACGCTCGTCGTTTGGTATGGCTTCATTCAGCTCCGGTTCCCAACGAT

CAAGGCGAGTTACATGATCCCCCATGTTGTGCAAAAAAGCGGTTAGCTCCTTCGGTCCTCCG

ATCGTTGTCAGAAGTAAGTTGGCCGCAGTGTTATCACTCATGGTTATGGCAGCACTGCATAA

```
TTCTCTTACTGTCATGCCATCCGTAAGATGCTTTTCTGTGACTGGTGAGTACTCAACCAAGT

CATTCTGAGAATAGTGTATGCGGCGACCGAGTTGCTCTTGCCCGGCGTCAATACGGGATAAT

ACCGCGCCACATAGCAGAACTTTAAAAGTGCTCATCATTGGAAAACGTTCTTCGGGGCGAAA

ACTCTCAAGGATCTTACCGCTGTTGAGATCCAGTTCGATGTAACCCACTCGTGCACCCAACT

GATCTTCAGCATCTTTTACTTTCACCAGCGTTTCTGGGTGAGCAAAAACAGGAAGGCAAAAT

GCCGCAAAAAAGGGAATAAGGGCGACACGGAAATGTTGAATACTCATACTCTTCCTTTTTCA

ATATTATTGAAGCATTTATCAGGGTTATTGTCTCATGAGCGGATACATATTTGAATGTATTT

AGAAAAATAAACAAATAGGGGTTCCGCGCACATTTTTGGCATTGGCAAAGTGCGGACTGCAT

AGTCACTGTGGTGCCGTACTTAGGGTACGCGTTCCTGAACGAAGCATCTGTGCTTCATTTTG

TAGAACAAAAATGCAACGCGAGAGCGCTAATTTTTCAAACAAAGAATCTGAGCTGCATTTTT

ACAGAACAGAAATGCAACGCGAAAGCGCTATTTTACCAACGAAGAATCTGTGCTTCATTTTT

GTAAAACAAAAATGCAACGCGAGAGCGCTAATTTTTCAAACAAAGAATCTGAGCTGCATTTT

TACAGAACAGAAATGCAACGCGAGAGCGCTATTTTACCAACAAAGAATCTATACTTCTTTTT

TGTTCTACAAAAATGCATCCCGAGAGCGCTATTTTTCTAACAAAGCATCTTAGATTACTTTT

TTTCTCCTTTGTGCGCTCTATAATGCAGTCTCTTGATAACTTTTTGCACTGTAGGTCCGTTA

AGGTTAGAAGAAGGCTACTTTGGTGTCTATTTTCTCTTCCATAAAAAAAGCCTGACTCCACT

TCCCGCGTTTACTGATTACTAGCGAAGCTGCGGGTGCATTTTTTCAAGATAAAGGCATCCCC

GATTATATTCTATACCGATGTGGATTGCGCATACTTTGTGAACAGAAAGTGATAGCGTTGAT

GATTCTTCATTGGTCAGAAAATTATGAACGGTTTCTTCTATTTTGTCTCTATATACTACGTA

TAGGAAATGTTTACATTTTCGTATTGTTTTCGATTCACTCTATGAATAGTTCTTACTACAAT

TTTTTTGTCTAAAGAGTAATACTAGAGATAAACATAAAAAATGTAGAGGTCGAGTTTAGATG

CAAGTTCAAGGAGCGAAAGGTGGATGGGTAGGTTATATAGGGATATAGCACAGAGATATATA

GCAAAGAGATACTTTTGAGCAATGTTTGTGGAAGCGGTATTCGCAATATTTTAGTAGCTCGT

TACAGTCCGGTGCGTTTTTGGTTTTTTGAAAGTGCGTCTTCAGAGCGCTTTTGGTTTTCAAA

AGCGCTCTGAAGTTCCTATACTTTCTAGAGAATAGGAACTTCGGAATAGGAACTTCAAAGCG

TTTCCGAAAACGAGCGCTTCCGAAAATGCAACGCGAGCTGCGCACATACAGCTCACTGTTCA

CGTCGCACCTATATCTGCGTGTTGCCTGTATATATATATACATGAGAAGAACGGCATAGTGC

GTGTTTATGCTTAAATGCGTACTTATATGCGTCTATTTATGTAGGATGAAAGGTAGTCTAGT

ACCTCCTGTGATATTATCCCATTCCATGCGGGGTATCGTATGCTTCCTTCAGCACTACCCTT

TAGCTGTTCTATATGCTGCCACTCCTCAATTGGATTAGTCTCATCCTTCAATGCTATCATTA

TGTCACCCGCAGTTCTGTGTCGTAGTCATCAACATAGCACCTATCCTTTGGCATCTCGGTGA

GCAAAAGGCCAGCAAAAGGCCAGGAACCGTAAAAAGGCCGCGTTGCTGGCGTTTTTCCATAG

GCTCCGCCCCCTGACGAGCATCACAAAAATCGACGCTCAAGTCAGAGGTGGCGAAACCCGA

CAGGACTATAAAGATACCAGGCGTTTCCCCCTGGAAGCTCCCTCGTGCGCTCTCCTGTTCCG

ACCCTGCCGCTTACCGGATACCTGTCCGCCTTTCTCCCTTCGGGAAGCGTGGCGCTTTCTCA

TAGCTCACGCTGTAGGTATCTCAGTTCGGTGTAGGTCGTTCGCTCCAAGCTGGGCTGTGTGC

ACGAACCCCCCGTTCAGCCCGACCGCTGCGCCTTATCCGGTAACTATCGTCTTGAGTCCAAC

CCGGTAAGACACGACTTATCGCCACTGGCAGCAGCCACTGGTAACAGGATTAGCAGAGCGAG

GTATGTAGGCGGTGCTACAGAGTTCTTGAAGTGGTGGCCTAACTACGGCTACACTAGAAGGA

CAGTATTTGGTATCTGCGCTCTGCTGAAGCCAGTTACCTTCGGAAAAAGAGTTGGTAGCTCT
```

-continued

```
TGATCCGGCAAACAAACCACCGCTGGTAGCGGTGGTTTTTTTGTTTGCAAGCAGCAGATTAC

GCGCAGAAAAAAGGATCTCAAGAAGATCCTTTGATCTTTTCTACGGGGTCTGACGCTCAGC

ACTTGCTACACTGTCAGGATAGCTTCCGTCACATGGTGGCGATCACCGTACATCTGAGTGAG

ACGTTAATTAAAGTAGACCGCTCACACATGGGCGGCCGCCGTCTCAAGGTGCAGTTCGCGTG

CAATTATAACGTCGTGGCAACTGTTATCAGTCGTACCGCGCCATTCGACTACGTCGTAAGGC

CGTTTCTGACAGAGTAAAATTCTTGAGGGAACTTTCACCATTATGGGAAATGCTTCAAGAAG

GTATTGACTTAAACTCCATCAAATGGTCAGGTCATTGAGTGTTTTTTATTTGTTGTATTTTT

TTTTTTTAGAGAAAATCCTCCAATATCAAATTAGGAATCGTAGTTTCATGATTTTCTGTTA

CACCTAACTTTTTGTGTGGTGCCCTCCTCCTTGTCAATATTAATGTTAAAGTGCAATTCTTT

TTCCTTATCACGTTGAGCCATTAGTATCAATTTGCTTACCTGTATTCCTTTACTATCCTCCT

TTTTCTCCTTCTTGATAAATGTATGTAGATTGCGTATATAGTTTCGTCTACCCTATGAACAT

ATTCCATTTTGTAATTTCGTGTCGTTTCTATTATGAATTTCATTTATAAAGTTTATGTACAA

ATATCATAAAAAAGAGAATCTTTTTAAGCAAGGATTTTCTTAACTTCTTCGGCGACAGCAT

CACCGACTTCGGTGGTACTGTTGGAACCACCTAAATCACCAGTTCTGATACCTGCATCCAAA

ACCTTTTTAACTGCATCTTCAATGGCCTTACCTTCTTCAGGCAAGTTCAATGACAATTTCAA

CATCATTGCAGCAGACAAGATAGTGGCGATAGGGTCAACCTTATTCTTTGGCAAATCTGGAG

CAGAACCGTGGCATGGTTCGTACAAACCAAATGCGGTGTTCTTGTCTGGCAAAGAGGCCAAG

GACGCAGATGGCAACAAACCCAAGGAACCTGGGATAACGGAGGCTTCATCGGAGATGATATC

ACCAAACATGTTGCTGGTGATTATAATACCATTTAGGTGGGTTGGGTTCTTAACTAGGATCA

TGGCGGCAGAATCAATCAATTGATGTTGAACCTTCAATGTAGGGAATTCGTTCTTGATGGTT

TCCTCCACAGTTTTTCTCCATAATCTTGAAGAGGCCAAAAGATTAGCTTTATCCAAGGACCA

AATAGGCAATGGTGGCTCATGTTGTAGGGCCATGAAAGCGGCCATTCTTGTGATTCTTTGCA

CTTCTGGAACGGTGTATTGTTCACTATCCCAAGCGACACCATCACCATCGTCTTCCTTTCTC

TTACCAAAGTAAATACCTCCCACTAATTCTCTGACAACAACGAAGTCAGTACCTTTAGCAAA

TTGTGGCTTGATTGGAGATAAGTCTAAAAGAGAGTCGGATGCAAAGTTACATGGTCTTAAGT

TGGCGTACAATTGAAGTTCTTTACGGATTTTTAGTAAACCTTGTTCAGGTCTAACACTACCG

GTACCCATTTAGGACCAGCCACAGCACCTAACAAAACGGCATCAACCTTCTTGGAGGCTTC

CAGCGCCTCATCTGGAAGTGGGACACCTGTAGCATCGATAGCAGCACCACCAATTAAATGAT

TTTCGAAATCGAACTTGACATTGGAACGAACATCAGAAATAGCTTTAAGAACCTTAATGGCT

TCGGCTGTGATTTCTTGACCAACGTGGTCACCTGGCAAAACGACGATCTTCTTAGGGGCAGA

CATAGGGGCAGACATTAGAATGGTATATCCTTGAAATATATATATATATTGCTGAAATGTAA

AAGGTAAGAAAAGTTAGAAAGTAAGACGATTGCTAACCACCTATTGGAAAAAACAATAGGTC

CTTAAATAATATTGTCAACTTCAAGTATTGTGATGCAAGCATTTAGTCATGAACGCTTCTCT

ATTCTATATGAAAAGCCGGTTCCGGCCTCTCACCTTTCCTTTTTCTCCCAATTTTTCAGTTG

AAAAAGGTATATGCGTCAGGCGACCTCTGAAATTAACAAAAAATTTCCAGTCATCGAATTTG

ATTCTGTGCGATAGCGCCCCTGTGTGTTCTCGTTATGTTGAGGAAAAAAATAATGGTTGCTA

AGAGATTCGAACTCTTGCATCTTACGATACCTGAGTATTCCCACAGTTAACTGCGGTCAAGA

TATTTCTTGAATCAGGCGCCTTAGACCGCTCGGCCAAACAACCAATTACTTGTTGAGAAATA

GAGTATAATTATCCTATAAATATAACGTTTTTGAACACACATGAACAAGGAAGTACAGGACA

ATTGATTTTGAAGAGAATGTGGATTTTGATGTAATTGTTGGGATTCCATTTTTAATAAGGCA

ATAATATTAGGTATGTGGATATACTAGAAGTTCTCCTCGACCGTCGA
```

SEQ ID NO: 2
Sequence for homologous recombination

GCACTTGCTACACTGTCAGGATAGCTTCCGTCACATGGTGGCGATCACC
GTACATCTGAG

SEQ ID NO: 3
Sequence for homologous recombination

AGGTGCAGTTCGCGTGCAATTATAACGTCGTGGCAACTGTTATCAGTCG
TACCGCGCCAT

SEQ ID NO: 4
XP_007369631.1 DNA sequence of *Dichomitus squalens*
Albincanol synthase codon optimized for its expression in *S. cerevisiae*

ATGGCTTCTATCCACAGAAGATACACTACTTTGATCTTGGACTTGGGTGACGTTTTGTTCAG

ATGGTCTCCAAAGACTGAAACTGCTATCCCACCACAACAATTGAAGGACATCTTGTCTTCTG

TTACTTGGTTCGAATACGAAAGAGGTAGATTGTCTCAAGAAGCTTGTTACGAAAGATGTGCT

GAAGAATTCAAGATCGAAGCTTCTGTTATCGCTGAAGCTTTCAAGCAAGCTAGAGGTTCTTT

GAGACCAAACGAAGAATTCATCGCTTTGATCAGAGACTTGAGAAGAGAAATGCACGGTGACT

TGACTGTTTTGGCTTTGTCTAACATCTCTTTGCCAGACTACGAATACATCATGTCTTTGTCT

TCTGACTGGACTACTGTTTTCGACAGAGTTTTCCCATCTGCTTTGGTTGGTGAAAGAAAGCC

ACACTTGGGTTGTTACAGAAAGGTTATCTCTGAAATGAACTTGGAACCACAAACTACTGTTT

TCGTTGACGACAAGTTGGACAACGTTGCTTCTGCTAGATCTTTGGGTATGCACGGTATCGTT

TTCGACAACCAAGCTAACGTTTTCAGACAATTGAGAAACATCTTCGGTGACCCAATCAGAAG

AGGTCAAGAATACTTGAGAGGTCACGCTGGTAAGTTGGAATCTTCTACTGACAACGGTTTGA

TCTTCGAAGAAACTTCACTCAATTGATCATCTACGAATTGACTCAAGACAGAACTTTGATC

TCTTTGTCTGAATGTCCAAGAACTTGGAACTTCTTCAGAGGTGAACCATTGTTCTCTGAAAC

TTTCCCAGACGACGTTGACACTACTTCTGTTGCTTTGACTGTTTTGCAACCAGACAGAGCTT

TGGTTAACTCTGTTTTGGACGAAATGTTGGAATACGTTGACGCTGACGGTATCATGCAAACT

TACTTCGACAGATCTAGACCAAGAATGGACCCATTCGTTTGTGTTAACGTTTTGTCTTTGTT

CTACGAAAACGGTAGAGGTCACGAATTGCCAAGAACTTTGGACTGGGTTTACGAAGTTTTGT

TGCACAGAGCTTACCACGGTGGTTCTAGATACTACTTGTCTCCAGACTGTTTCTTGTTCTTC

ATGTCTAGATTGTTGAAGAGAGCTGACGACCCAGCTGTTCAAGCTAGATTGAGACCATTGTT

CGTTGAAAGAGTTAACGAAAGAGTTGGTGCTGCTGGTGACTCTATGGACTTGGCTTTCAGAA

TCTTGGCTGCTGCTTCTGTTGGTGTTCAATGTCCAAGAGACTTGGAAAGATTGACTGCTGGT

CAATGTGACGACGGTGGTTGGGACTTGTGTTGGTTCTACGTTTTCGGTTCTACTGGTGTTAA

GGCTGGTAACAGAGGTTTGACTACTGCTTTGGCTGTTACTGCTATCCAAACTGCTATCGGTA

GACCACCATCTCCATCTCCATCTGCTGCTTCTTCTTTCAGACCATCTTCTCCATACAAG

TTCTTGGGTATCTCTAGACCAGCTTCTCCAATCAGATTCGGTGACTTGTTGAGACCATGGAG

AAAGATGTCTAGATCTAACTTGAAGTCTCAATAA

SEQ ID NO: 5
XP_007369631.1 Amino acid sequence of *Dichomitus squalens* Albincanol synthase

MASIHRRYTTLILDLGDVLFRWSPKTETAIPPQQLKDILSSVTWFEYERGRLSQEACYERCA

EEFKIEASVIAEAFKQARGSLRPNEEFIALIRDLRREMHGDLTVLALSNISLPDYEYIMSLS

SDWTTVFDRVFPSALVGERKPHLGCYRKVISEMNLEPQTTVFVDDKLDNVASARSLGMHGIV

FDNQANVFRQLRNIFGDPIRRGQEYLRGHAGKLESSTDNGLIFEENFTQLIIYELTQDRTLI

SLSECPRTWNFFRGEPLFSETFPDDVDTTSVALTVLQPDRALVNSVLDEMLEYVDADGIMQT

YFDRSRPRMDPFVCVNVLSLFYENGRGHELPRTLDWVYEVLLHRAYHGGSRYYLSPDCFLFF

MSRLLKRADDPAVQARLRPLFVERVNERVGAAGDSMDLAFRILAAASVGVQCPRDLERLTAG

QCDDGGWDLCWFYVFGSTGVKAGNRGLTTALAVTAIQTAIGRPPSPSPSAASSSFRPSSPYK

FLGISRPASPIRFGDLLRPWRKMSRSNLKSQ

SEQ ID NO: 6
XP_006461126 *Agaricus bisporus* Drimeol synthase DNA synthase codon optimized for its expression in *S. cerevisiae*

ATGGCTCCACCACAAAGACCATTCACTGCTATCGTTTTCGACATCGGTGACGTTTTGTTCCA

ATGGTCTGCTACTACTAAGACTTCTATCTCTCCAAAGACTTTGAGATCTATCTTGAACTGTC

CAACTTGGTTCGACTACGAAAGAGGTAGATTGGCTGAAAACGCTTGTTACGCTGCTATCTCT

CAAGAATTCAACGTTAACCCAGACGAAGTTAGAGACGCTTTCTCTCAAGCTAGAGACTCTTT

GCAAGCTAACCACGACTTCATCTCTTTGATCAGAGAATTGAAGGCTCAAGCTAACGGTAGAT

TGAGAGTTTACGCTATGTCTAACATCTCTTTGCCAGACTGGGAAGTTTTGAGAATGAAGCCA

GCTGACTGGGACATCTTCGACCACGTTTTCACTTCTGGTGCTGTTGGTGAAAGAAAGCCAAA

CTTGGCTTTCTACAGACACGTTATCGCTGCTACTGACTTGCAACCACACCAAACTATCTTCG

TTGACGACAAGTTGGAAAACGTTTTGTCTGCTAGATCTTTGGGTTTCACTGGTATCGTTTTC

GACGAACCATCTGAAGTTAAGAGAGCTTTGAGAAACTTGATCGGTGACCCAGTTCAAAGAGG

TGGTGAATTCTTGGTTAGAAACGCTGGTAAGTTGGGTTCTATCACTAGAACTACTGCTAAGC

ACGAATCTATCCCATTGGACGAAAACTTCGCTCAATTGTTGATCTTGGAAATCACTGGTAAC

AGAGCTTTGGTTAACTTGGTTGAACACCCACAAACTTGGAACTTCTTCCAAGGTAAGGGTCA

ATTGACTACTGAAGAATTCCCATTCGACTTGGACACTACTTCTTTGGGTTTGACTATCTTGA

AGAGATCTAGAGAAATCGCTGACTCTGTTATGGACGAAATGTTGGAATACGTTGACCCAGAC

GGTATCATCCAAACTTACTTCGACCACAGAAGACCAAGATTCGACCCAGTTGTTTGTGTTAA

CGCTTTGTCTTTGTTCTACGCTTACGGTAGAGGTGAACAATTGAGATCTACTTTGACTTGGG

TTCACGAAGTTTTGTTGAACAGAGCTTACTTGGACGGTACTAGATACTACGAAACTGCTGAA

TGTTTCTTGTACTTCATGTCTAGATTGTTGGCTACTTCTGGTGACCCAGACTTGCACTCTTT

GTTGAAGCCATTGTTGAAGGAAAGAGTTCAAGAAAGAATCGGTGCTGACGGTGACTCTTTGG

CTTTGGCTATGAGAATCTTGGCTTGTGACTTCGTTGGTATCAGAGACGAAGTTGACTTGAGA

ACTTTGTTGACTTTGCAATGTGAAGACGGTGGTTGGGAAGTTGGTTGGATGTACAAGTACGG

TTCTTCTGGTATCTCTATCGGTAACAGAGGTTTGGCTACTGCTTTGGCTATCAAGGCTGTTG

ACACTATGTTTCCAACCACAAATCAGATTCTCTGAATCTCCAACTGACACTTTGGTTGAAAAC

-continued

```
GCTATCCACAAGAGAAGACCATCTTTCTCTGAAAAGTTCTTGGGTAAGAGACCAAGATCTGG

TTCTTTCAGAAAGCCATTGCAATGGATCTTGCAAGGTTCTAAGTTGAGAAAGTCTGTTGAAA

TCGGTTCTTAA
```

SEQ ID NO: 7
XP_006461126 Protein sequence of *Agaricus bisporus*
Drimeol synthase DNA synthase

```
MAPPQRPFTAIVEDIGDVLFQWSATTKTSISPKTLRSILNCPTWFDYERGRLAENACYAAIS

QEFNVNPDEVRDAFSQARDSLQANHDFISLIRELKAQANGRLRVYAMSNISLPDWEVLRMKP

ADWDIFDHVFTSGAVGERKPNLAFYRHVIAATDLQPHQTIFVDDKLENVLSARSLGFTGIVE

DEPSEVKRALRNLIGDPVQRGGEFLVRNAGKLGSITRTTAKHESIPLDENFAQLLILEITGN

RALVNLVEHPQTWNFFQGKGQLTTEEFPFDLDTTSLGLTILKRSREIADSVMDEMLEYVDPD

GIIQTYFDHRRPRFDPVVCVNALSLFYAYGRGEQLRSTLTWVHEVLLNRAYLDGTRYYETAE

CFLYFMSRLLATSGDPDLHSLLKPLLKERVQERIGADGDSLALAMRILACDFVGIRDEVDLR

TLLTLQCEDGGWEVGWMYKYGSSGISIGNRGLATALAIKAVDTMFQPQIRFSESPTDTLVEN

AIHKRRPSFSEKFLGKRPRSGSFRKPLQWILQGSKLRKSVEIGS
```

SEQ ID NO: 8
CrDAT DNA sequence codon optimized for its expression in
*S. cerevisiae*

```
ATGGAAAGTGGTAAAATATCTGTAGAAACGGAAACCCTATCGAAAACCCTTATCAAGCCGTC

CTCGCCCACGCCACAGTCTCTTTCCCGTTACAACTTATCTTACAATGATCAGAACATTTATC

AGACCTGCGTATCTGTAGGGTTTCTTTTACGAAAATCCTGATGGCATCGAGATATCCACGATC

CGTGAGCAGCTGCAGAACAGCCTGTCCAAAACTCTGGTCTCATACTATCCCTTCGCAGGCAA

AGTAGTGAAGAACGACTACATACATTGTAACGACGATGGCATTGAGTTCGTCGAAGTCAGAA

TTAGATGCAGGATGAATGATATACTTAAATACGAACTACGTTCTTACGCTCGTGATTTAGTC

CTGCCAAAGAGGGTTACCGTGGGCTCTGAAGATACCACCGCTATCGTGCAGCTGTCCCATTT

CGACTGTGGCGGTTTGGCCGTGGCTTTTGGTATCTCCCACAAGGTGGCCGATGGTGGTACTA

TAGCCTCTTTCATGAAGGACTGGGCGGCCTCTGCTTGCTACTTGTCCTCAAGTCACCACGTT

CCAACGCCTCTATTGGTCTCAGACAGTATTTTCCCAAGACAGGACAACATAATATGCGAACA

ATTTCCCACCTCAAAGAATTGCGTGGAGAAGACATTCATTTTCCCACCAGAAGCAATCGAAA

AGTTAAAGAGTAAGGCCGTTGAATTCGGCATTGAGAAACCGACCAGAGTAGAGGTCCTGACT

GCATTCTTATCTAGATGCGCCACCGTAGCAGGTAAGTCGGCAGCTAAGAACAACAATTGTGG

TCAAAGCCTGCCCTTTCCGGTTCTACAGGCCATTAATTTGAGGCCGATTCTAGAATTGCCAC

AGAACTCTGTGGGTAATCTAGTTTCGATCTACTTCAGCAGGACAATTAAGGAAAACGACTAC

CTAAATGAAAAGGAGTACACTAAATTGGTGATAAACGAGTTGCGTAAAGAAAAGCAAAAGAT

CAAGAATTTGAGCAGAGAGAAGTTGACCTACGTCGCCCAGATGGAAGAGTTCGTTAAGTCAC

TTAAAGAGTTCGATATCTCCAACTTCCTAGATATCGATGCCTACTTAAGCGATAGTTGGTGC

AGGTTTCCTTTCTACGACGTCGACTTCGGATGGGGAAAGCCTATCTGGGTCTGCCTATTCCA
```

-continued

```
GCCTTACATCAAGAACTGCGTTGTTATGATGGACTATCCTTTCGGTGACGATTATGGTATCG

AGGCTATTGTTTCTTTCGAGCAAGAGAAAATGTCCGCGTTCGAGAAGAACGAACAGTTACTG

CAGTTTGTGTCTAACTAA
```

SEQ ID NO: 9
CrDAT Protein sequence

```
MESGKISVETETLSKTLIKPSSPTPQSLSRYNLSYNDQNIYQTCVSVGFFYENPDGIEISTI

REQLQNSLSKTLVSYYPFAGKVVKNDYIHCNDDGIEFVEVRIRCRMNDILKYELRSYARDLV

LPKRVTVGSEDTTAIVQLSHFDCGGLAVAFGISHKVADGGTIASFMKDWAASACYLSSSHHV

PTPLLVSDSIFPRQDNIICEQFPTSKNCVEKTFIFPPEAIEKLKSKAVEFGIEKPTRVEVLT

AFLSRCATVAGKSAAKNNNCGQSLPFPVLQAINLRPILELPQNSVGNLVSIYFSRTIKENDY

LNEKEYTKLVINELRKEKQKIKNLSREKLTYVAQMEEFVKSLKEFDISNFLDIDAYLSDSWC

RFPFYDVDFGWGKPIWVCLFQPYIKNCVVMMDYPFGDDYGIEAIVSFEQEKMSAFEKNEQLL

QFVSN
```

SEQ ID NO: 10
TcTAT DNA sequence codon optimized for its expression in *S. cerevisiae*

```
ATGGAGAAGACGGATTTACACGTGAACCTTATCGAAAAGGTTATGGTCGGTCCAAGCCCACC

TTTGCCGAAGACTACACTACAACTATCCTCAATCGATAACCTACCTGGTGTTAGAGGCTCGA

TCTTTAATGCCTTGTTAATATATAATGCTTCACCGTCTCCCACGATGATCTCCGCTGATCCA

GCTAAACCTATCAGAGAAGCTTTGGCCAAAATCCTGGTTTACTACCCACCTTTCGCTGGCAG

GCTACGTGAGACTGAGAATGGCGATCTAGAGGTAGAGTGCACGGGAGAGGGTGCGATGTTTC

TTGAAGCGATGGCCGATAATGAATTAAGTGTCTTAGGGGATTTCGACGACAGTAACCCTAGC

TTCCAGCAATTGTTGTTCTCCCTTCCACTGGACACTAACTTCAAGGATCTATCCCTGTTAGT

CGTGCAGGTGACAAGGTTTACATGCGGCGGGTTCGTCGTTGGGGTTTCATTTCACCACGGTG

TATGCGATGGGAGAGGAGCTGCACAATTTCTGAAGGGACTAGCCGAAATGGCAAGGGGAGAA

GTTAAGTTGTCGCTGGAGCCGATCTGGAATCGTGAACTAGTTAAGCTGGACGATCCCAAGTA

TTTGCAATTCTTTCACTTCGAATTCTTGAGAGCACCATCAATCGTCGAAAAGATAGTTCAAA

CCTACTTCATCATCGATTTCGAAACTATTAACTACATAAAGCAGTCAGTAATGGAAGAATGT

AAAGAATTCTGCAGCTCTTTTGAAGTTGCTTCTGCAATGACGTGGATAGCTAGGACCAGGGC

CTTTCAAATACCCGAGAGCGAGTACGTGAAAATCCTATTTGGTATGGACATGAGGAACTCTT

TTAACCCGCCTCTGCCGTCAGGTTATTATGGAAACTCAATTGGTACGGCTTGTGCAGTGGAC

AATGTTCAAGACTTGTTGAGTGGTTCACTACTGAGGGCAATAATGATAATCAAGAAATCAAA

GGTATCACTTAACGACAACTTTAAGAGCCGTGCTGTCGTTAAGCCTTCAGAACTTGACGTAA

ACATGAACCATGAGAATGTGGTGGCATTTGCTGACTGGTCAAGGCTGGGGTTCGACGAAGTC

GATTTTGGCTGGGGAAACGCGGTGTCTGTTTCCCCGGTACAGCAACAGTCGGCACTTGCAAT

GCAGAATTACTTCCTGTTCTTGAAGCCAAGCAAGAACAAGCCCGATGGAATTAAGATTCTAA

TGTTCCTACCATTGTCCAAGATGAAATCCTTCAAAATTGAAATGGAAGCGATGATGAAGAAG

TACGTCGCCAAGGTATAA
```

SEQ ID NO: 11
TcTAT Protein sequence

MEKTDLHVNLIEKVMVGPSPPLPKITTLQLSSIDNLPGVRGSIFNALLI

YNASPSPTMISADPAKPIREALAKILVYYPPFAGRLRETENGDLEVECT

GEGAMFLEAMADNELSVLGDEDDSNPSFQQLLFSLPLDTNFKDLSLLVV

QVTRFTCGGFVVGVSFHHGVCDGRGAAQFLKGLAEMARGEVKLSLEPIW

NRELVKLDDPKYLQFFHFEFLRAPSIVEKIVQTYFIIDFETINYIKQSV

MEECKEFCSSFEVASAMTWIARTRAFQIPESEYVKILFGMDMRNSFNPP

LPSGYYGNSIGTACAVDNVQDLLSGSLLRAIMIIKKSKVSLNDNFKSRA

VVKPSELDVNMNHENVVAFADWSRLGFDEVDFGWGNAVSVSPVQQQSAL

AMQNYFLFLKPSKNKPDGIKILMFLPLSKMKSFKIEMEAMMKKYVAKV

SEQ ID NO: 12
CrMAT DNA sequence codon optimized for its expression in *S. cerevisiae*

ATGGATTCTATTACTATGGTTGAAACCGAGACATTATCGAAGACATTGA

TTAAGCCATCTAGCCCAACCCCACAGAGTCTGTCACACTACAACCTGTC

TTACAACGATCAGAATATATATCCAGAGTATATATTTGCAGGCTTCTTC

TACAGCAACCCGGACGGACACGAGATCTCGACTATTAGAGAGCAGCTGC

AGAACTCTCTTAGCAAGACATTAGTATCTTATTATCCATTCGCTGGTAA

AGTGGTCAAGAACGATTACATTCACTGCAATGACGACGGAATAGAATTC

GTAGACGTCAGAATCCACTGCAGGATGAACGATATTCTTAAGCCTGAAT

TGAGGTCTTACGCTTCCGAGCTTATTCGTCCGAATAGAAGTACAGTGGG

GTCAGAGGACAGTACTGCGCTTGTCCAGTTATCTCACTTTGACTGTGGC

GGGGTAGCTGTCGCATTCGGTATATCTCACAAAGTCGCAGACGCAGCGA

CTATTCTGTCGTTTATAAAGGATTGGGCCGCTTCTACGTGTGACTTGTC

AAGTAGTCACGATGTGTCTACACCAGTACTAGTATCCGATTCCATATTC

CCCCGTCAAGATAACATCATCTGTGGCCAGTTCCCTGCTTCACCGAACT

GCGTGAGGAAGCGTTTCTTATTCAGCCCGGAAGCTATCGAAAGACTAAA

ATCGAAAGCCATTGAATTTGGGATCGAGAAGCCAACGAGGGTAGAGGTC

CTGACAGCATTCTTGTGCCGTTGCGCTACCGTTGCAGGTAAATCTGCGG

CCAAGAACAACAATTGTGGACAGTCACTGCCTTTCGCTGTTATTCAAGC

AGTCAACCTGAGGCCCTTACTAGAACTGCCAAAGAATTCCGTCGGCAAC

CTTATATCAATCTACTTTTCTACAATCAAAGAAAACGACACGGTGAACA

TCGAACAGGAGTTCACAAAATTAGTGATCGGAGAGTTGAGGAAGGCTAA

GGATAAGTTAAAGAACCTGTCGCAAGAGAAGCTGAATTACGTAGCTAGA

ATGCAAGATTTCGCGAATTGCCTGAAGGAATTGGACATAAGTTCATTCT

TCGACATGGAAAACGTGGACATAGACGCTTATTTATTTTCGAGCTGGTG

CAGGTTCCCCTTCTACGACATCGATTTCGGTCTGGGGAAGCCAATATGG

GTCTGCATGTTTCAGCCTCACTTTAAGAATTGTATAATTTTAATGGATT

ATCCCTTTGGTGACGATTACGGCATCGAAGCCCTAATTACGTTGGAACA

AGAGAAGATGCCCGCCTTCGAAAACAACGAGCTGCTGCTAAGCTTCGCC

AGCAACTAA

SEQ ID NO: 13
CrMAT Protein sequence

MDSITMVETETLSKTLIKPSSPTPQSLSHYNLSYNDQNIYPEYIFAGFF

YSNPDGHEISTIREQLQNSLSKTLVSYYPFAGKVVKNDYIHCNDDGIEF

VDVRIHCRMNDILKPELRSYASELIRPNRSTVGSEDSTALVQLSHFDCG

GVAVAFGISHKVADAATILSFIKDWAASTCDLSSSHDVSTPVLVSDSIF

PRQDNIICGQFPASPNCVRKRFLFSPEAIERLKSKAIEFGIEKPTRVEV

LTAFLCRCATVAGKSAAKNNNCGQSLPFAVIQAVNLRPLLELPKNSVGN

LISIYFSTIKENDTVNIEQEFTKLVIGELRKAKDKLKNLSQEKLNYVAR

MQDFANCLKELDISSFFDMENVDIDAYLFSSWCRFPFYDIDFGLGKPIW

VCMFQPHFKNCIILMDYPFGDDYGIEALITLEQEKMPAFENNELLLSFA

SN

SEQ ID NO: 14
LiAAT-4 DNA sequence codon optimized for its expression in *S. cerevisiae*

ATGGCCATGATAATCACGAAGCAAATATTAAGACCTAGTTCCCCGACGC

CCCAAGCCTTTAAGAATCACAAGCTGTCCTACTTAGACCAAATACAGGC

GCCTATTTACATACCTTTGTTGTTCTTCTATAAGAACGAGGAGTCAAAA

TACCCAGACCAGATCTCGCAAAGATTTAAGCAGAGTTTGTCCGAAATTT

TGACAATATTCTACCCTTTGGCTGGTACGATGAGGCATAACTCGTTCGT

GGACTGCAATGACAGGGGTGTCGAATTTGTAGAGGTCAGGGTCCATGCG

AGACTAGCCCAGTTCATTCAAGATCCTAAGATGGAAGAGCTTAAGCAAT

TGATACCTGTGGATTGTATATCTCACACTGACGATGATTTCTTATTGCT

AGTCAAGATTAGCTATTTTGACTGCGGTGAGGTCGTCGTTGGAGTCTGC

ATGTCGCACAAAATTGGTGACGGAATTAGTCTGGCAGCGTTTATGAACG

CTTGGGCAGCAACGTGTAGGGGAGAATCGTCTAGTGAGATCATTCACCC

ATCTTTTGATCTTGCTTTACACTTTCCGCCTAAAGACCACTTGTCTTCA

GCATCCTCATTCCGTGTGCCATAGCCCAGGAGAACATCATGACCAAGA

GGCTAGTATTTGATAGAGAAAGTTGGAGAAGCTGCGTAAGAGAATCGC

TGCCAGTTCTGATGGGTGAGAGACCCTAGCAGAGTTGAAGCTGTATCT

GTCTTTATTTGGAAAAGCTTAATTGAAGCCCACAAGGCCGAGTCACACA

TGACTGAGACACCAGCCGTTTCTATTGCTAGCCACGCCGTGAACTTAAG

GCCTAGAACAGTCCCACAAATGGACCAAACTTTCGGTAACTGCTACGCT

CCCGCTTCGGCCGTTGTCTCCTGGGATGAAGACTACGTACATCACAGTC

GTTTGAGGGCGGCCCTTAGAGAAATCGACGACGACTACATTAATAAGGT

CTTGAAAGCCGACAATAATTATTTAACGCAGGATCAAATTGGTGACTTG

TTTAAACCAGAAAACTCAGTTCTAAGTTCGTGGTGGCGTTTCCCAGTTT

-continued

```
ACAAGGTAGACTTTGGATGGGGTAAGCCAGTTTGGGTTTCTACGACGAC
CATCCAATACATGAACTTGATTATATTTACTTCGACGCCCTCAGAAGAC
GGCATAGAGGCGTGGGTAACTACTACTCACAATTTCTTCCAAGTTCTGC
AGGCAAACTATAATAAACTTGACACGTAA
```

SEQ ID NO: 15
LiAAT-4 Protein sequence

```
MAMIITKQILRPSSPTPQAFKNHKLSYLDQIQAPIYIPLLFFYKNEESK
YPDQISQRFKQSLSEILTIFYPLAGTMRHNSFVDCNDRGVEFVEVRVHA
RLAQFIQDPKMEELKQLIPVDCISHTDDDFLLLVKISYFDCGEVVVGVC
MSHKIGDGISLAAFMNAWAATCRGESSSEIIHPSEDLALHFPPKDHLSS
ASSFRVAIAQENIMTKRLVFDREKLEKLRKRIAASSDGVRDPSRVEAVS
VFIWKSLIEAHKAESHMTETPAVSIASHAVNLRPRTVPQMDQTFGNCYA
PASAVVSWDEDYVHHSRLRAALREIDDDYINKVLKADNNYLTQDQIGDL
FKPENSVLSSWWRFPVYKVDFGWGKPVWVSTTTIQYMNLIIFTSTPSED
GIEAWVTTTHNFFQVLQANYNKLDT
```

SEQ ID NO: 16
FgaAT DNA sequence codon optimized for its expression in *S. cerevisiae*

```
ATGAAGAAGCAGGTCACTTTTAAACCTTTCAGATTGTCACCAGTCGATC
ATAGTTTACCTAAGGTTTACATCTTCAAGTCTCTATATTTCAGAGGGGT
AGATGACACTGGTTCTCTTAGTAGACTACAGGATGGCATTGATCGTTTG
ATATCTTGTCTGCCTTTCCTGTCAGGCGAGGTGGTTCCATGTGCAGACA
TACCAGATAAGGTCGGTGTACTTCAAGTTCAGATGCCTTGCCCTTCCTT
GCAAGAAATTCCAATGCTGCTAGTCAAAAGTTATCCAAACCATACATGG
CCAGCAGCTTCTACCTCGGAAAGATGGAGAAACACCGCTTTGCTAGATC
AGTCGTATAGGCCATTGCCGGATTTTATACCCCCATCAAAGCCTAGACC
TGTTTTGAGATTTCAGGCGAACTTCCTGGCTGATGGTTTAATGCTATGT
ATGGGATATAATCATTCTGTATTCGACGAACAGGTGCGGGAACATTC
TGGAAATGTTGGCTGATTGTTGTAGAGCTAATCCAAACTCCATCTTAGC
ACTGCCAACAAACGGTGACATAGAGAGCGAGTTGAGAGGTTTACTGTCC
AGTCCAGGTGTAGCAGTTGCAAATGCCTCTCAGGAAGCCTACGCAATTA
ATTGTGCACACACGGAAGTAGAACCCGAACCCAGTTCAGCTATGCTTTA
CTGTTGGCCTTTCTTGCTGAGTTCTGAGAAGATTGAATGTTTACAGGAA
GCATGTAATAGTTTACTACCACATATCGTTCGTTTGTACTCTGGTACGC
AGAGTTCGCTTATAAACCAAGATACGAACTGGCCACATATTCTTTCATC
AAACGACGTGCTAACCGCTCTTTTAGCTGTTTCAATTGAAAAGGCTAGG
GAAGCAACAGGTGCCCTTGGTCATATGAGCAGATCATTGGCTATGGCTG
TTAACCTACGTGAGCGTTTAAAGCCTATGCCAAGACACTATTTGGGTAA
CCTAGTTACCACTGTGTGGGTATCACATCACCGTCCTGCCGTTAAGGAC
CTTGAAACAATGGTTTTACCAGTGCCAGCATGCAATAGGCACGAAATAG
ACAGAGACGACTTGTTGTGGATAACCCACGTGGCATTCCGTATTAGATT
AGGGCTGAACGCAATAAACGAAGAACATATTAGAGGTCTGATCCACTAC
TTGCATTCCCAAGACGATTGGGAACAGATTGGAATACATTTCACCGATC
CAATTTTCATTTCTTCCTGGCGTCACCTTAAGGTCTATGAACTAGACTT
CGGACCTACTATCGGTCATGCTGAACACTTTGAGATGGATGTCGGCACC
ACCGATGGTGTGTGTTGTTATGCCTGCTAACACCAGAGCCGTCGGCA
AGACTAAGAAGGCTCCTTGGGACATTAGAATCGTGTTAAACCCCGAAGT
GTTACAGGCACTAATAGCTAGTGCCATCTTTGGTTGGGCTATGGTCAAG
GACGCTTCGACATAA
```

SEQ ID NO: 17
FgaAT Protein sequence

```
MKKQVTFKPFRLSPVDHSLPKVYIFKSLYFRGVDDIGSLSRLQDGIDRL
ISCLPFLSGEVVPCADIPDKVGVLQVQMPCPSLQEIPMLLVKSYPNHTW
PAASTSERWRNTALLDQSYRPLPDFIPPSKPRPVLRFQANFLADGLMLC
MGYNHSVFDGTGAGNILEMLADCCRANPNSILALPTNGDIESELRGLLS
SPGVAVANASQEAYAINCAHTEVEPEPSSAMLYCWPFLLSSEKIECLQE
ACNSLLPHIVRLYSGTQSSLINQDTNWPHILSSNDVLTALLAVSIEKAR
EATGALGHMSRSLAMAVNLRERLKPMPRHYLGNLVTTVWVSHHRPAVKD
LETMVLPVPACNRHEIDRDDLLWITHVAFRIRLGLNAINEEHIRGLIHY
LHSQDDWEQIGIHFTDPIFISSWRHLKVYELDFGPTIGHAEHFEMDVGT
TDGVCVVMPANTRAVGKTKKAPWDIRIVLNPEVLQALIASAIFGWAMVK
DAST
```

SEQ ID NO: 18
GAO81666.1 DNA sequence codon optimized for its expression in *S. cerevisiae*

```
ATGGAAGAACATACCAGATCCTTTGAGCCATTTGACCTGGCCTGCTTAG
ATCATACTGTGGGCCGGTTTTCATGAATTTCTTCTTAAGTTTCAAGCC
TGCCAAGATCGAAGAGAGTCTTATCTCAATTGAAGAAGGTGTAACTAGG
TTAGTCAACAGACTGCCATTCCTGGCCGGTGACGTTGTTAATTCTGAAA
ACGTAGACGGTCGTGTTAATGTAATGAGGATTCAGCCAAGCTCGACATT
GATTAGAGAGATTCCCATGCTACACACAAAGCACCATCCTCATCATATT
TTGCCAATACACCTAGACAGATTAACCCAGGGTCCGACCAGGATCAAA
GGTTTGCTCCCTTGGACGATTCGTACGTACCACCAGTGTCTTTATTACC
TCTTGCTCCGGGCCCAAGGCCCGTAGTAAGATTCCAAACTAATGTTGTA
ATTGACGGGATTGTGCTTGCACTTGGGTTCCACCACTCAGTATTTGATG
CTACCGGAGTGGGTTTGTTGATCGAAATGTTGGCCACATGTTGTTCAAG
CGATTGTCCTGCCCTATCATCCCATATTGAACTGGAAGAAGAAATAAGG
CTAAGGCGTTCTGTGGACAAGATAGGTAACGGCGCTACTGATTTAGCAT
CCCAAAGAGATGAAGTTCAGGACCCAAATGGCAGTATCACTGAGTCCCC
AGCTCATGTGCCTATGGGTGACAGTAGCTGGGTACCCCCTAAACTATCT
```

```
GTTTACTCCTTTAATTTATCGGCTGCCGGTTTGGCTCATTTGAAGACAG
CCTGTAACAAGTTATTGCCCGCTATCCATGCGAGTCAAAATGGTTCACC
ACAAAGTGCGGAATCAGAAGGTGAGAAATTACAGCAAGAATTCGTTTCG
ACGAATGATGTTCTAACGGCTTTGTTGGCTACTTCCATTCACCAAGCGA
GGTCTAGAGTTACTGAAACGGAATTAGTTCCGACAAAAGCGAAACTTGC
GATGGCCGTTAATTTGAGGGAAAGGGCCAGTTCGTTACCCAAGACTTAT
TTGGGGAACTCGCTAACAGTTACAGAAGCTTTTGTGTATTCTTTAGCTG
CTACCGACGGTTTCGATGGTGTCCCCGAGAGACATTATCATCCTGACTT
GCGTAACGCCTTGCTATTAGAAATTGCTAGAGTTGCATTGCAATTGAGA
AAAGGGCTGGCAGCGATAGATGACGCGTATTTTAGGCAATTTGTGTCTA
GATTGAGGGCTAATCTAGACTGGTCACAGTTAGGTGCAAACCTGCCTGA
CACTATGGTGTCAAGCTGGAGACATTTGAAAGTATATCGTTTAGACTTC
GGTGCTAGATTGGGGAGAGTTGTAGAGTTCCATCCACAAACCGCTTTGG
TTGACGGTATTTGTATCATCCAACCTGAAAGGATAGCCCATGAGGATGA
TTCAGCTGATATGGCTCCAGAATCTGGGTGGGAAGTTTGTGTAACATTA
CAAAGCGATGCCATGGAGTGCTTCTTAAGAGGTGGGTTGTTCACAAGTC
TTTCTCAAGGTGCAATTAGAAGAGTTTAA
```

SEQ ID NO: 19
GAO81666.1 Protein sequence

```
MEEHTRSFEPFDLACLDHTVGPVFMNFFLSFKPAKIEESLISIEEGVTR
LVNRLPFLAGDVVNSENVDGRVNVMRIQPSSTLIREIPMLHTKHHPHHI
LPNTPRQINPGSDQDQRFAPLDDSYVPPVSLLPLAPGPRPVVRFQTNVV
IDGIVLALGFHHSVEDATGVGLLIEMLATCCSSDCPALSSHIELEEEIR
LRRSVDKIGNGATDLASQRDEVQDPNGSITESPAHVPMGDSSWVPPKLS
VYSFNLSAAGLAHLKTACNKLLPAIHASQNGSPQSAESEGEKLQQEFVS
TNDVLTALLATSIHQARSRVTETELVPTKAKLAMAVNLRERASSLPKTY
LGNSLTVTEAFVYSLAATDGFDGVPERHYHPDLRNALLLEIARVALQLR
KGLAAIDDAYFRQFVSRLRANLDWSQLGANLPDTMVSSWRHLKVYRLDF
GARLGRVVEFHPQTALVDGICIIQPERIAHEDDSADMAPESGWEVCVTL
QSDAMECFLRGGLFTSLSQGAIRRV
```

SEQ ID NO: 20
CfACT1-6 DNA sequence codon optimized for its expression in *S. cerevisiae*

```
ATGAAGGTAGAACGTTTCTCAAGAAAGTTGATAAAACCCCACACGCCTA
CTCCCGAGAACTTAAAGAAATATAAATTGTCTCTATTGGACAAATGCCT
TGGACACGACAACTTCGCGATCGTGTTGTTTTACGAATCTAAACCAAGA
AATAAGAGTGAGCTTGAGGAATCGTTAGAGAAGGTCTTGGTAGACTTTT
ATCCCTTGGCTGGGCGTCACACGATGAACGACCATATTGTCGACTGCTC
GGATGTCGGCGCTGTCTTTGTAGAAGCCGAGGCTTTAGATGTAGAGTTG
ACTATGGATGAGTTAGTCAAGAACATGGAAGCTCAAACTATACACCACT
TGTTGCCAAATCAGTACTTCAGTGCAGATGCTCCGAACCCGCTGCTTTC
CATCCAAGTTACGCACTTTCCTTCCGGTGGTTTGGCTATCGGAATCGCA
GTCTCGCACGCTGTATTTGATGGTTTCTCTTTGGGCGTGTTCGTAGCAG
CATGGTCAAAGGCGACCATGAACCCGGATAGGAAAATCAAAATAACACC
GTCATTCGACTTACCATCACTTCTGCCCTACAAAGACGACAACTTTGGT
TTGACTGCTGCTGAAATTGTCAGCCAGAGCGAGGACATCGTAGTTAAGA
GATTTATCTTCGGCAAGGAAGCCATCACGAGGTTGAGAAGTAAGCTTAG
TCCAAATAGGAACGGGAAGAAAATATCCAGGGTTAGGGTCGTTTGTGCA
GTCATTGTAAAGGCCTTGATGGGATTGGAGCGTGCCAAACACGGTAAGA
CGCGTGATTTCTTAATTACTCAATCAATTAACATGAGGGAGAGAACTAA
GGCGCCGCTGCAGAAACACGCCTGCGGCAACTTAGCAGTCTTGAGTTGC
ACGAGAAGAGTAGAGGCCGAGGAGATGATGGAGTTACAGAACCTAGTTA
ATTTGATCGGCGACAGTACCGAAAAGGACATCGCCGACTTTGCAGAATT
ATTATCACCAGATCAAGTGGGCAGAGACATTATAATCAAGATGATGAAG
TCATTCATGCAGTTCTTGGACAATGACATTTACAGCGTGTGCTTTACCG
ATTGGTCAAAGTTTGAATTTTACGAAGCGGACTTCGGCTTCGGGAAGCC
GGTTTGGATGGCAGCAGGCCCACAGAGACCCATTATCTCTACTGCAATA
TTGATGTCAGACAGGGAAGGCGACGGTATCGAGGCTTGGTTACATTTGA
ATAAGAACGACATGTTGATTTTCGAACAAGACGAGGAAATCAAGTTATT
CACTACATAA
```

SEQ ID NO: 21
CfACT1-6 Protein sequence

```
MKVERFSRKLIKPHTPTPENLKKYKLSLLDKCLGHDNFAIVLFYESKPR
NKSELEESLEKVLVDFYPLAGRHTMNDHIVDCSDVGAVEVEAEALDVEL
TMDELVKNMEAQTIHHLLPNQYFSADAPNPLLSIQVTHFPSGGLAIGIA
VSHAVEDGFSLGVFVAAWSKATMNPDRKIKITPSEDLPSLLPYKDDNFG
LTAAEIVSQSEDIVVKRFIFGKEAITRLRSKLSPNRNGKKISRVRVVCA
VIVKALMGLERAKHGKTRDFLITQSINMRERTKAPLQKHACGNLAVLSC
TRRVEAEEMMELQNLVNLIGDSTEKDIADFAELLSPDQVGRDIIIKMMK
SFMQFLDNDIYSVCFTDWSKFEFYEADFGFGKPVWMAAGPQRPIISTAI
LMSDREGDGIEAWLHLNKNDMLIFEQDEEIKLFTT
```

SEQ ID NO: 22
CfACT1-8 DNA sequence codon optimized for its expression in *S. cerevisiae*

```
ATGAAAGTCGAAAGGATTTCACGTAAATTCATCAAGCCATATACACCTA
CACCACAGAACCTTAAGAAGTACAAGCTATCCTTGCTGGATAAATGCAT
GGGACACATGGACTTCGCTGTAGTATTGTTTTACGAATCAAAGCCAAGA
AACAAGAATGAGCTGGAAGAATCACTAGAGAAAGTGTTAGTCGATTTCT
ATCCATTGGCAGGCAGGTATACCATGAACGACCACATTGTCGATTGCAG
CGATGAGGGCGCCGTTTTCGTTGAGGCAGAGGCCCCTAATGTTGAGCTT
```

-continued

ACAGTGGACCAGTTGGTTAAGAACATGGAAGCCCAGACAATCCACGACT

TCTTACCAGACCAATATTTTCCTGCTGACGCACCAAATCCGTTGCTAAG

TATTCAAGTAACGCACTTCCCTTGTGGTGGTTTAGCTATCGGGATTGTT

GTTAGTCACGCGGTCTTTGATGGATTCTCATTGGGCGTATTCTTAGCCG

CCTGGAGCAAAGCTACCATGAACCCTGAGAGGAAGATCGAAATCACCCC

TTCCTTCGATTTGCCTAGTCTTCTGCCCTACAAGGATGAATCTTTCGGT

TTAAATTTTAGCGAAATTGTCAAAGCTGAGAATATCGTAGTTAAACGTT

TGAATTTCGGGAAAGAGGCTATTACGCGTTTGAGGTCCAAGCTGTCTCC

TAACCAGAATGGTAAAACCATTTCCAGAGTGAGGGTAGTCTGCGCGGTG

ATAGTTAAGGCGTTGATGGGACTGGAGAGAGCAAAGACTAGAGACTTTA

TGATATGTCAGGGGATCAACATGAGAGAGAGGACGAAGGCGCCCCTGCA

GAAGCATGCGTGTGGCAACCTAGCAGTTTCGTCTTACACTAGAAGGGTA

GCGGCAGCGGAAGCAGAAGAACTGCAGTCCTTAGTGAATTTGATCGGGG

ACTCTATCGAAAAGTCAATCGCAGACTACGCTGATATACTTTCGAGTGA

TCAAGATGGGAGACACATCATTTCCACTATGATGAAGAGCTTTATGCAG

TTTGCTGCACCTGATATAAAAGCCATTTCATTTACCGACTGGTCAAAGT

TCGGCTTTTACCAAGTAGATTTTGGTTTTGGTAAACCAGTTTGGACCGG

CGTCCGTCCAGAACGTCCAATCTTCTCAGCCGCGATATTGATGAGTAAC

AGGGAAGGCGATGGCATCGAGGCTTGGCTTCATTTGGACAAGAACGATA

TGCTAATATTTGAGCAAGACGAAGAAATTAAGTTGTTGATAACGTAA

SEQ ID NO: 23
CfACT1-8 Protein sequence

MKVERISRKFIKPYTPTPQNLKKYKLSLLDKCMGHMDFAVVLFYESKPR

NKNELEESLEKVLVDFYPLAGRYTMNDHIVDCSDEGAVFVEAEAPNVEL

TVDQLVKNMEAQTIHDFLPDQYFPADAPNPLLSIQVTHFPCGGLAIGIV

VSHAVEDGFSLGVFLAAWSKATMNPERKIEITPSFDLPSLLPYKDESFG

LNFSEIVKAENIVVKRLNFGKEAITRLRSKLSPNQNGKTISRVRVVCAV

IVKALMGLERAKTRDFMICQGINMRERTKAPLQKHACGNLAVSSYTRRV

AAAEAEELQSLVNLIGDSIEKSIADYADILSSDQDGRHIISTMMKSFMQ

FAAPDIKAISFTDWSKFGFYQVDFGFGKPVWTGVRPERPIFSAAILMSN

REGDGIEAWLHLDKNDMLIFEQDEEIKLLITT

Optionally the C-terminal "T" may be missing
SEQ ID NO: 24
OAH94415.1 DNA sequence codon optimized for its expression in *S. cerevisiae*

ATGGATACCAAGAGGGTCGGTTATACAGTCGTTGATTTGAGTCAGTGGG

GCAGAAAAGAACACTTCGAAGCATTCCAGAGCTTCGCCCAGTGCACCTT

TTCCCAGACTGTTCAATTAGACATAACTTCCCTGCTGAAGACTGTCAAG

CAGAACGGATATAAATTCTACCCGACCTTTATCTACATAATAAGCCGTT

TAGTGAACAAGCATGCCGAATTCCGTATGGCCATGAAGGATGGTGAACT

-continued

GGTAATTTGGGACTCCGTAAACCCTGGTTACACAATCTTTCACGAACAG

ACCGAAACATTTTCATCTCTGTGGAGCTATTACCACAAGGACATCAATC

AGTTTCTTAAAACGTATTCTGAAGACATCGCTCAGTACGGGACGATCT

GGCGTACTTCCCCAAGGAGTTTATTGAAAATATGTTCTTCGTGTCAGCG

AACCCATGGGTGAGCTTCACAAGTTTCAACTTAAACGTGGCCAATATTA

ATAACTTCTTCGCACCGGTCTTTACAATCGGTAAATACTACACGCAGGG

CGACAAGGTGTTGATGCCGTTAGCTATTCAGGTCCATCATGCAGTCTGC

GACGGGTTTCATGTCGGCAGGTTATTGAACGAAATTCAGCAGTACTGCG

ATGAGGGATGCAAGTAA

SEQ ID NO: 25
OAH94415.1 Protein sequence

MDTKRVGYTVVDLSQWGRKEHFEAFQSFAQCTFSQTVQLDITSLLKTVK

QNGYKFYPTFIYIISRLVNKHAEFRMAMKDGELVIWDSVNPGYTIFHEQ

TETFSSLWSYYHKDINQFLKTYSEDIAQYGDDLAYFPKEFIENMFFVSA

NPWVSFTSFNLNVANINNFFAPVFTIGKYYTQGDKVLMPLAIQVHHAVC

DGFHVGRLLNEIQQYCDEGCK

SEQ ID NO: 116
DfACT13 native Nucleotide sequence

ATGGCCTGTGGAGGCGGCGTGAGGAATATTGAGGTGAAGGCGCAGGAGC

CCGTTTTGGTGCAGCCTTTATCTACAGCACAAAGCTCTGCCTATAATCT

TCTTACAAAACTGGACCAGACGCTCGCACAATTGGTGGTGCAGATTGTC

TTTGTCTTCGATGTGAAAAACCCCGTAACCCGCCGACCCCACGATGGCG

CCGATCCTGCCAAGCTTCTGAAGGAGGCTCTGAGGAAGGTCCTTGTGCC

CTTCTACCCGCTCGCTGGGCGTCTTTGCCTCTCGCCCGATGACGGCAGT

CTGTTCATTGACTGCAATGCTCAGGGGGTTTCCTTTGTTGAGGCCAATG

CCGACGCGGATATCTCCGAACTCGGCGACTTCTCGCAGCCCGATTTCGC

GACTCTGGGCTCCCTTGTCTTCCCCTTACCTCCTATAGCTTCGGATGAT

GGTCCTCTTCTATCTGCGCAGGTGACCAGATTCAAGTGTGGAGGATTTG

TGCTGGGCTTCGTATTCCATCATTGTTTATTTGATGGATTCGCACTTTC

GGAATTCCTAAATGCGTGGGCGGAGACTGCATGCGGCGTGCCTCTTTCT

ACACCTCCTGTCCTCGACAGAACTTTTCCGAGGGCGCGTTCTCCCTTGC

AAATCAAGTATCCCCACACCGAGTTCCTGGAAGTCGAAGATGTCTCTTT

GACTCAAAATATCTCTAACGATGCCATCAACCGGTCTTTCTGCTTTACT

TCGGCAAGTCTAGAGATACTCAAGAAGAAAGCCTTGGAGGATGGGGTGC

TATCAAAATGCACTACTTTTGAAGCTTTATCTGGGCTGATATGGAGGGC

CCGAACTAGAGCCCTGTGGAGCGATTACCCGGAGCACAAACTAAAGGTG

CTCATTGTCGTCGACCCGAGAGCACGTTTTGAGCCTCGTGTGGTGCCAA

AAGGGTATGTGGGCAATGCGGTGCTTTTTACATGTGCTTTCGCAAGCGC

AAGGGAGCTGGAAGAAAATCCCTTGTCACATGCAGTGAAGCATGTGCAA

CATGCCATCGGGCGTATGACGGAGGAGTACATGTTGTCGCAAATCGACT

-continued

ACATGGAGCATCAGAAGGTATGGTGCCCACCGCTAGGAGCTAGTACATC

TTTCATGACCAAATGGTCTAGGTTGGCCTTCAATATTCTAGACTTTGGG

TGGGGCAGGCCGAAGTATGTGGGGCCGGCCACGTCGCTGTCGATGGAGA

CGACTACTTTTGTATCTTATGGAAAGGGCATGAGTGTGGTGTTGGCTCT

TCCTCCAGAAGCAATGCGCAAATTTGAAAAAATCGTACATCCCTACCTC

AATCCATGA

SEQ ID NO: 117
DfACT13 Nucleotide sequence codon optimized for its expression in *S. cerevisiae*.

ATGGCATGTGGCGGTGGGGTCAGGAATATCGAAGTGAAGGCTCAAGAGC

CAGTCTTGGTGCAACCGTTAAGCACTGCTCAATCGTCAGCCTACAATTT

GTTAACAAAGTTAGACCAGACTTTGGCGCAATTGGTTGTCCAAATAGTG

TTTGTTTTCGATGTGAAGAACCCTGTGACAAGAAGGCCTCATGATGGAG

CCGATCCAGCTAAGTTATTGAAAGAGGCCTTAAGGAAAGTACTAGTACC

ATTCTATCCCCTTGCCGGAAGACTATGTCTTTCCCCAGACGATGGTAGT

CTATTCATAGACTGCAACGCTCAAGGTGTTTCATTTGTCGAAGCAAACG

CTGATGCCGACATCAGTGAGTTAGGTGATTTCTCCCAACCGGATTTTGC

GACCTTAGGTTCTTTAGTCTTCCCTCTTCCACCAATTGCGTCTGACGAT

GGACCATTGTTAAGTGCTCAAGTCACAAGATTCAAATGTGGTGGCTTCG

TTCTAGGTTTCGTCTTCCATCACTGTCTATTTGATGGTTTTGCCTTATC

TGAATTTCTTAATGCATGGGCTGAGACAGCGTGTGGAGTCCCGTTATCA

ACCCCACCTGTTTTAGATAGAACATTTCCTCGTGCTAGATCTCCCCTGC

AAATAAAGTACCCACATACAGAGTTCCTAGAGGTAGAAGATGTTTCATT

AACTCAGAACATCTCTAACGATGCTATCAACAGATCCTTCTGTTTTACA

TCAGCCTCTTTGGAAATTTTGAAGAAGAAGGCGCTAGAAGACGGGGTGT

TAAGCAAATGTACGACCTTCGAAGCTCTATCTGGCTTAATATGGAGAGC

ACGTACCAGAGCCTTATGGAGCGACTACCCCGAGCACAAGTTAAAGGTC

CTGATTGTCGTGGACCCTCGTGCCAGATTTGAACCGAGAGTGGTGCCAA

AAGGCTACGTAGGGAATGCAGTCTTGTTTACTTGTGCATTTGCTTCAGC

CAGAGAACTAGAAGAAAATCCATTATCTCATGCTGTTAAACACGTACAG

CACGCGATCGGCCGTATGACTGAGGAATATATGCTATCACAAATTGATT

ACATGGAGCACCAGAAGGTTTGGTGTCCCCACTAGGTGCGTCGACTTC

TTTTATGACTAAGTGGTCAAGGCTTGCCTTTAACATCTTAGATTTTGGT

TGGGGTAGACCTAAGTATGTTGGTCCGGCTACTTCATTGTCTATGGAAA

CAACTACATTCGTCTCCTATGGAAAGGGTATGAGCGTGGTGTTAGCCCT

ACCCCCAGAGGCAATGAGAAAGTTCGAAAAGATTGTACACCCTTATTTG

AACCCTTAA

SEQ ID NO: 118
DfACT13 Protein sequence

MACGGGVRNIEVKAQEPVLVQPLSTAQSSAYNLLTKLDQTLAQLVVQIV

FVFDVKNPVTRRPHDGADPAKLLKEALRKVLVPFYPLAGRLCLSPDDGS

LFIDCNAQGVSFVEANADADISELGDFSQPDFATLGSLVFPLPPIASDD

GPLLSAQVTRFKCGGFVLGFVFHHCLFDGFALSEFLNAWAETACGVPLS

TPPVLDRTFPRARSPLQIKYPHTEFLEVEDVSLTQNISNDAINRSFCFT

SASLEILKKKALEDGVLSKCTTFEALSGLIWRARTRALWSDYPEHKLKV

LIVVDPRARFEPRVVPKGYVGNAVLFTCAFASARELEENPLSHAVKHVQ

HAIGRMTEEYMLSQIDYMEHQKVWCPPLGASTSFMTKWSRLAFNILDFG

WGRPKYVGPATSLSMETTTFVSYGKGMSVVLALPPEAMRKFEKIVHPYL

NP

SEQ ID NO: 119
PYI04555.1 native Nucleotide sequence

ATGGGTGCCAGCGTCTCTTTCCAGCCCTTTGTGCCCACTCCCCTGGACC

ATGCTATGCCCCCAATTTACGTGTCTCAATTTCTATGCTTTCCTACCAC

AACTCCGCAATCCGCTATTCAAAGTCTCCAAGTGGGAATCGAGAGATTA

TTCGAACGCCTGCCATTCCTGGCGGGAGAGATTCTCATCAATGAACACA

CCGGAGCCATCAAAGTCCAGGCTCCCAGTGCTTTGATCGGGAAATTCC

CTACATGGCCCTCCGAGCCCATCCTGATCTTTACCTTCCAGCTAAGCAA

TGTGCAACCACACCAATCGAGAGACAGTTGAAGACCAACAGCCTTGATG

AATCCTACCATCCACTCCCGGCGGCACTTCCACTCTCCCAACCCCAGCC

CGTCATCCGATTCCAAGCAAACACCCTCGCAGACGGCATTCTCTTTGCA

GTCAGCTATCATCATTGCATATTCGATGGCACTGGATGCGGACAGATTC

TGGAAATGTTGGCTCAGTGCTGTTCGGCCTCCGACGATAAGATCTCCCT

GCCGACTGATTGCCACACCGATGTGCTCCTCCGCGAATACATCTCCAAT

CTAAGCCCTACTACCAACATCCCCCACGATTACACGCAAGCGTATAGCA

CTACGGTGCAACCGGACCCCGATGCCTCAGACCCAGACACGTCCCCCGC

CATACCCTCCTCACTCTACACAGAAGCATTCACCTTTCCCTCCCAACAA

ATCACCACTCTCCGTGATGCATGCAACCACCTCTTGCCCAAATTACCCA

GCACCAGCAACGCACATCCCCACAAACCAACACCGAATCCCCTATCATC

AAATGACGTCCTCACCGCACTAATAGCCCTATGCATCACACGCGCCACC

AACACCACCACCCCACCCCTCCAACCCAACAATCACAGTCTCTCAATGG

CCGTCAACCTCCGAACCCGCATCCAGCCCCAAGTACCAGATCACTTTCT

GGGAAACTTCGCCACGCTACTCCCAATACACTTTACCAGTCCAGTCCAC

ACCCAACAGTCTGATCTCCTCCTCACCACAGAACCCCCCGACCCCGCCC

TCATCCACCTAACCACCCTCGCCTCCCAAATCCGGTCCAGCCTATCCAC

AGTCAACACCGATTACATCTGCGGTCTCATGACGGATCTCCGAACCCGG

CGCAATGCAGGAGAAACAGCAGTCTTCTAATTGAAGGCATTAAGATTT

CCAGTTGGAGACATCTATCCGTCTACAAGCCGGACTTTGGCCCTGGGTT

SEQ ID NO: 120
PYI04555.1 Nucleotide sequence codon optimized for its expression in *S. cerevisiae*, encoding C-terminally extended protein variant of SEQ ID NO: 143.

```
GGGGAAAATAGCGGGGTTTGAGTTCCAGGCGGGGCTTATGGATAATTTG
GTGGTGATTTTGCCTTGGAGAAATGGGGATTGGGATGTGCGTGTTACGT
TGTTGGAGAGGGATATGCGCGGGTTTAGGGAGGATCGGTTGGTTAGGTG
GGCGTTGGGGTCTGGGTAG
```

SEQ ID NO: 120
PYI04555.1 Nucleotide sequence codon optimized for its expression in *S. cerevisiae*, encoding C-terminally extended protein variant of SEQ ID NO: 143.

```
ATGGGTGCGTCAGTTAGTTTTCAACCTTTCGTTCCTACCCCTTGGATC
ACGCCATGCCACCGATATACGTGTCACAGTTCTTGTGTTTCCCTACTAC
GACGCCGCAGTCAGCAATACAATCCCTACAGGTCGGTATTGAGCGTTTG
TTTGAAAGACTACCTTTTCTAGCCGGGGAAATTCTGATAAATGAGCACA
CAGGTGCAATAAAAGTTCAAGCTCCCTCTGCTCTGATTAGAGAAATTCC
GTACATGGCCTTAAGGGCTCATCCGGATTTGTATCTGCCTGCTAAGCAA
TGTGCAACTACTCCAATAGAGAGGCAGTTGAAAACTAACAGCCTTGATG
AGTCTTATCATCCATTACCTGCGGCACTACCATTGTCTCAACCACAACC
AGTCATCAGATTCCAAGCTAATACACTTGCTGACGGAATACTTTTCGCT
GTCAGTTACCACCATTGTATATTTGATGGAACGGGCTGCGGACAGATCC
TTGAAATGTTAGCCCAGTGTTGTTCGGCCTCAGACGATAAGATCAGCTT
GCCTACGGACTGTCATACAGATGTATTGTTGAGAGAATATATTTCGAAT
CTATCTCCAACCACGAATATCCCGCATGACTACACTCAAGCTTATTCTA
CTACAGTTCAACCAGATCCTGACGCATCCGATCCTGATACTAGCCCAGC
CATTCCGAGTTCGCTGTACACTGAAGCATTTACGTTTCCTTCACAACAG
ATTACCACACTAAGAGATGCGTGCAACCATTTATTGCCTAAATTACCAT
CTACTTCAAACGCACATCCCCACAAACCAACACCAAACCCGTTATCCTC
AAATGACGTTTTGACGGCACTGATCGCATTGTGCATCACCAGAGCTACT
AATACGACGACACCCCCATTACAACCAAACAACCATTCTCTTAGCATGG
CCGTCAATCTAAGGACTCGTATTCAACCCCAAGTCCCGGACCACTTTCT
TGGTAATTTTGCCACCTTGCTACCTATTCACTTCACAAGTCCAGTCCAT
ACGCAGCAATCAGATTTATTATTGACTACTGAGCCGCCAGACCCAGCAT
TGATCCACCTTACAACCCTTGCATCGCAAATTAGGTCTAGTTTATCGAC
CGTTAACACCGATTACATATGTGGCTTGATGACAGATCTGAGGACTAGG
AGAAACGCCGGTGAGAATTCCTCTTTGTTAATAGAAGGTATTAAGATTT
CTTCATGGAGACATCTTAGCGTTTACAAGCCAGATTTCGGACCTGGATT
AGGGAAGATTGCAGGATTTGAGTTTCAAGCTGGTTTAATGGACAACCTT
GTTGTGATATTGCCTTGGAGAAACGGTGATTGGGACGTGCGTGTAACTC
TTCTGGAGAGAGATATGAGGGGTTTTAGGGAAGACAGATTAGTCAGATG
GGCATTAGGTAGCGGAACAGGCCCCTTTTCCTTTGTCGATATCATGTAA
```

SEQ ID NO: 121
PYI04555.1 Protein sequence C-terminally extended protein variant of SEQ ID NO: 143.

```
MGASVSFQPFVPTPLDHAMPPIYVSQFLCFPTTTPQSAIQSLQVGIERL
FERLPFLAGEILINEHTGAIKVQAPSALIREIPYMALRAHPDLYLPAKQ
CATTPIERQLKTNSLDESYHPLPAALPLSQPQPVIRFQANTLADGILFA
VSYHHCIFDGTGCGQILEMLAQCCSASDDKISLPTDCHTDVLLREYISN
LSPTTNIPHDYTQAYSTTVQPDPDASDPDTSPAIPSSLYTEAFTFPSQQ
ITTLRDACNHLLPKLPSTSNAHPHKPTPNPLSSNDVLTALIALCITRAT
NTTTPPLQPNNHSLSMAVNLRTRIQPQVPDHFLGNFATLLPIHFTSPVH
TQQSDLLLTTEPPDPALIHLTTLASQIRSSLSTVNTDYICGLMTDLRTR
RNAGENSSLLIEGIKISSWRHLSVYKPDFGPGLGKIAGFEFQAGLMDNL
VVILPWRNGDWDVRVTLLERDMRGFREDRLVRWALGSGTGPFSFVDIM
```

SEQ ID NO: 122
ERR364415-1 _contig_8456 native Nucleotide sequence codon optimized for its expression in *S. cerevisiae*, encoding C-terminally extended protein variant of SEQ ID NO: 143.

```
ATGGCCCGGGCACCACCACCTCCGCCTCCTGGTCTCAGAATGAGAGACA
CAGTGCTCAGCATCGTGAAGCCGATACGGAAGACACAGCATTTGGAGAC
GATCGACGCAACGTTCGTCGATTTGATGAGAATGGACAGCTTTATACCC
GTGATTTTCGCCTACAGGCCTGCGGACAAGTCCGAGGCCGCGTACTCGC
GTCTCGTGAATCGCATCAAGGAGTCGCTCCAGAAGGTTTTGGTCCCCTT
TTTCGGGTTCGCGGGCCGCTGGGTTCCAAGCAGTGGCGGGAGCAGGCGG
CTCCTTGTGCAACGATGAGGGCGTTCCCTTCATTGAAGCGTTTGTGGACG
AAGAGTTGGACTCGGTGGTGAAGGCTTCCGCCGCATTCCAGCCGGTTAC
GGAGCTGAATGGCTTGGGCGTCCTCGGAATGGACATGACTTCATACGAT
CAAAGGATGCCACCGGAAGGTGGGCAACCTTGCGTCGTTGCTCAAGTCA
CACGGTTCAAATGTGGGGGAGTGGTTCTGGGGGTGGCTTTCAATCACAC
TCACACTGACGGCCAGGGATTCTACACCTTCATGCGAGCATGGTCCGAC
TTCTCTCGAACCAACGGAACGGCAATCAAGGTGGACCACAACCGGGCCC
TGCCAGAACTGGCTTCCCTCTCACAGTTCTTCATCAAACAGCACGACCG
AATAGGAGGCAAAACTTCTACCGATCGAGTCAACGATCATTGTTCTAAA
GTTCCGGAACGGCTGGCTTTGAAAGCTTTCGAGGTTCGTGCGTCTAAGA
TCAAAGCCGCAAAGCTAGCAGCCGAAGATGGAGGGGTTGGGTATGTCAG
CACGGTAGATTGCATTGTGGCTCACTTATGGAAAACTCTTGCCAGATTG
CCGCCCGTCGTGTTGGATGGGAGGGAGATTACGGTCTTCTCGCCTGTGG
AGGGGAGGAACAGATTCTTGGACCCGCCAAGACCCAATATGTGTGGAAA
TTGTTTTGCAGCAATGGTGACCCCCAAAATCCCAACCCAGGAGTTGCTG
GAGATGCCTCTCGCTGCAATTGCAGGCAAGCAACGGGAGAAATTATCCA
CAACCCGAAGGGAGGAATGGTTTGGACAGCAAAGCTTTAGGGAGCTGGC
CTCCGCGATGAACACCAGCAAATCTGCTCTACTTATTGTGACCTCGTGG
TTCAACTTTCCCATGTATGAGATCGACTTTGGAGCTGGCAAACCATTTT
```

-continued

TTGCATCCACTACGAACATGATTTCTCCTATCAACGGCGTGTGTTGTGG

AGTCATTGCACCCCCAACTCCTGGGAGCTGCTCCTCCATTGCCACTCTG

TACATTTTGTGCCTTCCCGCGGTACTAGAGGCTCTTGAAAATGTTCCAG

ATTTCCTATCCTTCTTCGTTCCTCACCCAAATCACAAAGATAACTCGCA

ATAG

SEQ ID NO: 123
ERR364415-1 _contig_8456 Nucleotide sequence codon optimized for its expression in *S. cerevisiae*, encoding C-terminally extended protein variant of SEQ ID NO: 144.

ATGGCCAGGGCTCCACCCCCACCACCACCGGGCTTGCGTATGAGAGATA

CGGTCCTATCAATCGTCAAACCTATAAGAAAGACTCAACACCTAGAGAC

AATTGATGCAACATTCGTAGATTTAATGAGAATGGACTCATTTATCCCT

GTGATCTTCGCTTATAGACCTGCAGATAAGAGCGAGGCTGCGTACTCTA

GATTAGTTAATAGGATAAAAGAAAGCTTACAGAAAGTACTAGTACCATT

CTTTGGATTTGCTGGAAGGTGGGTGCCTTCTTCCGGTGGCTCAAGGCGT

CTGCTATGCAATGACGAAGGTGTCCCTTTTATTGAGGCGTTTGTAGACG

AAGAACTGGACTCTGTCGTTAAGGCTTCAGCTGCCTTCCAACCTGTAAC

TGAACTTAATGGTCTAGGTGTGTTGGGTATGGATATGACTAGTTATGAT

CAAAGAATGCCCCCTGAAGGCGGTCAACCGTGCGTCGTAGCTCAGGTAA

CGAGATTTAAATGCGGCGGTGTGGTATTGGGTGTAGCATTCAACCATAC

CCATACTGACGGGCAGGGCTTTTATACTTTTATGCGTGCATGGTCGGAT

TTCAGTAGAACGAATGGTACCGCAATTAAAGTCGATCACAACAGGGCAC

TACCCGAATTAGCATCTTTGAGTCAGTTCTTTATTAAGCAGCATGATAG

AATTGGTGGGAAAACTTCCACCGATAGAGTCAATGACCACTGTAGCAAA

GTCCCTGAAAGACTAGCACTAAAGGCTTTTGAAGTTAGGGCGTCCAAAA

TCAAGGCAGCAAAACTAGCCGCAGAAGATGGTGGTGTAGGCTACGTCTC

GACGGTGGATTGTATTGTTGCTCATCTATGGAAGACACTAGCTCGTTTG

CCACCAGTTGTGTTAGACGGTCGTGAGATCACTGTGTTTAGCCCAGTAG

AAGGCAGAAATAGGTTTCTTGATCCGCCCCGTCCGAACATGTGTGGTAA

TTGTTTCGCTGCAATGGTAACCCCTAAAATCCCAACACAAGAATTGTTA

GAGATGCCATTAGCCGCCATTGCCGGCAAGCAGAGAGAGAAACTATCTA

CCACGAGACGTGAAGAGTGGTTCGGACAGCAATCATTCAGGGAGTTGGC

TTCAGCTATGAATACTTCTAAATCAGCTTTGTTAATCGTGACATCTTGG

TTTAACTTCCCGATGTATGAAATCGATTTTGGTGCCGGTAAGCCGTTCT

TCGCTAGTACGACTAATATGATTTCTCCTATAAATGGAGTTTGTTGTGG

TGTCATAGCCCCGCCCACCCCCGGTTCCTGTTCATCCATAGCGACATTA

TACATTTTATGTTTACCAGCCGTGTTAGAAGCTCTTGAAAATGTCCCAG

ATTTCCTTTCGTTCTTCGTACCGCATCCAAACCATAAAGACAACAGCCA

AACAGGCCCCTTTTCCTTTGTCGATATCATGTAA

SEQ ID NO: 124
ERR364415-1 _contig_8456 Protein sequence C-terminally extended protein variant of SEQ ID NO: 144.

MARAPPPPPPGLRMRDTVLSIVKPIRKTQHLETIDATFVDLMRMDSFIP

VIFAYRPADKSEAAYSRLVNRIKESLQKVLVPFFGFAGRWVPSSGGSRR

LLCNDEGVPFIEAFVDEELDSVVKASAAFQPVTELNGLGVLGMDMTSYD

QRMPPEGGQPCVVAQVTRFKCGGVVLGVAFNHTHTDGQGFYTFMRAWSD

FSRTNGTAIKVDHNRALPELASLSQFFIKQHDRIGGKTSTDRVNDHCSK

VPERLALKAFEVRASKIKAAKLAAEDGGVGYVSTVDCIVAHLWKTLARL

PPVVLDGREITVFSPVEGRNRFLDPPRPNMCGNCFAAMVTPKIPTQELL

EMPLAAIAGKQREKLSTTRREEWFGQQSFRELASAMNTSKSALLIVTSW

FNFPMYEIDFGAGKPFFASTTNMISPINGVCCGVIAPPTPGSCSSIATL

YILCLPAVLEALENVPDFLSFFVPHPNHKDNSQTGPFSFVDIM

SEQ ID NO: 125
XP_001258079.1 native Nucleotide sequence

ATGACCGTGACCATCAGTTTCGAGCCATATGTGGGCTCCTCTGTCGATG

CTCTAAGCATCCCTCTCTATCTTCGATGTCAACTCGTCTTCAAACTTTC

TAAGCCACTTGCTGCGGTGCCTCTGCTTGAGTCTGGAGTTAATCGTCTT

GTACAAGCGTTACCCTTCCTCTCGGGCGAGTTCACGGCCGTGCCAGCAT

CCGACGGTGGGAAAGAAATTCTTCTCGTTCGCCCTGTGCTCAACTTCGA

GCTCAGCCGTATACTCAAGATCAAGTACCATGAAACATCCCTACGACAT

GTATGCAAACAGATGAACAGGCCAAGCAGCCAGGGTGGTGACCTTCCGC

ATGAGCCATACATGCCCTACCCACGACTTCCAGATCCTTCACGCCCTCA

ACCCATCGTCGGGTTCCAAGTCAACGTTCACACGGATGGCATCATTCTC

TCCGTTGCTACGCATCACTGTTCCTTTGACGCAACAGGGATGGGATCAA

TCGTCCAAAACCTCGCGGCTTGTTGCCGTTCTCCTCCGAGCGACGAGCC

TGACTTGACCACGTCGCCAGCCCAGGAAGCAGAAGCAAGAAAAGTCCTC

TCGCAAGTCCGCGAGACGCCTTTTGATCCAAAGATGTTCCCGGAGTACA

GACCCTTGGACAGTATGCTGTCCTATTACAAAGGCGTCCAGTCAGCGCT

CCAGGGTCGTCAAACCACTATCGTCAATCGATGTTTCACAATCGCCGCC

GACAAGATCAACGCGCTCAAAAGGCGCTGCAATCAACTGATACCGGAAA

TGGTGAAGAAGTATGGGCTTTCAACTGAGGATGCCATTGGGAGCGCCTG

GGTCTCGAGTAATGATGTTGTTGCTGCCCTCTTGTGGACATGTATCAAT

CGAGCGCGATATCCCGAAATCCGCGAGCGCAGCGTTCACCAGCTCCCAC

CAGACCTCCTACATGCGACATCTAGCCTGGGTGTGCCAGTGAACGTTCG

CTCTCGACTGTCGCCGCCCTTACCCAAATCGACTTTAGGTAACGCCGTG

TGTCTTCTCCGGGAGAAGGTCCCGCTGCAATTTTTCGCTTTGCCTAGTC

ATGCCAACATGGAGGCCACTTCTAGCGTTTGCGCAGACCATTCCGGAGA

CGACGAATGGGCCTTGTCCTTCTGTCGAGTCGCCTACGGACTCAGAGCG

AAGCTGAACGCAATTGATGACGACTATATCCGCGACTATATCTCCTACG

TGCAAAAGTCTCCGTGCCATCTGTCAGTGACACTGGATACAGAGAACCT

GTACCTCAGTAACTGGCGCGAGATCGGTGTGTATGATGCTGATTTTGGA

GGCATGCTGGGCAAGCCGCTACGGATGAGAGCTCCGGATGGATACACCG

ATGGCCTGATTTTTGTGATGGCGCAGCGGAGCGAAGATAAGTCTGCACC

GTGGGAGTTTAATATCTCGCTGGAGGCATCGACAATGAAGCGTATTGTG

CATGATCCCCTCTGGTGCAAGTATGTTGAGCTGGATGCGTTCTGGCATG

GAGAAGAATGA

SEQ ID NO: 126
XP_001258079.1 Nucleotide sequence codon optimized for its expression in *S. cerevisiae*.

ATGACCGTCACGATTTCATTCGAACCATATGTGGGATCTAGCGTGGACG

CGCTGTCCATACCCTTGTATCTAAGGTGCCAACTGGTGTTCAAATTATC

CAAGCCTCTTGCAGCCGTGCCCCTGCTAGAATCTGGGGTAAACCGTCTA

GTACAAGCATTACCATTCTTGTCTGGTGAATTTACTGCTGTCCCTGCAA

GCGATGGTGGGAAGGAAATCTTACTTGTTAGACCAGTCTTAAATTTCGA

ACTAAGTCGTATACTGAAGATCAAATACCACGAAACATCCTTAAGACAC

GTATGCAAGCAGATGAACAGACCATCCTCGCAAGGTGGTGACTTGCCAC

ACGAACCGTATATGCCATACCCCAGGTTACCAGATCCATCTAGGCCTCA

ACCAATCGTGGGTTTTCAAGTCAATGTCCACACTGACGGTATAATCCTG

AGTGTAGCAACTCACCATTGCAGTTTTGACGCCACGGGATGGGAAGTA

TTGTACAGAACTTGGCCGCATGCTGTAGATCTCCGCCATCGGACGAGCC

AGATTTAACTACAAGCCCTGCTCAAGAAGCAGAAGCTAGGAAGGTCCTG

AGCCAAGTTAGAGAAACACCATTCGACCCAAAGATGTTTCCCGAATATA

GGCCCTTAGACTCTATGTTATCTTATTACAAAGGTGTCCAGTCTGCTTT

GCAGGGTCGTCAAACTACTATCGTTAACAGATGTTTCACTATCGCTGCT

GATAAGATAAACGCCTTAAAGAGGAGATGTAACCAACTTATTCCGGAAA

TGGTAAAGAAATACGGATTGAGTACAGAAGATGCTATCGGTTCTGCATG

GGTCTCTTCTAATGACGTGGTTGCCGCACTTTTGTGGACCTGTATTAAT

CGTGCTAGATACCCAGAGATTAGAGAAAGAAGTGTACATCAGCTTCCAC

CAGACTTGTTGCATGCTACATCTTCATTGGGTGTACCTGTTAATGTTAG

ATCTAGACTTTCACCACCCTTACCCAAATCCACTCTTGGGAATGCGGTC

TGCCTGCTAAGGGAGAAGGTACCTTTGCAATTCTTCGCTCTTCCGAGTC

ACGCAAACATGGAAGCAACCAGTTCAGTTTGCGCTGACCATTCAGGGGA

TGATGAATGGGCGTTGAGCTTTTGTAGGGTAGCTTATGGTCTGCGTGCA

AAATTGAACGCGATCGATGATGATTACATAAGGGATTACATTAGTTATG

TACAGAAGTCGCCCTGTCATCTTTCAGTTACACTAGATACTGAGAACTT

ATACCTGTCTAATTGGAGAGAAATAGGCGTCTACGATGCAGACTTCGGT

GGTATGCTAGGGAAACCATTGCGTATGAGAGCTCCGGATGGCTACACTG

ACGGTTTGATTTTCGTTATGGCCCAAAGATCTGAAGACAAGTCAGCTCC

GTGGGAATTCAACATATCCCTTGAGGCTTCTACAATGAAAAGGATTGTA

CATGATCCGCTGTGGTGTAAATATGTTGAATTGGATGCCTTTTGGCATG

GGGAAGAGTAA

SEQ ID NO: 127
XP_001258079.1 Protein sequence

MTVTISFEPYVGSSVDALSIPLYLRCQLVFKLSKPLAAVPLLESGVNRL

VQALPFLSGEFTAVPASDGGKEILLVRPVLNFELSRILKIKYHETSLRH

VCKQMNRPSSQGGDLPHEPYMPYPRLPDPSRPQPIVGFQVNVHTDGIIL

SVATHHCSFDATGMGSIVQNLAACCRSPPSDEPDLTTSPAQEAEARKVL

SQVRETPFDPKMFPEYRPLDSMLSYYKGVQSALQGRQTTIVNRCFTIAA

DKINALKRRCNQLIPEMVKKYGLSTEDAIGSAWVSSNDVVAALLWTCIN

RARYPEIRERSVHQLPPDLLHATSSLGVPVNVRSRLSPPLPKSTLGNAV

CLLREKVPLQFFALPSHANMEATSSVCADHSGDDEWALSFCRVAYGLRA

KLNAIDDDYIRDYISYVQKSPCHLSVTLDTENLYLSNWREIGVYDADFG

GMLGKPLRMRAPDGYTDGLIFVMAQRSEDKSAPWEFNISLEASTMKRIV

HDPLWCKYVELDAFWHGEE

SEQ ID NO: 128
XP_001217250.1 native Nucleotide sequence

ATGGCAACCTTCGACCATATCGAGGATGTCATCGGCCAGCTACCTATGC

TGAAGAGCTACACCCATATCTTGCTGTGCTTTCCCCTCGCTGAGAGCCA

ACTCAATGAAGCCATCGAGAGCCTTGAATCTGCTGTACGTCAGGTTATA

AAAACCTTTTCGTTCTTGGCTGGCAAAGTAGTCAACGAAGGCAAGGGAC

CCAACAGCTCGGGTACTTTCAGGGTCGCTCCCTGTGAGACGTGGGAGTC

CCCAGATCATCAATTTGTGCGAGTCGTTGATCGCTCTTTCATGCTGGCC

TCCTACGATGAGATCCGCGGAGCACAGGCACCTGCTTCCATGCTCCCAG

GAAGTCAACTCGGGTATCGGTGGCTTTTCCAGCGCATTATCACGAGAC

AGAGGACGATCCCGCGCCGGTCCTGGACATTCAGTGCAATTTGATACGG

GGCGGACTGCTACTTGACATCGCTGCCCAACACAACATTATCGATGCGA

GCGGTATCTTTCAAATTGCCAGCTTGATCGCTCTTTCCATGCGAGGCGA

GTCAATTCCTGAGGATGTCATCAAGGAAGGGAACCGTGATCGACGCAAT

ATCATTCCACTACTAGAGGCAGATGAGCCTCTTCTTGATCACAGCGAGC

TCAAAGCCAGCAGCGCGGTGCAAAATCCGCCGCCCGTCAACTTCCTCCA

GGGGTATAAATGGCAAATCTTCAAGCTCTCTGCCGAGGTGTTAACTCGA

ATTACCGCTGAAGGACGACGACAGCCACAGGAGTTTGTCCCCTCCGTCA

CATTTGTCTCGGCAAACGATTGCTTGACAGCCTTTCTGTGGCAACGGGT

GATAGCCATGCGCCTGAAGCGGCTCCATACGCCCGAGGCCGTATCCAAA

CTGAGCCGTGCTGTTGATCTTCGGCGGGCGATGGGCATTACCCCAGCAT

ACATGGGCCATATGATTCGTGTCGCAAATACTAGTCTCACTTTTCAAGA

```
AATTGTGGCATGCTCTTTATCCAGGCTTGCATCTCTGCTCCGCAAGAGC

ATCATCGATGTCAGCCAGCCGTATGCGATTCGGAGCTACGTGACCTTTA

TTGCAAATGAGACGGATAAATCAAAGATTGCGTATGCGGGTGCTTTCAA

TCCTTGCACCGACATGTCGTGCTCGTCCATTGCACACATCACTGCTCCT

GAATTCGGTCGTTTGGGAGCGCCTGACTTTATAAGGAGGCCTACCTACG

GGCCTCTGCCGTGCTGCACCTATGTCGCTCCCGATAAGAACGATGGAGC

TTTGGATCAAAACCAGGCATGGTCAGACGTTGTGAAGCGCATCGGTTGA
```

SEQ ID NO: 129
XP_001217250.1 Nucleotide sequence codon optimized for its expression in S. cerevisiae.

```
ATGGCCACCTTCGACCACATTGAGGACGTGATAGGACAATTGCCCATGC

TAAAGAGCTACACACATATTTTACTTTGCTTTCCGTTGGCAGAATCTCA

ACTGAACGAGGCGATTGAATCTTTGGAGTCAGCAGTCAGACAAGTAATT

AAGACGTTTTCATTCCTTGCAGGTAAGGTTGTTAATGAAGGCAAAGGTC

CGAATTCCTCTGGTACGTTCCGTGTTGCTCCGTGTGAAACTTGGGAATC

TCCTGATCATCAATTTGTTCGTGTTGTAGATAGGAGCTTTATGTTGGCC

TCGTATGATGAGATCCGTGGTGCTCAAGCCCCCGCTTCCATGTTACCTG

GGTCACAACTGGGGTATAGGGTAGCATTCCCAGCCCATTATCATGAAAC

TGAAGACGATCCAGCTCCAGTTCTAGATATCCAGTGTAATTTGATAAGA

GGTGGTCTGCTTCTAGATATAGCGGCCCAACACAACATAATTGATGCTT

CCGGGATATTTCAAATCGCTAGTCTGATCGCCTTAAGCATGAGAGGAGA

AAGTATCCCTGAAGATGTTATCAAAGAAGGAAACAGAGATAGAAGGAAT

ATCATTCCGTTATTGGAAGCCGATGAGCCTTTATTAGACCATAGTGAAT

TGAAGGCATCCAGCGCCGTTCAGAACCCGCCACCAGTTAATTTCTTGCA

AGGTTATAAATGGCAGATTTTCAAACTGTCCGCTGAGGTATTGACCCGT

ATTACTGCCGAAGGACGTAGACAACCACAAGAATTTGTGCCCTCAGTGA

CCTTTGTGTCCGCAAACGACTGCTTGACTGCTTTCTTGTGGCAGCGTGT

GATAGCTATGAGGCTAAAGAGATTGCATACCCCCGAGGCCGTTTCCAAG

CTATCTAGAGCCGTGGATTTAAGAAGGGCCATGGGTATAACCCCTGCAT

ACATGGGCCATATGATAAGAGTCGCAAACACATCCTTAACCTTTCAAGA

AATTGTCGCATGTAGTTTATCACGTCTTGCGAGCTTACTTAGAAAATCT

ATCATTGATGTGTCCCAACCATATGCGATCAGATCATACGTCACCTTCA

TAGCAAACGAAACAGACAAATCTAAGATAGCCTATGCCGGGGCATTTAA

CCCGTGTACTGATATGTCATGTTCATCCATAGCTCATATTACGGCACCG

GAGTTTGGTAGGTTAGGGGCGCCTGACTTCATTAGGAGACCCACTTATG

GCCCACTACCTTGCTGTACTTACGTAGCTCCTGACAAGAATGACGGTGC

ATTGGATCAGAATCAAGCATGGTCAGATGTCGTAAAGAGGATAGGTTAA
```

SEQ ID NO: 130
XP_001217250.1 Protein sequence

```
MATFDHIEDVIGQLPMLKSYTHILLCFPLAESQLNEAIESLESAVRQVI

KTFSFLAGKVVNEGKGPNSSGTFRVAPCETWESPDHQFVRVVDRSFMLA

SYDEIRGAQAPASMLPGSQLGYRVAFPAHYHETEDDPAPVLDIQCNLIR

GGLLLDIAAQHNIIDASGIFQIASLIALSMRGESIPEDVIKEGNRDRRN

IIPLLEADEPLLDHSELKASSAVQNPPPVNFLQGYKWQIFKLSAEVLTR

ITAEGRRQPQEFVPSVTFVSANDCLTAFLWQRVIAMRLKRLHTPEAVSK

LSRAVDLRRAMGITPAYMGHMIRVANTSLTFQEIVACSLSRLASLLRKS

IIDVSQPYAIRSYVTFIANETDKSKIAYAGAFNPCTDMSCSSIAHITAP

EFGRLGAPDFIRRPTYGPLPCCTYVAPDKNDGALDQNQAWSDVVKRIG
```

SEQ ID NO: 131
BAU61551.1 native Nucleotide sequence

```
ATGTCCAAGCCCTTATTCGAAGCGTATCCTCTCACAGGGCTTGATCATA

CGATTCCTCCATGTTATGTTCGCTTCCTTCTAACTTTCCCCGTGCCGGA

TGTGGCATTGGCTGTCAATCAGCTGCAAAAGGGAGCTGAAAATTTAATC

GAGAAACTTCCTTTCCTGGCCGGATATTTGGCTTCATGCGAGACCCCCG

GCGTACGCCCAGGGCAGCTCGAGATTCGACCTCCCGCTGGGGAAAGGAG

ACCTGTCTGCCTCGTCGCACATCACTCGAACTCCTATCTCGCAGATTCC

AGTGCGACGTCGACGACGGAACAGCTGGGCACCGCCAACGAGAACTATC

TCCCTGTCCCGTTCTTCCCGGAGCTAGACAAGCCGGTGCCCATCTTCCG

GGTTAAGGTGAATGCCATGACGGACGGCATCATTCTGGGATTTGCGTTC

CACCATAGCGTGATCGATGCCACCGGGATGGGCACCATTGTCCGGGACT

TTGCCAGATGCTGCCGTGGCCCTGATGGCGGTCCCCTGGAAATCAGTCT

GGAGTCTCAGCAGGACTCTAGAGAGAAGCTGAGACACTCCGGAGGACCT

CCCGATCCGCGGTTTGACCACAATGGGGAGTACCCTCGTGGCGTCTC

TGCCCGCCGACCTCGAAGCCATGAAGCAGGTCTTGATCCAGACGGCCCG

TCTCATGTCAACGCAGTATTTCCGCATCCCTGCCAGCCTAGTTAACACG

CTAAAGGAATCCTGCAATCGGATGCTTCGGGAATCACCAGCGCTCAGGG

ACGAAGGGAGAATCCATGGATTTCGAGCAACGATCTGGTGGTGTCGCT

GTTGTGGCTGTGTCTGAATCGCGTTCGGTATCCTGAAGATAATACCAAC

GTCATTCCTCCTTCCGATTCCTCGGTCTGCATGGCCGTGAATATCCGAG

GGCGTTTGCAGTCGCCCATTGATCCAGGATACGTTGGCAACGCCATCGT

CCTTCTCCGGGAGAGCGTTGGCATGAATGCTTTTCTGCATAAACCGGGC

GACGATGATCCCCTGGGCGCCCAATGTTACGAAACAGCGAAACGGCTAG

GCCGAGAAGCGTGGGAAGCAGCCCTGGTGCGCATCGCCCTGGCCATCCG

CCGCAAGCTCAACACCATAAACGCGAGTTACGTGCGCAGTGTTATATCC

TATCTGGAGGACGTGCCCGACCTGTCCACTGTGGCGTTTGGCCAGACGG

ACTACCACATCAGCAGCTGGCGGATATTGGCGTCTACGAGGCTGATTT

TGGTGGCCACATGGGCCATCCCAGCGAAATGCGAGTACCAGATGGGATG
```

-continued
GTCGATGGCATGTTTTACATCTTACCTCGAAGGCAGGGAACACACCCTT

GCTGGGAGATCCATGTTACTATCCACCAGGACACAATGAAGCGACTCAT

TGCAGACCCTGTGTGGGCACGATATACAGTGAGAAAGCCTTCATCACTC

TGCCGGGATGAATGA

SEQ ID NO: 132
BAU61551.1 Nucleotide sequence codon optimized for its expression in *S. cerevisiae*.

ATGTCAAAGCCTCTGTTTGAAGCATACCCCCTAACTGGTCTAGATCATA
CTATACCCCCTTGTTACGTCAGGTTCTTATTAACTTTCCCAGTTCCAGA
TGTAGCCCTTGCTGTTAACCAATTACAGAAAGGCGCCGAAAATTTAATA
GAGAAATTGCCTTTTCTTGCAGGGTACCTAGCTAGCTGTGAAACACCTG
GCGTAAGACCGGGGCAGTTAGAAATCAGGCCACCAGCAGGTGAAAGAAG
ACCAGTGTGTTTGGTCGCACATCACAGTAACTCGTACCTTGCGGATTCT
TCTGCAACAAGTACGACGGAGCAATTGGGAACAGCTAACGAAAATTACC
TTCCCGTACCATTCTTTCCAGAGTTGGACAAACCTGTTCCAATATTCCG
TGTCAAAGTTAACGCTATGACAGATGGGATTATCTTGGGGTTCGCTTTC
CACCATAGTGTAATAGATGCTACGGGAATGGGTACAATAGTTAGGGACT
TCGCCAGGTGCTGCAGAGGTCCTGATGGTGGGCCCTTAGAGATAAGTCT
AGAAAGCCAACAAGATTCGAGAGAAAAGCTGAGGCACTCAGGCGGTCCG
CCAGATCCCAGATTCGATCATAACGGAGAATACCCATTGGTGGCCTCAC
TGCCAGCGGACTTAGAAGCTATGAAACAAGTTTTAATCCAAACAGCGAG
GCTGATGAGTACACAATACTTTAGAATACCTGCTAGCCTTGTGAACACT
TTAAAAGAGTCATGTAATAGAATGCTTCGTGAATCCCCTGCACTGAGGG
ATGAAGGTGAAAACCCGTGGATTAGTTCTAACGATTTAGTAGTGAGTCT
ACTGTGGCTTTGTTTGAACAGGGTGAGGTACCCCGAAGACAATACAAAT
GTGATTCCACCCTCTGACAGTTCTGTTTGCATGGCTGTAAATATAAGAG
GGAGATTACAGTCGCCGATCGATCCAGGTTATGTTGGTAATGCTATTGT
ATTATTAAGAGAATCTGTTGGAATGAATGCCTTTCTACATAAACCTGGT
GATGACGACCCGCTTGGTGCCCAATGTTACGAGACAGCTAAAAGACTTG
GAAGAGAAGCATGGGAAGCAGCATTAGTCAGGATTGCTTTGGCAATTAG
GCGTAAGTTGAACACTATTAATGCTTCCTATGTCAGATCAGTTATTAGC
TACTTAGAGGATGTGCCCGATCTATCAACCGTTGCCTTCGGGCAAACTG
ATTATCATATCTCCAGTTGGAGAGACATTGGAGTTTACGAGGCTGACTT
TGGTGGTCATATGGGCCATCCATCTGAGATGAGAGTCCCTGACGGGATG
GTCGATGGTATGTTTTACATACTACCTAGAAGACAAGGTACTCACCCAT
GTTGGGAAATTCATGTGACTATACACCAGGATACCATGAAAAGACTGAT
CGCTGATCCGGTTTGGGCAAGATATACCGTTAGAAAGCCTAGTTCTTTG
TGCAGGGACGAGTAA

SEQ ID NO: 133
BAU61551.1 Protein sequence

MSKPLFEAYPLTGLDHTIPPCYVRFLLTFPVPDVALAVNQLQKGAENLI
EKLPFLAGYLASCETPGVRPGQLEIRPPAGERRPVCLVAHHSNSYLADS
SATSTTEQLGTANENYLPVPFFPELDKPVPIFRVKVNAMTDGIILGFAF
HHSVIDATGMGTIVRDFARCCRGPDGGPLEISLESQQDSREKLRHSGGP
PDPREDHNGEYPLVASLPADLEAMKQVLIQTARLMSTQYFRIPASLVNI
LKESCNRMLRESPALRDEGENPWISSNDLVVSLLWLCLNRVRYPEDNTN
VIPPSDSSVCMAVNIRGRLQSPIDPGYVGNAIVLLRESVGMNAFLHKPG
DDDPLGAQCYETAKRLGREAWEAALVRIALAIRRKLNTINASYVRSVIS
YLEDVPDLSTVAFGQTDYHISSWRDIGVYEADFGGHMGHPSEMRVPDGM
VDGMFYILPRRQGTHPCWEIHVTIHQDTMKRLIADPVWARYTVRKPSSL
CRDE

SEQ ID NO: 134
PsSalAT native Nucleotide sequence

ATGGCAACAATGTATAGTGCTGCTGTTGAAGTGATCTCTAAGGAAACCA
TTAAACCCACAACTCCAACCCCATCTCAACTTAAAAACTTCAATCTGTC
ACTTCTCGATCAATGTTTTCCTTTATATTATTATGTTCCAATCATTCTT
TTCTACCCAGCCACCGCCGCTAATAGTACCGGTAGCAGTAACCATCATG
ATGATCTTGACTTGCTTAAGAGTTCTCTTTCCAAAACACTAGTTCACTT
TTATCCAATGGCTGGTAGGATGATAGACAATATTCTGGTCGACTGTCAT
GACCAAGGGATTAACTTTTACAAAGTTAAAATTAGAGGTAAAATGTGTG
AGTTCATGTCGCAACCGGATGTGCCACTAAGCCAGCTTCTTCCCTCTGA
AGTTGTTTCCGCGAGTGTCCCTAAGGAAGCACTGGTGATCGTTCAAGTG
AACATGTTTGACTGTGGTGGAACAGCCATTTGTTCGAGTGTATCACATA
AGATTGCCGATGCAGCTACAATGAGTACGTTCATTCGTAGTTGGGCAAG
CACCACTAAAACATCTCGTAGTGGGGGTTCAACTGCTGCCGTTACAGAT
CAGAAATTGATTCCTTCTTTCGACTCGGCATCTCTATTCCCACCTAGTG
AACGATTGACATCTCCATCAGGGATGTCAGAGATACCATTTTCCAGTAC
CCCAGAGGATACAGAAGATGATAAAACTGTCAGCAAGAGATTTGTGTTC
GATTTTGCAAAGATAACATCTGTACGTGAAAAGTTGCAAGTATTGATGC
ATGATAACTACAAAAGCCGCAGGCAAACAAGGGTTGAGGTGGTTACTTC
TCTAATATGGAAGTCCGTGATGAAATCCACTCCAGCCGGTTTTTTACCA
GTGGTACATCATGCCGTGAACCTTAGAAAGAAAATGGACCCACCATTAC
AAGATGTTTCATTCGGAAATCTATCTGTAACTGTTTCGGCGTTCTTACC
AGCAACAACAACGACAACAACAAATGCGGTCAACAAGACAATCAATAGT
ACGAGTAGTGAATCACAAGTGGTACTTCATGAGTTACATGATTTTATAG
CTCAGATGAGGAGTGAAATAGATAAGGTCAAGGGTGATAAAGGTAGCTT
GGAGAAAGTCATTCAAAATTTTGCTTCTGGTCATGATGCTTCAATAAAG
AAAATCAATGATGTTGAAGTGATAAACTTTTGGATAAGTAGCTGGTGCA

-continued
GGATGGGATTATACGAGATTGATTTTGGTTGGGGAAAGCCAATTTGGGT

AACAGTTGATCCAAATATCAAGCCGAACAAGAATTGTTTTTTCATGAAT

GATACGAAATGTGGTGAAGGAATAGAAGTTTGGGCGAGCTTTCTTGAGG

ATGATATGGCTAAGTTCGAGCTTCACCTAAGTGAAATCCTTGAATTGAT

TTGA

SEQ ID NO: 135
PsSalAT Nucleotide sequence codon optimized for its expression in *S. cerevisiae*.

ATGGCAACAATGTACTCAGCTGCAGTTGAGGTTATATCTAAGGAAACGA
TAAAACCAACCACTCCAACCCCAAGCCAATTGAAGAATTTCAATTTATC
TTTATTAGACCAGTGCTTTCCCTTGTACTACTATGTCCCCATCATCTTG
TTCTACCCTGCGACTGCTGCAAACTCCACTGGTTCCTCGAACCACCATG
ATGATCTAGATCTTCTGAAGAGCTCCCTTAGCAAGACACTTGTTCACTT
CTACCCTATGGCCGGTAGGATGATCGATAACATATTGGTTGACTGCCAC
GATCAGGGTATCAATTTCTATAAAGTTAAAATCAGGGGCAAGATGTGTG
AATTCATGTCTCAGCCTGATGTGCCACTGTCGCAGCTGCTACCTAGTGA
AGTGGTATCCGCATCTGTCCCAAAAGAGGCCTTGGTCATAGTCCAAGTT
AATATGTTCGATTGCGGTGGGACGGCCATCTGCTCGTCGGTCAGTCATA
AGATCGCAGACGCCGCAACCATGTCAACATTTATTAGATCTTGGGCGAG
TACCACCAAAACTTCAAGGTCTGGCGGGTCAACCGCCGCTGTTACTGAC
CAGAAGTTGATTCCTAGCTTTGATTCGGCAAGCTTATTCCCACCTTCCG
AAAGGTTGACTTCACCAAGCGGGATGTCTGAGATACCATTTTCTTCAAC
CCCTGAAGATACCGAGGACGACAAAACAGTTAGCAAAAGATTCGTGTTT
GACTTTGCAAAGATAACATCTGTTAGAGAAAAGCTTCAGGTATTAATGC
ACGACAACTACAAAAGCAGGCGTCAGACCAGGGTTGAGGTCGTAACGAG
CCTGATCTGGAAGAGTGTCATGAAGTCAACACCAGCTGGGTTCCTTCCC
GTCGTGCATCATGCGGTAAATTTGAGGAAGAAGATGGACCCACCATTGC
AGGATGTCTCCTTCGGCAACCTGAGTGTTACTGTCTCAGCATTCTTGCC
CGCCACAACTACCACCACCACAAATGCCGTTAATAAGACAATAAATTCA
ACTTCATCGGAGAGTCAGGTGGTGCTACATGAATTGCACGATTTTATCG
CACAAATGAGAAGTGAGATAGACAAAGTTAAAGGCGATAAGGGTAGCCT
AGAAAAGGTGATTCAGAACTTTGCCTCTGGTCATGACGCTTCAATAAAG
AAAATAAATGACGTAGAGGTCATAAATTTCTGGATATCTTCATGGTGCA
GAATGGGCTTGTATGAGATCGACTTCGGCTGGGGCAAGCCGATTTGGGT
TACAGTTGACCCTAATATCAAGCCAAATAAGAATTGCTTCTTTATGAAC
GACACAAAATGCGGAGAAGGAATAGAGGTATGGGCAAGCTTCCTGGAAG
ACGACATGGCCAAGTTTGAATTGCACTTATCGGAGATATTGGAATTGAT
CTAA

SEQ ID NO: 136
PsSalAT Protein sequence

MATMYSAAVEVISKETIKPTTPTPSQLKNFNLSLLDQCFPLYYYVPIIL
FYPATAANSTGSSNHHDDLDLLKSSLSKTLVHFYPMAGRMIDNILVDCH
DQGINFYKVKIRGKMCEFMSQPDVPLSQLLPSEVVSASVPKEALVIVQV
NMEDCGGTAICSSVSHKIADAATMSTFIRSWASTTKTSRSGGSTAAVTD
QKLIPSFDSASLFPPSERLTSPSGMSEIPFSSTPEDTEDDKTVSKREVF
DFAKITSVREKLQVLMHDNYKSRRQTRVEVVTSLIWKSVMKSTPAGFLP
VVHHAVNLRKKMDPPLQDVSFGNLSVTVSAFLPATTTTTTNAVNKTINS
TSSESQVVLHELHDFIAQMRSEIDKVKGDKGSLEKVIQNFASGHDASIK
KINDVEVINFWISSWCRMGLYEIDFGWGKPIWVTVDPNIKPNKNCFFMN
DTKCGEGIEVWASFLEDDMAKFELHLSEILELI

SEQ ID NO: 137
AstC Nucleotide sequence codon optimized for its expression in *S. cerevisiae*.

ATGACTAAGATCAACCCATACAAGGGTATCTTGGTTGAATTGAAGGACA
TCGTTTTCACTTCTTCTTCTGACCAAATCAAGTTGCCAATCAACACTTT
CAAGTCTATCTTGTGTTGTGGTGCTACTGCTCAATACCAATGTGGTAAG
ATCAACAGAGCTCAATACTACTCTAGATTGGCTAGAGACTTCGCTTTGT
CTTTGGCTGACGTTACTGCTTTGTTCGACACTGTTCAAGCTACTATCAG
ACCAGAAGAATCTTTCTTGGCTTTCTTGGCTGAATTGAAGTCTAGATTC
GGTGAACAATTGAAGTTGTACGCTGTTGCTAACATGTCTAGAGAAGACT
ACGCTATGTTGAAGTCTTTGCCAATCGACTGGTCTTTGTTCGACGGTGT
TTTCTTGTCTGCTGACTTGGGTATGAGAAAGCCAGAATTGAGATTCTTC
AGACACGTTTTGGAATCTATCTCTATGAAGCCAGAAGACACTATCTTGG
TTGACAACGACACTGACAACATCTTGTGTGCTTTGTCTATGGGTTTGAA
GGGTATCTTGTTCGGTTCTACTTCTGTTCCACAAGCTTTGACTAACTTG
TTGGAATACGACCACATCTCTAGAGCTGAACAATTCTTGAGATCTCACG
CTAAGTCTTTGCACTCTGTTACTCACACTGGTGTTACTATCAGAGAAAA
CTTCGCTCAATTGTTGATCTTGGAAGCTACTGGTGACATCGACTTGGTT
GAATTGGAATACCACCCAACTACTTGGAACTACTTCATCGGTACTCCAG
TTTTGACTCAAACTGAATTCCCACACGACTTGGACACTACTTCTTTGGC
TACTACTGTTTTGGACAGACCAAAGGACATCGCTAACGAAATCATGGAC
GAAATGTTGAAGTACAGATCTGACGACGACTTGATGTTGACTTTCTTCA
CTGACTTCAAGAACAGAGTTGACCCAGTTGTTTGTTGTAACGTTTTGTC
TTTGTTCTACAAGTACGGTAGAGGTCACGAATTGCACCACACTTTGGCT
TGGGTTAGACAAGTTTTGATCAGAAGAGCTTACATCAACGGTACTGCTT
TCTACCCAATGCCAGAAGCTTTCTTGTACTTCTTCTTCAGATTCTTGCA
ACACATCACTCACTTGCCACAATTGTACGACGGTTTGAAGGTTTTGTTG
AAGGAAAGATTGCAAGAAGAGTTGGTGTTCCAGTTGACCCAATCTCTT
TGTCTATGAGATTGATCGCTTGTAACGGTGTTGGTATCCACGACAGAAT

GGGTTTGAACGCTTTGTTGTCTATGCAAAACCCAGACGGTTCTTGGGAC

TTGGGTACTATGTACCACTACGCTTCTAAGAGATTGCCAATCGGTAACC

AAGGTGTTTCTACTGCTATGGCTATCAAGGCTATCAAGCAATGTCAAGC

TAACCAATGTGCTGGTATCTAA

SEQ ID NO: 138
AstC Protein sequence

MTKINPYKGILVELKDIVFTSSSDQIKLPINTFKSILCCGATAQYQCGK

INRAQYYSRLARDFALSLADVTALFDTVQATIRPEESFLAFLAELKSRF

GEQLKLYAVANMSREDYAMLKSLPIDWSLFDGVFLSADLGMRKPELRFF

RHVLESISMKPEDTILVDNDTDNILCALSMGLKGILFGSTSVPQALTNL

LEYDHISRAEQFLRSHAKSLHSVTHTGVTIRENFAQLLILEATGDIDLV

ELEYHPTTWNYFIGTPVLTQTEFPHDLDTTSLATTVLDRPKDIANEIMD

EMLKYRSDDDLMLTFFTDFKNRVDPVVCCNVLSLFYKYGRGHELHHTLA

WVRQVLIRRAYINGTAFYPMPEAFLYFFFRFLQHITHLPQLYDGLKVLL

KERLQERVGVPVDPISLSMRLIACNGVGIHDRMGLNALLSMQNPDGSWD

LGTMYHYASKRLPIGNQGVSTAMAIKAIKQCQANQCAGI

SEQ ID NO: 139
AstI Nucleotide sequence codon optimized for its expression in *S. cerevisiae*.

ATGACTAGACAATCTCACTACCAAGCTATCATCTTGGACTTGGGTAACG

TTGTTTTCGAATGGGACACTTCTCAAAACCCACCAACTGCTGCTCCAAA

CCAAATCTCTTTGTTGAGAACTTCTATGAAGTCTCCAGTTTACCACTCT

TACGAAAGAGGTCAATTGTCTACTGAAGAATGTCACAGATTGTTGGGTG

AATCTTTGCACGTTGACCCAGGTCAAATCAAGGAAGCTTTCGACTTGGC

TAGACAATCTTTGAGATCTAACCCAGCTTTGTTGGACTTCATCAGACAA

TTGAAGCAAACTAGAGGTGTTGCTGTTTACGCTATGTCTAACATCCCAC

AAGCTGAAATCGAATACTTGAAGGAATCTAGAGCTGGTGACATGGAAGT

TTTCGACGAAGTTTTCGCTTCTGGTTACGTTGGTTCTAGAAAGCCAGAA

ACTGAATTCTACAGAAGAGTTATGGGTGAAATCGGTTTGAAGGCTGAAA

GAGTTGTTTTCGTTGACGACAAGGAAGAAAACGTTGACGTTGCTAGAGG

TTTGGGTTTGTACGGTGTTTGTTTCGGTGGTGTTGAAGAATTGAGAGGT

CACTTGTTGGGTATCTAA

SEQ ID NO: 140
AstI Protein sequence

MTRQSHYQAIILDLGNVVFEWDTSQNPPTAAPNQISLLRTSMKSPVYHS

YERGQLSTEECHRLLGESLHVDPGQIKEAFDLARQSLRSNPALLDFIRQ

LKQTRGVAVYAMSNIPQAEIEYLKESRAGDMEVEDEVFASGYVGSRKPE

TEFYRRVMGEIGLKAERVVFVDDKEENVDVARGLGLYGVCFGGVEELRG

HLLGI

SEQ ID NO: 139
AstI Nucleotide sequence codon optimized for its expression in *S. cerevisiae*.

ATGTGTACTACTTTCAAGGCTGCTATCTTCGACATGGGTGGTGTTTTGT

TCACTTGGAACCCAATCGTTGACACTCAAGTTTCTTTGAAGGACTTGGG

TACTATCATCAACTCTGAAACTTGGGAACAATTCGAAAGAGGTAAGATC

GAACCAGACGACTGTTACCACCAATTGGGTTCTCAAATCGGTTTGCCAG

GTTCTGAAATCGCTGCTACTTTCAGACAAACTACTGGTTGTTTGAGACC

AGACGCTAGAATGACTTCTTTGTTGAGAGAATTGAAGGGTCAAGGTGTT

GCTGTTTACATGATGACTAACATCCCAGCTCCAGACTTCCACCAATTGA

GAGAAATGCACTACGAATGGGACTTGTTCGACGGTATCTTCGCTTCTGC

TTTGGAAGGTATGAGAAAGCCAGACTTGGAATTCTACGAACACGTTTTG

AAGCAAATCGACACTTCTGCTGCTGAAACTATCTTCGTTGACGACAAGT

TGGAAAACGTTATCGCTGCTCAAGCTGTTGGTATGGTTGGTTTGCACTT

GACTGACTCTTTGGCTACTTGTATGGAATTGAGACAATTGGTTGGTTGT

TAA

SEQ ID NO: 142
AstK Protein sequence

MCTTFKAAIFDMGGVLFTWNPIVDTQVSLKDLGTIINSETWEQFERGKI

EPDDCYHQLGSQIGLPGSEIAATFRQTTGCLRPDARMTSLLRELKGQGV

AVYMMTNIPAPDFHQLREMHYEWDLFDGIFASALEGMRKPDLEFYEHVL

KQIDTSAAETIFVDDKLENVIAAQAVGMVGLHLTDSLATCMELRQLVGC

SEQ ID NO: 142
PYI04555.1 Protein sequence not C-terminally extended.

MGASVSFQPFVPTPLDHAMPPIYVSQFLCFPTTTPQSAIQSLQVGIERL

FERLPFLAGEILINEHTGAIKVQAPSALIREIPYMALRAHPDLYLPAKQ

CATTPIERQLKTNSLDESYHPLPAALPLSQPQPVIRFQANTLADGILFA

VSYHHCIFDGTGCGQILEMLAQCCSASDDKISLPTDCHTDVLLREYISN

LSPTTNIPHDYTQAYSTTVQPDPDASDPDTSPAIPSSLYTEAFTFPSQQ

ITTLRDACNHLLPKLPSTSNAHPHKPTPNPLSSNDVLTALIALCITRAT

NTTTPPLQPNNHSLSMAVNLRTRIQPQVPDHFLGNFATLLPIHFTSPVH

TQQSDLLLTTEPPDPALIHLTTLASQIRSSLSTVNTDYICGLMTDLRTR

RNAGENSSLLIEGIKISSWRHLSVYKPDFGPGLGKIAGFEFQAGLMDNL

VVILPWRNGDWDVRVTLLERDMRGFREDRLVRWALGSG

SEQ ID NO: 143
ERR364415-1_contig_8546 Protein sequence not C-terminally extended.

MARAPPPPPPGLRMRDTVLSIVKPIRKTQHLETIDATFVDLMRMDSFIP

VIFAYRPADKSEAAYSRLVNRIKESLQKVLVPFFGFAGRWVPSSGGSRR

LLCNDEGVPFIEAFVDEELDSVVKASAAFQPVTELNGLGVLGMDMTSYD

QRMPPEGGQPCVVAQVTRFKCGGVVLGVAFNHTHTDGQGFYTFMRAWSD

-continued

FSRTNGTAIKVDHNRALPELASLSQFFIKQHDRIGGKTSTDRVNDHCSK

VPERLALKAFEVRASKIKAAKLAAEDGGVGYVSTVDCIVAHLWKTLARL

PPVVLDGREITVFSPVEGRNRFLDPPRPNMCGNCFAAMVTPKIPTQELL

EMPLAAIAGKOREKLSTTRREEWFGQQSFRELASAMNTSKSALLIVTSW

FNFPMYEIDFGAGKPFFASTTNMISPINGVCCGVIAPPTPGSCSSIATL

YILCLPAVLEALENVPDFLSFFVPHPNHKDNSQ

Further sequences applicable in the invention are listed below. The "previous" SEQ ID NOs refer to those as used in the respective patent document.

1. Albicanyl diphosphate synthases as described in PCT/CN2018/088902 (filed May 29, 2018) are:
DfHAD, DfHAD-9 (V274A) and DfHAD-8 (K532R) of *Dryopteris fragrans*

| Previous SEQ ID NO | Name | Type | Current SEQ ID NO |
|---|---|---|---|
| 1 | DfHAD | NA | 26 |
| 2 | DfHAD | AA | 27 |
| 3 | DfHAD-8 (K532R) | NA | 28 |
| 4 | DfHAD-8 (K532R) | AA | 29 |
| 5 | DfHAD-9 (V274A) | NA | 30 |
| 6 | DfHAD-9 (V274A) | AA | 31 |
| 7 | DfHAD codon optimized for *E. coli* | NA | 32 |
| 8 | DfHAD codon optimized for Tobacco | NA | 33 |
| 9 | DfHAD-8 (K532R) codon optimized for *E. coli* | NA | 34 |
| 10 | DfHAD-9 (V274A) codon optimized for *E. coli* | NA | 35 |
| 17 | DfHAD-His-GST | NA | 36 |
| 18 | DfHAD-His-GST | AA | 37 |

NA = Nucleic Acid
AA = Amino Acid

2. Drimane synthases (i.e. albicanol synthases or drimenol synthases) as described in PCT/EP2018/064344 (filed May 31, 2018) are

| Previous SEQ ID NO (AA) | Name or NCBI accession number | Source | Current SEQ ID NO (AA) | Current SEQ ID NO (NA) |
|---|---|---|---|---|
| 1 | CvTps1 | *Cryptoporus volvatus* | 38 | 39, 40, 41 |
| 5 | LoTps1 | *Laricifomes officinalis* | 42 | 43, 44, 45, 95 |
| 9 | OCH93767.1 | *Obba rivulosa* | 46 | 47, 48 |
| 12 | EMD37666.1 | *Gelatoporia subvermispora* | 49 | 50, 51, 96 |
| 15 | EMD37666-B | *Gelatoporia subvermispora* | 52 | 53 |
| 17 | XP_001217376.1 | *Aspergillus terreus* | 54 | 55, 56, 97 |
| 20 | OJJ98394.1 | *Aspergillus aculeatus* | 57 | 58, 59 |
| 23 | GAO87501.1 | *Aspergillus udagawae* | 60 | 61, 62 |
| 26 | XP_008034151.1 | *Trametes versicolor* | 63 | 64, 65 |
| 29 | XP_007369631.1 | *Dichomitus squalens* | 66 | 67, 68, 93 |
| 32 | ACg006372 | *Antrodia cinnamomea* | 69 | 70, 71 |
| 35 | KIA75676.1 | *Aspergillus ustus* | 72 | 73, 74 |
| 38 | XP_001820867.2 | *Aspergillus oryzae* | 75 | 76, 77 |
| 41 | CEN60542.1 | *Aspergillus calidoustus* | 78 | 79, 80 |
| 44 | XP_009547469.1 | *Heterobasidion irregulare* | 81 | 82, 83 |
| 47 | KLO09124.1 | *Schizopora paradoxa* | 84 | 85, 86 |
| 50 | OJI95797.1 | *Aspergillus versicolor* | 87 | 88, 89 |
| 63 | XP_006461126 | *Agaricus bisporus* | 90 | 91, 92, 94 |

AA = Amino Acid

3. Drimenol synthases as described in WO2015/169871 are

| Previous SEQ ID NO (AA) | Name | Source | Current SEQ ID NO (AA) | Current SEQ ID NO (NA) |
|---|---|---|---|---|
| 2 | D1Tps589 | *Drimys lanceolota* | 99 | 98, 100 |
| 8 | SCH51_3228_11 | *Drimys winteri* | 105 | 104, 106 |
| 5 | SCH51_3228_9 | *Drimys winteri* | 102 | 101, 103 |
| 11 | SCH51_998_28 | *Drimys winteri* | 108 | 107, 109 |
| 14 | SCH52_13163_6 | *Drimys lanceolota* | 111 | 110, 112 |

4. Drimenol synthases as described in WO 2015/176959 are
VaTPS3 (SEQ ID NO:6) of *Valeriana amurensis*

| Previous SEQ ID NO (AA) | Name | Source | Current SEQ ID NO (AA) | Current SEQ ID NO (NA) |
|---|---|---|---|---|
| 6 | VaTPS3 | *Valeriana amurensis* | 114 | 113, 115 |

The invention claimed is:

1. A biocatalytic method of producing a drimanyl acetate compound comprising the steps of
   (1) contacting in the presence of an acetyl group donor a drimanyl alcohol with a polypeptide having acetyl transferase activity of the enzyme class EC 2.3.1 capable of transferring an acetyl group from said acetyl group donor to said drimanyl alcohol to obtain a drimanyl acetate; and
   (2) optionally isolating a drimanyl acetate compound from the reaction product of step (1);
   wherein said acetyl group donor is acetyl-Coenzyme A (acetyl-CoA); and
   wherein said acetyl transferase is selected from the group consisting of
   a) polypeptides comprising an amino acid sequence selected from the group consisting of SEQ ID NO: 9, 17, 118, 124, 144, 23, 21, 11, 19, 13, 15, 25, 121, 143, 127, 130, 133, and 136; and
   b) polypeptides having acetyl transferase activity and comprising an amino acid sequence showing a degree of sequence identity of at least 80% to at least one of said amino acid sequences selected from the group consisting of SEQ ID NO: 9, 17, 118, 124, 144, 23, 21, 11, 19, 13, 15, 25, 121, 143, 127, 130, 133, and 136;
   wherein the biocatalytic method is performed in an aqueous environment.

2. The method of claim 1, wherein said drimanyl acetate compound is selected from the group consisting of albicanyl acetate, drimenyl acetate, and bicyclofarnesyl acetate, each in stereoisomerically pure form or as a mixture of at least two stereoisomers thereof, and combinations thereof comprising at least two members of said group.

3. The method of claim 1, wherein said drimanyl alcohol is selected from the group consisting of albicanol, drimenol, and bicyclofarnesol, each in stereoisomerically pure form or as a mixture of at least two stereoisomers thereof, and combinations thereof comprising at least two members of said group.

4. The method of claim 1, further comprising, prior to step 1) the biocatalytic formation of said drimanyl alcohol compound.

5. The method of claim 4, wherein said enzymatic synthesis of said drimanyl alcohol is catalysed by one or more polypeptides having the ability to convert said non-cyclic sesquiterpene precursor to at least one drimanyl alcohol in one or more enzymatic steps.

6. The method of claim 5, wherein said at least one drimanyl alcohol is produced in a single or more enzymatic steps from FPP.

7. The method of claim 6, wherein said at least one drimanyl alcohol is produced by an enzymatic conversion of FPP, catalysed by
   a) a polypeptide having drimane sesquiterpene synthase activity forming said drimanyl alcohol; or
   b) a combination of a polypeptide having drimanyl phosphate synthase activity forming at least one drimanyl phosphate intermediate, and a polypeptide having phosphatase activity converting said at least one drimanyl phosphate intermediate to at least one drimanyl alcohol.

8. The method of claim 7, wherein
a) said polypeptide having drimane sesquiterpene synthase activity is selected from the group consisting of a polypeptide having albicanol synthase activity, drimenol synthase activity, bicyclofarnesol synthase activity and any combination of such activities; and
b) said combination of polypeptides comprises a drimanyl diphosphate synthase activity and a phosphatase.

9. The method of claim 8, wherein said drimane sesquiterpene synthase is selected from the group consisting of
a) a polypeptide having albicanol synthase activity and comprising an amino acid sequence of SEQ ID NO: 5 or a mutant or variant polypeptide having albicanol synthase activity and comprising an amino acid sequence having at least 40% sequence identity to SEQ ID NO: 5; and
b) a polypeptide having drimenol synthase activity and comprising an amino acid sequence of SEQ ID NO: 7 or a mutant or variant polypeptide having drimenol synthase activity and comprising an amino acid sequence having at least 40% sequence identity to SEQ ID NO: 7.

10. The method of claim 1, wherein said acetyl transferase is selected from the group consisting of
a) polypeptides comprising an amino acid sequence selected from the group consisting of SEQ ID NO: 9, 17, 118, 124, 144, 23, 21, 11, 19, 13, 15, 25, 121, 143, 127, 130, 133, and 136; and
b) polypeptides having acetyl transferase activity and comprising an amino acid sequence showing a degree of sequence identity of at least 90% to at least one of said amino acid sequences selected from the group consisting of SEQ ID NO: 9, 17, 118, 124, 144, 23, 21, 11, 19, 13, 15, 25, 121, 143, 127, 130, 133, and 136.

11. The method of claim 1, wherein said acetyl transferase is selected from the group consisting of
a) polypeptides comprising an amino acid sequence selected from the group consisting of SEQ ID NO: 9, 17, 118, 124, 144, 23, 21, 11, 19, 13, 15, 25, 121, 143, 127, 130, 133, and 136; and
b) polypeptides having acetyl transferase activity and comprising an amino acid sequence showing a degree of sequence identity of at least 95% to at least one of said amino acid sequences selected from the group consisting of SEQ ID NO: 9, 17, 118, 124, 144, 23, 21, 11, 19, 13, 15, 25, 121, 143, 127, 130, 133, and 136.

* * * * *